US012668739B2

(12) United States Patent
Itoi et al.

(10) Patent No.: US 12,668,739 B2
(45) Date of Patent: Jun. 30, 2026

(54) ORGANIC ELECTROLUMINESCENT ELEMENT AND ELECTRONIC DEVICE USING SAME

(71) Applicant: IDEMITSU KOSAN CO., LTD., Tokyo (JP)

(72) Inventors: Hiroaki Itoi, Sodegaura (JP); Yuki Nakano, Sodegaura (JP); Satomi Tasaki, Sodegaura (JP); Taro Yamaki, Sodegaura (JP)

(73) Assignee: IDEMITSU KOSAN CO., LTD., Tokyo (JP)

(*) Notice: Subject to any disclaimer, the term of this patent is extended or adjusted under 35 U.S.C. 154(b) by 1060 days.

(21) Appl. No.: 17/632,913

(22) PCT Filed: Aug. 7, 2020

(86) PCT No.: PCT/JP2020/030495
§ 371 (c)(1),
(2) Date: Feb. 4, 2022

(87) PCT Pub. No.: WO2021/025163
PCT Pub. Date: Feb. 11, 2021

(65) Prior Publication Data

US 2022/0289704 A1 Sep. 15, 2022

(30) Foreign Application Priority Data

| | | |
|---|---|---|
| Aug. 8, 2019 | (JP) | 2019-146848 |
| Aug. 8, 2019 | (JP) | 2019-146849 |
| May 20, 2020 | (JP) | 2020-088409 |
| May 20, 2020 | (JP) | 2020-088410 |

(51) Int. Cl.
*H01L 51/54* (2006.01)
*C07C 13/62* (2006.01)
(Continued)

(52) U.S. Cl.
CPC .............. *C09K 11/06* (2013.01); *C07C 13/62* (2013.01); *C07C 15/62* (2013.01); *C07C 49/76* (2013.01); *C07C 211/54* (2013.01); *C07C 255/50* (2013.01); *C07C 321/26* (2013.01); *C07D 209/86* (2013.01); *C07D 213/16* (2013.01); *C07D 215/06* (2013.01); *C07D 223/24* (2013.01); *C07D 235/08* (2013.01); *C07D 277/66* (2013.01); *C07D 279/22* (2013.01); *C07D 311/82* (2013.01);
(Continued)

(58) Field of Classification Search
None
See application file for complete search history.

(56) References Cited

U.S. PATENT DOCUMENTS

2015/0001479 A1* 1/2015 Lee .......................... C07C 13/62 549/384
2015/0069344 A1 3/2015 Kim et al.
(Continued)

FOREIGN PATENT DOCUMENTS

JP 2010-059147 A 3/2010
KR 2017-0120767 A 11/2017
(Continued)

OTHER PUBLICATIONS

International Preliminary Report on Patentability and Written Opinion issued in corresponding International Patent Application No. PCT/JP2020/030492 dated Feb. 17, 2022.
(Continued)

*Primary Examiner* — Andrew K Bohaty
(74) *Attorney, Agent, or Firm* — Foley & Lardner LLP

(57) ABSTRACT

An organic electroluminescence device comprising: a cathode, an anode, and an organic layer disposed between the cathode and the anode, wherein the organic layer comprises a compound represented by the following formula (1), and a compound A having a Stokes shift of 20 nm or smaller and an emission peak wavelength of 440 nm to 465 nm (at least one of $Ar_1$ and $Ar_2$ is a monovalent group having a structure represented by the following formula (2)).

(1)

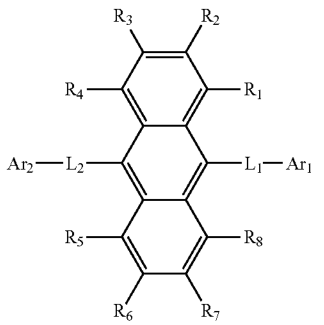

(2)

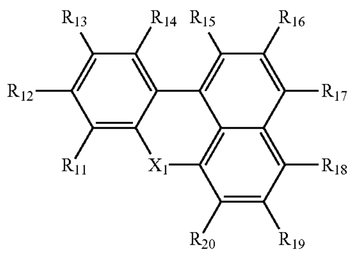

20 Claims, 1 Drawing Sheet

(51) Int. Cl.

| | |
|---|---|
| ***C07C 15/62*** | (2006.01) |
| ***C07C 49/76*** | (2006.01) |
| ***C07C 211/54*** | (2006.01) |
| ***C07C 255/50*** | (2006.01) |
| ***C07C 321/26*** | (2006.01) |
| ***C07D 209/86*** | (2006.01) |
| ***C07D 213/16*** | (2006.01) |
| ***C07D 215/06*** | (2006.01) |
| ***C07D 223/24*** | (2006.01) |
| ***C07D 235/08*** | (2006.01) |
| ***C07D 277/66*** | (2006.01) |
| ***C07D 279/22*** | (2006.01) |
| ***C07D 311/82*** | (2006.01) |
| ***C07D 333/54*** | (2006.01) |
| ***C07D 335/12*** | (2006.01) |
| ***C07D 405/10*** | (2006.01) |
| ***C07D 405/14*** | (2006.01) |
| ***C07D 407/10*** | (2006.01) |
| ***C07D 409/04*** | (2006.01) |
| ***C07D 409/10*** | (2006.01) |
| ***C07D 487/22*** | (2006.01) |
| ***C07D 493/04*** | (2006.01) |
| ***C07F 5/02*** | (2006.01) |
| ***C07F 7/08*** | (2006.01) |
| ***C07F 9/28*** | (2006.01) |
| ***C09K 11/06*** | (2006.01) |
| ***H10K 50/11*** | (2023.01) |
| ***H10K 85/40*** | (2023.01) |
| ***H10K 85/60*** | (2023.01) |

(52) U.S. Cl.

CPC ......... *C07D 333/54* (2013.01); *C07D 335/12* (2013.01); *C07D 405/10* (2013.01); *C07D 405/14* (2013.01); *C07D 407/10* (2013.01); *C07D 409/04* (2013.01); *C07D 409/10* (2013.01); *C07D 487/22* (2013.01); *C07D 493/04* (2013.01); *C07F 5/027* (2013.01); *C07F 7/081* (2013.01); *C07F 7/0812* (2013.01); *C07F 9/28* (2013.01); *H10K 50/11* (2023.02); *H10K 85/40* (2023.02); *H10K 85/60* (2023.02); *H10K 85/615* (2023.02); *H10K 85/621* (2023.02); *H10K 85/622* (2023.02); *H10K 85/623* (2023.02); *H10K 85/624* (2023.02); *H10K 85/625* (2023.02); *H10K 85/631* (2023.02); *H10K 85/649* (2023.02); *H10K 85/652* (2023.02); *H10K 85/653* (2023.02); *H10K 85/654* (2023.02); *H10K 85/655* (2023.02); *H10K 85/656* (2023.02); *H10K 85/6572* (2023.02); *H10K 85/6574* (2023.02); *H10K 85/6576* (2023.02); *H10K 85/658* (2023.02); *C07B 2200/05* (2013.01)

(56) References Cited

U.S. PATENT DOCUMENTS

| | | | | |
|---|---|---|---|---|
| 2015/0236274 | A1* | 8/2015 | Hatakeyama ...... | H10K 85/6572 548/405 |
| 2015/0333268 | A1 | 11/2015 | Han et al. | |
| 2016/0190481 | A1 | 6/2016 | Han et al. | |
| 2017/0331051 | A1 | 11/2017 | Han et al. | |
| 2017/0352820 | A1* | 12/2017 | Kim .................. | H10K 85/6574 |

FOREIGN PATENT DOCUMENTS

| | | | |
|---|---|---|---|
| KR | 2017-0126081 | A | 11/2017 |
| KR | 2019-0055685 | A | 5/2019 |
| KR | 2019-0118514 | A | 10/2019 |
| WO | WO-2018/066536 | A1 | 4/2018 |
| WO | WO-2018/088472 | A1 | 5/2018 |
| WO | WO-2019/035268 | A1 | 2/2019 |
| WO | WO-2019/111971 | A1 | 6/2019 |

OTHER PUBLICATIONS

International Preliminary Report on Patentability and Written Opinion issued in corresponding International Patent Application No. PCT/JP2020/030495 dated Feb. 17, 2022.

International Search Report issued in corresponding International Patent Application No. PCT/JP2020/030492 dated Oct. 13, 2020.

International Search Report issued in corresponding International Patent Application No. PCT/JP2020/030495 dated Nov. 2, 2020.

* cited by examiner

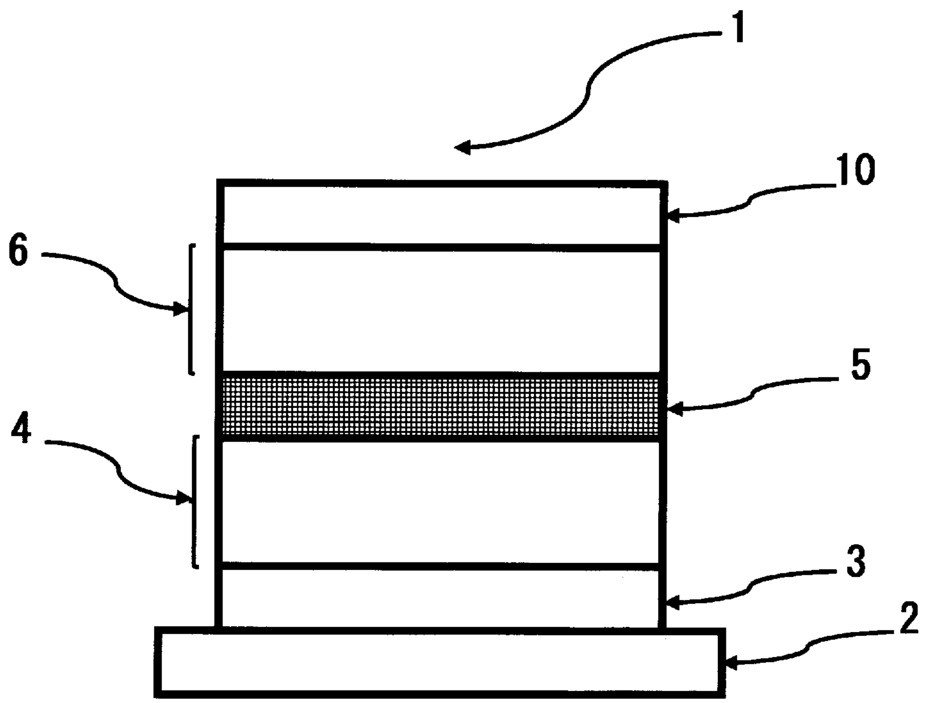
1
10
6
5
4
3
2

ORGANIC ELECTROLUMINESCENT ELEMENT AND ELECTRONIC DEVICE USING SAME

CROSS-REFERENCE TO RELATED APPLICATIONS

The present application claims priority under 35 U.S.C. § 371 to International Patent Application No. PCT/JP2020/030495, filed Aug. 7, 2020, which claims priority to and the benefit of Japanese Patent Application Nos. 2019-146848 and 2019-146849, both filed on Aug. 8, 2019, 2020-088409 and 2020-088410, both filed on May 20, 2020. The contents of these applications are hereby incorporated by reference in their entireties.

TECHNICAL FIELD

The invention relates to an organic electroluminescence device and an electronic apparatus using the same.

BACKGROUND ART

When voltage is applied to an organic electroluminescence device (hereinafter, referred to as an organic EL device in several cases), holes and electrons are injected into an emitting layer from an anode and a cathode, respectively. Then, thus injected holes and electrons are recombined in the emitting layer, and excitons are formed therein.

Patent Documents 1 and 2 disclose that a compound having a benzoxanthene structure is used as a material for an emitting layer of an organic EL device.

RELATED ART DOCUMENTS

Patent Documents

[Patent Document 1] US 2015/001479 A1

[Patent Document 2] US 2015/0693444 A1

SUMMARY OF THE INVENTION

It is an object of the invention to provide an organic EL device having high luminous efficiency and an electronic apparatus using the organic EL device.

According to the invention, the following organic EL device and electronic apparatus are provided.

1. An organic electroluminescence device comprising:

a cathode;

an anode; and an organic layer disposed the cathode and the anode, wherein the organic layer comprises a compound represented by the following formula (1), and a compound A having a Stokes shift of 20 nm or smaller and an emission peak wavelength of 440 nm to 465 nm.

(1)

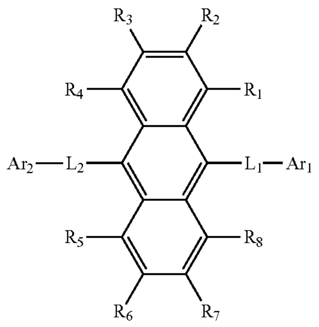

wherein in the formula (1), one or more sets of adjacent two or more of $R_1$ to $R_8$ form a substituted or unsubstituted, saturated or unsaturated ring by bonding with each other, or do not form a substituted or unsubstituted, saturated or unsaturated ring;

$R_1$ to $R_8$ that do not form the substituted or unsubstituted, saturated or unsaturated ring are independently a hydrogen atom or a substituent R;

the substituent R is a halogen atom, a cyano group, a nitro group, a substituted or unsubstituted alkyl group including 1 to 50 carbon atoms, a substituted or unsubstituted alkenyl group including 2 to 50 carbon atoms, a substituted or unsubstituted alkynyl group including 2 to 50 carbon atoms, a substituted or unsubstituted cycloalkyl group including 3 to 50 ring carbon atoms, $—Si(R_{901})(R_{902})(R_{903})$, $—O—(R_{904})$, $—S—(R_{905})$, $—N(R_{906})(R_{907})$, a substituted or unsubstituted aryl group including 6 to 50 ring carbon atoms, or a substituted or unsubstituted monovalent heterocyclic group including 5 to 50 ring atoms;

$R_{901}$ to $R_{907}$ are independently a hydrogen atom, a substituted or unsubstituted alkyl group including 1 to 50 carbon atoms, a substituted or unsubstituted cycloalkyl group including 3 to 50 ring carbon atoms, a substituted or unsubstituted aryl group including 6 to 50 ring carbon atoms, or a substituted or unsubstituted monovalent heterocyclic group including 5 to 50 ring atoms;

when two or more of each of $R_{901}$ to $R_{907}$ are present, the two or more of each of $R_{901}$ to $R_{907}$ are the same as or different from each other;

$L_1$ and $L_2$ are independently a single bond, a substituted or unsubstituted arylene group including 6 to 50 ring carbon atoms, or a substituted or unsubstituted divalent heterocyclic group including 5 to 50 ring atoms;

at least one of $Ar_1$ and $Ar_2$ is a monovalent group having a structure represented by the following formula (2);

(2)

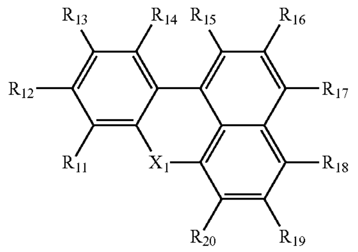

wherein in the formula (2), $X_1$ is O, S, or $C(R_{21})(R_{22})$;

one of $R_{11}$ to $R_{20}$ is a single bond which bonds with $L_1$ or $L_2$;

one or more sets of adjacent two or more of $R_{11}$ to $R_{14}$ and adjacent two or more of $R_{15}$ to $R_{20}$ that are not a single bond which bonds with $L_1$ or $L_2$ form a substituted or unsubstituted, saturated or unsaturated ring by bonding with each other, or do not form a substituted or unsaturated, saturated or unsaturated ring;

$R_{21}$ and $R_{22}$ form a substituted or unsubstituted, saturated or unsaturated ring by bonding with each other, or do not form a substituted or unsubstituted, saturated or unsaturated ring;

$R_{21}$ and $R_{22}$ that do not form the substituted or unsubstituted, saturated or unsaturated ring, and $R_{11}$ to $R_{20}$ that do not form the substituted or unsubstituted, saturated or unsaturated ring and that are not a single bond which bonds with $L_1$ or $L_2$ are independently a hydrogen atom or a substituent R;

the substituent R is as defined in the formula (1);

$Ar_1$ or $Ar_2$ which is not the monovalent group having a structure represented by the formula (2) is a substituted or unsubstituted aryl group including 6 to 50 ring carbon atoms, or a substituted or unsubstituted monovalent heterocyclic group including 5 to 50 ring atoms.

2. An electronic apparatus equipped with the organic electroluminescence device according to 1.

According to the invention, an organic EL device having high luminous efficiency and an electronic apparatus using the organic EL device can be provided.

BRIEF DESCRIPTION OF THE DRAWINGS

The Figure is a diagram showing a schematic configuration of an organic EL device according to an aspect of the invention.

MODE FOR CARRYING OUT THE INVENTION

Hereinafter, each aspect for carrying out the invention will be described. It should be noted that an embodiment in which two or more of the individual embodiments of the invention described below are combined is also an embodiment of the invention.

[Definition]

In this specification, a hydrogen atom includes its isotopes different in the number of neutrons, namely, a protium, a deuterium and a tritium.

In this specification, at a bondable position in a chemical formula where a symbol such as "R", or "D" representing a deuterium atom is not indicated, a hydrogen atom, that is, a protium atom, a deuterium atom or a tritium atom is bonded.

In this specification, the number of ring carbon atoms represents the number of carbon atoms forming a subject ring itself among the carbon atoms of a compound having a structure in which atoms are bonded in a ring form (for example, a monocyclic compound, a fused ring compound, a cross-linked compound, a carbocyclic compound, or a heterocyclic compound). When the subject ring is substituted by a substituent, the carbon contained in the substituent is not included in the number of ring carbon atoms. The same shall apply to "the number of ring carbon atoms" described below, unless otherwise specified. For example, a benzene ring has 6 ring carbon atoms, a naphthalene ring includes 10 ring carbon atoms, a pyridine ring includes 5 ring carbon atoms, and a furan ring includes 4 ring carbon atoms. Further, for example, a 9,9-diphenylfluorenyl group includes 13 ring carbon atoms, and a 9,9'-spirobifluorenyl group includes 25 ring carbon atoms.

When a benzene ring is substituted by, for example, an alkyl group as a substituent, the number of carbon atoms of the alkyl group is not included in the number of ring carbon atoms of the benzene ring. Therefore, the number of ring carbon atoms of the benzene ring substituted by the alkyl group is 6. When a naphthalene ring is substituted by, for example, an alkyl group as a substituent, the number of carbon atoms of the alkyl group is not included in the number of ring carbon atoms of the naphthalene ring. Therefore, the number of ring carbon atoms of the naphthalene ring substituted by the alkyl group is 10.

In this specification, the number of ring atoms represents the number of atoms forming a subject ring itself among the atoms of a compound having a structure in which atoms are bonded in a ring form (for example, the structure includes a monocyclic ring, a fused ring and a ring assembly) (for example, a monocyclic compound, a fused ring compound, a cross-linked compound, a carbocyclic compound and a heterocyclic compound). The number of ring atoms does not include atoms that do not form the ring (for example, a hydrogen atom which terminates a bond of the atoms forming the ring), or atoms contained in a substituent when the ring is substituted by the substituent. The same shall apply to "the number of ring atoms" described below, unless otherwise specified. For example, the number of atoms of a pyridine ring is 6, the number of atoms of a quinazoline ring is 10, and the number of a furan ring is 5. For example, hydrogen atoms bonded to a pyridine ring and atoms constituting a substituent substituted on the pyridine ring are not included in the number of ring atoms of the pyridine ring. Therefore, the number of ring atoms of a pyridine ring with which a hydrogen atom or a substituent is bonded is 6. For example, hydrogen atoms and atoms constituting a substituent which are bonded with a quinazoline ring is not included in the number of ring atoms of the quinazoline ring. Therefore, the number of ring atoms of a quinazoline ring with which a hydrogen atom or a substituent is bonded is 10.

In this specification, "XX to YY carbon atoms" in the expression "a substituted or unsubstituted ZZ group including XX to YY carbon atoms" represents the number of carbon atoms in the case where the ZZ group is unsubstituted by a substituent, and does not include the number of carbon atoms of a substituent in the case where the ZZ group is substituted by the substituent. Here, "YY" is larger than "XX", and "XX" means an integer of 1 or more and "YY" means an integer of 2 or more.

In this specification, "XX to YY atoms" in the expression "a substituted or unsubstituted ZZ group including XX to YY atoms" represents the number of atoms in the case where the ZZ group is unsubstituted by a substituent, and does not include the number of atoms of a substituent in the case where the ZZ group is substituted by the substituent. Here, "YY" is larger than "XX", and "XX" means an integer of 1 or more and "YY" means an integer of 2 or more.

In this specification, the unsubstituted ZZ group represents the case where the "substituted or unsubstituted ZZ group" is a "ZZ group unsubstituted by a substituent", and the substituted ZZ group represents the case where the "substituted or unsubstituted ZZ group"is a" ZZ group substituted by a substituent".

In this specification, a term "unsubstituted" in the case of "a substituted or unsubstituted ZZ group" means that hydrogen atoms in the ZZ group are not substituted by a substituent. Hydrogen atoms in a term "unsubstituted ZZ group" are a protium atom, a deuterium atom, or a tritium atom.

In this specification, a term "substituted" in the case of "a substituted or unsubstituted ZZ group" means that one or more hydrogen atoms in the ZZ group are substituted by a substituent. Similarly, a term "substituted" in the case of "a BB group substituted by an AA group" means that one or more hydrogen atoms in the BB group are substituted by the AA group.

"Substituent as Described in this Specification"

Hereinafter, the substituent described in this specification will be explained.

The number of ring carbon atoms of the "unsubstituted aryl group" described in this specification is 6 to 50, preferably 6 to 30, and more preferably 6 to 18, unless otherwise specified.

The number of ring atoms of the "unsubstituted heterocyclic group" described in this specification is 5 to 50, preferably 5 to 30, and more preferably 5 to 18, unless otherwise specified.

The number of carbon atoms of the "unsubstituted alkyl group" described in this specification is 1 to 50, preferably 1 to 20, and more preferably 1 to 6, unless otherwise specified.

The number of carbon atoms of the "unsubstituted alkenyl group" described in this specification is 2 to 50, preferably 2 to 20, and more preferably 2 to 6, unless otherwise specified.

The number of carbon atoms of the "unsubstituted alkynyl group" described in this specification is 2 to 50, preferably 2 to 20, and more preferably 2 to 6, unless otherwise specified.

The number of ring carbon atoms of the "unsubstituted cycloalkyl group" described in this specification is 3 to 50, preferably 3 to 20, and more preferably 3 to 6, unless otherwise specified.

The number of ring carbon atoms of the "unsubstituted arylene group" described in this specification is 6 to 50, preferably 6 to 30, and more preferably 6 to 18, unless otherwise specified.

The number of ring atoms of the "unsubstituted divalent heterocyclic group" described in this specification is 5 to 50, preferably 5 to 30, and more preferably 5 to 18, unless otherwise specified.

The number of carbon atoms of the "unsubstituted alkylene group" described in this specification is 1 to 50, preferably 1 to 20, and more preferably 1 to 6, unless otherwise specified.

"Substituted or Unsubstituted Aryl Group"

Specific examples of the "substituted or unsubstituted aryl group" described in this specification (specific example group G1) include the following unsubstituted aryl groups (specific example group G1A), substituted aryl groups (specific example group G1B), and the like. (Here, the unsubstituted aryl group refers to the case where the "substituted or unsubstituted aryl group" is an "aryl group unsubstituted by a substituent", and the substituted aryl group refers to the case where the "substituted or unsubstituted aryl group" is an "aryl group substituted by a substituent".). In this specification, in the case where simply referred as an "aryl group", it includes both a "unsubstituted aryl group" and a "substituted aryl group."

The "substituted aryl group" means a group in which one or more hydrogen atoms of the "unsubstituted aryl group" are substituted by a substituent. Specific examples of the "substituted aryl group" include, for example, groups in which one or more hydrogen atoms of the "unsubstituted aryl group" of the following specific example group G1A are substituted by a substituent, the substituted aryl groups of the following specific example group G1B, and the like. It should be noted that the examples of the "unsubstituted aryl group" and the examples of the "substituted aryl group" enumerated in this specification are mere examples, and the "substituted aryl group" described in this specification also includes a group in which a hydrogen atom bonded with a carbon atom of the aryl group itself in the "substituted aryl group" of the following specific group G1B is further substituted by a substituent, and a group in which a hydrogen atom of a substituent in the "substituted aryl group" of the following specific group G1B is further substituted by a substituent.

Unsubstituted aryl group (specific example group G1A):

a phenyl group,
a p-biphenyl group,
a m-biphenyl group,
an o-biphenyl group,
a p-terphenyl-4-yl group,
a p-terphenyl-3-yl group,
a p-terphenyl-2-yl group,
a m-terphenyl-4-yl group,
a m-terphenyl-3-yl group,
a m-terphenyl-2-yl group,
an o-terphenyl-4-yl group,
an o-terphenyl-3-yl group,
an o-terphenyl-2-yl group,
a 1-naphthyl group,
a 2-naphthyl group,
an anthryl group,
a benzanthryl group,
a phenanthryl group,
a benzophenanthryl group,
a phenalenyl group,
a pyrenyl group,
a chrysenyl group,
a benzochrysenyl group,
a triphenylenyl group,
a benzotriphenylenyl group,
a tetracenyl group,
a pentacenyl group,
a fluorenyl group,
a 9,9'-spirobifluorenyl group,
a benzofluorenyl group,
a dibenzofluorenyl group,
a fluoranthenyl group,
a benzofluoranthenyl group,
a perylenyl group, and a monovalent aryl group derived by removing one hydrogen atom from the ring structures represented by any of the following general formulas (TEMP-1) to (TEMP-15).
(TEMP-1)
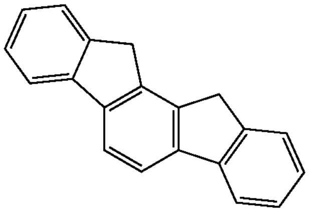
(TEMP-2)
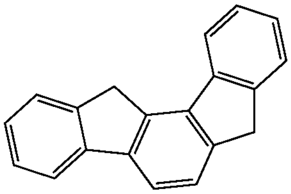
(TEMP-3)
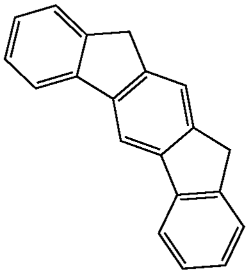
(TEMP-4)
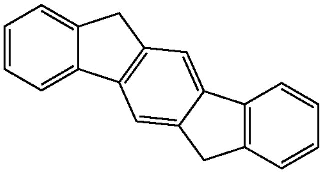
(TEMP-5)
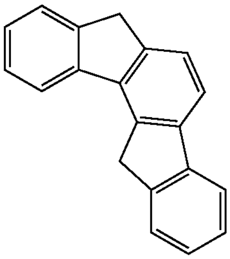
(TEMP-6)
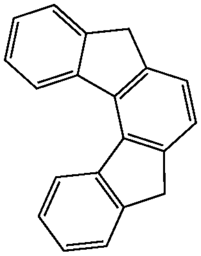
-continued
(TEMP-7)
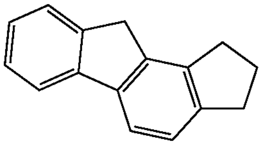
(TEMP-8)
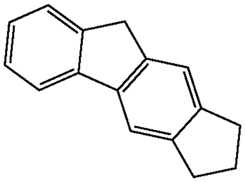
(TEMP-9)
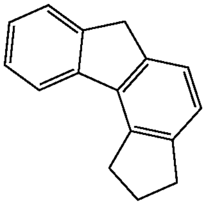
(TEMP-10)
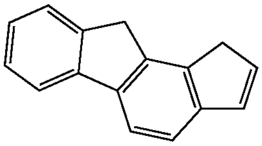
(TEMP-11)
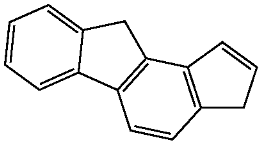
(TEMP-12)
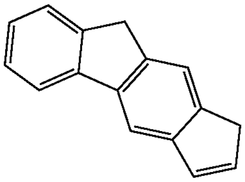
(TEMP-13)
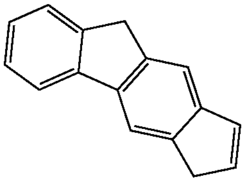
(TEMP-14)
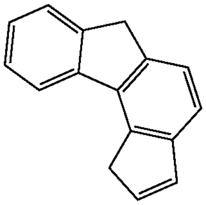

-continued (TEMP-15)

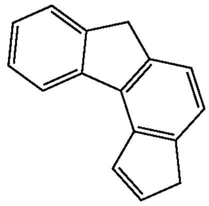

Substituted Aryl Group (Specific Example Group G1B):

an o-tolyl group,
a m-tolyl group,
a p-tolyl group,
a p-xylyl group,
a m-xylyl group,
an o-xylyl group,
a p-isopropylphenyl group,
a m-isopropylphenyl group,
an o-isopropylphenyl group,
a p-t-butylphenyl group,
a m-t-butylphenyl group,
an o-t-butylphenyl group,
a 3,4,5-trimethylphenyl group,
a 9,9-dimethylfluorenyl group,
a 9,9-diphenylfluorenyl group,
a 9,9-bis(4-methylphenyl)fluorenyl group,
a 9,9-bis(4-isopropylphenyl)fluorenyl group,
a 9,9-bis(4-t-butylphenyl)fluorenyl group,
a cyanophenyl group,
a triphenylsilylphenyl group,
a trimethylsilylphenyl group,
a phenyinaphthyl group,
a naphthylphenyl group, and
a group in which one or more hydrogen atoms of a monovalent group derived from the ring structures represented by any of the general formulas (TEMP-1) to (TEMP-15) are substituted by a substituent.

"Substituted or Unsubstituted Heterocyclic Group"

The "heterocyclic group" described in this specification is a ring group having at least one hetero atom in the ring atom. Specific examples of the hetero atom include a nitrogen atom, an oxygen atom, a sulfur atom, a silicon atom, a phosphorus atom, and a boron atom.

The "heterocyclic group" in this specification is a monocyclic group or a fused ring group.

The "heterocyclic group" in this specification is an aromatic heterocyclic group or a non-aromatic heterocyclic group.

Specific examples of the "substituted or unsubstituted heterocyclic group" (specific example group G2) described in this specification include the following unsubstituted heterocyclic group (specific example group G2A), the following substituted heterocyclic group (specific example group G2B), and the like. (Here, the unsubstituted heterocyclic group refers to the case where the "substituted or unsubstituted heterocyclic group" is a "heterocyclic group unsubstituted by a substituent", and the substituted heterocyclic group refers to the case where the "substituted or unsubstituted heterocyclic group"is a" heterocyclic group substituted by a substituent".). In this specification, in the case where simply referred as a "heterocyclic group", it includes both the "unsubstituted heterocyclic group" and the "substituted heterocyclic group."

The "substituted heterocyclic group" means a group in which one or more hydrogen atom of the "unsubstituted heterocyclic group" are substituted by a substituent. Specific examples of the "substituted heterocyclic group" include a group in which a hydrogen atom of "unsubstituted heterocyclic group" of the following specific example group G2A is substituted by a substituent, the substituted heterocyclic groups of the following specific example group G2B, and the like. It should be noted that the examples of the "unsubstituted heterocyclic group" and the examples of the "substituted heterocyclic group" enumerated in this specification are mere examples, and the "substituted heterocyclic group" described in this specification includes groups in which hydrogen atom bonded with a ring atom of the heterocyclic group itself in the "substituted heterocyclic group" of the specific example group G2B is further substituted by a substituent, and a group in which hydrogen atom of a substituent in the "substituted heterocyclic group" of the specific example group G2B is further substituted by a substituent.

Specific example group G2A includes, for example, the following unsubstituted heterocyclic group containing a nitrogen atom (specific example group G2A1), the following unsubstituted heterocyclic group containing an oxygen atom (specific example group G2A2), the following unsubstituted heterocyclic group containing a sulfur atom (specific example group G2A3), and the monovalent heterocyclic group derived by removing one hydrogen atom from the ring structures represented by any of the following general formulas (TEMP-16) to (TEMP-33) (specific example group G2A4).

Specific example group G2B includes, for example, the following substituted heterocyclic group containing a nitrogen atom (specific example group G2B1), the following substituted heterocyclic group containing an oxygen atom (specific example group G2B2), the following substituted heterocyclic group containing a sulfur atom (specific example group G2B3), and the following group in which one or more hydrogen atoms of the monovalent heterocyclic group derived from the ring structures represented by any of the following general formulas (TEMP-16) to (TEMP-33) are substituted by a substituent (specific example group G2B4).

Unsubstituted Heterocyclic Group Containing a Nitrogen Atom (Specific Example Group G2A1):

a pyrrolyl group,
an imidazolyl group,
a pyrazolyl group,
a triazolyl group,
a tetrazolyl group,
an oxazolyl group,
an isoxazolyl group,
an oxadiazolyl group,
a thiazolyl group,
an isothiazolyl group,
a thiadiazolyl group,
a pyridyl group,
a pyridazinyl group,
a pyrimidinyl group,
a pyrazinyl group,
a triazinyl group,
an indolyl group,
an isoindolyl group,
an indolizinyl group,
a quinolizinyl group,
a quinolyl group,
an isoquinolyl group,
a cinnolyl group,
a phthalazinyl group, a quinazolinyl group,
a quinoxalinyl group,
a benzimidazolyl group,
an indazolyl group,
a phenanthrolinyl group,
a phenanthridinyl group,
an acridinyl group,
a phenazinyl group,
a carbazolyl group,
a benzocarbazolyl group,
a morpholino group,
a phenoxazinyl group,
a phenothiazinyl group,
an azacarbazolyl group, and
a diazacarbazolyl group.

Unsubstituted Heterocyclic Group Containing an Oxygen Atom (Specific Example Group G2A2):

a furyl group,
an oxazolyl group,
an isoxazolyl group,
an oxadiazolyl group,
a xanthenyl group,
a benzofuranyl group,
an isobenzofuranyl group,
a dibenzofuranyl group,
a naphthobenzofuranyl group,
a benzoxazolyl group,
a benzisoxazolyl group,
a phenoxazinyl group,
a morpholino group,
a dinaphthofuranyl group,
an azadibenzofuranyl group,
a diazadibenzofuranyl group,
an azanaphthobenzofuranyl group, and
a diazanaphthobenzofuranyl group.

Unsubstituted Heterocyclic Group Containing a Sulfur Atom (Specific Example Group G2A3):

a thienyl group,
a thiazolyl group,
ani isothiazolyl group,
a thiadiazolyl group,
a benzothiophenyl group (benzothienyl group),
an isobenzothiophenyl group (isobenzothienyl group),
a dibenzothiophenyl group (dibenzothienyl group),
a naphthobenzothiophenyl group (naphthobenzothienyl group),
a benzothiazolyl group,
a benzisothiazolyl group,
a phenothiazinyl group,
a dinaphthothiophenyl group (dinaphthothienyl group),
an azadibenzothiophenyl group (azadibenzothienyl group),
a diazadibenzothiophenyl group (diazadibenzothienyl group),
an azanaphthobenzothiophenyl group (azanaphthobenzothienyl group), and
a diazanaphthobenzothiophenyl group (diazanaphthobenzothienyl group).

Monovalent Heterocyclic Group Derived by Removing One Hydrogen Atom from the Ring Structures Represented by any of the Following General Formulas (TEMP-16) to (TEMP-33) (Specific Example Group G2A4):

(TEMP-16)

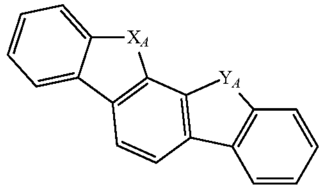

(TEMP-17)

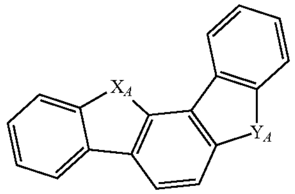

(TEMP-18)

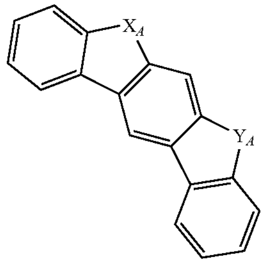

(TEMP-19)

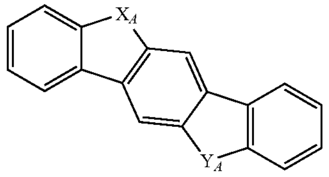

(TEMP-20)

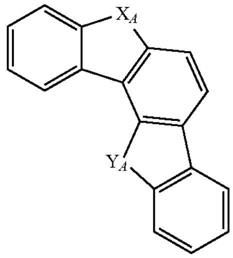

(TEMP-21)

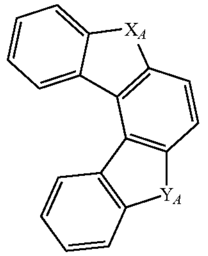

(TEMP-22)

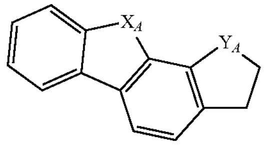

-continued (TEMP-23)

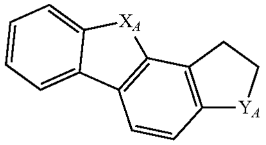

(TEMP-24)

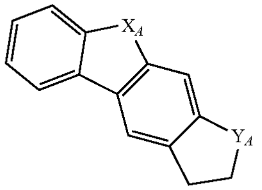

(TEMP-25)

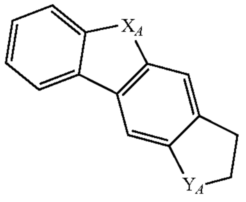

(TEMP-26)

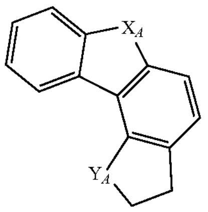

(TEMP-27)

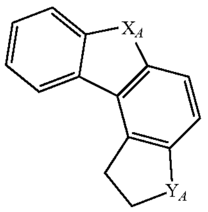

(TEMP-28)

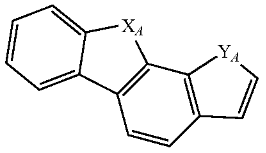

(TEMP-29)

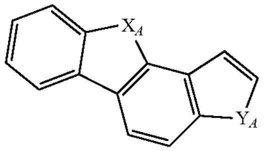

(TEMP-30)

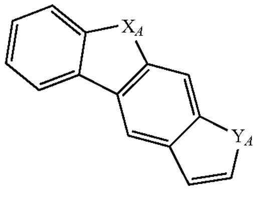

-continued (TEMP-31)

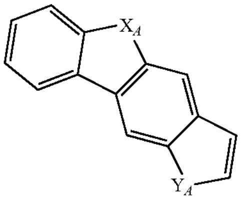

(TEMP-32)

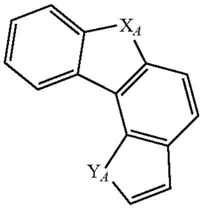

(TEMP-33)

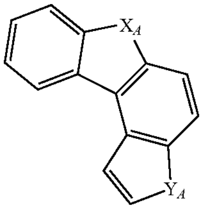

In the general formulas (TEMP-16) to (TEMP-33), $X_A$ and $Y_A$ are independently an oxygen atom, a sulfur atom, NH, or $CH_2$. Provided that at least one of $X_A$ and $Y_A$ is an oxygen atom, a sulfur atom, or NH.

In the general formulas (TEMP-16) to (TEMP-33), when at least one of $X_A$ and $Y_A$ is NH or $CH_2$, the monovalent heterocyclic group derived from the ring structures represented by any of the general formulas (TEMP-16) to (TEMP-33) includes a monovalent group derived by removing one hydrogen atom from these NH or $CH_2$.

Substituted Heterocyclic Group Containing a Nitrogen Atom (Specific Example Group G2B1):

a (9-phenyl)carbazolyl group,
a (9-biphenylyl)carbazolyl group,
a (9-phenyl)phenylcarbazolyl group,
a (9-naphthyl)carbazolyl group,
a diphenylcarbazol-9-yl group,
a phenylcarbazol-9-yl group,
a methylbenzimidazolyl group,
an ethylbenzimidazolyl group,
a phenyltriazinyl group,
a biphenylyltriazinyl group,
a diphenyltriazinyl group,
a phenylquinazolinyl group, and
a biphenylylquinazolinyl group.

Substituted Heterocyclic Group Containing an Oxygen Atom (Specific Example Group G2B2):

a phenyldibenzofuranyl group,
a methyldibenzofuranyl group,
a t-butyldibenzofuranyl group, and
a monovalent residue of spiro[9H-xanthene-9,9'-[9H]fluorene].

Substituted Heterocyclic Group Containing a Sulfur Atom (Specific Example Group G2B3):

a phenyldibenzothiophenyl group,
a methyldibenzothiophenyl group,
a t-butyldibenzothiophenyl group, and
a monovalent residue of spiro[9H-thioxanthene-9,9'-[9H]fluorene].

Group in which One or More Hydrogen Atoms of the Monovalent Heterocyclic Group Derived from the Ring Structures Represented by any of the Following General Formulas (TEMP-16) to (TEMP-33) are Substituted by a Substituent (Specific Example Group G2B4):

The "one or more hydrogen atoms of the monovalent heterocyclic group" means one or more hydrogen atoms selected from hydrogen atoms bonded with ring carbon atoms of the monovalent heterocyclic group, a hydrogen atom bonded with a nitrogen atom when at least one of $X_A$ and $Y_A$ is NH, and hydrogen atoms of a methylene group when one of $X_A$ and $Y_A$ is $CH_2$.

"Substituted or Unsubstituted Alkyl Group"

Specific examples of the "substituted or unsubstituted alkyl group" (specific example group G3) described in this specification include the following unsubstituted alkyl groups (specific example group G3A) and the following substituted alkyl groups (specific example group G3B). (Here, the unsubstituted alkyl group refers to the case where the "substituted or unsubstituted alkyl group"is an" alkyl group unsubstituted by a substituent", and the substituted alkyl group refers to the case where the "substituted or unsubstituted alkyl group" is an "alkyl group substituted by a substituent".). In this specification, in the case where simply referred as an "alkyl group" includes both the "unsubstituted alkyl group" and the "substituted alkyl group."

The "substituted alkyl group" means a group in which one or more hydrogen atoms in the "unsubstituted alkyl group" are substituted by a substituent. Specific examples of the "substituted alkyl group" include groups in which one or more hydrogen atoms in the following "unsubstituted alkyl group" (specific example group G3A) are substituted by a substituent, the following substituted alkyl group (specific example group G3B), and the like. In this specification, the alkyl group in the "unsubstituted alkyl group" means a linear alkyl group. Thus, the "unsubstituted alkyl group" includes a straight-chain "unsubstituted alkyl group" and a branched-chain "unsubstituted alkyl group". It should be noted that the examples of the "unsubstituted alkyl group" and the examples of the "substituted alkyl group" enumerated in this specification are mere examples, and the "substituted alkyl group" described in this specification includes a group in which hydrogen atom of the alkyl group itself in the "substituted alkyl group" of the specific example group G3B is further substituted by a substituent, and a group in which hydrogen atom of a substituent in the "substituted alkyl group" of the specific example group G3B is further substituted by a substituent.

Unsubstituted Alkyl Group (Specific Example Group G3A):

- a methyl group,
- an ethyl group,
- a n-propyl group,
- an isopropyl group,
- a n-butyl group,
- an isobutyl group,
- a s-butyl group, and
- a t-butyl group.

Substituted Alkyl Group (Specific Example Group G3B):

- a heptafluoropropyl group (including isomers),
- a pentafluoroethyl group,
- a 2,2,2-trifluoroethyl group, and
- a trifluoromethyl group.

"Substituted or Unsubstituted Alkenyl Group"

Specific examples of the "substituted or unsubstituted alkenyl group" described in this specification (specific example group G4) include the following unsubstituted alkenyl group (specific example group G4A), the following substituted alkenyl group (specific example group G4B), and the like. (Here, the unsubstituted alkenyl group refers to the case where the "substituted or unsubstituted alkenyl group"is a" alkenyl group unsubstituted by a substituent", and the "substituted alkenyl group" refers to the case where the "substituted or unsubstituted alkenyl group" isa "alkenyl group substituted by a substituent."). In this specification, in the case where simply referred as an "alkenyl group" includes both the "unsubstituted alkenyl group" and the "substituted alkenyl group."

The "substituted alkenyl group" means a group in which one or more hydrogen atoms in the "unsubstituted alkenyl group" are substituted by a substituent. Specific examples of the "substituted alkenyl group" include a group in which the following "unsubstituted alkenyl group" (specific example group G4A) has a substituent, the following substituted alkenyl group (specific example group G4B), and the like. It should be noted that the examples of the "unsubstituted alkenyl group" and the examples of the "substituted alkenyl group" enumerated in this specification are mere examples, and the "substituted alkenyl group" described in this specification includes a group in which a hydrogen atom of the alkenyl group itself in the "substituted alkenyl group" of the specific example group G4B is further substituted by a substituent, and a group in which a hydrogen atom of a substituent in the "substituted alkenyl group" of the specific example group G4B is further substituted by a substituent.

Unsubstituted Alkenyl Group (Specific Example Group G4A):

- a vinyl group,
- an allyl group,
- a 1-butenyl group,
- a 2-butenyl group, and
- a 3-butenyl group.

Substituted Alkenyl Group (Specific Example Group G4B):

- a 1,3-butanedienyl group,
- a 1-methylvinyl group,
- a 1-methylallyl group,
- a 1,1-dimethylallyl group,
- a 2-methylally group, and
- a 1,2-dimethylallyl group.

"Substituted or Unsubstituted Alkynyl Group"

Specific examples of the "substituted or unsubstituted alkynyl group" described in this specification (specific example group G5) include the following unsubstituted alkynyl group (specific example group G5A) and the like. (Here, the unsubstituted alkynyl group refers to the case where the "substituted or unsubstituted alkynyl group" is an "alkynyl group unsubstituted by a substituent".). In this specification, in the case where simply referred as an "alkynyl group" includes both the "unsubstituted alkynyl group" and the "substituted alkynyl group."

The "substituted alkynyl group" means a group in which one or more hydrogen atoms in the "unsubstituted alkynyl group" are substituted by a substituent. Specific examples of the "substituted alkynyl group" include a group in which one or more hydrogen atoms in the following "unsubstituted alkynyl group" (specific example group G5A) are substituted by a substituent, and the like.

Unsubstituted Alkynyl Group (Specific Example Group G5A):

- an ethynyl group.

"Substituted or Unsubstituted Cycloalkyl Group"

Specific examples of the "substituted or unsubstituted cycloalkyl group" described in this specification (specific example group G6) include the following unsubstituted cycloalkyl group (specific example group G6A), the following substituted cycloalkyl group (specific example group G6B), and the like. (Here, the unsubstituted cycloalkyl group refers to the case where the "substituted or unsubstituted cycloalkyl group" is a "cycloalkyl group unsubstituted by a substituent", and the substituted cycloalkyl group refers to the case where the "substituted or unsubstituted cycloalkyl group"is a" cycloalkyl group substituted by a substituent".). In this specification, in the case where simply referred as a "cycloalkyl group" includes both the "unsubstituted cycloalkyl group" and the "substituted cycloalkyl group."

The "substituted cycloalkyl group" means a group in which one or more hydrogen atoms in the "unsubstituted cycloalkyl group" are substituted by a substituent. Specific examples of the "substituted cycloalkyl group" include a group in which one or more hydrogen atoms in the following "unsubstituted cycloalkyl group" (specific example group G6A) are substituted by a substituent, and examples of the following substituted cycloalkyl group (specific example group G6B), and the like. It should be noted that the examples of the "unsubstituted cycloalkyl group" and the examples of the "substituted cycloalkyl group" enumerated in this specification are mere examples, and the "substituted cycloalkyl group" in this specification includes a group in which one or more hydrogen atoms bonded with the carbon atom of the cycloalkyl group itself in the "substituted cycloalkyl group" of the specific example group G6B are substituted by a substituent, and a group in which a hydrogen atom of a substituent in the "substituted cycloalkyl group" of specific example group G6B is further substituted by a substituent.

Unsubstituted Cycloalkyl Group (Specific Example Group G6A):

a cyclopropyl group,
a cyclobutyl group,
a cyclopentyl group,
a cyclohexyl group,
a 1-adamantyl group,
a 2-adamantyl group,
a 1-norbomyl group, and
a 2-norbomyl group.

Substituted Cycloalkyl Group (Specific Example Group G6B):

a 4-methylcyclohexyl group.

"Group Represented by —Si ($R_{901}$)($R_{902}$)($R_{903}$)"

Specific examples of the group represented by —Si($R_{901}$)($R_{902}$)($R_{903}$) described in this specification (specific example group G7) include:

—Si(G1)(G1)(G1),
—Si(G1)(G2)(G2),
—Si(G1)(G1)(G2),
—Si(G2)(G2)(G2),
—Si(G3)(G3)(G3), and
—Si(G6)(G6)(G6).

G1 is the "substituted or unsubstituted aryl group" described in the specific example group G1.

G2 is the "substituted or unsubstituted heterocyclic group" described in the specific example group G2.

G3 is the "substituted or unsubstituted alkyl group" described in the specific example group G3.

G6 is the "substituted or unsubstituted cycloalkyl group" described in the specific example group G6.

Plural G1's in —Si(G1)(G1)(G1) are the same or different.

Plural G2's in —Si(G1)(G2)(G2) are the same or different.

Plural G1's in —Si(G1)(G1)(G2) are the same or different.

Plural G2's in —Si(G2)(G2)(G2) are be the same or different.

Plural G3's in —Si(G3)(G3)(G3) are the same or different.

Plural G6's in —Si(G6)(G6)(G6) are be the same or different.

"Group Represented by —O—($R_{904}$)"

Specific examples of the group represented by —O—($R_{904}$) in this specification (specific example group G8) include:

—O(G1),
—O(G2),
—O(G3), and
—O(G6).

G1 is the "substituted or unsubstituted aryl group" described in the specific example group G1.

G2 is the "substituted or unsubstituted heterocyclic group" described in the specific example group G2.

G3 is the "substituted or unsubstituted alkyl group" described in the specific example group G3.

G6 is the "substituted or unsubstituted cycloalkyl group" described in the specific example group G6.

"Group Represented by —S—($R_{905}$)"

Specific examples of the group represented by —S—($R_{905}$) in this specification (specific example group G9) include:

—S(G1),
—S(G2),
—S(G3), and
—S(G6).

G1 is the "substituted or unsubstituted aryl group" described in the specific example group G1.

G2 is the "substituted or unsubstituted heterocyclic group" described in the specific example group G2.

G3 is the "substituted or unsubstituted alkyl group" described in the specific example group G3.

G6 is the "substituted or unsubstituted cycloalkyl group" described in the specific example group G6.

"Group Represented by —N($R_{906}$)($R_{907}$)"

Specific examples of the group represented by —N($R_{906}$)($R_{907}$) in this specification (specific example group G10) include:

—N(G1)(G1),
—N(G2)(G2),
—N(G1)(G2),
—N(G3)(G3), and
—N(G6)(G6).

G1 is the "substituted or unsubstituted aryl group" described in the specific example group G1.

G2 is the "substituted or unsubstituted heterocyclic group" described in the specific example group G2.

G3 is the "substituted or unsubstituted alkyl group" described in the specific example group G3.

G6 is the "substituted or unsubstituted cycloalkyl group" described in the specific example group G6.

Plural G1's in —N(G1)(G1) are the same or different.

Plural G2's in —N(G2)(G2) are the same or different.

Plural G3's in —N(G3)(G3) are the same or different.

Plural G6's in —N(G6)(G6) are the same or different.

"Halogen Atom"

Specific examples of the "halogen atom" described in this specification (specific example group G11) include a fluorine atom, a chlorine atom, a bromine atom, an iodine atom, and the like.

"Substituted or Unsubstituted Fluoroalkyl Group"

The "substituted or unsubstituted fluoroalkyl group" described in this specification is a group in which at least one hydrogen atom bonded with a carbon atom constituting the alkyl group in the "substituted or unsubstituted alkyl group" is substituted by a fluorine atom, and includes a group in which all hydrogen atoms bonded with a carbon atom constituting the alkyl group in the "substituted or unsubstituted alkyl group" are substituted by a fluorine atom (a perfluoro group). The number of carbon atoms of the "unsubstituted fluoroalkyl group" is 1 to 50, preferably 1 to 30, more preferably 1 to 18, unless otherwise specified in this specification. The "substituted fluoroalkyl group" means a group in which one or more hydrogen atoms of the "fluoroalkyl group" are substituted by a substituent. The "substituted fluoroalkyl group" described in this specification also includes a group in which one or more hydrogen atoms bonded with a carbon atom of the alkyl chains in the "substituted fluoroalkyl group" are further substituted by a substituent, and a group in which one or more hydrogen atom of a substituent in the "substituted fluoroalkyl group" are further substituted by a substituent. Specific examples of the "unsubstituted fluoroalkyl group" include a group in which one or more hydrogen atoms in the "alkyl group" (specific group G3) are substituted by a fluorine atom, and the like.

"Substituted or Unsubstituted Haloalkyl Group"

The "substituted or unsubstituted haloalkyl group" described in this specification is a group in which at least one hydrogen atom bonded with a carbon atom constituting the alkyl group in the "substituted or unsubstituted alkyl group" is substituted by a halogen atom, and also includes a group in which all hydrogen atoms bonded with a carbon atom constituting the alkyl group in the "substituted or unsubstituted alkyl group" are substituted by a halogen atom. The number of carbon atoms of the "unsubstituted haloalkyl group" is 1 to 50, preferably 1 to 30, more preferably 1 to 18, unless otherwise specified in this specification. The "substituted haloalkyl group" means a group in which one or more hydrogen atoms of the "haloalkyl group" are substituted by a substituent. The "substituted haloalkyl group" described in this specification also includes a group in which one or more hydrogen atoms bonded with a carbon atom of the alkyl chain in the "substituted haloalkyl group" are further substituted by a substituent, and a group in which one or more hydrogen atoms of a substituent in the "substituted haloalkyl group" are further substituted by a substituent. Specific examples of the "unsubstituted haloalkyl group" include a group in which one or more hydrogen atoms in the "alkyl group" (specific example group G3) are substituted by a halogen atom, and the like. A haloalkyl group is sometimes referred to as an alkyl halide group.

"Substituted or Unsubstituted Alkoxy Group"

Specific examples of the "substituted or unsubstituted alkoxy group" described in this specification include a group represented by —O(G3), wherein G3 is the "substituted or unsubstituted alkyl group" described in the specific example group G3. The number of carbon atoms of the "unsubstituted alkoxy group" is 1 to 50, preferably 1 to 30, more preferably 1 to 18, unless otherwise specified in this specification.

"Substituted or Unsubstituted Alkylthio Group"

Specific examples of the "substituted or unsubstituted alkylthio group" described in this specification include a group represented by —S(G3), wherein G3 is the "substituted or unsubstituted alkyl group" described in the specific example group G3. The number of carbon atoms of the "unsubstituted alkylthio group" is 1 to 50, preferably 1 to 30, more preferably 1 to 18, unless otherwise specified in this specification.

"Substituted or Unsubstituted Aryloxy Group"

Specific examples of the "substituted or unsubstituted aryloxy group" described in this specification include a group represented by —O(G1), wherein G1 is the "substituted or unsubstituted aryl group" described in the specific example group G1. The number of ring carbon atoms of the "unsubstituted aryloxy group" is 6 to 50, preferably 6 to 30, more preferably 6 to 18, unless otherwise specified in this specification.

"Substituted or Unsubstituted Arylthio Group"

Specific examples of the "substituted or unsubstituted arylthio group" described in this specification include a group represented by —S(G1), wherein G1 is a "substituted or unsubstituted aryl group" described in the specific example group G1. The number of ring carbon atoms of the "unsubstituted arylthio group" is 6 to 50, preferably 6 to 30, more preferably 6 to 18, unless otherwise specified in this specification.

"Substituted or Unsubstituted Trialkylsilyl Group"

Specific examples of the "trialkylsilyl group" described in this specification include a group represented by —Si(G3)(G3)(G3), where G3 is the "substituted or unsubstituted alkyl group" described in the specific example group G3. Plural G3's in —Si(G3)(G3)(G3) are the same or different. The number of carbon atoms in each alkyl group of the "trialkylsilyl group" is 1 to 50, preferably 1 to 20, more preferably 1 to 6, unless otherwise specified in this specification.

"Substituted or Unsubstituted Aralkyl Group"

Specific examples of the "substituted or unsubstituted aralkyl group" described in this specification is a group represented by -(G3)-(G1), wherein G3 is the "substituted or unsubstituted alkyl group" described in the specific example group G3, and G1 is the "substituted or unsubstituted aryl group" described in the specific example group G1. Therefore, the "aralkyl group" is a group in which a hydrogen atom of the "alkyl group" is substituted by an "aryl group" as a substituent, and is one form of the "substituted alkyl group." The "unsubstituted aralkyl group" is the "unsubstituted alkyl group" substituted by the "unsubstituted aryl group", and the number of carbon atoms of the "unsubstituted aralkyl group" is 7 to 50, preferably 7 to 30, more preferably 7 to 18, unless otherwise specified in this specification.

Specific examples of the "substituted or unsubstituted aralkyl group" include a benzyl group, a 1-phenylethyl group, a 2-phenylethyl group, a 1-phenylisopropyl group, a 2-phenylisopropyl group, a phenyl-t-butyl group, an α-naphthylmethyl group, a 1-α-naphthylethyl group, a 2-α-naphthylethyl group, a 1-α-naphthylisopropyl group, a 2-α-naphthylisopropyl group, a β-naphthylmethyl group, a 1-β-naphthylethyl group, a 2-β-naphthylethyl group, a 1-β-naphthylisopropyl group, a 2-β-naphthylisopropyl group, and the like.

Unless otherwise specified in this specification, examples of the substituted or unsubstituted aryl group described in this specification preferably include a phenyl group, a p-biphenyl group, a m-biphenyl group, an o-biphenyl group, a p-terphenyl-4-yl group, a p-terphenyl-3-yl group, a p-terphenyl-2-yl group, a m-terphenyl-4-yl group, a m-terphenyl-3-yl group, a m-terphenyl-2-yl group, an o-terphenyl-4-yl group, an o-terphenyl-3-yl group, an o-terphenyl-2-yl group, a 1-naphthyl group, a 2-naphthyl group, an anthryl group, a phenanthryl group, a pyrenyl group, a chrysenyl group, a triphenylenyl group, a fluorenyl group, a 9,9'-spirobifluorenyl group, 9,9-dimethylfluorenyl group, 9,9-diphenylfluorenyl group, and the like.

Unless otherwise specified in this specification, examples of the substituted or unsubstituted heterocyclic groups described in this specification preferably include a pyridyl group, a pyrimidinyl group, a triazinyl group, a quinolyl group, an isoquinolyl group, a quinazolinyl group, a benzimidazolyl group, a phenanthrolinyl group, a carbazolyl group (a 1-carbazolyl group, a 2-carbazolyl group, a 3-carbazolyl group, a 4-carbazolyl group, or a 9-carbazolyl group), a benzocarbazolyl group, an azacarbazolyl group, a diazacarbazolyl group, a dibenzofuranyl group, a naphthobenzofuranyl group, an azadibenzofuranyl group, a diazadibenzofuranyl group, a dibenzothiophenyl group, a naphthobenzothiophenyl group, an azadibenzothiophenyl group, a diazadibenzothiophenyl group, a (9-phenyl)carbazolyl group (a (9-phenyl)carbazol-1-yl group, a (9-phenyl)carbazol-2-yl group, a (9-phenyl)carbazol-3-yl group, or a (9-phenyl)carbazol-4-yl group), a (9-biphenylyl)carbazolyl group, a (9-phenyl)phenylcarbazolyl group, a diphenylcarbazol-9-yl group, a phenylcarbazol-9-yl group, a phenyltriazinyl group, a biphenylyltriazinyl group, a diphenyltriazinyl group, a phenyldibenzofuranyl group, a phenyldibenzothiophenyl group, and the like.

In this specification, the carbazolyl group is specifically any of the following groups, unless otherwise specified in this specification.

(TEMP-Cz1)

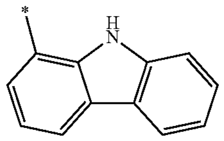

(TEMP-Cz2)

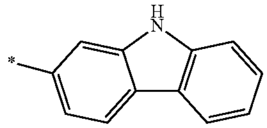

(TEMP-Cz3)

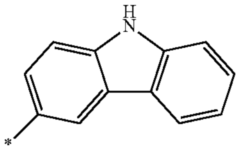

(TEMP-Cz4)

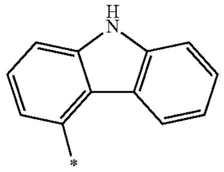

(TEMP-Cz5)

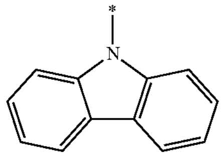

In this specification, the (9-phenyl)carbazolyl group is specifically any of the following groups, unless otherwise specified in this specification.

(TEMP-Cz6)

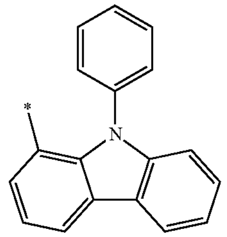

(TEMP-Cz7)

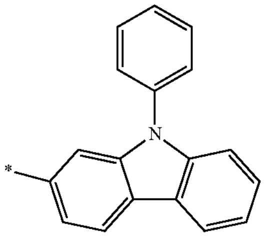

(TEMP-Cz8)

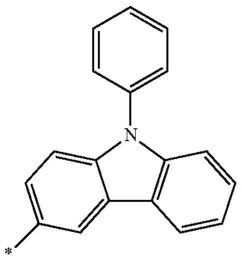

(TEMP-Cz9)

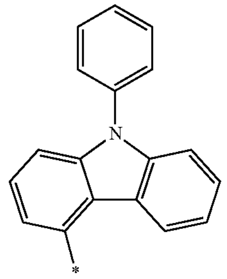

In the general formulas (TEMP-Cz1) to (TEMP-Cz9), * represents a bonding position.

In this specification, the dibenzofuranyl group and the dibenzothiophenyl group are specifically any of the following groups, unless otherwise specified in this specification.

(TEMP-34)

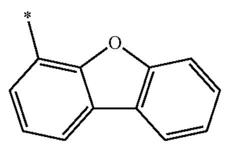

(TEMP-35)

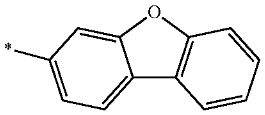

-continued (TEMP-36)

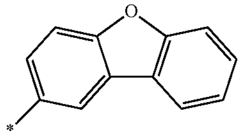

(TEMP-37)

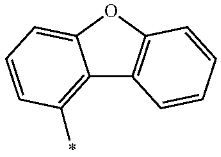

(TEMP-38)

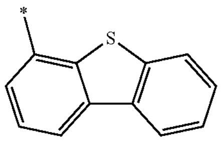

(TEMP-39)

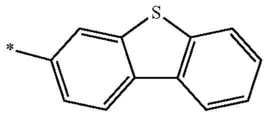

(TEMP-40)

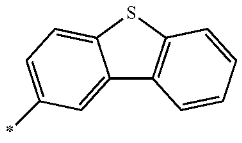

(TEMP-41)

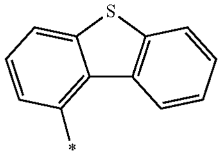

In the general formulas (TEMP-34) to (TEMP-41), * represents a bonding position.

The substituted or unsubstituted alkyl group described in this specification is preferably a methyl group, an ethyl group, a propyl group, an isopropyl group, a n-butyl group, an isobutyl group, a t-butyl group, or the like, unless otherwise specified in this specification.

"Substituted or Unsubstituted Arylene Group"

The "substituted or unsubstituted arylene group" described in this specification is a divalent group derived by removing one hydrogen atom on the aryl ring of the "substituted or unsubstituted aryl group", unless otherwise specified. Specific examples of the "substituted or unsubstituted arylene group" (specific example group G12) include a divalent group derived by removing one hydrogen atom on the aryl ring of the "substituted or unsubstituted aryl group" described in the specific example group G1, and the like.

"Substituted or Unsubstituted Divalent Heterocyclic Group"

The "substituted or unsubstituted divalent heterocyclic group" described in this specification is a divalent group derived by removing one hydrogen atom on the heterocyclic ring of the "substituted or unsubstituted heterocyclic group", unless otherwise specified. Specific examples of the "substituted or unsubstituted divalent heterocyclic group" (specific example group G13) include a divalent group derived by removing one hydrogen atom on the heterocyclic ring of the "substituted or unsubstituted heterocyclic group" described in the specific example group G2, and the like.

"Substituted or Unsubstituted Alkylene Group"

The "substituted or unsubstituted alkylene group" described in this specification is a divalent group derived by removing one hydrogen atom on the alkyl chain of the "substituted or unsubstituted alkyl group", unless otherwise specified. Specific examples of the "substituted or unsubstituted alkylene group" (specific example group G14) include a divalent group derived by removing one hydrogen atom on the alkyl chain of the "substituted or unsubstituted alkyl group" described in the specific example group G3, and the like.

The substituted or unsubstituted arylene group described in this specification is preferably any group of the following general formulas (TEMP-42) to (TEMP-68), unless otherwise specified in this specification.

(TEMP-42)

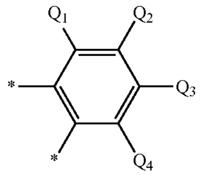

(TEMP-43)

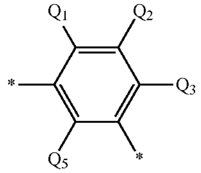

(TEMP-44)

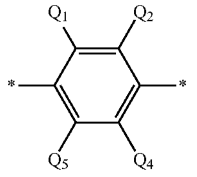

(TEMP-45)

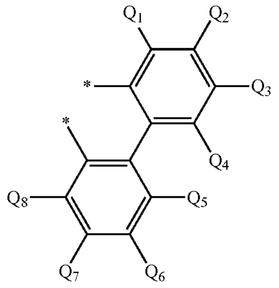

(TEMP-46)

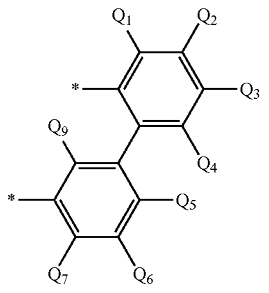

-continued
(TEMP-47)
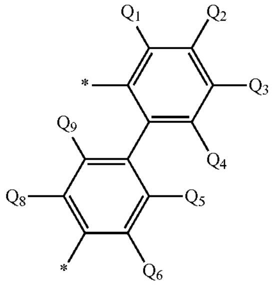
(TEMP-48)
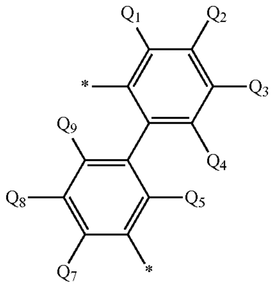
(TEMP-49)
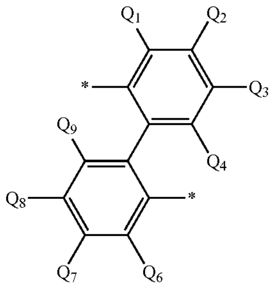
(TEMP-50)
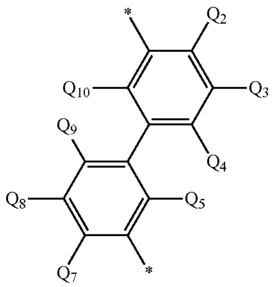
(TEMP-51)
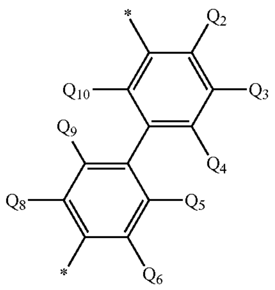
-continued
(TEMP-52)
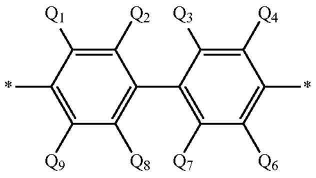
In the general formulas (TEMP-42) to (TEMP-52), $Q_1$ to $Q_{10}$ are independently a hydrogen atom or a substituent.
In the general formulas (TEMP-42) to (TEMP-52), * represents a bonding position.
(TEMP-53)
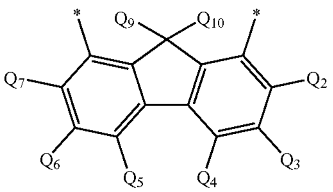
(TEMP-54)
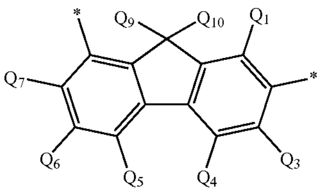
(TEMP-55)
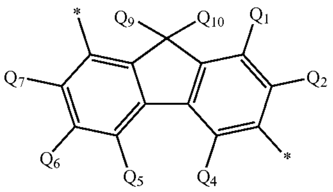
(TEMP-56)
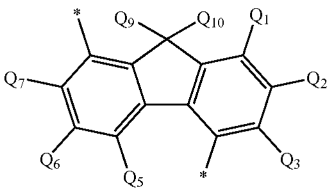
(TEMP-57)
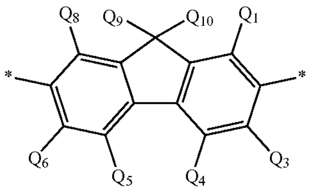
(TEMP-58)
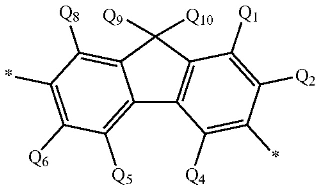

-continued (TEMP-59)

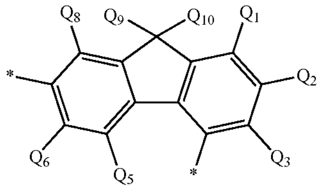

(TEMP-60)

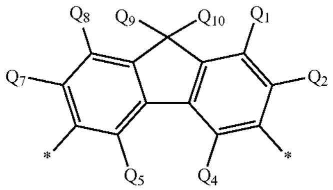

(TEMP-61)

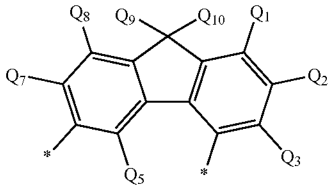

(TEMP-62)

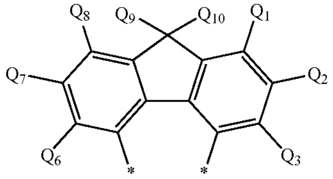

In the general formulas (TEMP-53) to (TEMP-62), $Q_1$ to $Q_{10}$ are independently a hydrogen atom or a substituent.

$Q_9$ and $Q_{10}$ may be bonded with each other via a single bond to form a ring.

In the general formulas (TEMP-53) to (TEMP-62), * represents a bonding position.

(TEMP-63)

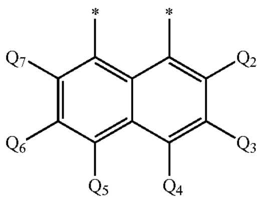

(TEMP-64)

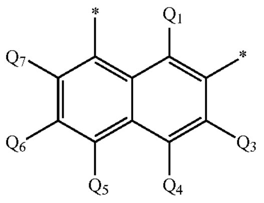

(TEMP-65)

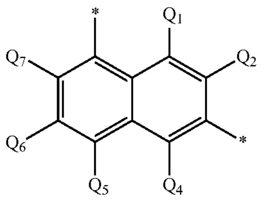

-continued (TEMP-66)

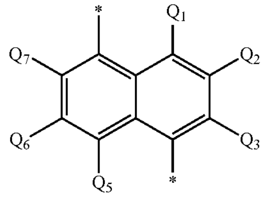

(TEMP-67)

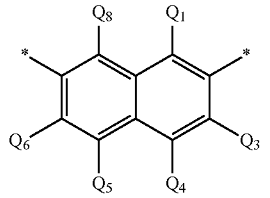

(TEMP-68)

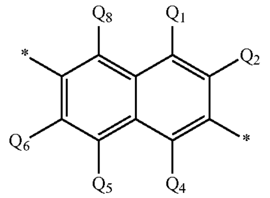

In the general formulas (TEMP-63) to (TEMP-68), $Q_1$ to $Q_8$ are independently a hydrogen atom or a substituent.

In the general formulas (TEMP-63) to (TEMP-68), * represents a bonding position.

The substituted or unsubstituted divalent heterocyclic group described in this specification is preferably any group of the following general formulas (TEMP-69) to (TEMP-102), unless otherwise specified in this specification.

(TEMP-69)

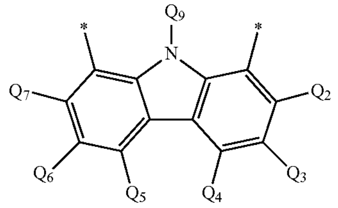

(TEMP-70)

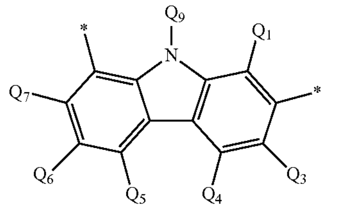

(TEMP-71)

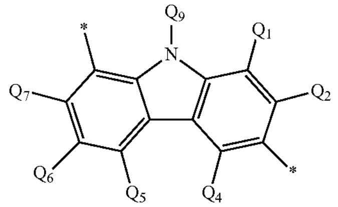

-continued
(TEMP-72)
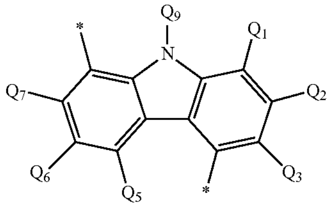
(TEMP-73)
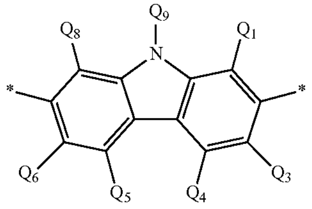
(TEMP-74)
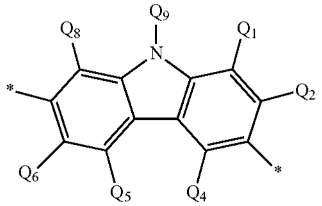
(TEMP-75)
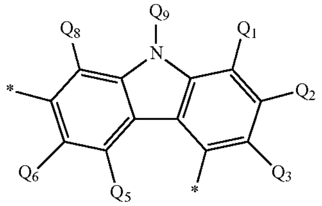
(TEMP-76)
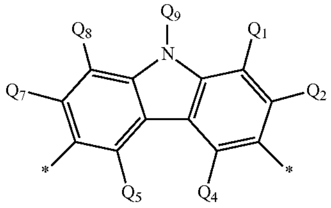
(TEMP-77)
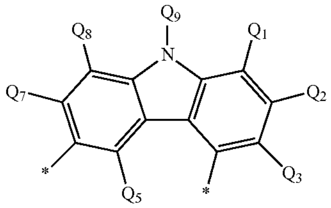
(TEMP-78)
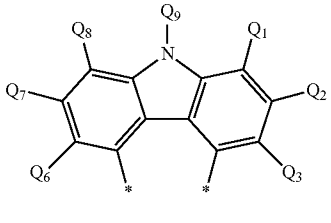
-continued
(TEMP-79)
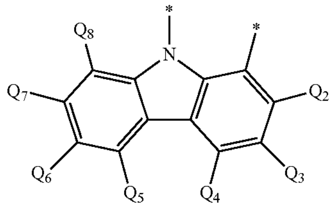
(TEMP-80)
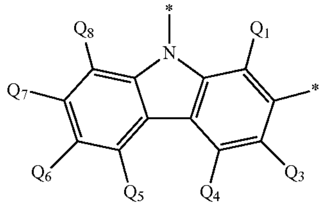
(TEMP-81)
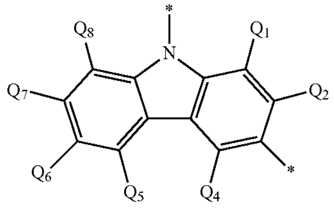
(TEMP-82)
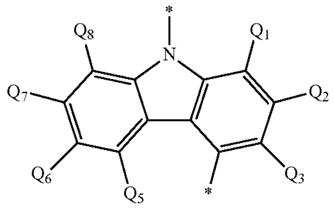
In the general formulas (TEMP-69) to (TEMP-82), $Q_1$ to $Q_9$ are independently a hydrogen atom or a substituent.
(TEMP-83)
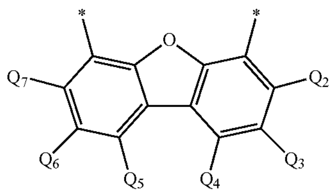
(TEMP-84)
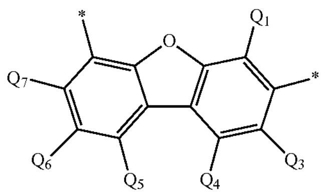
(TEMP-85)
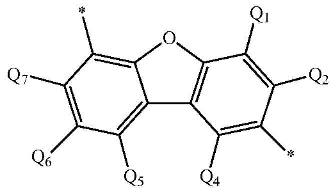

-continued
(TEMP-86)
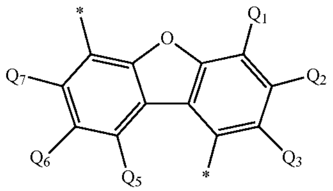
(TEMP-87)
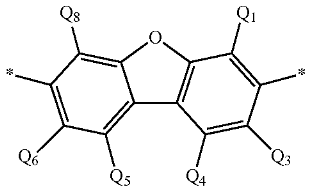
(TEMP-88)
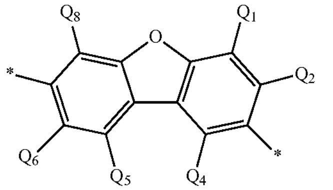
(TEMP-89)
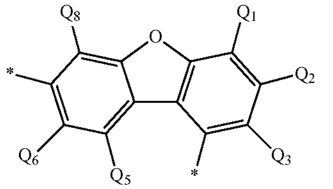
(TEMP-90)
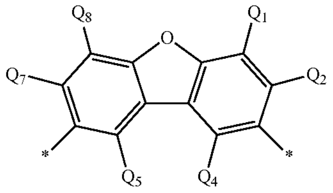
(TEMP-91)
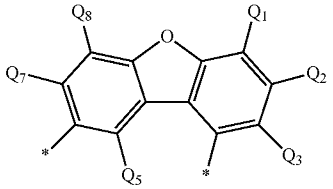
(TEMP-92)
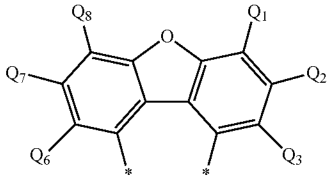
(TEMP-93)
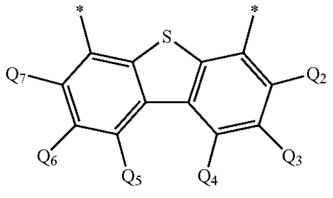
-continued
(TEMP-94)
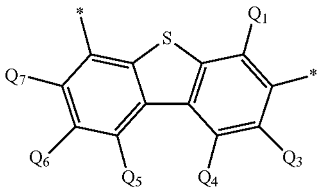
(TEMP-95)
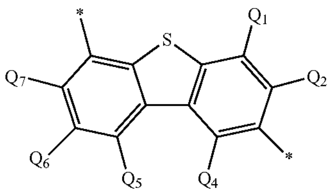
(TEMP-96)
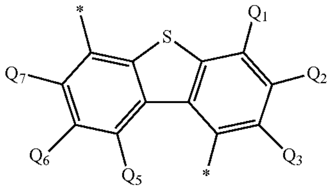
(TEMP-97)
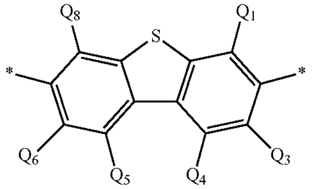
(TEMP-98)
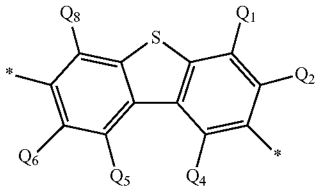
(TEMP-99)
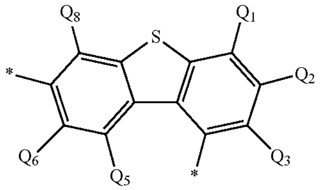
(TEMP-100)
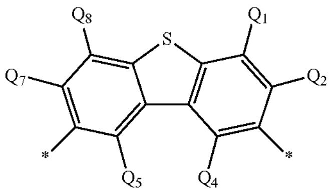
(TEMP-101)
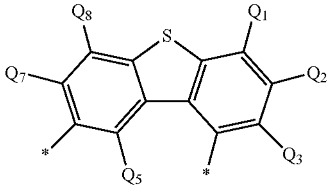

-continued (TEMP-102)

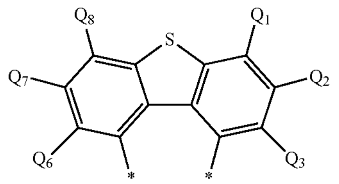

In the general formulas (TEMP-83) to (TEMP-102), $Q_1$ to $Q_8$ are independently a hydrogen atom or a substituent.

The above is the explanation of the "Substituent described in this specification."

"the Case where Bonded with Each Other to Form a Ring"

In this specification, the case where "one or more sets of adjacent two or more form a substituted or unsubstituted monocycle by bonding with each other, form a substituted or unsubstituted fused ring by bonding with each other, or do not bond with each other" means the case where "one or more sets of adjacent two or more form a substituted or unsubstituted monocycle by bonding with each other"; the case where "one or more sets of adjacent two or more form a substituted or unsubstituted fused ring by bonding with each other"; and the case where "one or more sets of adjacent two or more do not bond with each other."

The case where "one or more sets of adjacent two or more form a substituted or unsubstituted monocycle by bonding with each other" and the case where "one or more sets of adjacent two or more form a substituted or unsubstituted fused ring by bonding with each other" in this specification (these cases may be collectively referred to as "the case where forming a ring by bonding with each other") will be described below. The case of an anthracene compound represented by the following general formula (TEMP-103) in which the mother skeleton is an anthracene ring will be described as an example.

(TEMP-103)

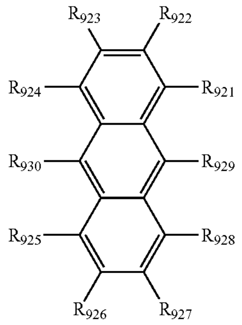

For example, in the case where "one or more sets of adjacent two or more among $R_{921}$ to $R_{930}$ form a ring by bonding with each other", the one set of adjacent two includes a pair of $R_{921}$ and $R_{922}$, a pair of $R_{922}$ and $R_{923}$, a pair of $R_{923}$ and $R_{924}$, a pair of $R_{924}$ and $R_{930}$, a pair of $R_{930}$ and $R_{925}$, a pair of $R_{925}$ and $R_{926}$, a pair of $R_{926}$ and $R_{927}$, a pair of $R_{927}$ and $R_{928}$, a pair of $R_{928}$ and $R_{929}$, and a pair of $R_{929}$ and $R_{921}$.

The "one or more sets" means that two or more sets of the adjacent two or more sets may form a ring at the same time. For example, $R_{921}$ and $R_{922}$ form a ring $Q_A$ by bonding with each other, and at the same, time $R_{925}$ and $R_{926}$ form a ring $Q_B$ by bonding with each other, the anthracene compound represented by the general formula (TEMP-103) is represented by the following general formula (TEMP-104).

(TEMP-104)

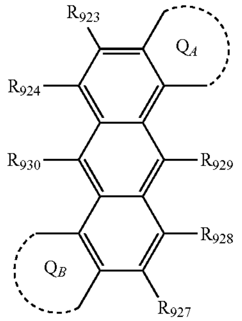

The case where the "set of adjacent two or more" form a ring includes not only the case where the set (pair) of adjacent "two" is bonded with as in the above-mentioned examples, but also the case where the set of adjacent "three or more" are bonded with each other. For example, it means the case where $R_{921}$ and $R_{922}$ form a ring $Q_A$ by bonding with each other, and $R_{922}$ and $R_{923}$ form a ring Qc by bonding with each other, and adjacent three ($R_{921}$, $R_{922}$ and $R_{923}$) form rings by bonding with each other and together fused to the anthracene mother skeleton. In this case, the anthracene compound represented by the general formula (TEMP-103) is represented by the following general formula (TEMP-105). In the following general formula (TEMP-105), the ring $Q_A$ and the ring Qc share $R_{922}$.

(TEMP-105)

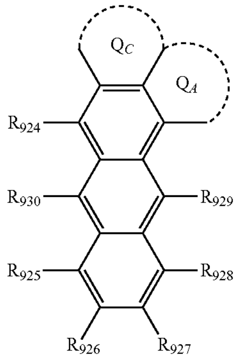

The "monocycle" or "fused ring" formed may be a saturated ring or an unsaturated ring, as a structure of the formed ring alone. Even when the "one pair of adjacent two" forms a "monocycle" or a "fused ring", the "monocycle" or the "fused ring" may form a saturated ring or an unsaturated ring. For example, the ring $Q_A$ and the ring $Q_B$ formed in the general formula (TEMP-104) are independently a "monocycle" or a "fused ring." The ring $Q_A$ and the ring Qc formed in the general formula (TEMP-105) are"fused ring." The ring $Q_A$ and ring Qc of the general formula (TEMP-105) are fused ring by fusing the ring $Q_A$ and the ring Qc together. When the ring $Q_A$ of the general formula (TMEP-104) is a benzene ring, the ring $Q_A$ is a monocycle. When the ring $Q_A$ of the general formula (TMEP-104) is a naphthalene ring, the ring $Q_A$ is a fused ring.

The "unsaturated ring" means an aromatic hydrocarbon ring or an aromatic heterocyclic ring. The "saturated ring" means an aliphatic hydrocarbon ring, or a non-aromatic heterocyclic ring.

Specific examples of the aromatic hydrocarbon ring include a structure in which the group listed as a specific example in the specific example group G1 is terminated by a hydrogen atom.

Specific examples of the aromatic heterocyclic ring include a structure in which the aromatic heterocyclic group listed as a specific example in the example group G2 is terminated by a hydrogen atom.

Specific examples of the aliphatic hydrocarbon ring include a structure in which the group listed as a specific example in the specific example group G6 is terminated by a hydrogen atom.

The term "to form a ring" means forming a ring only with plural atoms of the mother skeleton, or with plural atoms of the mother skeleton and one or more arbitrary elements in addition. For example, the ring $Q_A$ shown in the general formula (TEMP-104), which is formed by bonding $R_{921}$ and $R_{922}$ with each other, is a ring formed from the carbon atom of the anthracene skeleton with which $R_{921}$ is bonded, the carbon atom of the anthracene skeleton with which $R_{922}$ is bonded, and one or more arbitrary elements. For example, in the case where the ring $Q_A$ is formed with $R_{921}$ and $R_{922}$, when a monocyclic unsaturated ring is formed with the carbon atom of the anthracene skeleton with which $R_{921}$ is bonded, the carbon atom of the anthracene skeleton with which $R_{922}$ is bonded, and four carbon atoms, the ring formed with $R_{921}$ and $R_{922}$ is a benzene ring.

Here, the "arbitrary element" is preferably at least one element selected from the group consisting of a carbon element, a nitrogen element, an oxygen element, and a sulfur element, unless otherwise specified in this specification. In the arbitrary element (for example, a carbon element or a nitrogen element), a bond which does not form a ring may be terminated with a hydrogen atom or the like, or may be substituted with "arbitrary substituent" described below. When an arbitrary element other than a carbon element is contained, the ring formed is a heterocyclic ring.

The number of "one or more arbitrary element(s)" constituting a monocycle or a fused ring is preferably 2 or more and 15 or less, more preferably 3 or more and 12 or less, and still more preferably 3 or more and 5 or less, unless otherwise specified in this specification.

The "monocycle" is preferable among the "monocycle" and the "fused ring", unless otherwise specified in this specification.

The "unsaturated ring" is preferable among the "saturated ring" and the "unsaturated ring", unless otherwise specified in this specification.

Unless otherwise specified in this specification, the "monocycle" is preferably a benzene ring.

Unless otherwise specified in this specification, the "unsaturated ring" is preferably a benzene ring.

Unless otherwise specified in this specification, when "one or more sets of adjacent two or more" are "bonded with each other to form a substituted or unsubstituted monocycle" or "bonded with each other to form a substituted or unsubstituted fused ring", this specification, one or more sets of adjacent two or more are preferably bonded with each other to form a substituted or unsubstituted "unsaturated ring" from plural atoms of the mother skeleton and one or more and 15 or less elements which is at least one kind selected from a carbon elements, a nitrogen element, an oxygen element, and a sulfur element.

The substituent in the case where the above-mentioned "monocycle" or "fused ring" has a substituent is, for example, an "arbitrary substituent" described below. Specific examples of the substituent which the above-mentioned "monocycle" or "fused ring" has include the substituent described above in the "Substituent described in this specification" section.

The substituent in the case where the above-mentioned "saturated ring" or "unsaturated ring" has a substituent is, for example, an "arbitrary substituent" described below. Specific examples of the substituent which the above-mentioned "monocycle" or "fused ring" has include the substituent described above in the "Substituent described in this specification" section.

The foregoing describes the case where "one or more sets of adjacent two or more form a substituted or unsubstituted monocycle by bonding with each other" and the case where "one or more sets of adjacent two or more form a substituted or unsubstituted fused ring by bonding with each other" (the case where "forming a ring by bonding with each other").

Substituent in the Case of "Substituted or Unsubstituted"

In one embodiment in this specification, the substituent (in this specification, sometimes referred to as an "arbitrary substituent") in the case of "substituted or unsubstituted" is, for example, a group selected from the group consisting of:

- an unsubstituted alkyl group including 1 to 50 carbon atoms,
- an unsubstituted alkenyl group including 2 to 50 carbon atoms,
- an unsubstituted alkynyl group including 2 to 50 carbon atoms,
- an unsubstituted cycloalkyl group including 3 to 50 ring carbon atoms,
- $—Si(R_{901})(R_{902})(R_{903})$,
- $—O—(R_{904})$,
- $—S—(R_{905})$,
- $—N(R_{906})(R_{907})$,
- a halogen atom, a cyano group, a nitro group,
- an unsubstituted aryl group including 6 to 50 ring carbon atoms, and
- an unsubstituted heterocyclic group including 5 to 50 ring atoms, wherein, $R_{901}$ to $R_{907}$ are independently

- a hydrogen atom,
- a substituted or unsubstituted alkyl group including 1 to 50 carbon atoms,
- a substituted or unsubstituted cycloalkyl group including 3 to 50 ring carbon atoms,
- a substituted or unsubstituted aryl group including 6 to 50 ring carbon atoms, or
- a substituted or unsubstituted heterocyclic group including 5 to 50 ring atoms.

When two or more Roi's are present, the two or more $R_{901}$'s may be the same or different.

When two or more $R_{902}$'s are present, the two or more $R_{902}$'s may be the same or different.

When two or more $R_{903}$'s are present, the two or more $R_{903}$'s may be the same or different.

When two or more $R_{904}$'s are present, the two or more $R_{904}$'s may be the same or different.

When two or more $R_{905}$'s are present, the two or more $R_{905}$'s may be the same or different.

When two or more $R_{906}$'s are present, the two or more $R_{906}$'s may be the same or different.

When two or more $R_{907}$'s are present, the two or more $R_{907}$'s may be the same or different.

In one embodiment, the substituent in the case of "substituted or unsubstituted" is a group selected from the group consisting of:

an alkyl group including 1 to 50 carbon atoms, an aryl group including 6 to 50 ring carbon atoms, and a heterocyclic group including 5 to 50 ring atoms.

In one embodiment, the substituent in the case of "substituted or unsubstituted" is a group selected from the group consisting of:

an alkyl group including 1 to 18 carbon atoms, an aryl group including 6 to 18 ring carbon atoms, and a heterocyclic group including 5 to 18 ring atoms.

Specific examples of each of the arbitrary substituents include specific examples of substituent described in the section "Substituent described in this specification" above.

Unless otherwise specified in this specification, adjacent arbitrary substituents may form a "saturated ring" or an "unsaturated ring", preferably form a substituted or unsubstituted saturated 5-membered ring, a substituted or unsubstituted saturated 6-membered ring, a substituted or unsubstituted unsaturated 5-membered ring, or a substituted or unsubstituted unsaturated 6-membered ring, more preferably form a benzene ring.

Unless otherwise specified in this specification, the arbitrary substituent may further have a substituent. The substituent which the arbitrary substituent further has is the same as that of the above-mentioned arbitrary substituent.

In this specification, the numerical range represented by "AA to BB" means the range including the numerical value AA described on the front side of "AA to BB" as the lower limit and the numerical value BB described on the rear side of "AA to BB" as the upper limit.

[Organic EL Device]

The organic EL device according to an aspect of the invention includes: a cathode;

an anode; and an organic layer disposed between the cathode and the anode, wherein the organic layer contains a compound represented by the formula (1), and a compound A having a Stokes shift of 20 nm or smaller and an emission peak wavelength of 440 nm to 465 nm.

The formula (1), each substituent in the formula (1), and a compound A will be described later.

Here, "Stokes shift (SS)" is the difference between the local-maximum wavelength of the absorption spectrum and the local-maximum wavelength of the fluorescence spectrum, and can be measured by the method described in Examples.

When the compound represented by the formula (1) is combined with the compound A having a small Stokes shift (SS) and an emission peak wavelength of 440 nm to 465 nm, that is, which emits blue light, energy transfer is more likely to occur and sufficient efficiency can be obtained as compared with the case where combined with a compound which emits blue light having a large Stokes shift (SS).

However, for example, depending on a compound combined with the compound A having the above characteristics in an emitting layer, the effect of the compound A is not sufficiently exhibited in some cases.

In the invention, the compound represented by the formula (1) was selected as a compound that allows the compound A having the above characteristics to exhibit the effect and can achieve high luminous efficiency when used in an organic EL device. By using the compound represented by the formula (1) in combination with the compound A, a blue fluorescent organic EL device having high luminous efficiency is obtained.

In one embodiment, the Stokes shift of the compound A is 15 nm or smaller. The smaller the Stokes shift, the better the energy transfer efficiency. The lower limit value of the Stokes shift is not particularly limited, and is preferably 5 nm or more, for example.

A schematic configuration of an organic EL device will be described with reference to The Figure.

The organic EL device 1 includes a substrate 2, an anode 3, an emitting layer 5, a cathode 10, an organic layer 4 disposed between the anode 3 and the emitting layer 5, and an organic layer 6 disposed between the emitting layer 5 and the cathode 10.

The compound represented by the formula (1) and the compound A are contained in the organic layers 4 to 6 disposed between the anode 3 and the cathode 10, and are preferably contained in the emitting layer 5.

Each of the compound represented by the formula (1) and the compound A contained in the organic layer may be used alone, or in combination of two or more kinds, respectively.

[Compound Represented by Formula (1)]

Next, the compound represented by the formula (1) will be described.

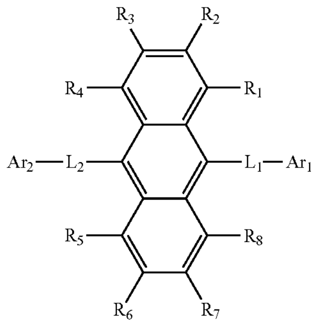

(1)

In the formula (1), one or more sets of adjacent two or more of $R_1$ to $R_8$ form a substituted or unsubstituted, saturated or unsaturated ring by bonding with each other, or do not form a substituted or unsubstituted, saturated or unsaturated ring.

$R_1$ to $R_8$ that do not form the substituted or unsubstituted, saturated or unsaturated ring are independently a hydrogen atom or a substituent R.

The substituent R is a halogen atom, a cyano group, a nitro group, a substituted or unsubstituted alkyl group including 1 to 50 carbon atoms, a substituted or unsubstituted alkenyl group including 2 to 50 carbon atoms, a substituted or unsubstituted alkynyl group including 2 to 50 carbon atoms, a substituted or unsubstituted cycloalkyl group including 3 to 50 ring carbon atoms, $-Si(R_{901})(R_{902})(R_{903})$, $-O-(R_{904})$, $-S-(R_{905})$, $-N(R_{906})(R_{907})$, a substituted or unsubstituted aryl group including 6 to 50 ring carbon atoms, or a substituted or unsubstituted monovalent heterocyclic group including 5 to 50 ring atoms.

$R_{901}$ to $R_{907}$ are independently a hydrogen atom, a substituted or unsubstituted alkyl group including 1 to 50 carbon atoms, a substituted or unsubstituted cycloalkyl group including 3 to 50 ring carbon atoms, a substituted or unsubstituted aryl group including 6 to 50 ring carbon atoms, or a substituted or unsubstituted monovalent heterocyclic group including 5 to 50 ring atoms. When two or more of each of $R_{901}$ to $R_{907}$ are present, the two or more of each of $R_{901}$ to $R_{907}$ are the same as or different from each other.

$L_1$ and $L_2$ are independently a single bond, a substituted or unsubstituted arylene group including 6 to 50 ring carbon atoms, or a substituted or unsubstituted divalent heterocyclic group including 5 to 50 ring atoms.

At least one of $Ar_1$ and $Ar_2$ is a monovalent group having a structure represented by the following formula (2).

(2)

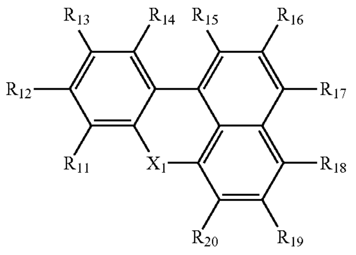

In the formula (2), $X_1$ is O, S, or $C(R_{21})(R_{22})$.

One of $R_{11}$ to $R_{20}$ is a single bond which bonds with $L_1$ or $L_2$.

One or more sets of adjacent two or more of $R_{11}$ to $R_{14}$ and adjacent two or more of $R_{15}$ to $R_{20}$ that are not a single bond which bonds with $L_1$ or $L_2$ form a substituted or unsubstituted, saturated or unsaturated ring by bonding with each other, or do not form a substituted or unsaturated, saturated or unsaturated ring.

$R_{21}$ and $R_{22}$ form a substituted or unsubstituted, saturated or unsaturated ring by bonding with each other, or do not form a substituted or unsubstituted, saturated or unsaturated ring.

$R_{21}$ and $R_{22}$ that do not form the substituted or unsubstituted, saturated or unsaturated ring, and $R_{11}$ to $R_{20}$ that do not form the substituted or unsubstituted, saturated or unsaturated ring and that are not a single bond which bonds with $L_1$ or $L_2$ are independently a hydrogen atom or a substituent R.

The substituent R is as defined in the formula (1).

$Ar_1$ or $Ar_2$ which is not the monovalent group having a structure represented by the formula (2) is a substituted or unsubstituted aryl group including 6 to 50 ring carbon atoms, or a substituted or unsubstituted monovalent heterocyclic group including 5 to 50 ring atoms.

The position to be a single bond which bonds with $L_1$ or $L_2$ in the formula (2) is not particularly limited.

In one embodiment, one of $R_{12}$ to $R_{20}$ in the formula (2) is a single bond which bonds with $L_1$ or $L_2$.

In one embodiment, $Ar_1$ or $Ar_2$ is a monovalent group represented by the following formula (2-$R_{12}$), (2-$R_{13}$), (2-$R_{14}$), (2-$R_{17}$), or (2-$R_{18}$).

(2-$R_{12}$)

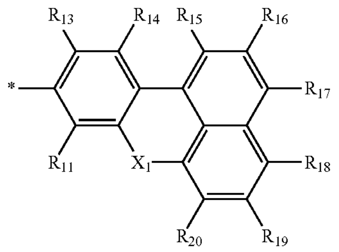

(2-$R_{13}$)

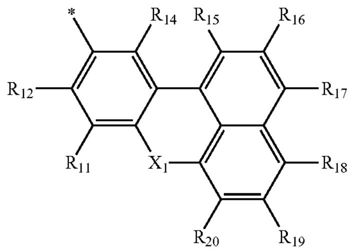

(2-$R_{14}$)

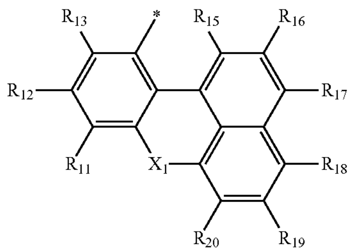

(2-$R_{17}$)

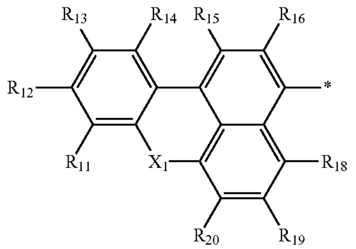

(2-$R_{18}$)

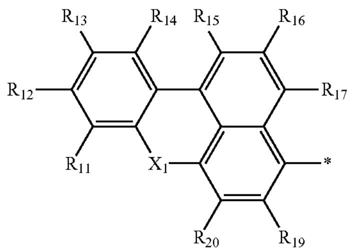

In the formulas (2-$R_{12}$), (2-$R_{13}$), (2-$R_{14}$), (2-$R_{17}$), and (2-$R_{18}$), $X_1$, and $R_{11}$ to $R_{20}$ are as defined in the formula (2).

* is bonded with $L_1$ or $L_2$.

In one embodiment, the compound represented by the formula (1) is one or more compounds selected from the group consisting of a compound represented by the following formula (1-1) and a compound represented by the following formula (1-2).

(1-1)

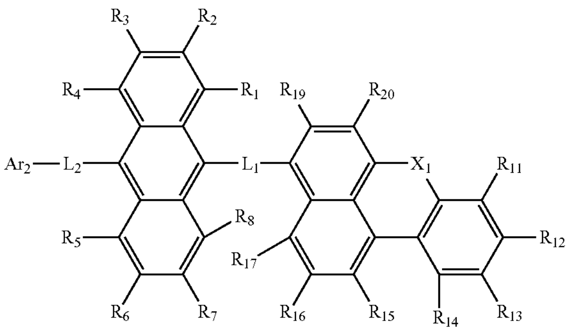

(1-2)

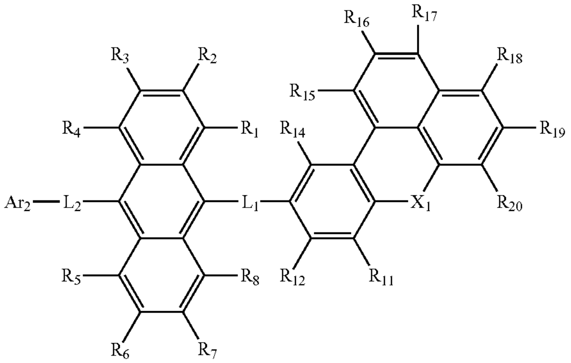

In the formulas (1-1) and (1-2), $R_1$ to $R_8$, $L_1$, $L_2$, $Ar_2$, $X_1$, and $R_{11}$ to $R_{20}$ are as defined in the formula (1) or (2), respectively.

In one embodiment, $L_1$ and $L_2$ are independently a single bond, or a substituted or unsubstituted arylene group including 6 to 14 ring carbon atoms.

In one embodiment, $L_1$ and $L_2$ are independently a single bond, a substituted or unsubstituted phenylene group, a substituted or unsubstituted naphthylene group, a substituted or unsubstituted fluorenylene group, a substituted or unsubstituted phenanthrylene group, or a substitute or unsubstituted biphenyldiyl group.

In one embodiment, either or both of $L_1$ and $L_2$ are single bonds.

In one embodiment, the compound represented by the formula (1) is a compound represented by the following formula (1-1-1).

(1-1-1)

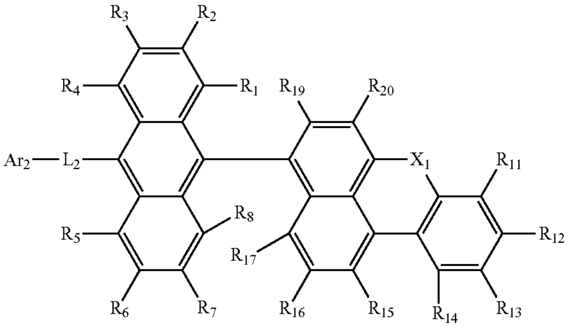

In the formula (1-1-1), $R_1$ to $R_8$, $L_2$, $Ar_2$, $X_1$, $R_{11}$ to $R_{17}$, $R_{19}$, and $R_{20}$ are as defined in the formula (1) or (2), respectively.

In one embodiment, the compound represented by the formula (1) is a compound represented by the following formula (1-1-2).

(1-1-2)

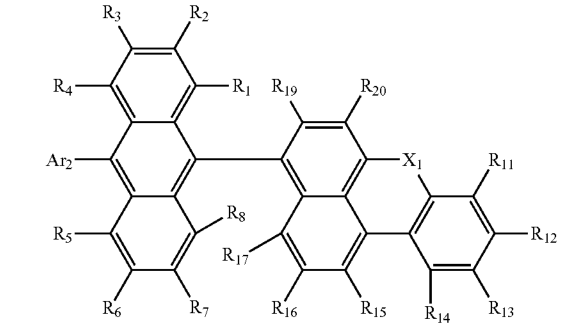

In the formula (1-1-2), $R_1$ to $R_8$, $Ar_2$, $X_1$, $R_{11}$ to $R_{17}$, $R_{19}$, and $R_{20}$ are as defined in the formula (1) or (2), respectively.

In one embodiment, $L_2$ is a single bond.

In one embodiment, $Ar_2$ is a substituted or unsubstituted phenyl group, a substituted or unsubstituted naphthyl group, a substituted or unsubstituted fluorenyl group, a substituted or unsubstituted phenanthryl group, a substituted or unsubstituted biphenyl group.

a substituted or unsubstituted chrysenyl group, a substituted or unsubstituted benzophenanthrenyl group, a substituted or unsubstituted benzotriphenylenyl group, a substituted or unsubstituted dibenzofuranyl group, a substituted or unsubstituted naphthobenzofuranyl group, a substituted or unsubstituted carbazolyl group, or a substituted or unsubstituted benzo[def]carbazolyl group.

In one embodiment, $Ar_2$ is a group represented by any of the following formulas ($Ar_2$-11) to ($Ar_2$-14).

($Ar_2$-11)

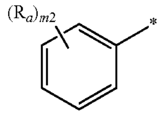

-continued (Ar$_2$-12)

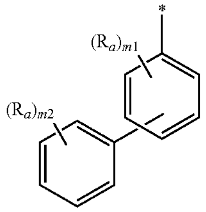

(Ar$_2$-13)

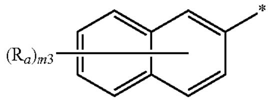

(Ar$_2$-14)

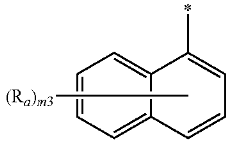

In the formulas (Ar$_2$-11) to (Ar$_2$-14),

* is bonded with $L_2$.

$R_a$ is a substituent.

The substituent $R_a$ is a halogen atom, a cyano group, a nitro group, a substituted or unsubstituted alkyl group including 1 to 50 carbon atoms, a substituted or unsubstituted alkenyl group including 2 to 50 carbon atoms, a substituted or unsubstituted alkynyl group including 2 to 50 carbon atoms, a substituted or unsubstituted cycloalkyl group including 3 to 50 ring carbon atoms, —Si($R_{901}$)($R_{902}$)($R_{903}$),

—O—($R_{904}$),

—S—($R_{905}$),

—N($R_{906}$)($R_{907}$), a substituted or unsubstituted aryl group including 6 to 50 ring carbon atoms, or a substituted or unsubstituted monovalent heterocyclic group including 5 to 50 ring atoms.

$R_{901}$ to $R_{907}$ are as defined in the formula (1).

m1 is an integer of 0 to 4.

m2 is an integer of 0 to 5.

m3 is an integer of 0 to 7.

When each of m1 to m3 is 2 or more, a plurality of $R_a$'s may be the same as or different from each other.

When each of m1 to m3 is 2 or more, a plurality of adjacent $R_a$'s form a substituted or unsubstituted, saturated or unsaturated ring by bonding with each other, or do not form a substituted or unsubstituted, saturated or unsaturated ring.

In one embodiment, $Ar_2$-$L_2$- is selected from the following groups:

a substituted or unsubstituted phenyl group in which $L_2$ is a single bond and $Ar_2$ is a substituted or unsubstituted phenyl group, a substituted or unsubstituted naphthyl group in which $L_2$ is a single bond and $Ar_2$ is a substituted or unsubstituted naphthyl group, a substituted or unsubstituted phenylnaphthyl group in which $L_2$ is a substituted or unsubstituted naphthyl group and $Ar_2$ is a phenyl group, a substituted or unsubstituted biphenyl group in which $L_2$ is a single bond and $Ar_2$ is a substituted or unsubstituted biphenyl group, or a substituted or unsubstituted biphenyl group in which $L_2$ is a substituted or unsubstituted phenylene group and $Ar_2$ is a substituted or unsubstituted phenyl group, a substituted or unsubstituted naphthylphenyl group in which $L_2$ is a substituted or unsubstituted phenyl group and $Ar_2$ is a substituted or unsubstituted naphthyl group, a substituted or unsubstituted fluorenyl group in which $L_2$ is a single bond and $Ar_2$ is a substituted or unsubstituted fluorenyl group, a substituted or unsubstituted phenanthryl group in which $L_2$ is a single bond and $Ar_2$ is a substituted or unsubstituted phenanthryl group, a substituted or unsubstituted phenylphenanthryl group in which $L_2$ is a substituted or unsubstituted phenanthryl group and $Ar_2$ is a substituted or unsubstituted phenyl group, a substituted or unsubstituted benzophenanthryl group in which $L_2$ is a single bond and $Ar_2$ is a substituted or unsubstituted benzophenanthryl group, a substituted or unsubstituted benzotriphenylenyl group in which $L_2$ is a single bond and $Ar_2$ is a substituted or unsubstituted benzotriphenylenyl group, a substituted or unsubstituted chrysenyl group in which $L_2$ is a single bond and $Ar_2$ is a substituted or unsubstituted chrysenyl group, a substituted or unsubstituted dibenzofuranyl group in which $L_2$ is a single bond and $Ar_2$ is a substituted or unsubstituted dibenzofuranyl group, a substituted or unsubstituted phenyldibenzofuranyl group in which $L_2$ is a substituted or unsubstituted dibenzofuranyl group and $Ar_2$ is a substituted or unsubstituted phenyl group, a substituted or unsubstituted naphthobenzofuranyl group in which $L_2$ is a single bond and $Ar_2$ is a substituted or unsubstituted naphthobenzofuranyl group, a substituted or unsubstituted carbazolyl group in which $L_2$ is a single bond and $Ar_2$ is a substituted or unsubstituted carbazolyl group, a substituted or unsubstituted carbazolyl-phenyl group, in which $L_2$ is a substituted or unsubstituted phenyl group and $Ar_2$ is a substituted or unsubstituted carbazolyl group; or a substituted or unsubstituted benzo[def]carbazolyl-phenyl group wherein $L_2$ is a substituted or unsubstituted phenyl group and $Ar_2$ is a substituted or unsubstituted benzo[def]carbazolyl group.

In one embodiment, the compound represented by the formula (1) is a compound represented by the following formula (1-3).

(1-3)

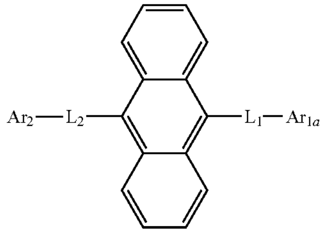

In the formula (1-3), $Ar_2$, $L_1$, and $L_2$ are as defined in the formula (1).

$Ar_{1a}$ is a monovalent group having a structure represented by the following formula (2-2).

(2-2)

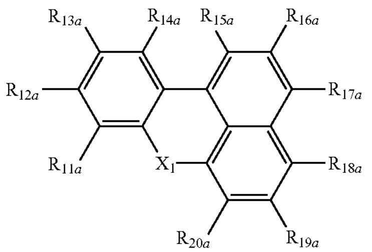

In the formula (2-2), $X_1$ is as defined in the formula (2).

One of $R_{11a}$ to $R_{20a}$ is a single bond which bonds with $L_1$.

$R_{11a}$ to $R_{20a}$ that are not a single bond which bonds with $L_1$ are hydrogen atoms.

In one embodiment, $X_1$ is O or S.

In one embodiment, the hydrogen atom at any position of the compound represented by the formula (1) may be a deuterium atom. Specifically, one or more of $R_1$ to $R_8$ that are hydrogen atoms, $R_{11}$ to $R_{20}$ that are hydrogen atoms, hydrogen atoms possessed by the substituted or unsubstituted, saturated or unsaturated ring formed by bonding one or more sets of adjacent two or more of $R_1$ to $R_8$ with each other, hydrogen atoms possessed by $R_1$ to $R_8$ that are the substituents R, hydrogen atoms possessed by the substituted or unsubstituted, saturated or unsaturated ring formed by bonding one or more sets of adjacent two or more of $R_{11}$ to $R_{20}$ with each other, hydrogen atoms possessed by $R_{11}$ to $R_{20}$ that are the substituents R, hydrogen atoms possessed by $L_1$, hydrogen atoms possessed by $L_2$, hydrogen atoms possessed by $Ar_1$, and hydrogen atoms possessed by $Ar_2$ are deuterium atoms.

In one embodiment, the compound represented by the formula (1) is a compound represented by the following formula (1-A).

(1-A)

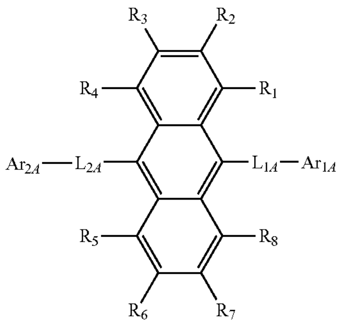

In the formula (1-A), one or more sets of adjacent two or more of $R_1$ to $R_8$ form a substituted or unsubstituted, saturated or unsaturated ring by bonding with each other, or do not form a substituted or unsubstituted, saturated or unsaturated ring.

$R_1$ to $R_8$ that do not form the substituted or unsubstituted, saturated or unsaturated ring are independently a hydrogen atom or a substituent R.

The substituent R is a halogen atom, a cyano group, a nitro group, a substituted or unsubstituted alkyl group including 1 to 50 carbon atoms, a substituted or unsubstituted alkenyl group including 2 to 50 carbon atoms, a substituted or unsubstituted alkynyl group including 2 to 50 carbon atoms, a substituted or unsubstituted cycloalkyl group including 3 to 50 ring carbon atoms, $—Si(R_{901})(R_{902})(R_{903})$, $—O—(R_{904})$, $—N(R_{905})(R_{907})$, a substituted or unsubstituted aryl group including 6 to 50 ring carbon atoms, or a substituted or unsubstituted monovalent heterocyclic group including 5 to 50 ring atoms.

$R_{901}$ to $R_{907}$ are independently a hydrogen atom, a substituted or unsubstituted alkyl group including 1 to 50 carbon atoms, a substituted or unsubstituted cycloalkyl group including 3 to 50 ring carbon atoms, a substituted or unsubstituted aryl group including 6 to 50 ring carbon atoms, or a substituted or unsubstituted monovalent heterocyclic group including 5 to 50 ring atoms. When two or more of each of $R_{901}$ to $R_{907}$ are present, the two or more of each of $R_{901}$ to $R_{907}$ are the same as or different from each other.

$L_{1A}$ and $L_{2A}$ are independently a single bond, or a linking group having a structure represented by any of the following formulas (L-1) to (L-9).

(L-1)

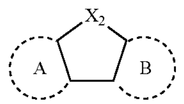

(L-2)

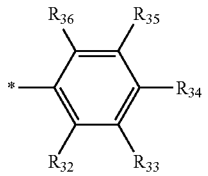

(L-3)

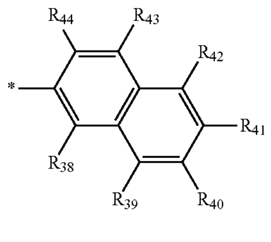

-continued (L-4)

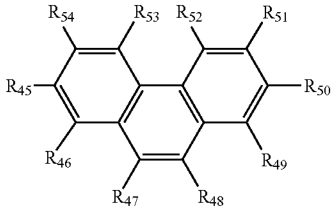

(L-5)

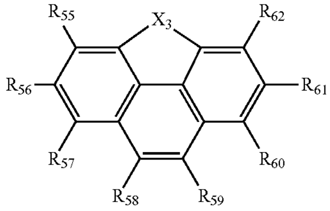

(L-6)

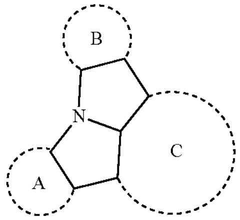

(L-7)

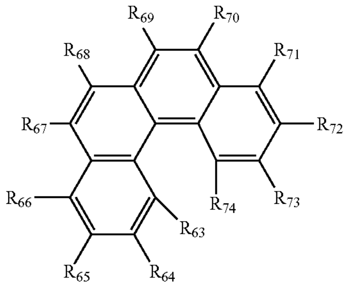

(L-8)

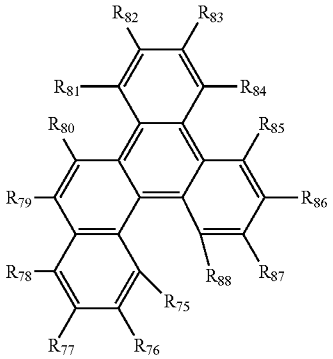

-continued (L-9)

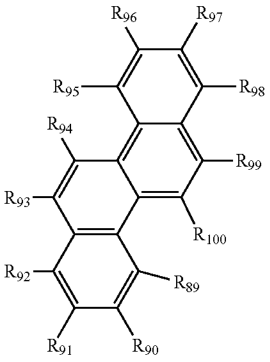

In the formula (L-1), a ring A and a ring B are independently a substituted or unsubstituted aromatic hydrocarbon ring including 6 to 14 ring carbon atoms, or a substituted or unsubstituted heterocycle including 5 to 50 ring atoms.

$X_2$ is O, S, $N(R_{1a})$, or $C(R_{2a})(R_{3a})$.

One of $R_{1a}$ to $R_{3a}$ and the atoms that constitute the aromatic hydrocarbon ring or the heterocycle of the ring A and the ring B and that can form a single bond is bonded with the anthracene skeleton via a single bond, and one of the remaining is a single bond which bonds with $Ar_{1A}$ or $Ar_{2A}$ or bonded with $Ar_{1A}$ or $Ar_{2A}$ via a single bond.

$R_{1a}$ to $R_{3a}$ that are not a single bond which bonds with the anthracene skeleton and $Ar_{1A}$ or $Ar_{2A}$, and the atoms that constitute the aromatic hydrocarbon ring or the heterocycle of the ring A and the ring B and that can form a single bond are independently a hydrogen atom or a substituent R, or bonded with a hydrogen atom or a substituent R.

$R_{1a}$ to $R_{3a}$ that are not a single bond are independently a hydrogen atom or a substituent R.

The substituent R is as defined above.

In the formula (L-2),

* is a single bond which bonds with an anthracene skeleton.

One of $R_{32}$ to $R_{36}$ is a single bond which bonds with $Ar_{1A}$ or $Ar_{2A}$.

$R_{32}$ to $R_{36}$ that are not a single bond which bonds with $Ar_{1A}$ or $Ar_{2A}$ are independently a hydrogen atom or a substituent R.

The substituent R is as defined above.

In the formula (L-3),

* is a single bond which bonds with an anthracene skeleton.

One of $R_{38}$ to $R_{44}$ is a single bond which bonds with $Ar_{1A}$ or $Ar_{2A}$.

$R_{38}$ to $R_{44}$ that are not a single bond which bonds with the anthracene skeleton and $Ar_{1A}$ or $Ar_{2A}$ are independently a hydrogen atom or a substituent R.

The substituent R is as defined above.

In the formula (L-4), one of $R_{45}$ to $R_{54}$ is a single bond which bonds with the anthracene skeleton and one of the remaining is a single bond which bonds with $Ar_{1A}$ or $Ar_{2A}$.

$R_{45}$ to $R_{54}$ that are not a single bond which bonds with the anthracene skeleton and $Ar_{1A}$ or $Ar_{2A}$ are independently a hydrogen atom or a substituent R.

The substituent R is as defined above.

In the formula (L-5), $X_3$ is O, S, $N(R_{1a})$ or $C(R_{2a})(R_{3a})$.

One of $R_{1a}$ to $R_{3a}$ and $R_{55}$ to $R_{62}$ is a single bond which bonds with the anthracene skeleton and one of the remaining is a single bond which bonds with $Ar_{1A}$ or $Ar_{2A}$.

$R_{1a}$ to $R_{3a}$ and $R_{55}$ to $R_{62}$ that are not a single bond which bonds with the anthracene skeleton and $Ar_{1A}$ or $Ar_{2A}$ are independently a hydrogen atom or a substituent R.

The substituent R is as defined above.

In the formula (L-6), a ring a, a ring b, and a ring c are independently a substituted or unsubstituted aromatic hydrocarbon ring including 6 to 14 ring carbon atoms, or a substituted or unsubstituted heterocycle including 5 to 50 ring atoms.

One of the atoms that constitute the aromatic hydrocarbon ring or the heterocycle of the ring A, the ring B, and the ring C and that can form a single bond is bonded with the anthracene skeleton via a single bond, and one of the remaining is bonded with $Ar_{1A}$ or $Ar_{2A}$ via a single bond.

The atoms that are not bonded with the anthracene skeleton and $Ar_{1A}$ or $Ar_{2A}$ via a single bond, that constitute the aromatic hydrocarbon ring or the heterocycle of the ring A, the ring B, and the ring C, and that can form a single bond are independently bonded with a hydrogen atom or a substituent R.

The substituent R is as defined above.

In the formula (L-7), one of $R_{63}$ to $R_{74}$ is a single bond which bonds with the anthracene skeleton and one of the remaining is a single bond which bonds with $Ar_{1A}$ or $Ar_{2A}$.

$R_{63}$ to $R_{74}$ which are not a single bond which bonds with the anthracene skeleton and $Ar_1$ or $Ar_{2A}$ are independently a hydrogen atom or a substituent R.

The substituent R is as defined above.

In the formula (L-8), one of $R_{75}$ to $R_{88}$ is a single bond which bonds with the anthracene skeleton and one of the remaining is a single bond which bonds with $Ar_{1A}$ or $Ar_{2A}$.

$R_{75}$ to $R_{88}$ which are not a single bond which bonds with the anthracene skeleton and $Ar_{1A}$ or $Ar_{2A}$ are independently a hydrogen atom or a substituent R.

The substituent R is as defined above.

In the formula (L-9), one of $R_{89}$ to $R_{100}$ is a single bond which bonds with the anthracene skeleton and one of the remaining is a single bond which bonds with $Ar_{1A}$ or $Ar_{2A}$.

$R_{89}$ to $R_{100}$ that are not a single bond which bonds with the anthracene skeleton and $Ar_{1A}$ or $Ar_{2A}$ are independently a hydrogen atom or a substituent R.

The substituent R is as defined above.

$Ar_1$ is a monovalent group having a structure represented by the following formula (2-A).

(2-A)

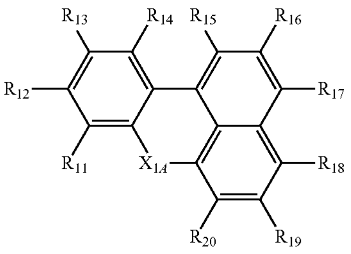

In the formula (2-A), $X_{1A}$ is O or S.

One of $R_{11}$ to $R_{20}$ is a single bond which bonds with $L_{1A}$.

One or more sets of adjacent two or more of $R_{11}$ to $R_{14}$ and adjacent two or more of $R_{15}$ to $R_{20}$ that are not a single bond which bonds with $L_{1A}$ form a substituted or unsubstituted, saturated or unsaturated ring by bonding with each other, or do not form a substituted or unsaturated, saturated or unsaturated ring.

$R_{11}$ to $R_{20}$ that are not a single bond which bonds with $L_{1A}$ and that do not form the substituted or unsubstituted, saturated or unsaturated ring are independently a hydrogen atom or a substituent R.

The substituent R is as defined above.

$Ar_{2A}$ is a monovalent group having a structure represented by any of the following formulas ($Ar_2$-1) to ($Ar_2$-10). Provided that, when $L_{2A}$ is a single bond, $Ar_{2A}$ is not a group having a structure represented by the following formula ($Ar_2$-10).

($Ar_2$-1)

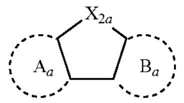

($Ar_2$-2)

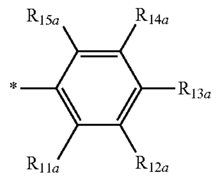

($Ar_2$-3)

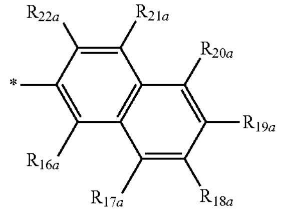

($Ar_2$-4)

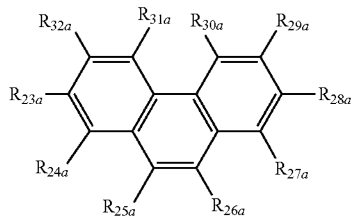

($Ar_2$-5)

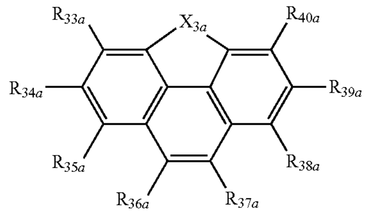

($Ar_2$-6)

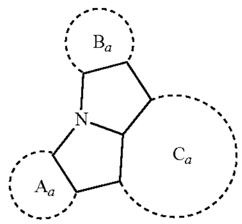

-continued (Ar$_2$-7)

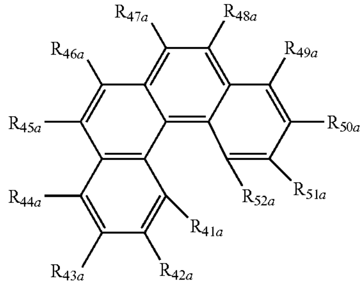

(Ar$_2$-8)

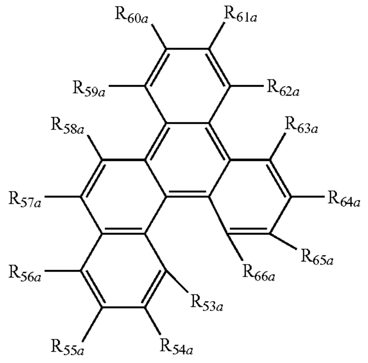

(Ar$_2$-9)

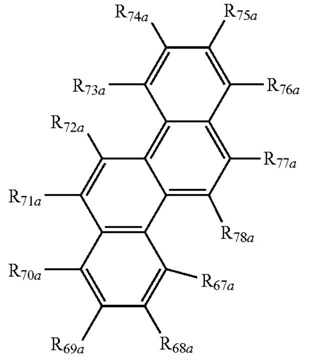

(Ar$_2$-10)

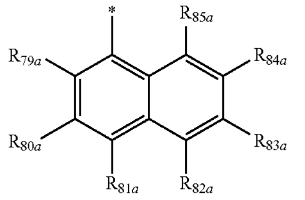

In the formula (Ar$_2$-1), a ring $A_a$ and a ring $B_a$ are independently a substituted or unsubstituted aromatic hydrocarbon ring including 6 to 14 ring carbon atoms, or a substituted or unsubstituted heterocycle including 5 to 50 ring atoms.

$X_{2a}$ is O, S, N($R_{1a}$), or C($R_{2a}$)($R_{3a}$).

One of $R_{1a}$ to $R_{3a}$ and the atoms that constitute the aromatic hydrocarbon ring or the heterocycle of the ring $A_a$ and the ring $B_a$ and that can form a single bond is a single bond which bonds with $L_{2A}$ or bonded with $L_{2A}$ via a single bond.

$R_{1a}$ to $R_{3a}$ and the atoms which constitute the hydrocarbon ring or the heterocyclic of the ring $A_a$ and the ring $B_a$, which are not bonded with $L_{2A}$ by a single bond, and which can form a single bond are independently bonded with a hydrogen atom or a substituent R.

The substituent R is as defined above.

In the formula (Ar$_2$-2),

* is a single bond which bonds with $L_{2A}$.

$R_{11a}$ to $R_{15a}$ are independently a hydrogen atom or a substituent R.

The substituent R is as defined above.

In the formula (Ar$_2$-3),

* is a single bond which bonds with $L_{2A}$.

$R_{16a}$ to $R_{22a}$ are independently a hydrogen atom or a substituent R.

The substituent R is as defined above.

In the formula (Ar$_2$-4), one of $R_{23a}$ to $R_{32a}$ is a single bond which bonds with $L_{2A}$.

$R_{23a}$ to $R_{32a}$ that are not a single bond which bonds with $L_{2A}$ are independently a hydrogen atom or a substituent R.

The substituent R is as defined above.

In the formula (Ar$_2$-5), $X_{3a}$ is O, S, N($R_{1a}$), or C($R_{2a}$)($R_{3a}$).

One of $R_{1a}$ to $R_{3a}$ and $R_{33a}$ to $R_{40a}$ is a single bond which bonds with $L_{2A}$.

$R_{1a}$ to $R_{3a}$ and $R_{33a}$ to $R_{40a}$ that are not a single bond which bonds with $L_{2A}$ are independently a hydrogen atom r a substituent R.

The substituent R is as defined above.

In the formula (Ar$_2$-6), a ring $A_a$, a ring $B_a$, and a ring $C_a$ are independently a substituted or unsubstituted aromatic hydrocarbon ring including 6 to 14 ring carbon atoms, or a substituted or unsubstituted heterocycle including 5 to 50 ring atoms.

One of the atoms that constitute the aromatic hydrocarbon ring or the heterocycle of the ring $A_a$, the ring $B_a$, and the ring $C_a$ and that can form a single bond is bonded with $L_a$ via a single bond.

The atoms that constitute the aromatic hydrocarbon ring or the heterocycle of the ring $A_a$, the ring $B_a$, and the ring $C_a$, that are not bonded with $L_{2A}$ via a single bond, and that can form a single bond are independently bonded with a hydrogen atom or a substituent R.

The substituent R is as defined above.

In the formula (Ar$_2$-7), one of $R_{41a}$ to $R_{52a}$ is a single bond which bonds with $L_{2A}$.

$R_{41a}$ to $R_{52a}$ that are not a single bond which bonds with $L_{2A}$ are independently a hydrogen atom or a substituent R.

The substituent R is as defined above.

In the formula (Ar$_2$-8), one of $R_{53a}$ to $R_{66a}$ is a single bond which bonds with $L_{2A}$.

$R_{53a}$ to $R_{66a}$ that are not a single bond which bonds with $L_{2A}$ are independently a hydrogen atom or a substituent R.

The substituent R is as defined above.

In the formula (Ar$_2$-9), one of $R_{67a}$ to $R_{78a}$ is a single bond which bonds with $L_{2A}$.

$R_{67a}$ to $R_{78a}$ that are not a single bond which bonds with $L_{2A}$ are independently a hydrogen atom or a substituent R.

The substituent R is as defined above.

In the formula (Ar$_2$-10),

* is a single bond which bonds with $L_{2A}$.

$R_{79a}$ to $R_{85a}$, are independently a hydrogen atom or a substituent R.

The substituent R is as defined above.

In one embodiment, one of $R_{11}$ to $R_{20}$ in the formula (2-A) is a single bond which bonds with $L_{1A}$.

In one embodiment, $Ar_{1A}$ is a monovalent group having a structure represented by the following formula (2-$R_{12}$), (2-$R_{13}$), (2-$R_{14}$), (2-$R_{17}$), or (2-$R_{18}$).

(2-$R_{12}$)

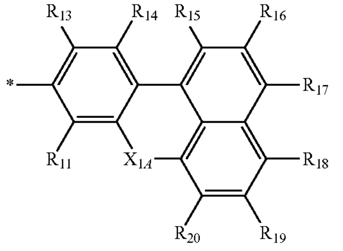

(2-$R_{13}$)

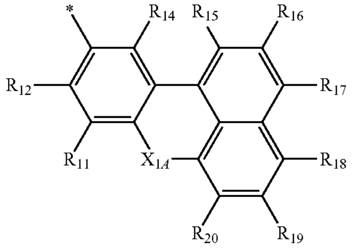

(2-$R_{14}$)

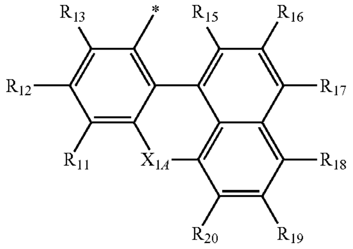

(2-$R_{17}$)

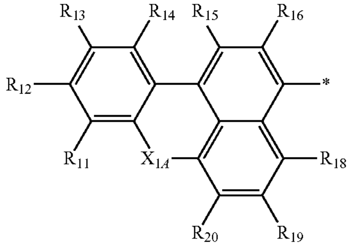

(2-$R_{18}$)

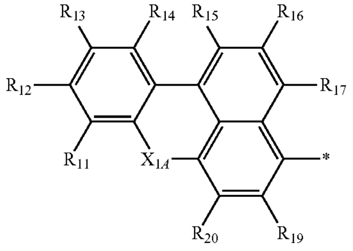

In the formulas (2-$R_{12}$), (2-$R_{13}$), (2-$R_{14}$), (2-$R_{17}$), and (2-$R_{18}$), $X_{1A}$ and $R_{11}$ to $R_{20}$ are as defined in the formula (2-A).

* is bonded with $L_{1A}$.

In one embodiment, the compound represented by the formula (1-A) is one or more compounds selected from the group consisting of a compound represented by the following formula (1-A-1) and a compound represented by the following formula (1-A-2).

(1-A-1)

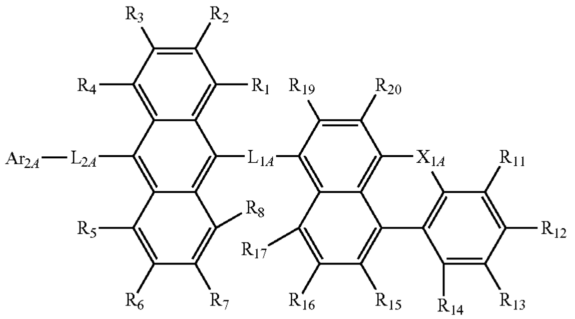

(1-A-2)

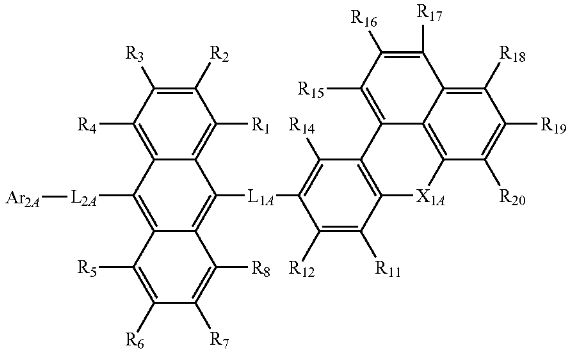

In the formulas (1-A-1) and (1-A-2), $R_1$ to $R_8$, $L_{1A}$, $L_{2A}$, $Ar_{2A}$, $X_{1A}$, and $R_{11}$ to $R_{20}$ are as defined in the formula (1-A) or (2-A), respectively.

In one embodiment, $L_{1A}$ is a single bond, or a linking group having a structure represented by the formula (L-1), (L-2), (L-3), or (L-4).

In one embodiment, $L_{1A}$ is a single bond, or a substituted or unsubstituted phenylene group, a substituted or unsubstituted naphthylene group, a substituted or unsubstituted fluorenylene group, a substituted or unsubstituted phenanthrylene group, or a substitute or unsubstituted biphenyldiyl group.

In one embodiment, $L_{1A}$ is a single bond.

In one embodiment, the compound represented by the formula (1-A) is a compound represented by the following formula (1-A-1-1).

(1-A-1-1)

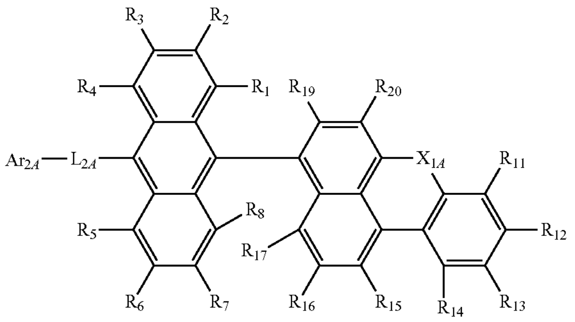

In the formula (1-A-1-1), $R_1$ to $R_8$, $L_{2A}$, $Ar_2$, $X_{1A}$, $R_{11}$ to $R_{17}$, $R_{19}$, and $R_{20}$ are as defined in the formula (1-A) or (2-A), respectively.

In one embodiment, $L_{2A}$ is a single bond, or a linking group having a structure represented by the formula (L-1), (L-2), or (L-4).

In one embodiment, $L_{2A}$ is a single bond, a substituted or unsubstituted phenylene group, a substituted or unsubstituted naphthylene group, a substituted or unsubstituted fluorenylene group, a substituted or unsubstituted phenanthrylene group, or a substitute or unsubstituted biphenyldiyl group.

In one embodiment, $L_{2A}$ is a single bond.

In one embodiment, the compound represented by the formula (1-A) is a compound represented by the following formula (1-A-1-2).

(1-A-1-2)

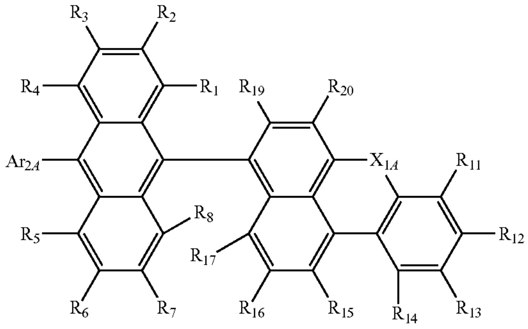

In the formula (1-A-1-2), $R_1$ to $R_8$, $Ar_{2A}$, $X_{1A}$, $R_{11}$ to $R_{17}$, $R_{19}$, and $R_{20}$ are as defined in the formula (1-A) or (2-A), respectively.

In one embodiment, $Ar_{2A}$ is a monovalent group having a structure represented by the formula ($Ar_2$-1), ($Ar_2$-2), ($Ar_2$-3), ($Ar_2$-4), ($Ar_2$-5), ($Ar_2$-7), ($Ar_2$-8), or ($Ar_2$-9).

In one embodiment, $Ar_{2A}$ is a substituted or unsubstituted phenyl group, a substituted or unsubstituted 2-naphthyl group, a substituted or unsubstituted fluorenyl group, a substituted or unsubstituted phenanthryl group, a substituted or unsubstituted biphenyl group.

a substituted or unsubstituted chrysenyl group, a substituted or unsubstituted benzophenanthrenyl group, a substituted or unsubstituted benzotriphenylenyl group, a substituted or unsubstituted dibenzofuranyl group, a substituted or unsubstituted naphthobenzofuranyl group, a substituted or unsubstituted carbazolyl group, or a substituted or unsubstituted benzo[def]carbazolyl group.

In one embodiment, $Ar_{2A}$ is a group represented by any of the following formulas ($Ar_{2A}$-11) to ($Ar_{2A}$-13).

($Ar_{2A}$-11)

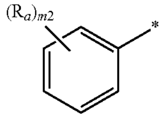

-continued ($Ar_{2A}$-12)

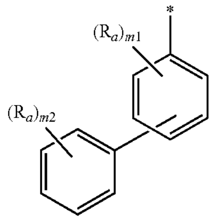

($Ar_{2A}$-13)

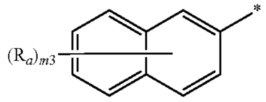

In the formula ($Ar_{2A}$-11) to ($Ar_{2A}$-13),

* is bonded with $L_{2A}$.

$R_a$ is a substituent.

The substituent $R_a$ is a halogen atom, a cyano group, a nitro group, a substituted or unsubstituted alkyl group including 1 to 50 carbon atoms, a substituted or unsubstituted alkenyl group including 2 to 50 carbon atoms, a substituted or unsubstituted alkynyl group including 2 to 50 carbon atoms, a substituted or unsubstituted cycloalkyl group including 3 to 50 ring carbon atoms, —$Si(R_{901})(R_{902})(R_{903})$,

—O—($R_{904}$),

—S—($R_{905}$),

—$N(R_{906})(R_{907})$, a substituted or unsubstituted aryl group including 6 to 50 ring carbon atoms, or a substituted or unsubstituted monovalent heterocyclic group including 5 to 50 ring atoms.

$R_{901}$ to $R_{907}$ are as defined in the formula (1-A).

m1 is an integer of 0 to 4.

m2 is an integer of 0 to 5.

m3 is an integer of 0 to 7.

When each of m1 to m3 is 2 or more, a plurality of $R_a$'s may be the same as or different from each other.

When each of m1 to m3 is 2 or more, a plurality of adjacent $R_a$'s form a substituted or unsubstituted, saturated or unsaturated ring by bonding with each other, or do not form a substituted or unsubstituted, saturated or unsaturated ring.

In one embodiment, $Ar_{2A}$-$L_{2A}$- is selected from the following groups:

a substituted or unsubstituted phenyl group in which $L_{2A}$ is a single bond and $Ar_{2A}$ is a substituted or unsubstituted phenyl group, a substituted or unsubstituted 2-naphthyl group in which $L_{2A}$ is a single bond and $Ar_{2A}$ is a substituted or unsubstituted 2-naphthyl group, a substituted or unsubstituted phenylnaphthyl group in which $L_{2A}$ is a substituted or unsubstituted 2-naphthyl group and $Ar_{2A}$ is a substituted or unsubstituted phenyl group, a substituted or unsubstituted biphenyl group in which $L_{2A}$ is a single bond and $Ar_{2A}$ is a substituted or unsubstituted biphenyl group, or a substituted or unsubstituted biphenyl group in which $L_{2A}$ is a substituted or unsubstituted phenylene group and $Ar_{2A}$ is a substituted or unsubstituted phenyl group, a substituted or unsubstituted naphthylphenyl group in which $L_{2A}$ is a substituted or unsubstituted phenyl group and $Ar_{2A}$ is a substituted or unsubstituted naphthyl group, a substituted or unsubstituted fluorenyl group in which $L_{2A}$ is a single bond and $Ar_{2A}$ is a substituted or unsubstituted fluorenyl group, a substituted or unsubstituted phenanthryl group in which $L_{2A}$ is a single bond and $Ar_{2A}$ is a substituted or unsubstituted phenanthryl group, a substituted or unsubstituted phenylphenanthryl group in which $L_{2A}$ is a substituted or unsubstituted phenanthryl group and $Ar_{2A}$ is a substituted or unsubstituted phenyl group, a substituted or unsubstituted benzophenanthryl group in which $L_{2A}$ is a single bond and $Ar_{2A}$ is a substituted or unsubstituted benzophenanthryl group, a substituted or unsubstituted benzotriphenylenyl group in which $L_{2A}$ is a single bond and $Ar_{2A}$ is a substituted or unsubstituted benzotriphenylenyl group, a substituted or unsubstituted chrysenyl group in which $L_{2A}$ is a single bond and $Ar_{A2}$ is a substituted or unsubstituted chrysenyl group, a substituted or unsubstituted dibenzofuranyl group in which $L_{2A}$ is a single bond and $Ar_{2A}$ is a substituted or unsubstituted dibenzofuranyl group, a substituted or unsubstituted phenyldibenzofuranyl group in which $L_{2A}$ is a substituted or unsubstituted dibenzofuranyl group and $Ar_{2A}$ is a substituted or unsubstituted phenyl group, a substituted or unsubstituted naphthobenzofuranyl group in which $L_{2A}$ is a single bond and $Ar_{2A}$ is a substituted or unsubstituted naphthobenzofuranyl group, a substituted or unsubstituted carbazolyl group in which $L_{2A}$ is a single bond and $Ar_{2A}$ is a substituted or unsubstituted carbazolyl group, a substituted or unsubstituted carbazolyl-phenyl group in which $L_{2A}$ is a substituted or unsubstituted phenyl group and $Ar_{2A}$ is a substituted or unsubstituted carbazolyl group; or a substituted or unsubstituted benzo[def]carbazolyl-phenyl group wherein $L_{2A}$ is a substituted or unsubstituted phenyl group and $Ar_{2A}$ is a substituted or unsubstituted benzo[def]carbazolyl group.

In one embodiment, $R_1$ to $R_8$, and $R_{11}$ to $R_{20}$ that are not a single bond which bonds with $L_{1A}$ and that do not form the substituted or unsubstituted, saturated or unsaturated ring are hydrogen atoms.

In one embodiment, the compound represented by the formula (1-A) is a compound represented by the following formula (1-A-4).

(1-A-4)

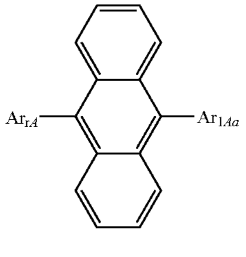

In the formula (1-A-4), $Ar_{2A}$ is as defined in the formula (1-A).

$Ar_{1Aa}$ is a monovalent group having a structure represented by the following formula (2-A-1).

(2-A-1)

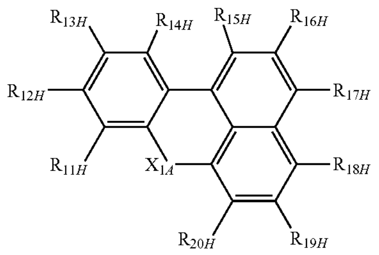

In the formula (2-A-1), $X_{1A}$ is as defined in the formula (2-A).

One of $R_{11H}$ to $R_{20H}$ is a single bond which bonds with the anthracene skeleton.

$R_{11H}$ to $R_{20H}$ that are not a single bond which bonds with the anthracene skeleton are hydrogen atoms.

In one embodiment, one or more of $R_1$ to $R_8$ which are hydrogen atoms, $R_{11}$ to $R_{20}$ that are hydrogen atoms, hydrogen atoms possessed by the substituted or unsubstituted, saturated or unsaturated ring formed by bonding one or more sets of adjacent two or more of $R_1$ to $R_8$ with each other, hydrogen atoms possessed by $R_1$ to $R_8$ which are substituents R, hydrogen atoms possessed by the substituted or unsubstituted, saturated or unsaturated ring formed by bonding one or more sets of adjacent two or more of $R_{11}$ to $R_{20}$ with each other, hydrogen atoms possessed by $R_{11}$ to $R_{20}$ which are substituents R, hydrogen atoms possessed by $L_{1A}$, hydrogen atoms possessed by $L_{2A}$, and hydrogen atoms possessed by $Ar_{2A}$ are deuterium atoms.

Specific examples of the compound represented by the formula (1) will be described below, but these are merely examples, and the compound represented by the formula (1) is not limited to the following specific examples.

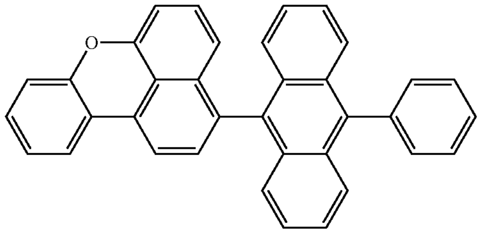

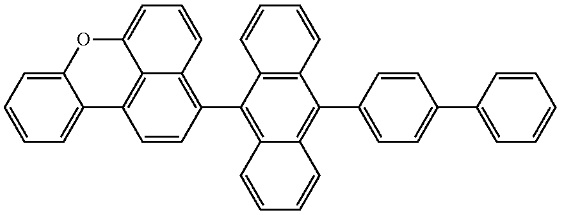

-continued
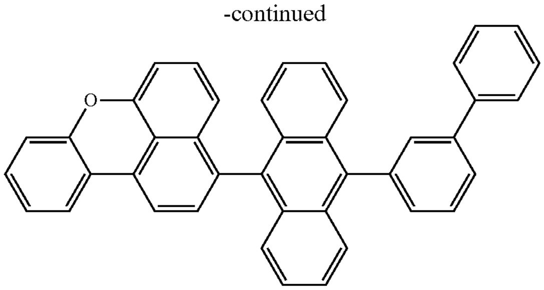
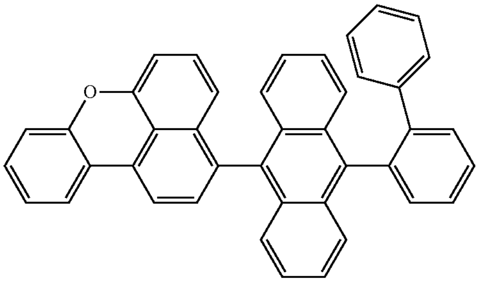
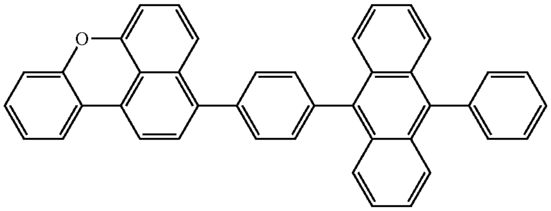
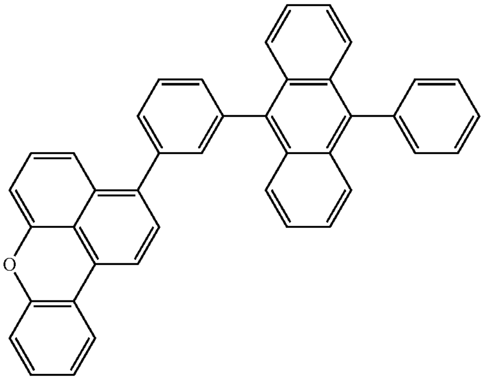
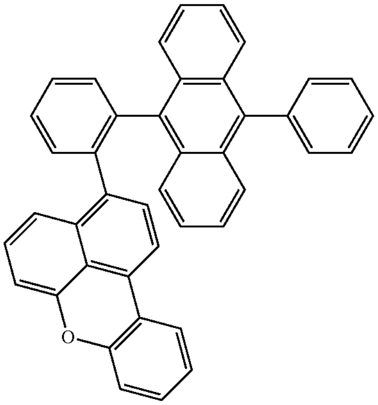
-continued
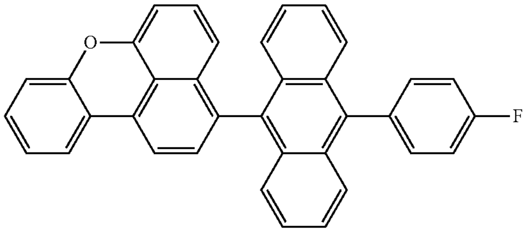
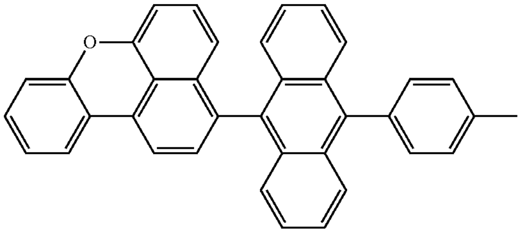
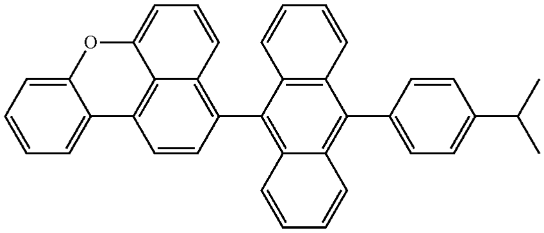
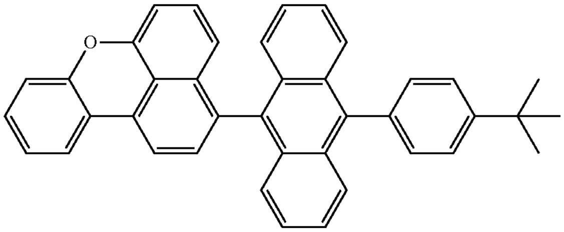
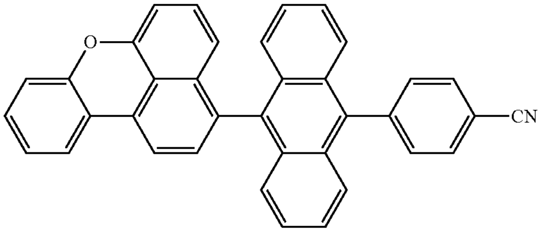
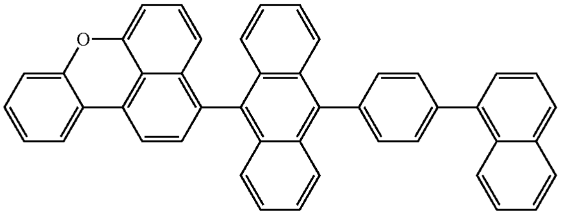
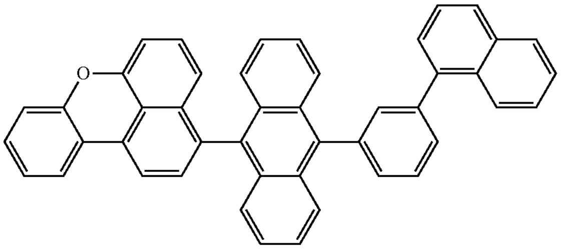

-continued
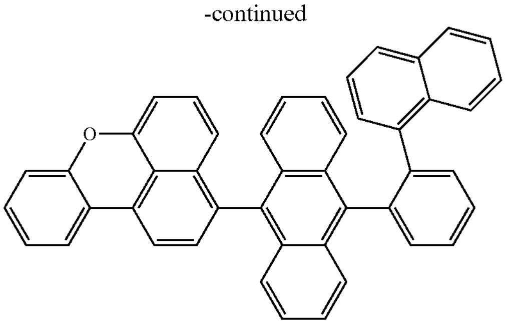
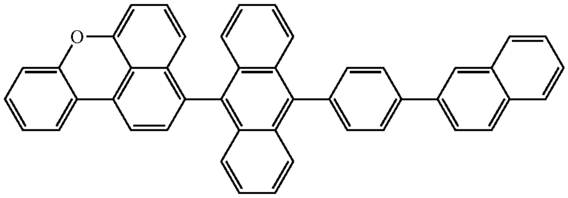
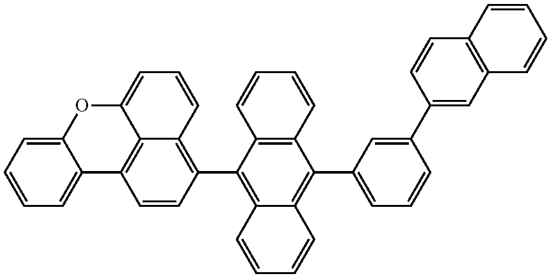
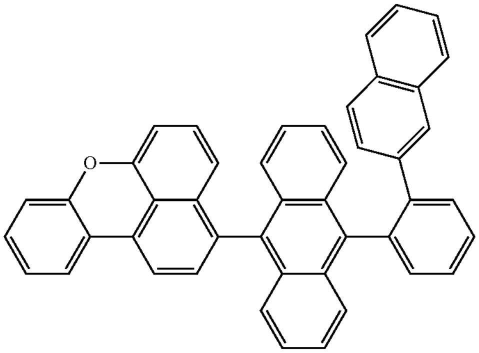
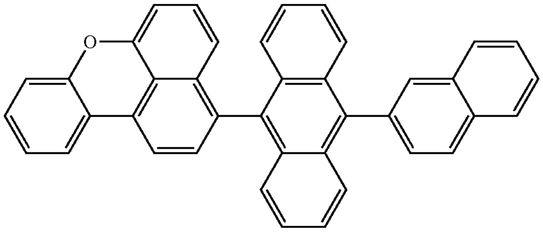
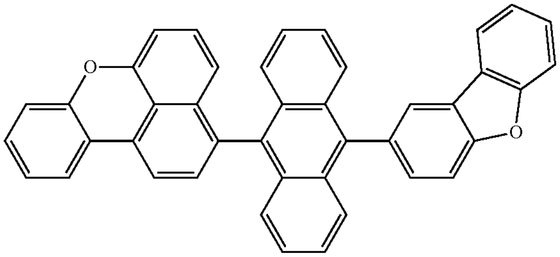
-continued
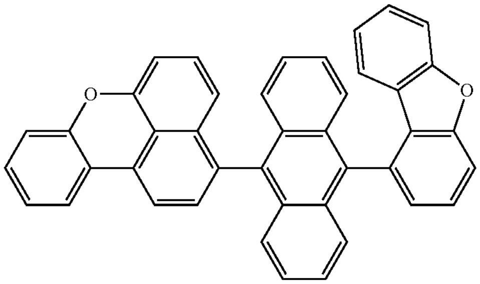
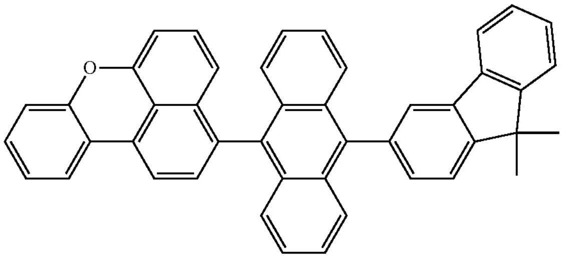
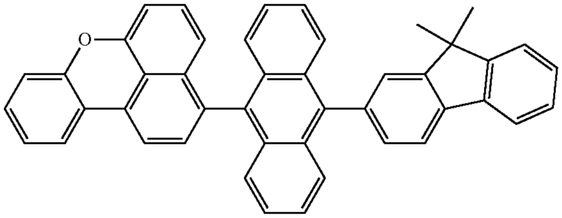
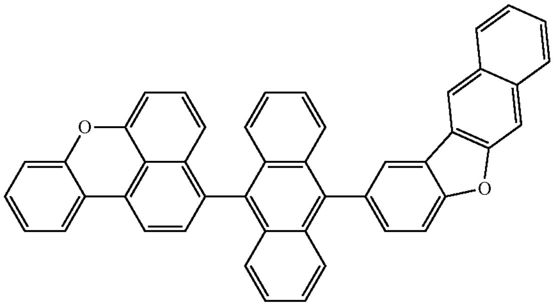
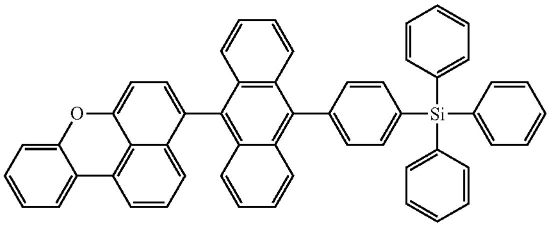
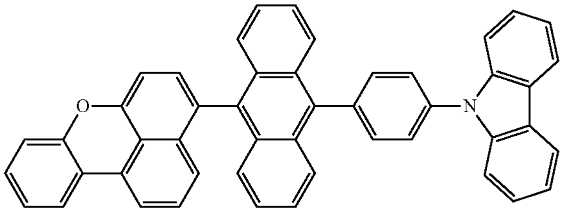
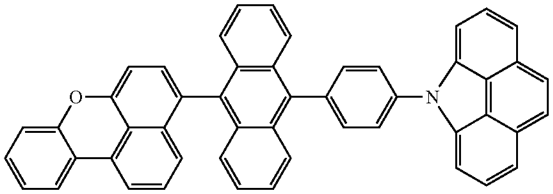

-continued
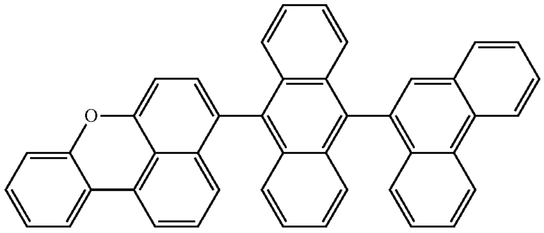
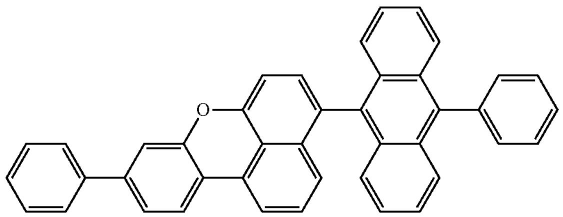
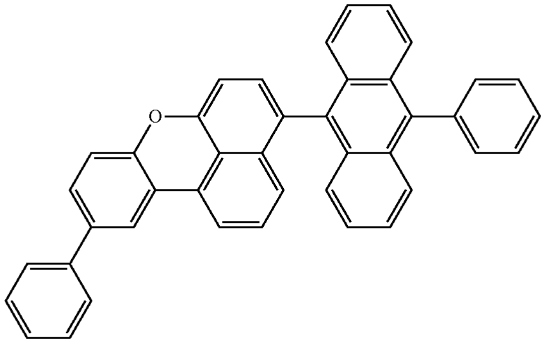
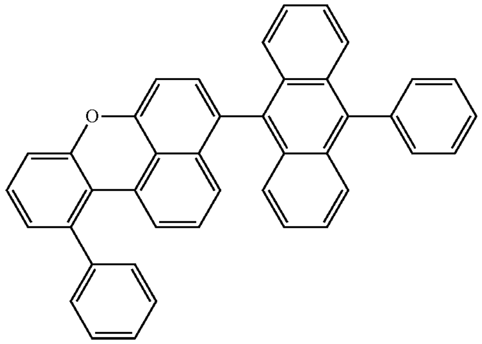
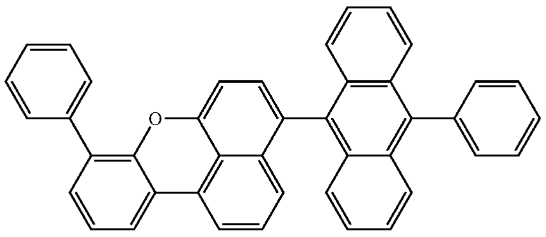
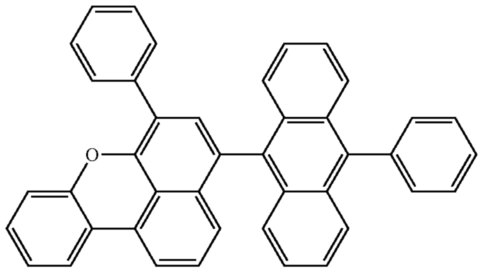
-continued
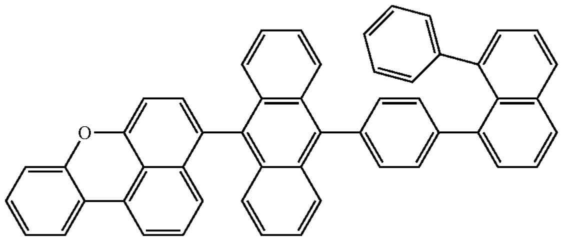
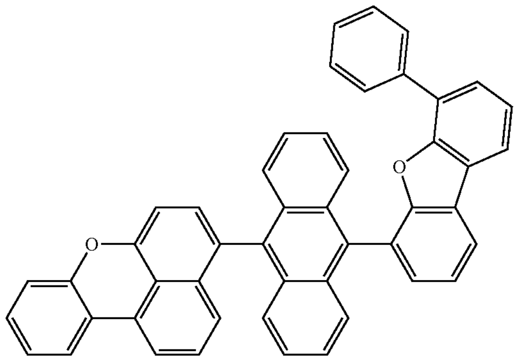
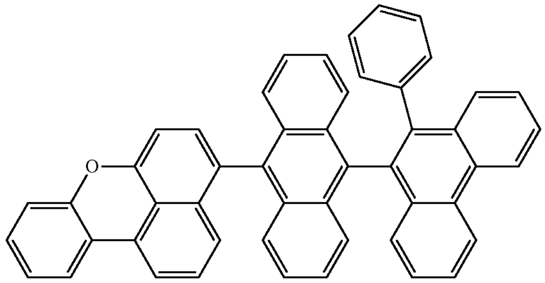
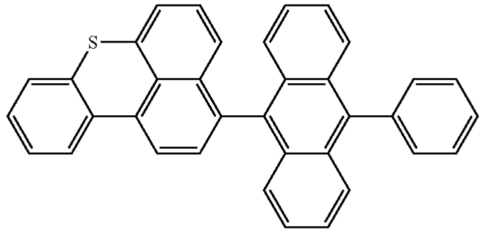
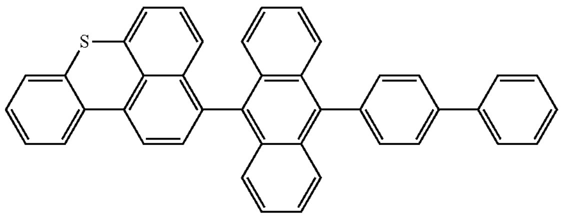
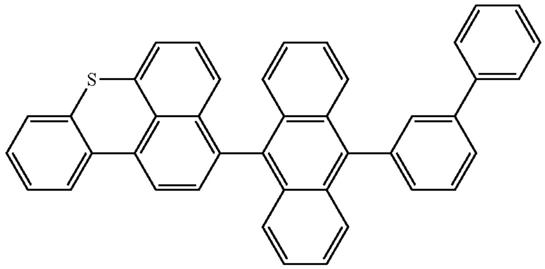

-continued
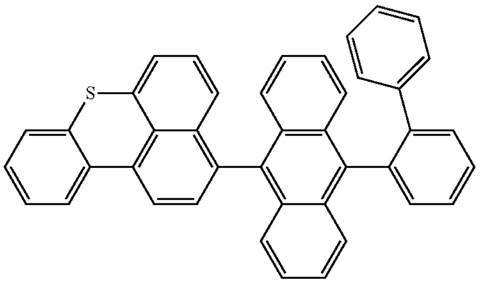
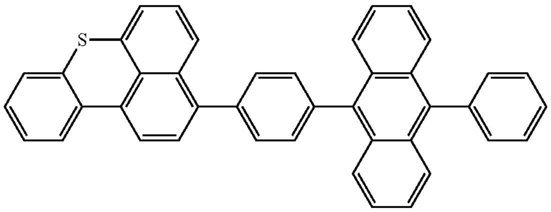
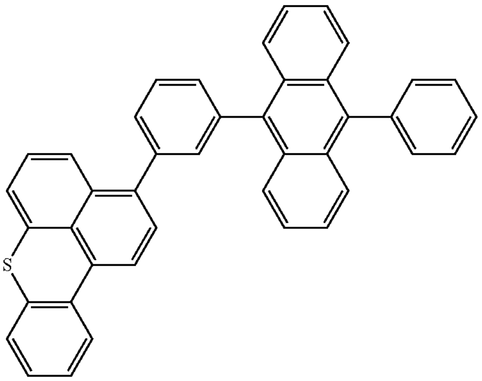
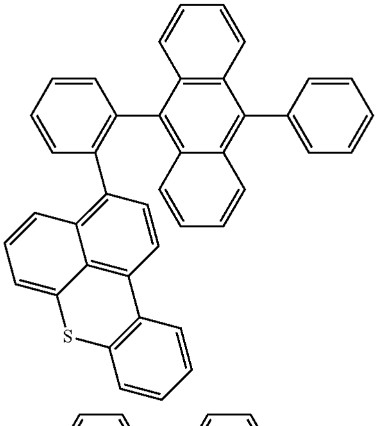
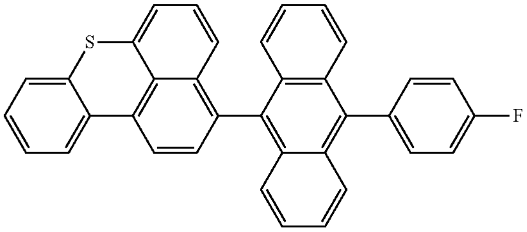
-continued
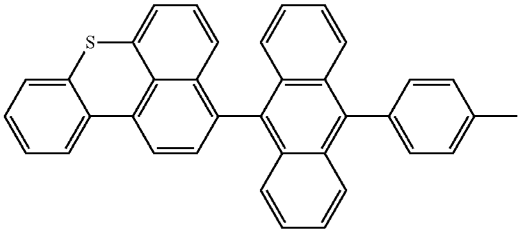
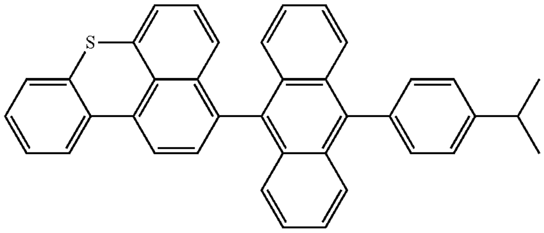
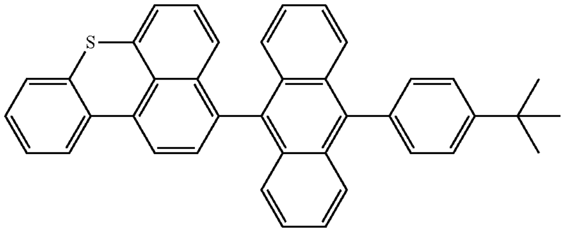
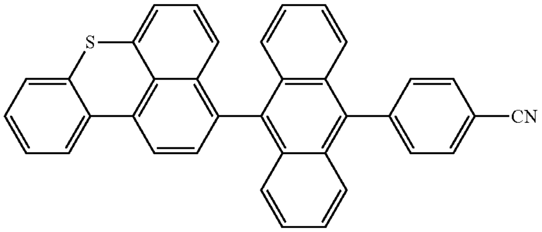
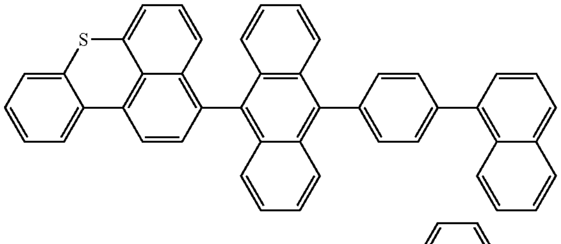
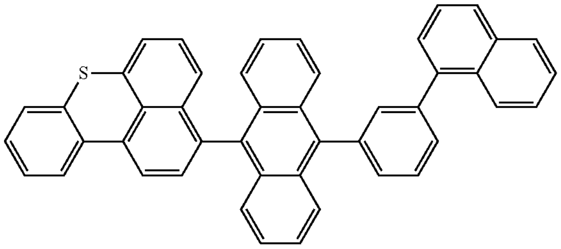
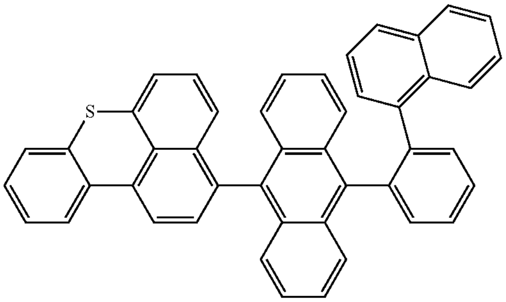

-continued
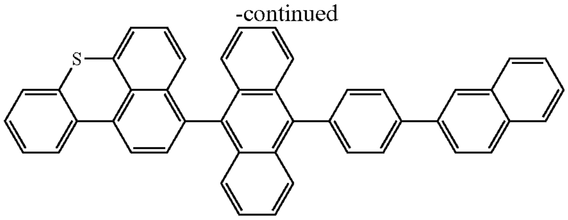
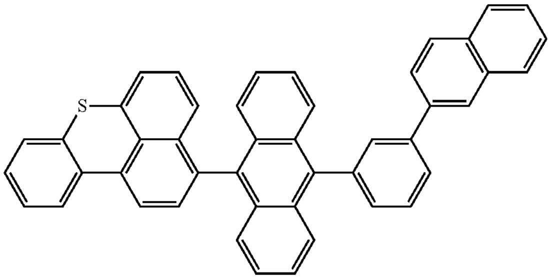
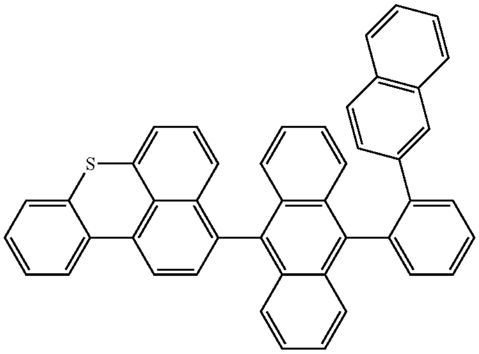
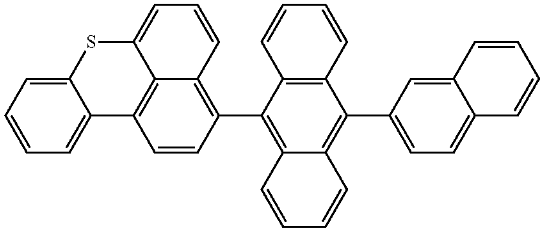
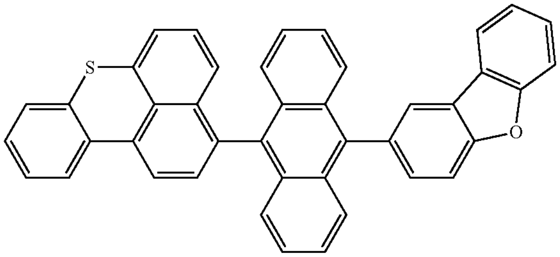
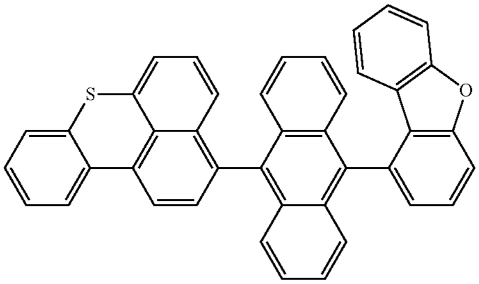
-continued
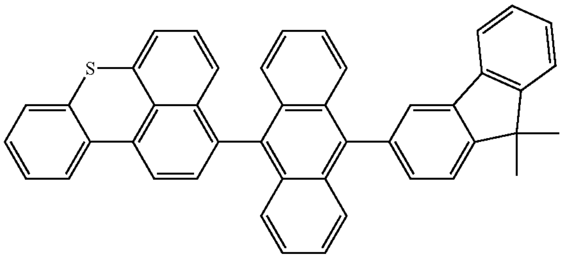
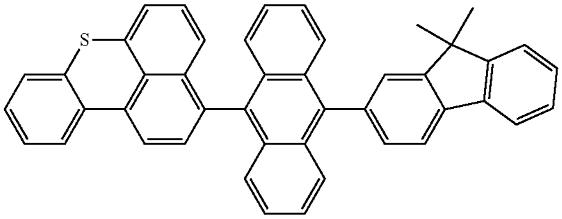
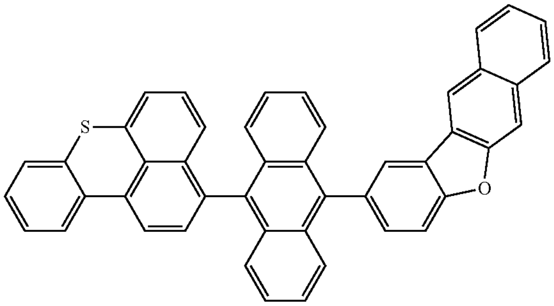
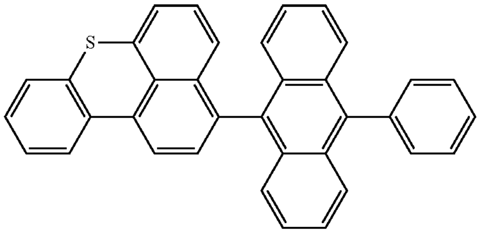
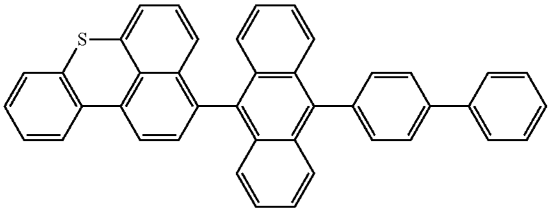
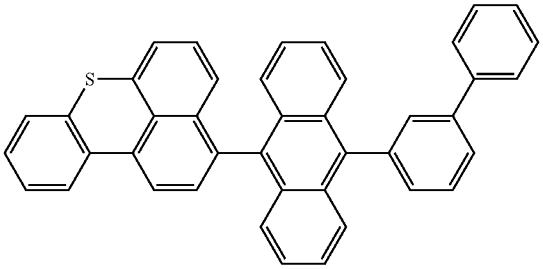

-continued
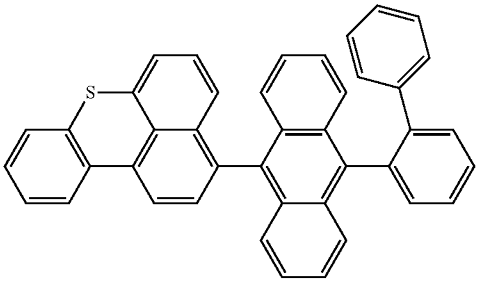
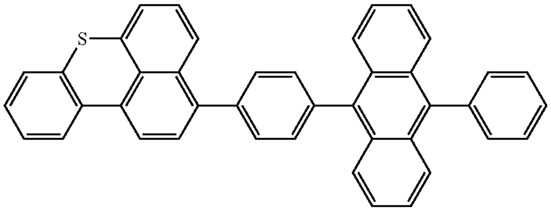
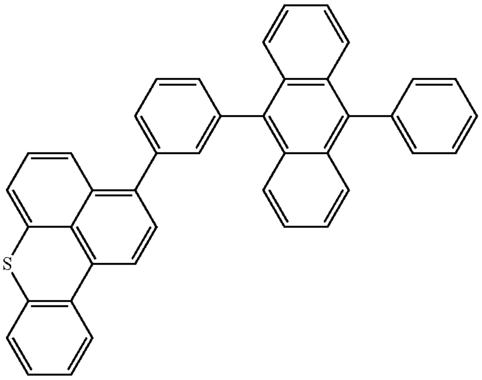
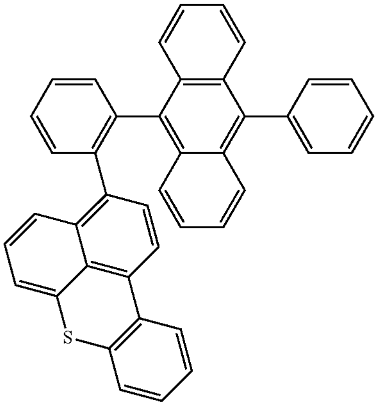
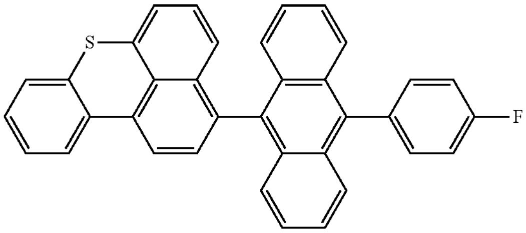
-continued
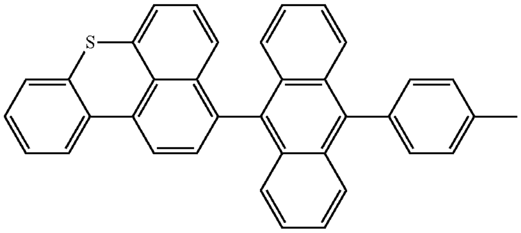
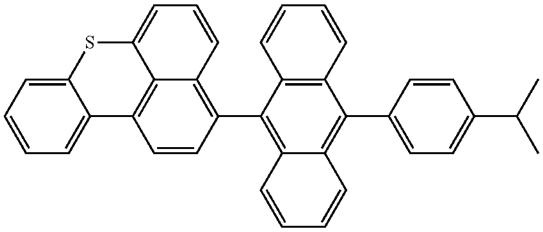
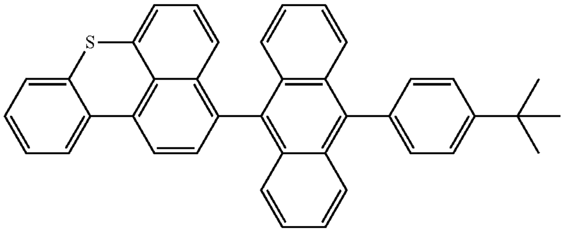
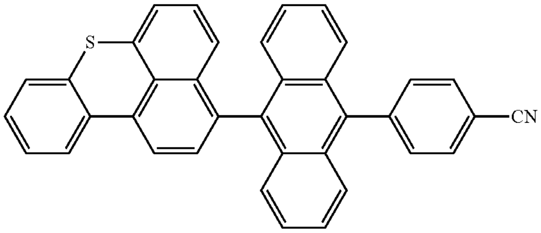
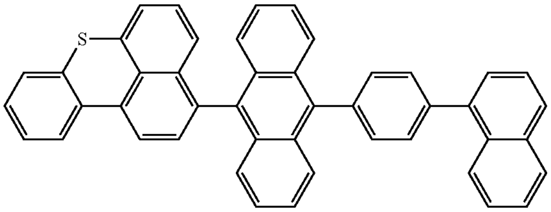
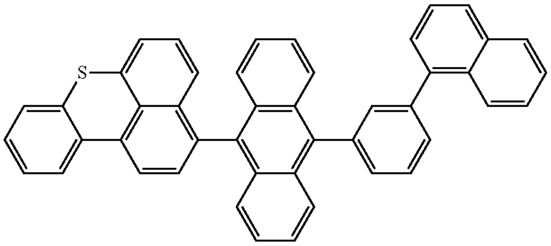
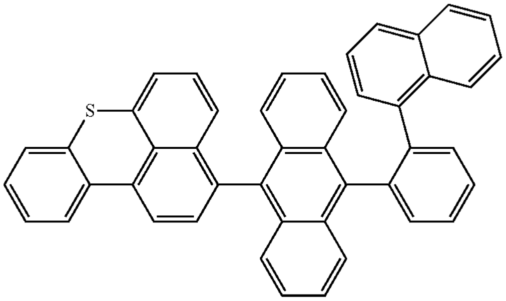

-continued
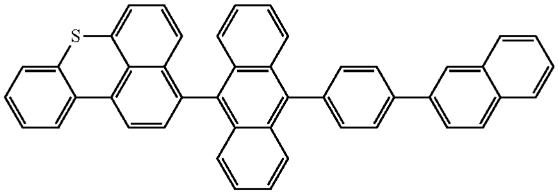
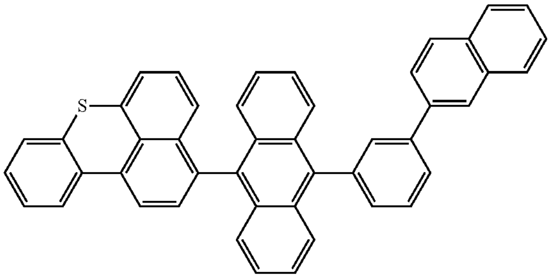
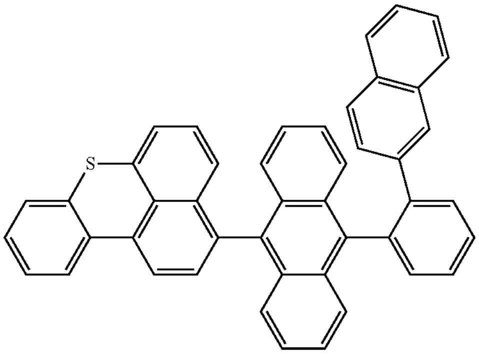
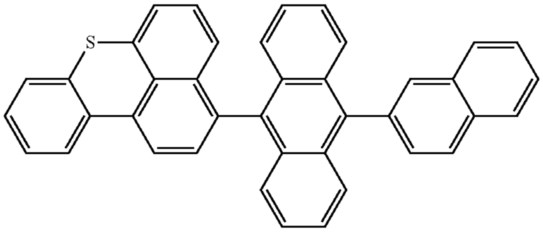
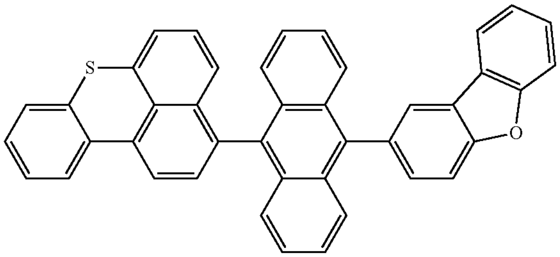
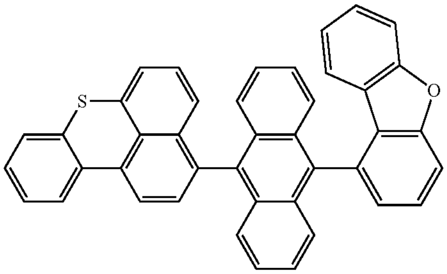
-continued
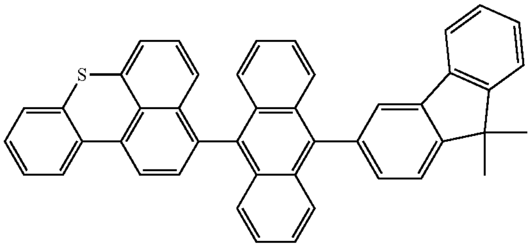
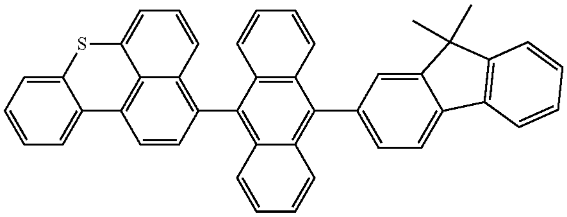
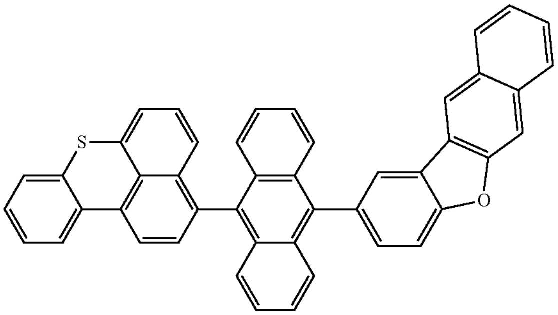
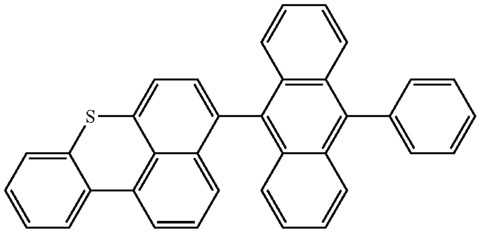
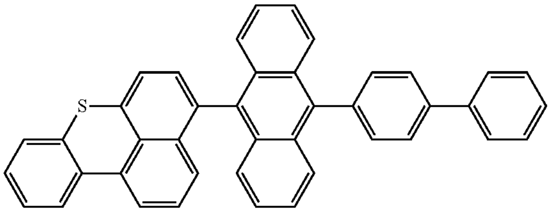
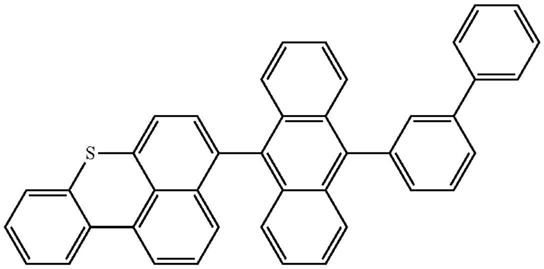

-continued
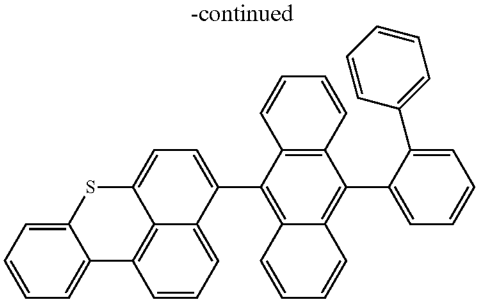
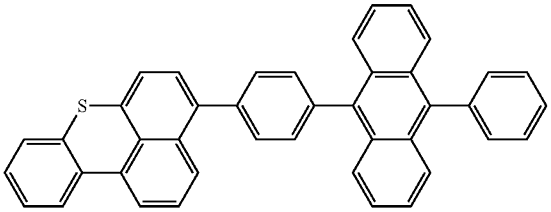
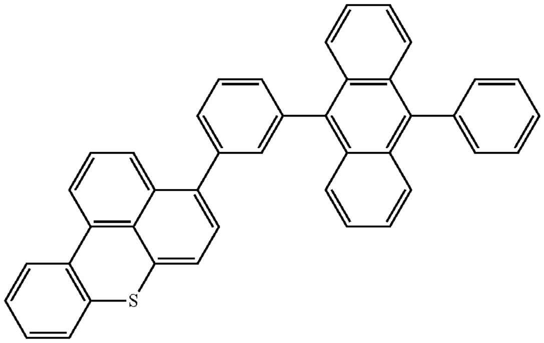
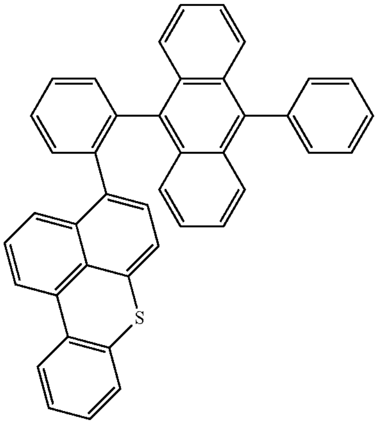
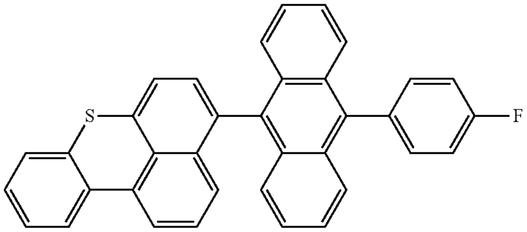
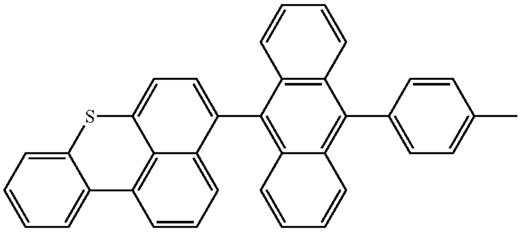
-continued
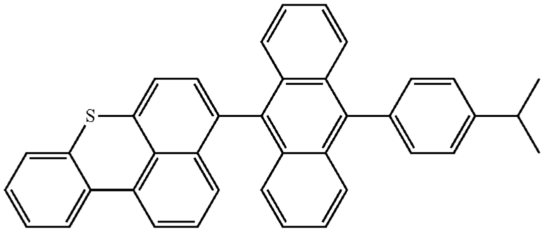
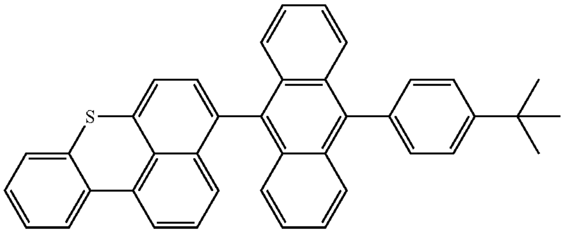
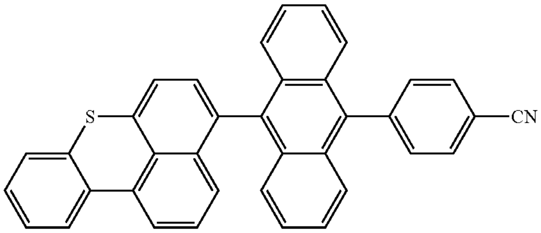
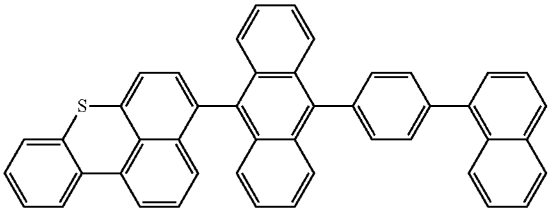
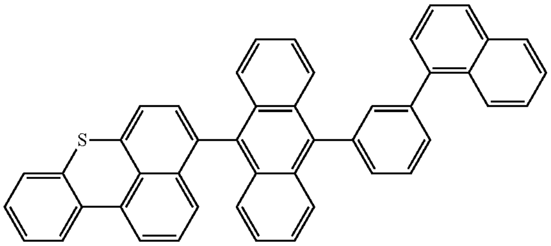
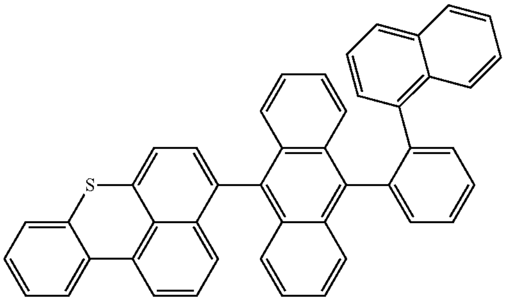
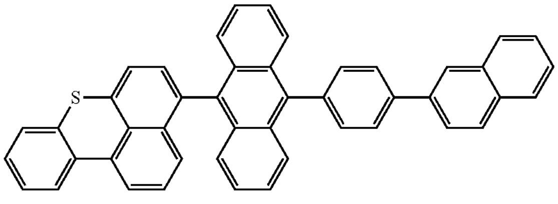

-continued
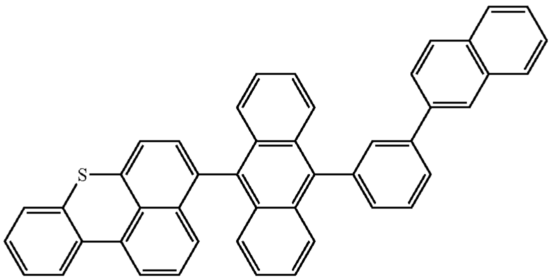
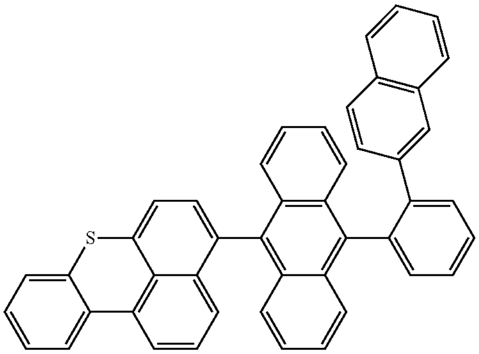
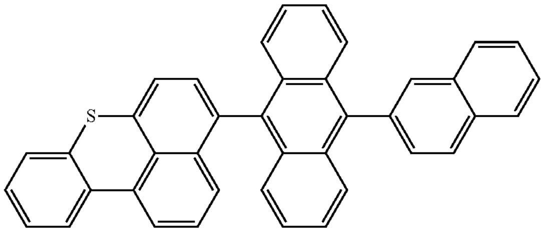
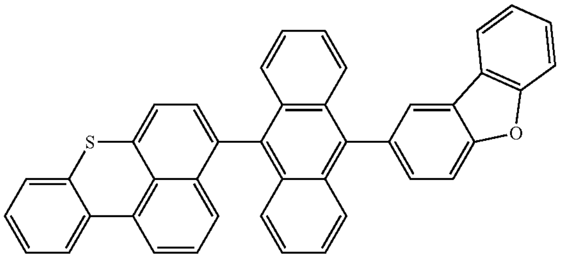
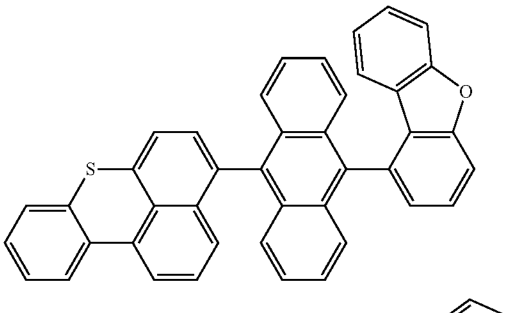
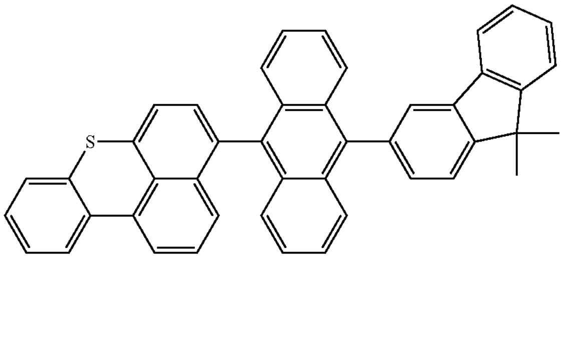
-continued
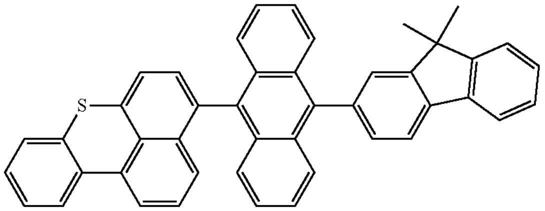
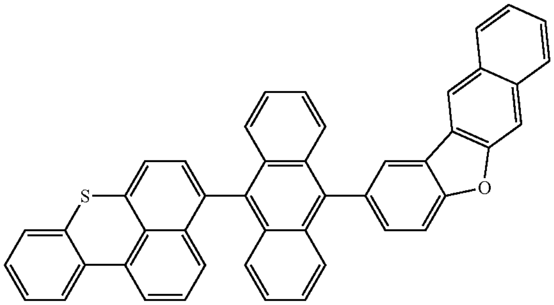
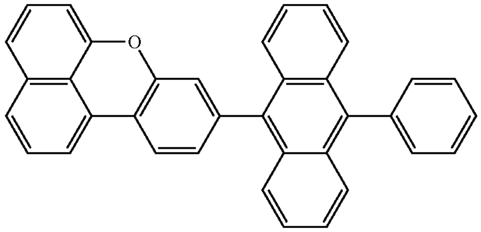
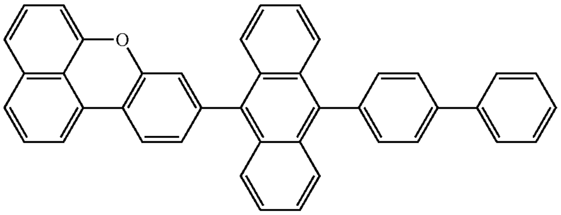
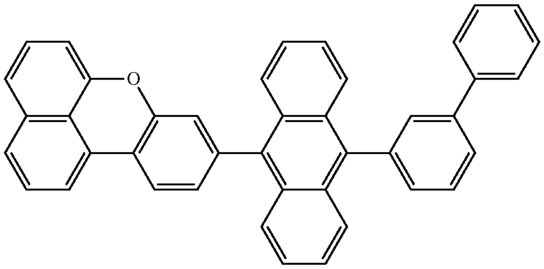
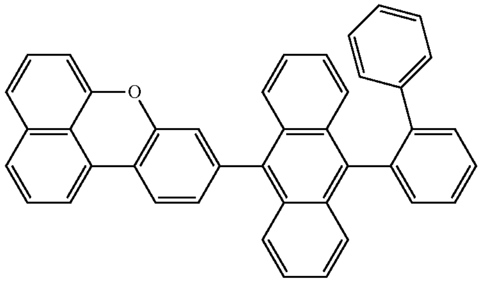
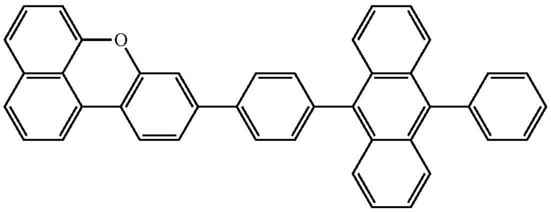

-continued
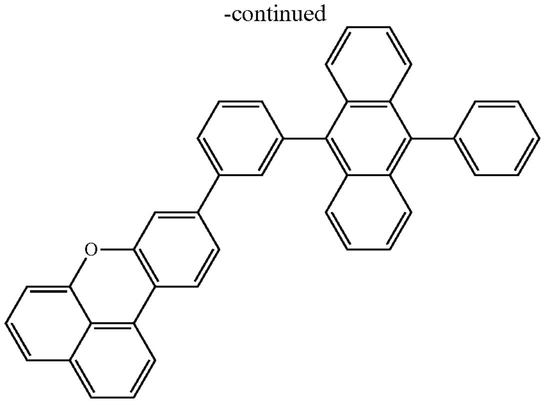
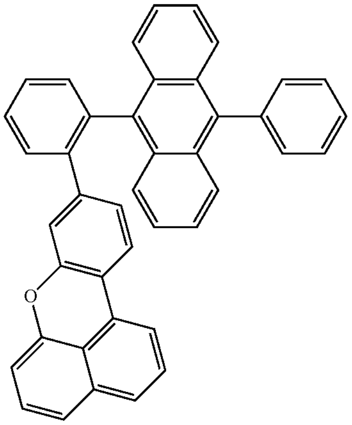
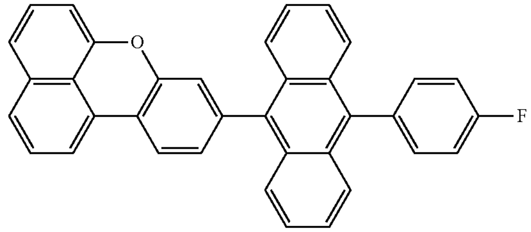
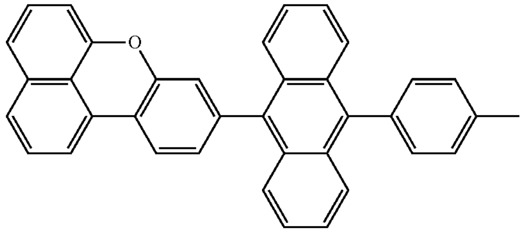
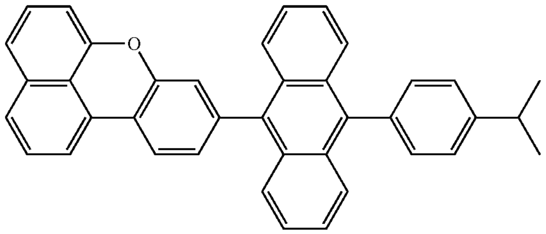
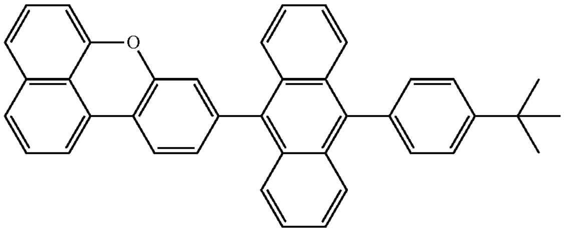
-continued
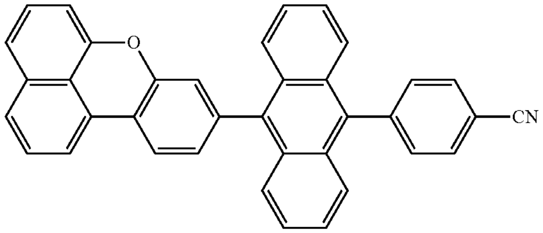
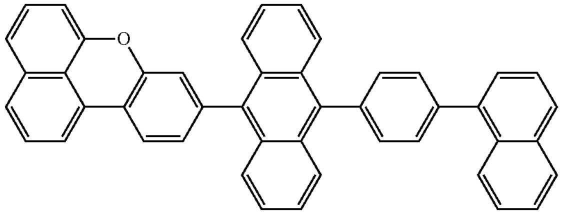
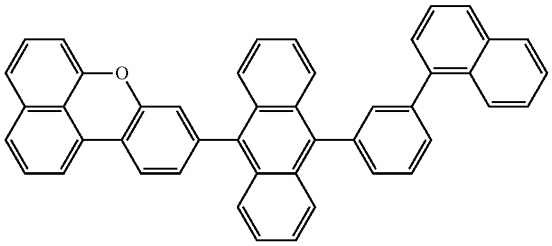
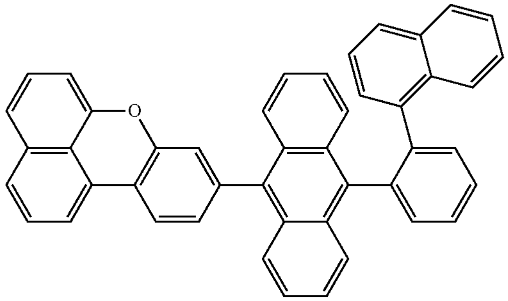
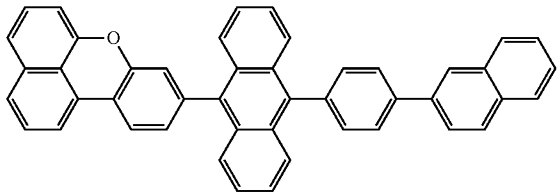
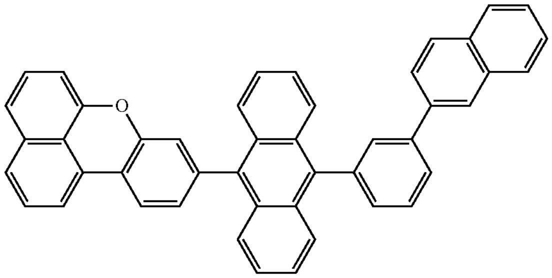

-continued
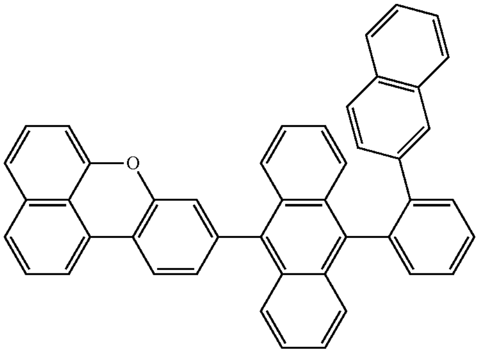
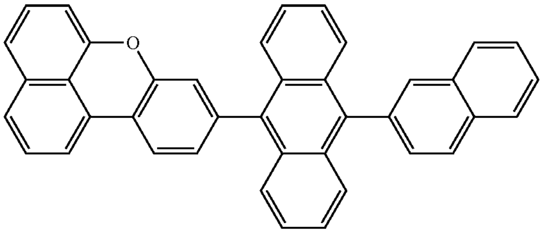
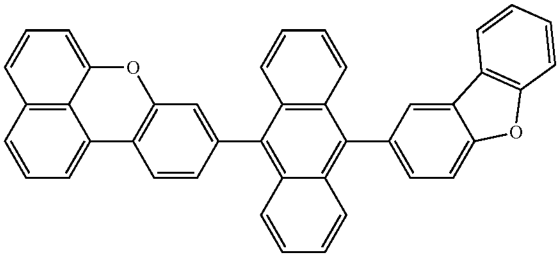
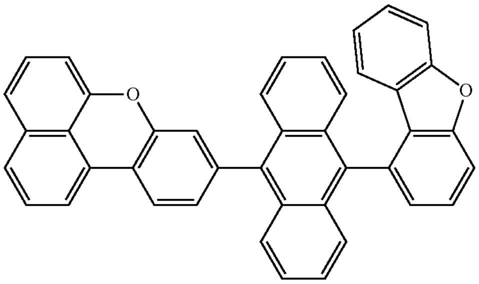
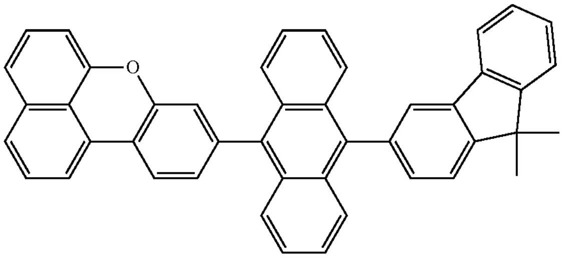
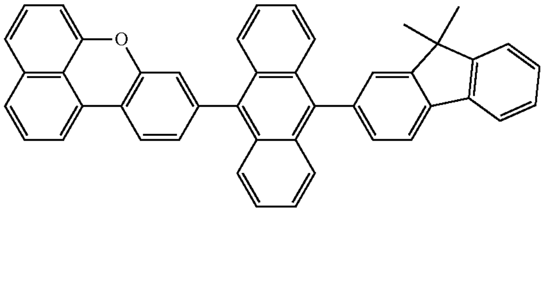
-continued
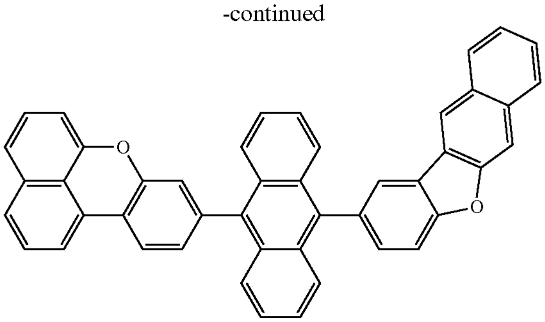
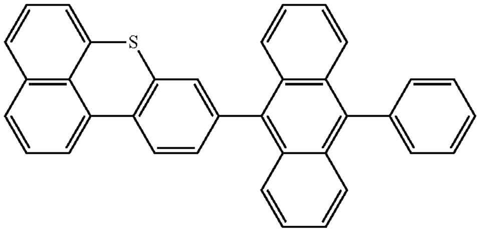
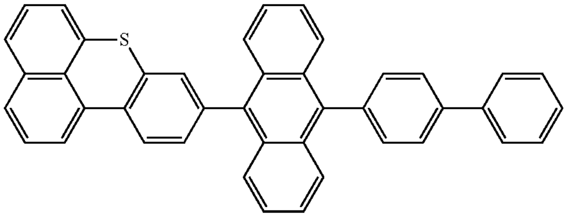
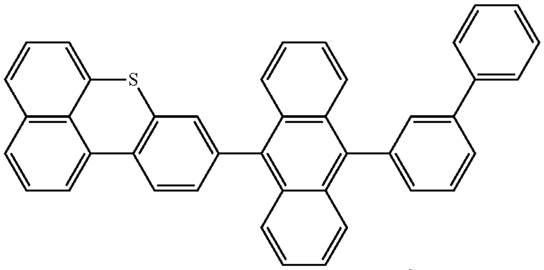
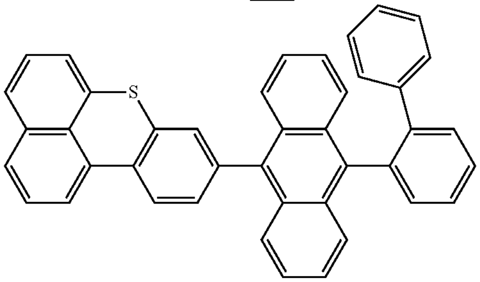
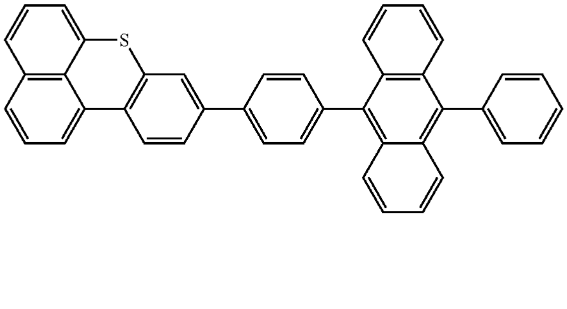

-continued
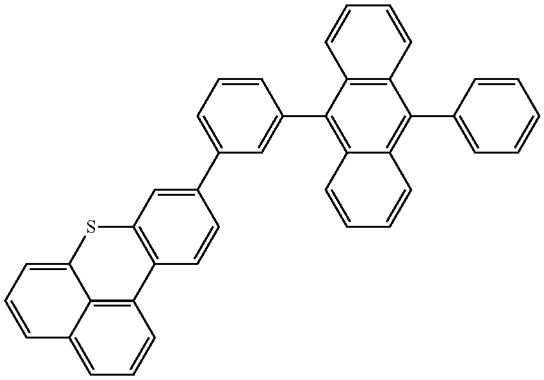
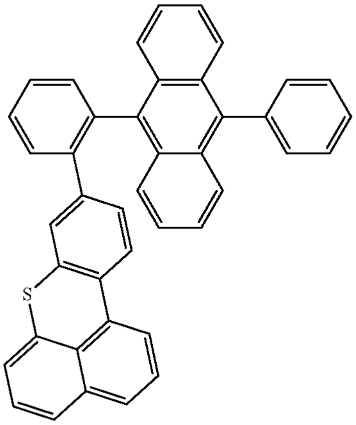
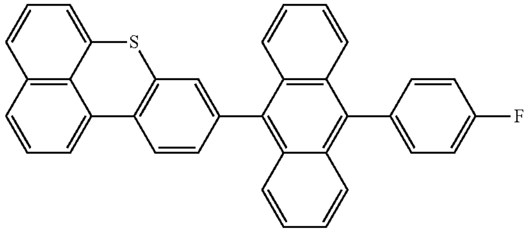
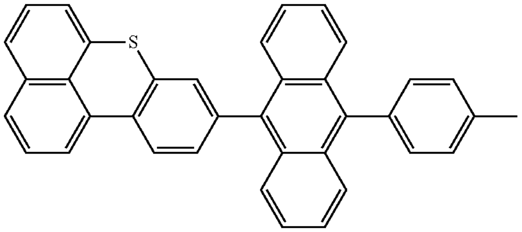
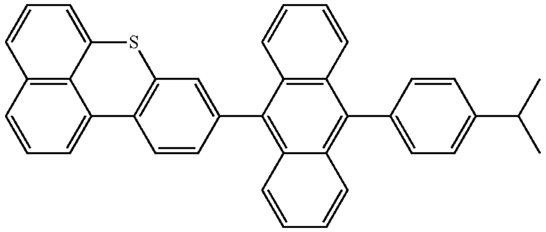
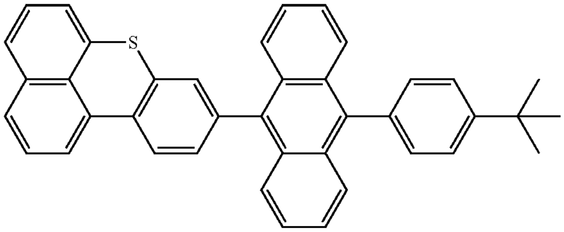
-continued
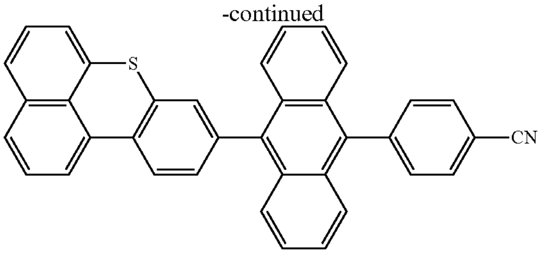
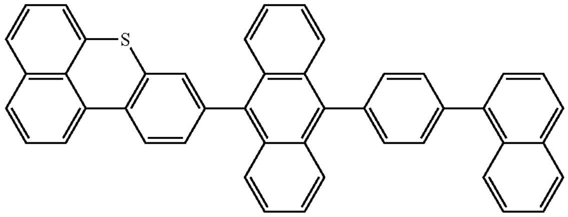
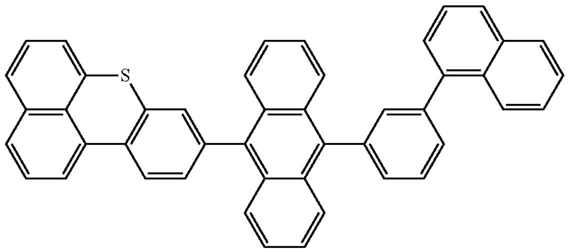
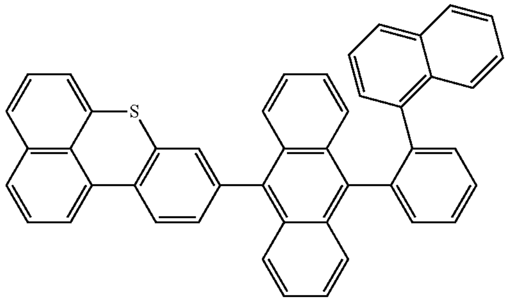
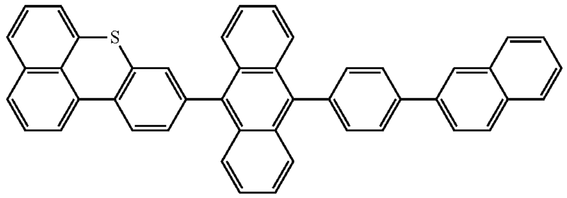
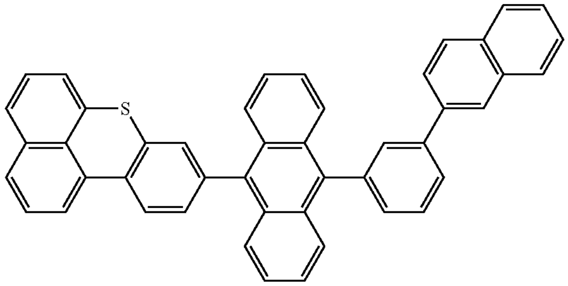

-continued
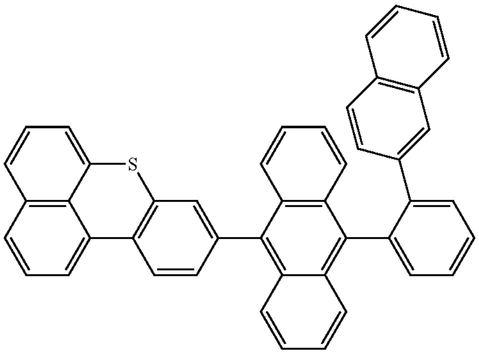
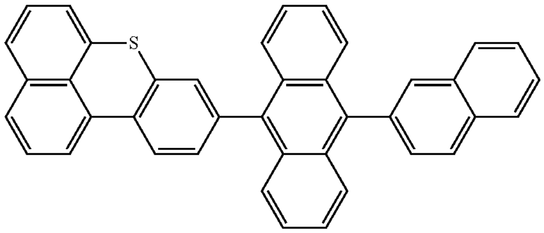
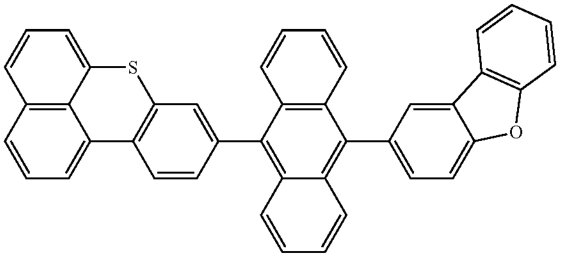
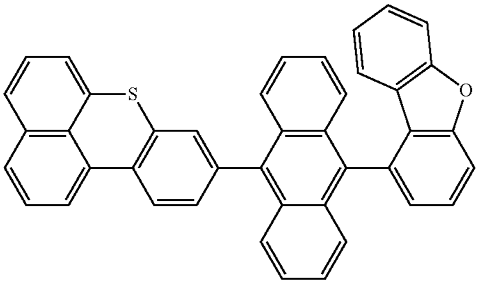
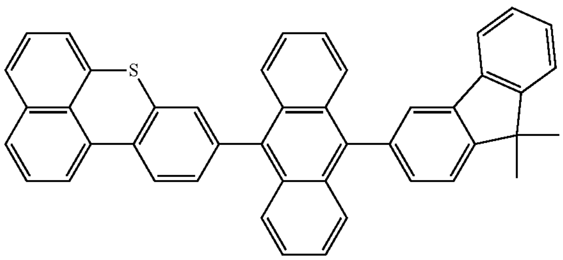
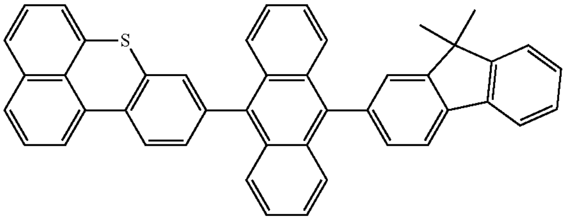
-continued
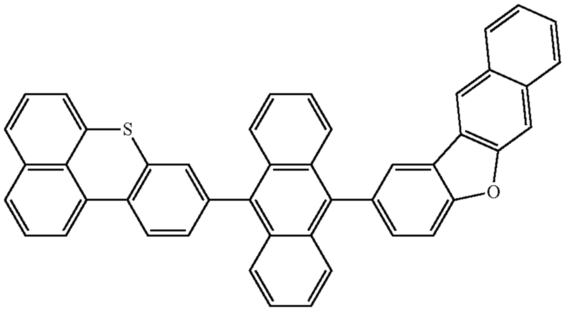
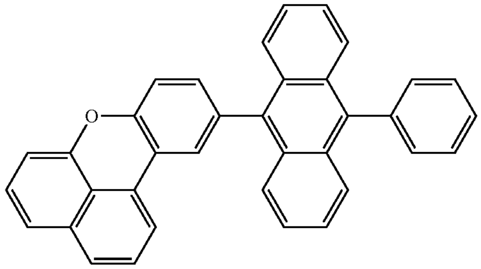
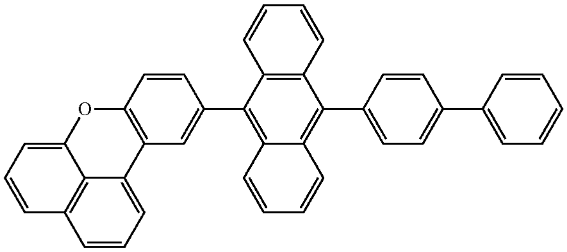
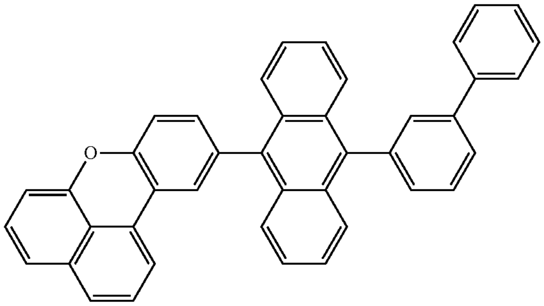
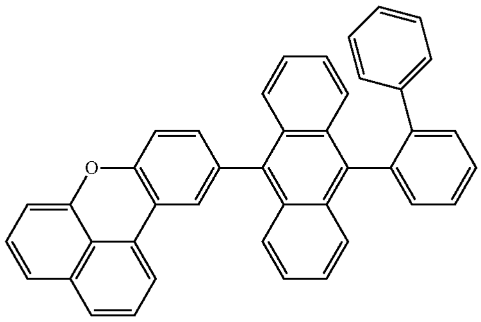
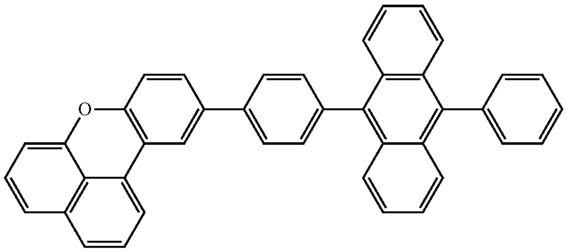

-continued
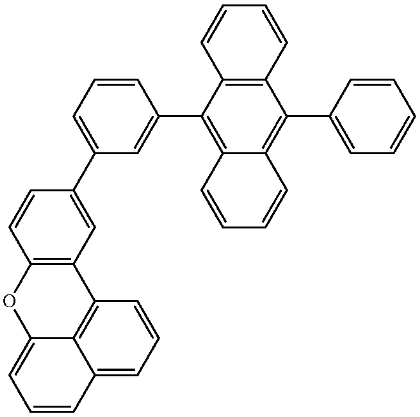
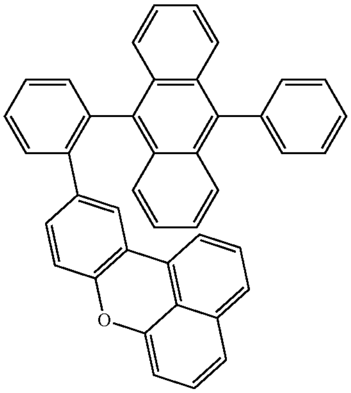
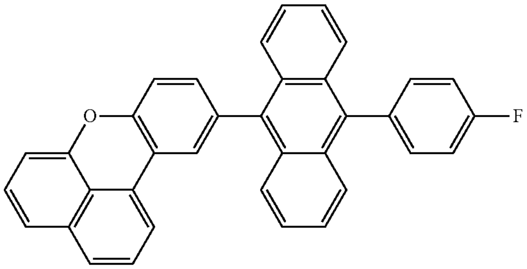
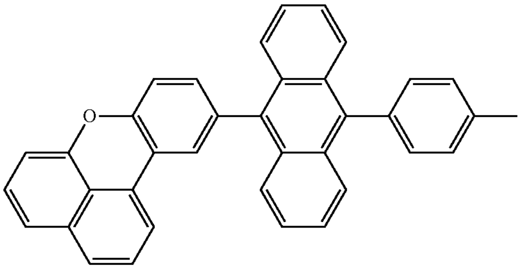
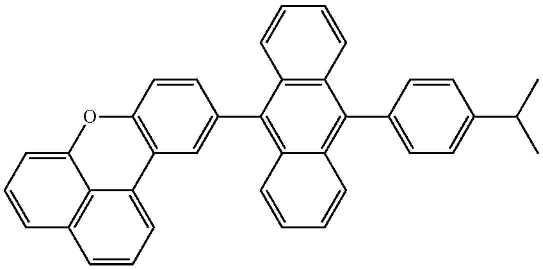
-continued
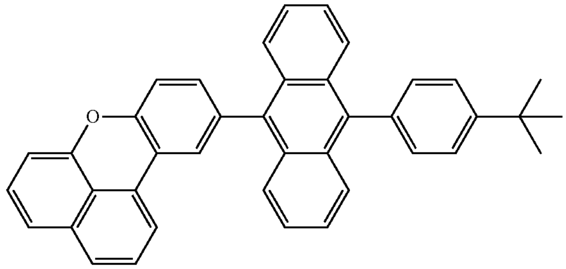
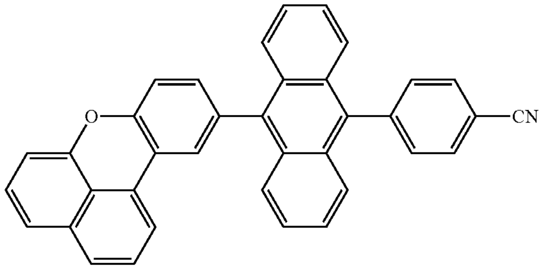
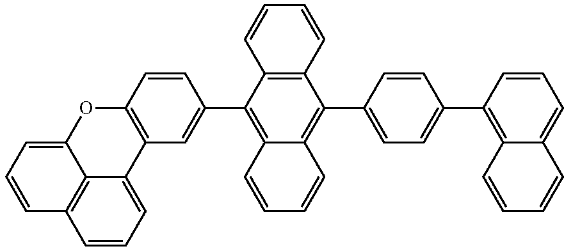
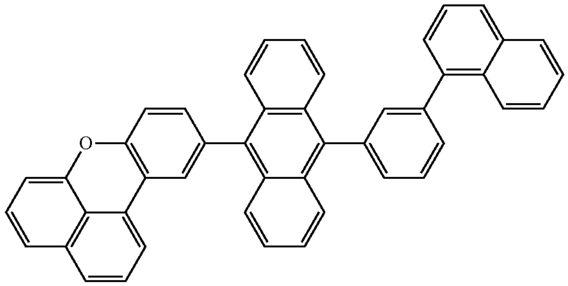
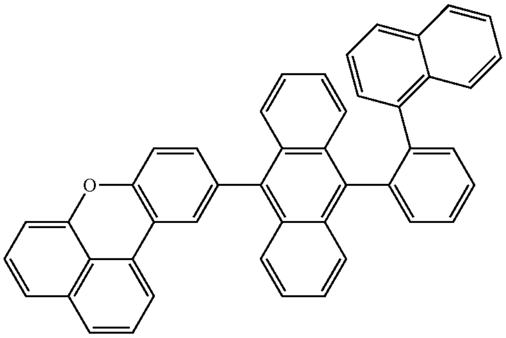
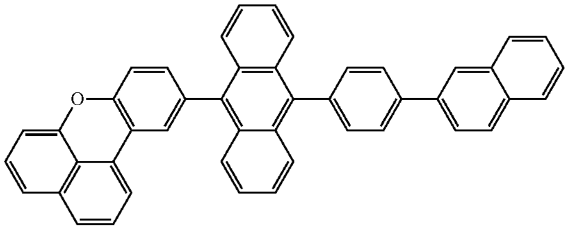

-continued
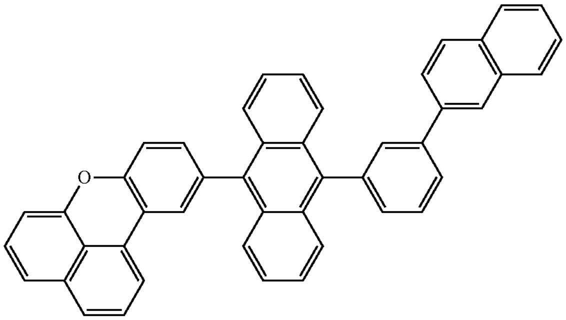
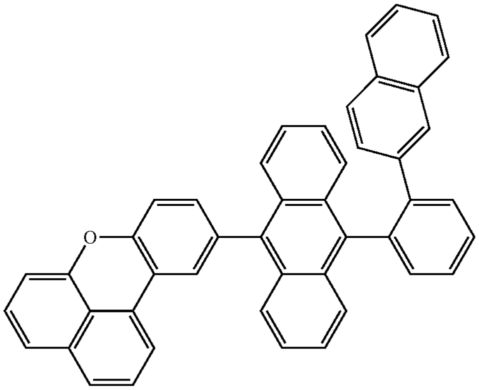
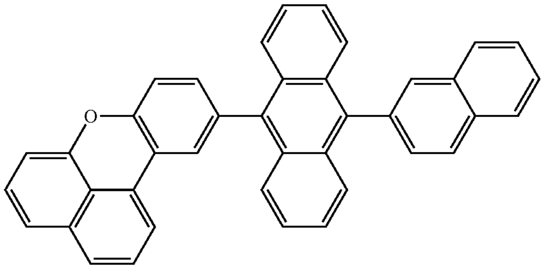
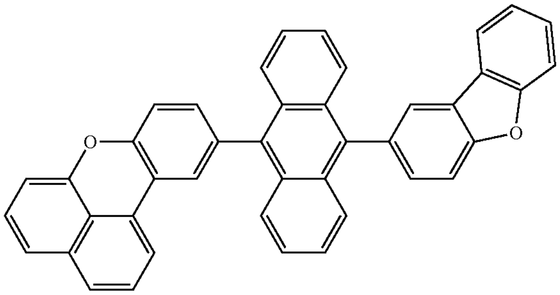
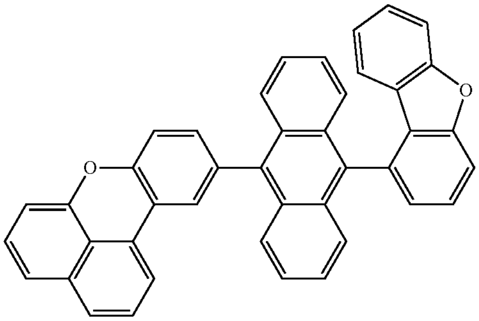
-continued
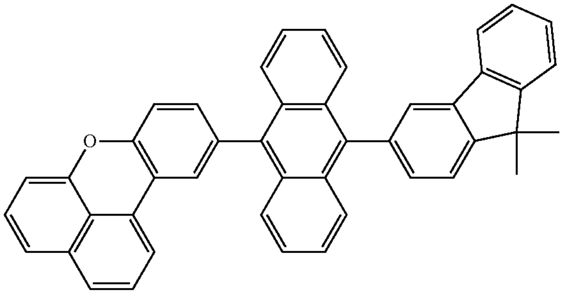
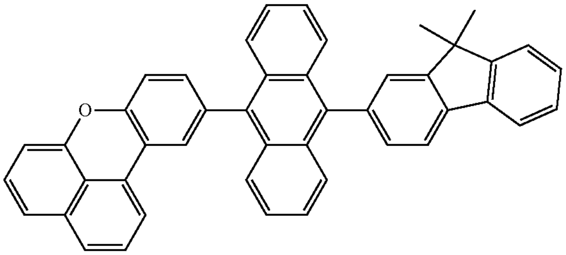
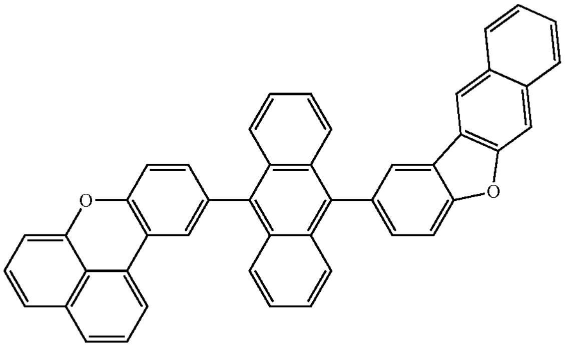
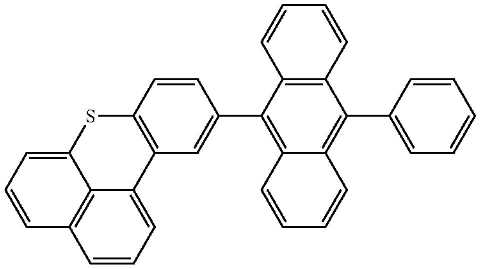
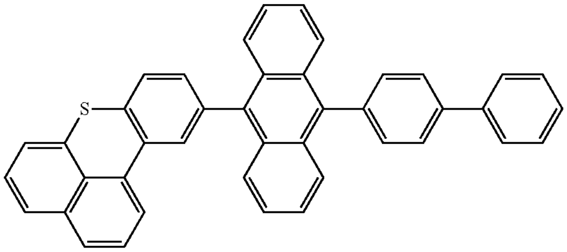
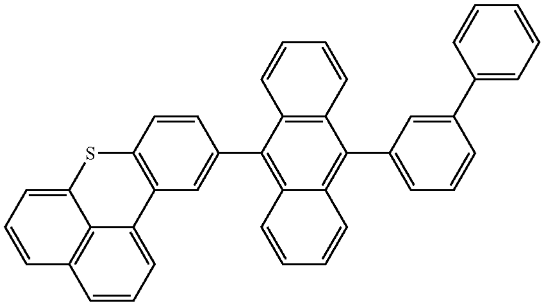

-continued
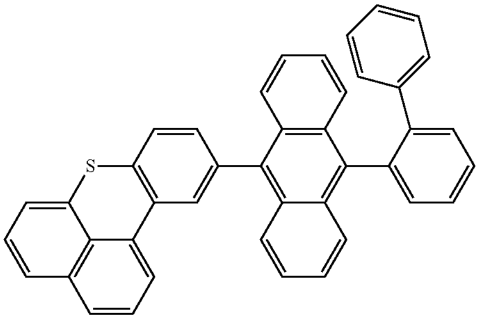
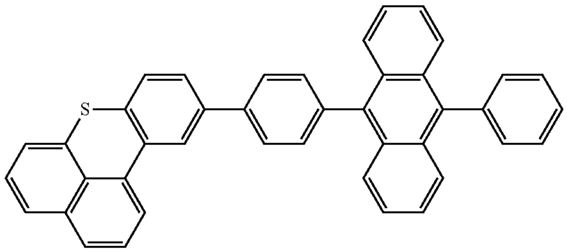
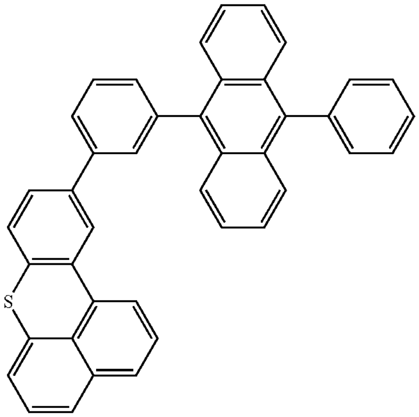
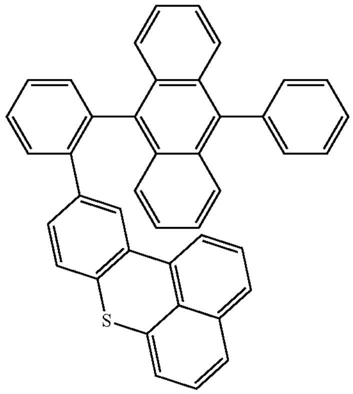
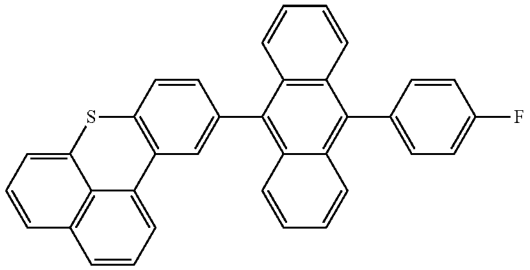
-continued
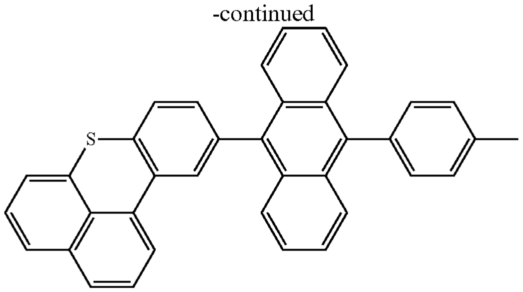
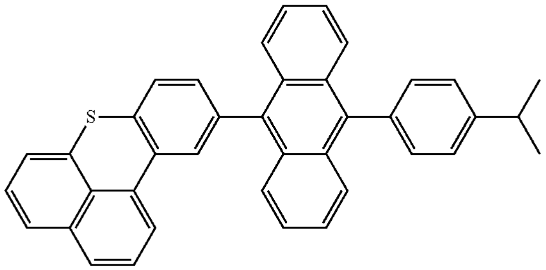
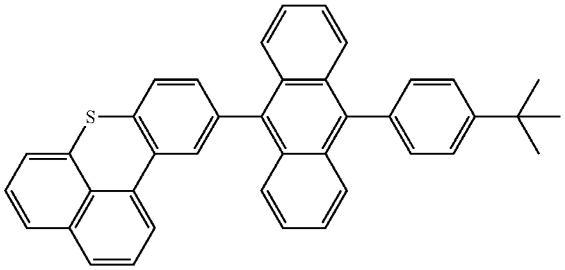
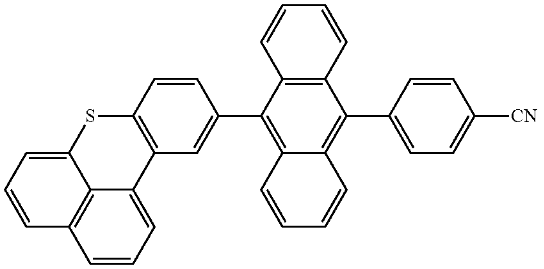
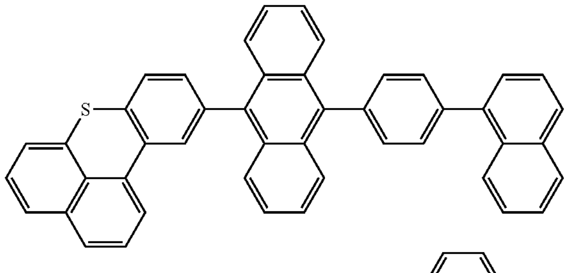
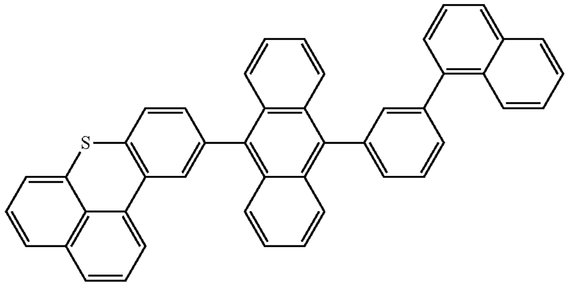

-continued
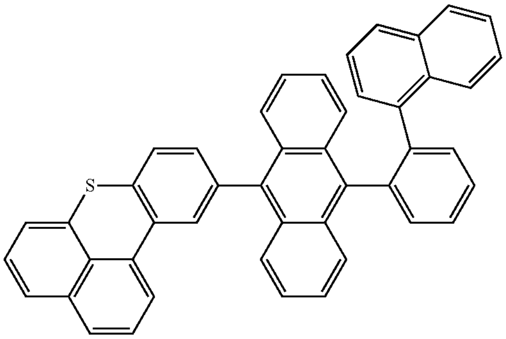
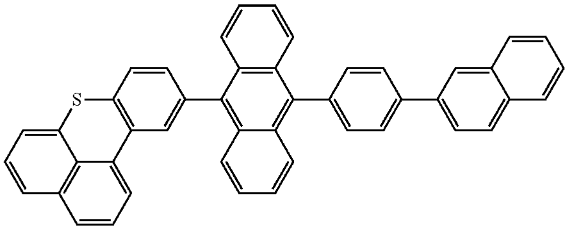
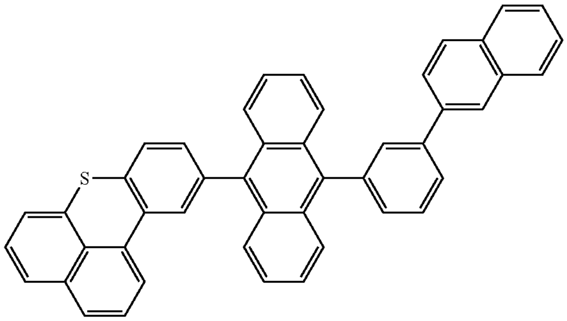
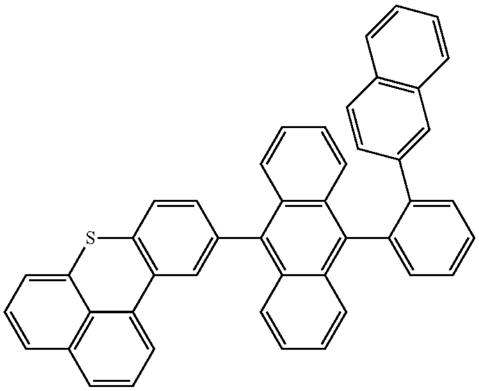
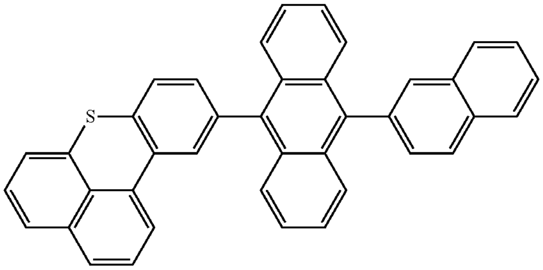
-continued
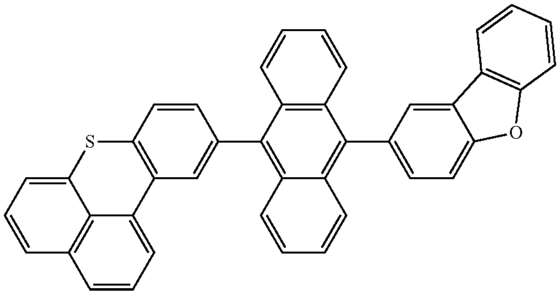
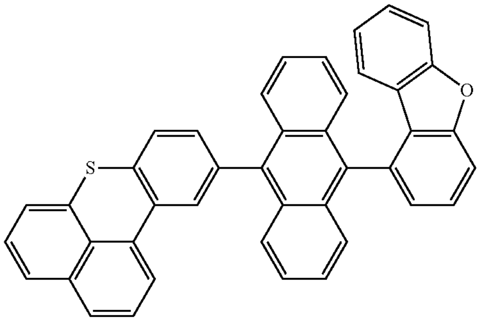
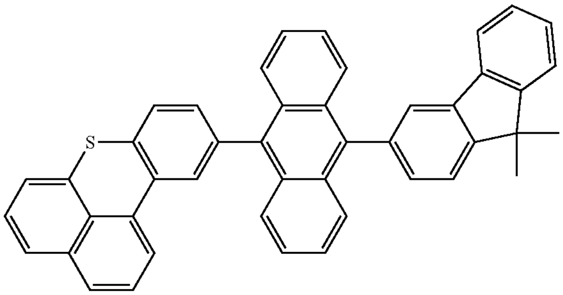
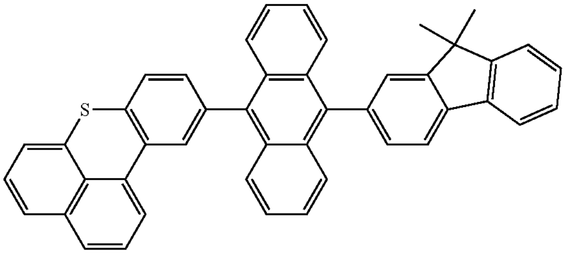
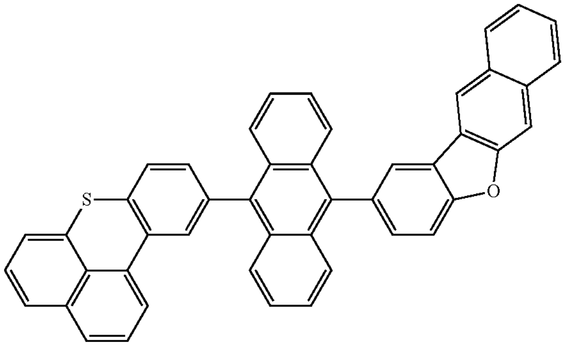

-continued
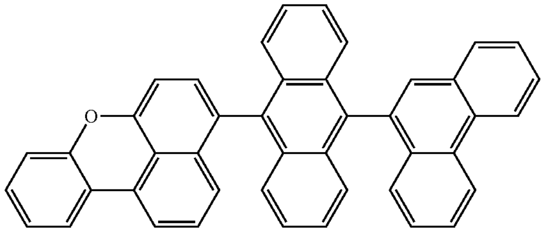
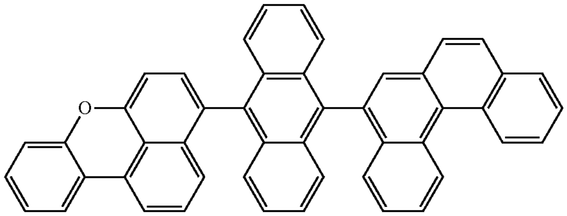
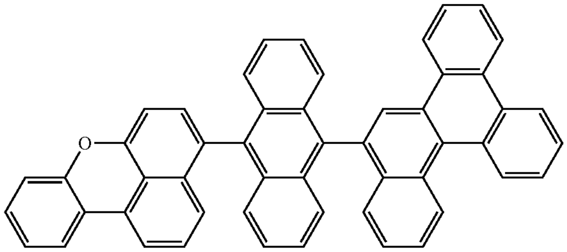
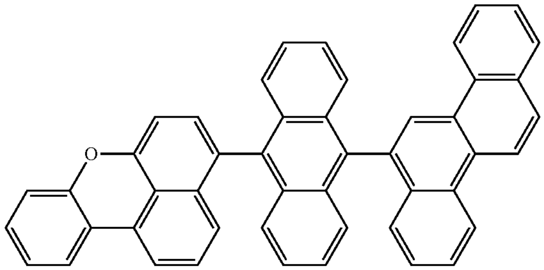
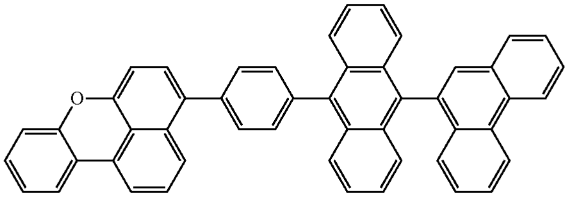
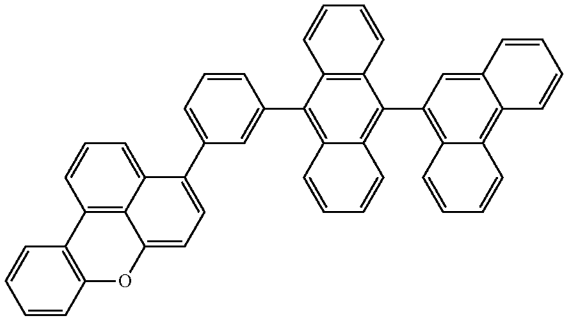
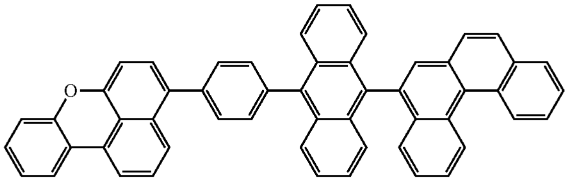
-continued
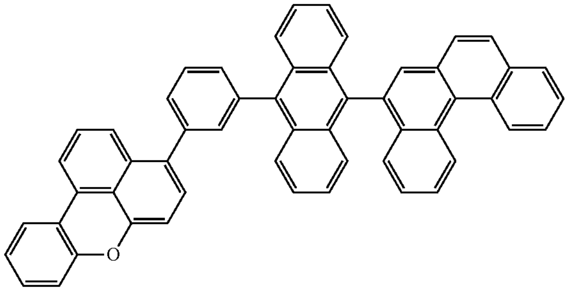
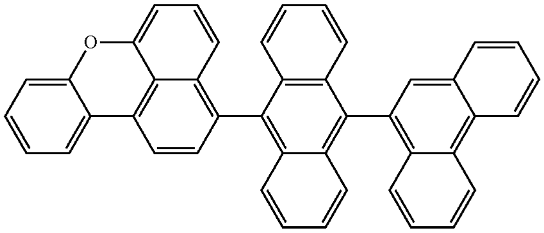
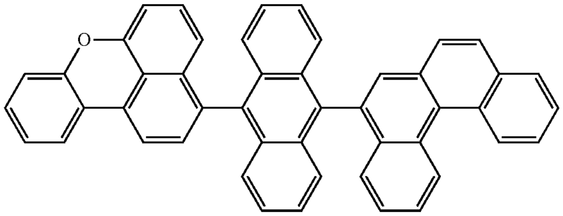
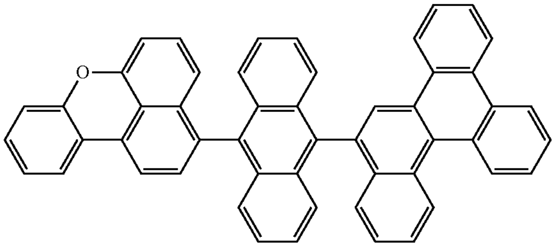
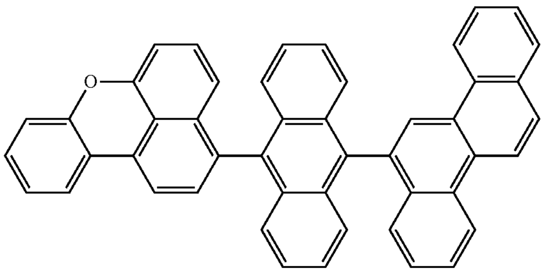
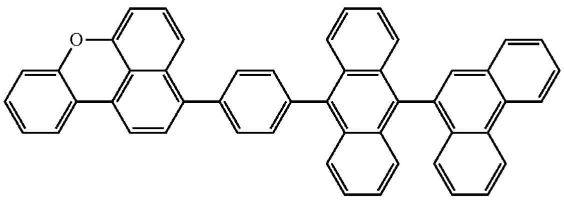

-continued
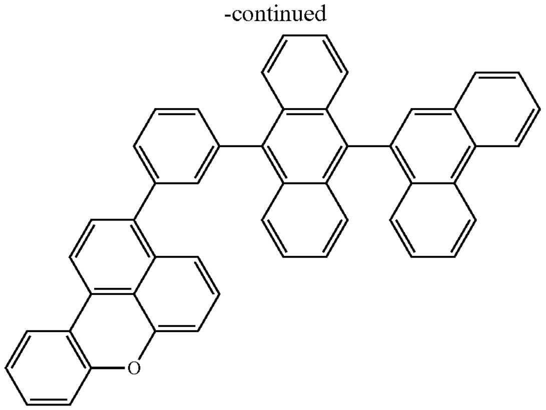
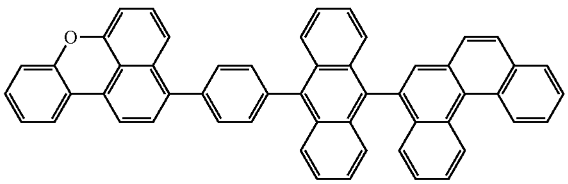
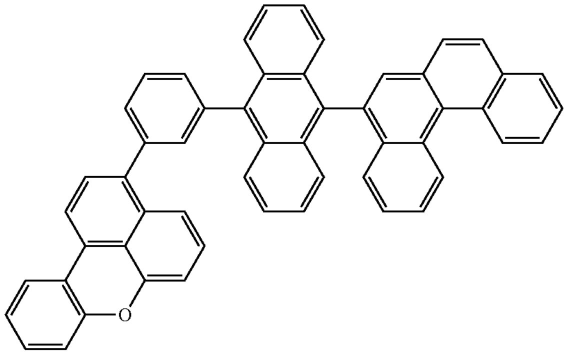
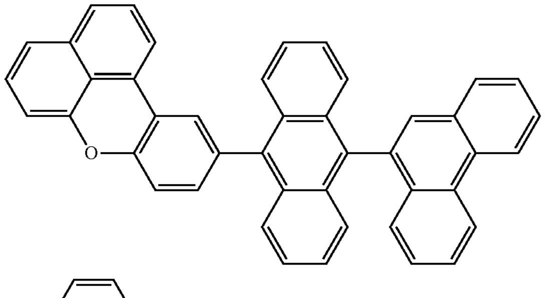
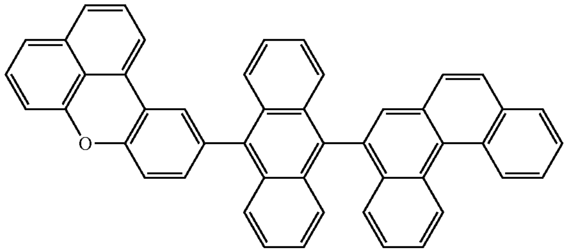
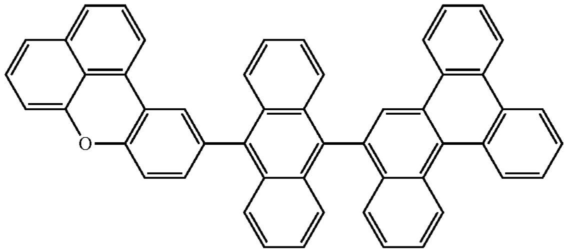
-continued
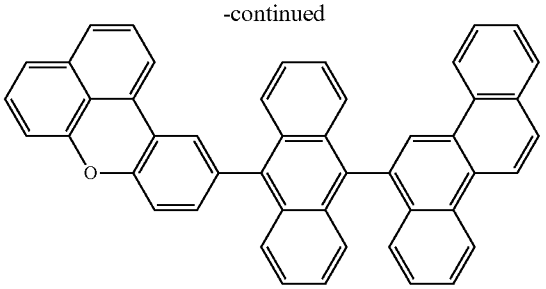
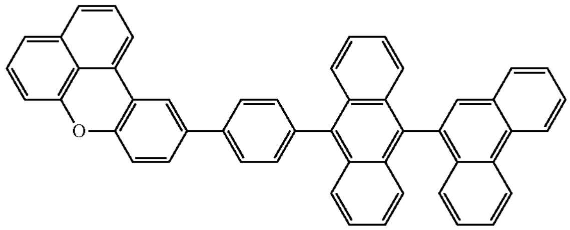
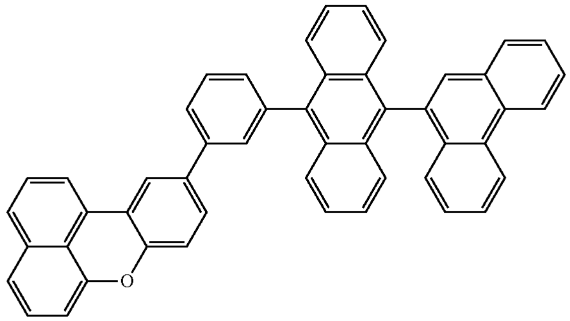
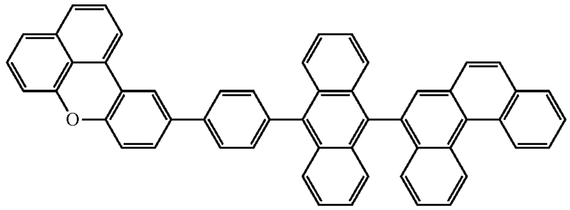
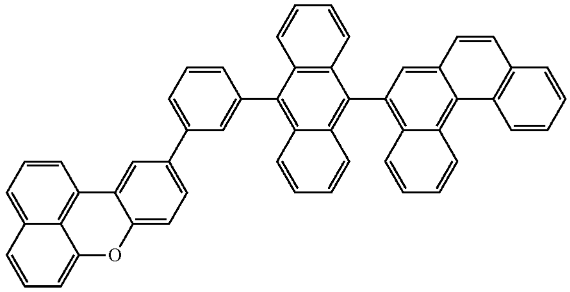
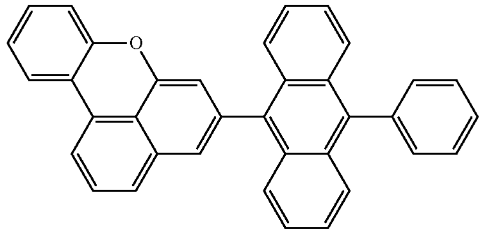

-continued
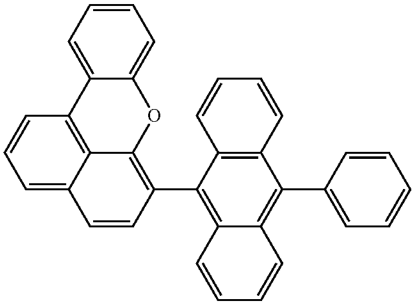
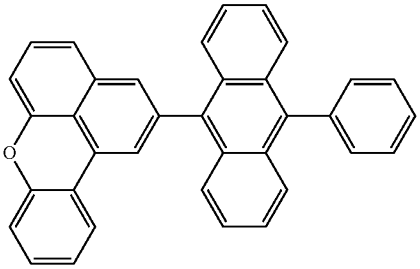
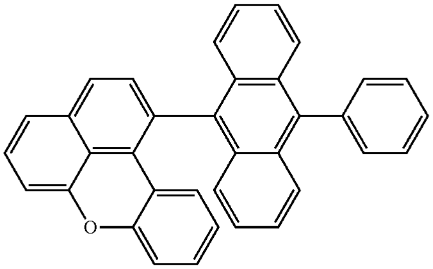
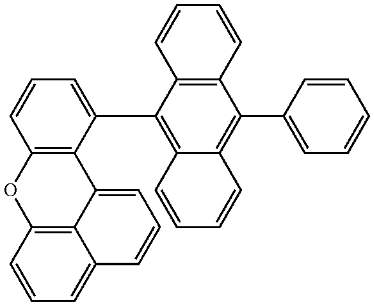
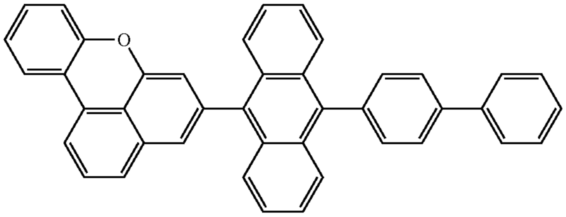
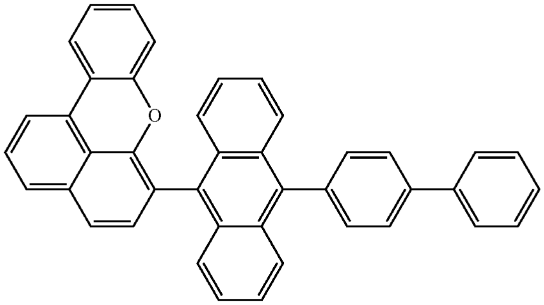
-continued
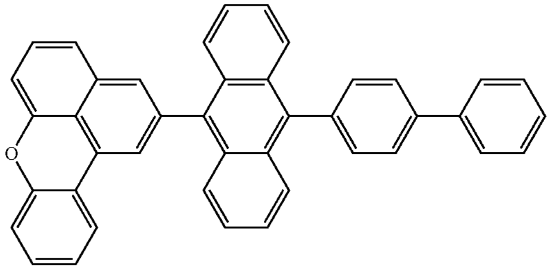
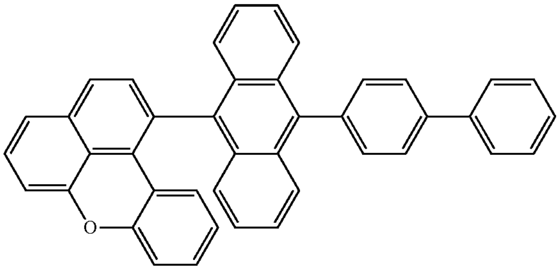
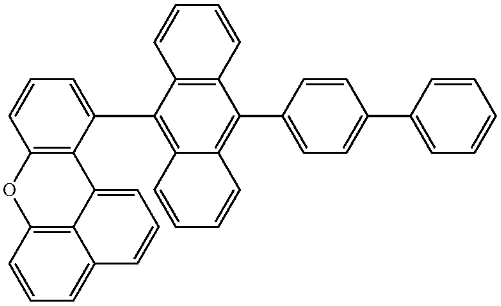
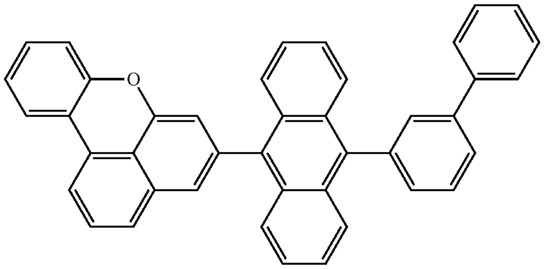
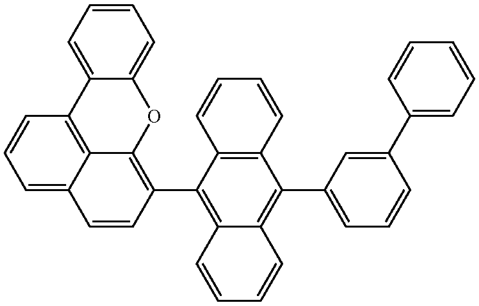
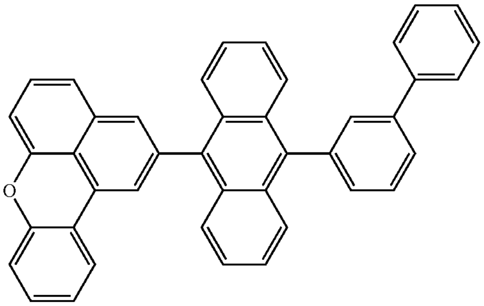

-continued
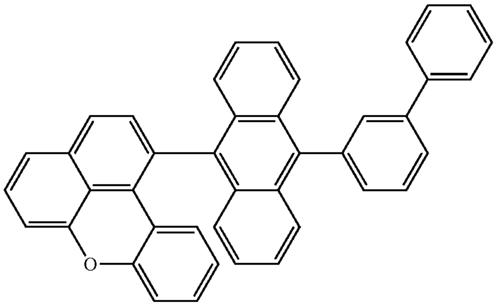
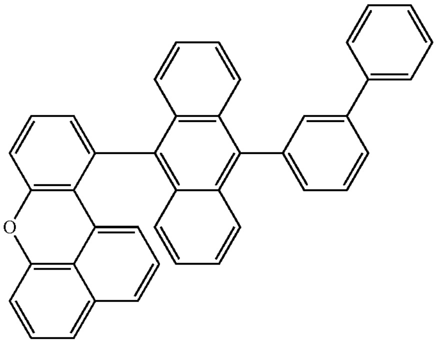
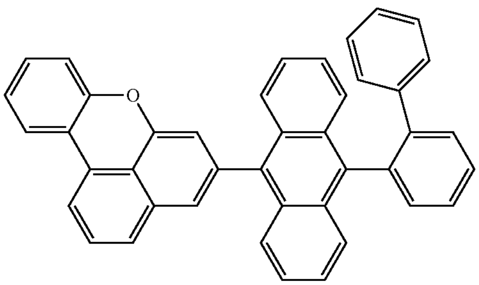
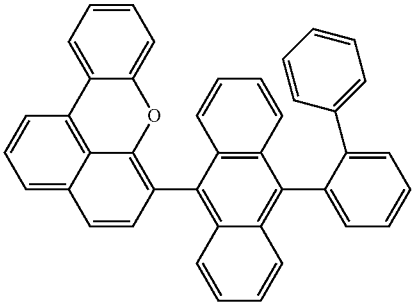
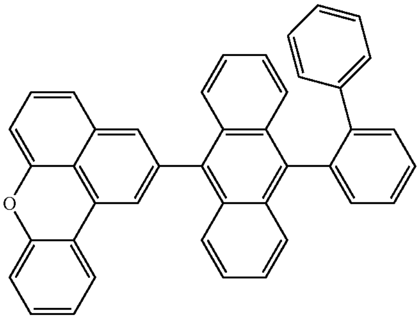
-continued
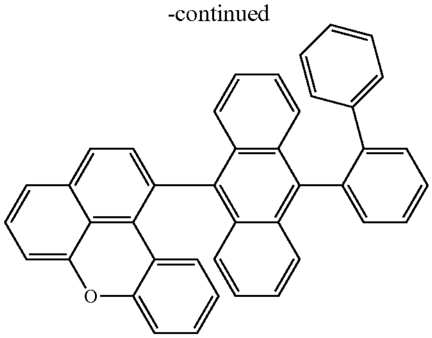
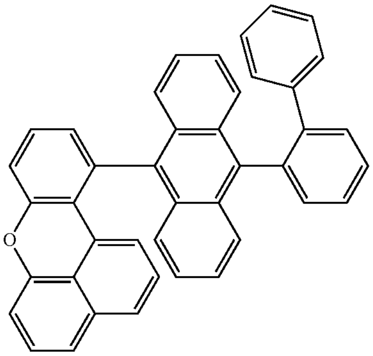
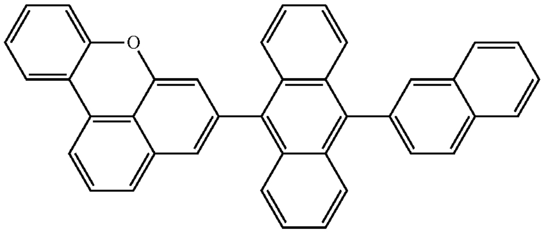
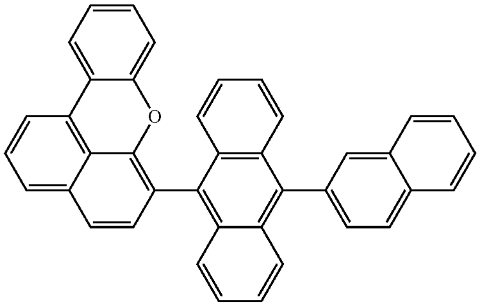
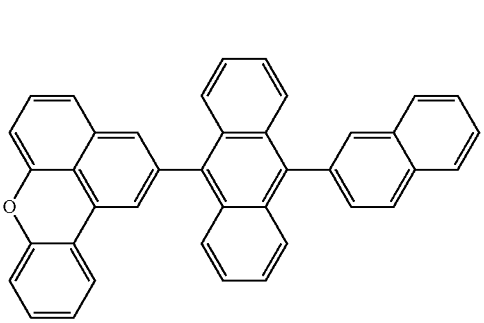

-continued
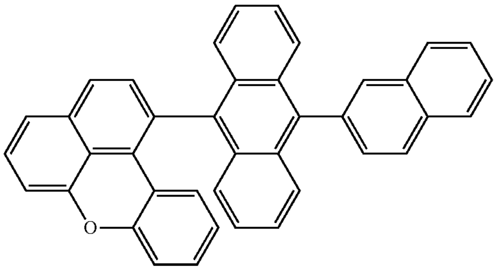
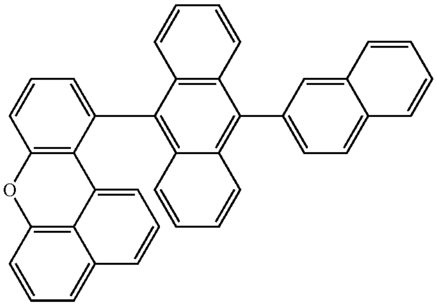
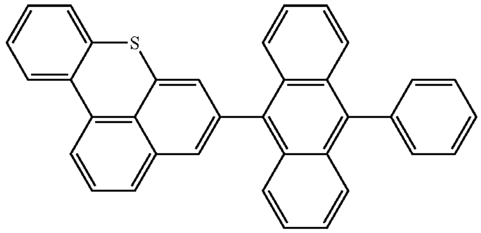
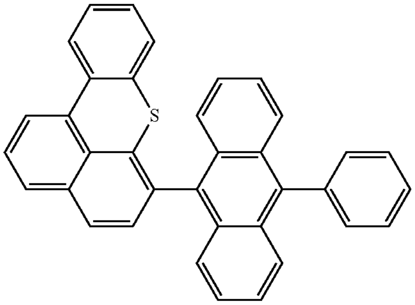
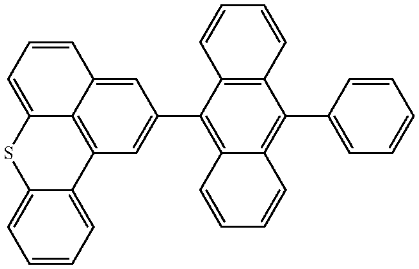
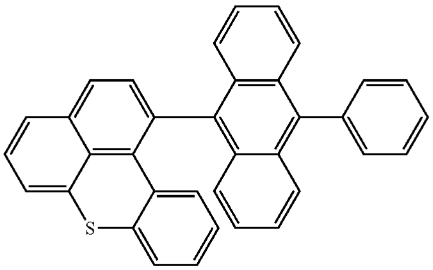
-continued
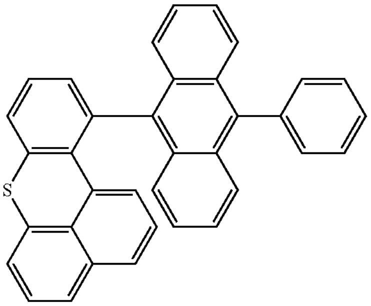
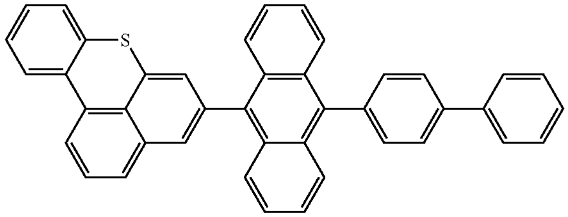
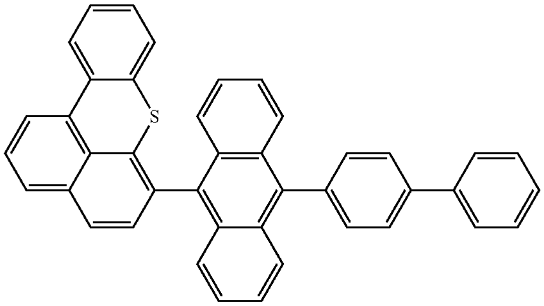
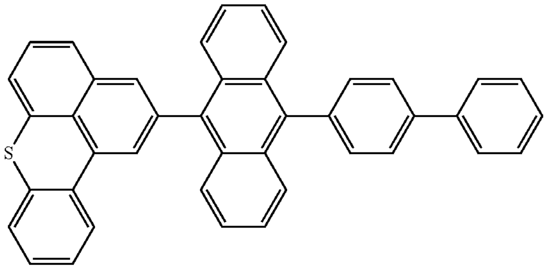
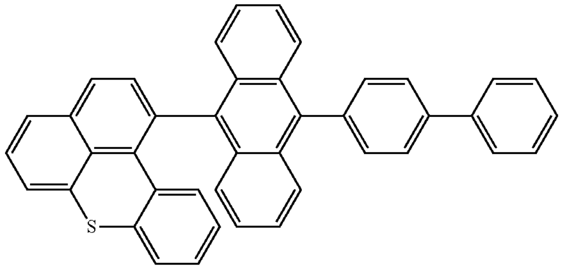
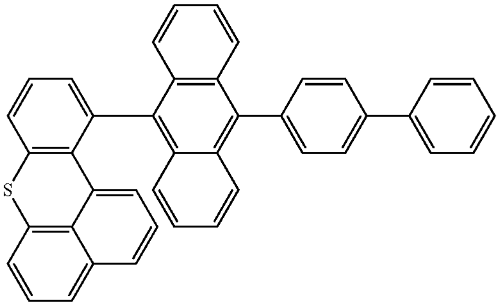

-continued
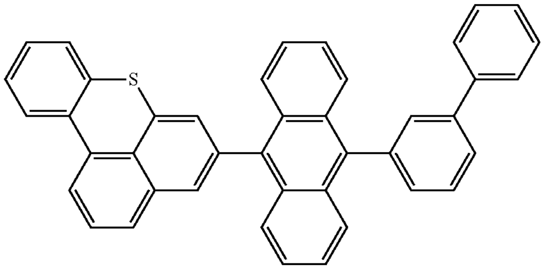
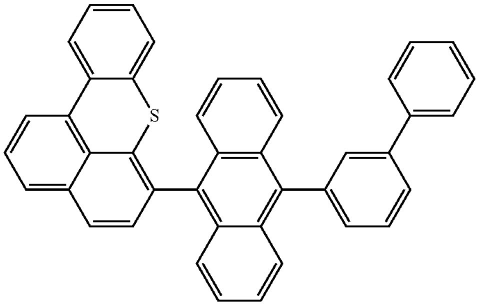
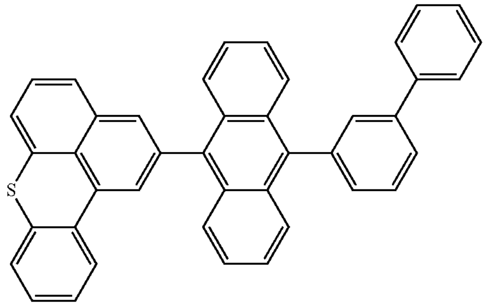
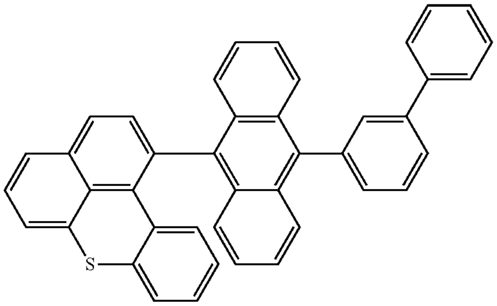
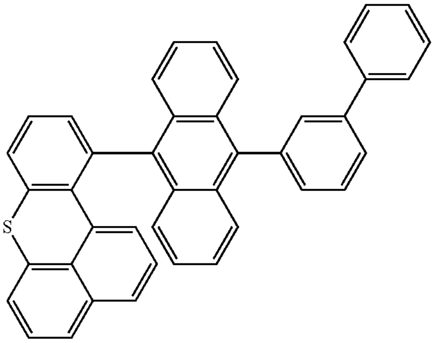
-continued
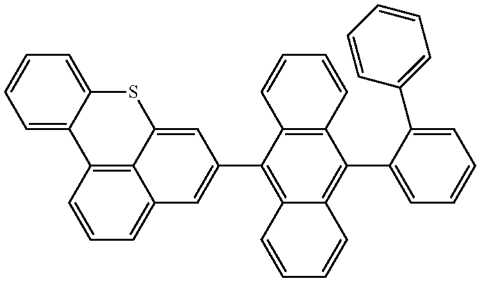
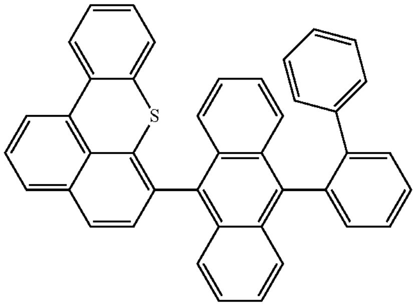
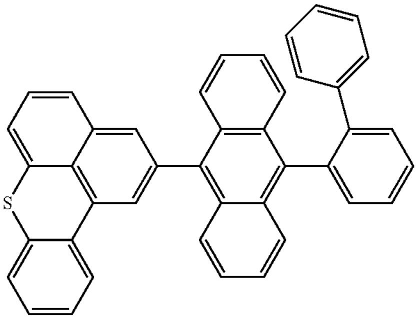
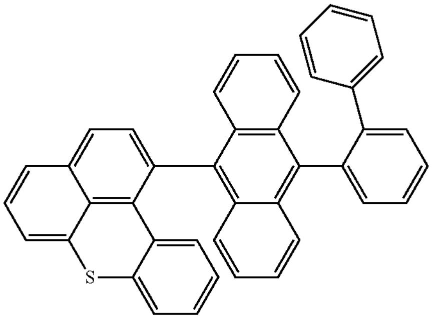
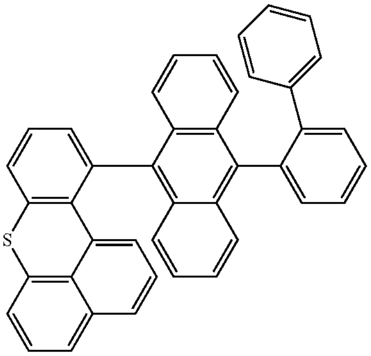

-continued
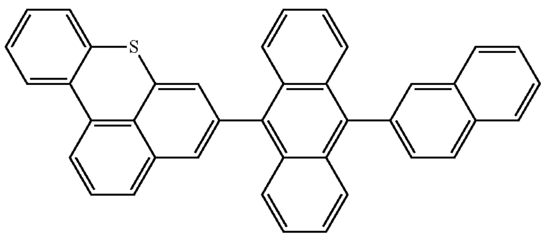
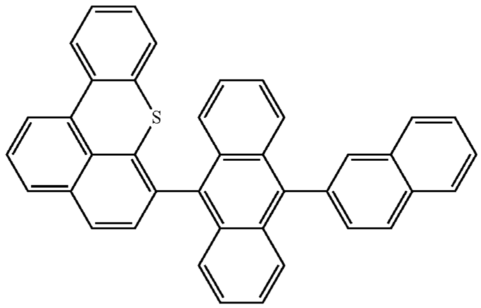
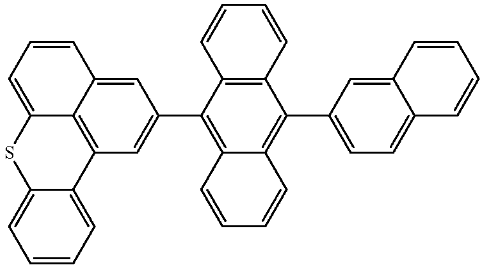
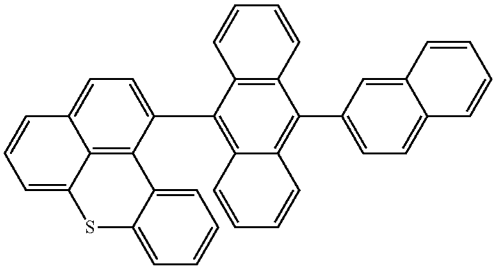
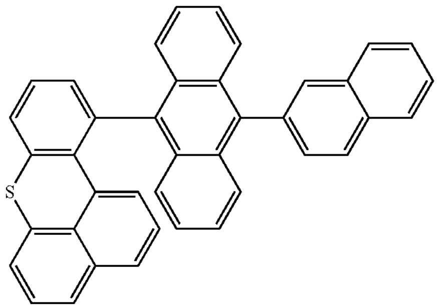
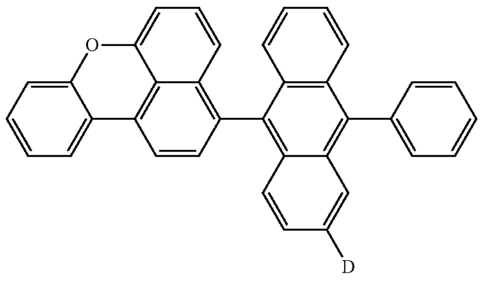
-continued
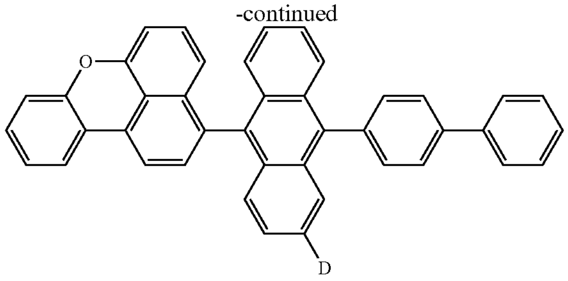
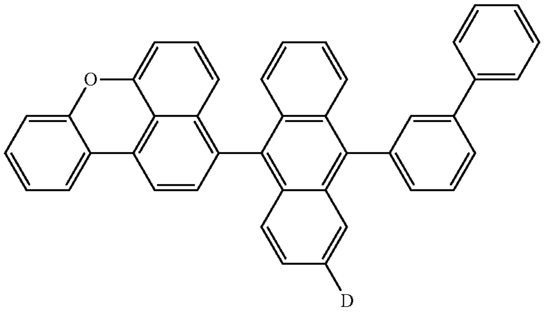
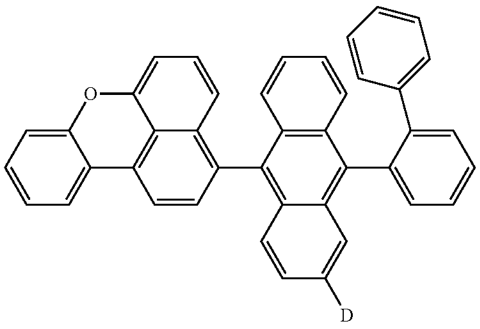
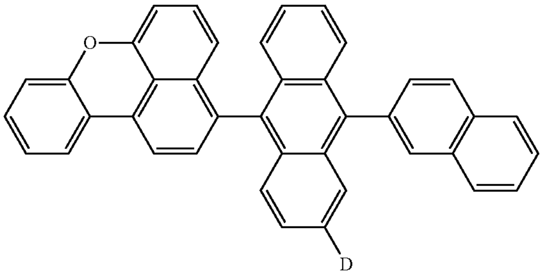
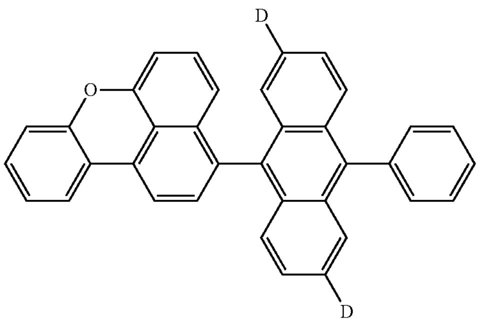

-continued
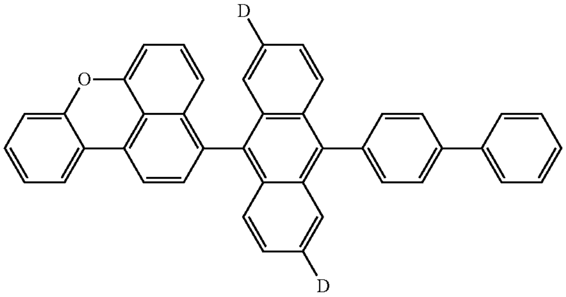
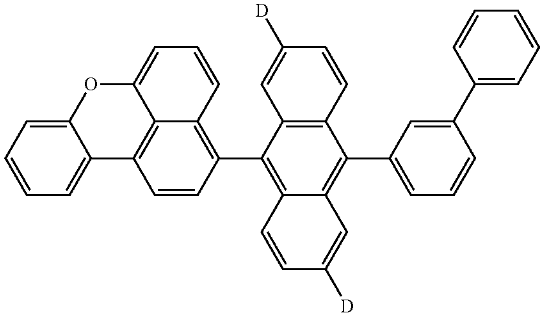
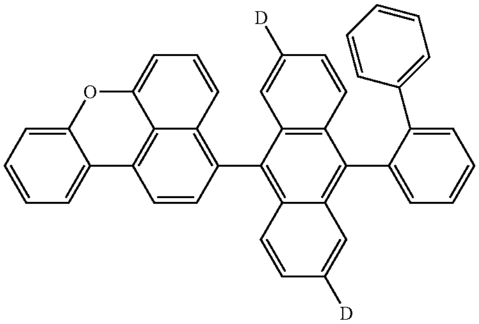
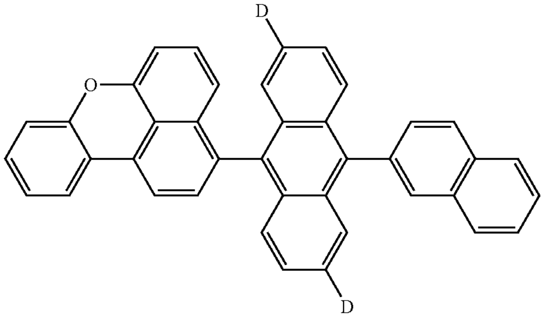
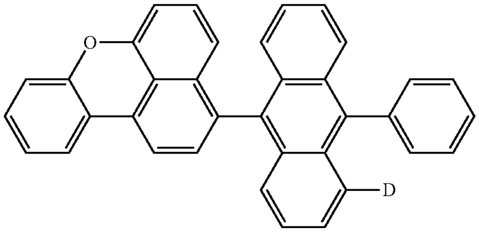
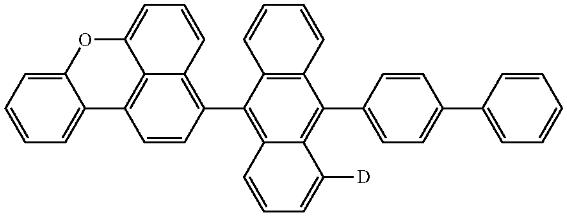
-continued
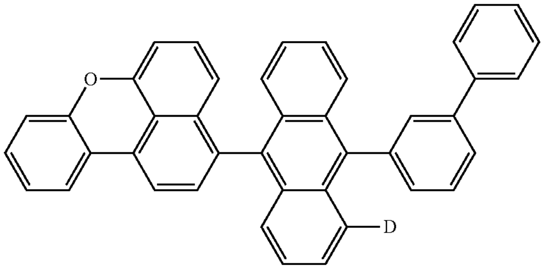
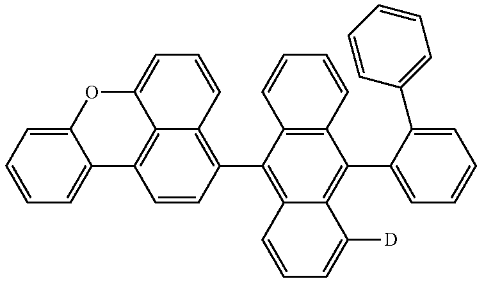
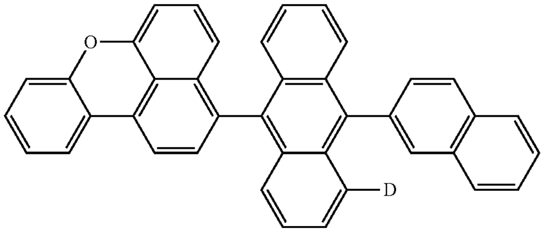
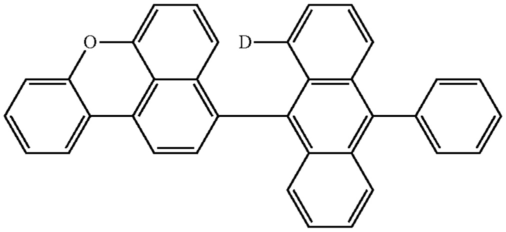
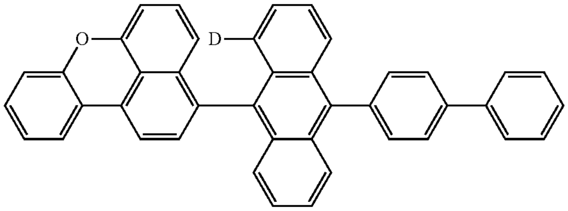
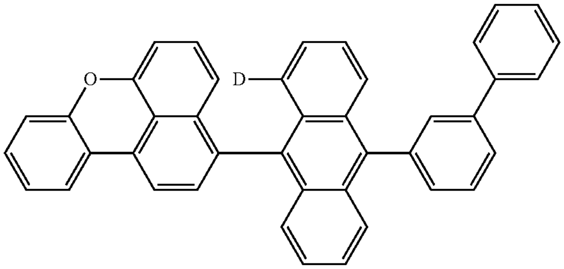

-continued
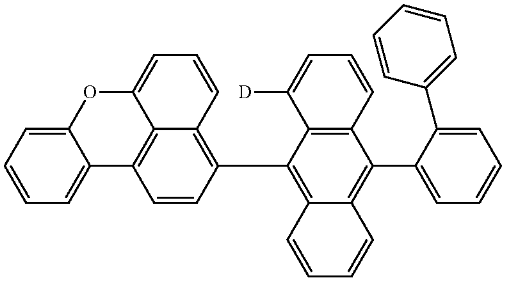
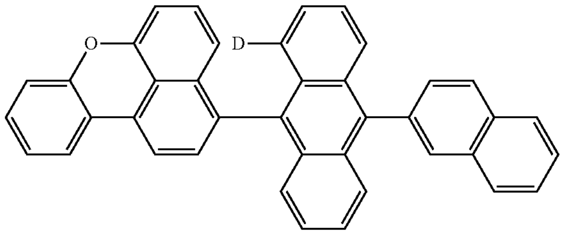
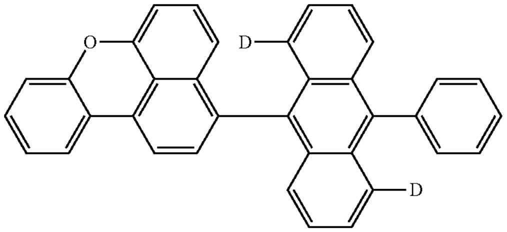
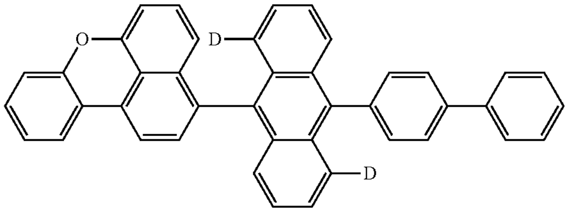
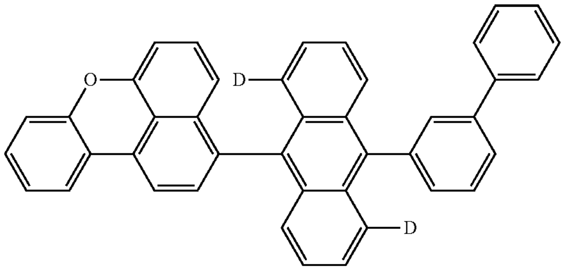
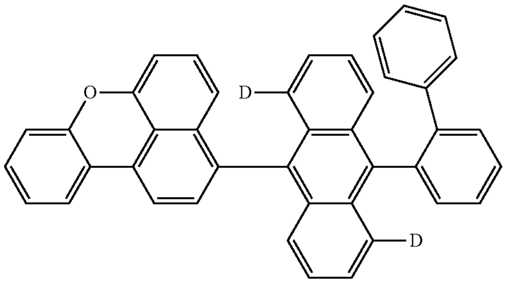
-continued
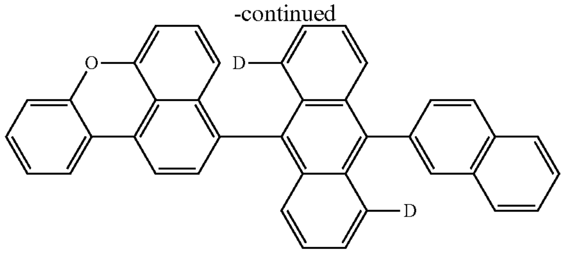
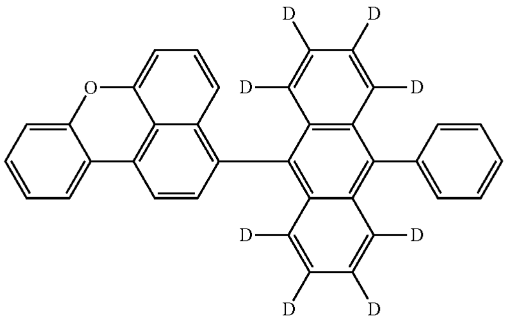
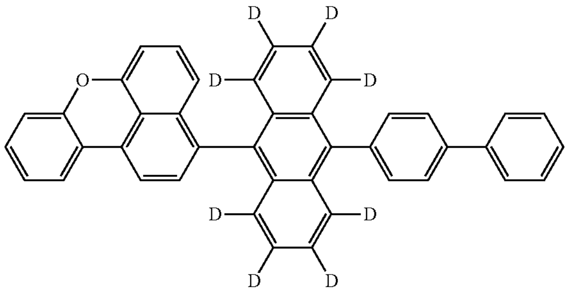
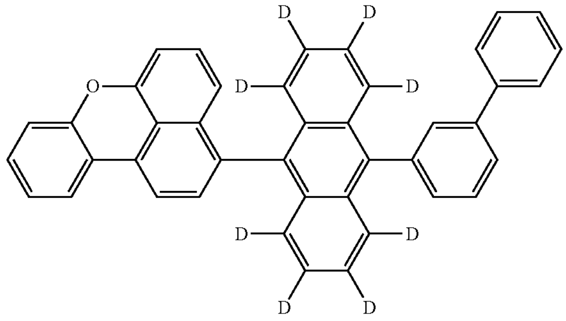

-continued
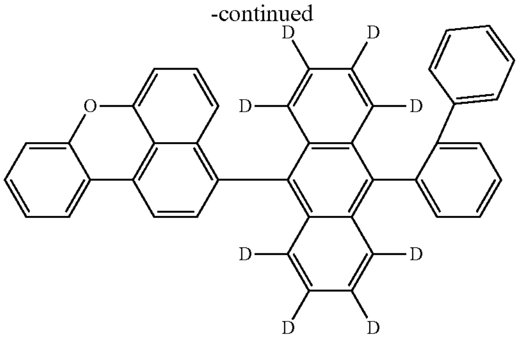
-continued
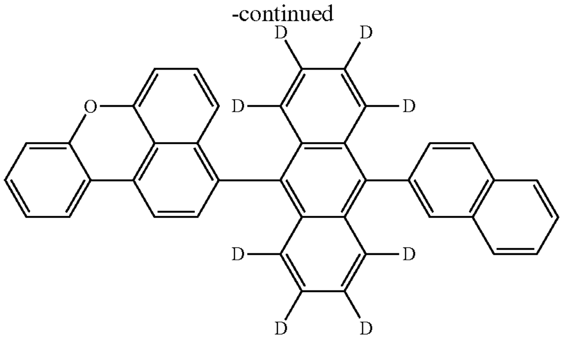
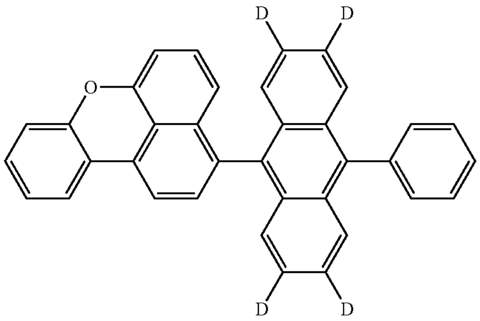
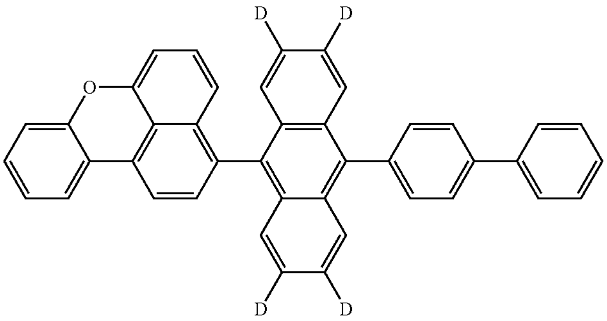
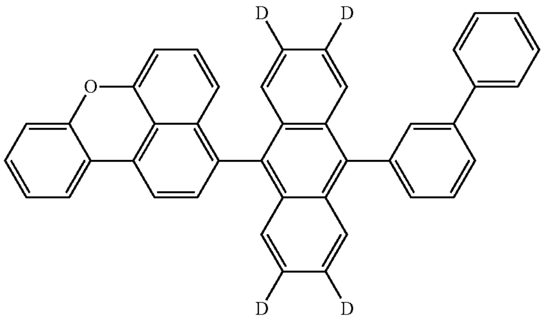
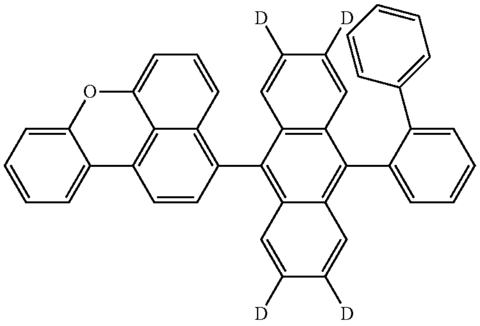
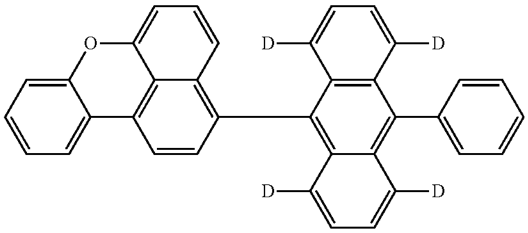
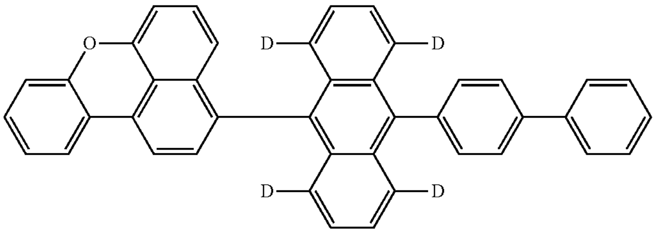
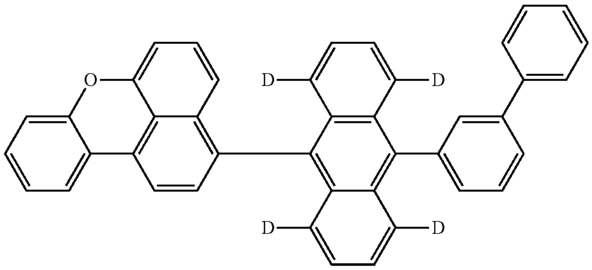
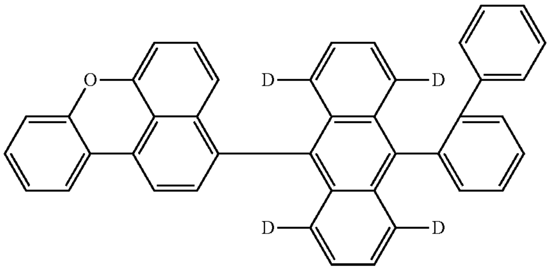

-continued
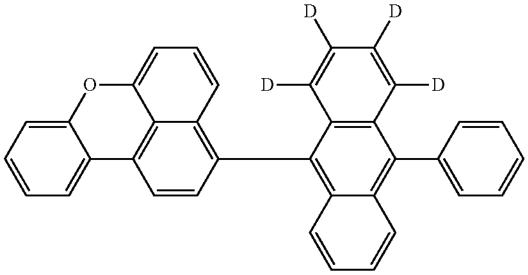
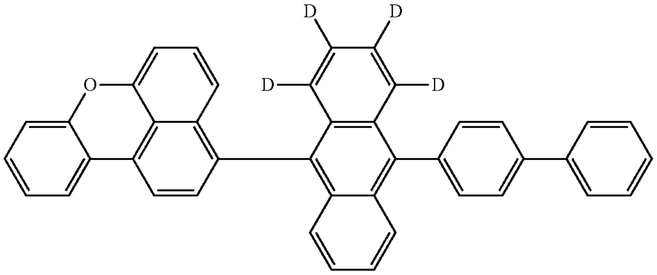
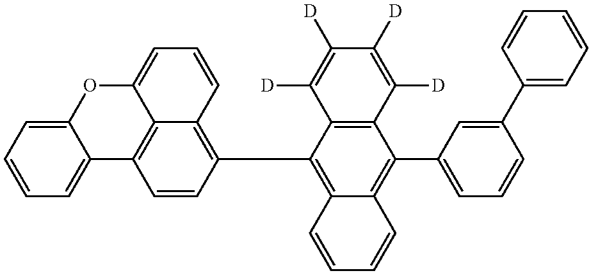
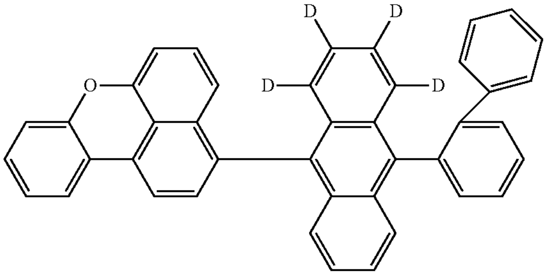
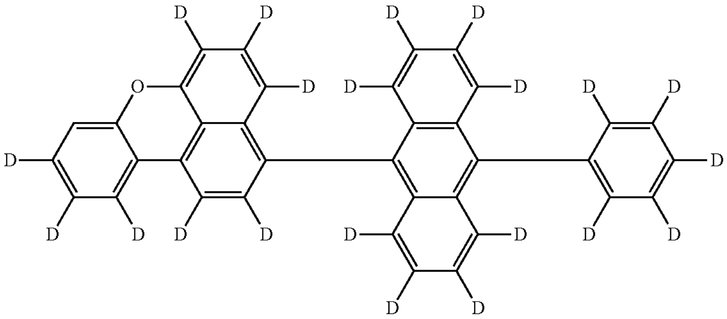
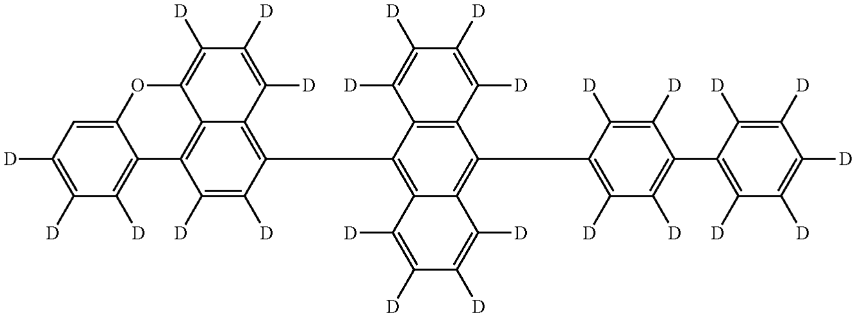
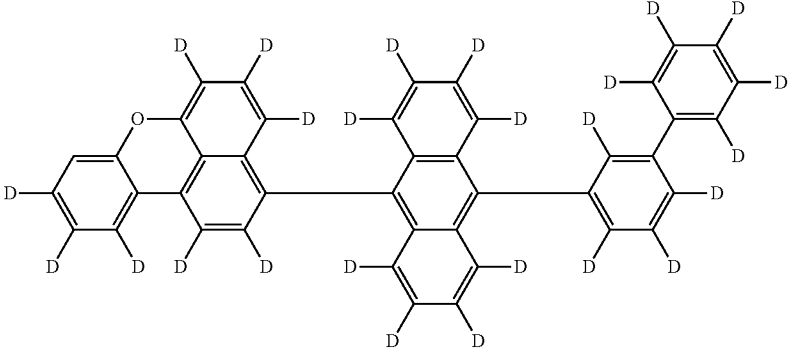

-continued
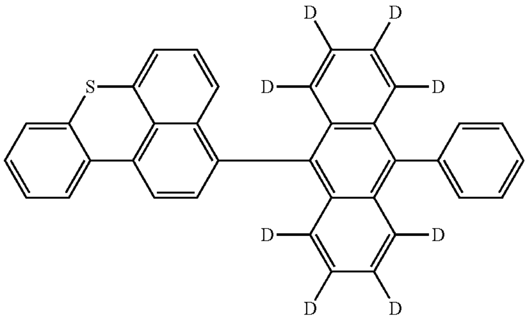
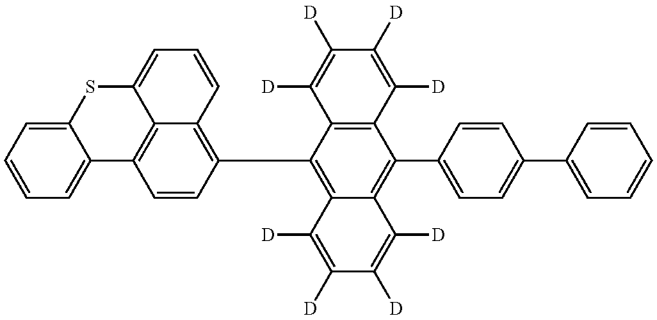
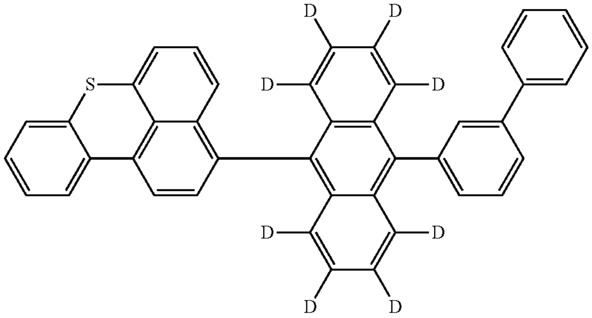
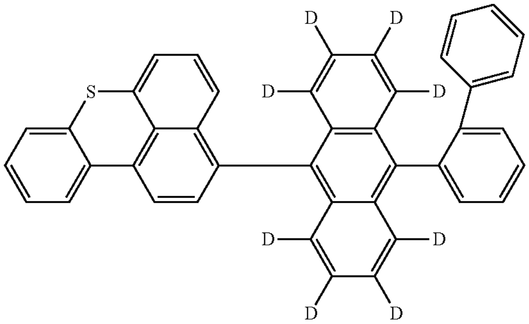
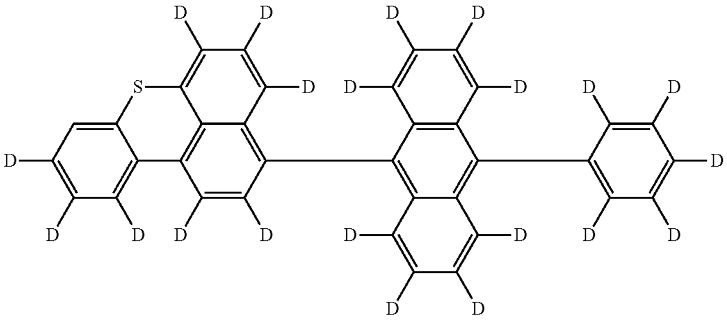
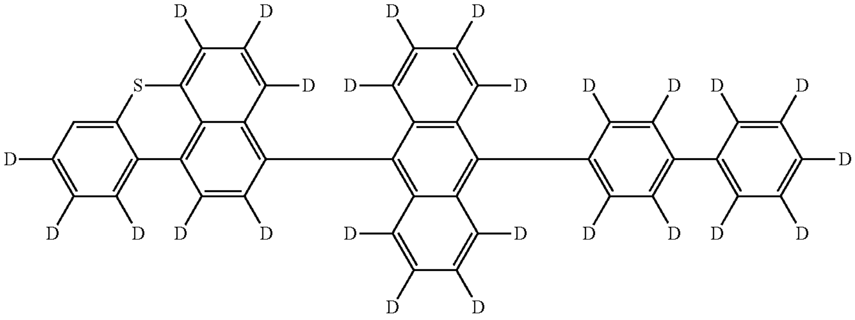
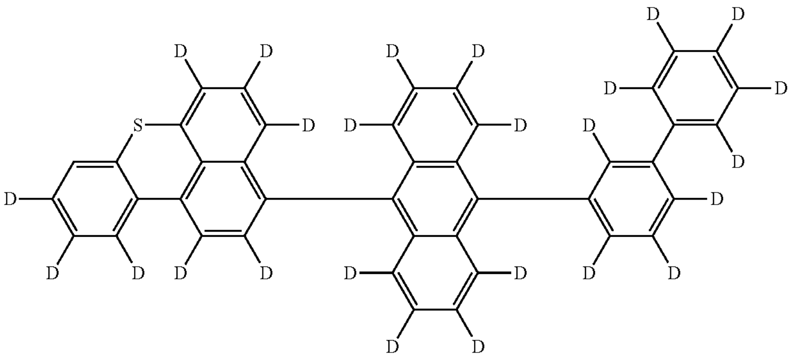

-continued
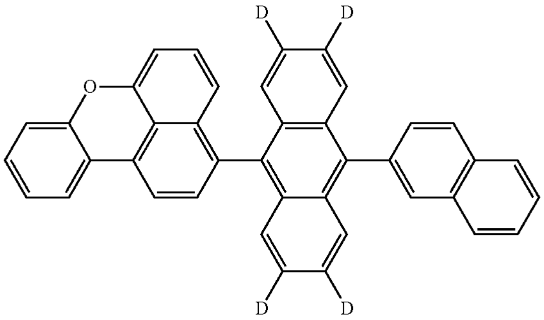
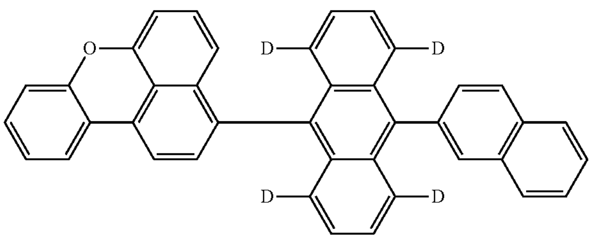
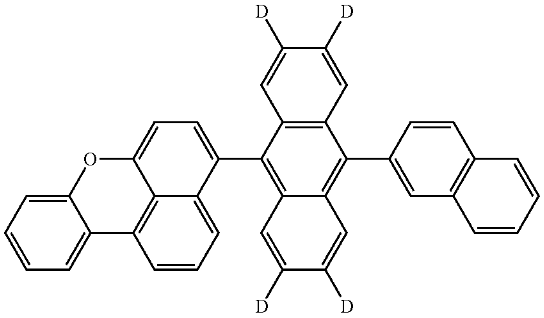
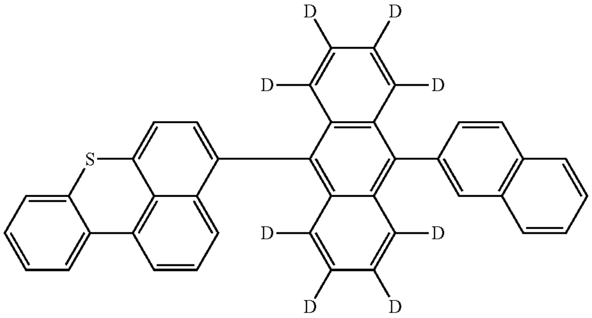
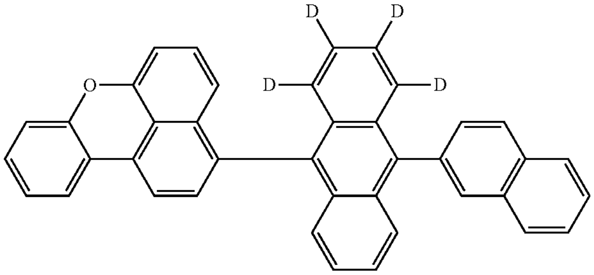
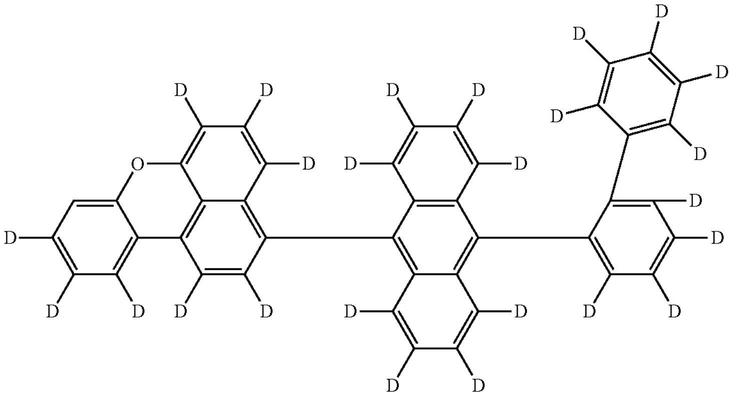
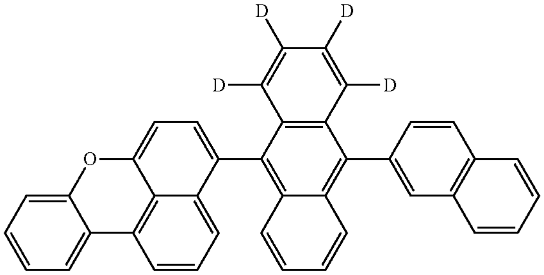

-continued
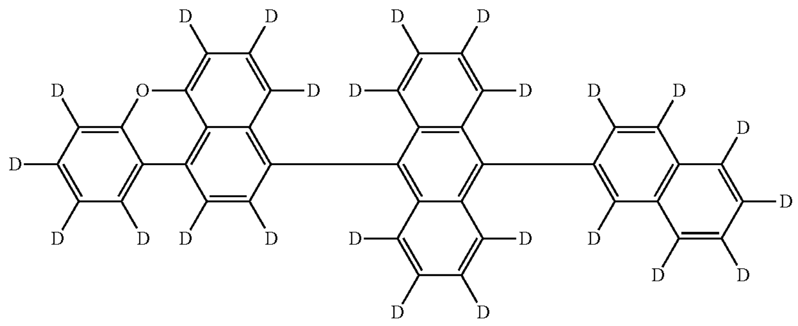
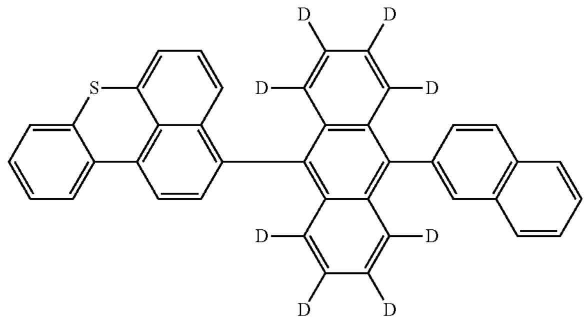
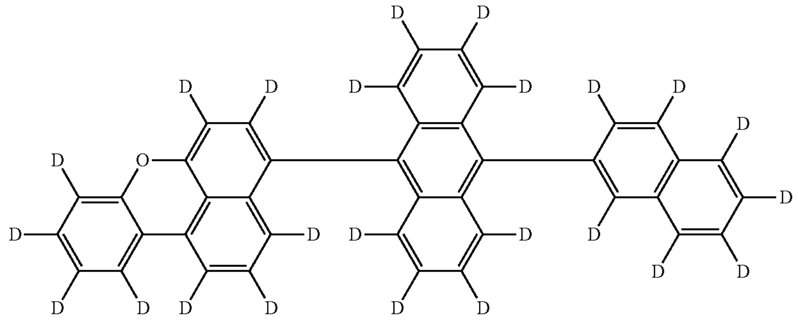
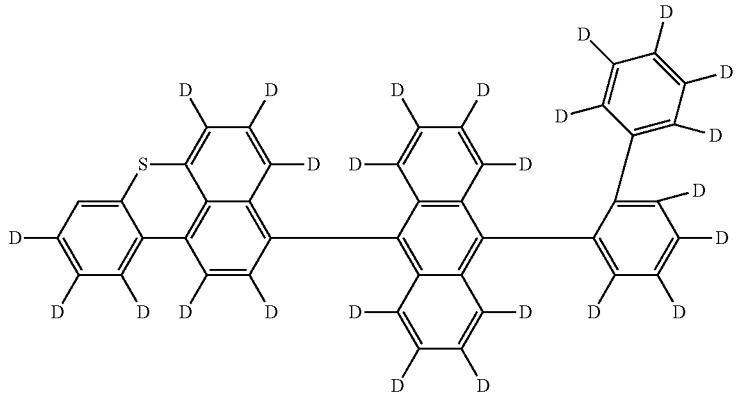
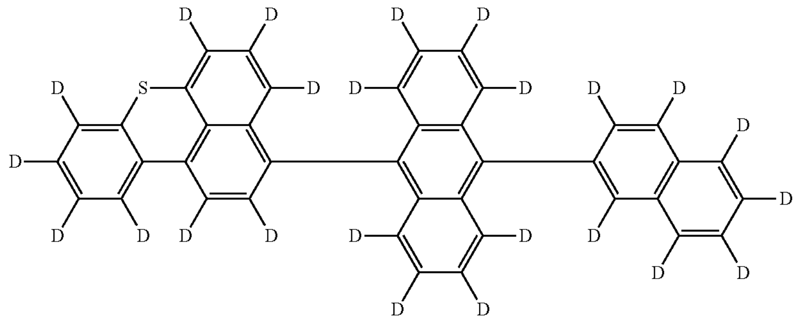

-continued
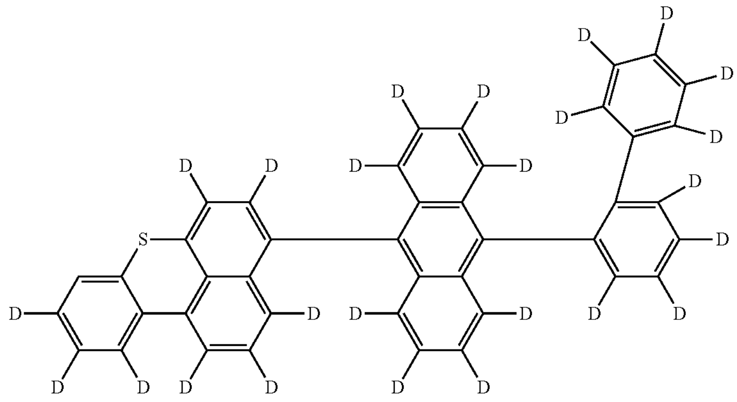
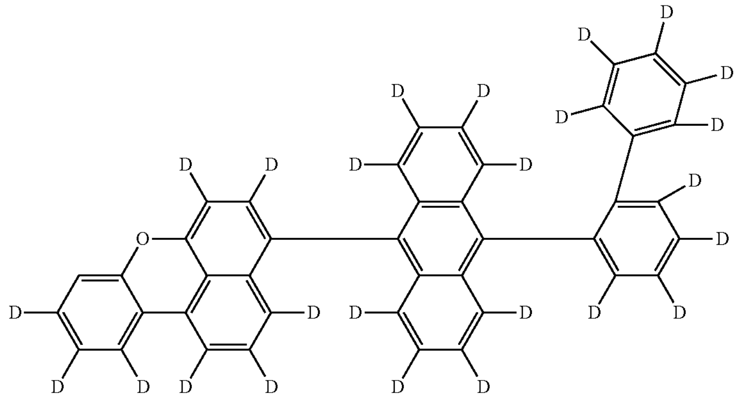
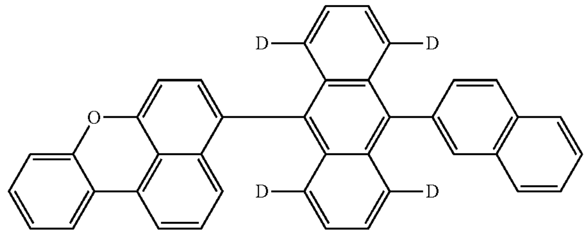
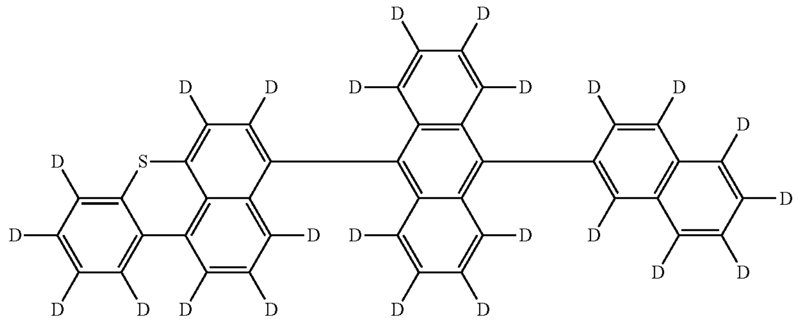
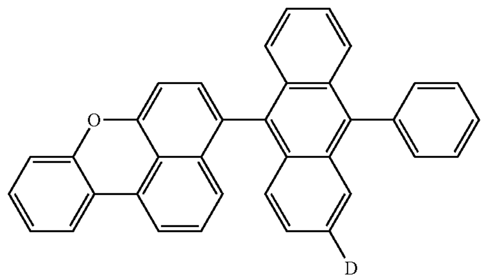
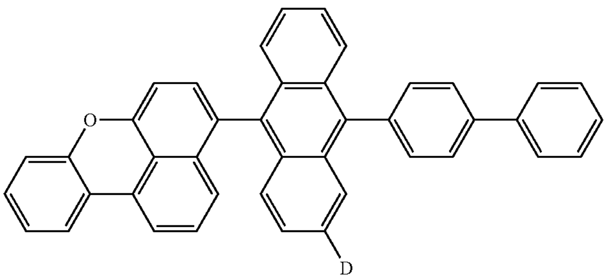

-continued
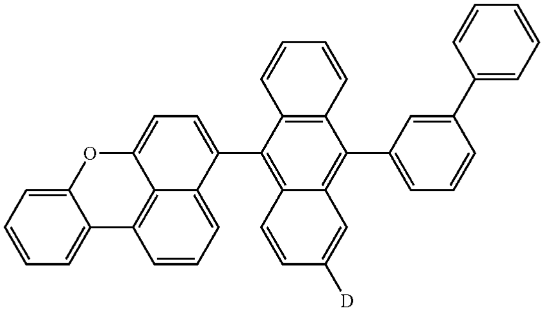
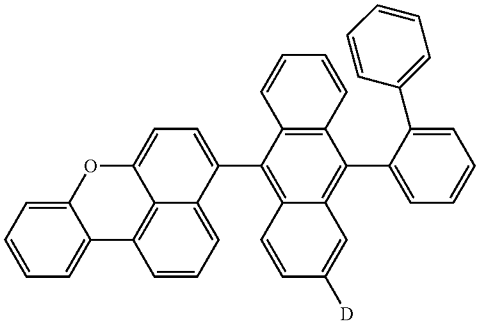
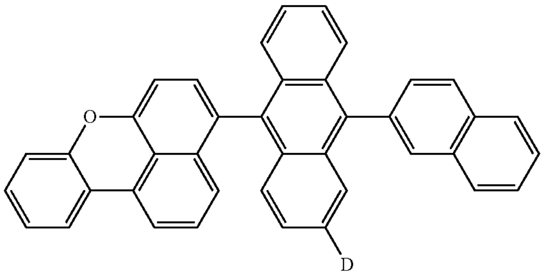
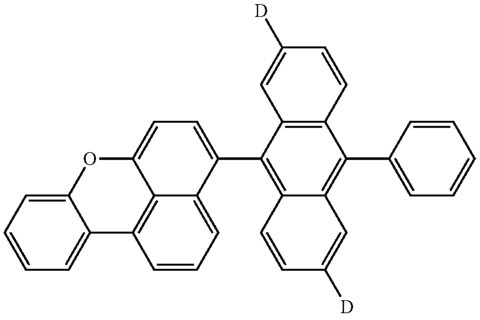
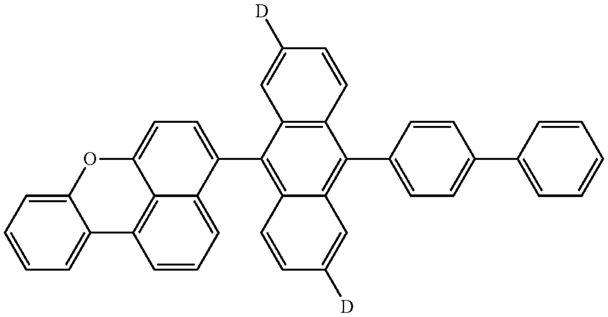
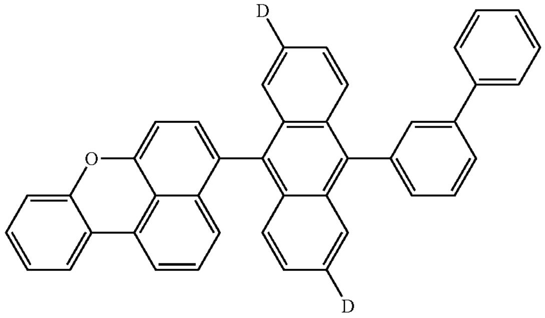
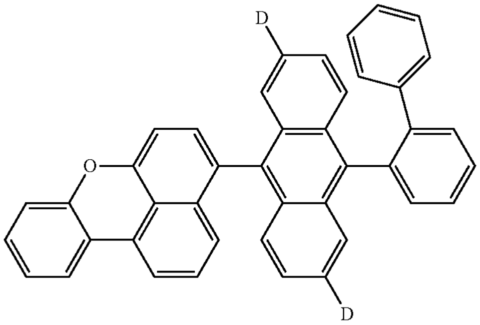
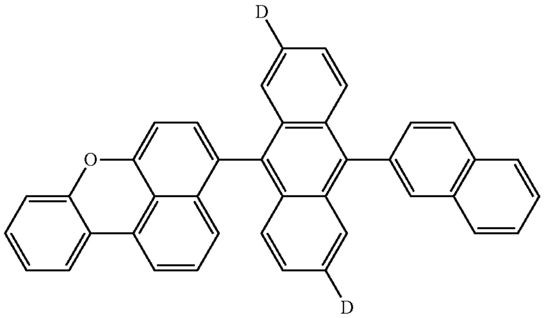
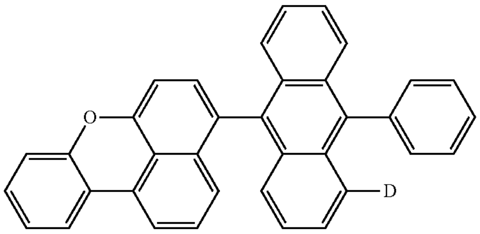
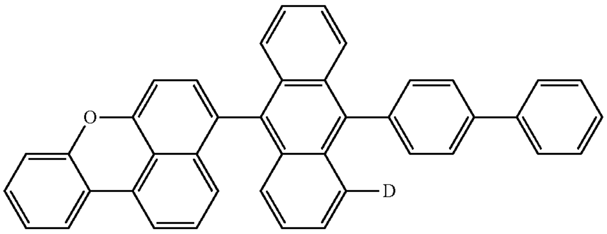

-continued
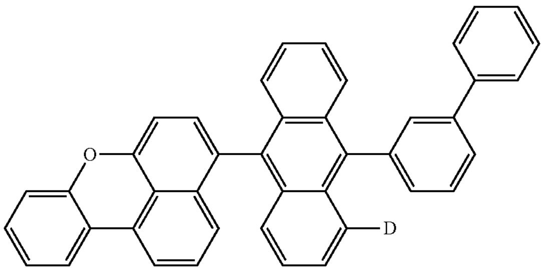
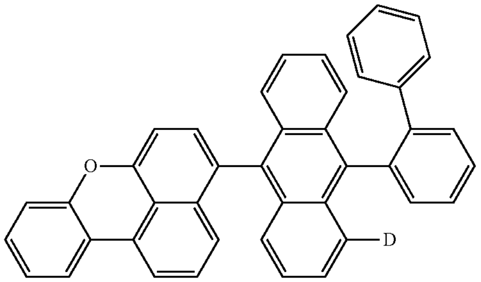
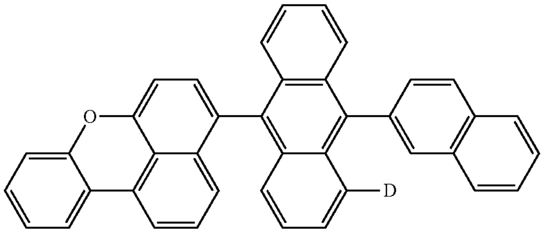
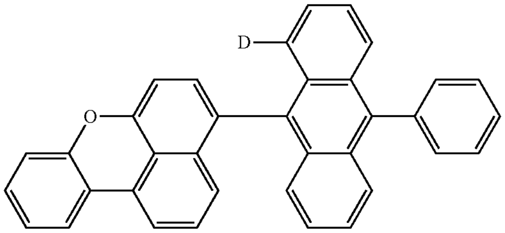
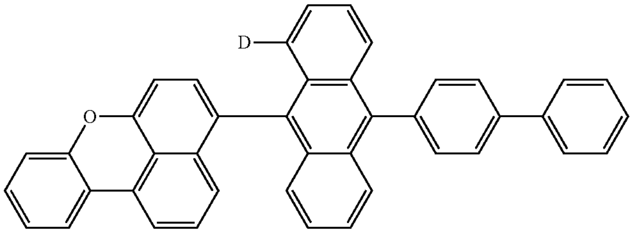
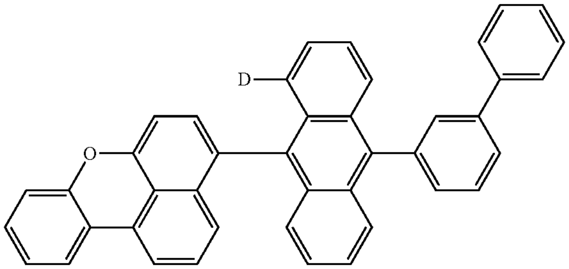
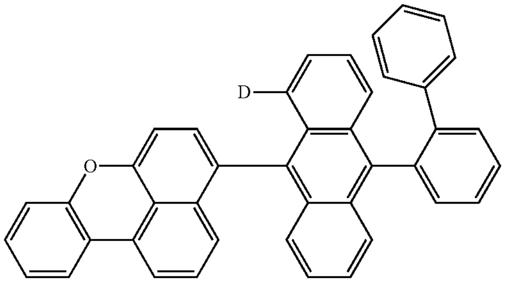
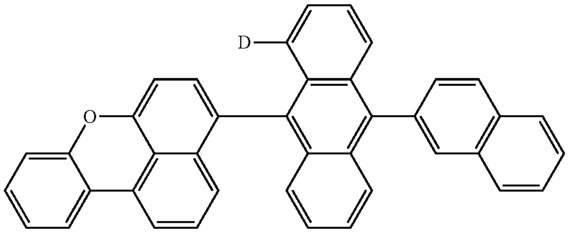
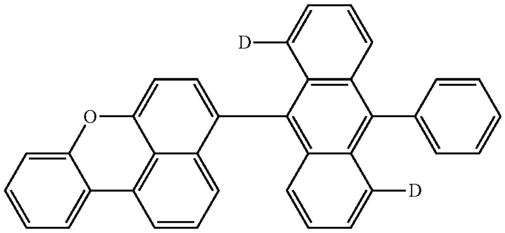
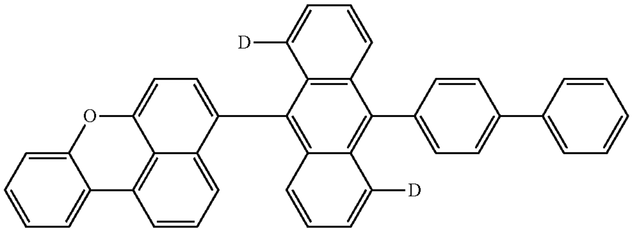

-continued
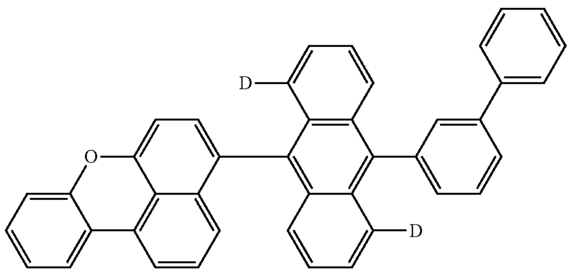
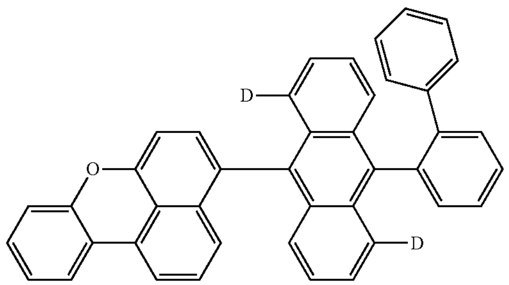
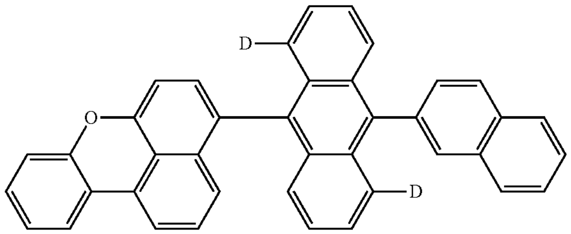
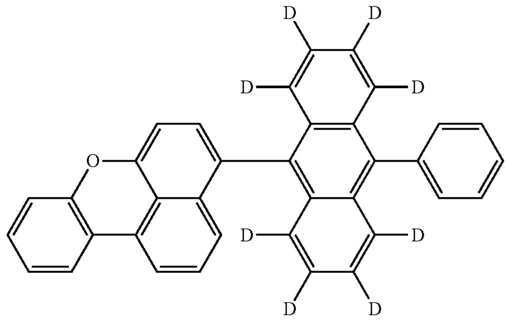
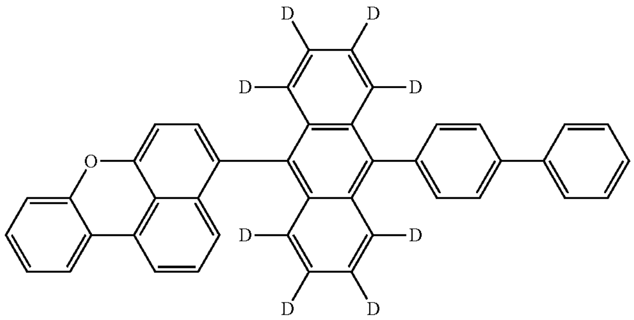
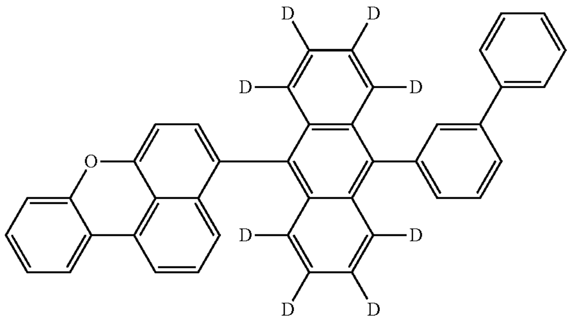
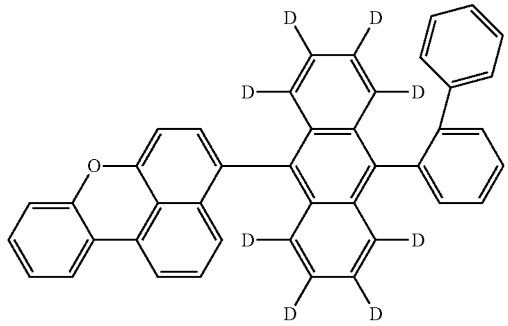
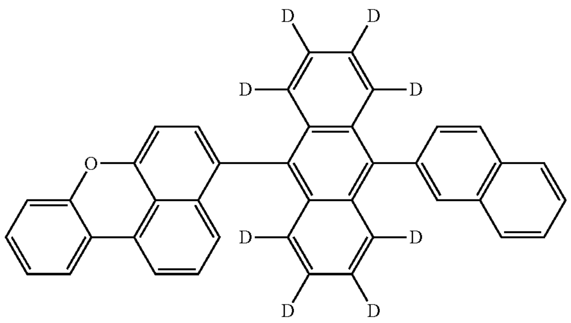
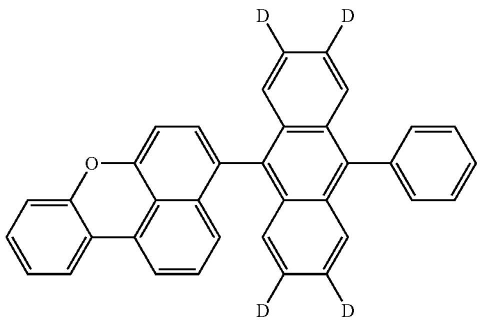

-continued
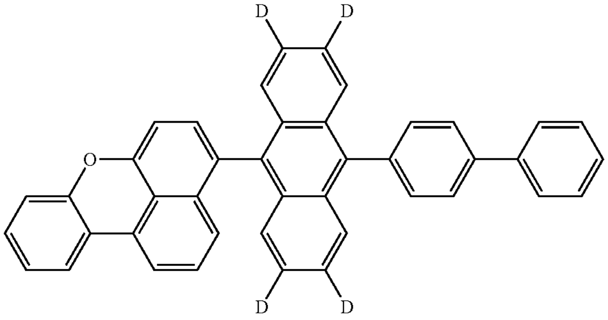
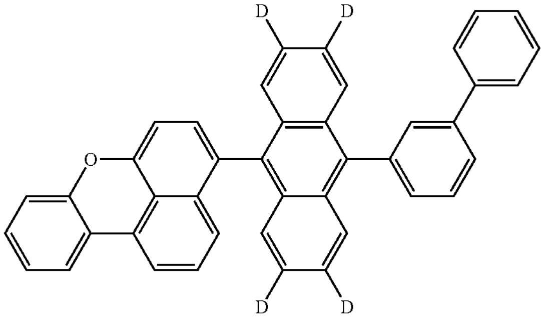
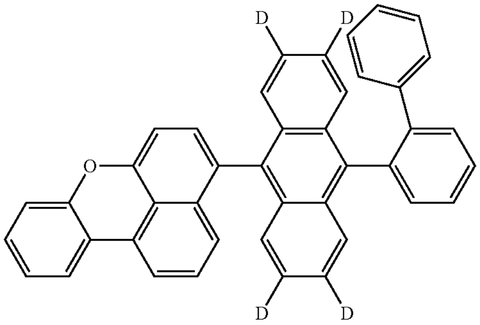
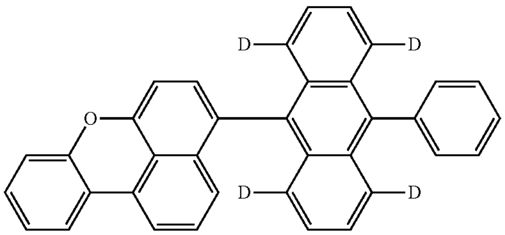
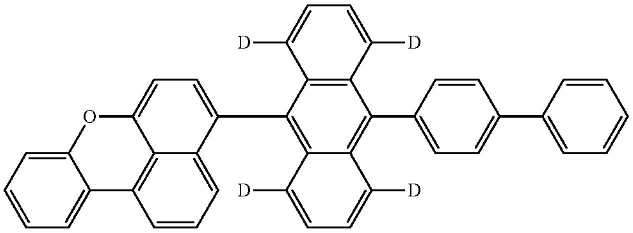
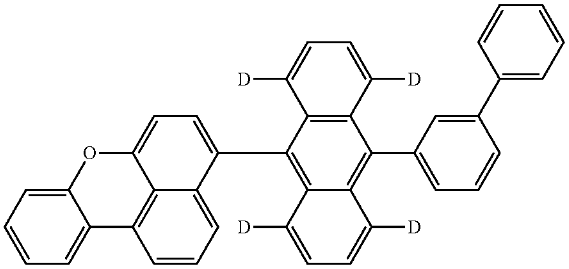
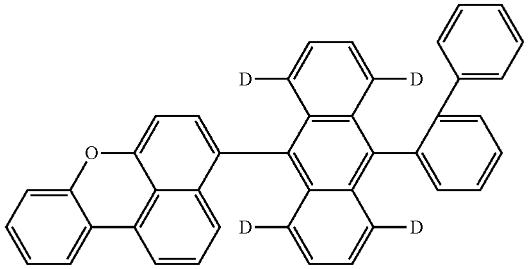
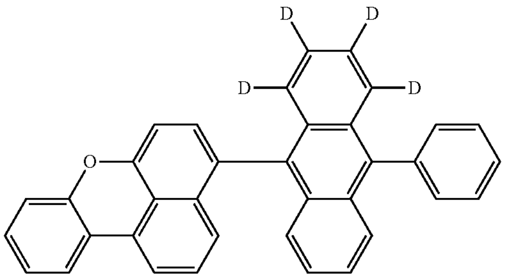
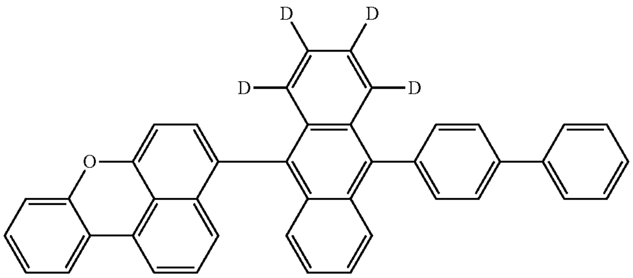
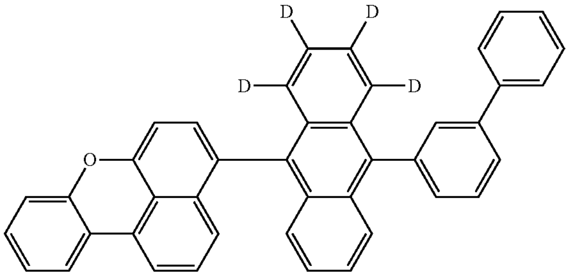
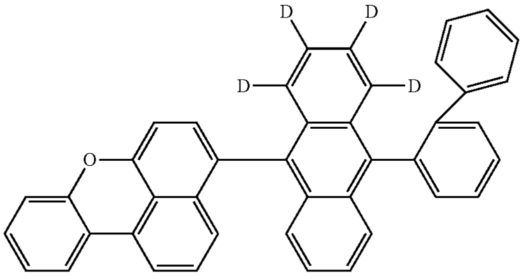

-continued
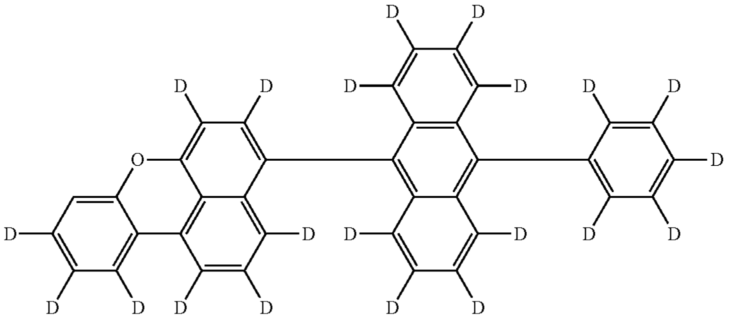
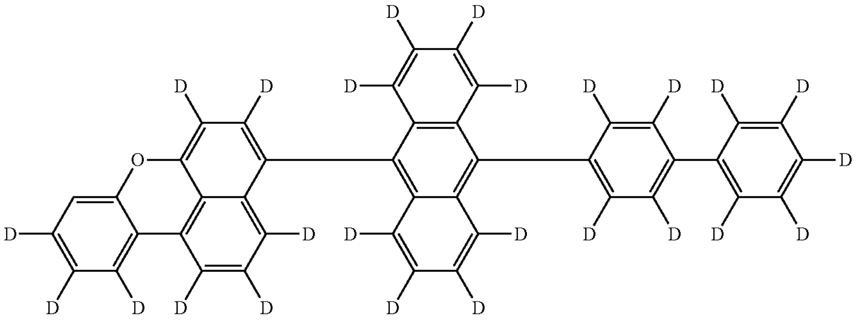
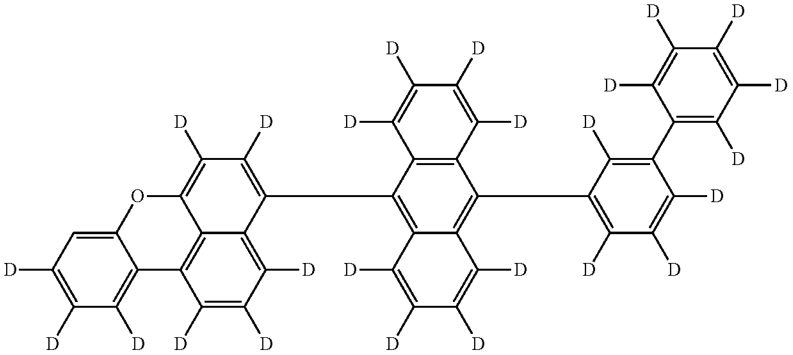
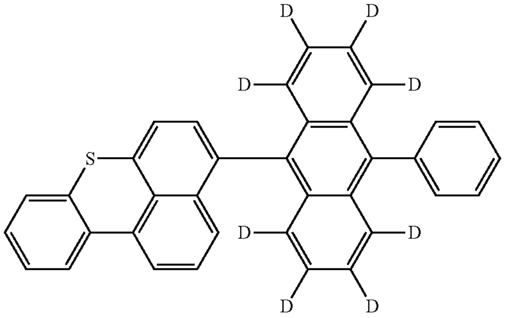
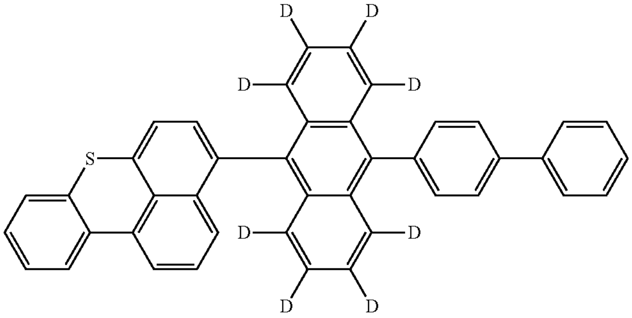
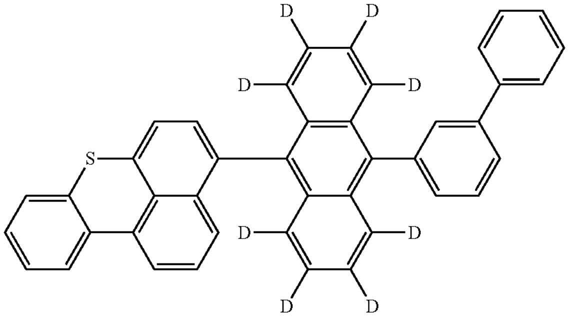
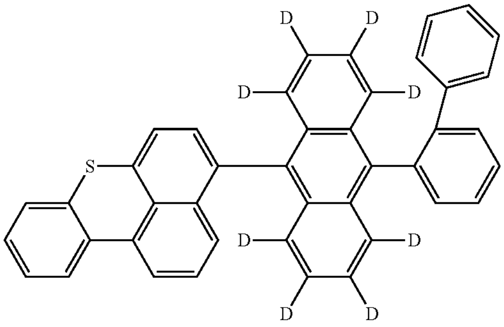

-continued
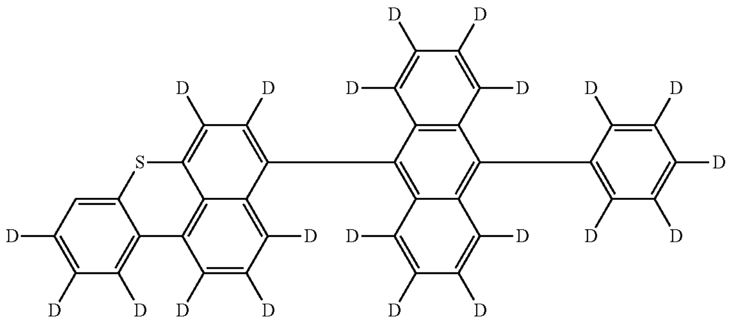
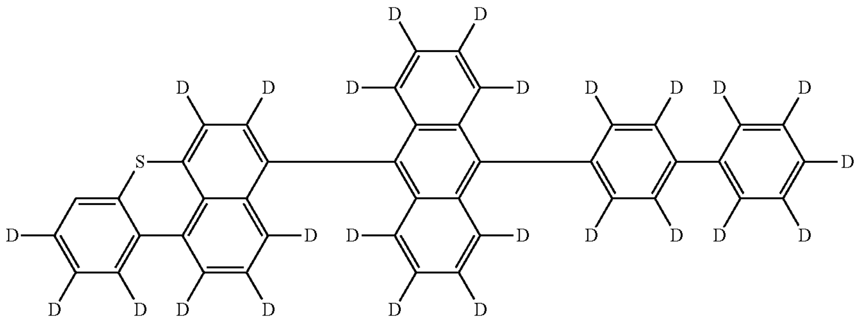
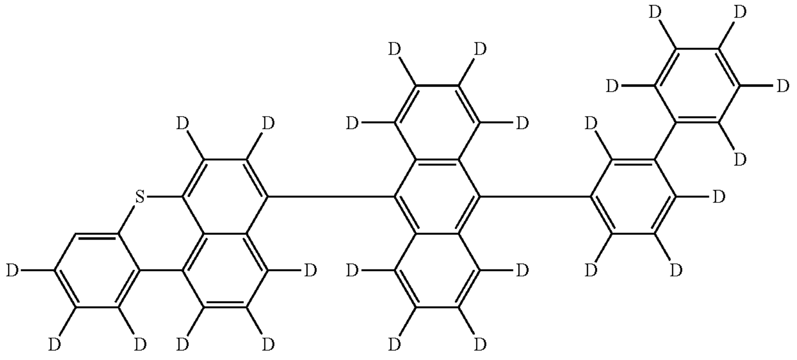
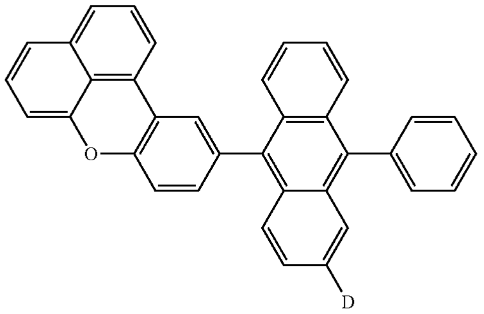
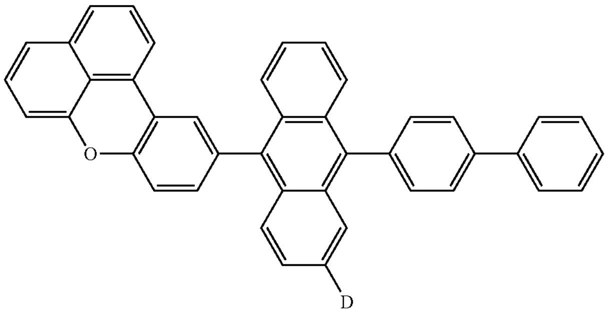
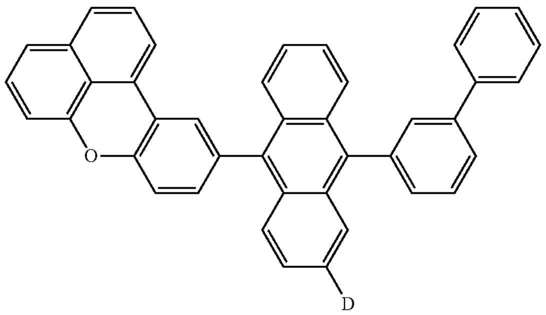
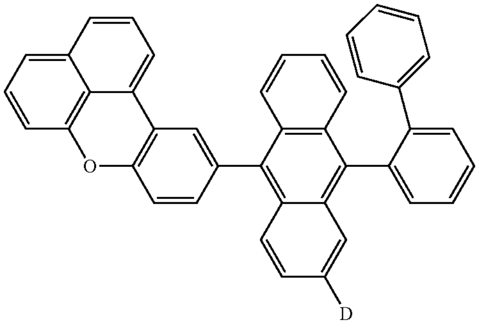

-continued
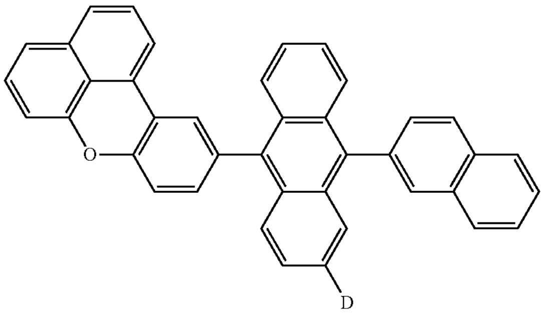
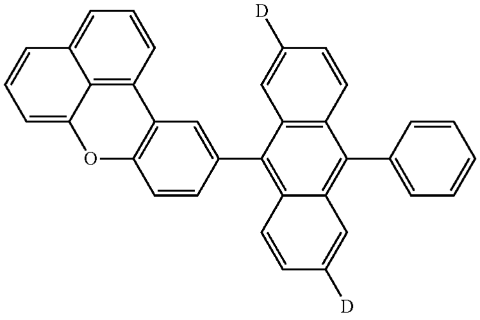
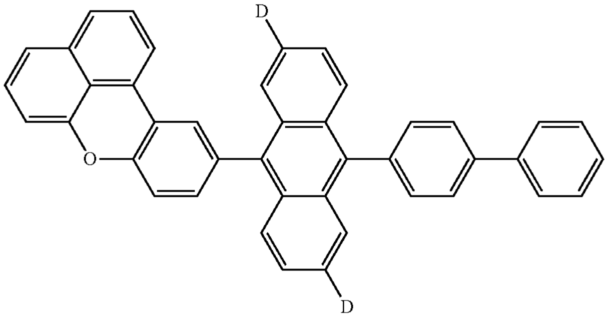
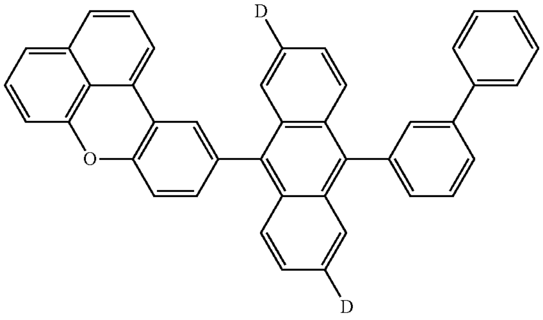
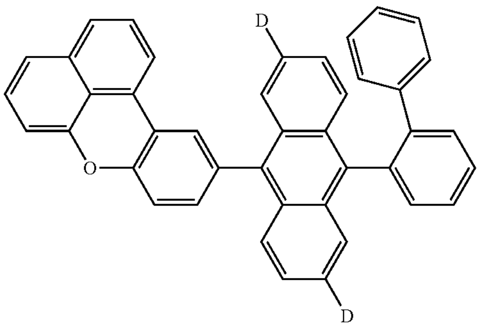
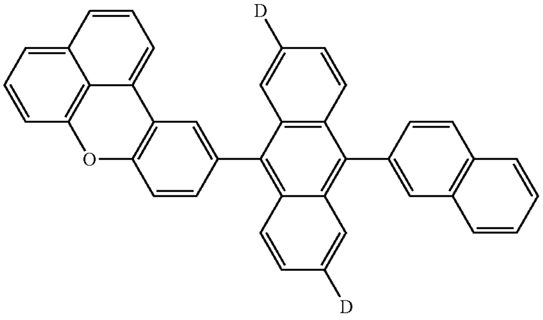
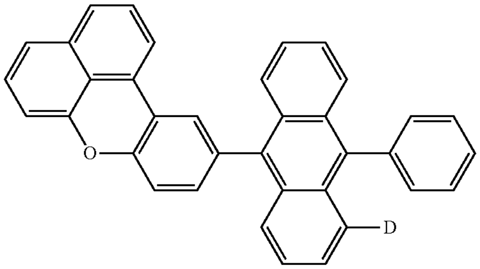
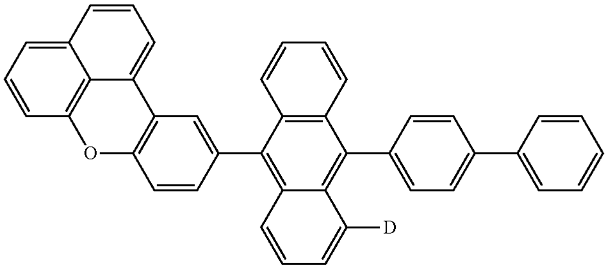
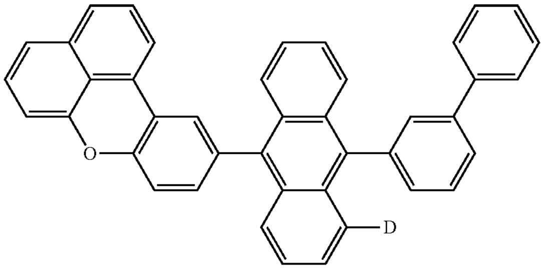
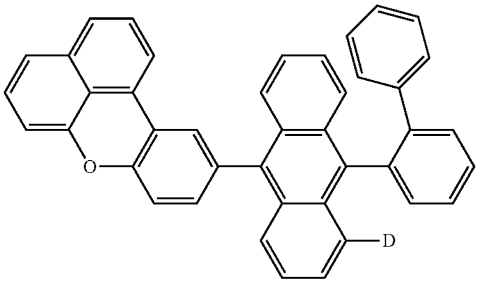

-continued
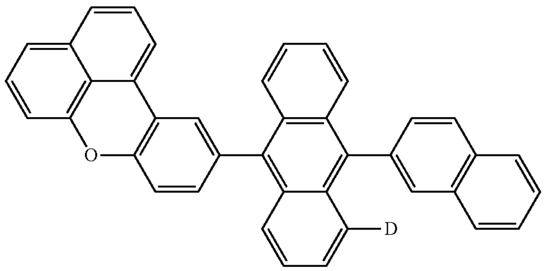
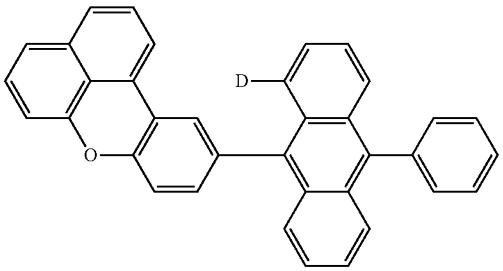
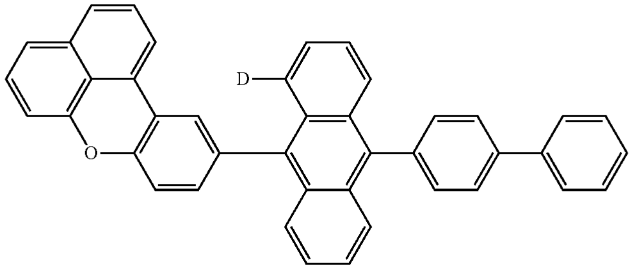
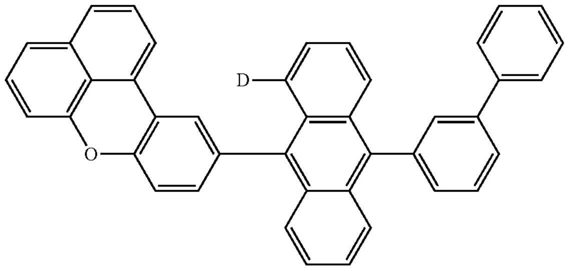
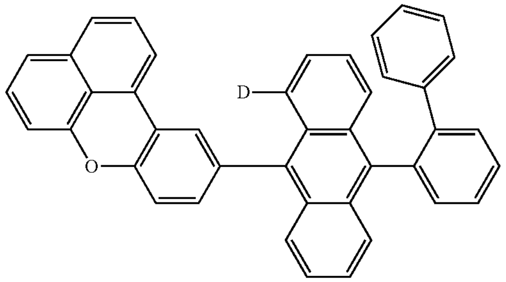
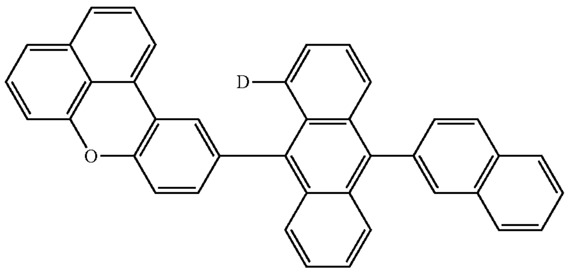
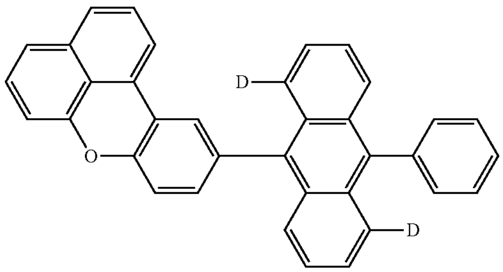
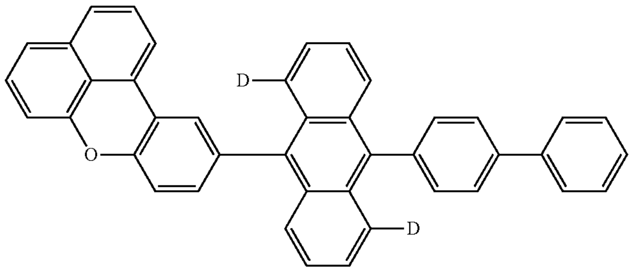
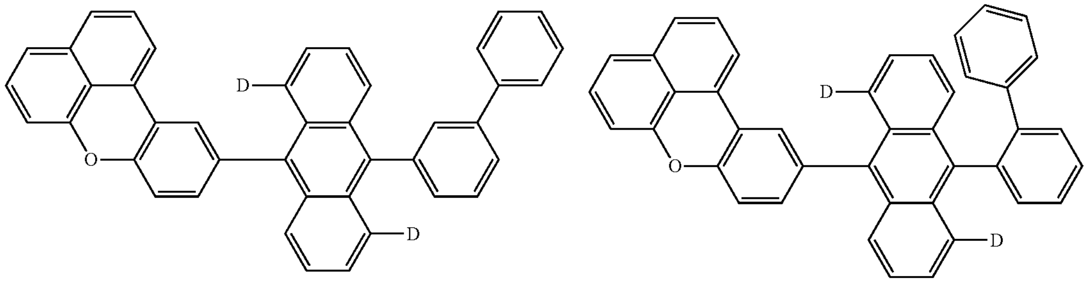

-continued
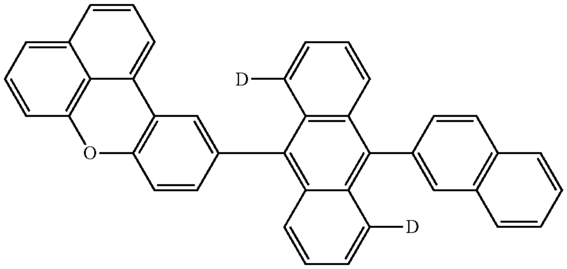
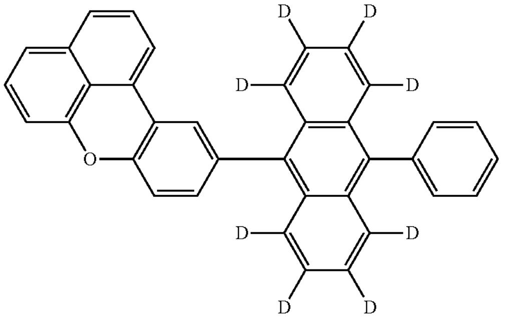
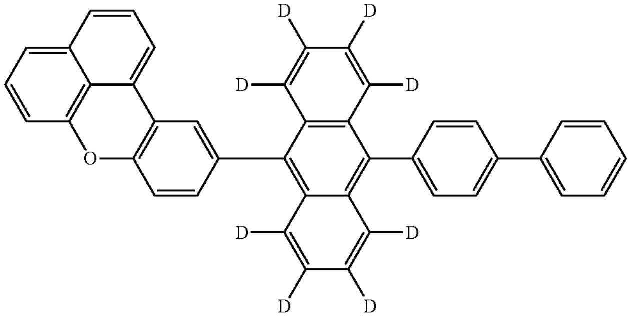
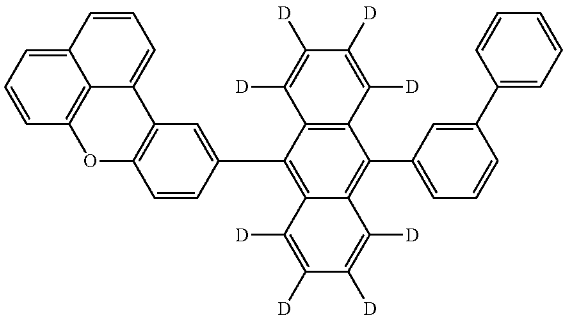
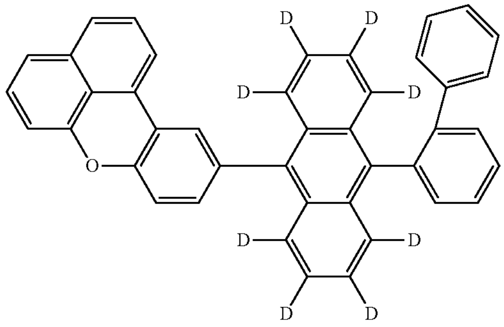
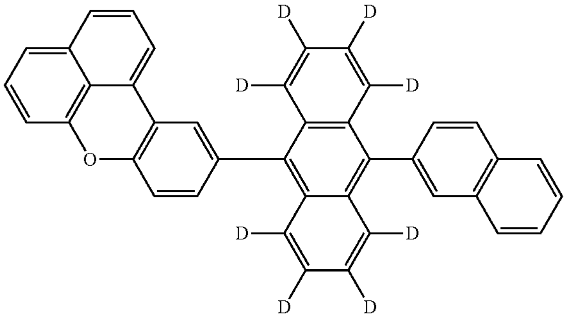
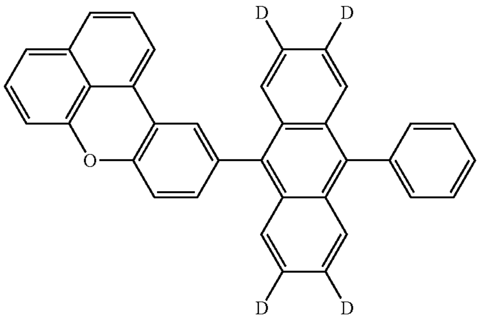
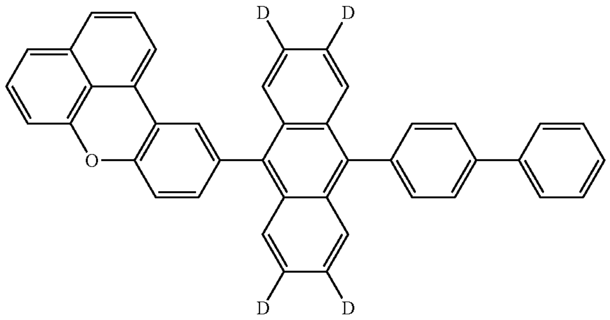

-continued
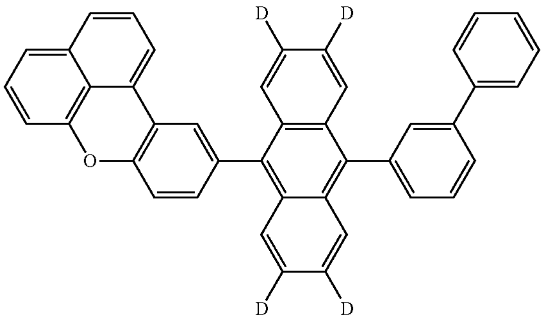
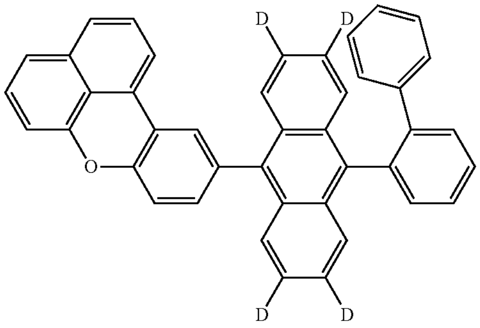
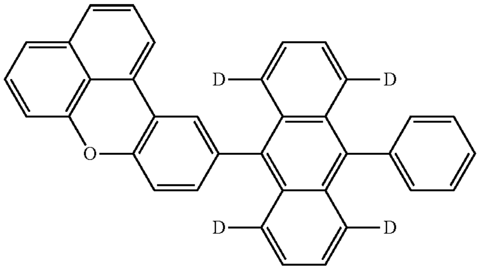
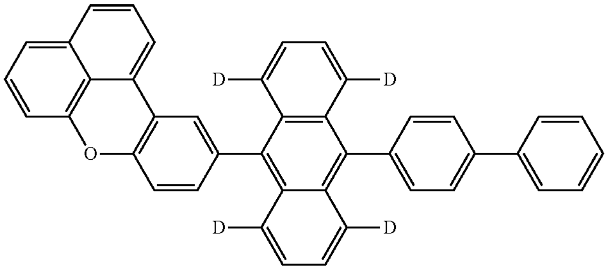
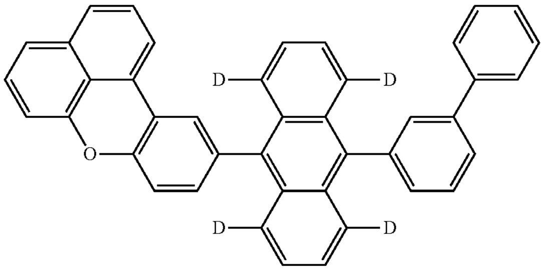
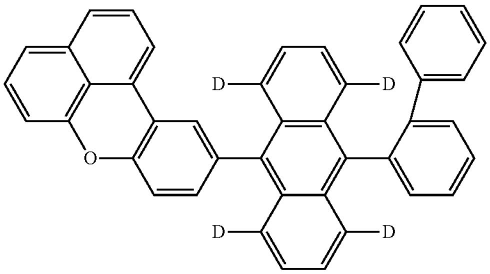
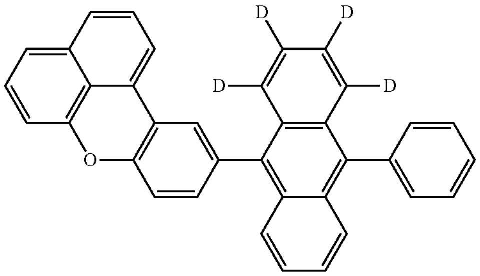
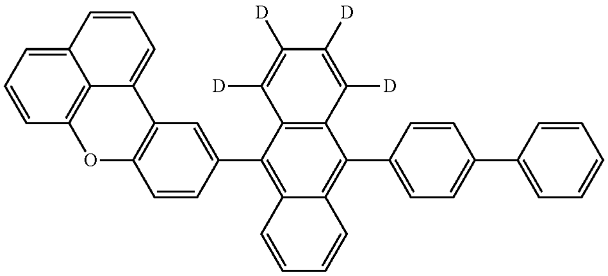
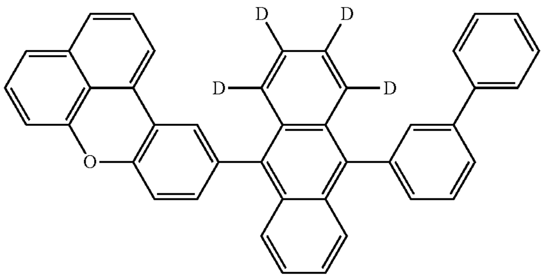
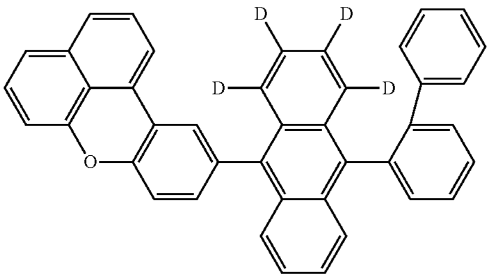

-continued
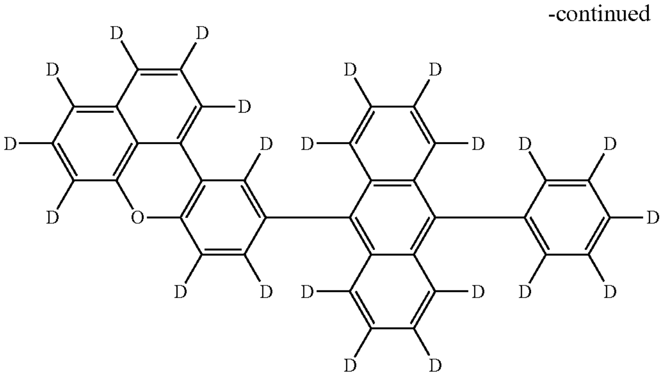
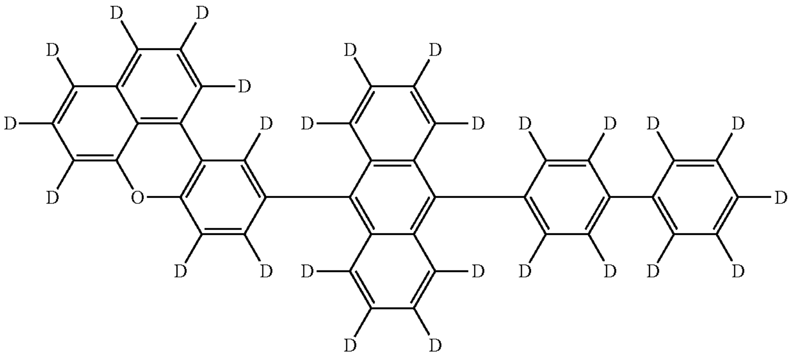
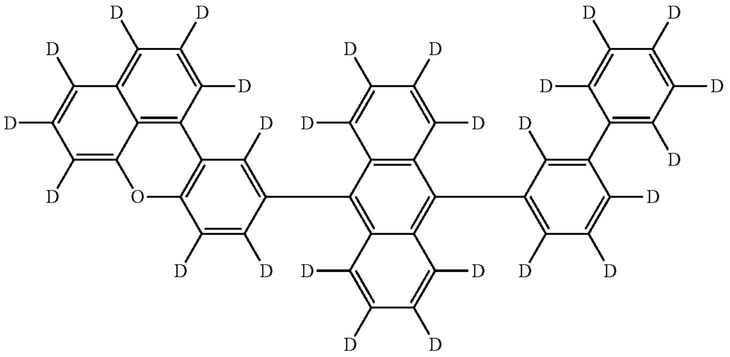
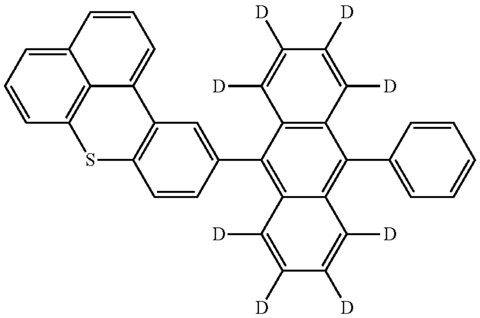
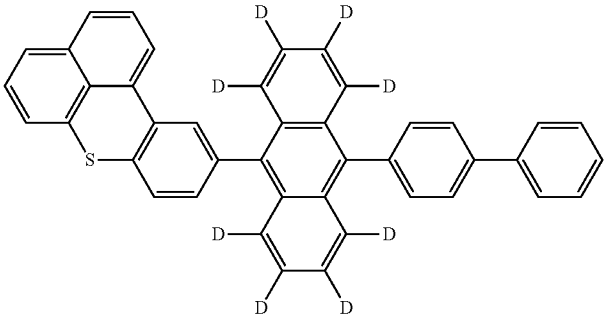
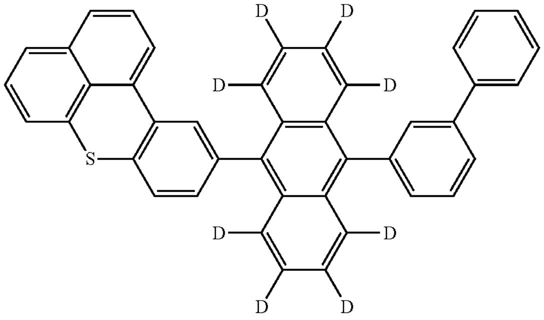
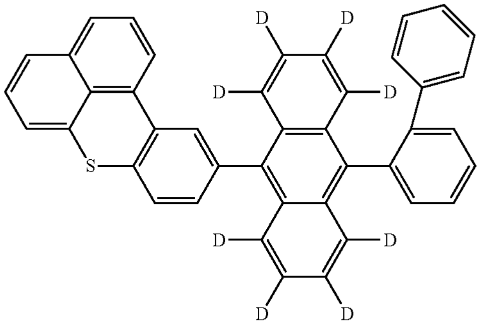

-continued
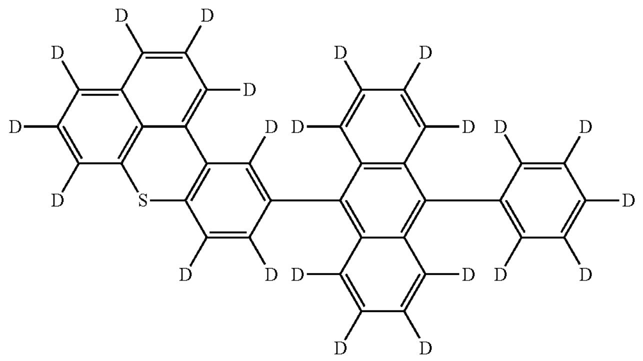
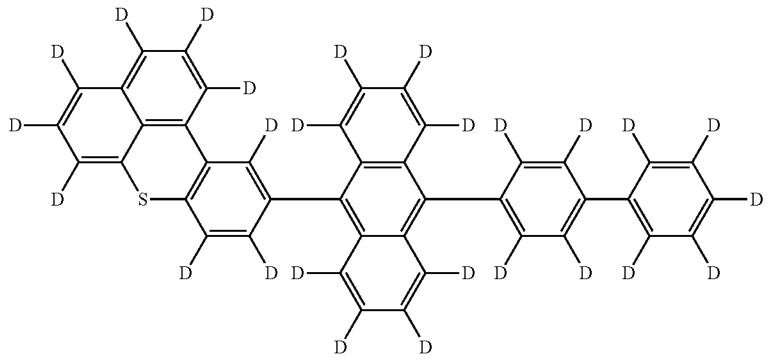
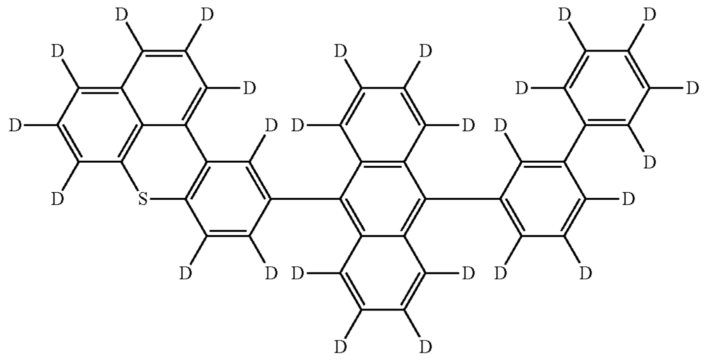
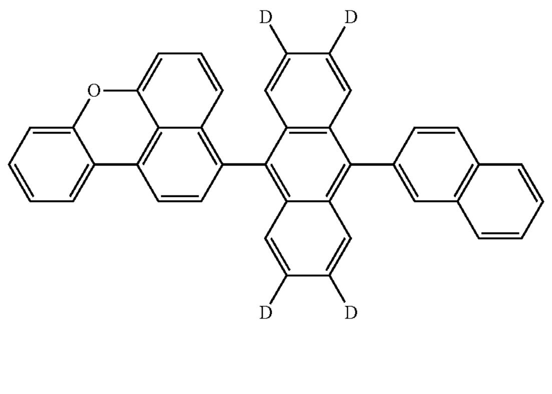
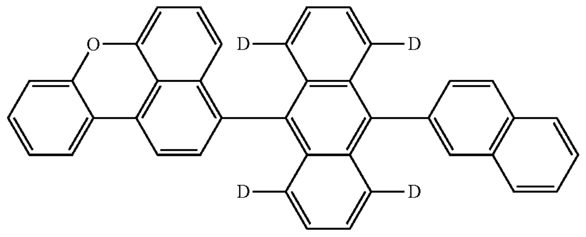

-continued
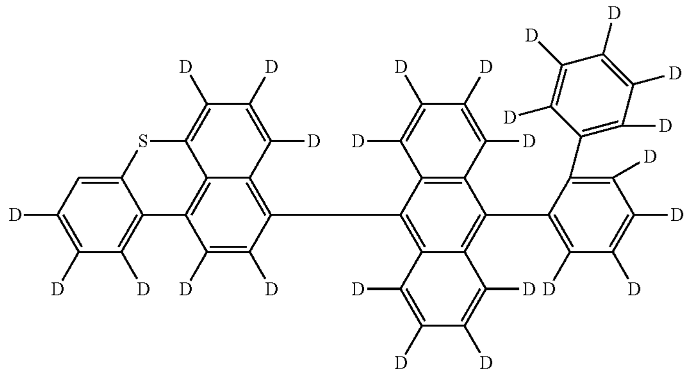
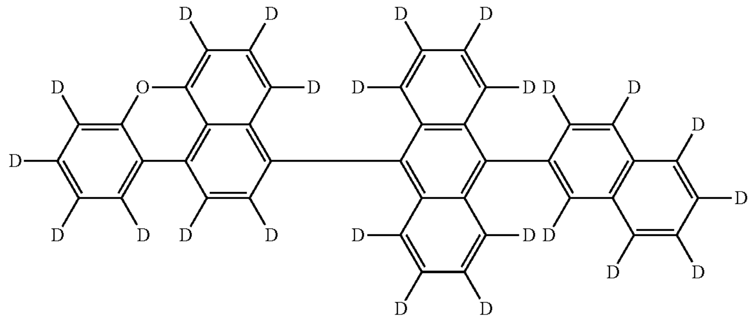
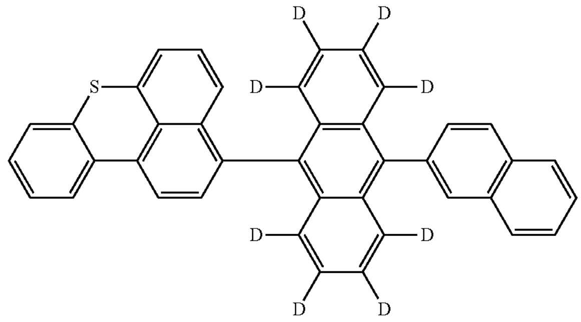
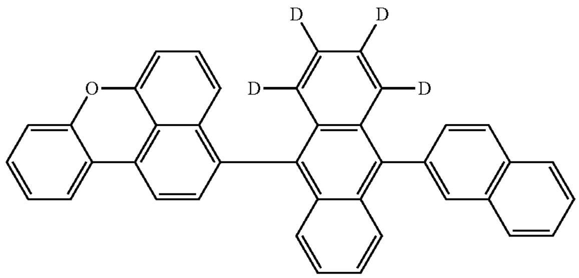
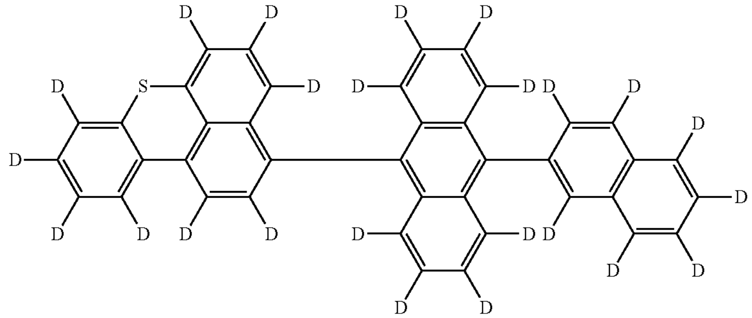
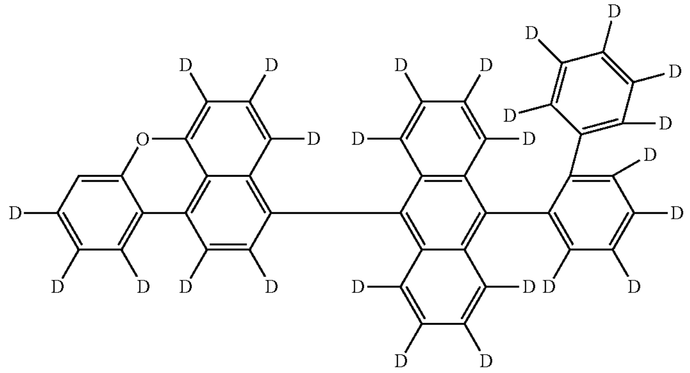

-continued
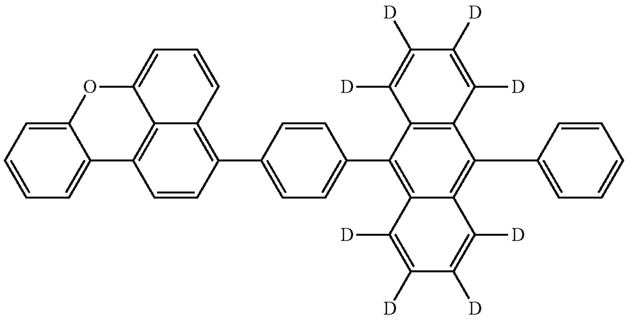
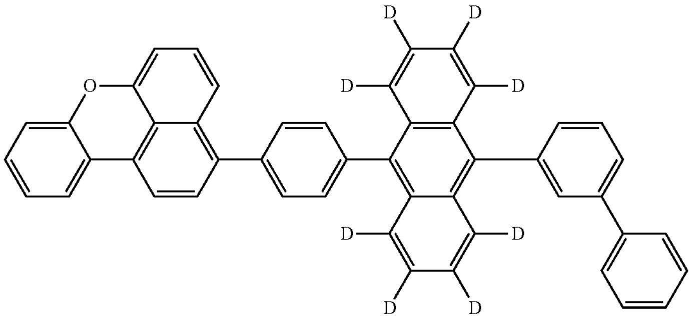
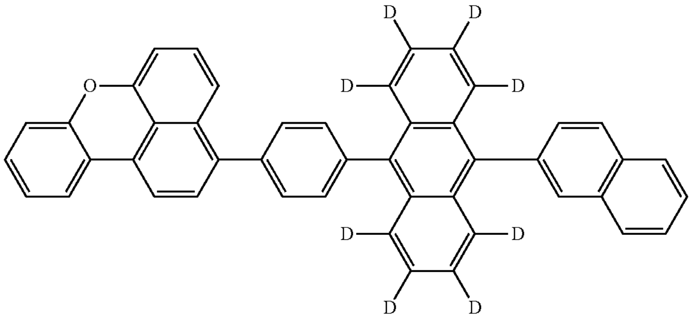
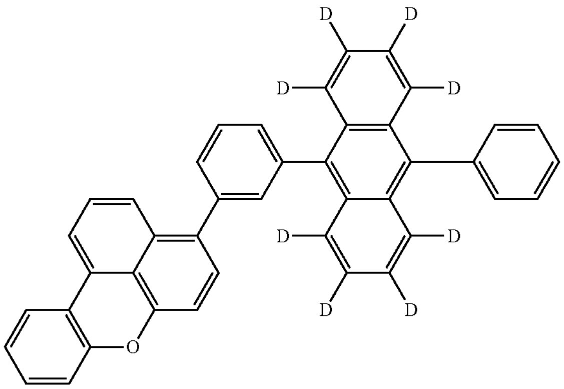
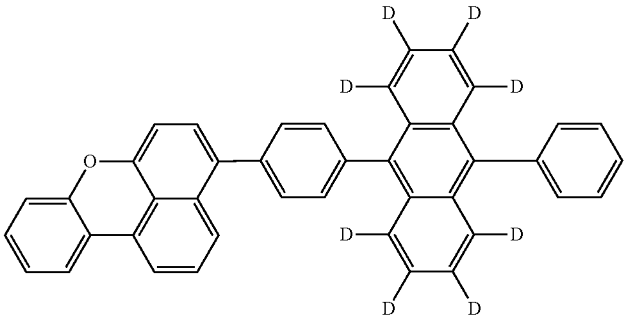

-continued
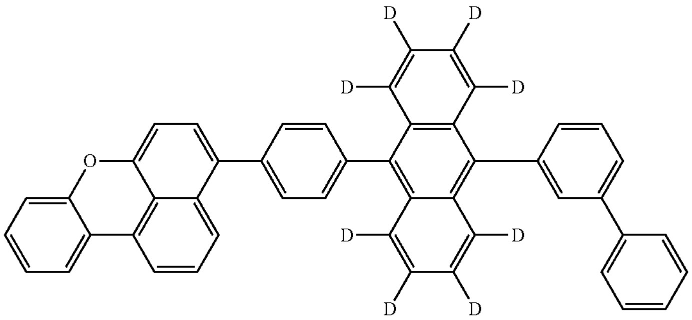
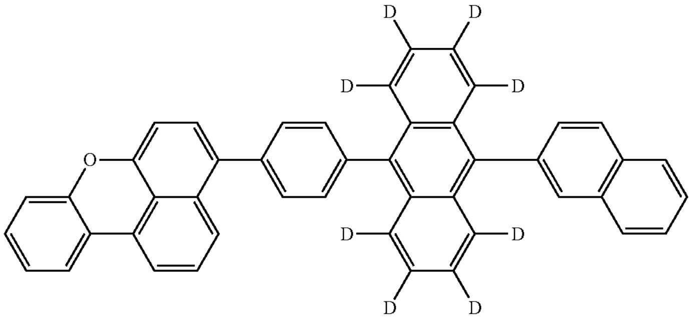
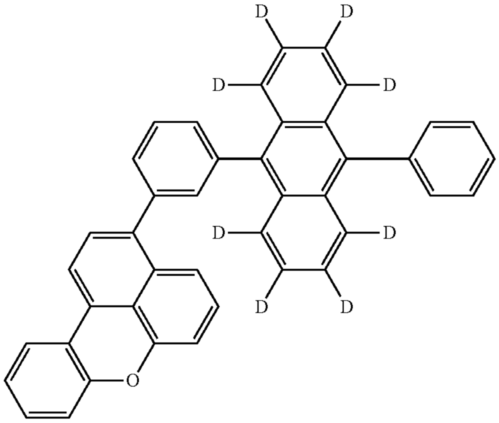
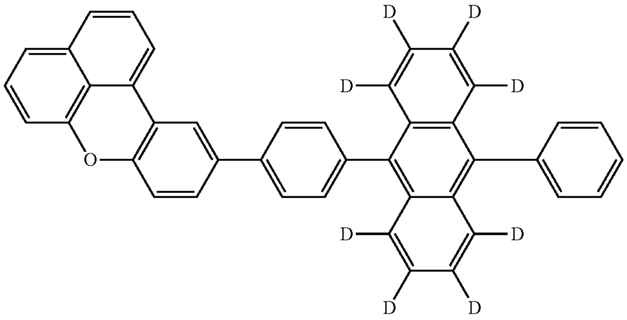
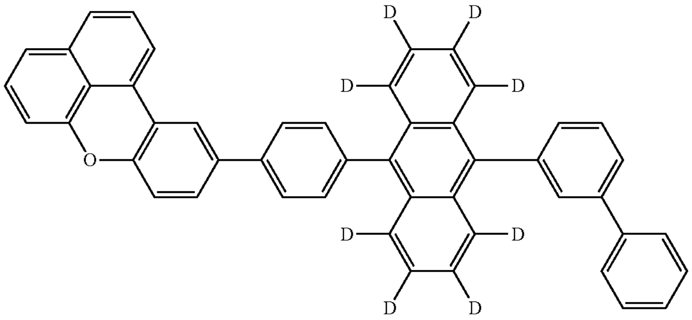
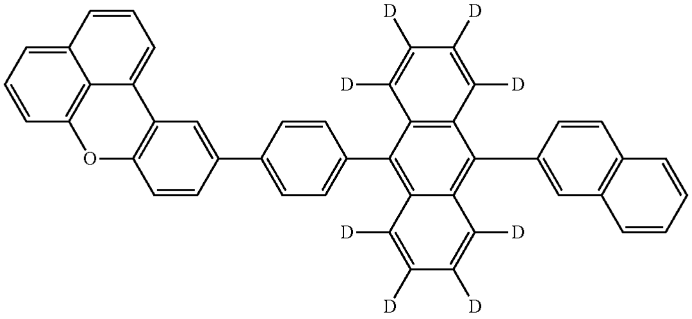

-continued
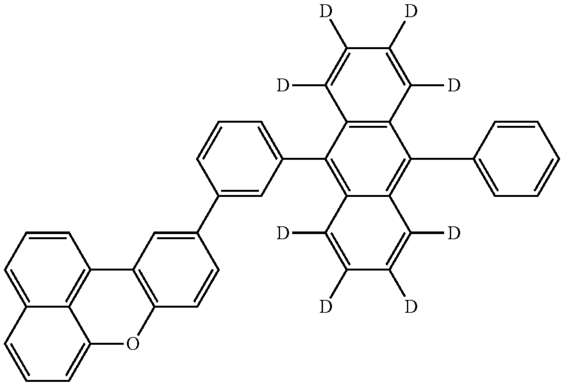
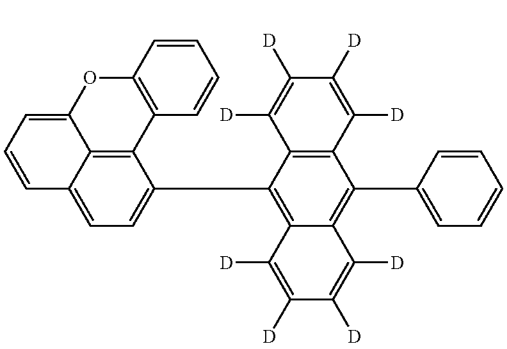
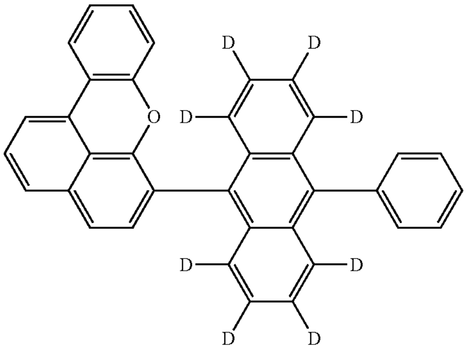
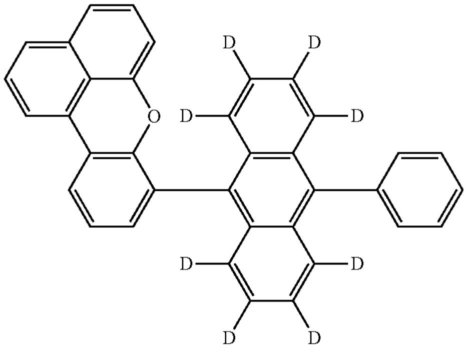
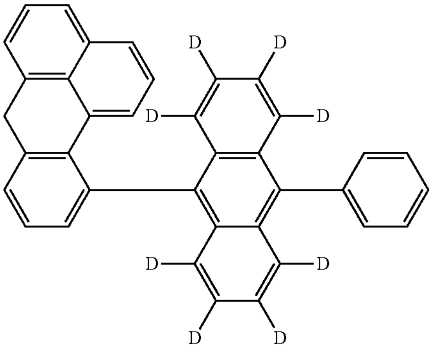
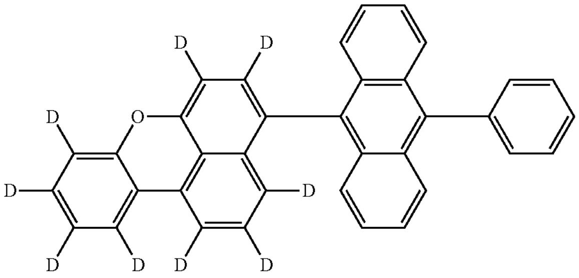
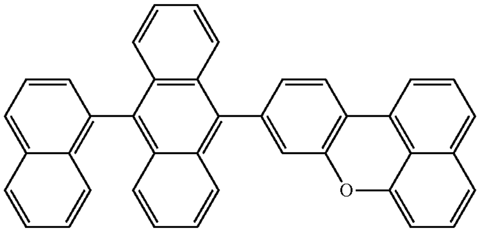
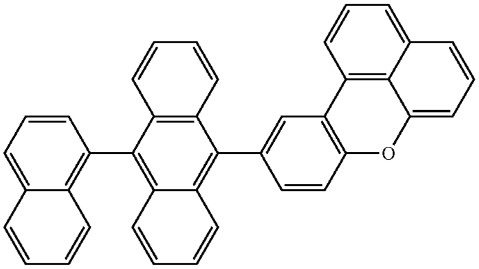

-continued
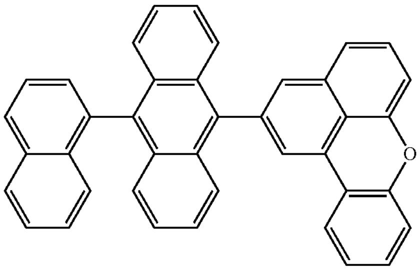
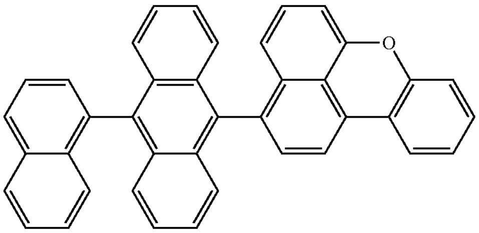
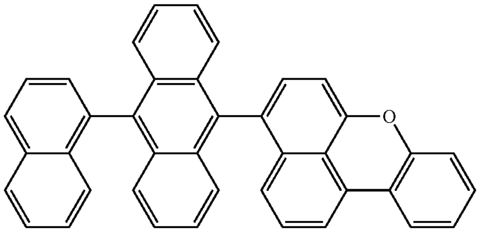
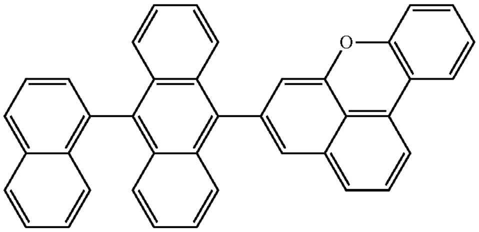
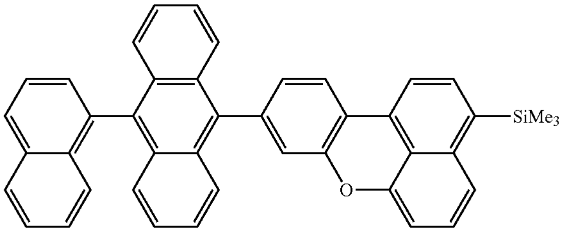
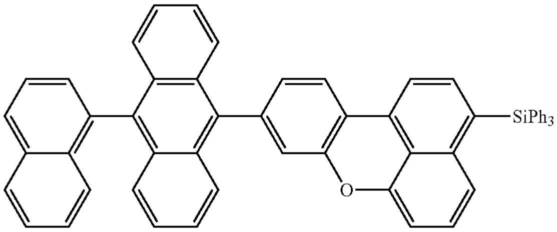
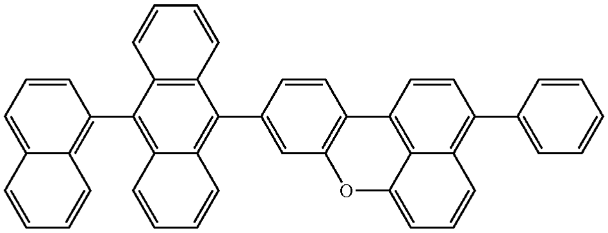
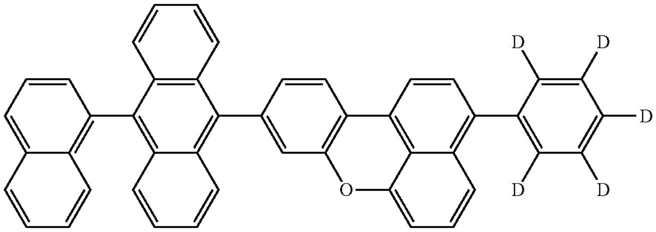
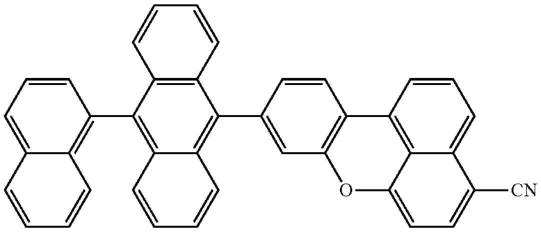
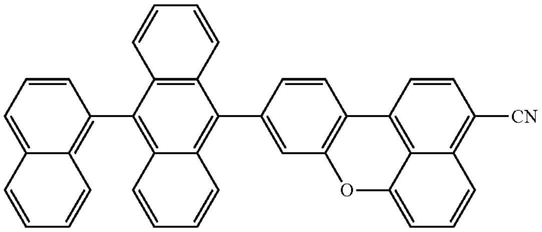
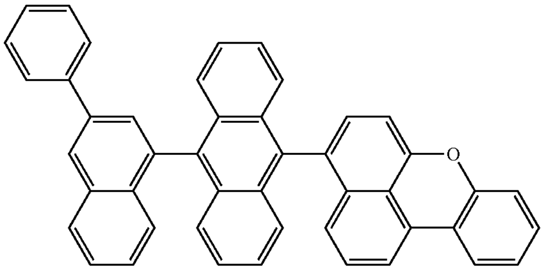
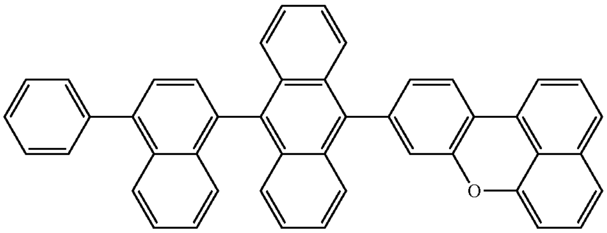

-continued
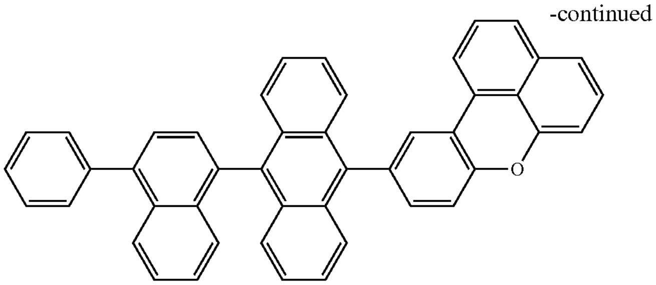
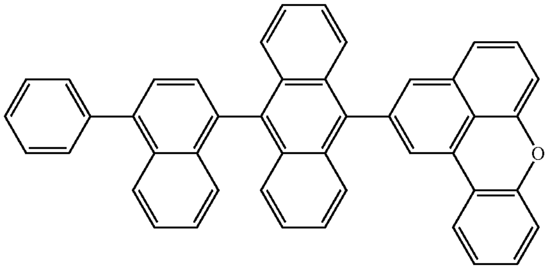
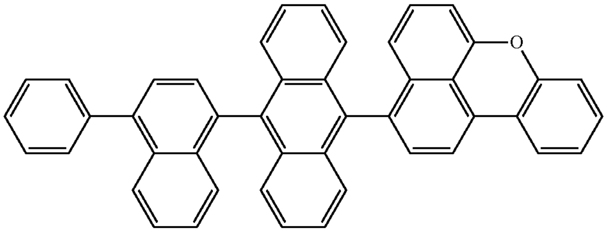
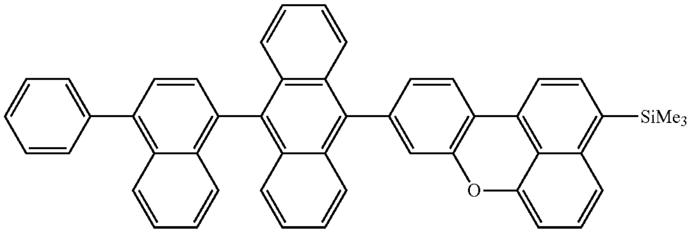
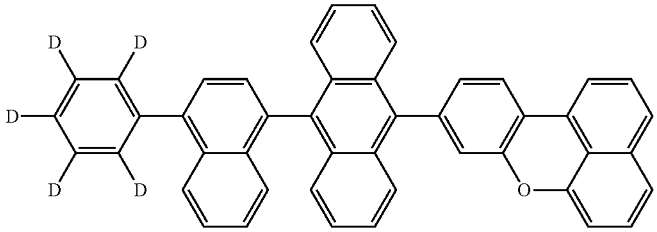
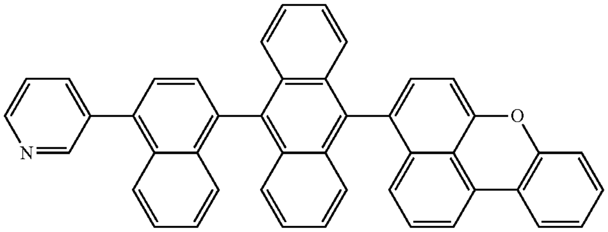
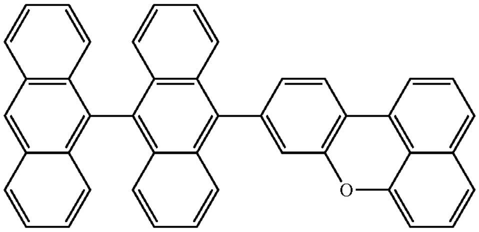
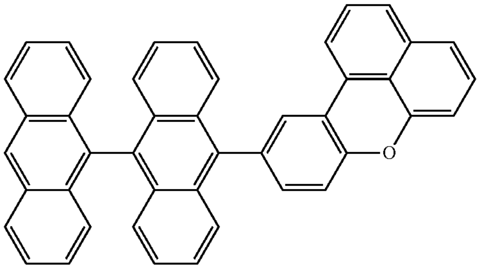
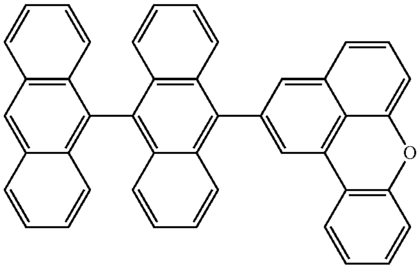
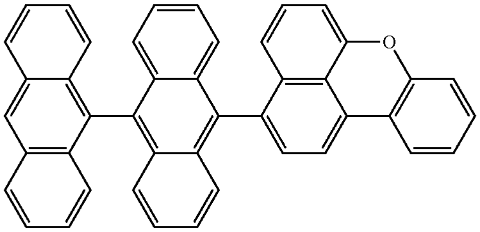
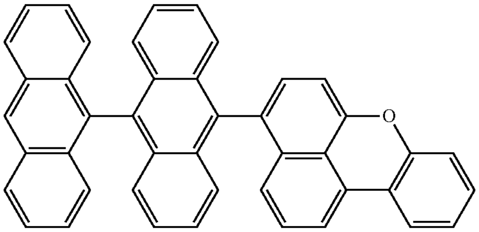

-continued
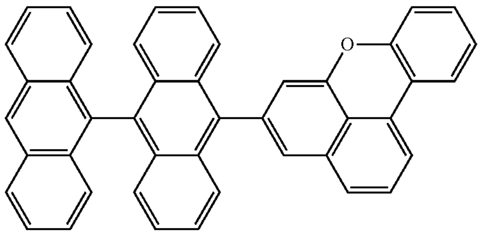
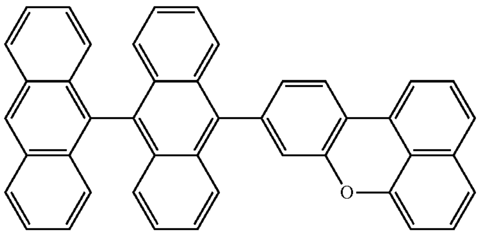
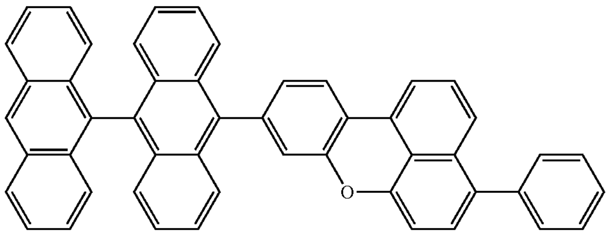
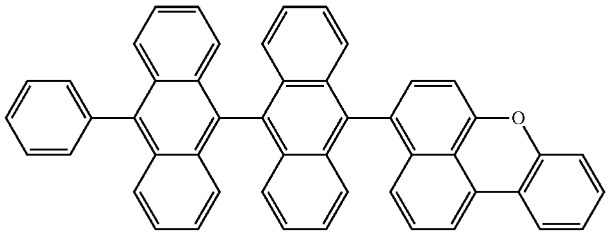
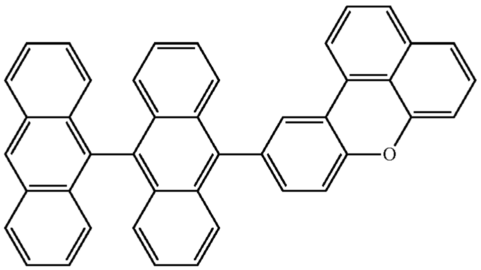
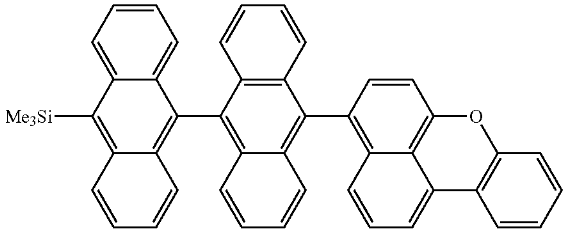
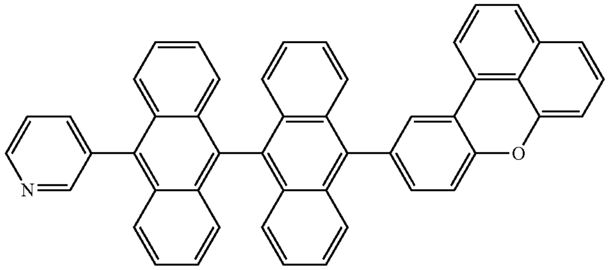
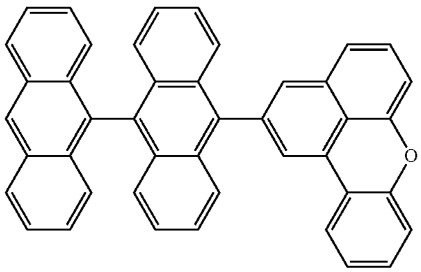
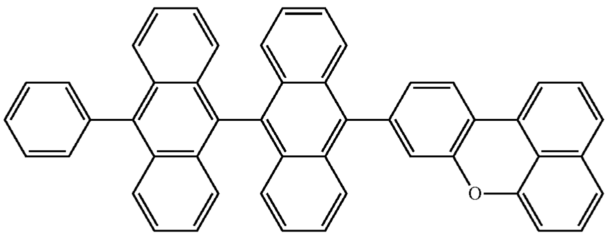
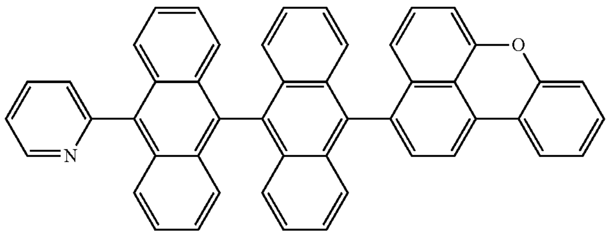
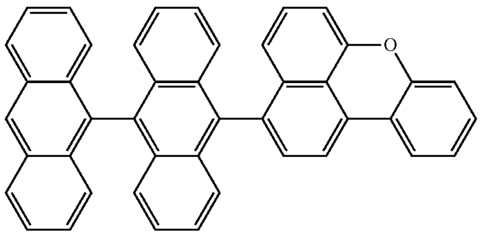

-continued
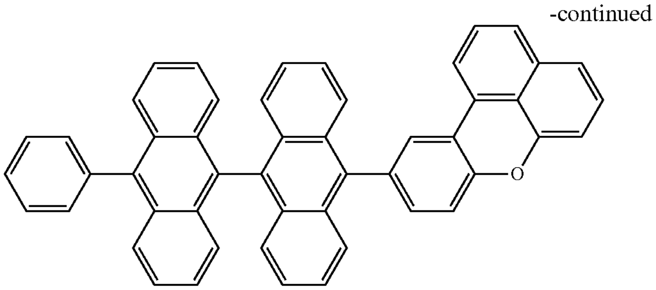
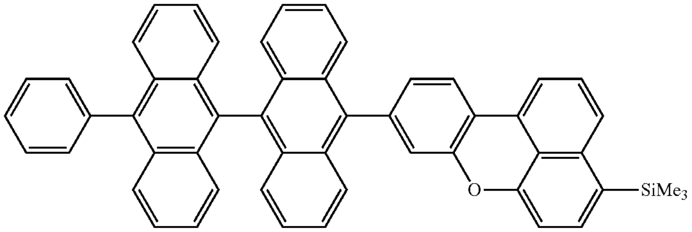
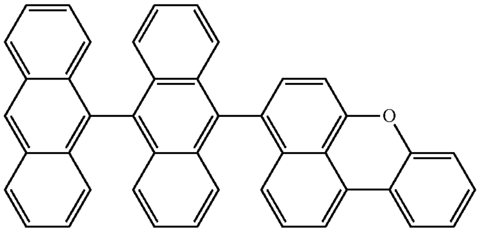
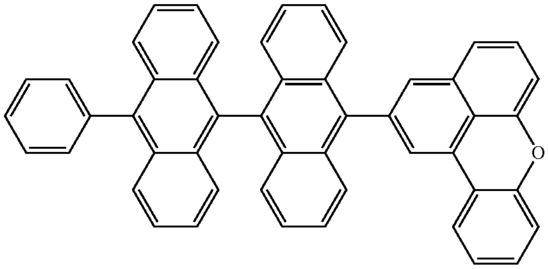
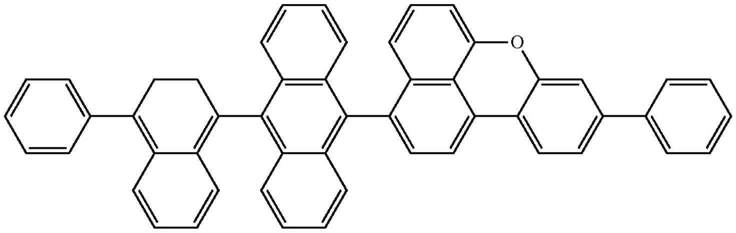
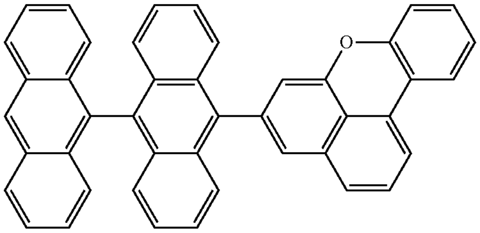
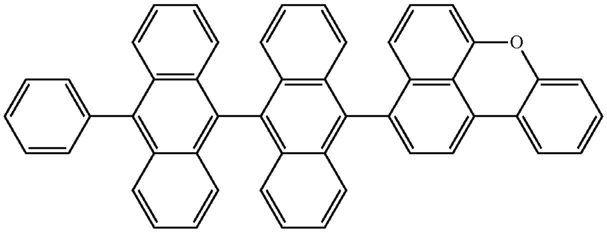
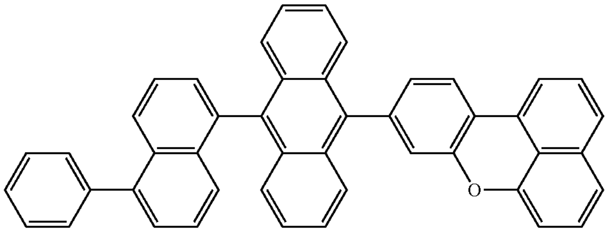
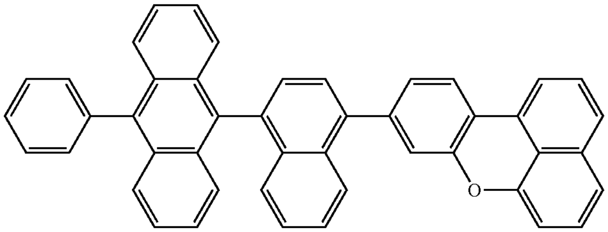

-continued
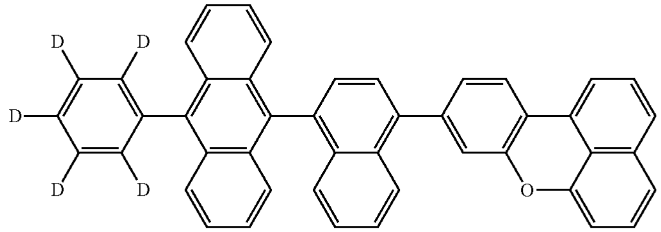
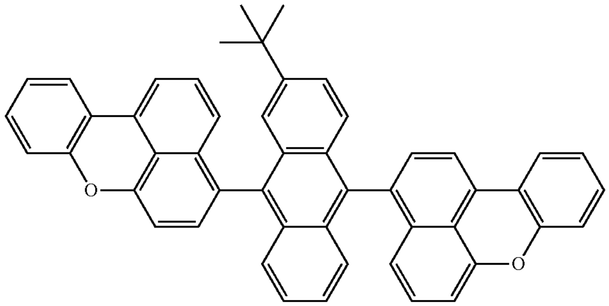
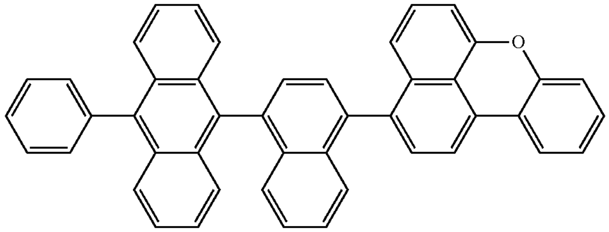
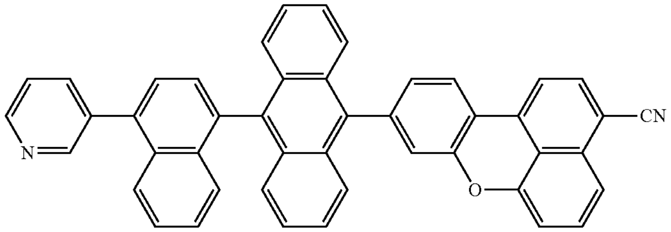
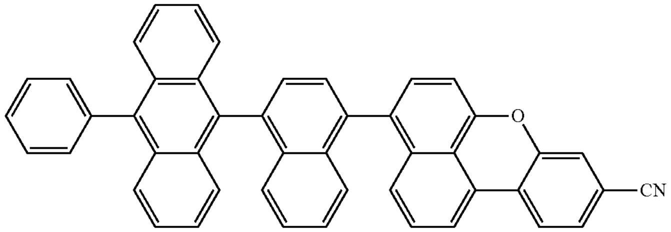
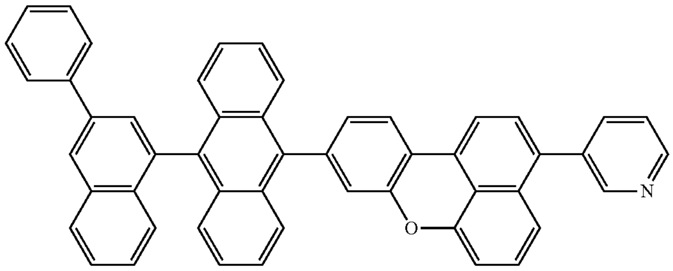

-continued
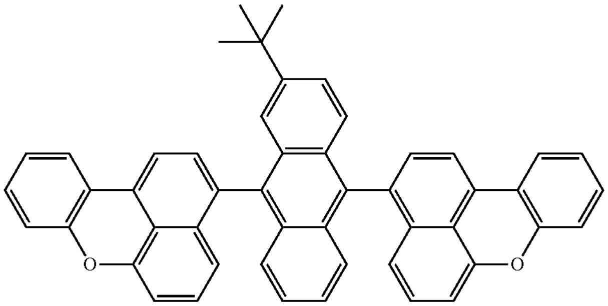
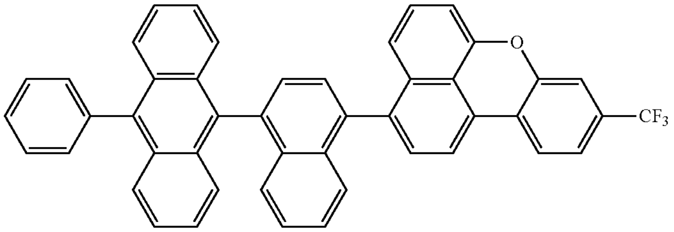
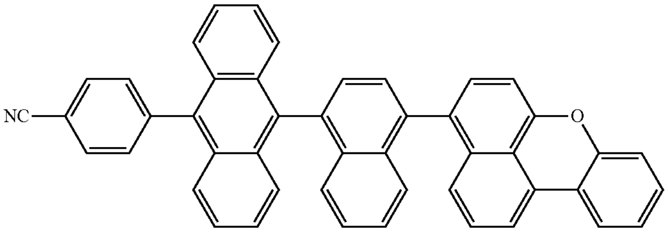
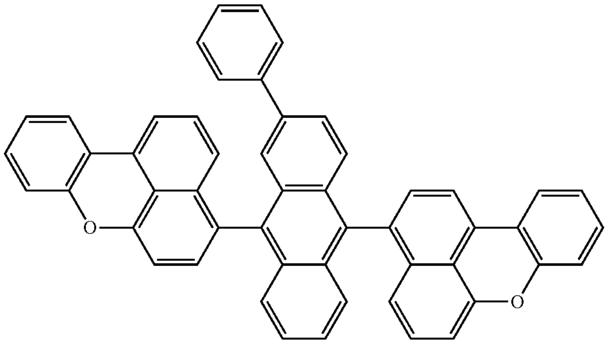
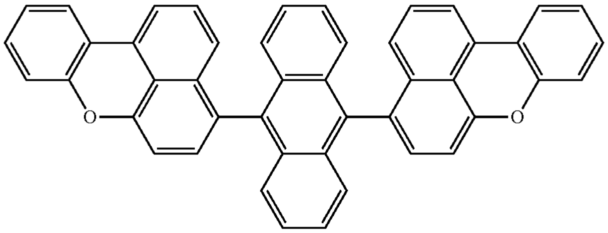
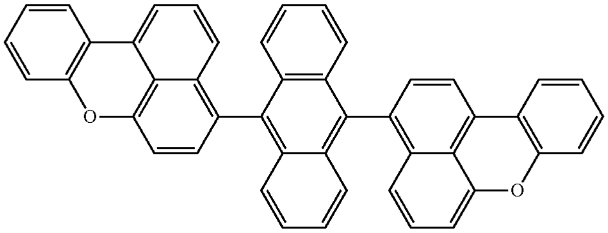

-continued
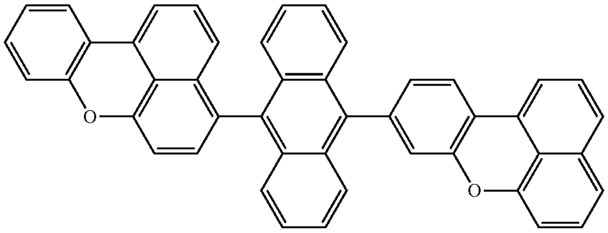
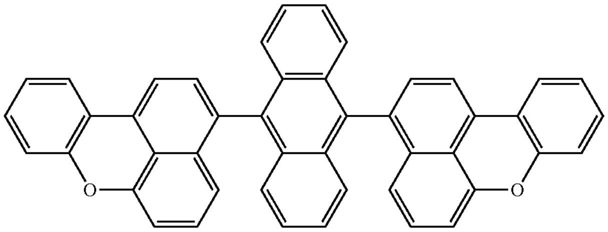
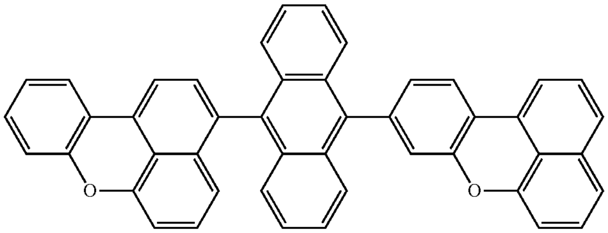
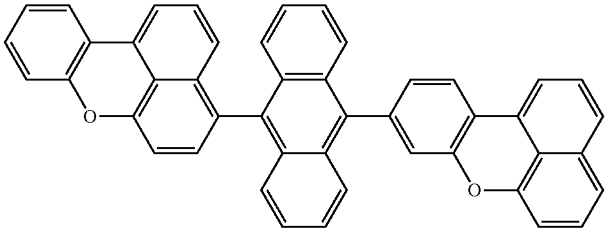
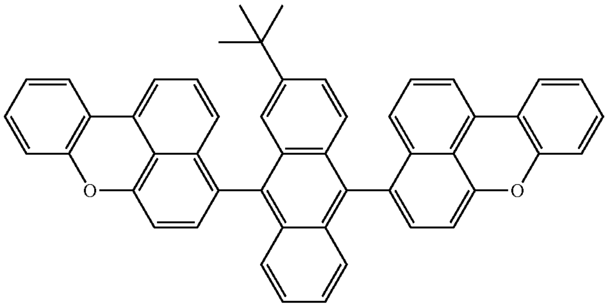
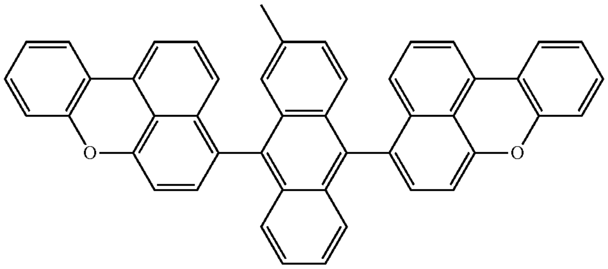

-continued
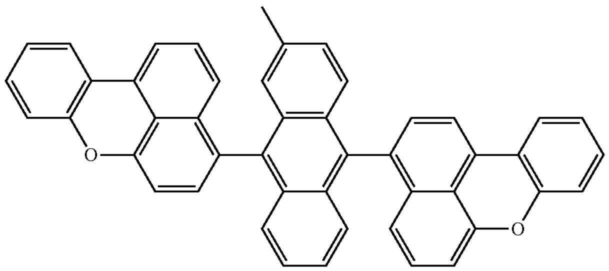
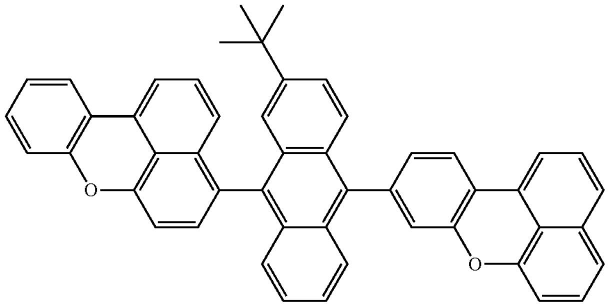
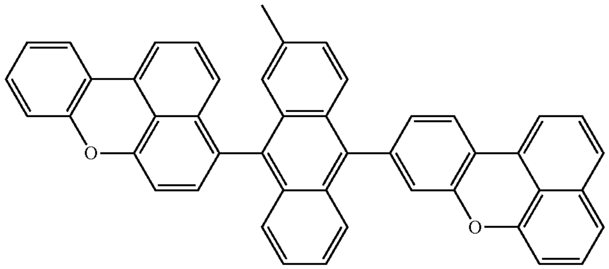
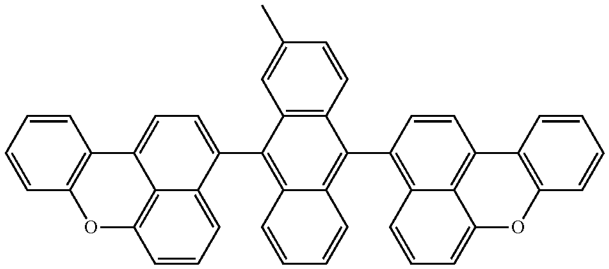
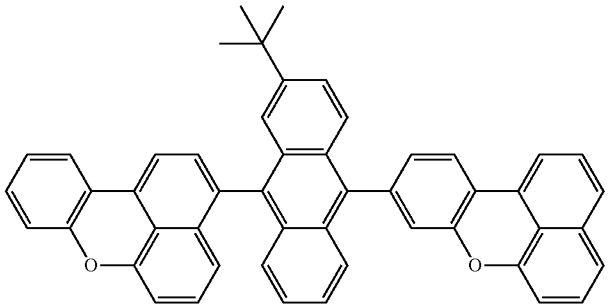
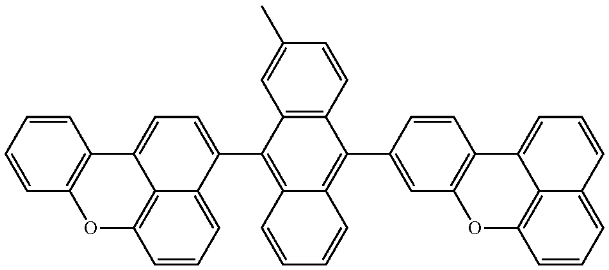

-continued
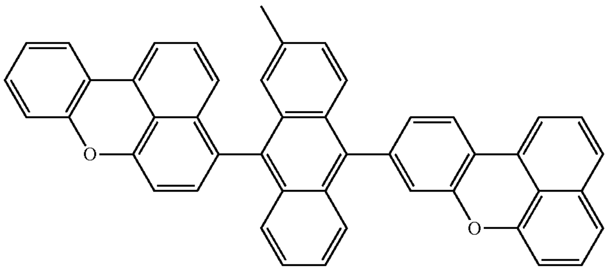
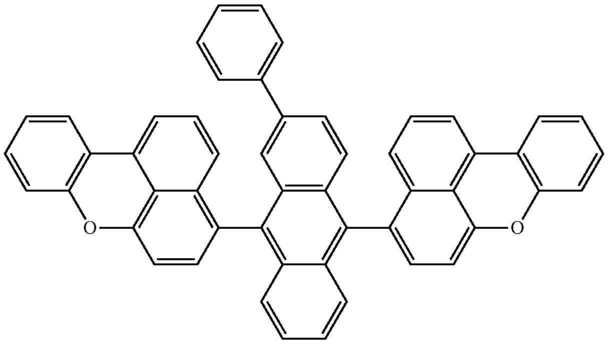
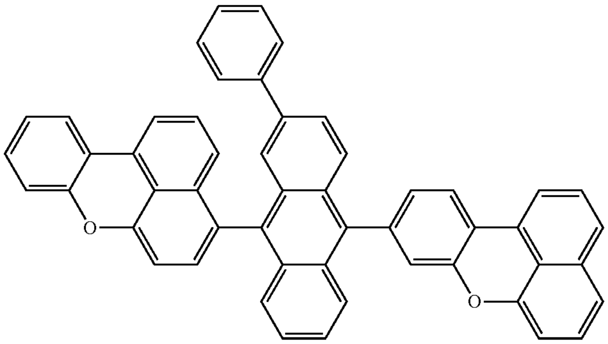
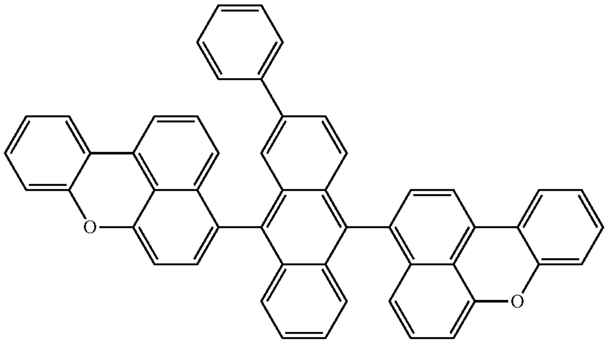

-continued
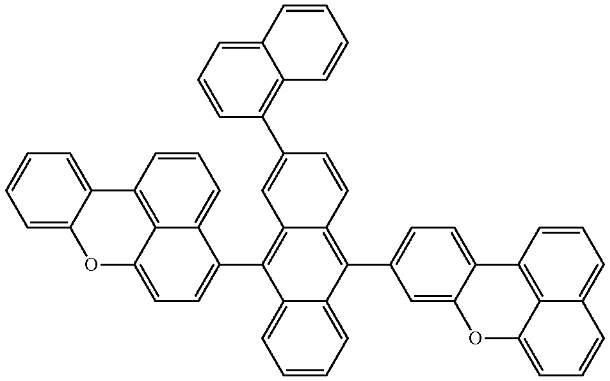
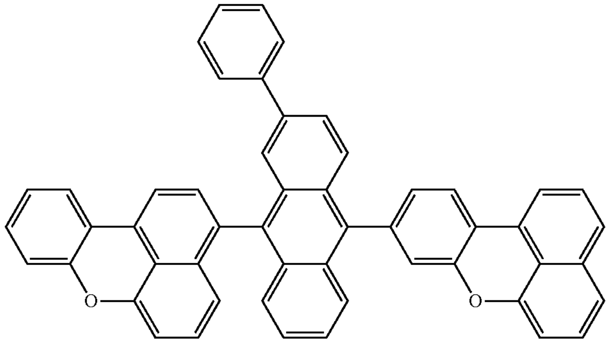
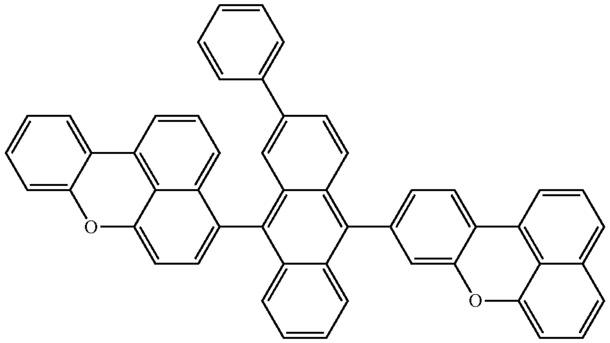
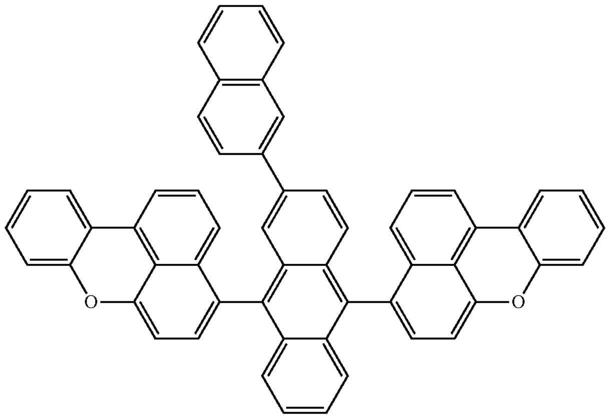

-continued
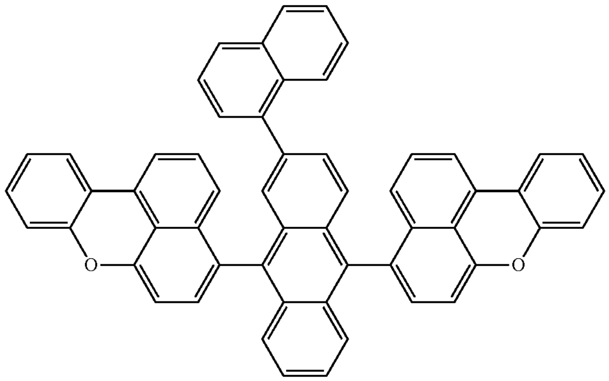
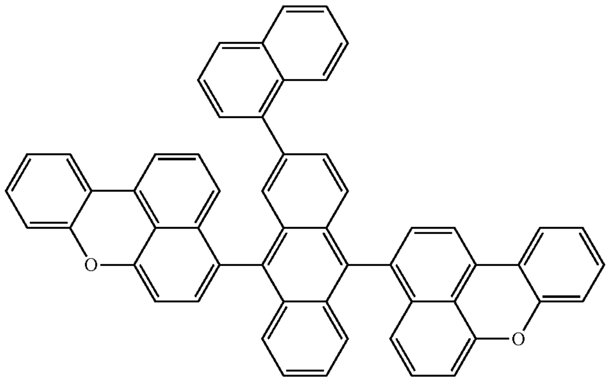
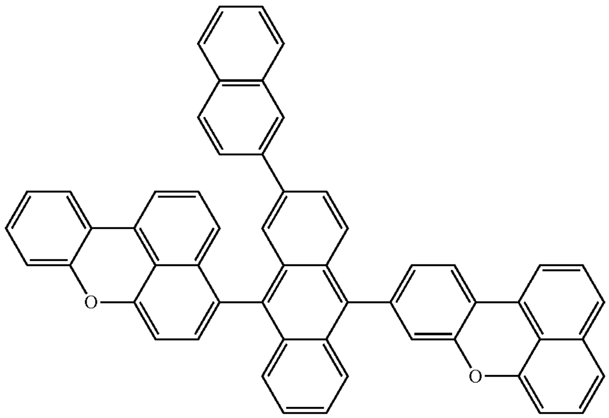
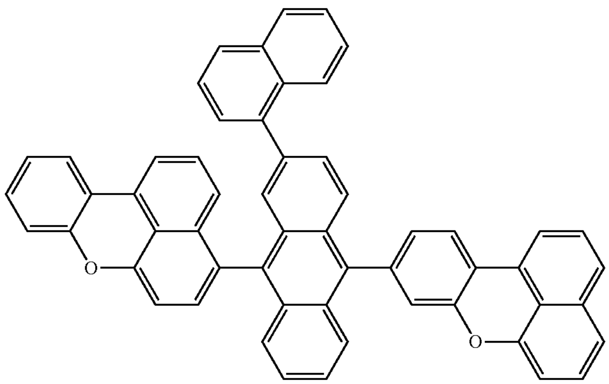

-continued
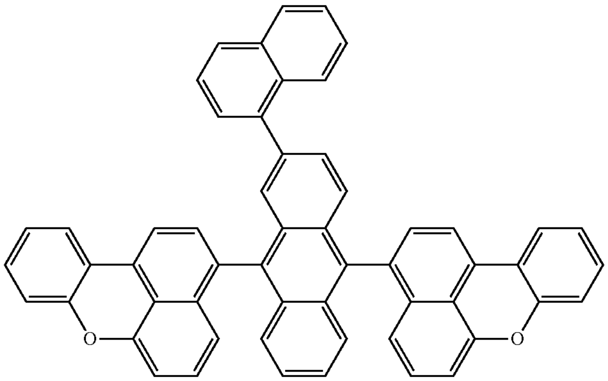
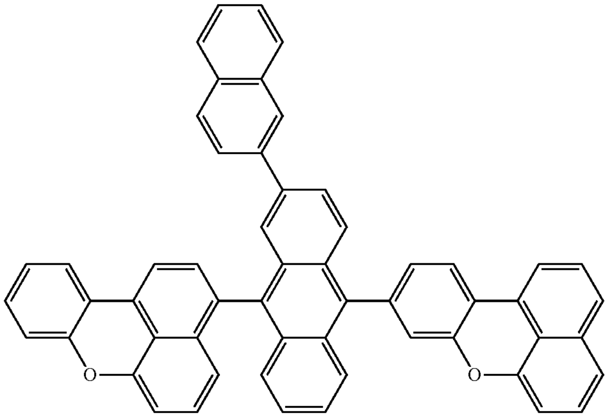
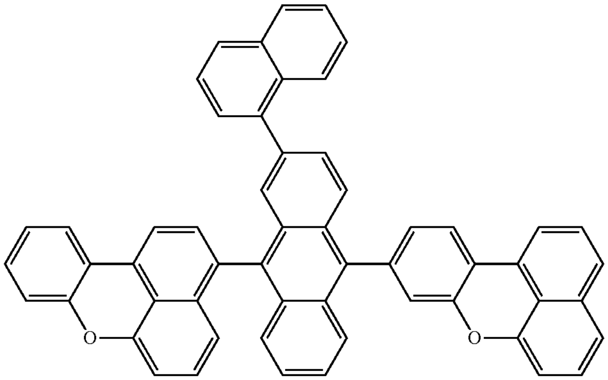
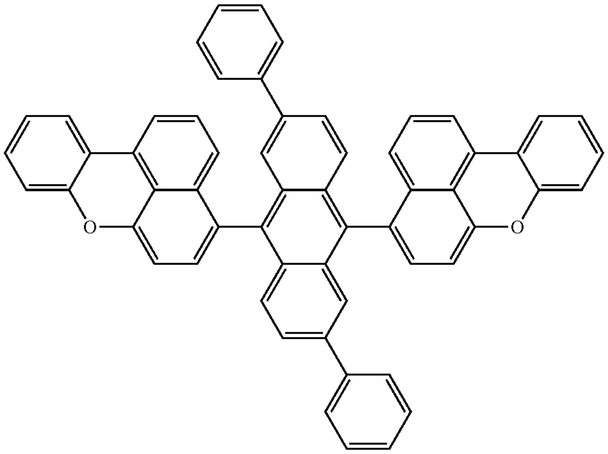

-continued
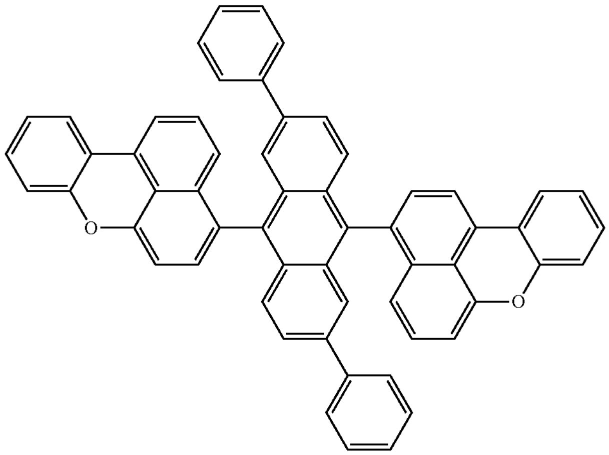
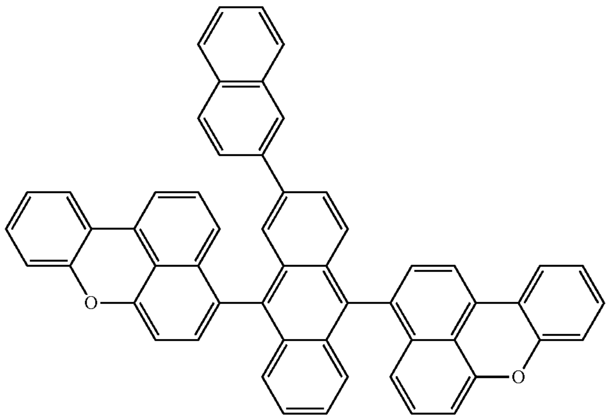
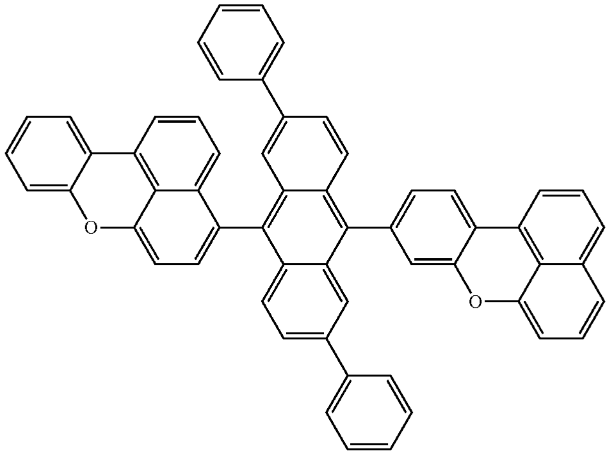

-continued
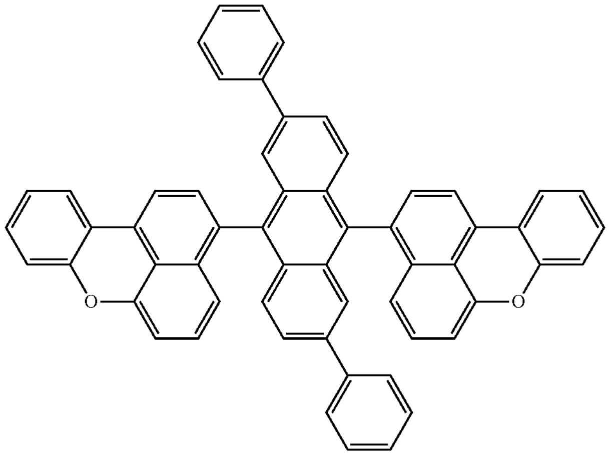
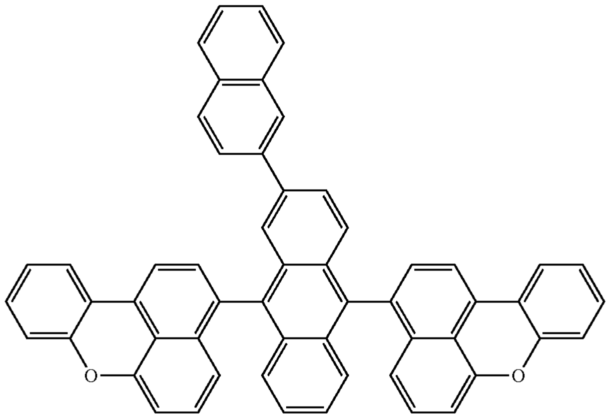
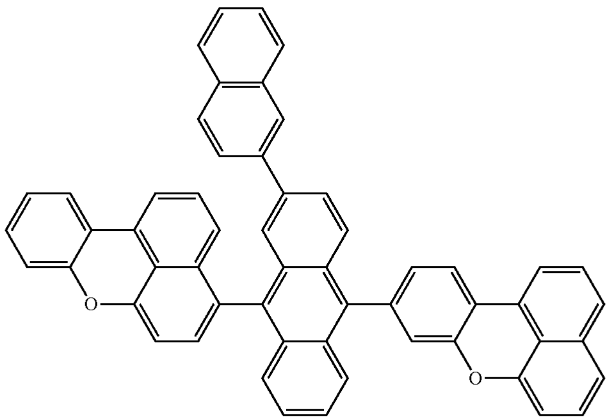

-continued
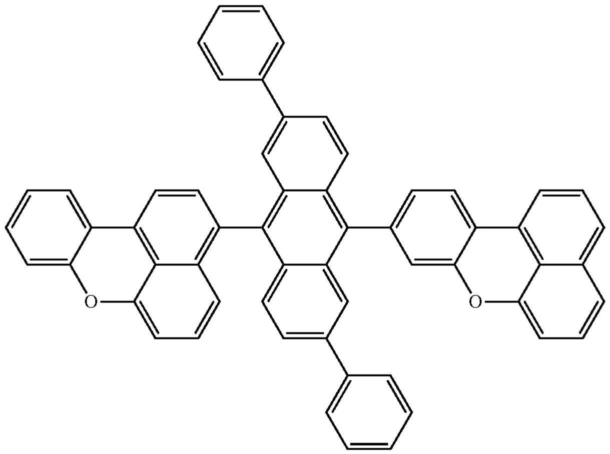
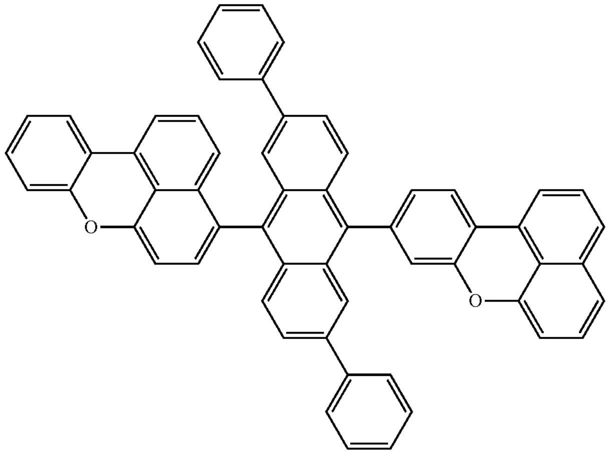
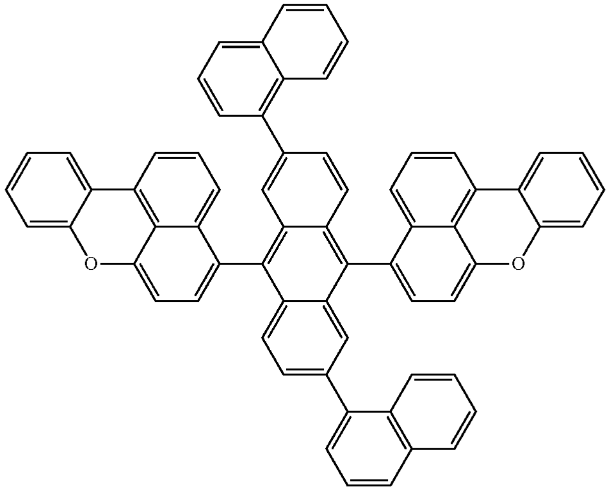

-continued
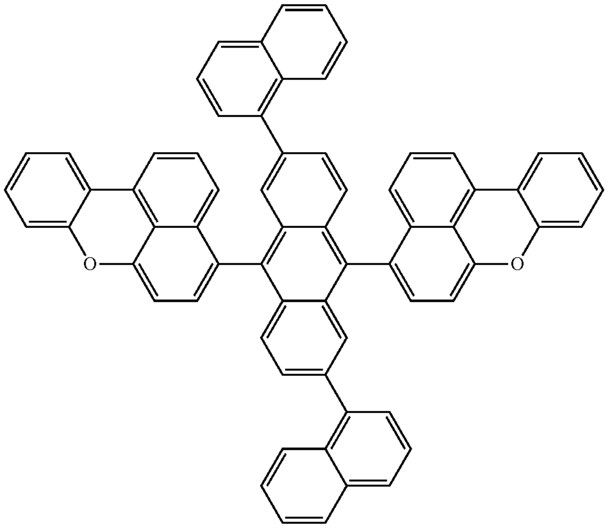
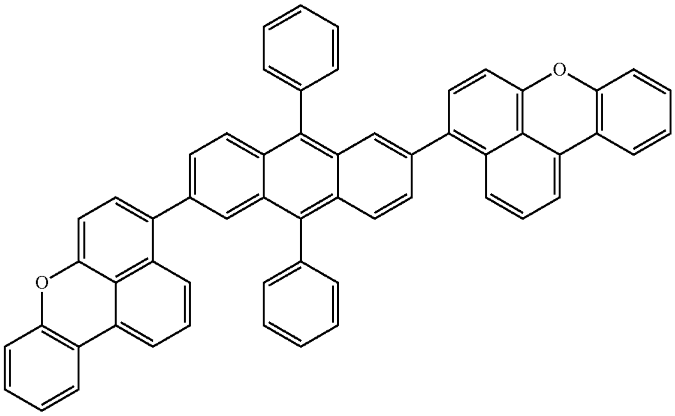
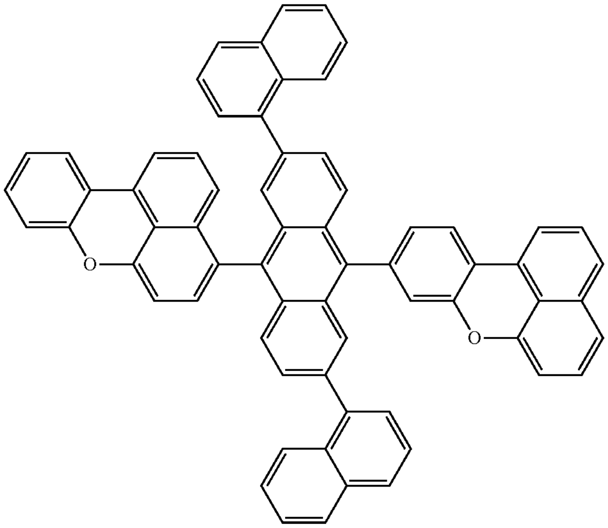

-continued
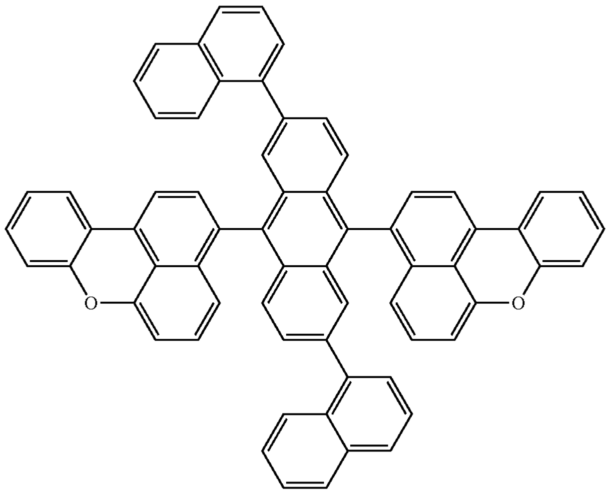
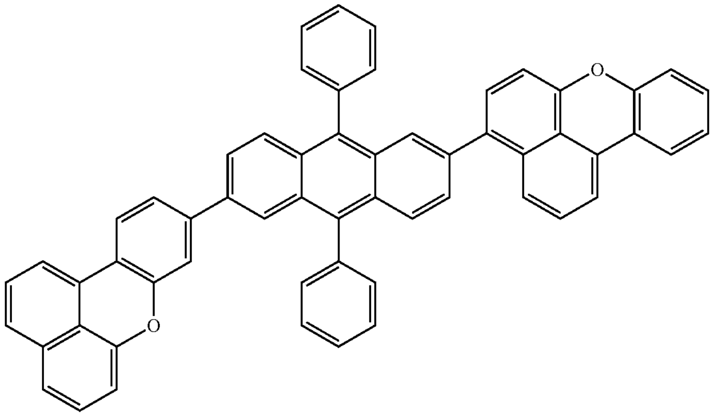
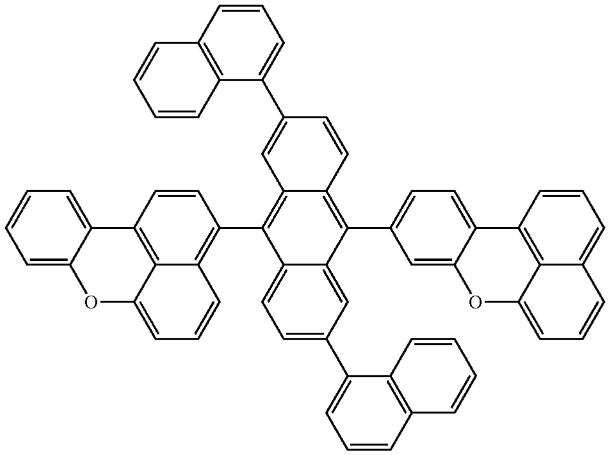

-continued
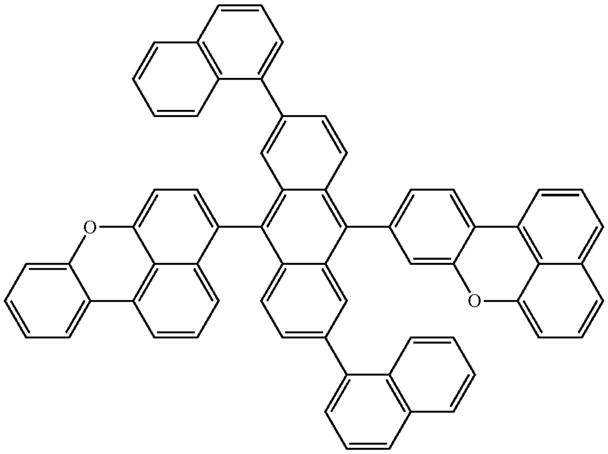
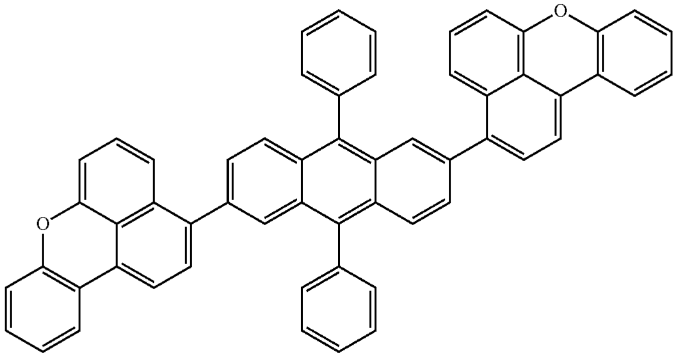
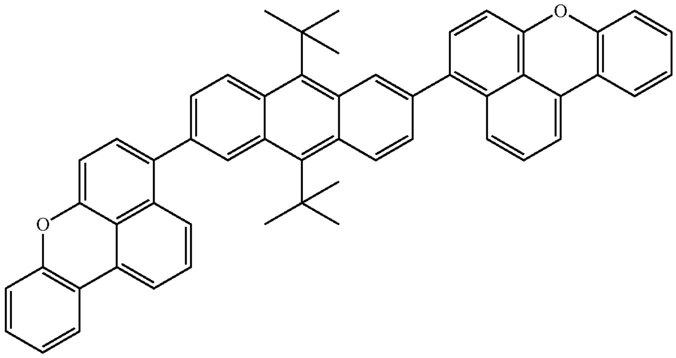
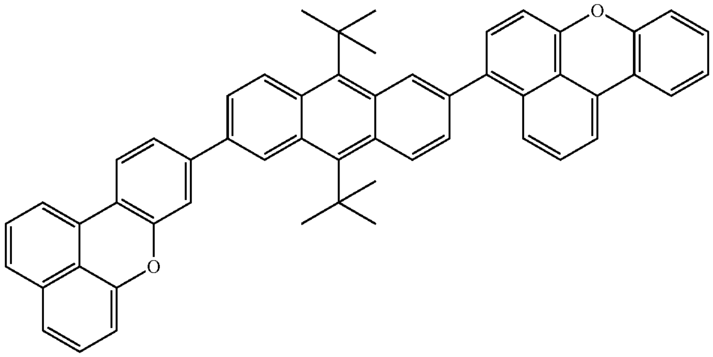

-continued
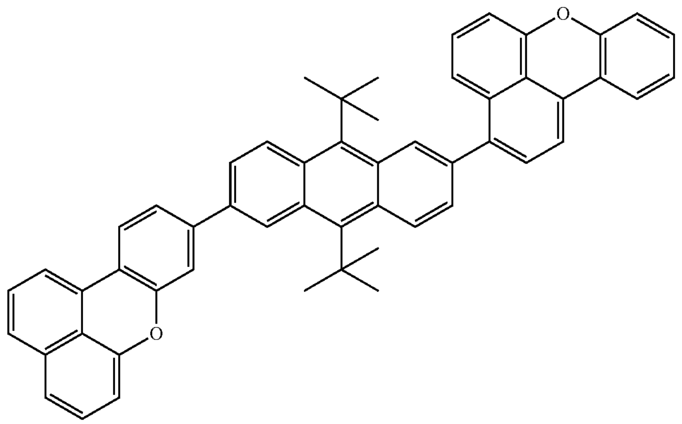
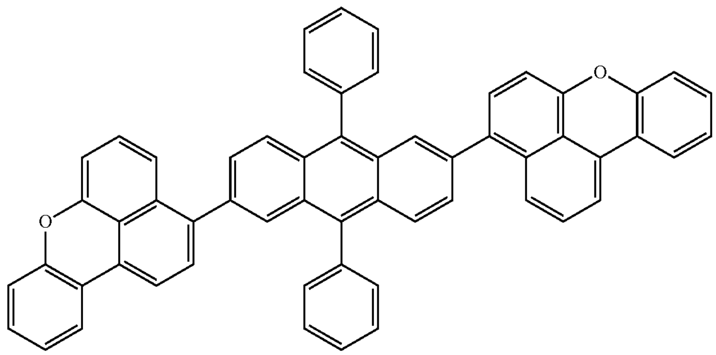
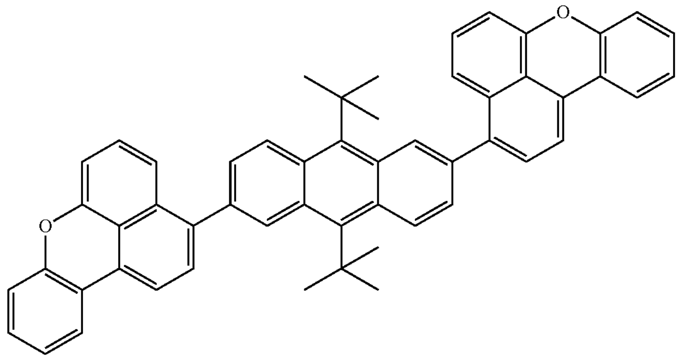
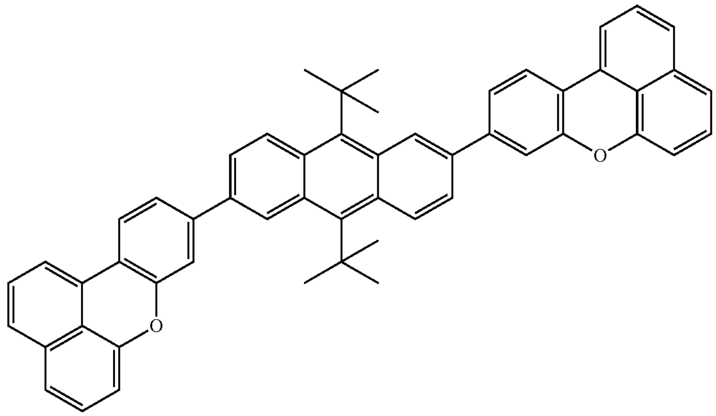

-continued
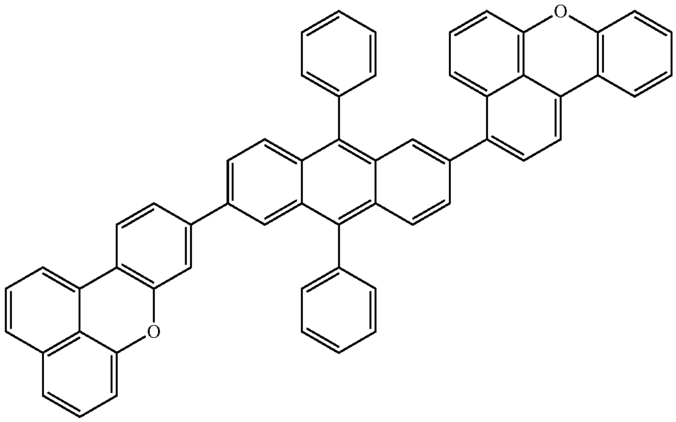
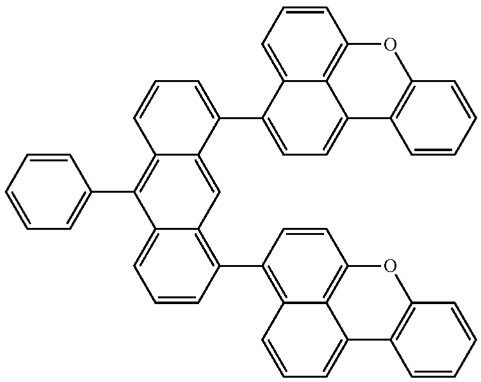
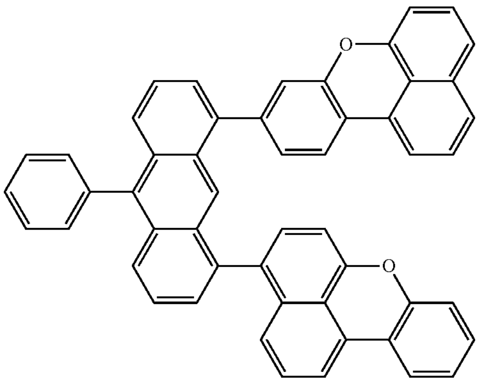
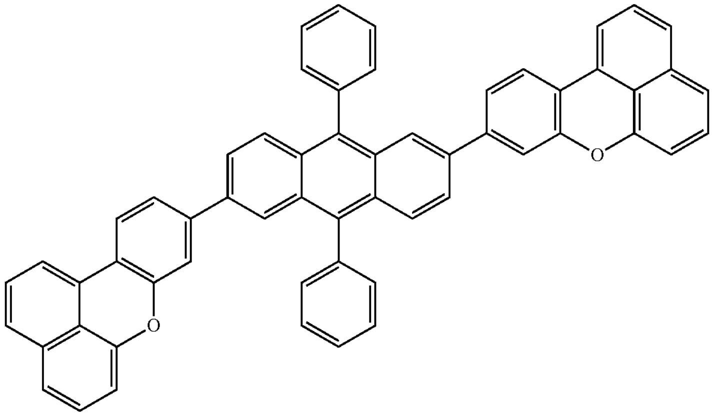
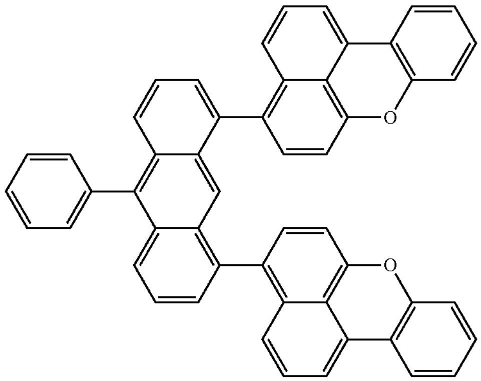
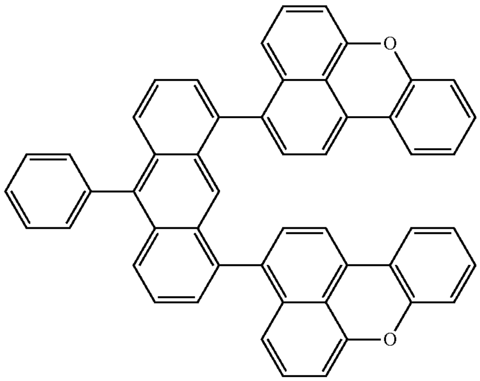

-continued
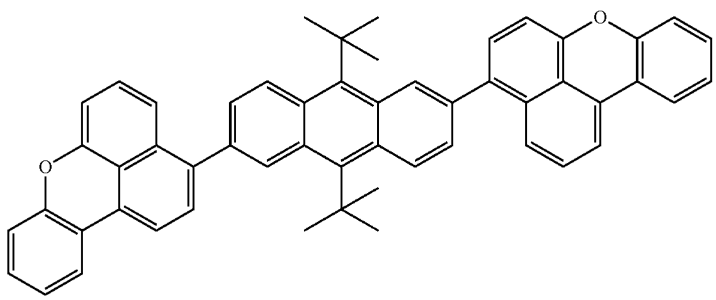
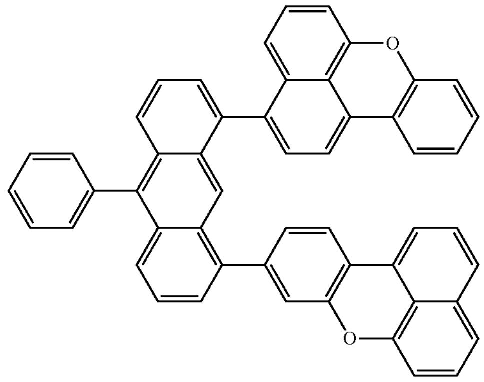
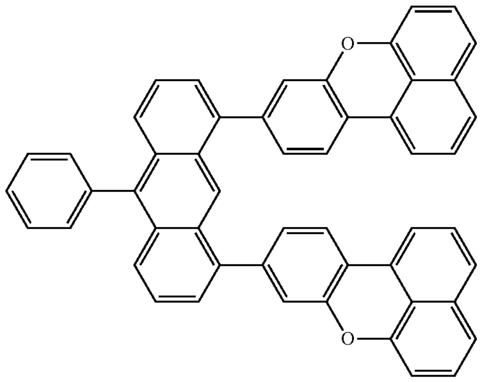
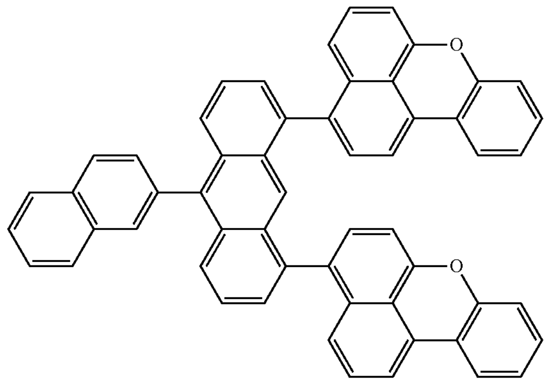
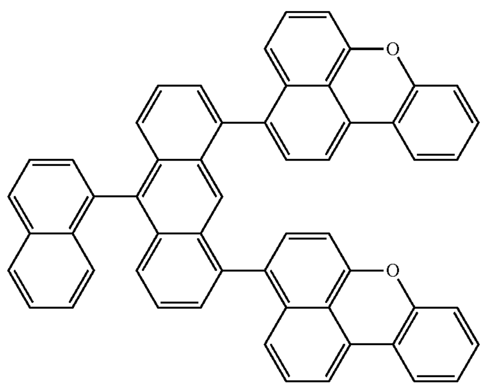
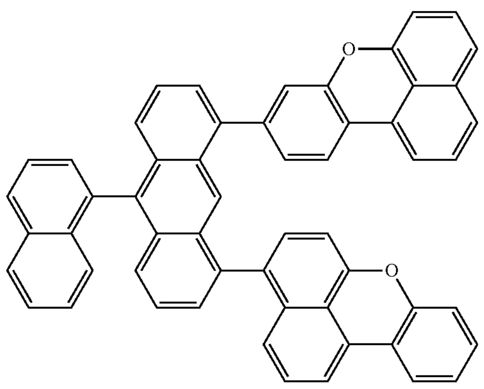

-continued
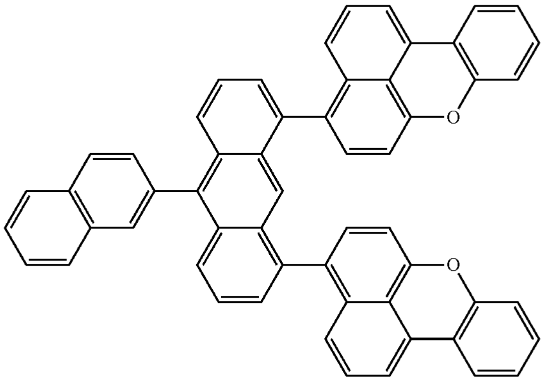
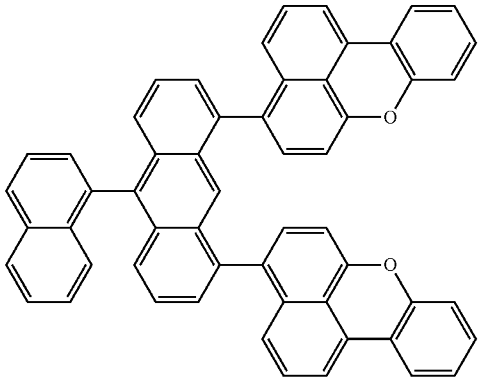
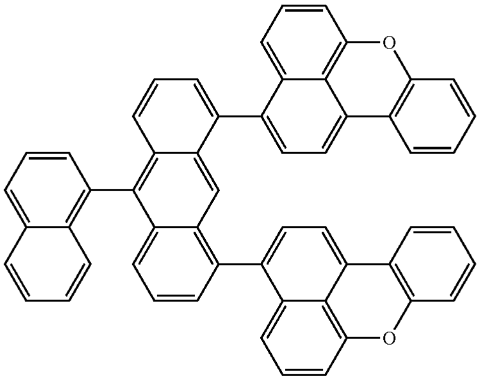
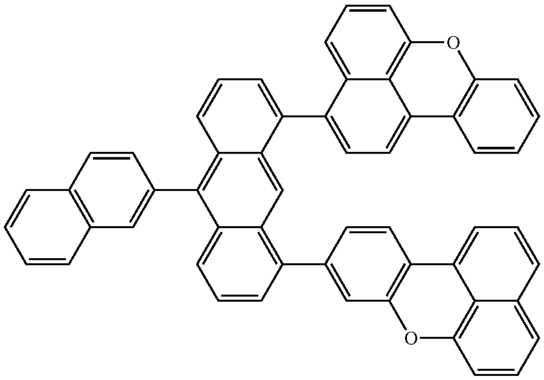
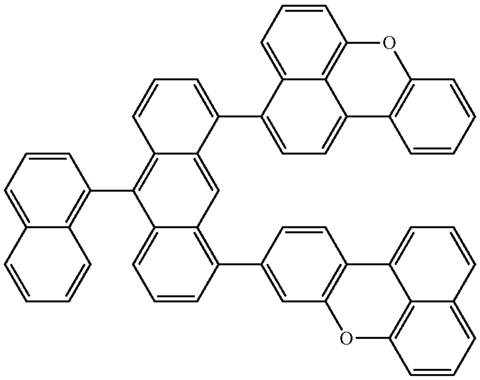
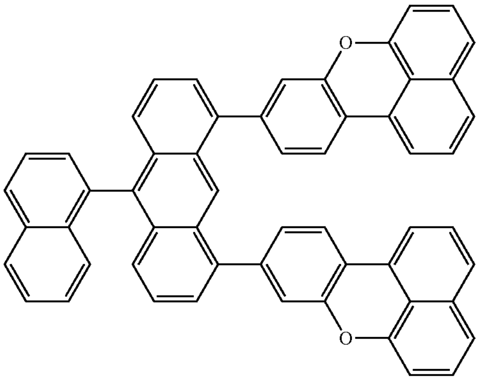
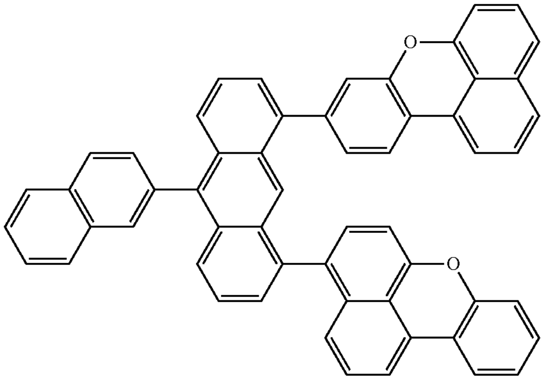

-continued
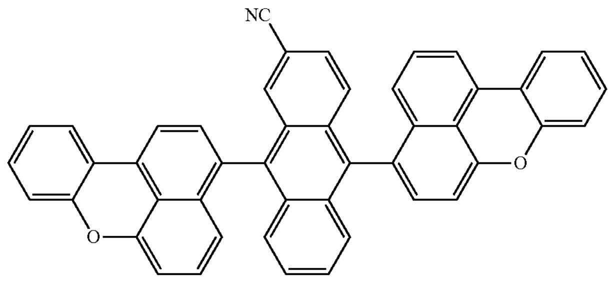
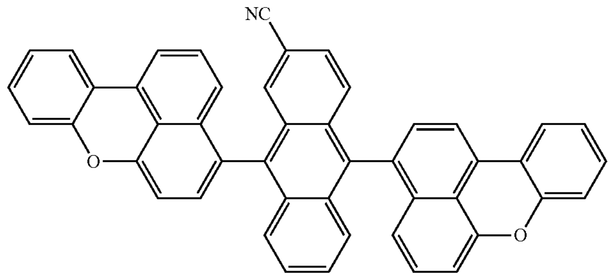
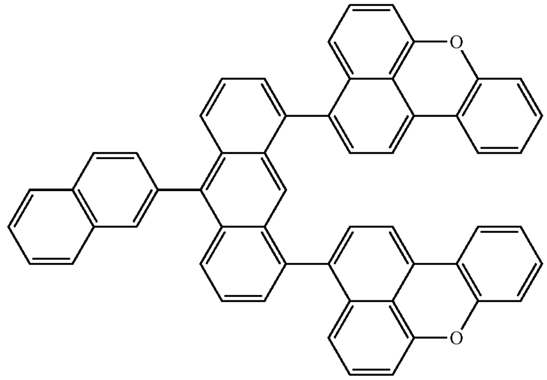
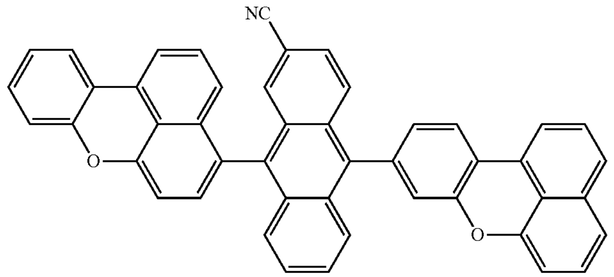
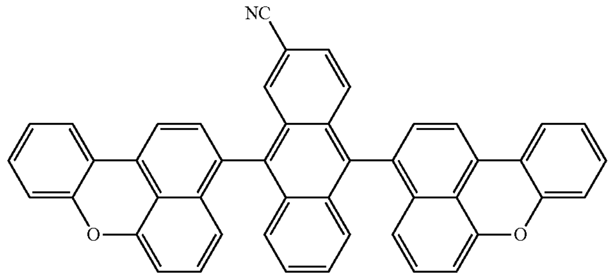

-continued
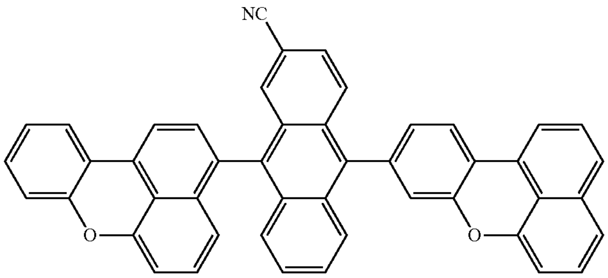
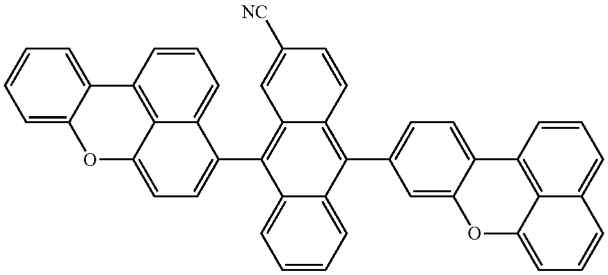
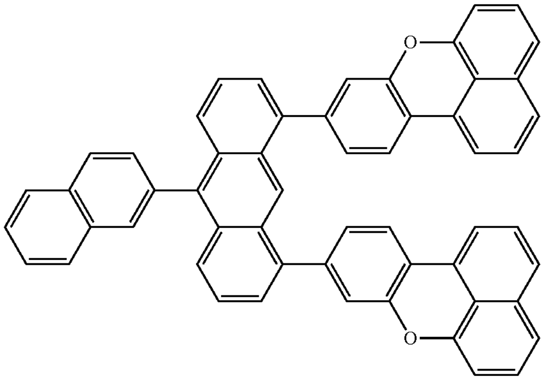
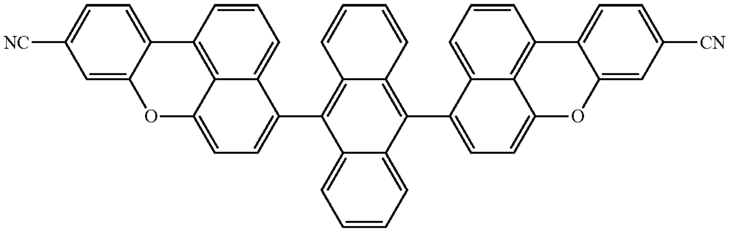
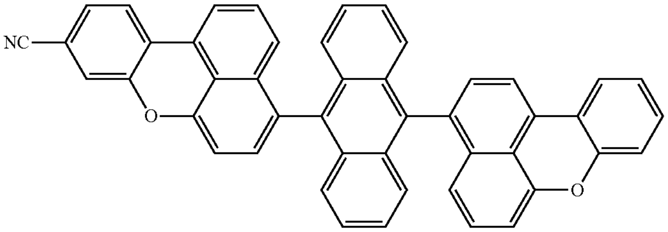
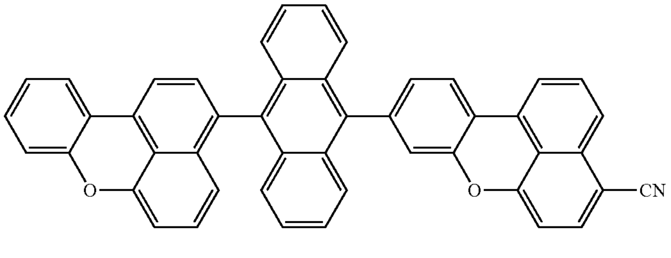

-continued
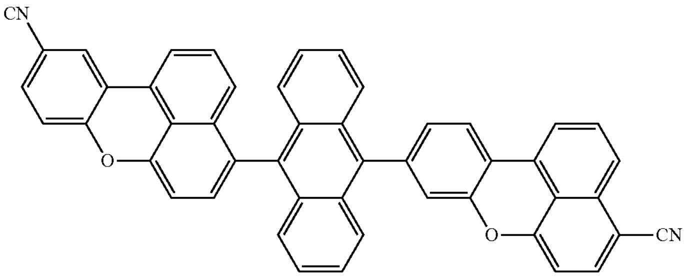
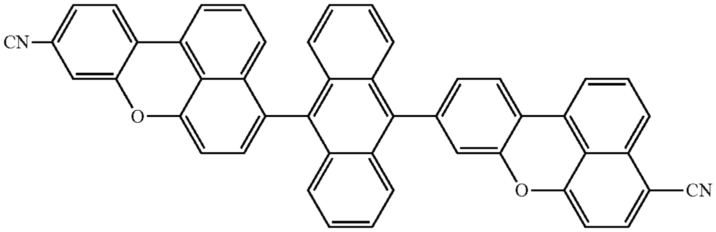
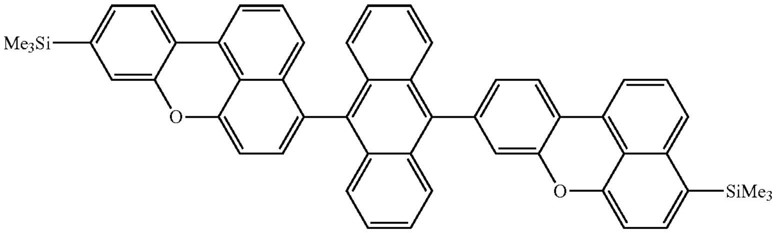
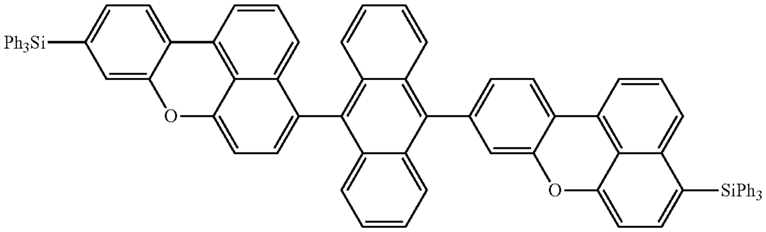
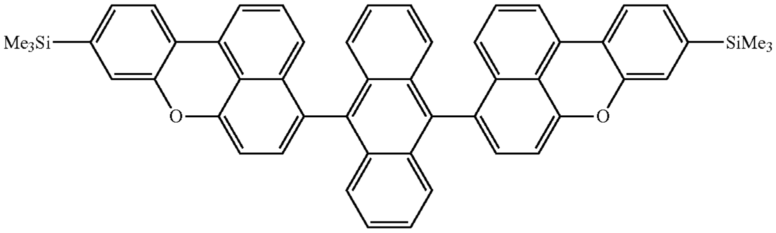
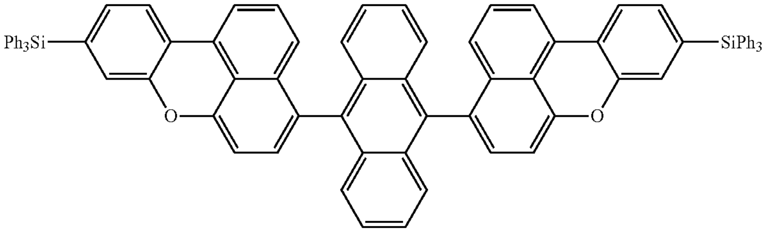
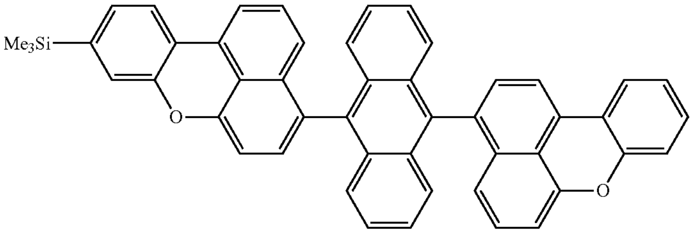

-continued
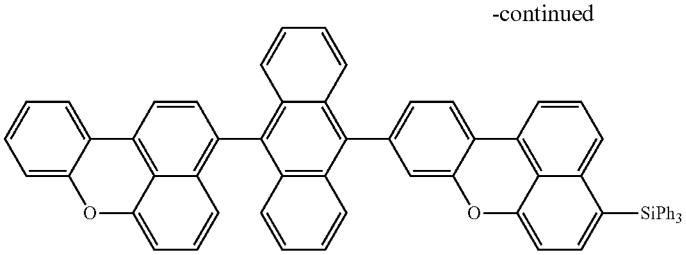
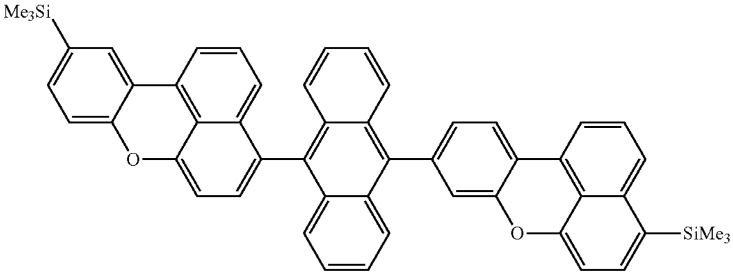
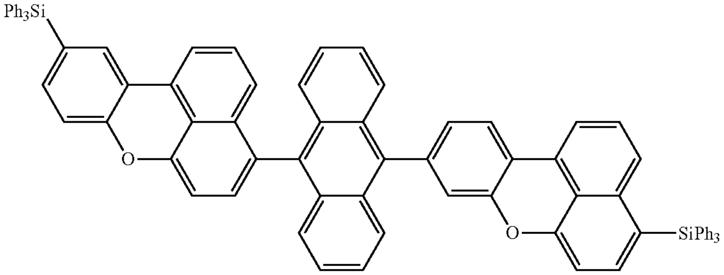
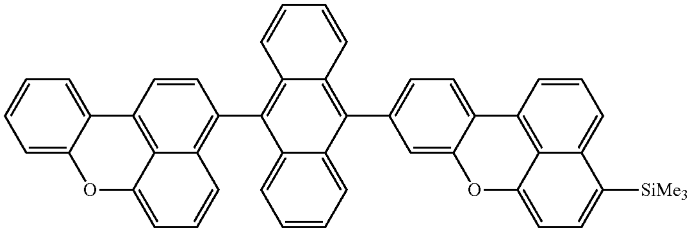
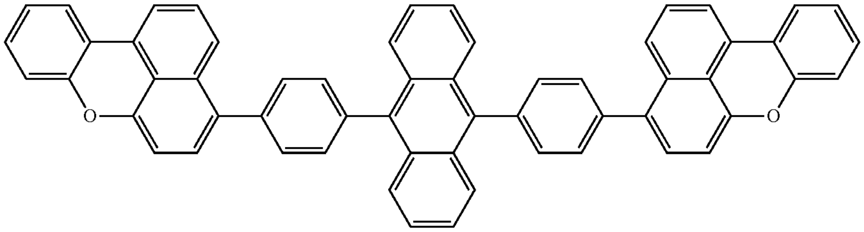
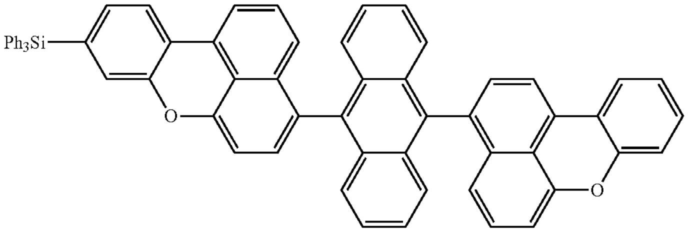
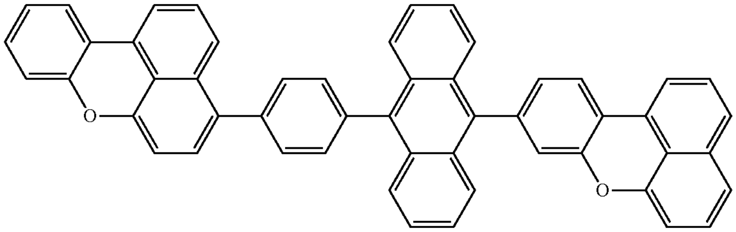

-continued
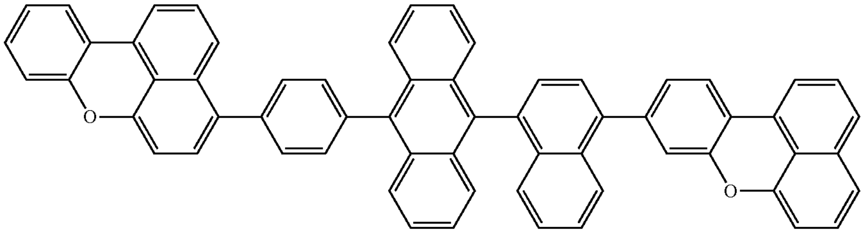
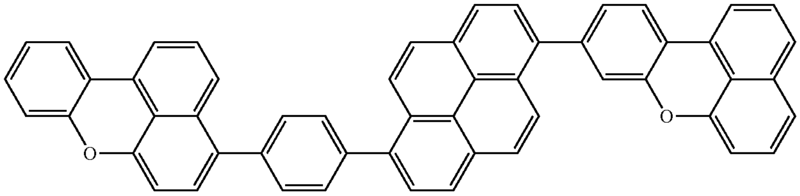
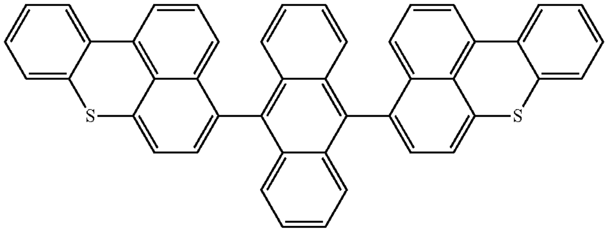
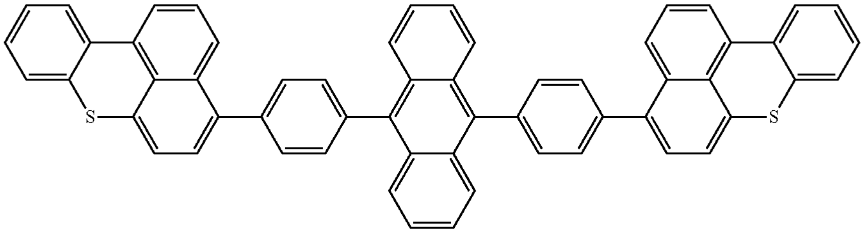
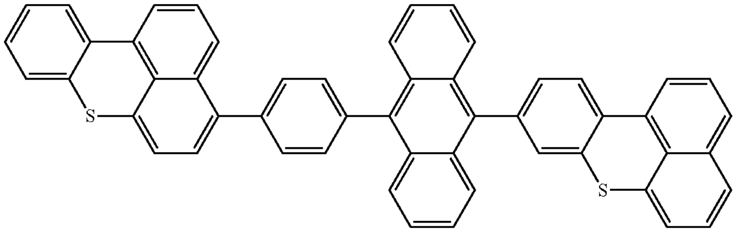
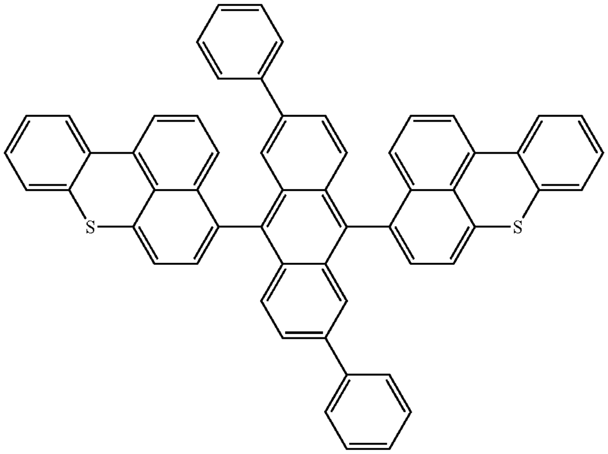

-continued
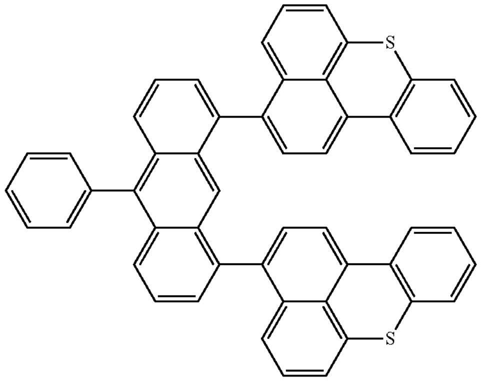
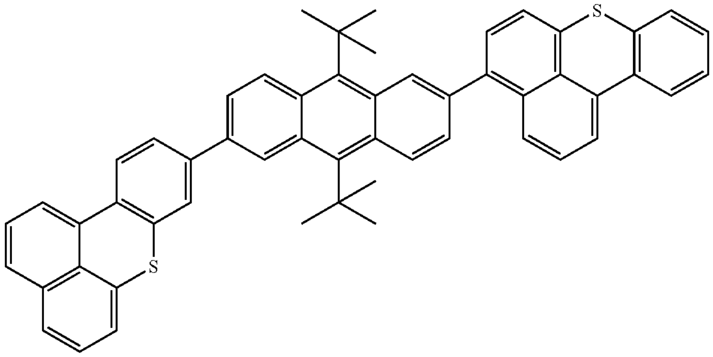
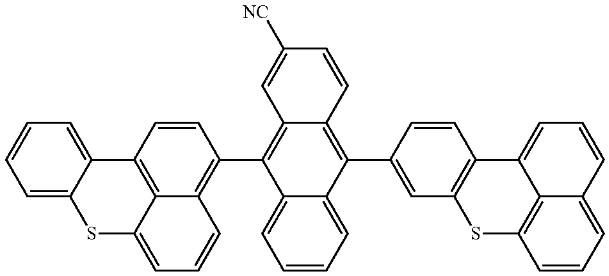
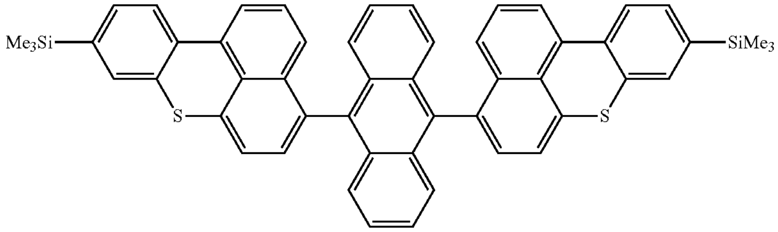
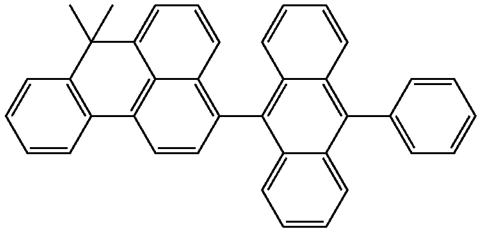
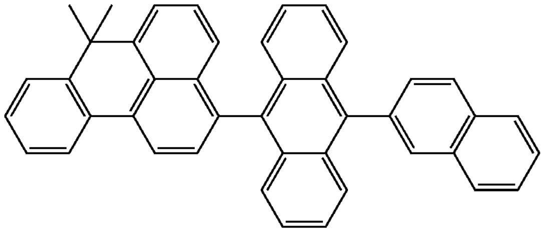
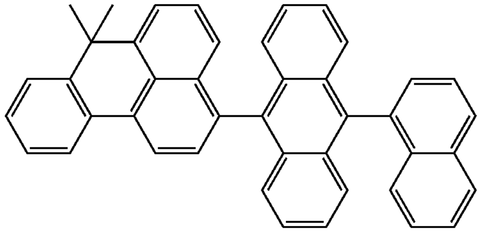
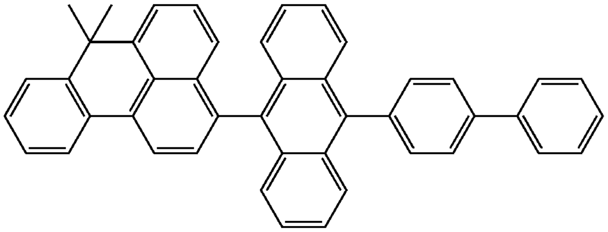

-continued
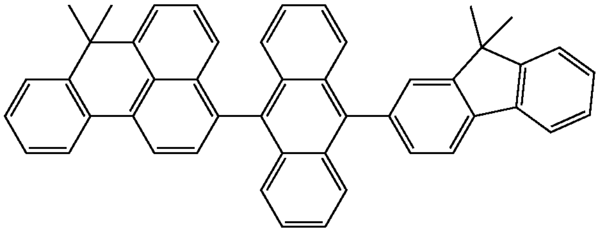
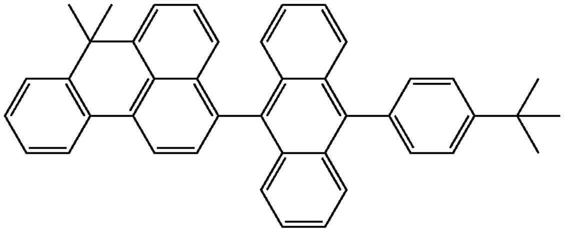
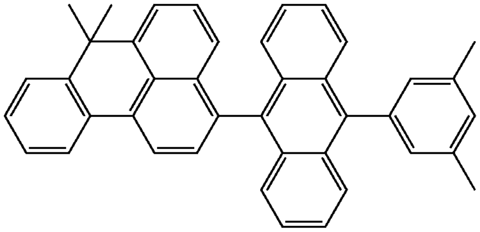
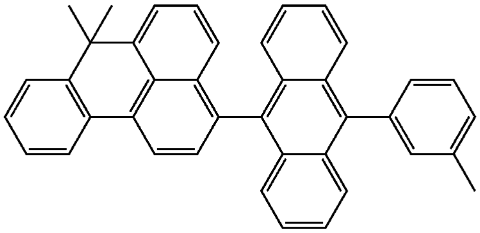
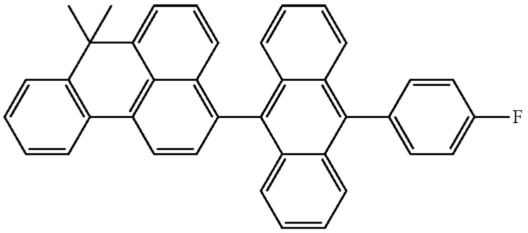
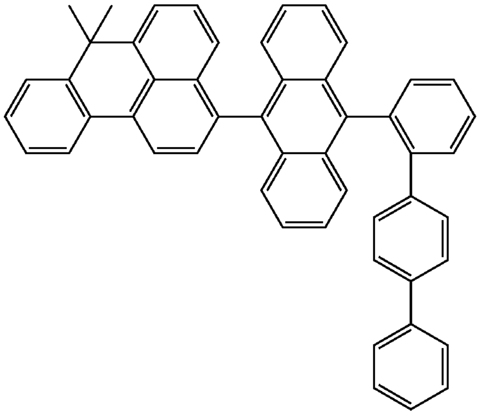
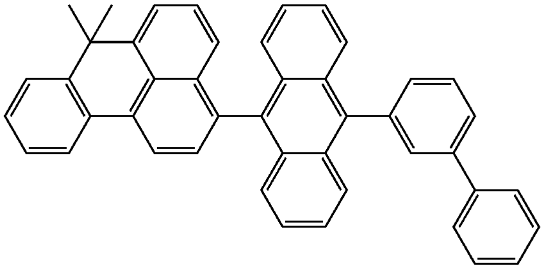
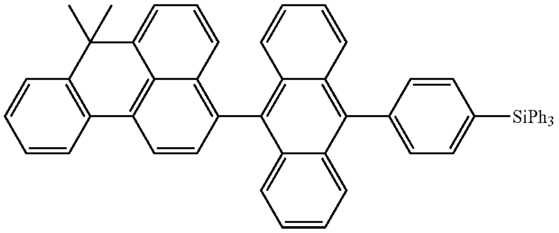
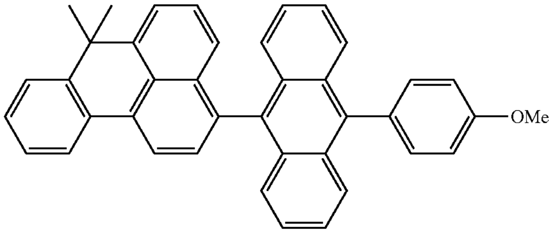

-continued
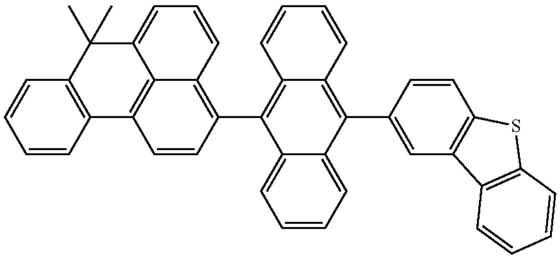
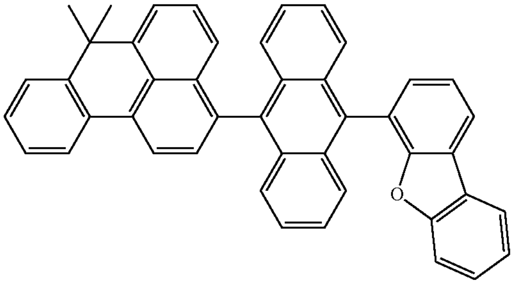
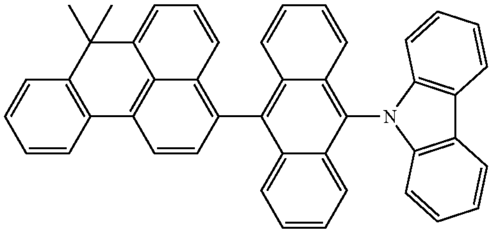
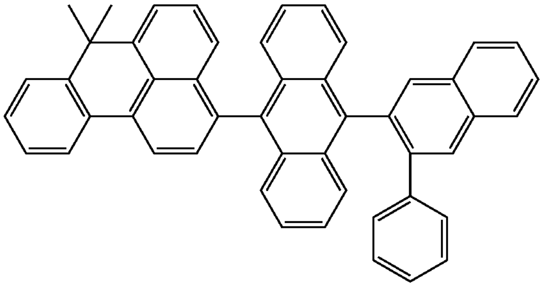
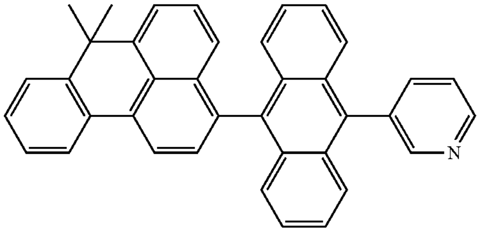
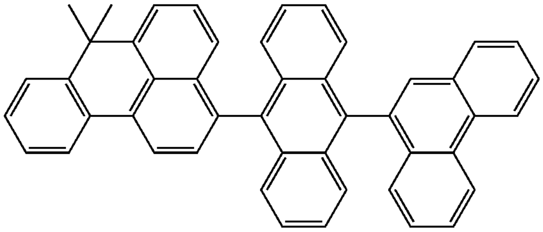
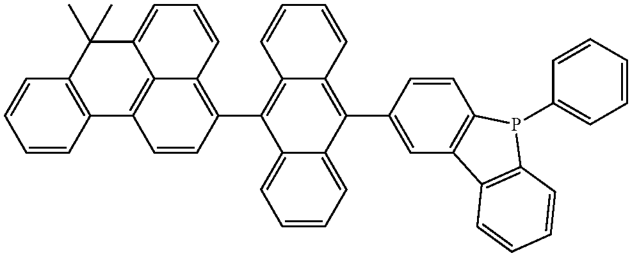
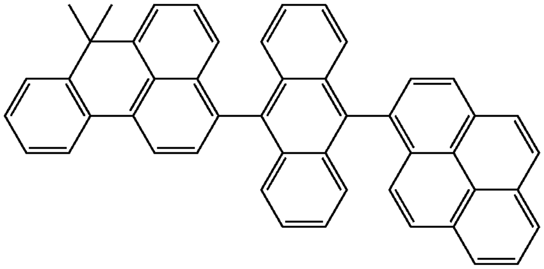
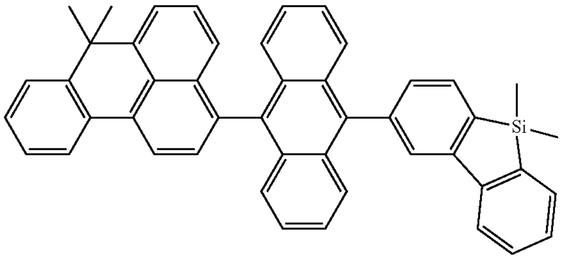

-continued
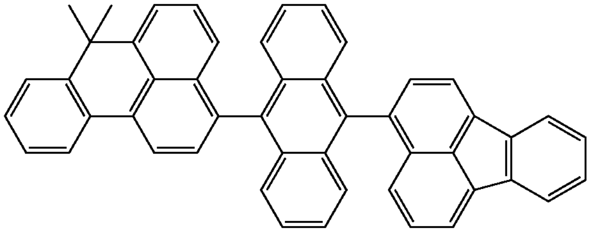
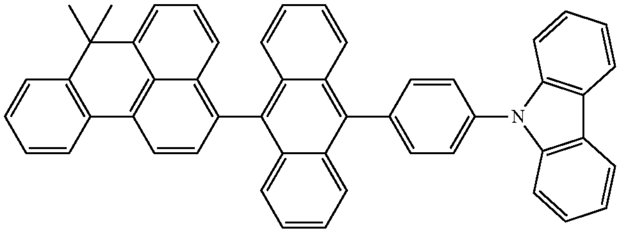
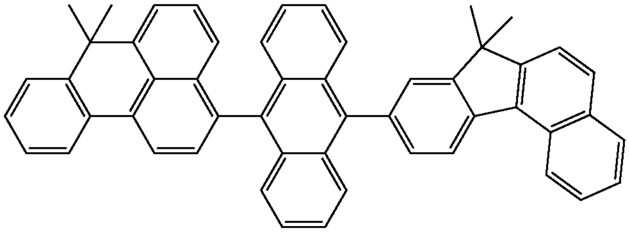
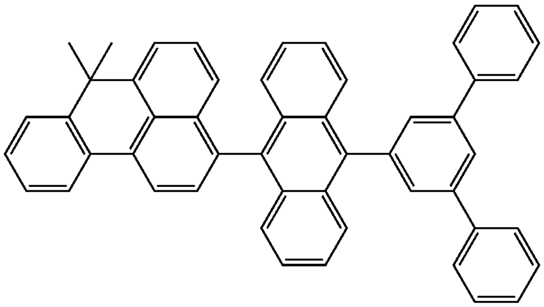
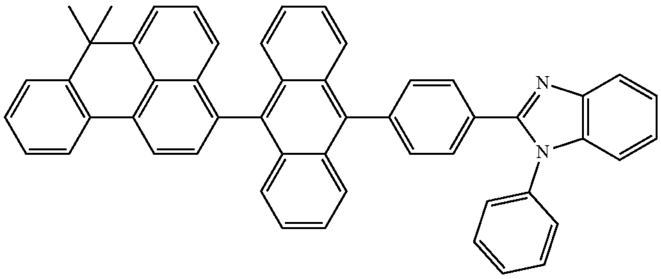
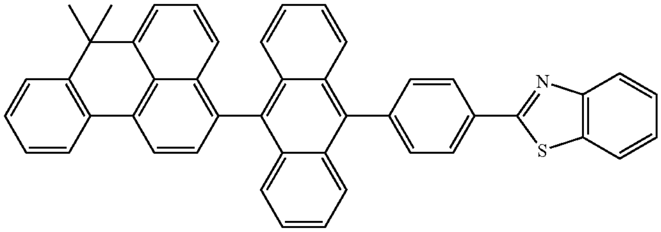

-continued
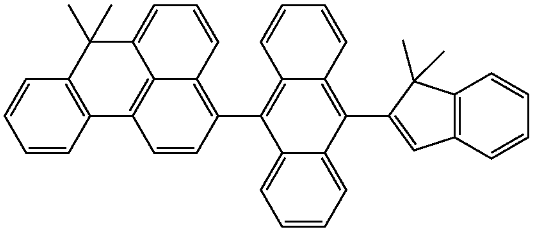
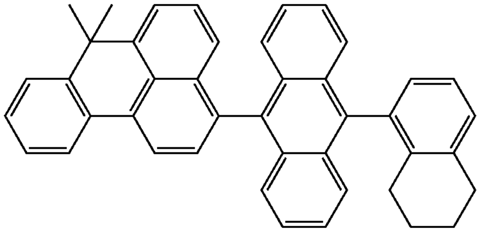
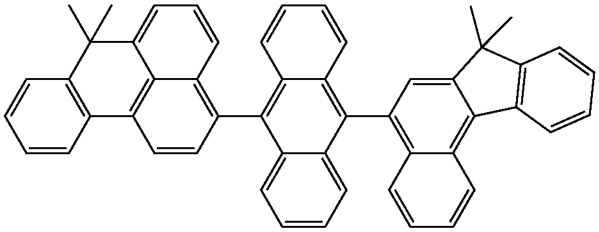
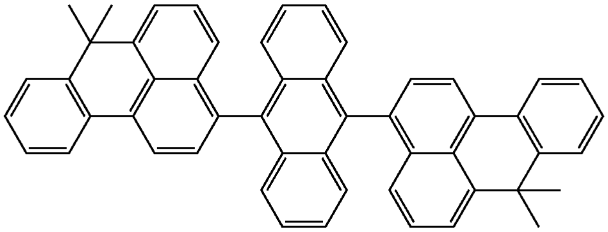
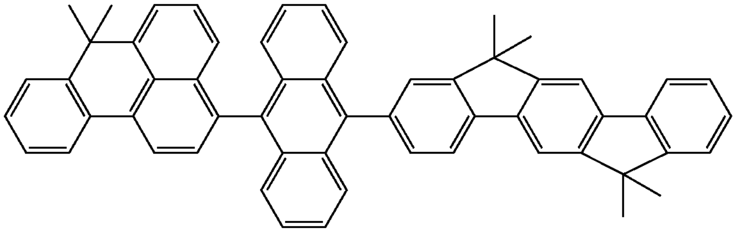
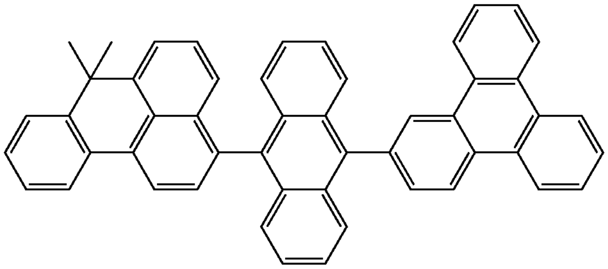
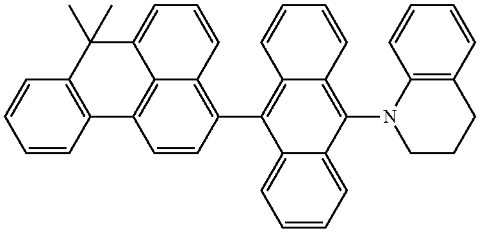
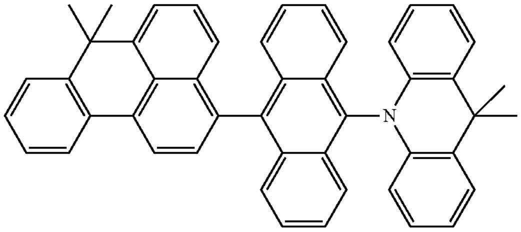
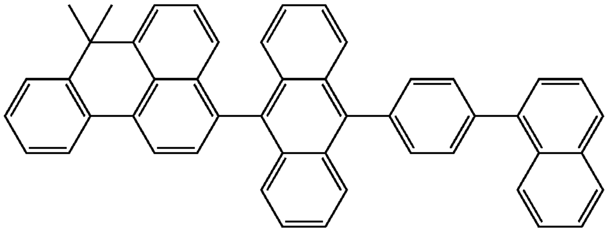

-continued
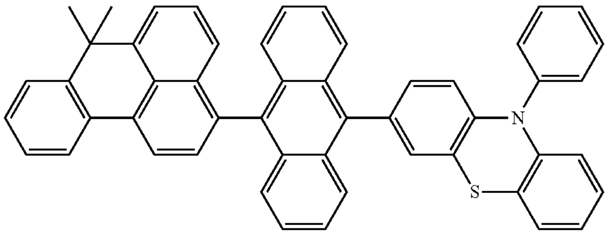
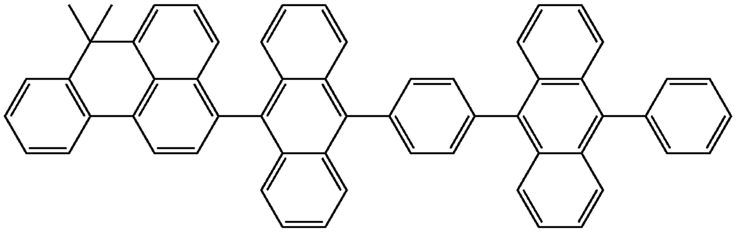
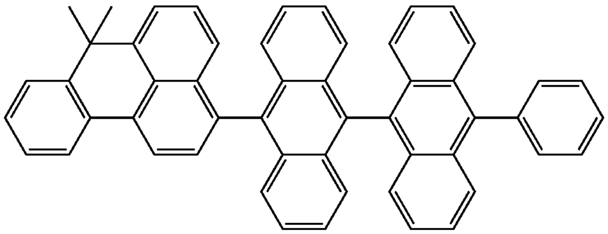
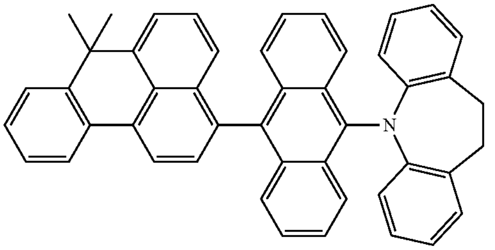
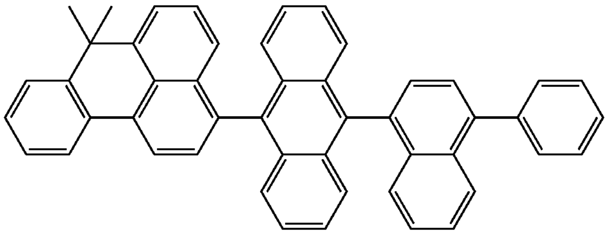
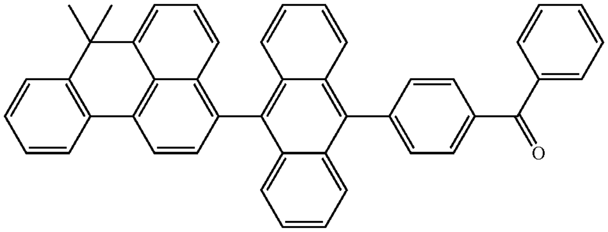
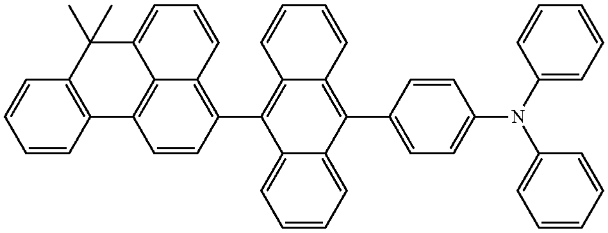
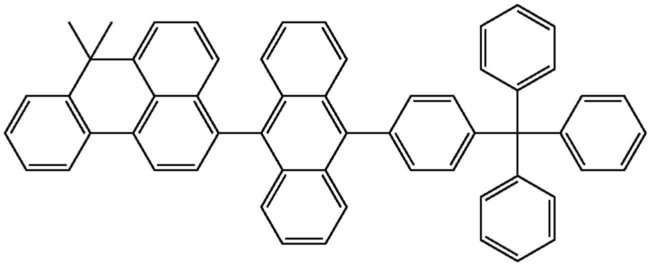

-continued
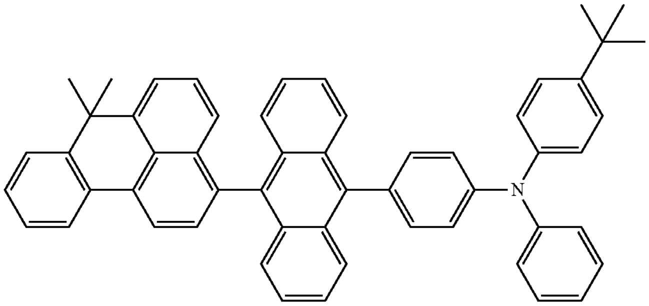
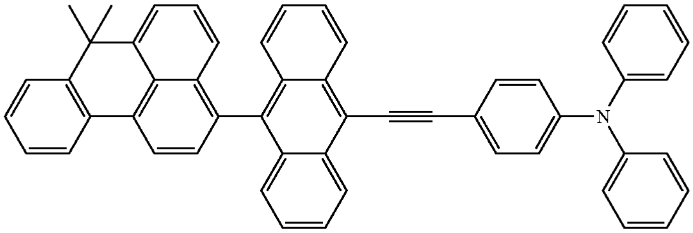
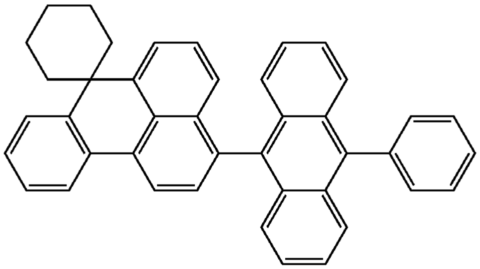
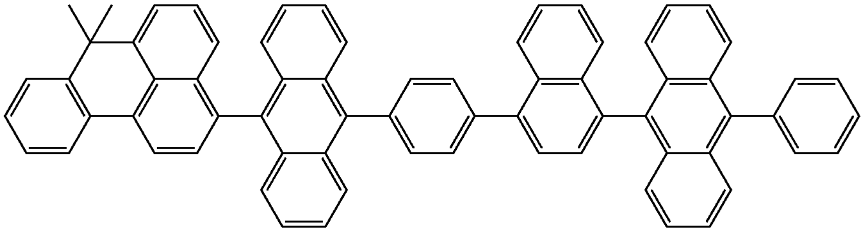
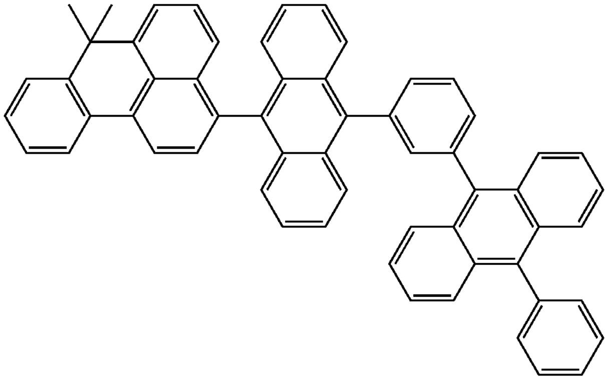
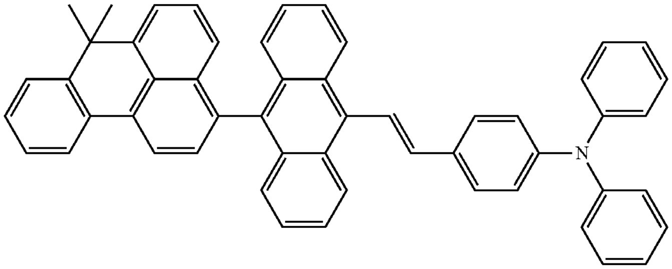

-continued
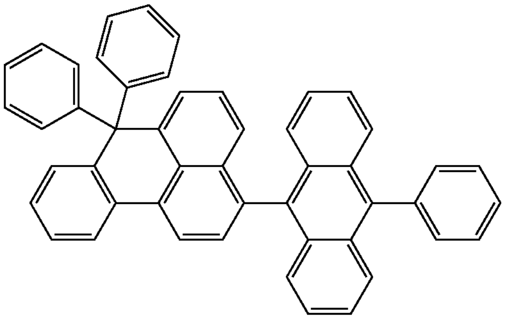
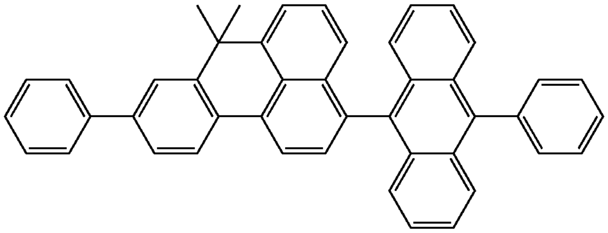
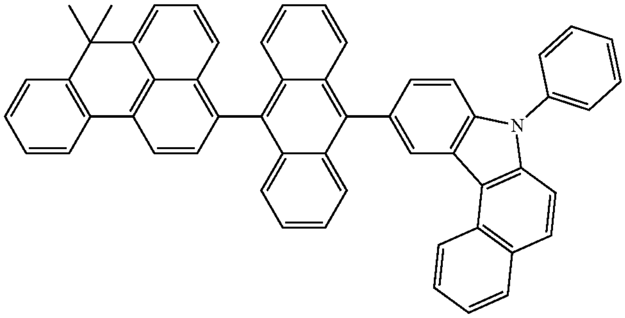
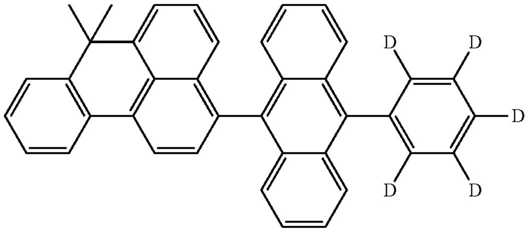
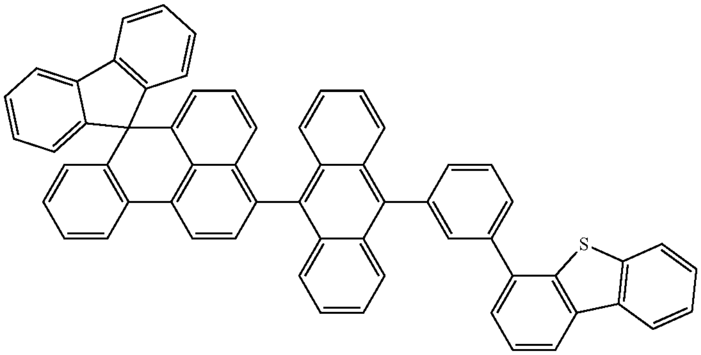
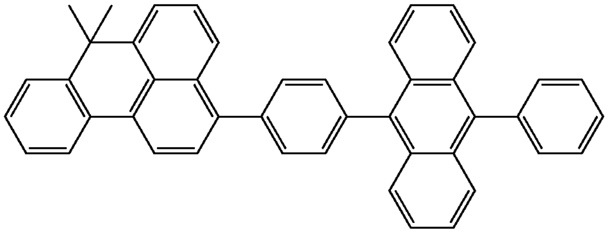

-continued
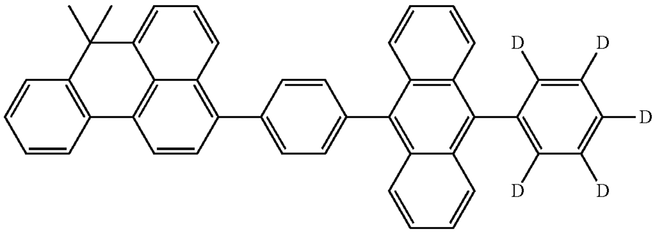
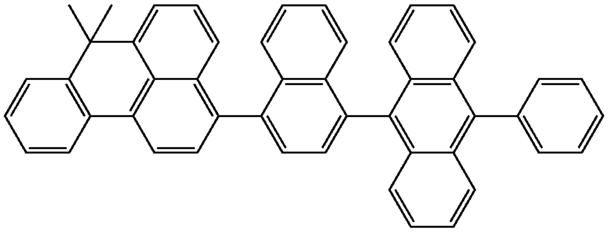
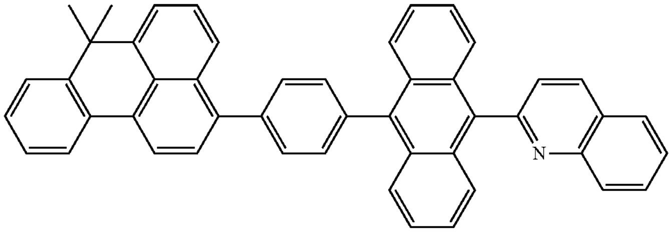
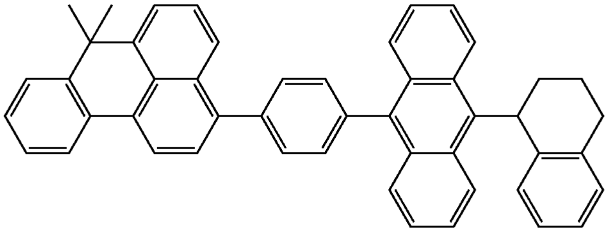
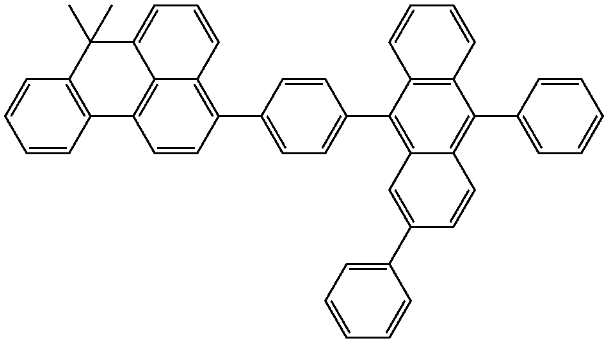
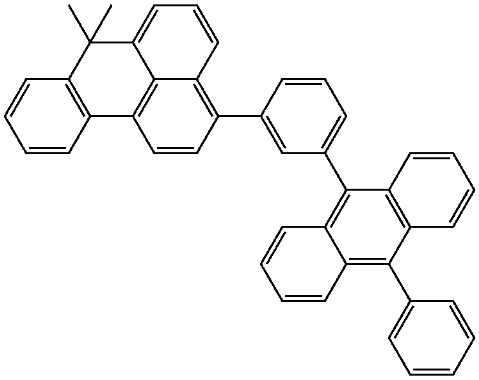
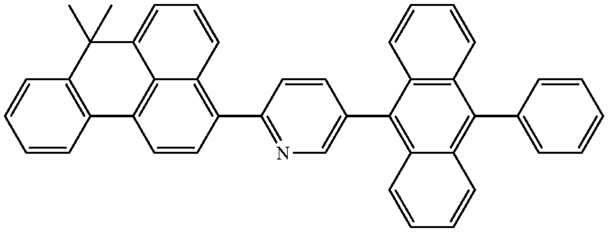

-continued
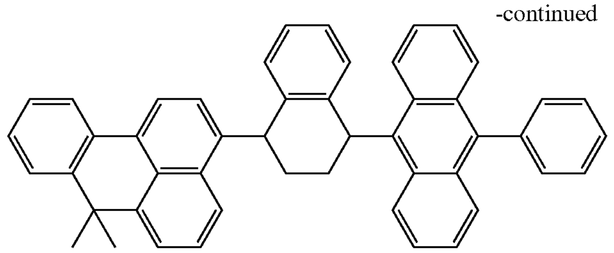
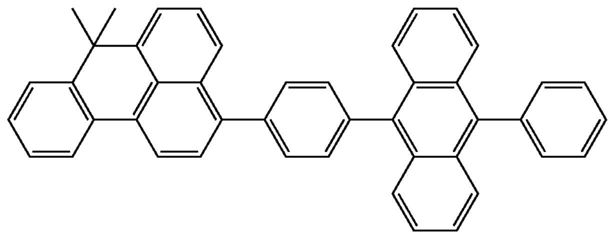
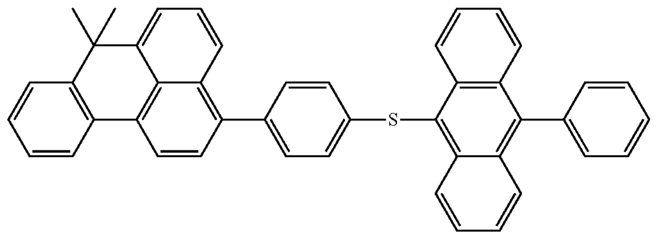
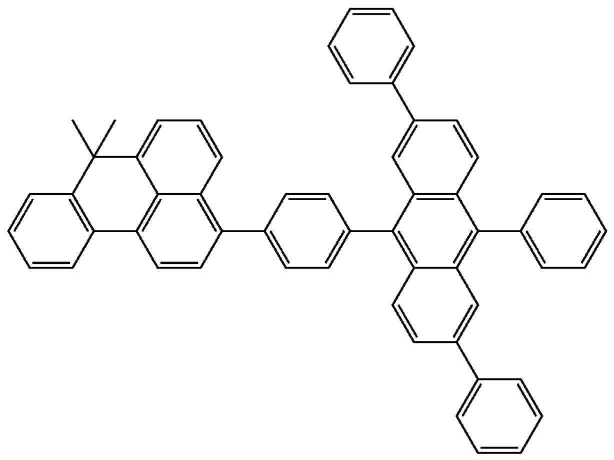

The compound represented by the formula (1) can be synthesized using, for example, a known alternative reaction or a raw material adapted to the target product, following the reaction of Examples described later.

[Compound A]

The compound A is not particularly limited as long as it has a Stokes shift of 20 nm or smaller and the emission peak wavelength of 440 nm to 465 nm.

In one embodiment, the compound A is one or more selected from the group consisting of a compound represented by the following formula (11), a compound represented by the following formula (21), a compound represented by the following formula (31), and a compound represented by the following formula (41).

(Compound Represented by Formula (11))

(11)

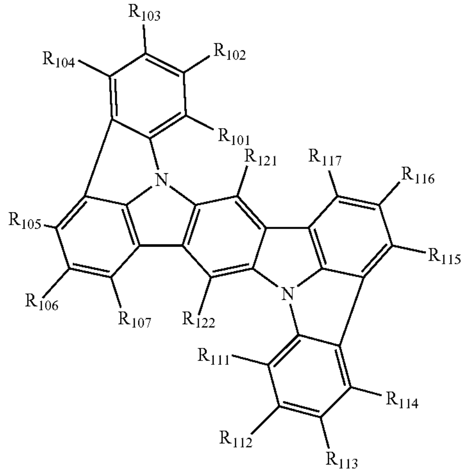

In the formula (11), one or more sets of adjacent two or more of $R_{101}$ to $R_{107}$ and $R_{111}$ to $R_{17}$ form a substituted or unsubstituted, saturated or unsaturated ring by bonding with each other, or do not form a substituted or unsubstituted, saturated or unsaturated ring;

$R_{121}$ and $R_{122}$, and $R_{101}$ to $R_{107}$ and $R_{111}$ to $R_{117}$ that do not form the substituted or unsubstituted, saturated or unsaturated ring are independently a hydrogen atom or a substituent R.

The substituent R is as defined in the formula (1).

In one embodiment, the compound represented by the formula (11) is a compound represented by the following formula (12).

(12)

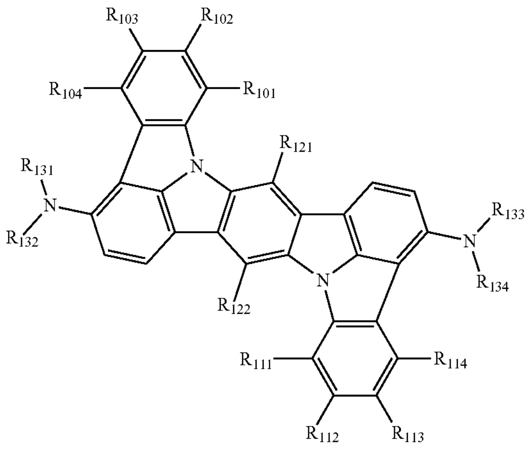

In the formula (12), $R_{101}$ to $R_{104}$, $R_{111}$ to $R_{114}$, $R_{121}$, and $R_{122}$ are as defined in the formula (11).

$R_{131}$ to $R_{134}$ are independently a substituted or unsubstituted aryl group including 6 to 50 ring carbon atoms, or a substituted or unsubstituted monovalent heterocyclic group including 5 to 50 ring atoms.

In one embodiment, the compound represented by the formula (11) is a compound represented by the following formula (13).

(13)

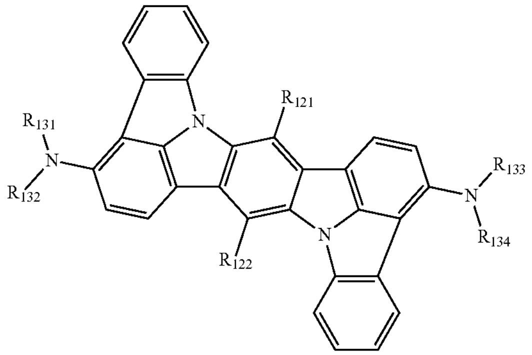

In the formula (13), $R_{121}$ and $R_{122}$ are as defined in the formula (1), and $R_{131}$ to $R_{134}$ are as defined in the formula (12).

In one embodiment, $R_{131}$ to $R_{134}$ in the formulas (12) and (13) are independently a substituted or unsubstituted aryl group (preferably phenyl group) including 6 to 50 ring carbon atoms.

In one embodiment, $R_{121}$ and $R_{122}$ in the formulas (11) to (13) are hydrogen atoms.

In one embodiment, the substituent in the case of "substituted or unsubstituted" in the formulas (11) to (13) is a substituted or unsubstituted alkyl group including 1 to 50 carbon atoms, a substituted or unsubstituted alkenyl group including 2 to 50 carbon atoms, a substituted or unsubstituted alkynyl group including 2 to 50 carbon atoms, a substituted or unsubstituted cycloalkyl group including 3 to 50 ring carbon atoms, a substituted or unsubstituted aryl group including 6 to 50 ring carbon atoms, or a substituted or unsubstituted monovalent heterocyclic group including 5 to 50 ring atoms.

Specific examples of the compound represented by the formula (11) will be described below, but these are merely examples, and the compound represented by the formula (11) is not limited to the following specific examples.

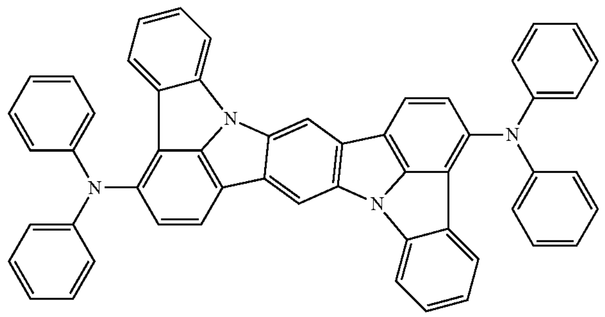
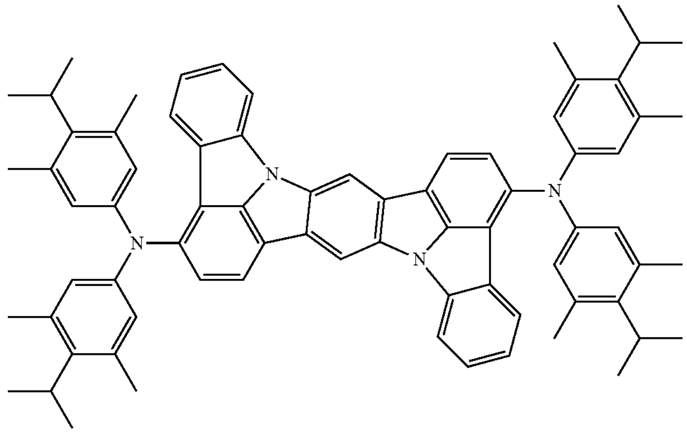
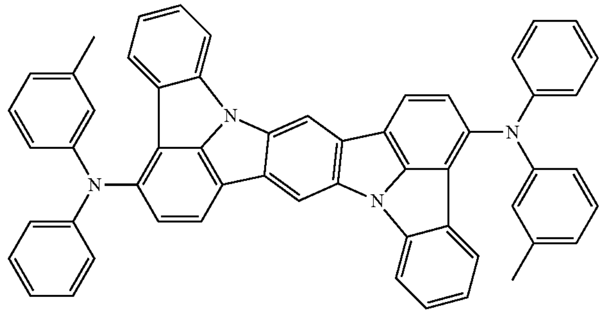
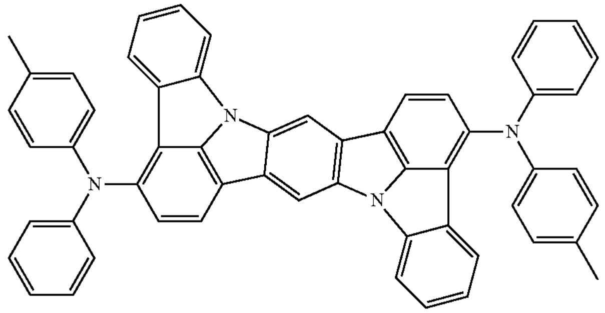
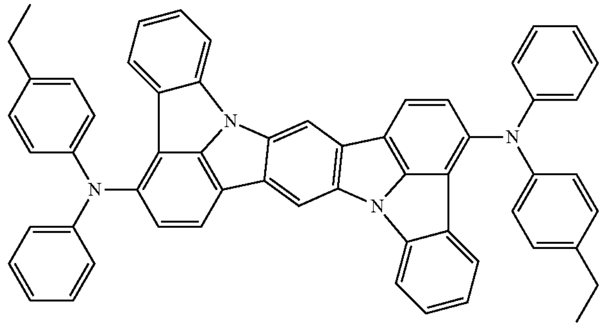

-continued
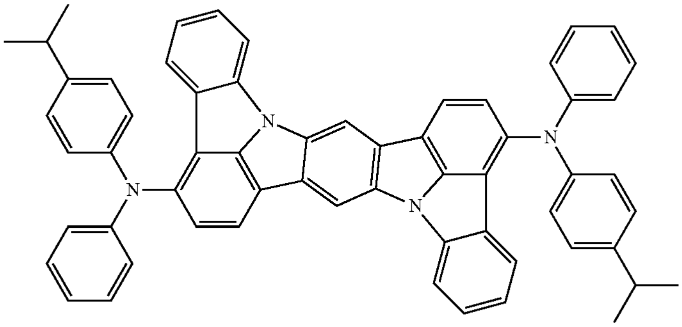
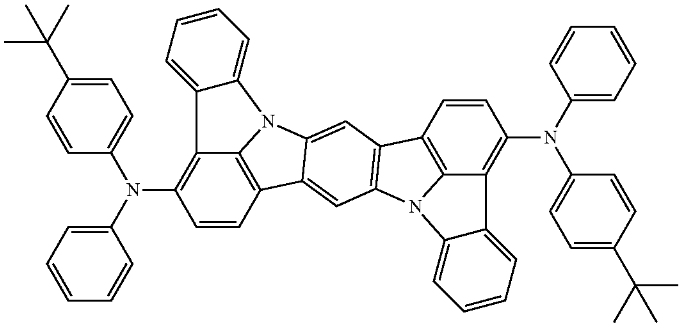
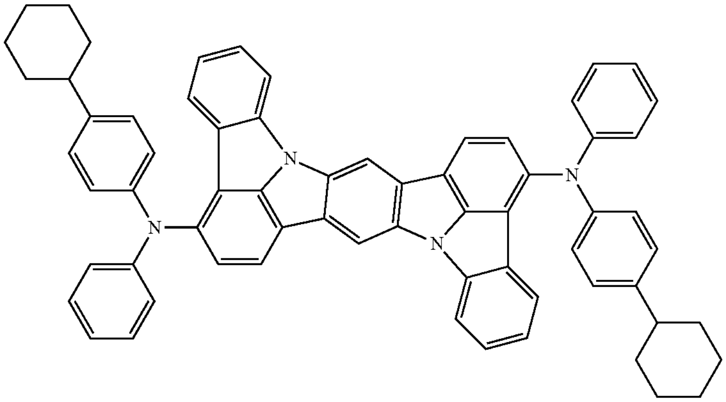
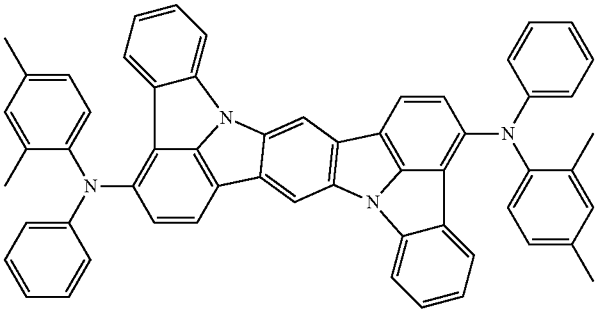

-continued
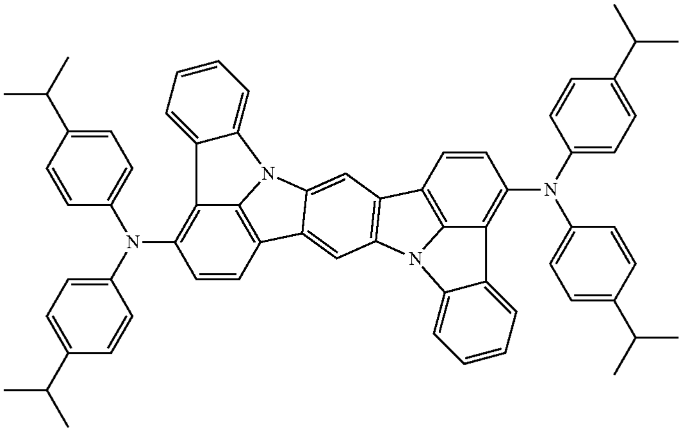
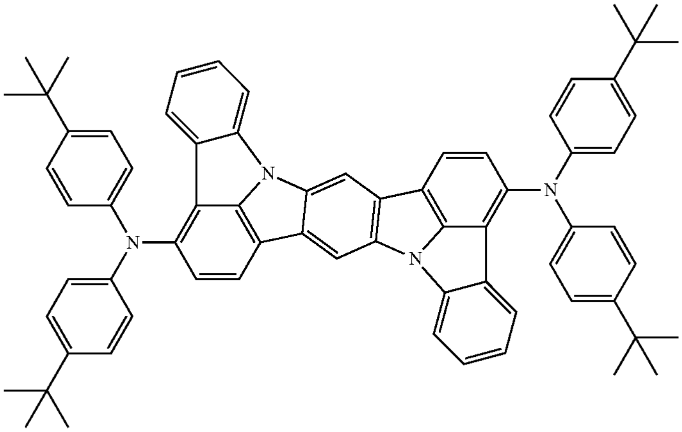
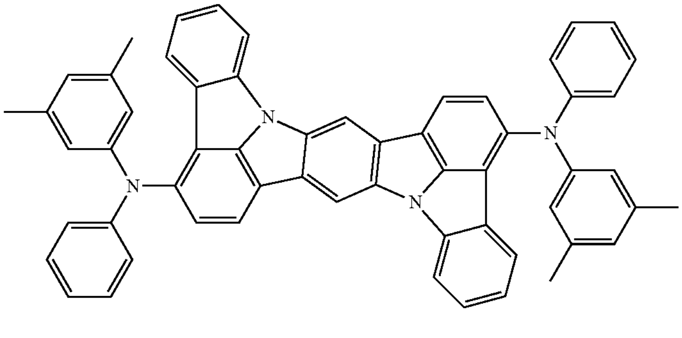
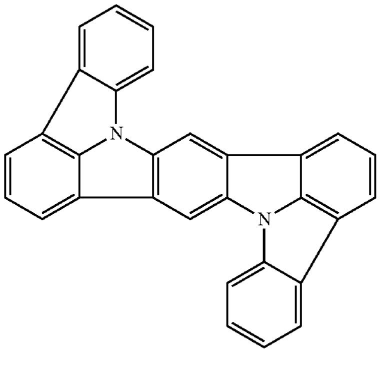

-continued
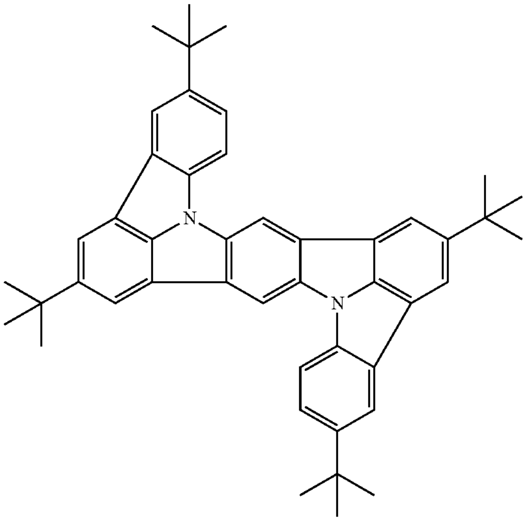
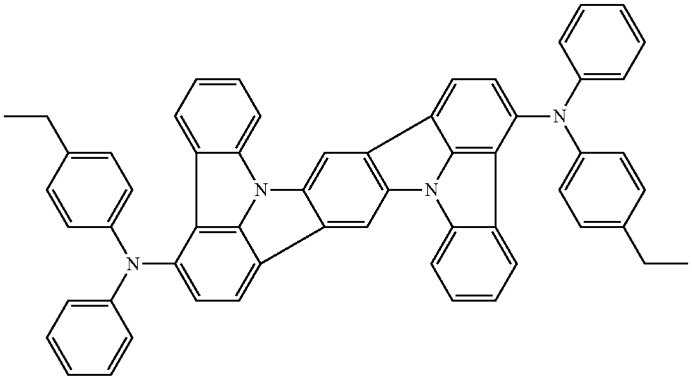
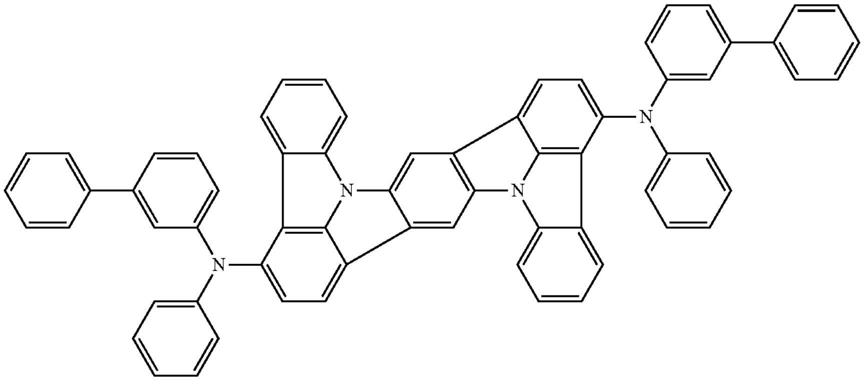
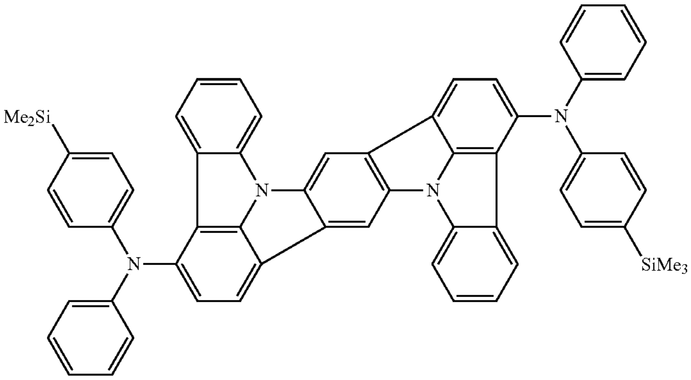

-continued
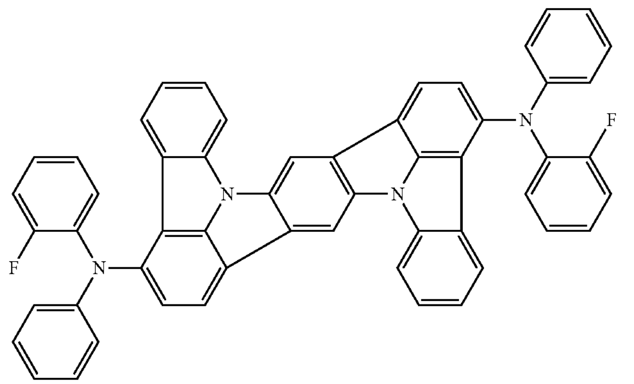
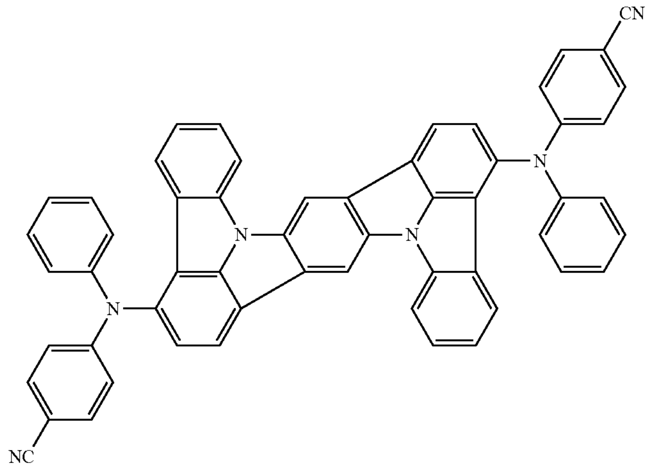
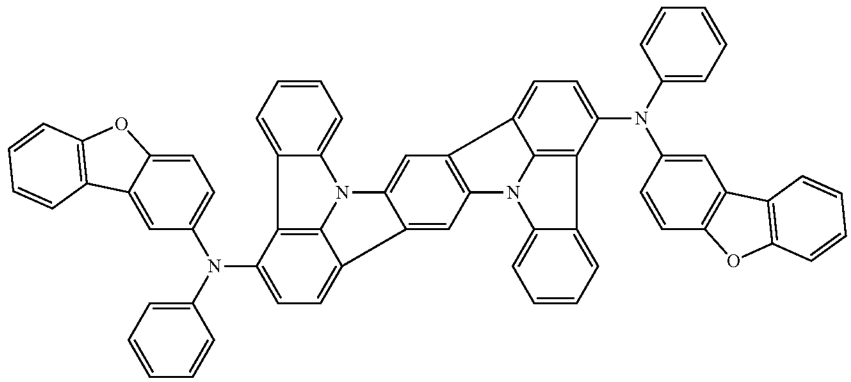
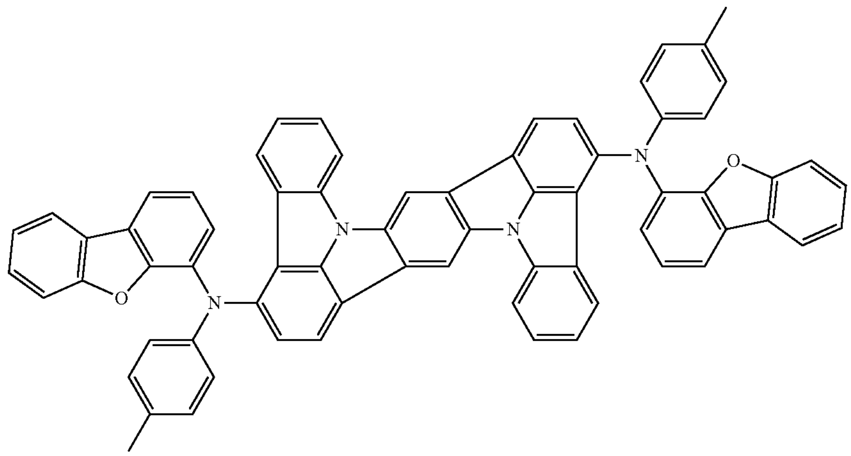

-continued
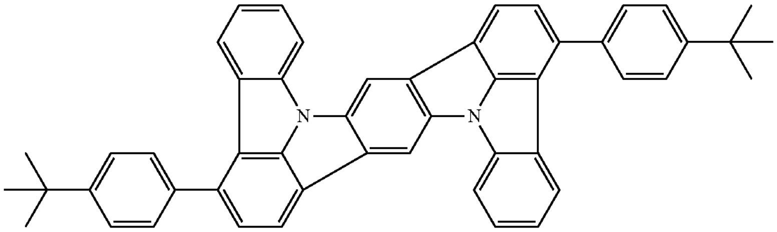
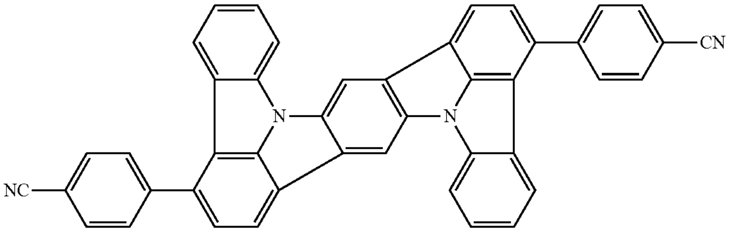
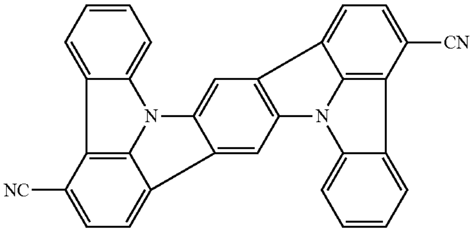
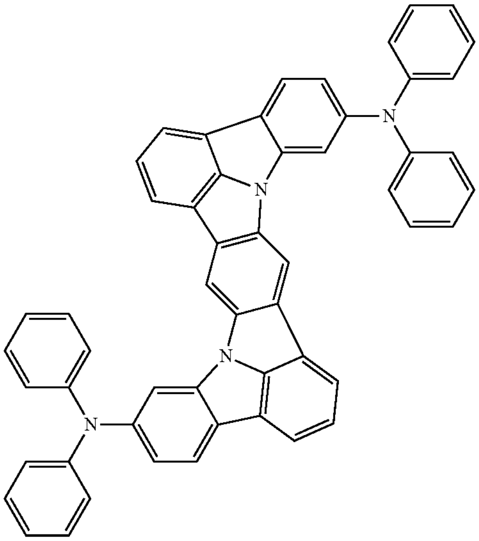
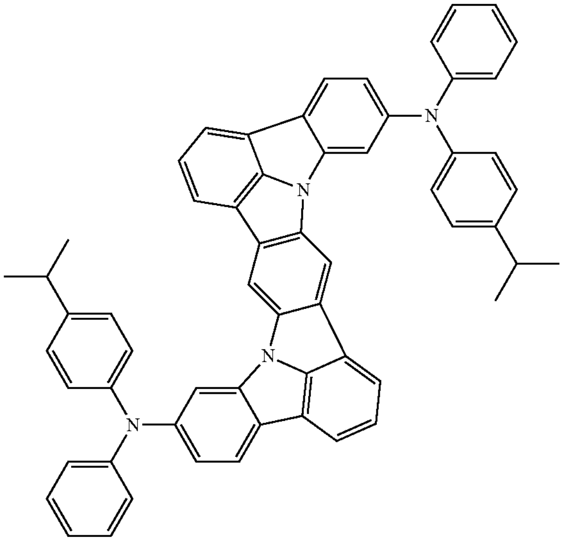
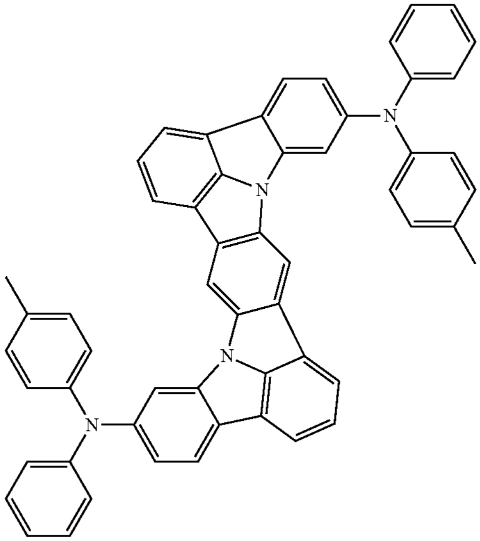

-continued
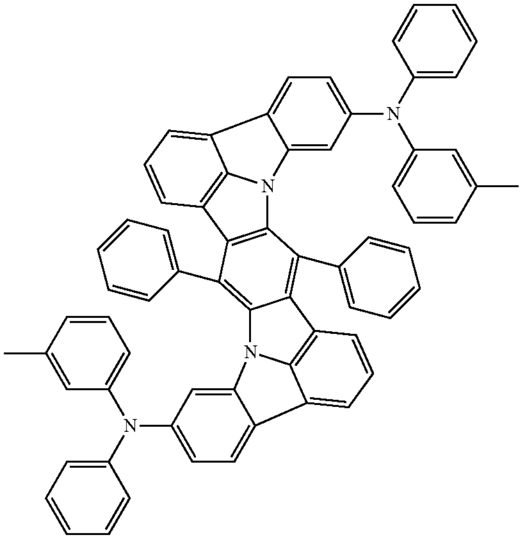
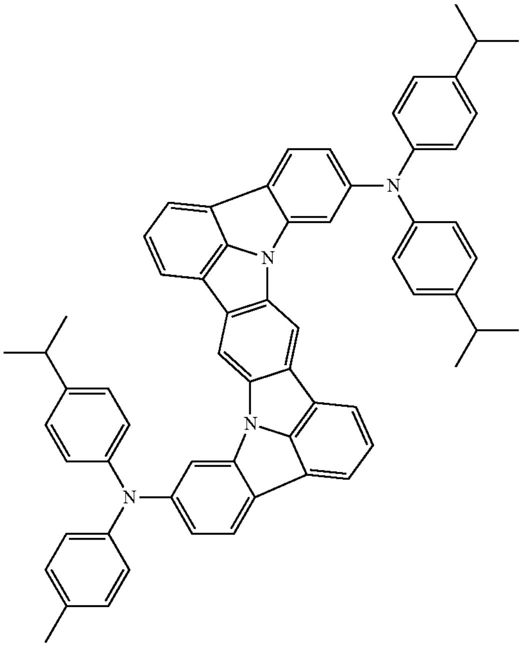
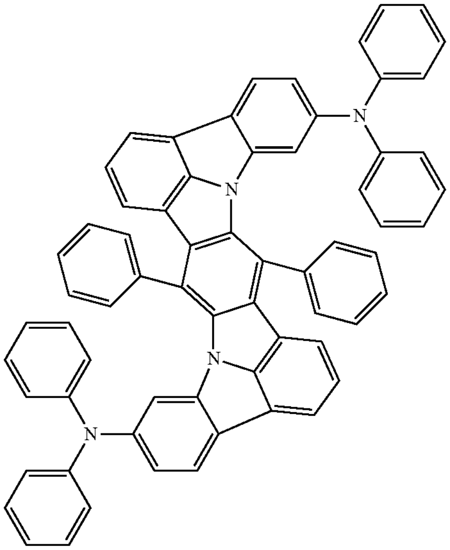
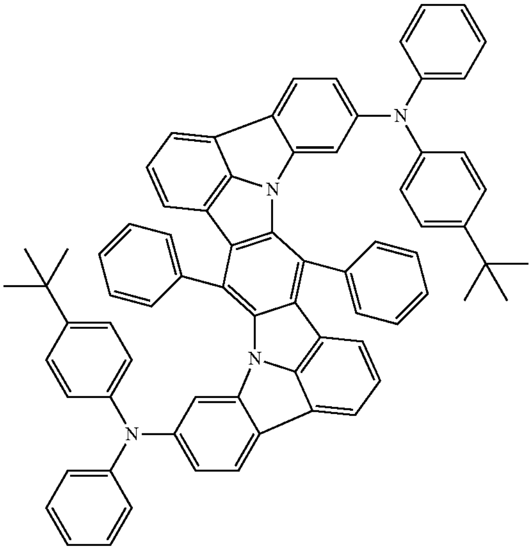

-continued
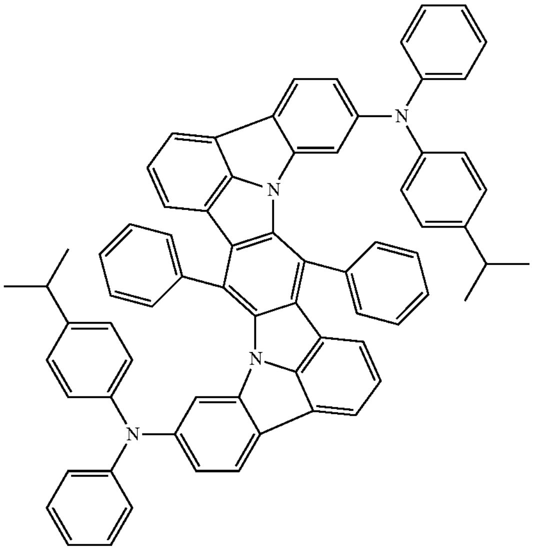
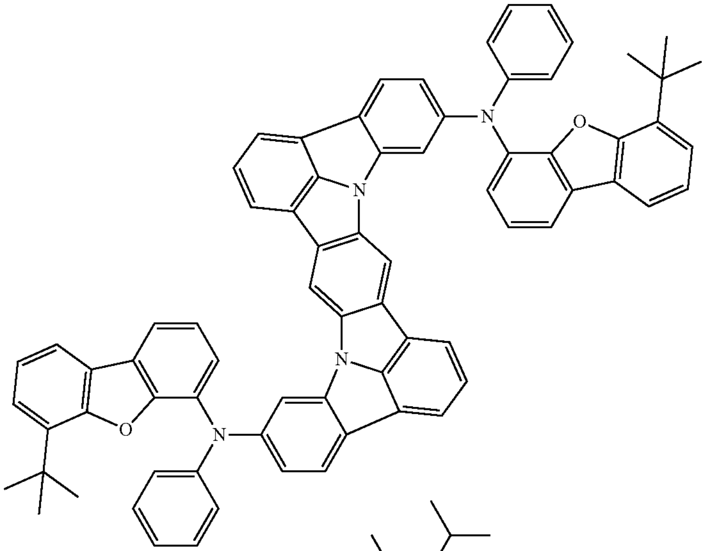
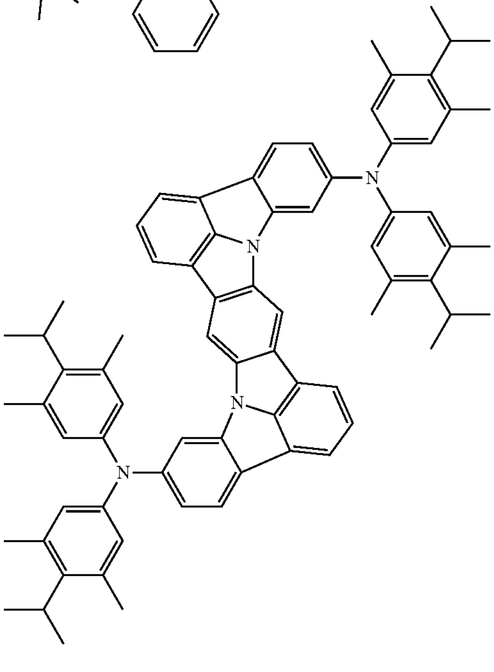
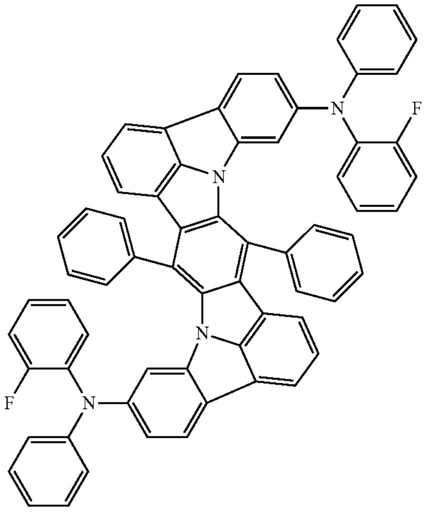

-continued
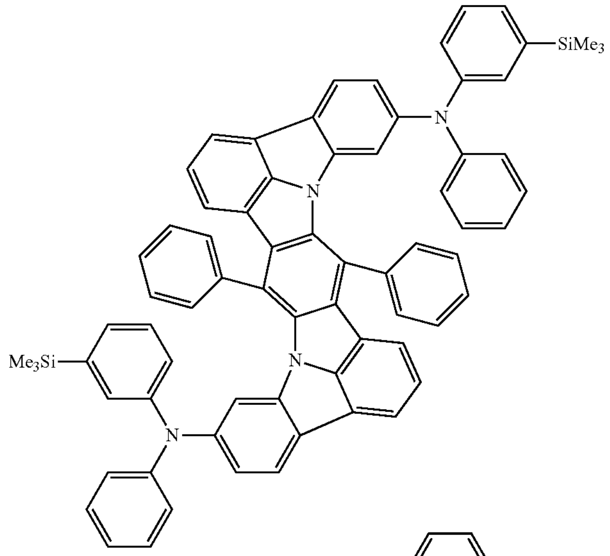
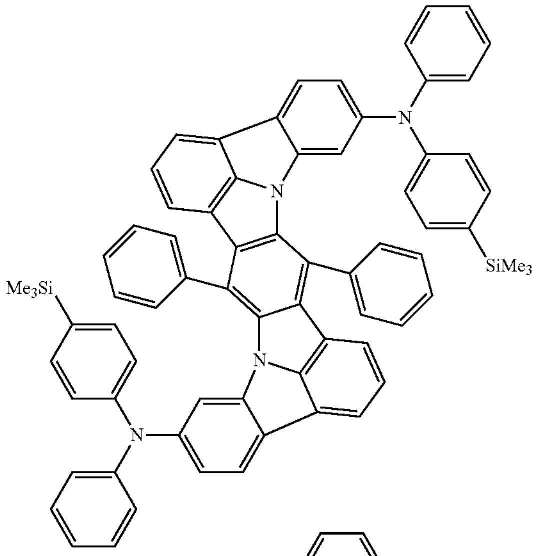
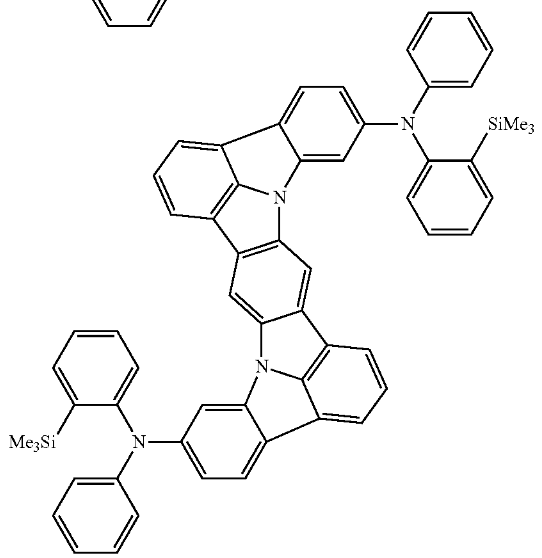
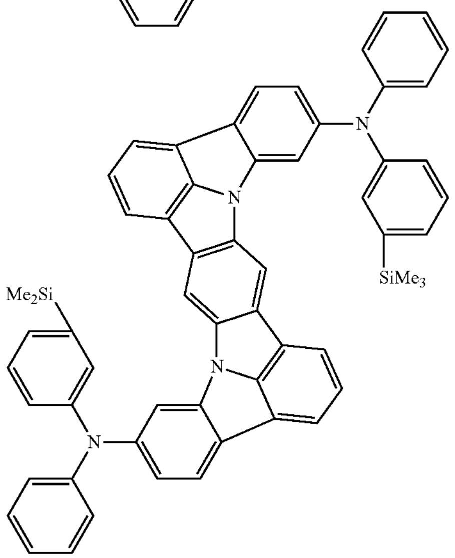
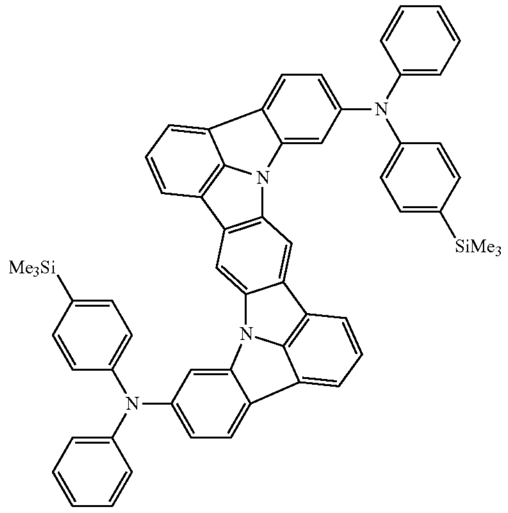
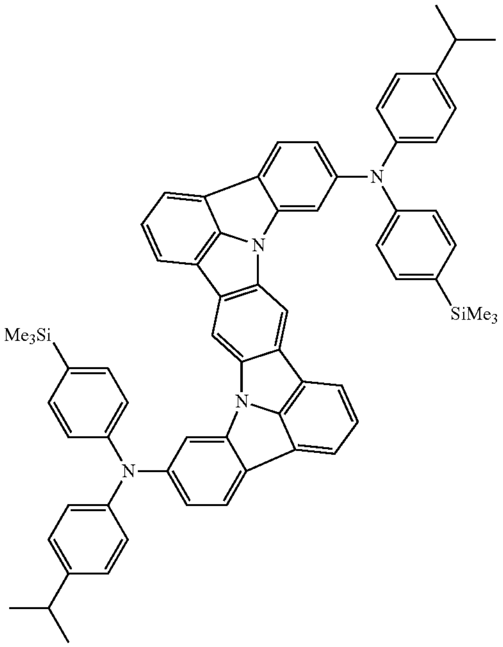

-continued
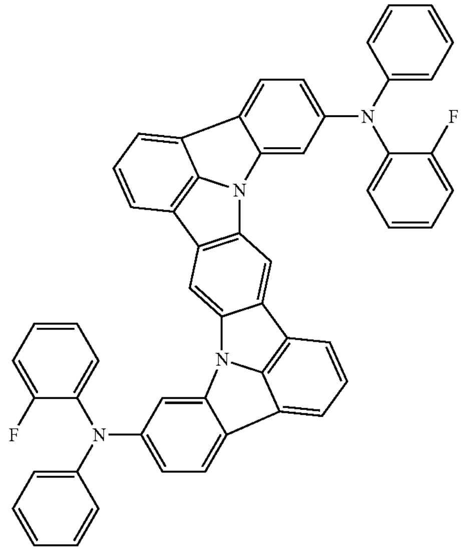
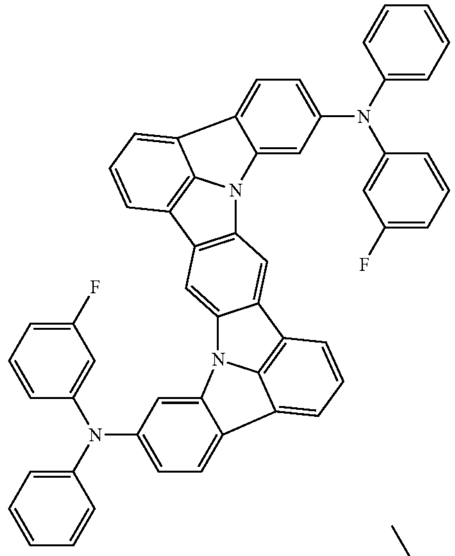
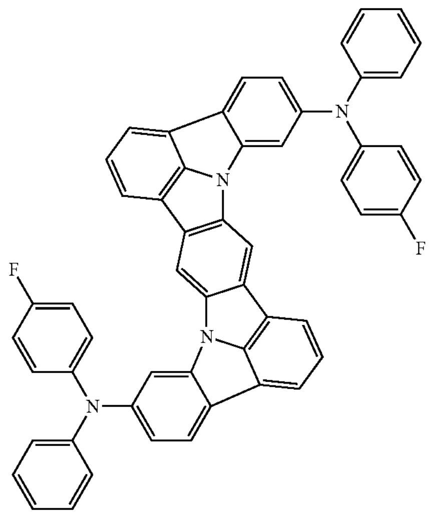
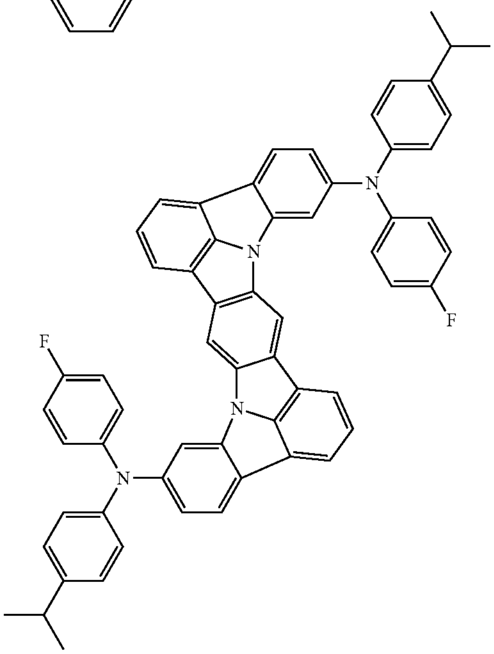
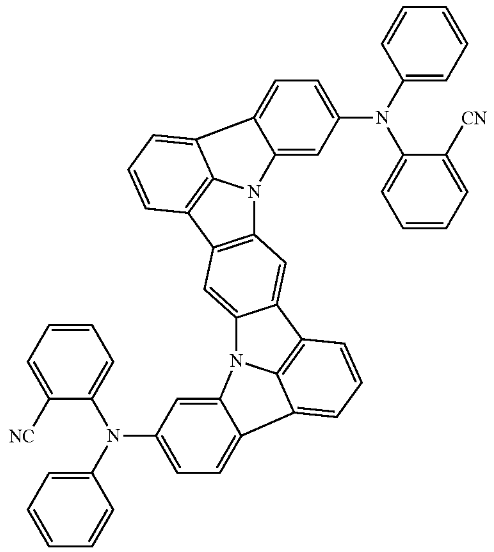
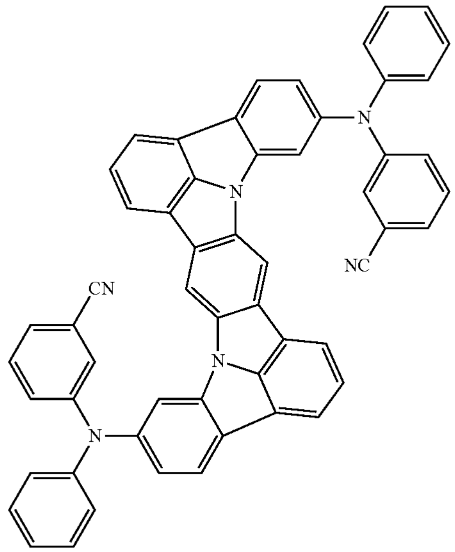

-continued
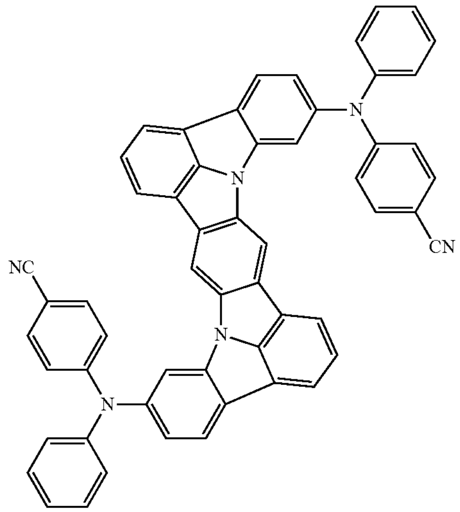
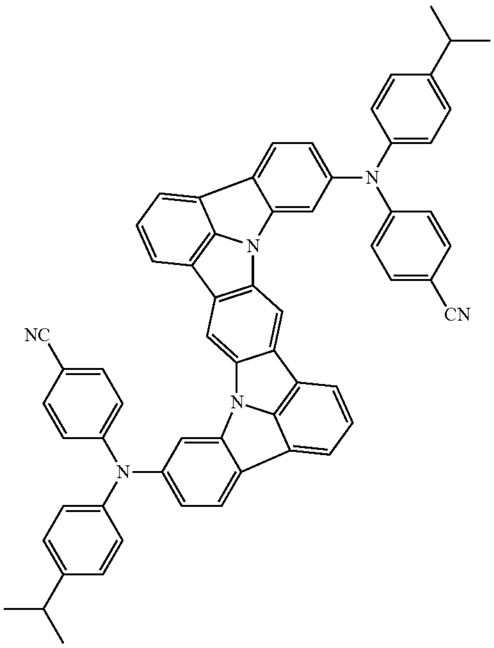
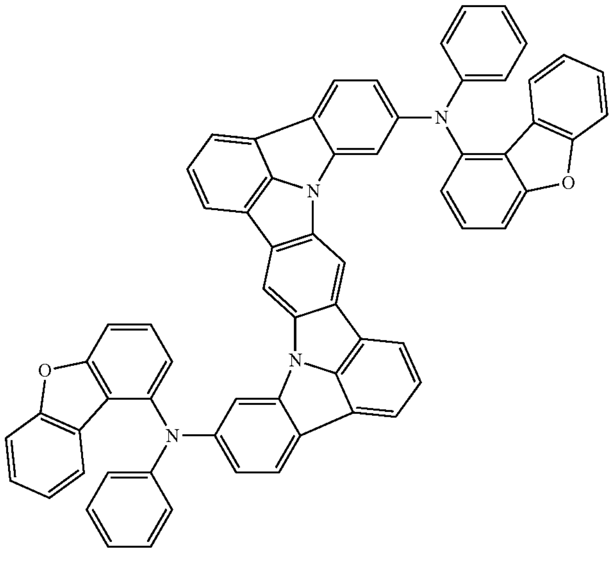

-continued
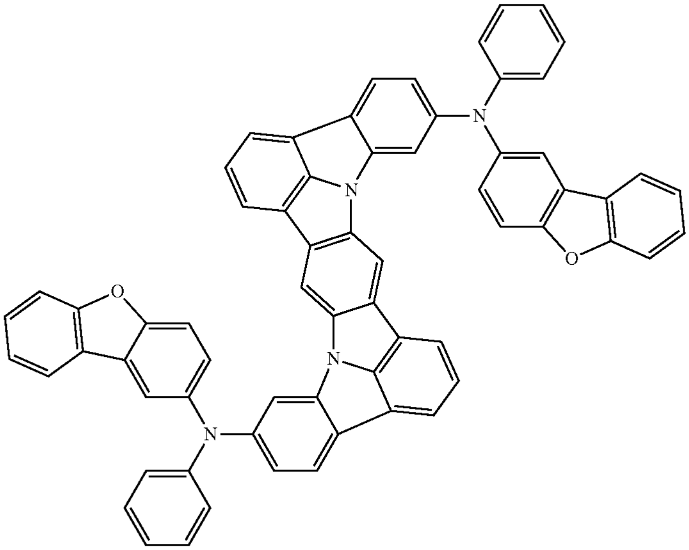
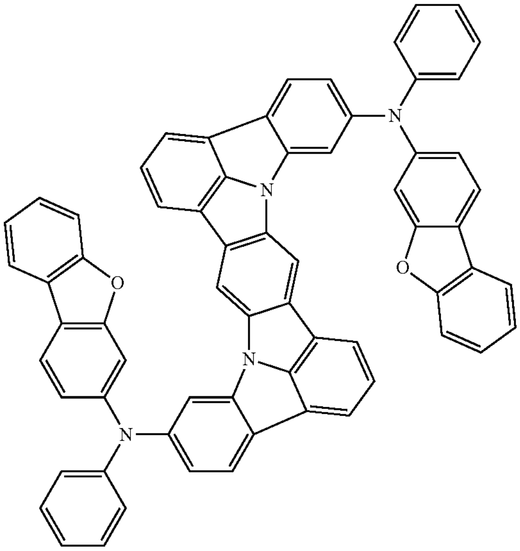
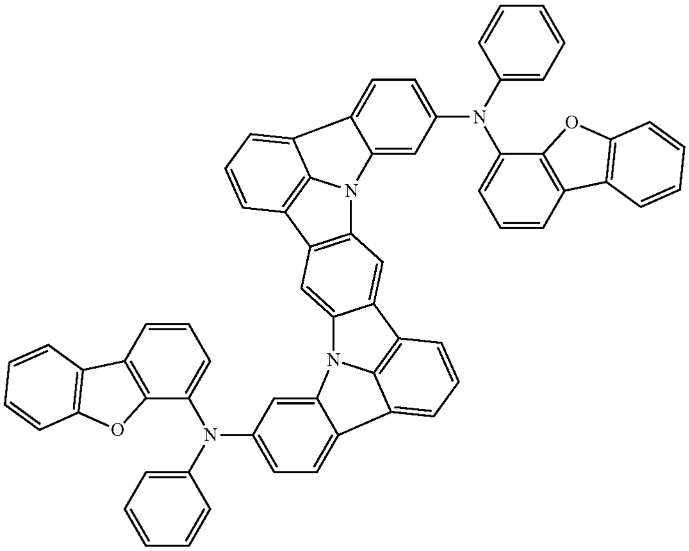

-continued
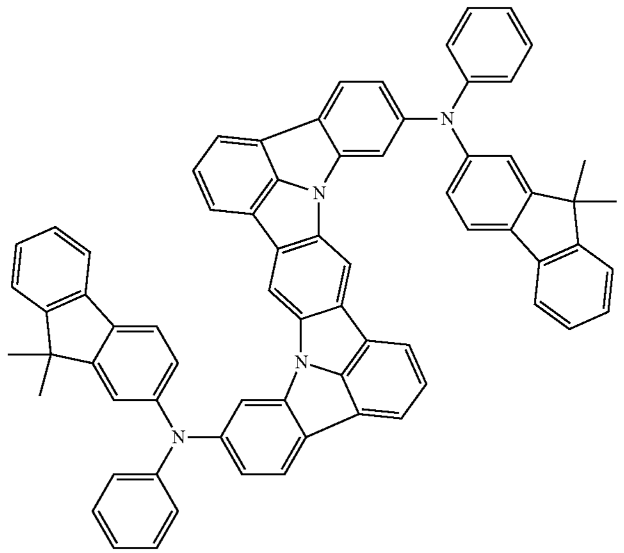
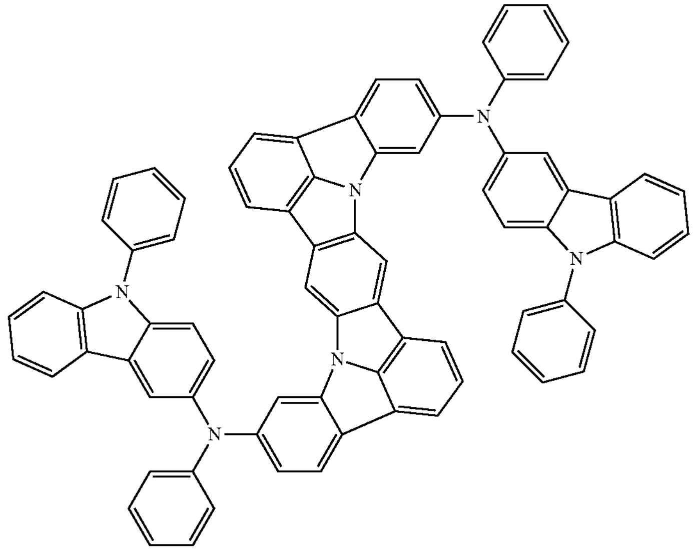
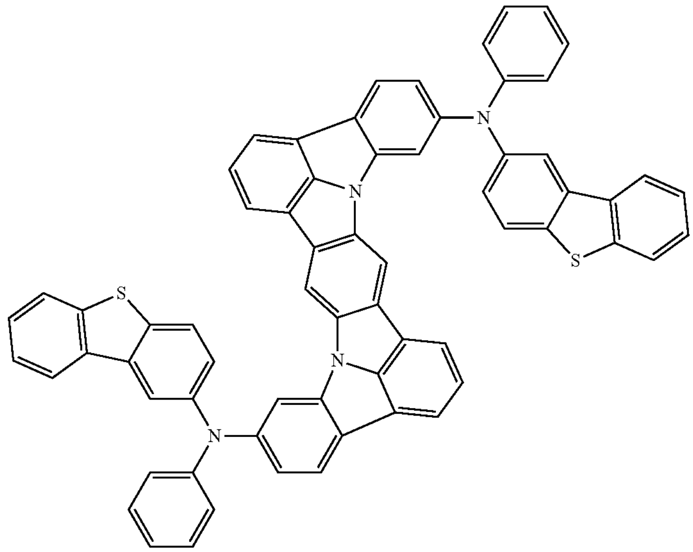

-continued
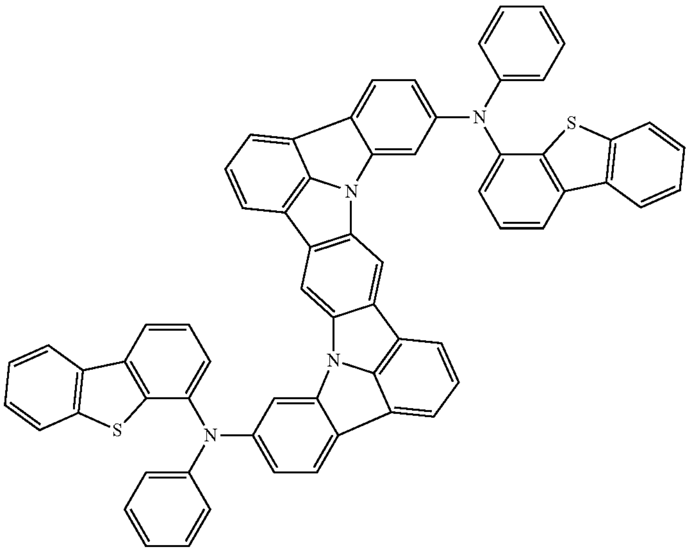
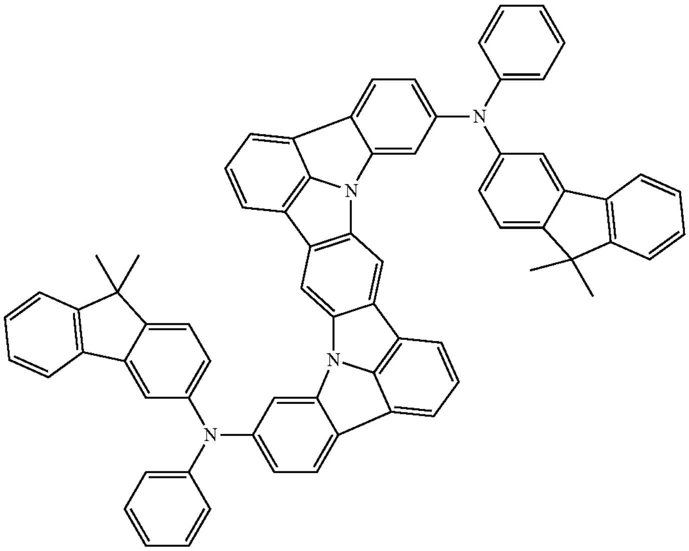
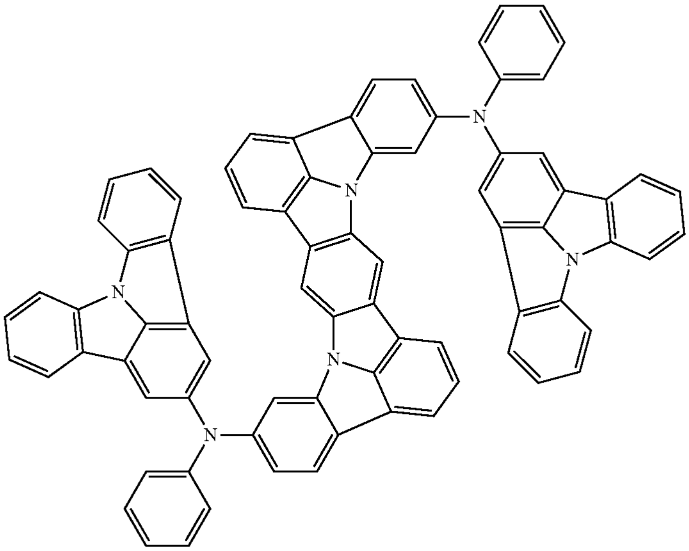

-continued
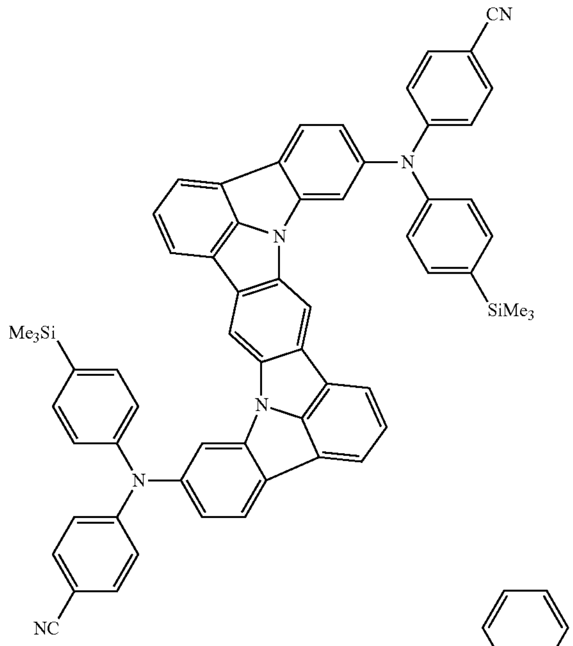
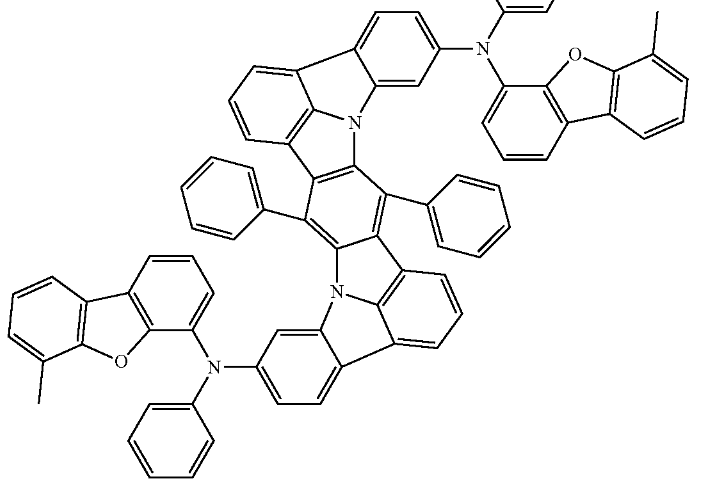
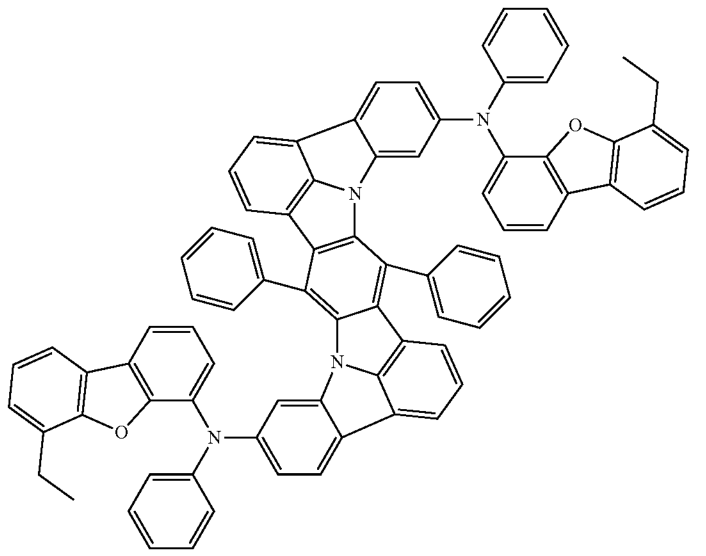

-continued
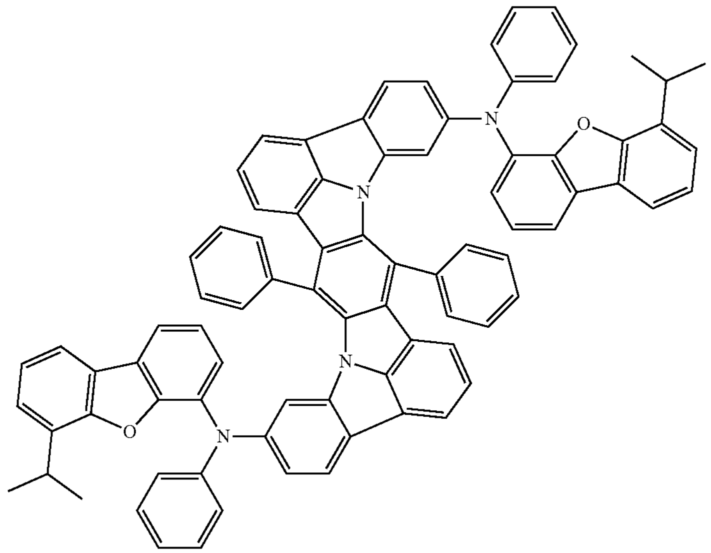
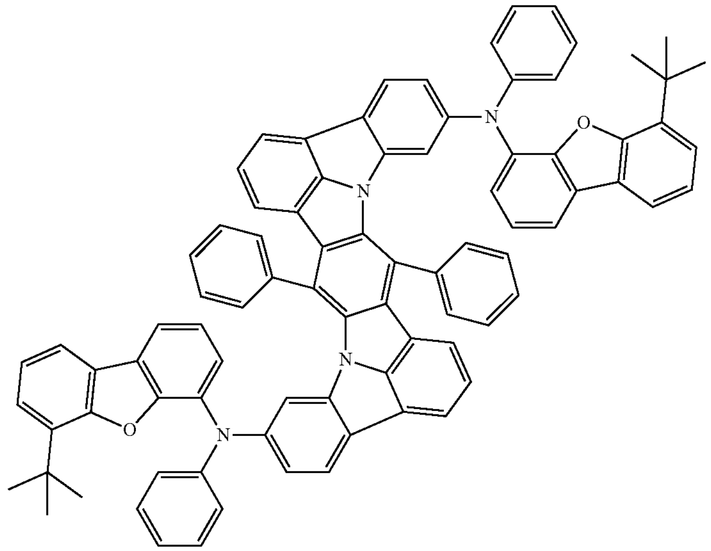
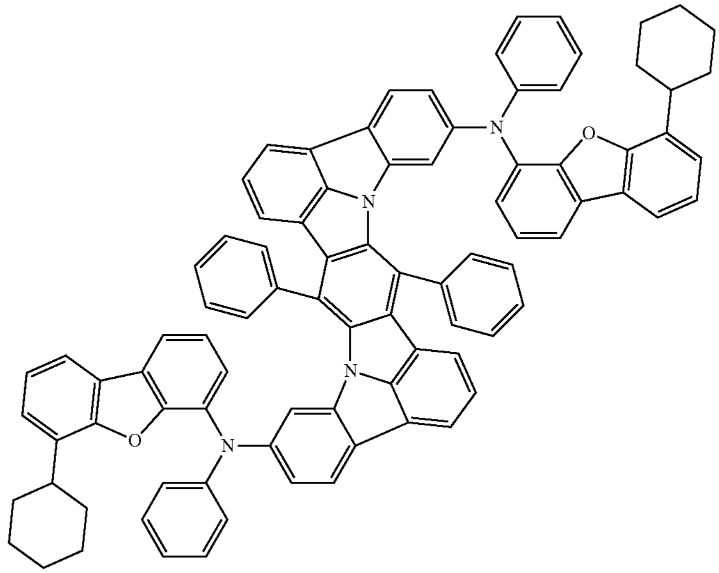

-continued
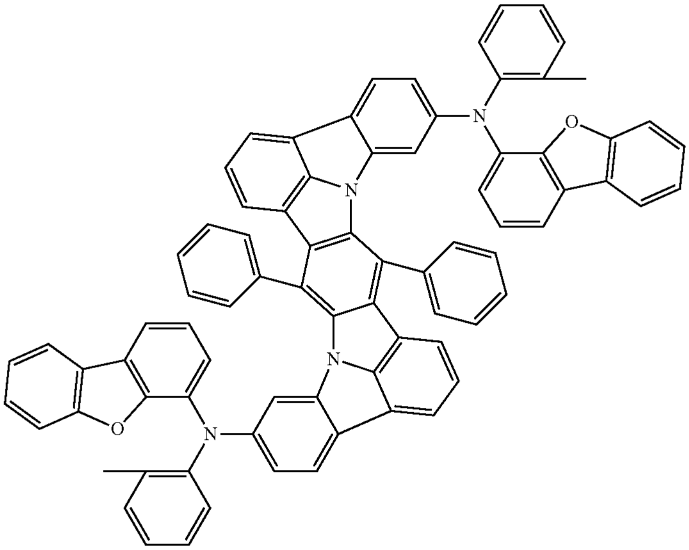
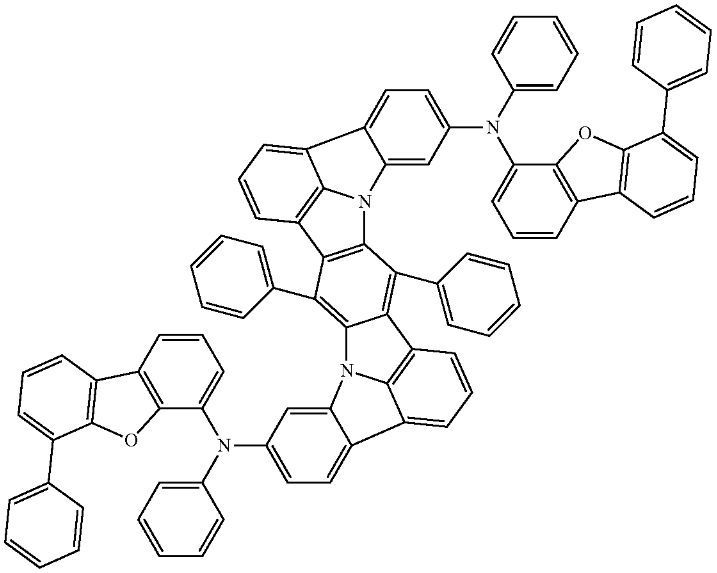
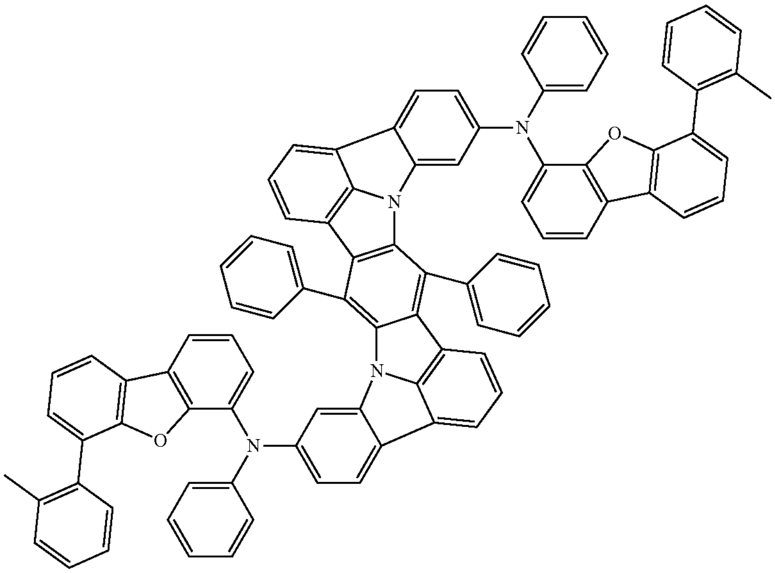

-continued
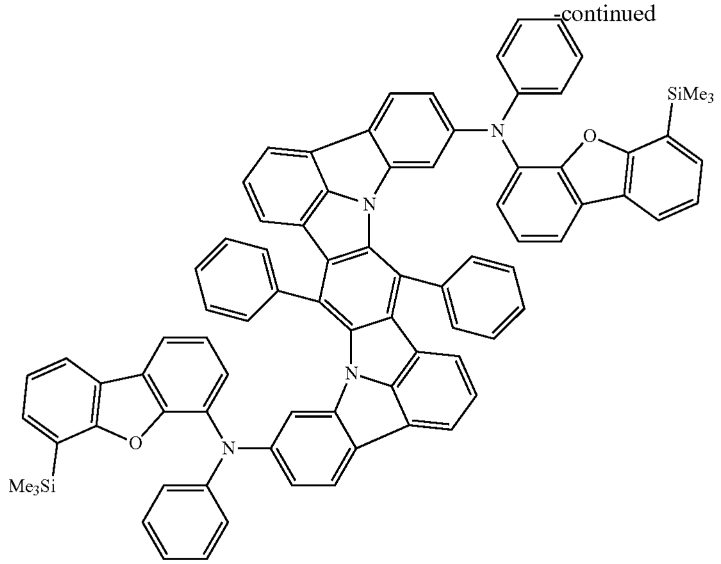
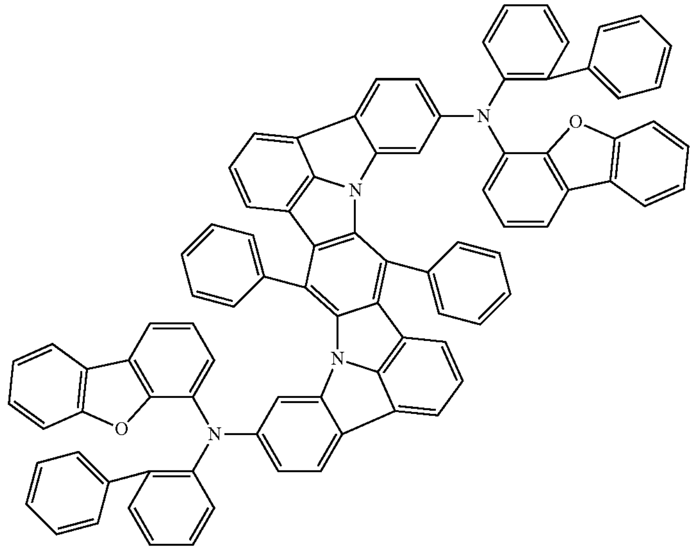
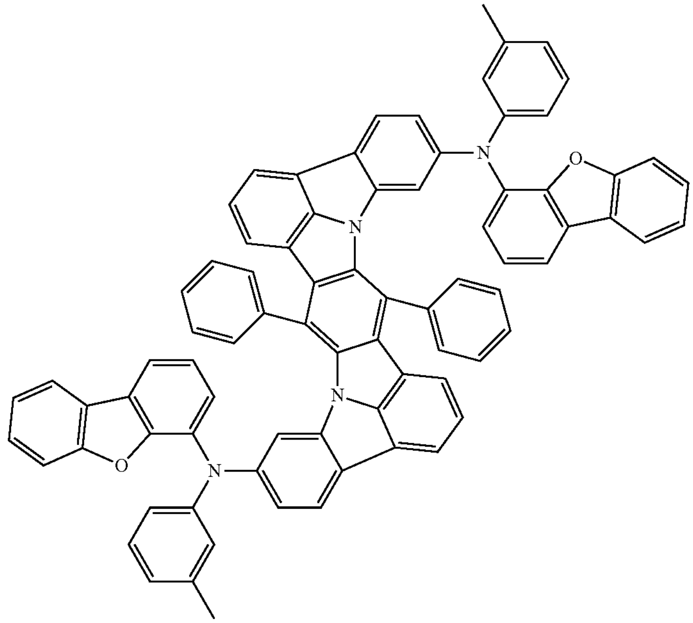

-continued
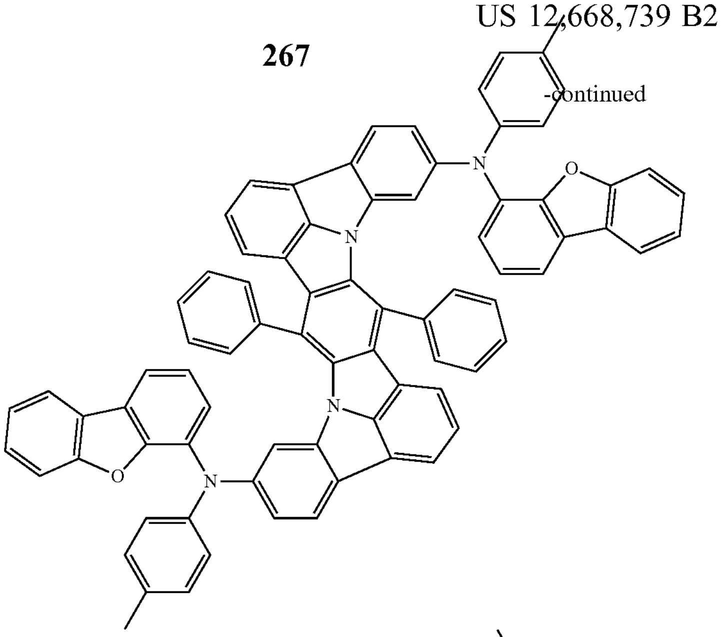
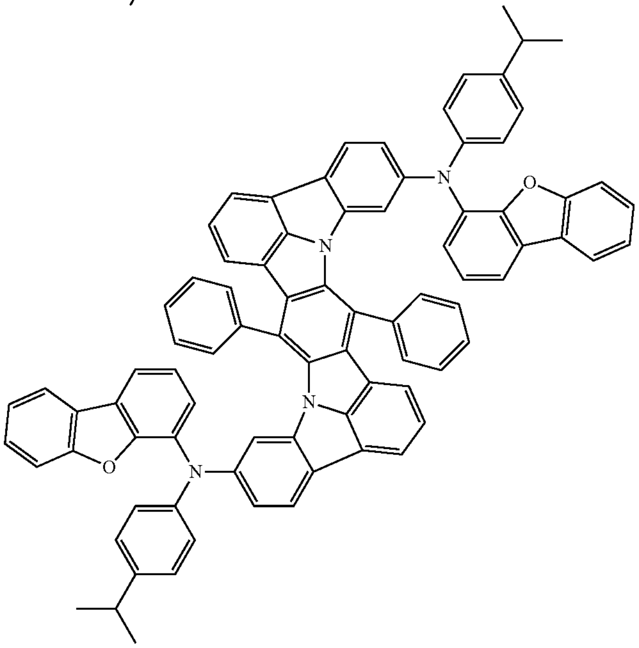
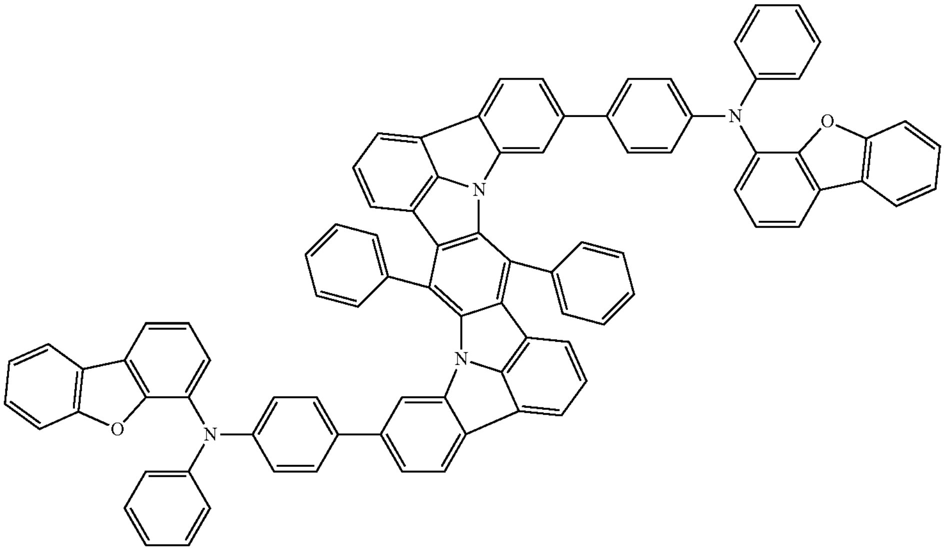

-continued
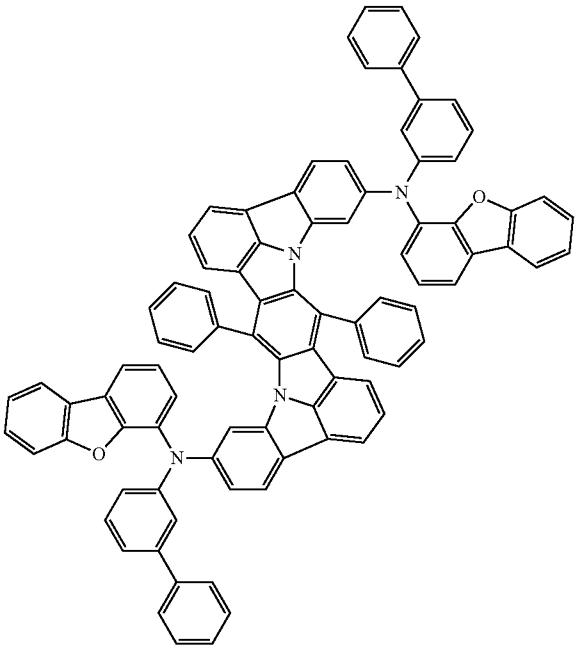
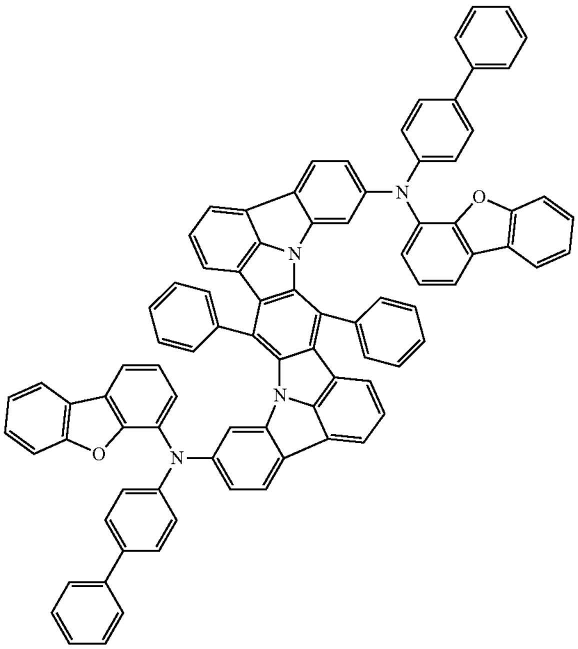
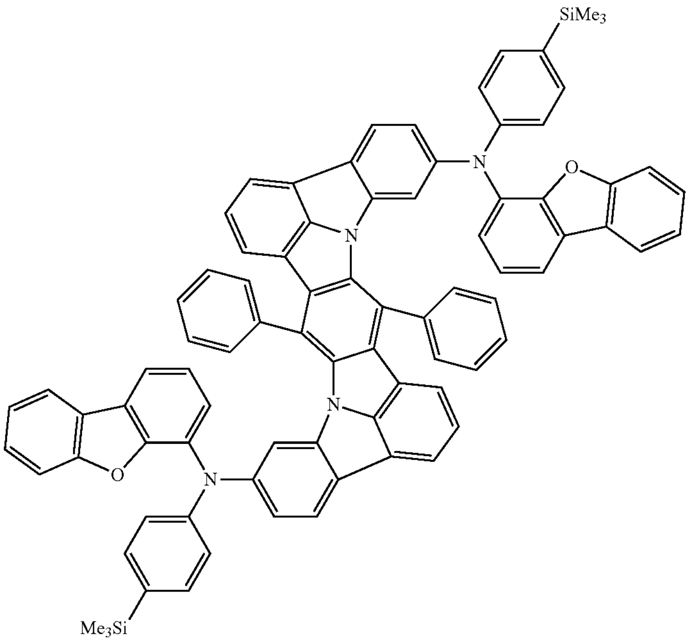

-continued
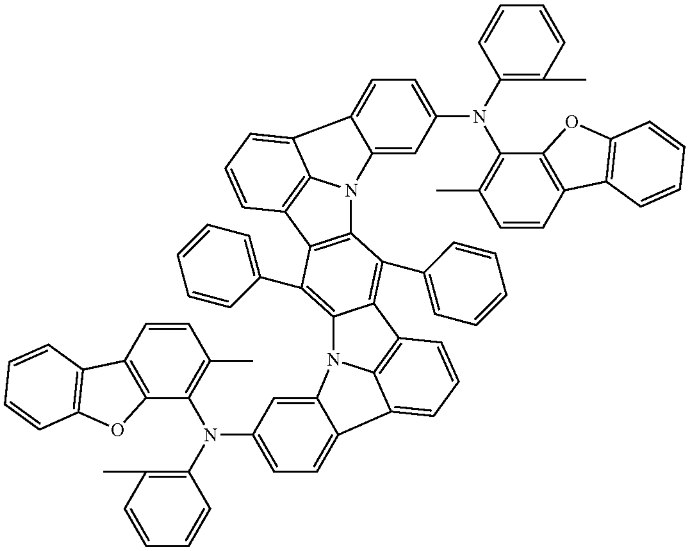
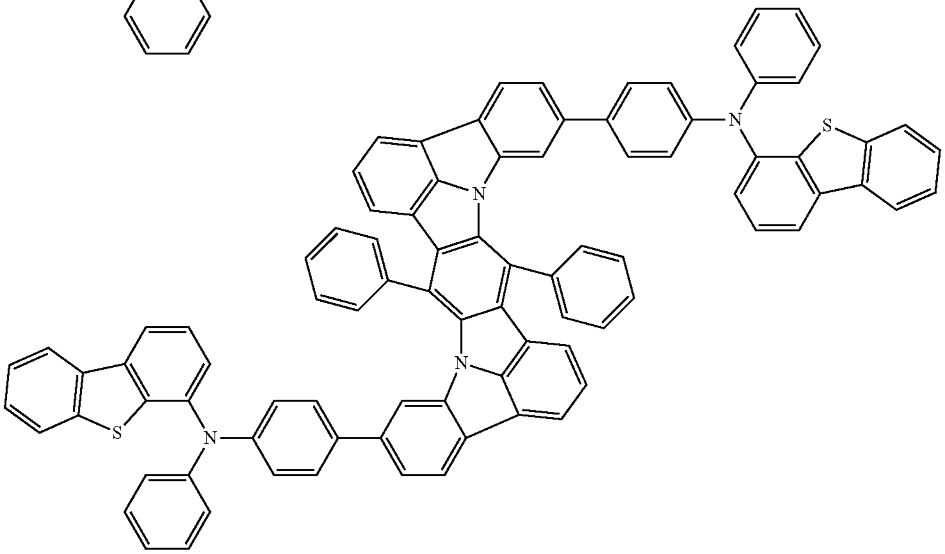
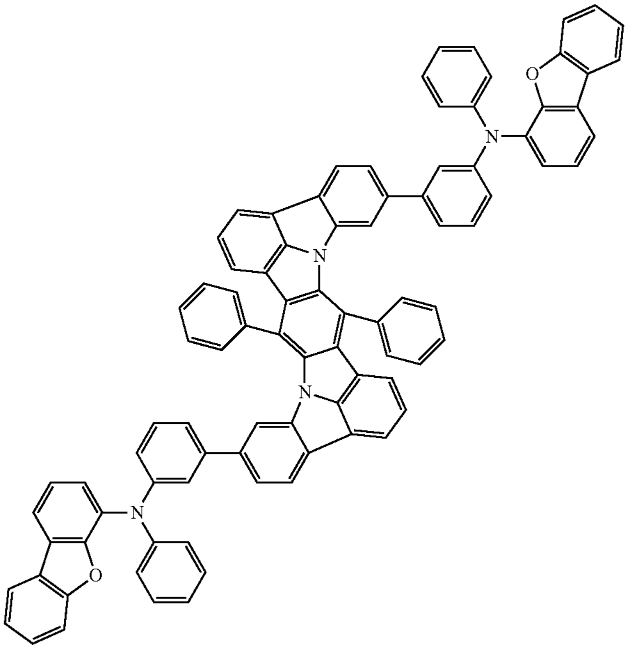

-continued
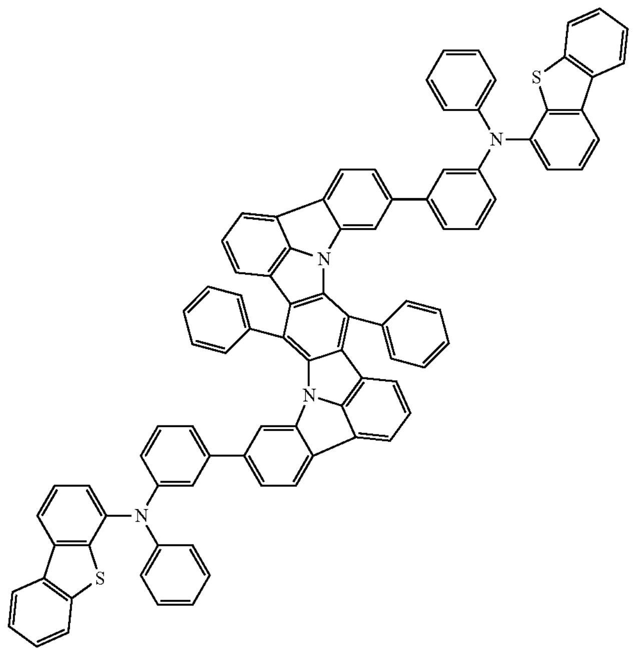
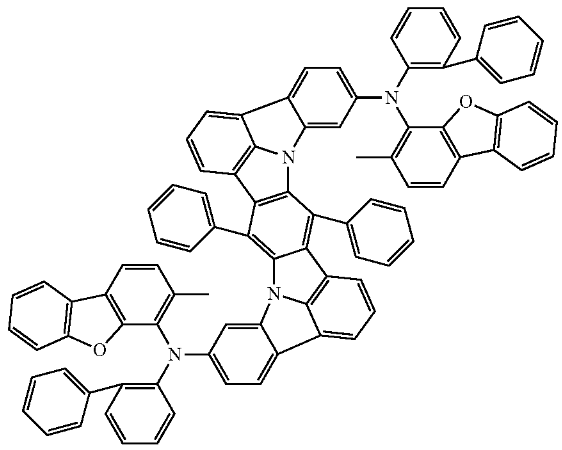
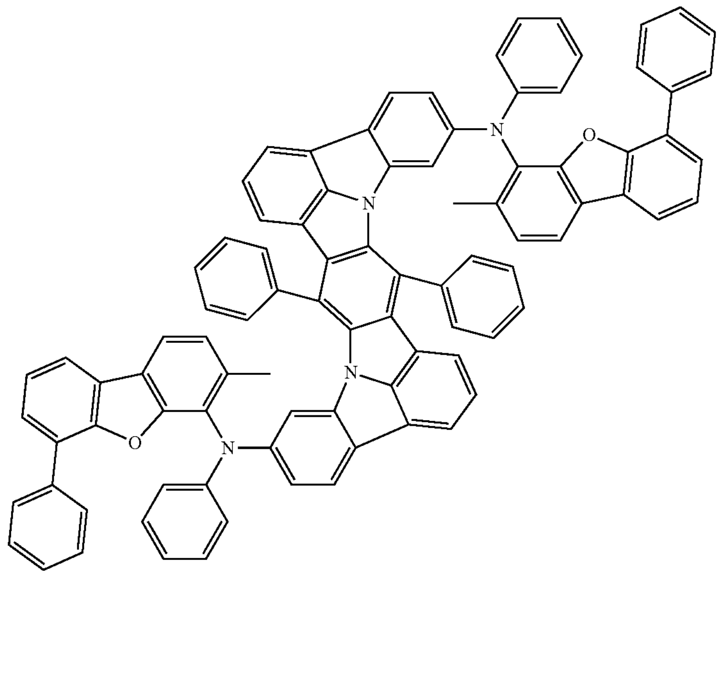

-continued
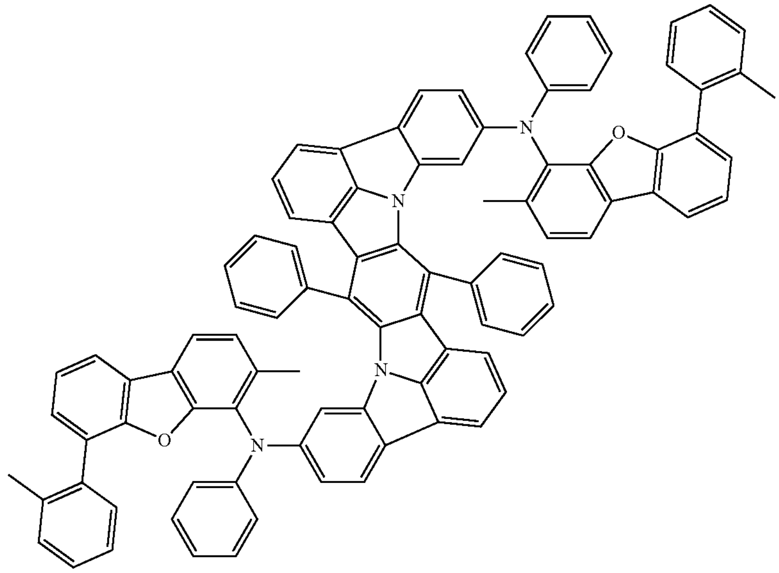
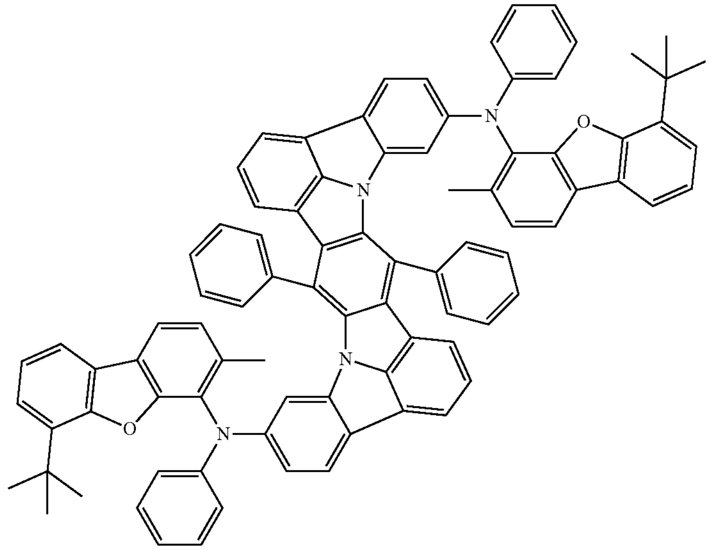
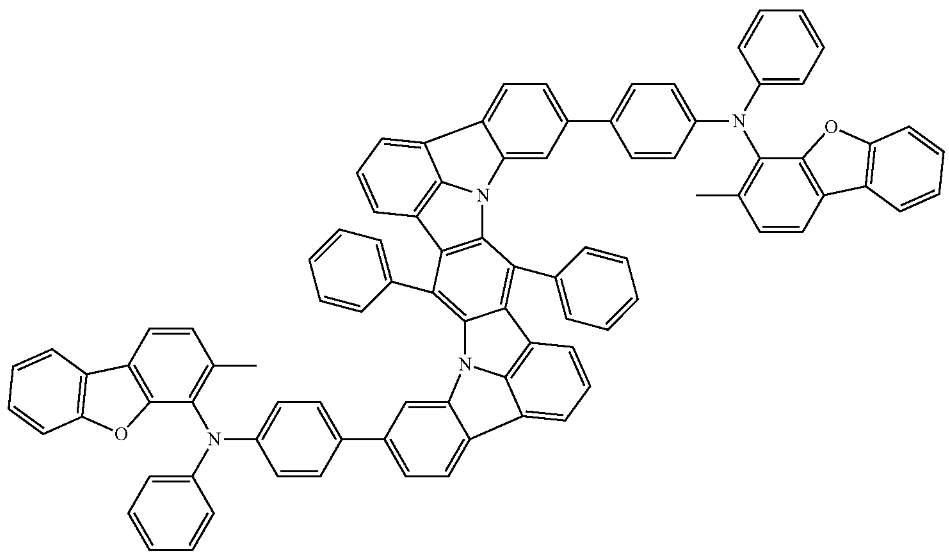

-continued
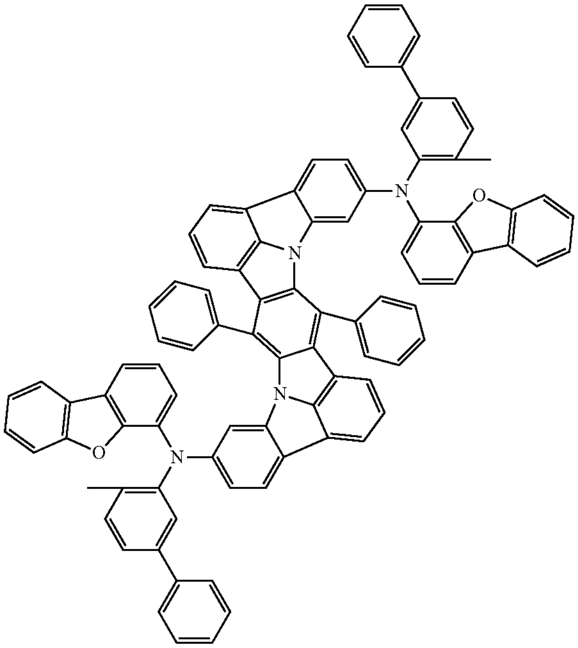
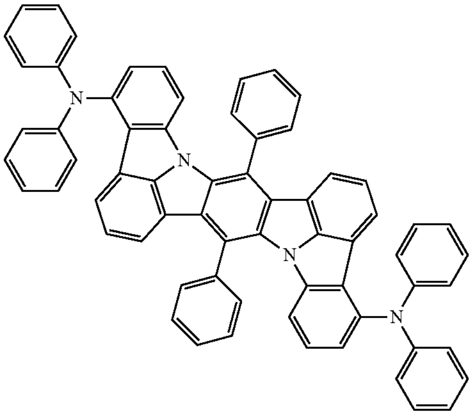
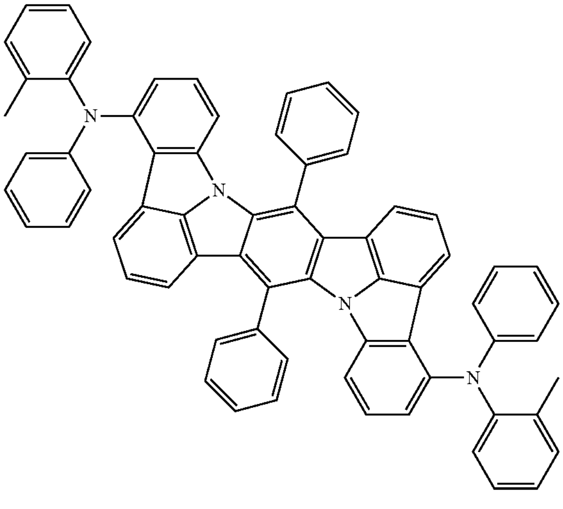
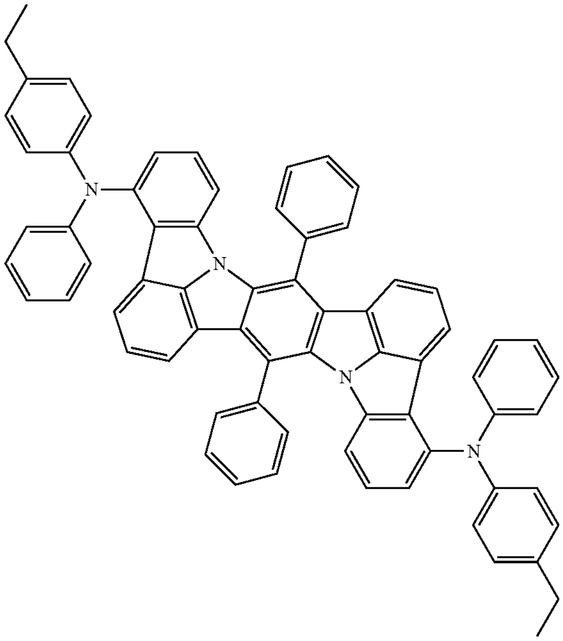

-continued
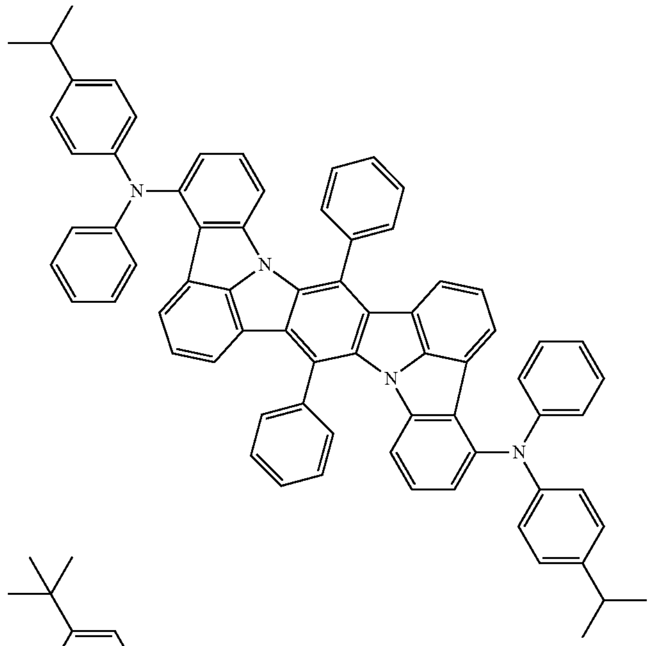
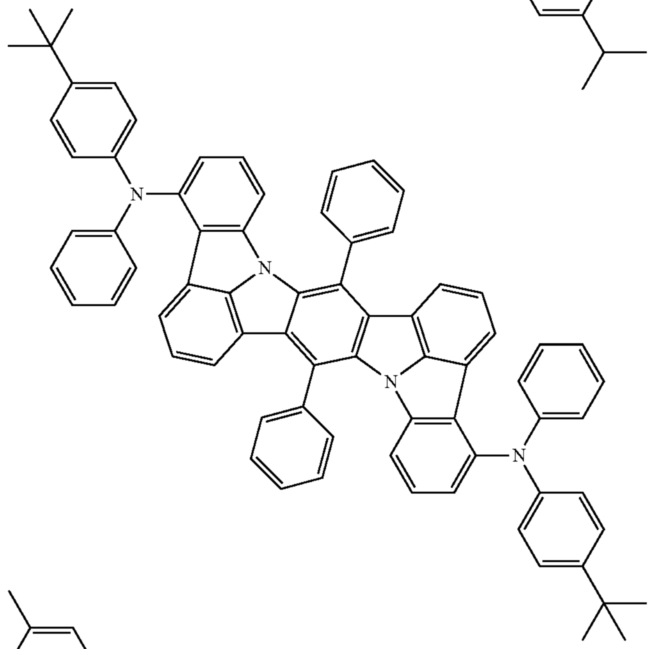
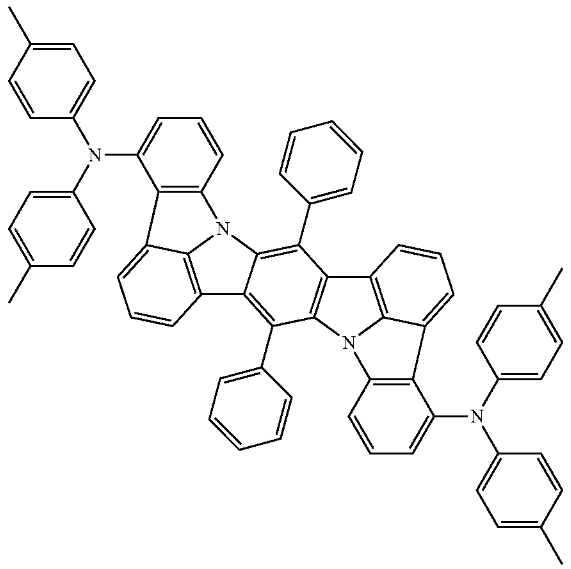

-continued
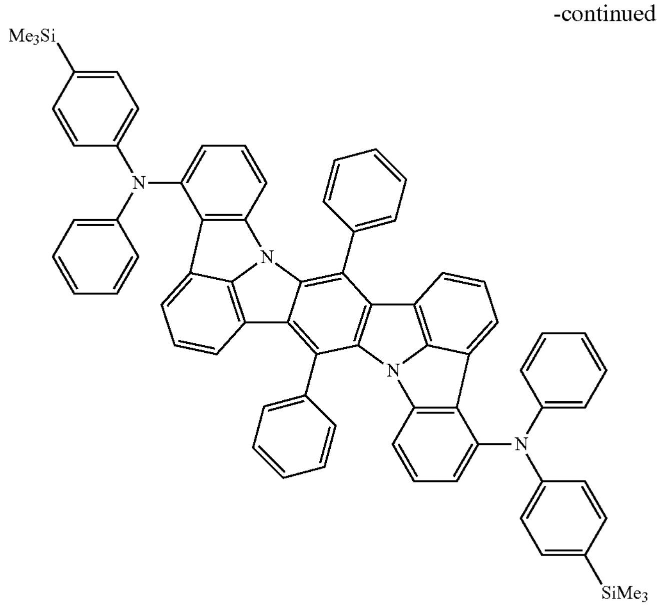
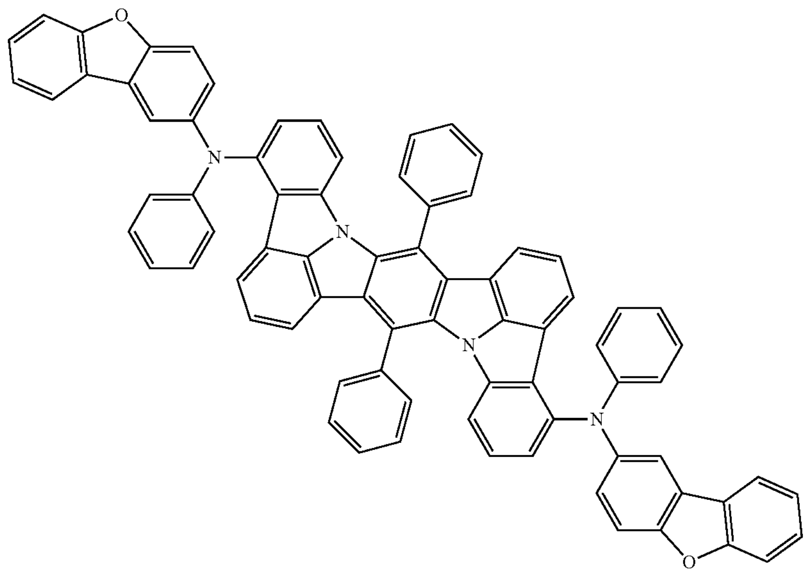
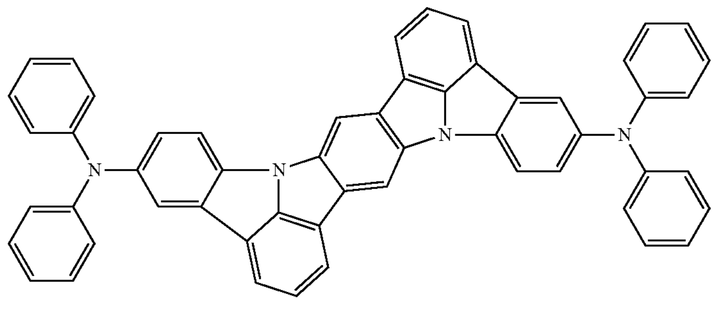

-continued
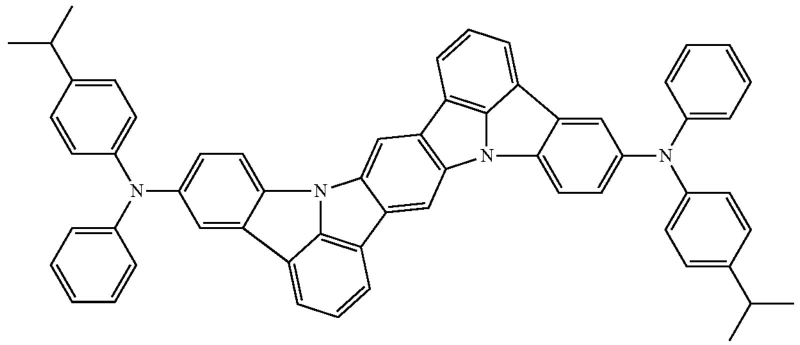
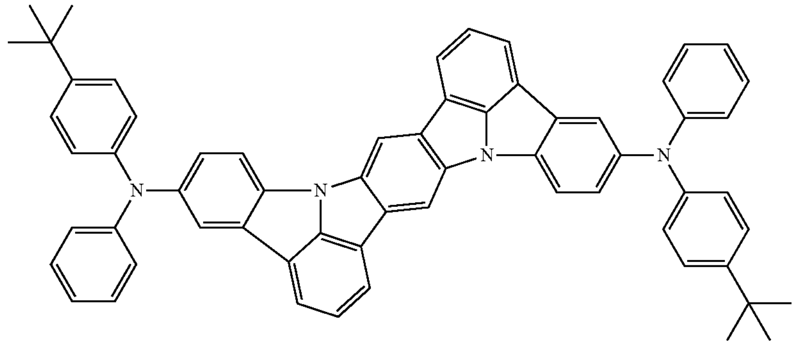
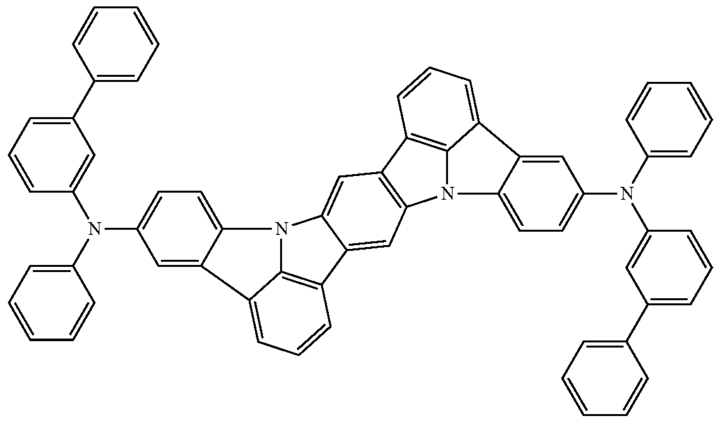
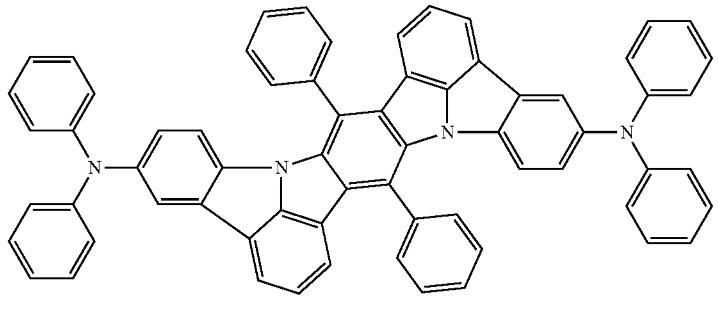

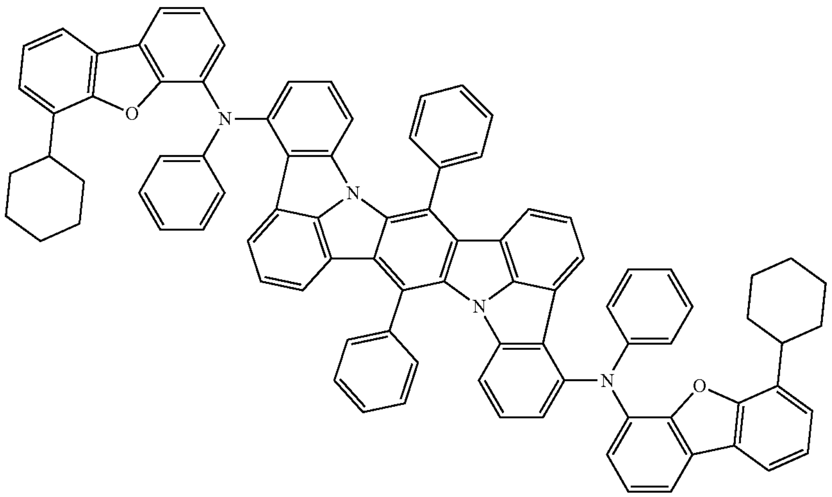
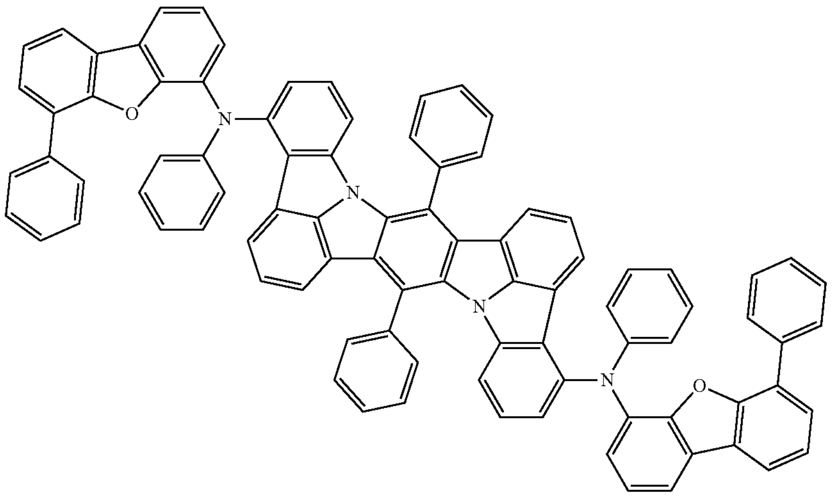
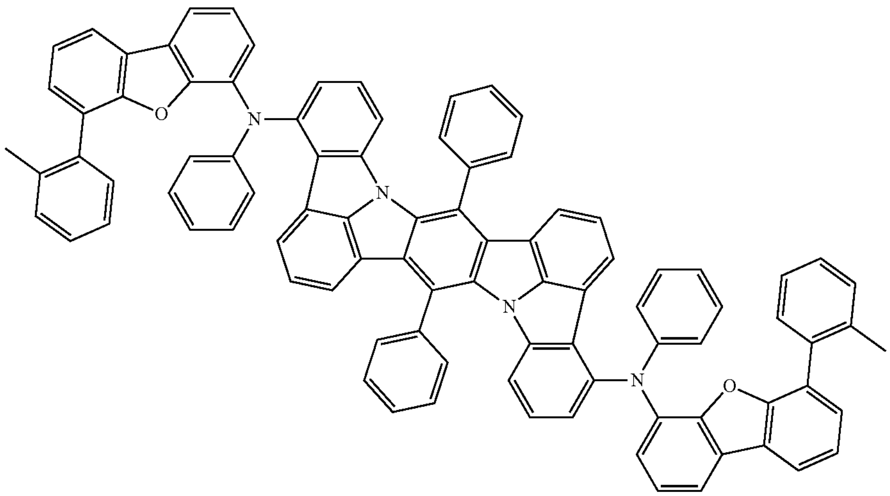

-continued
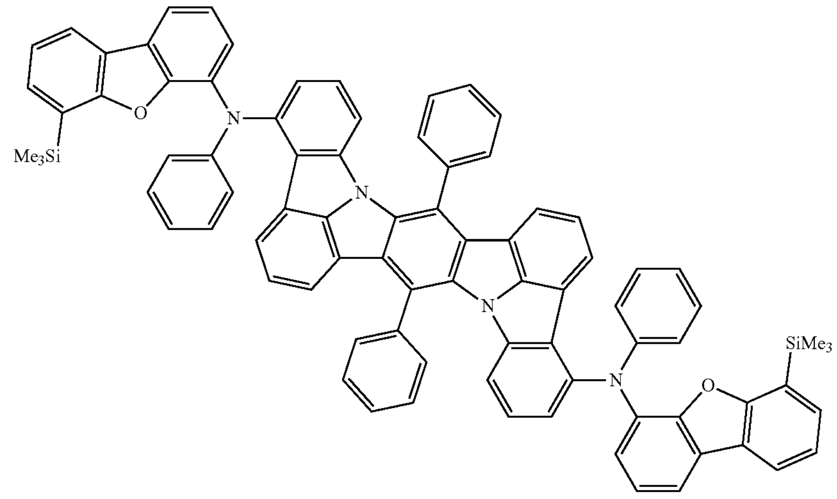
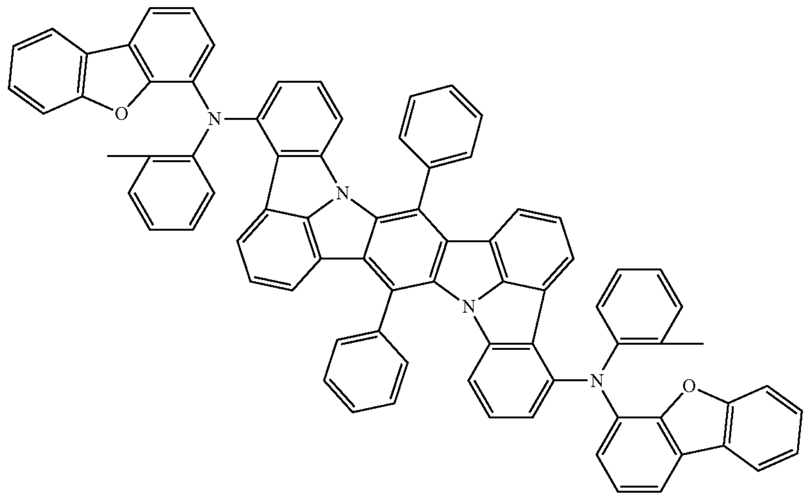
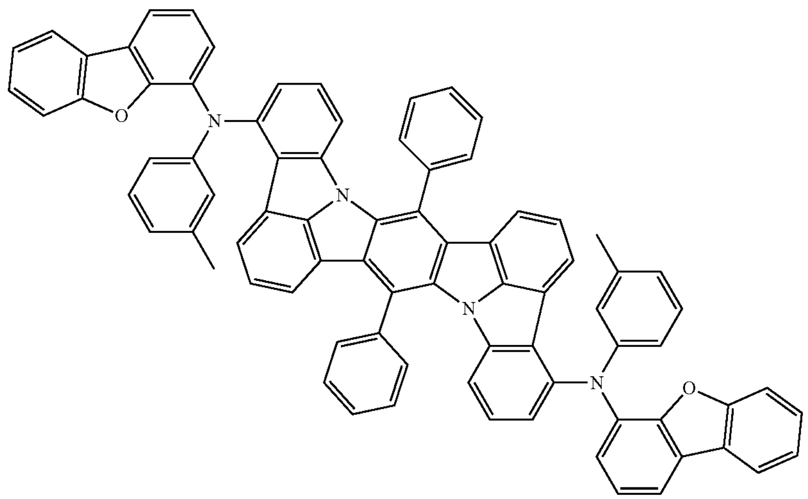

-continued
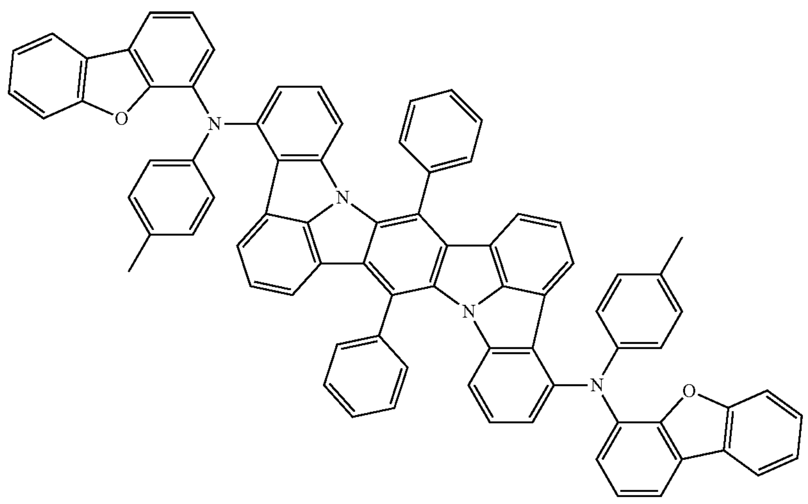
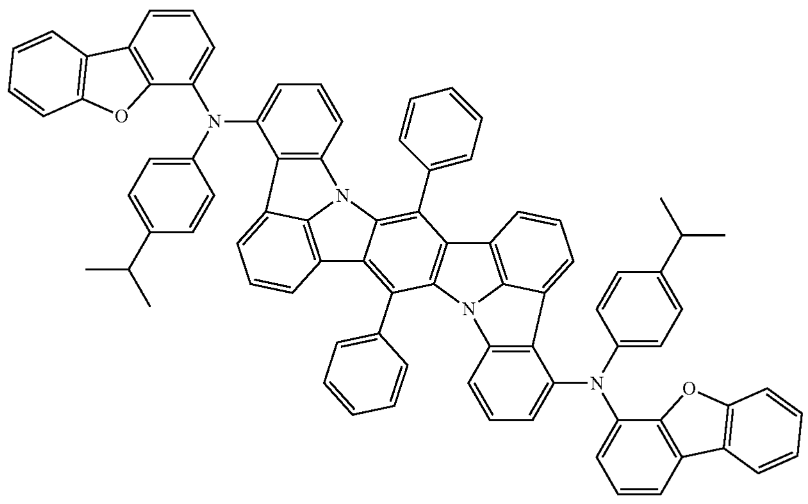
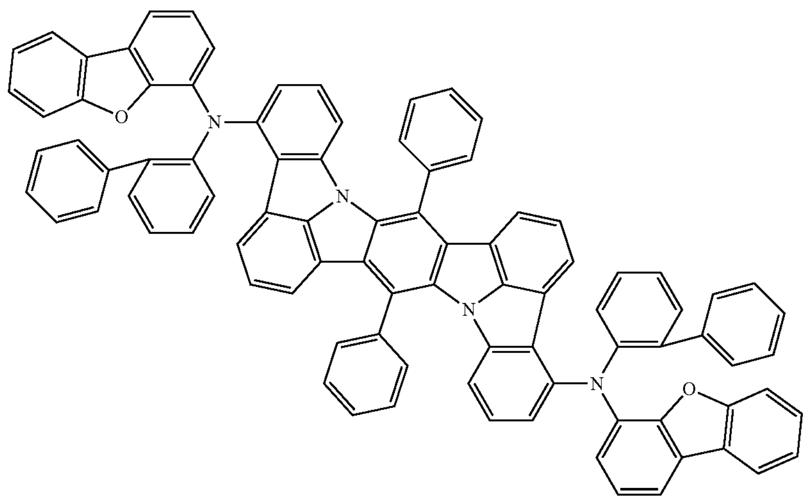

-continued
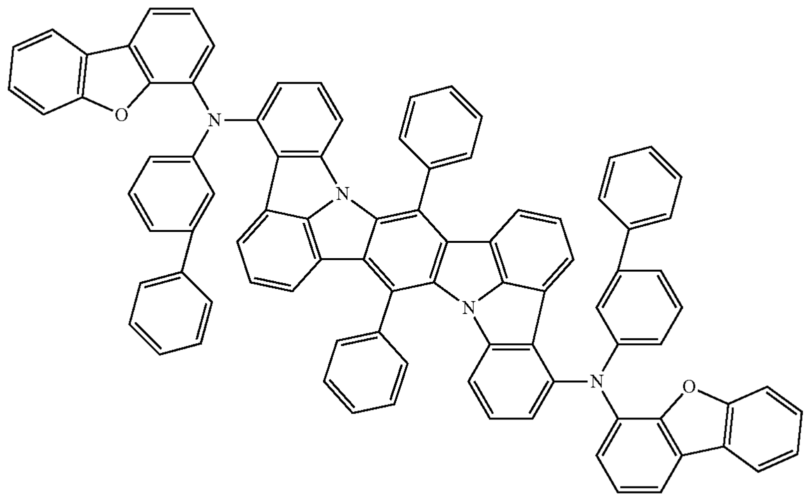
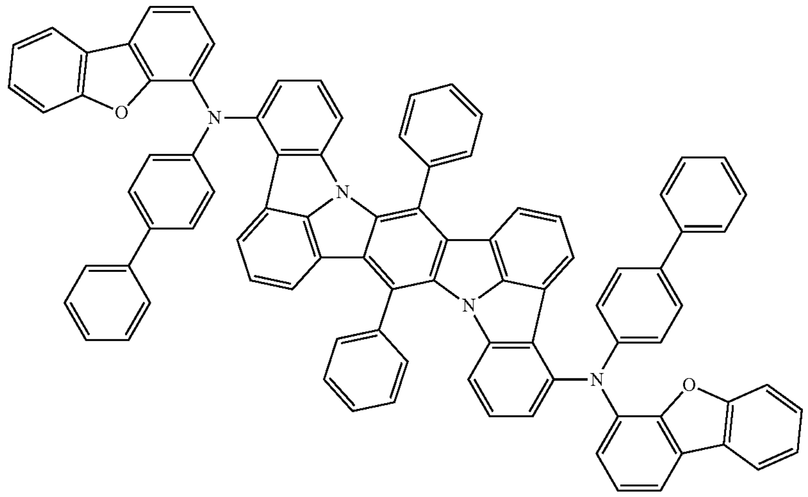
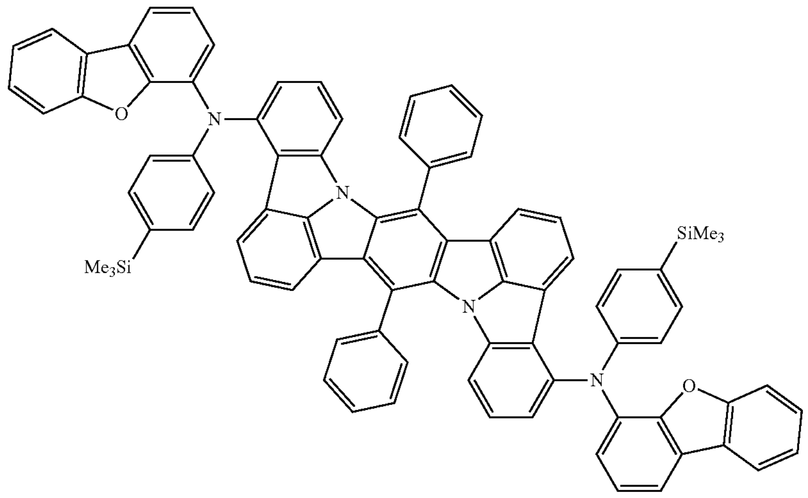

-continued
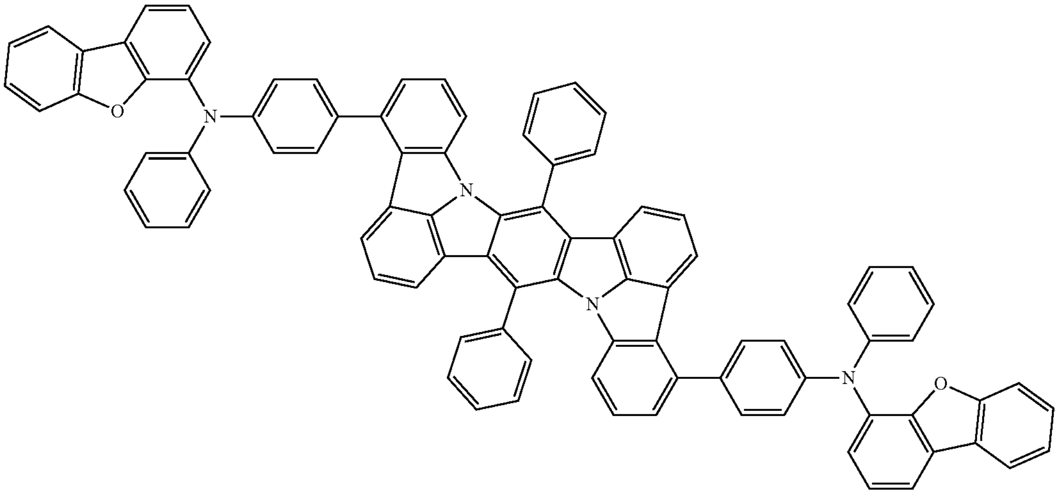
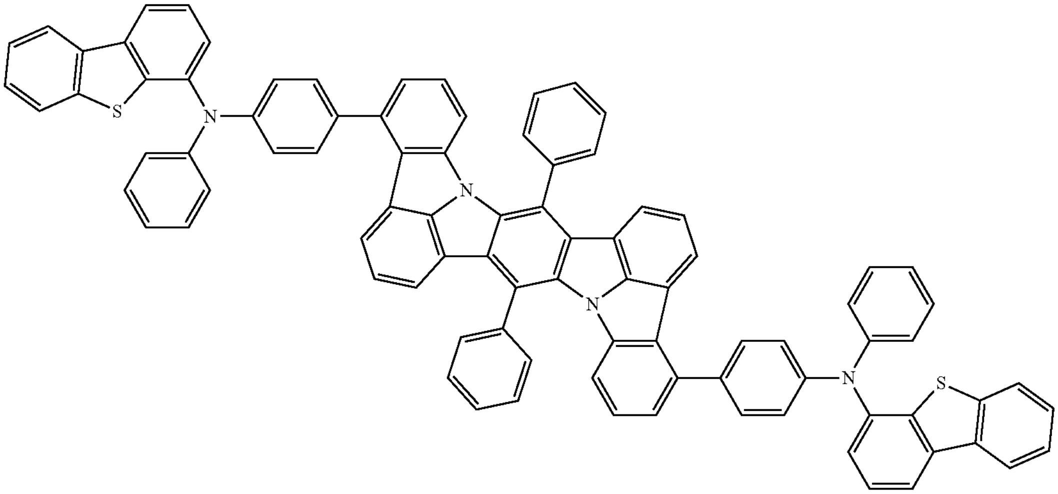
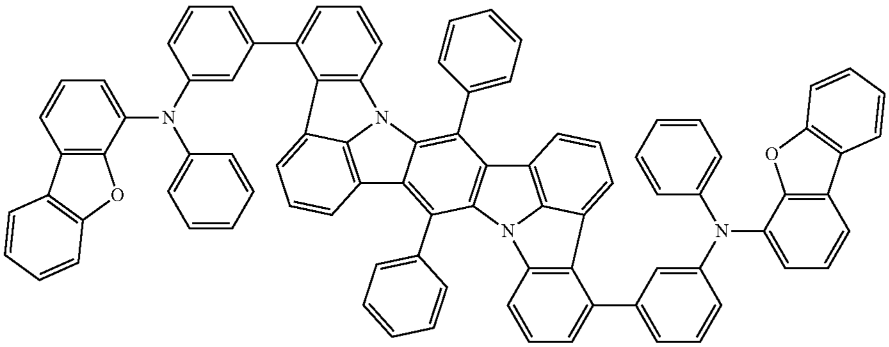
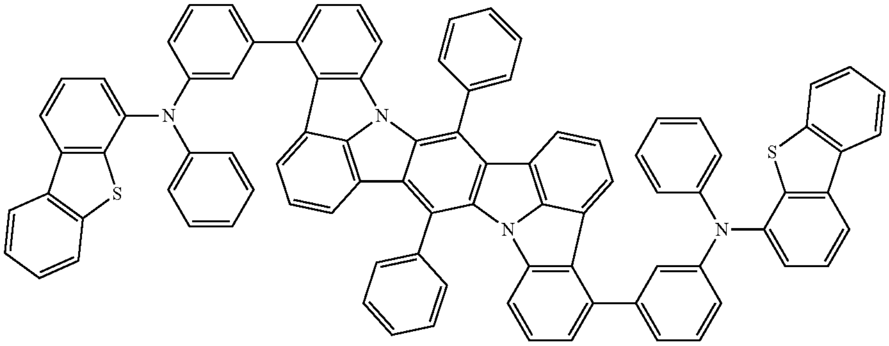

-continued
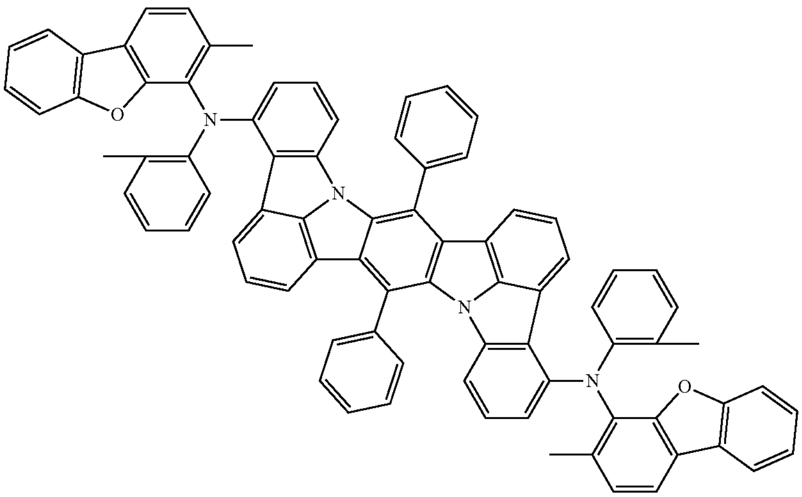
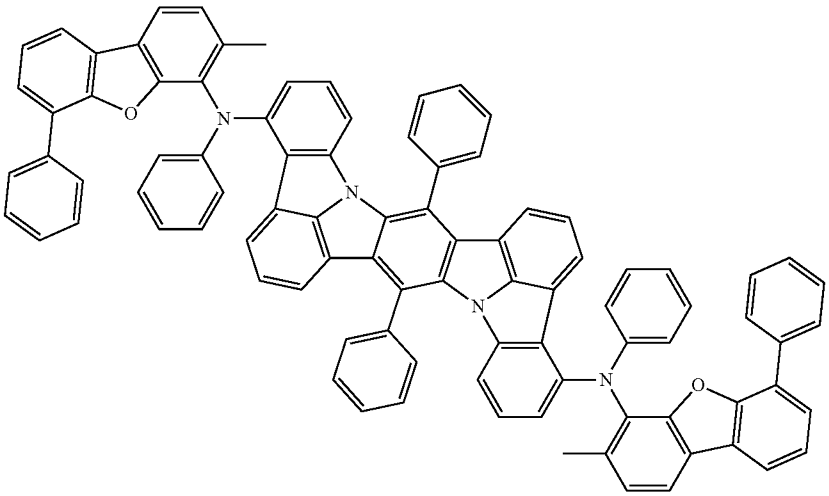
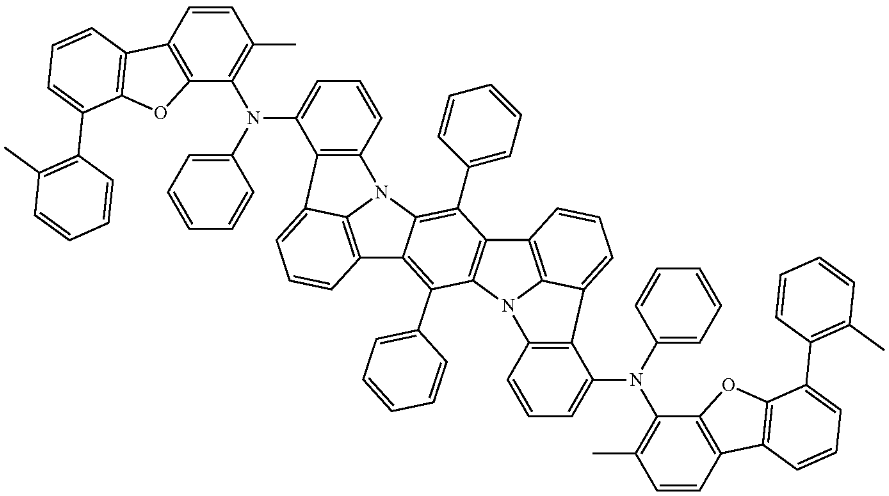

-continued
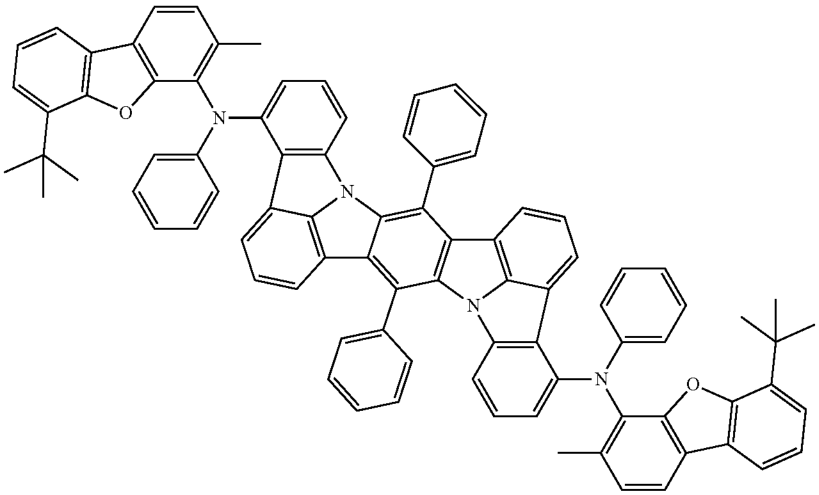
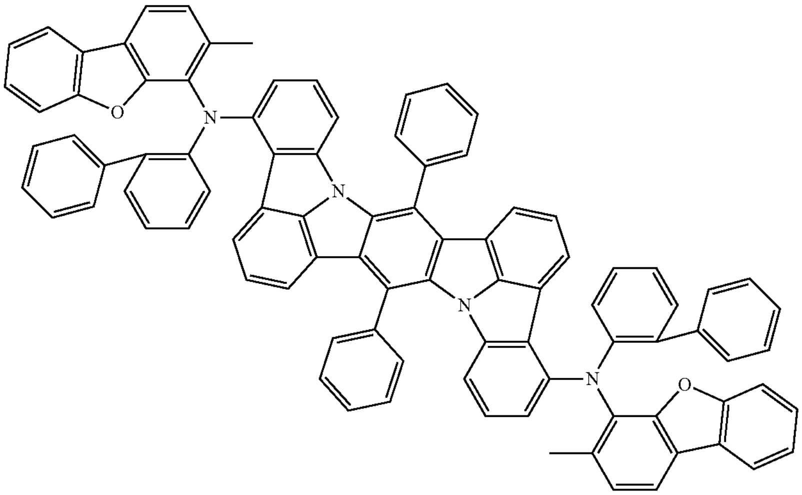
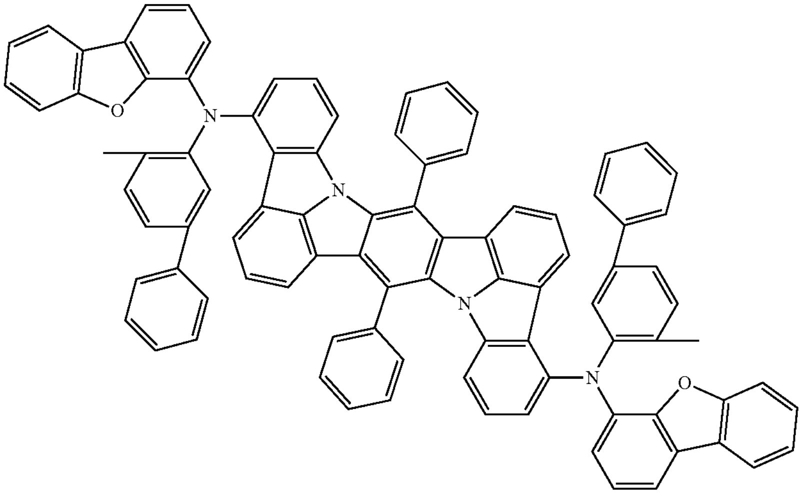

-continued
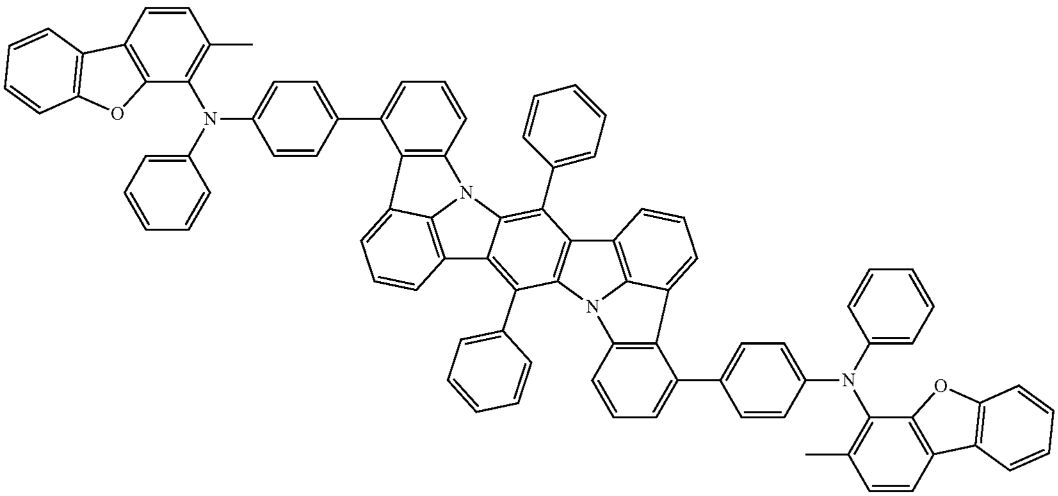
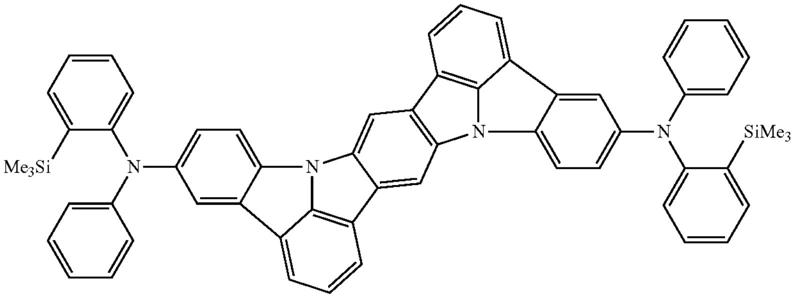
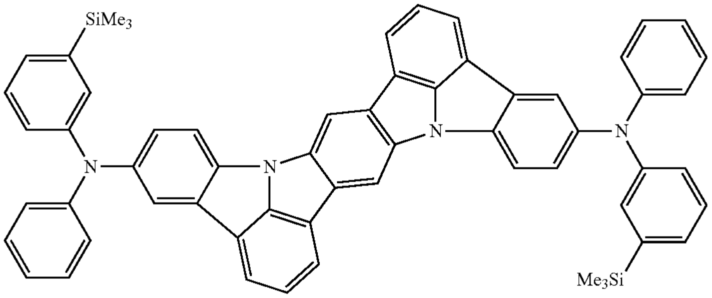
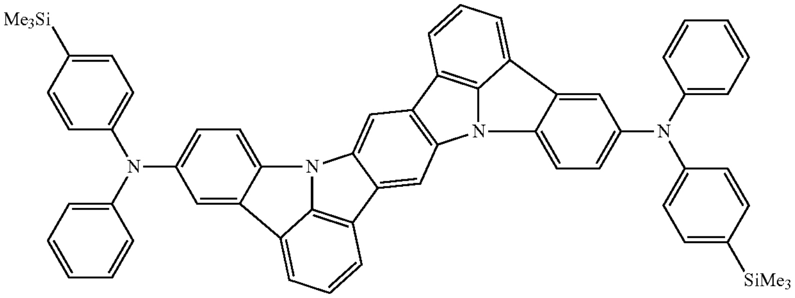

-continued
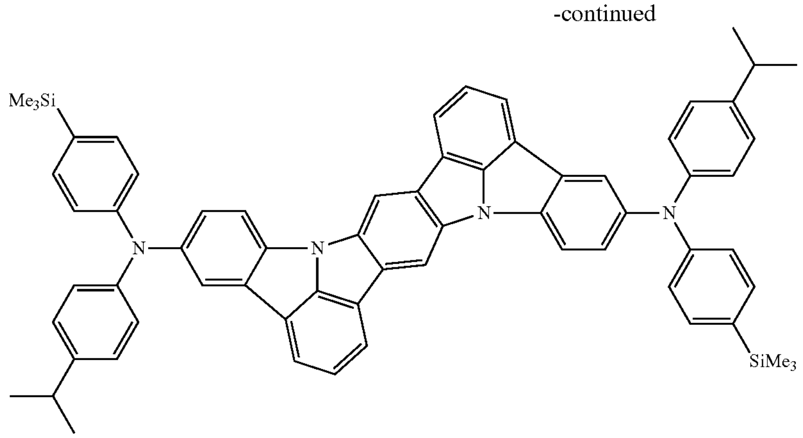
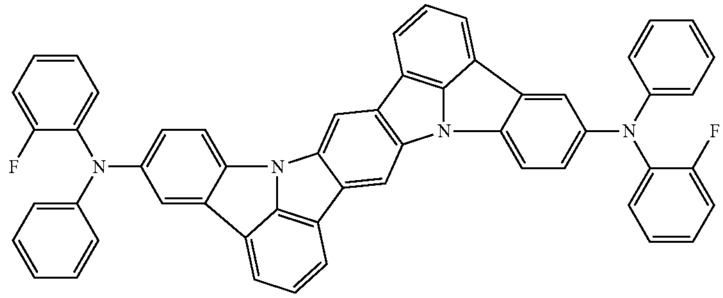
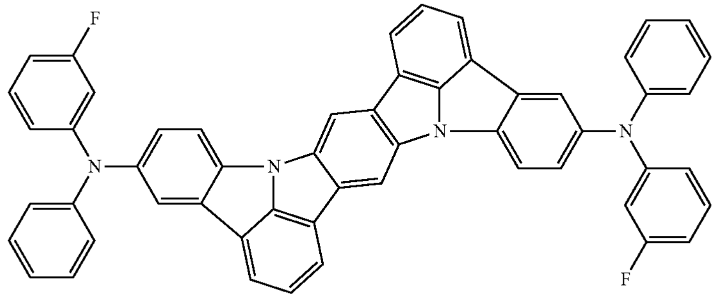
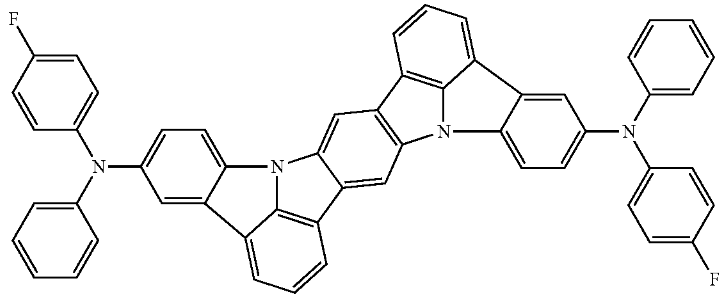
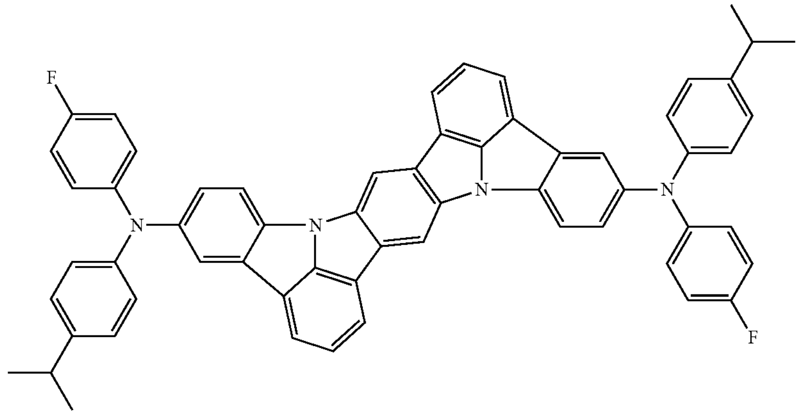

-continued
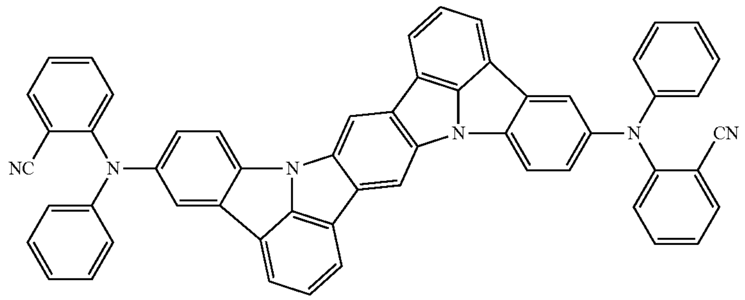
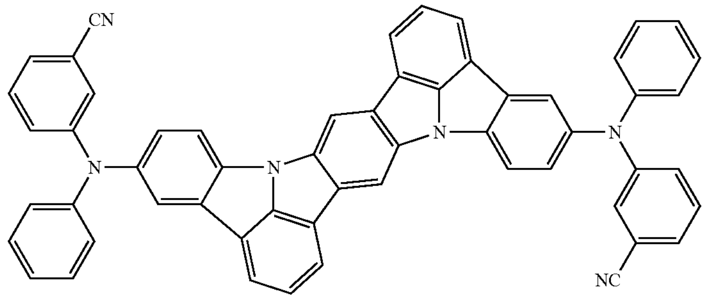
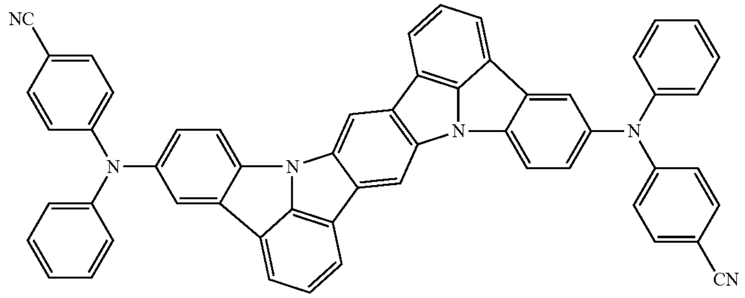
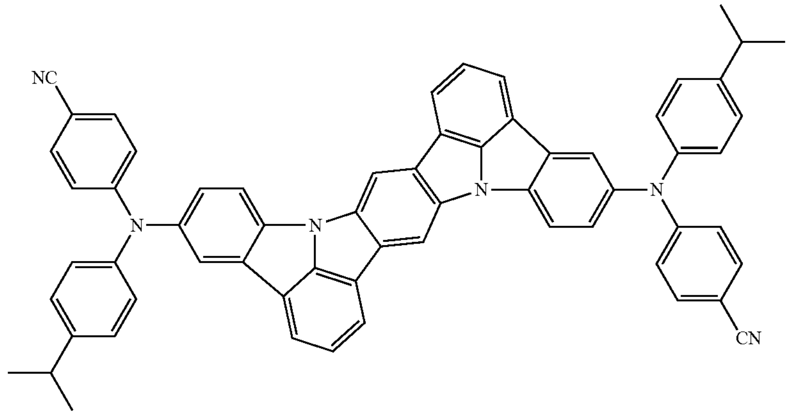
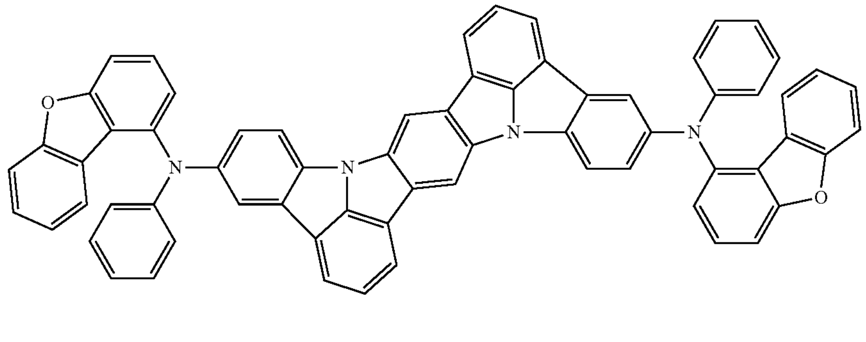

-continued
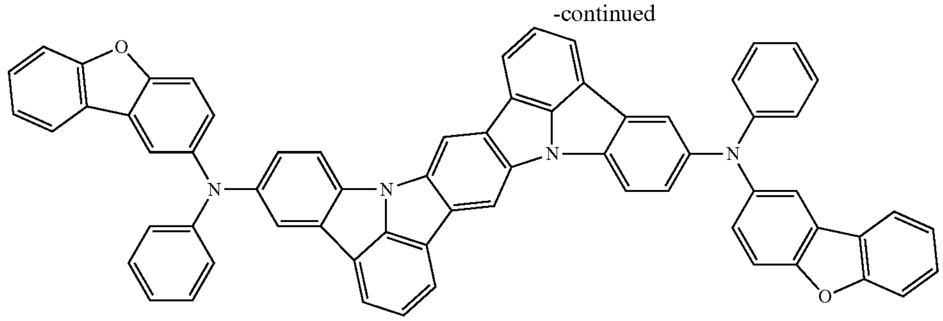
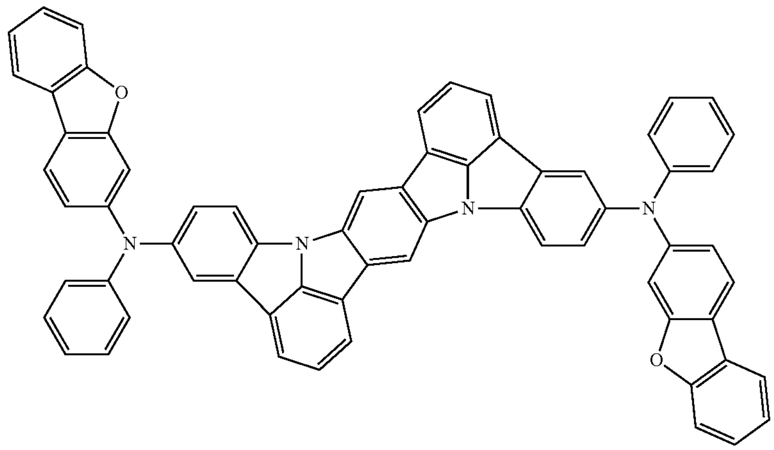
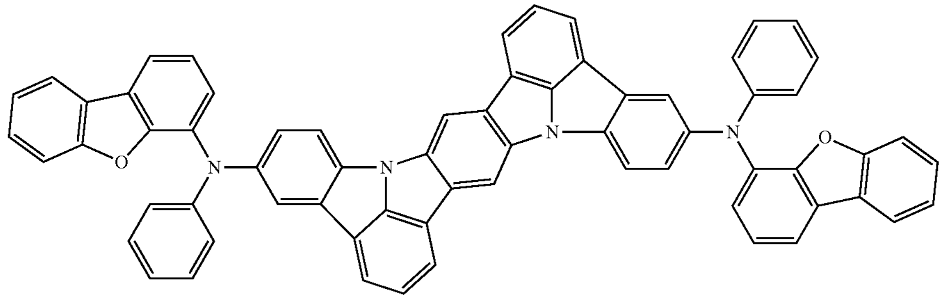
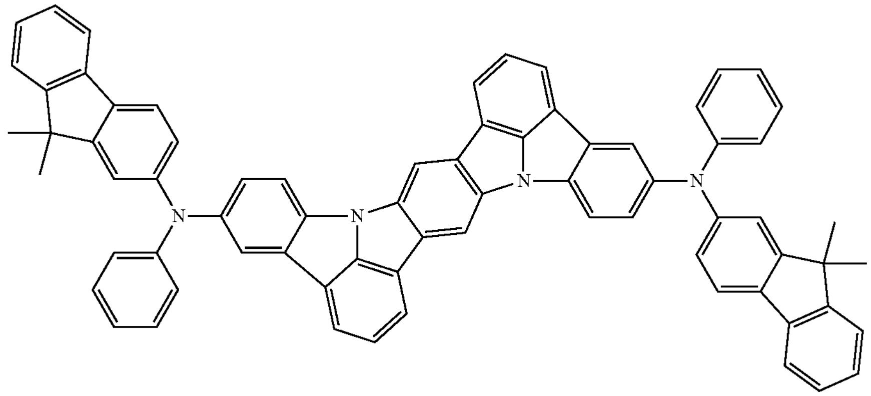

-continued
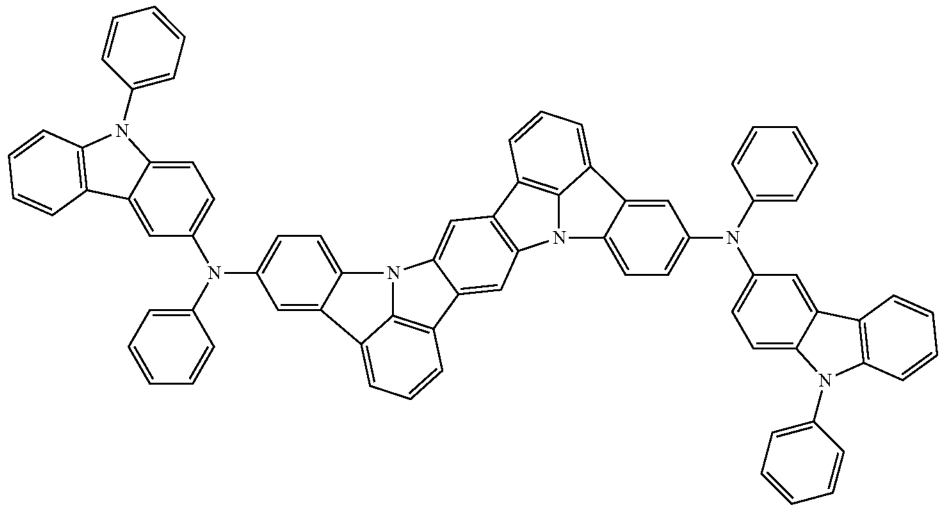
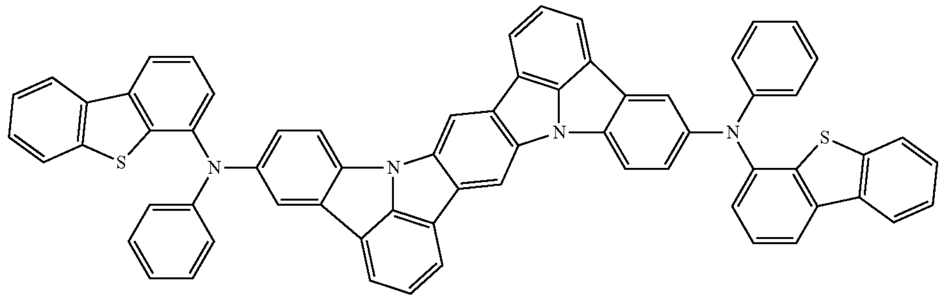
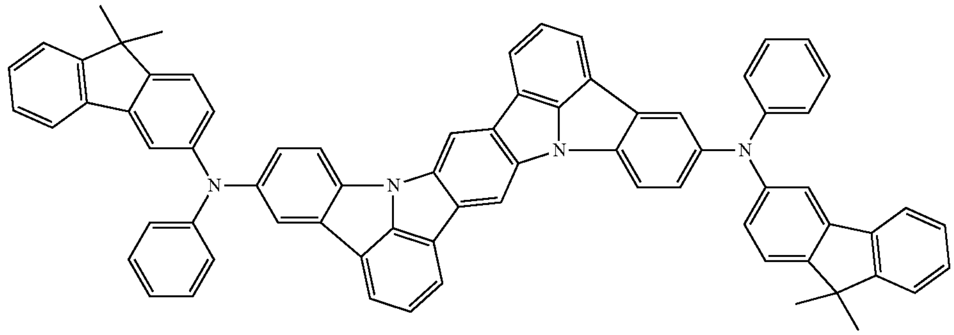
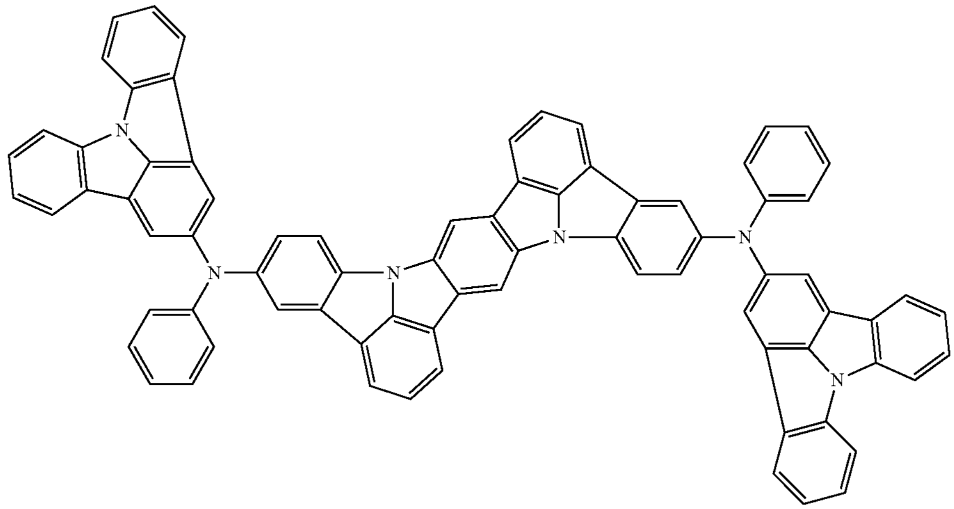

-continued
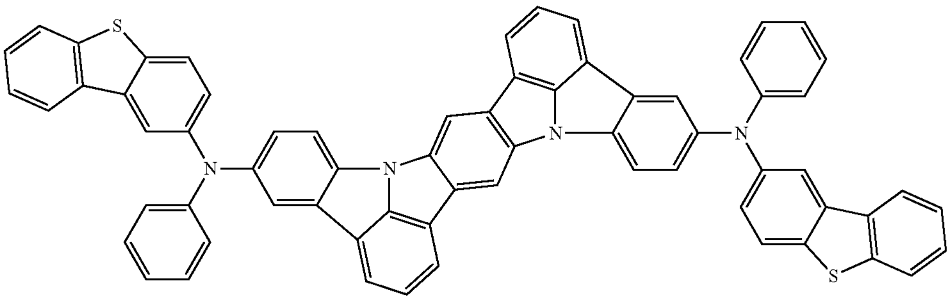
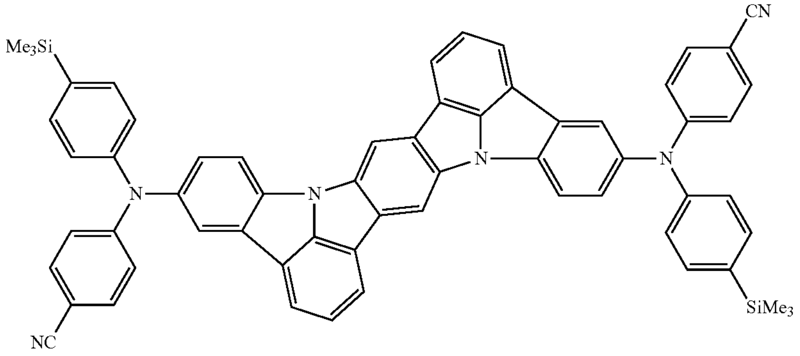
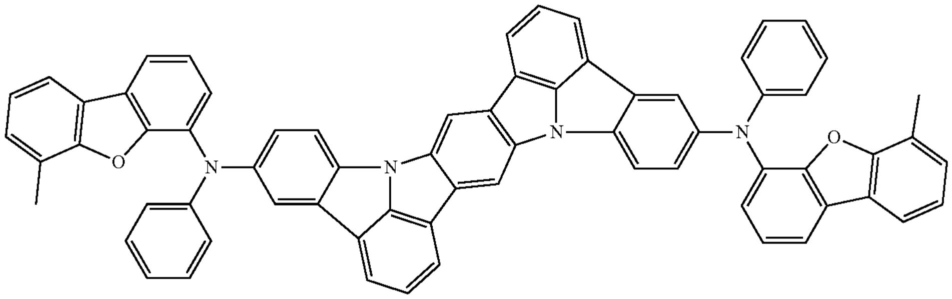
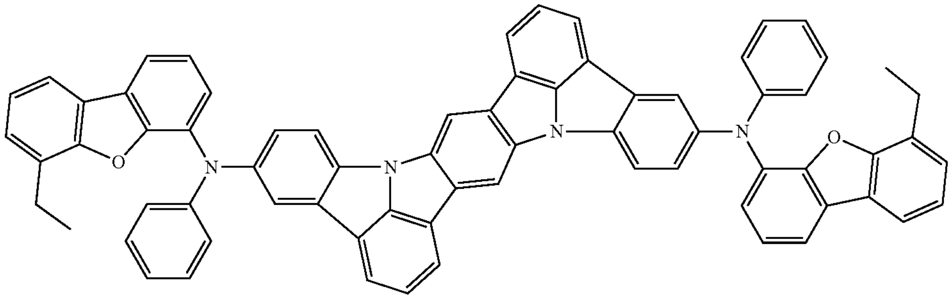
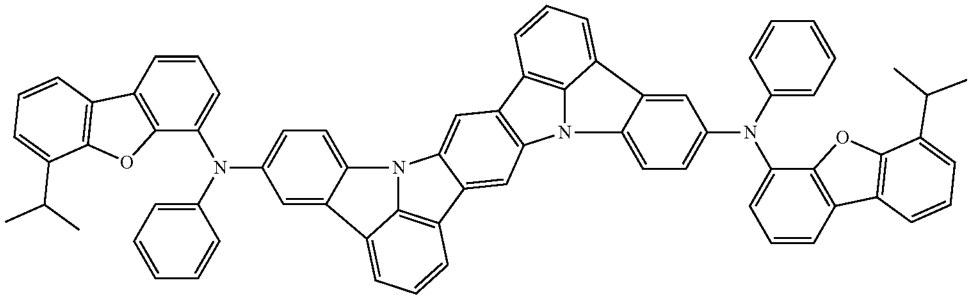

-continued
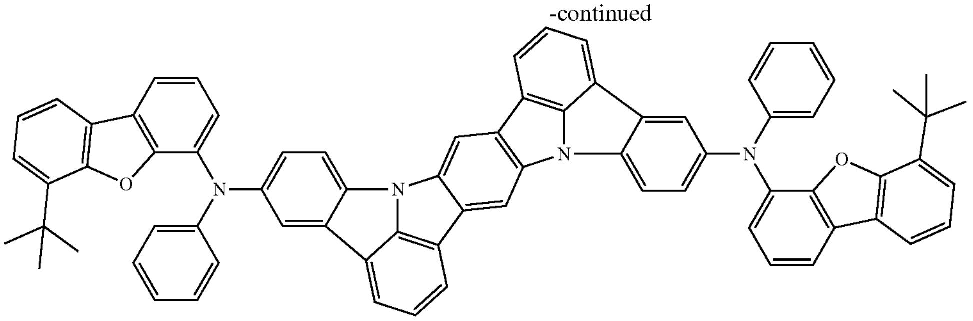
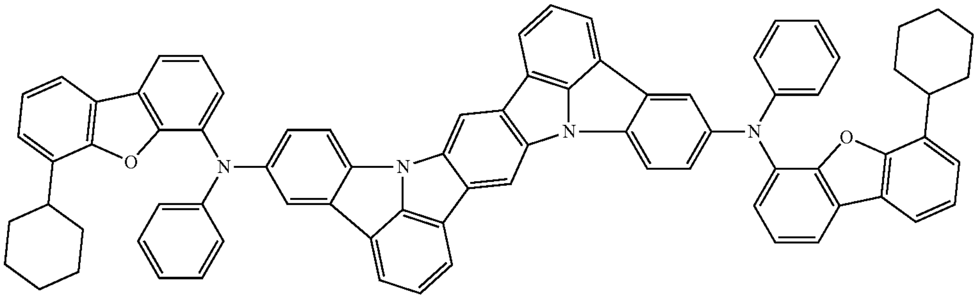
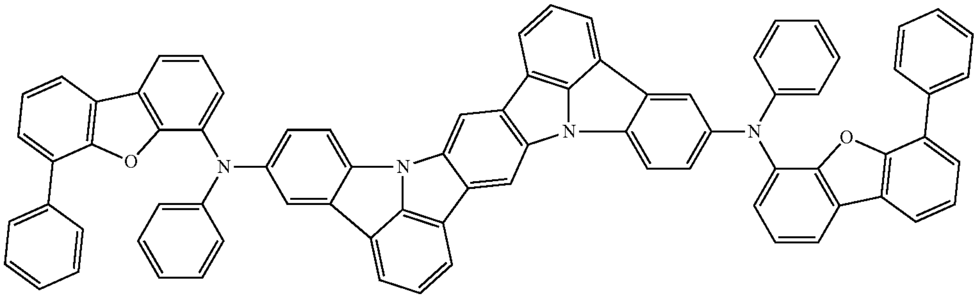
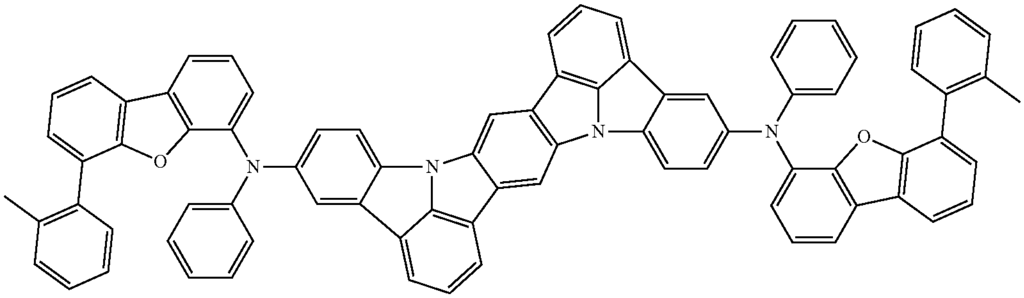
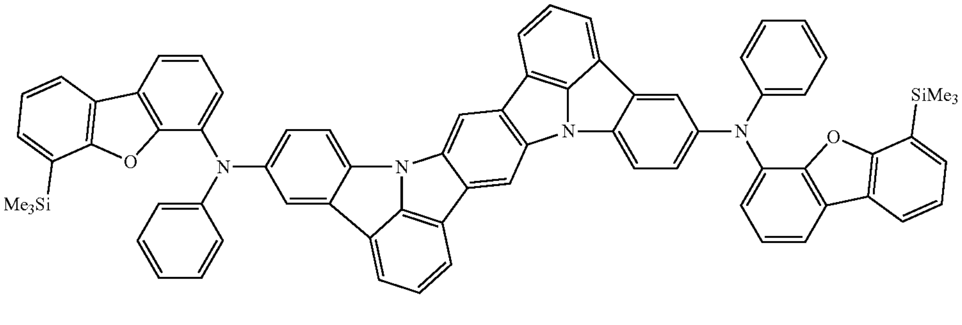

-continued
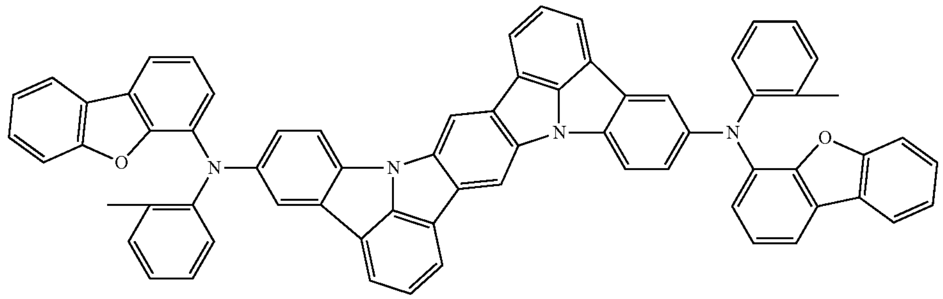
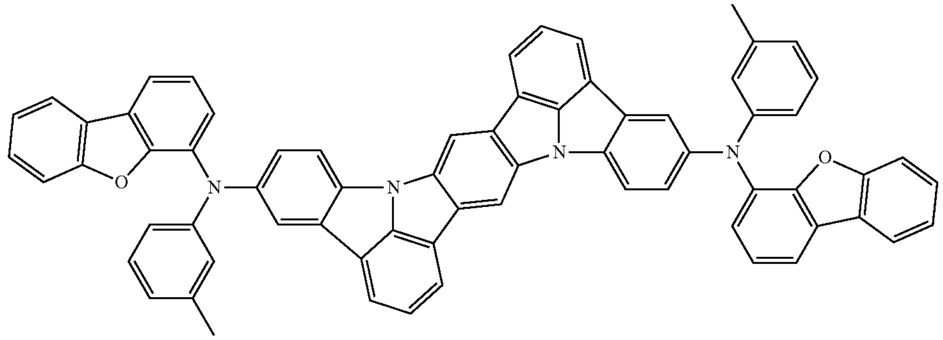
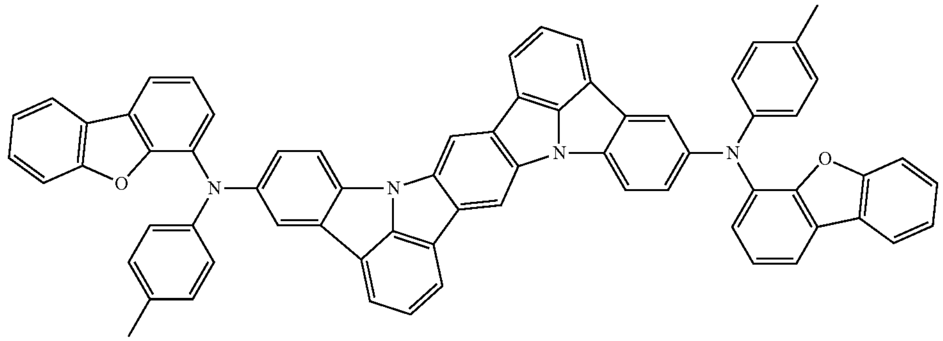
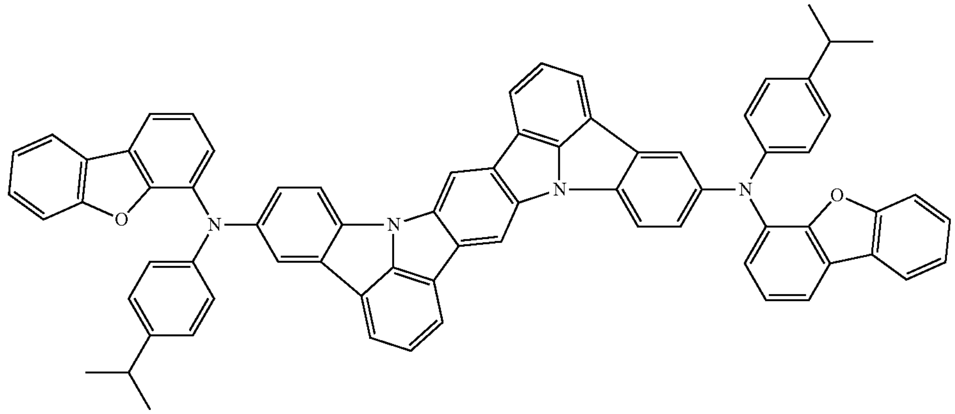
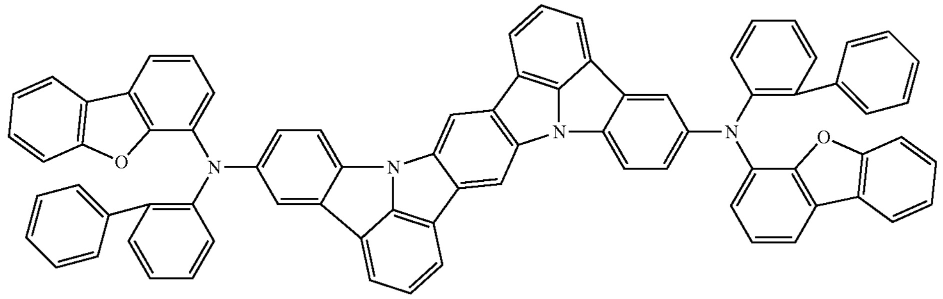

-continued
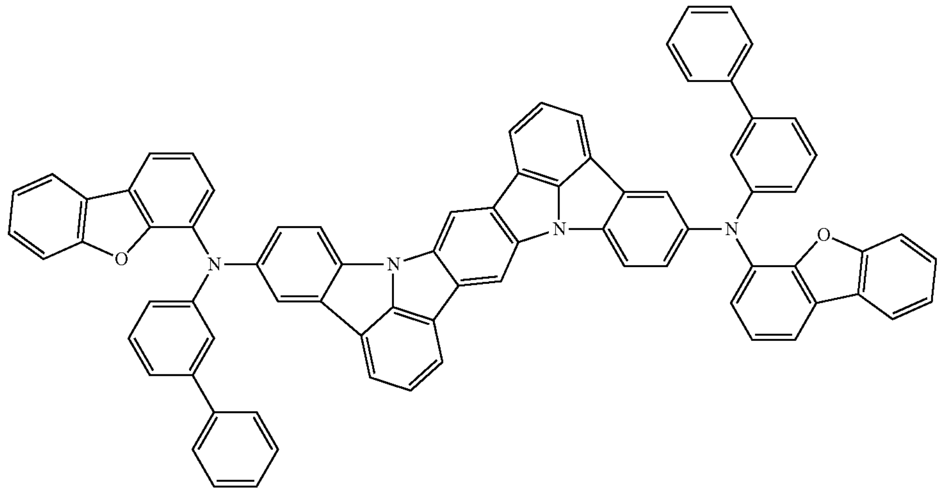
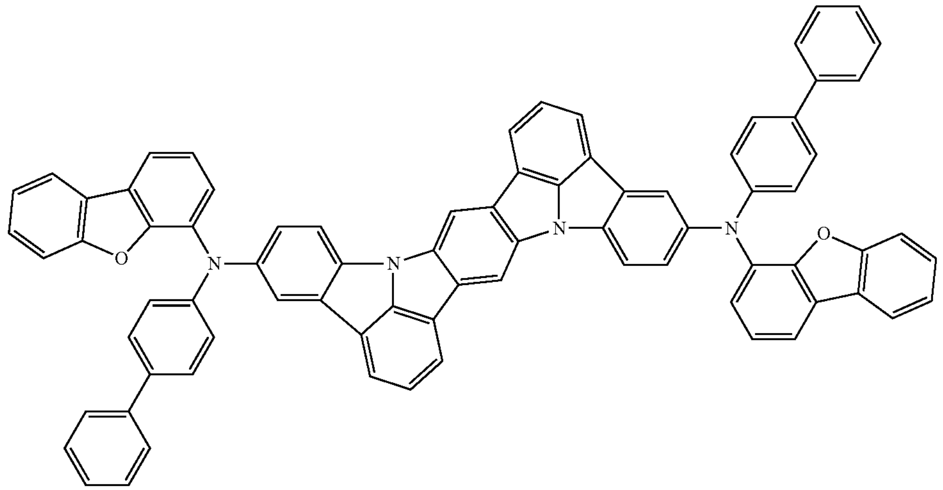
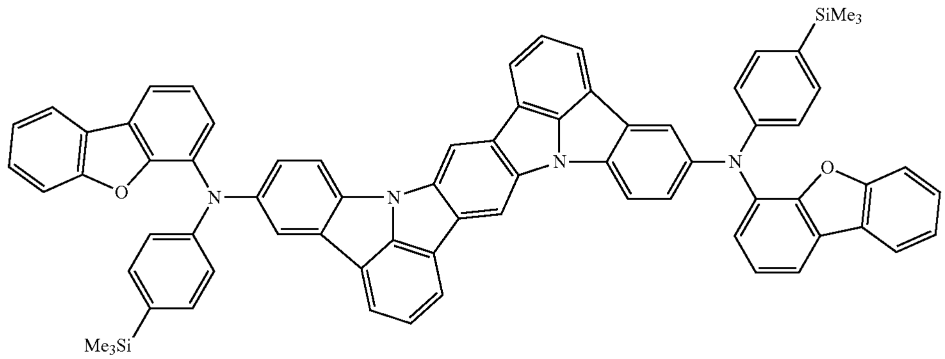
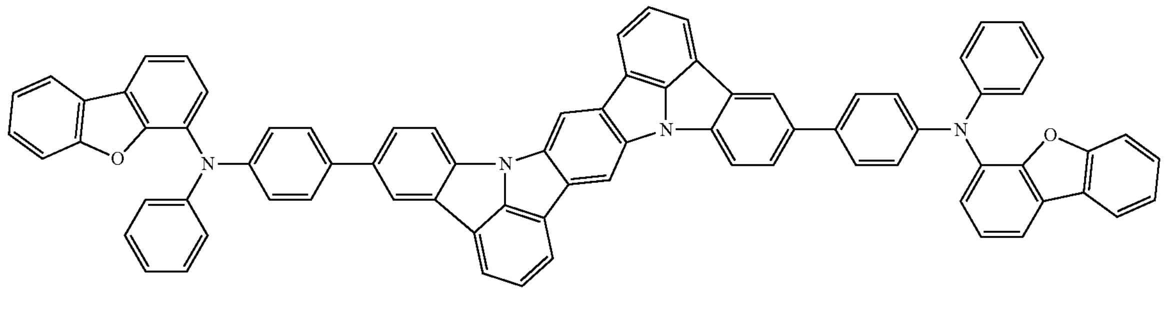

-continued
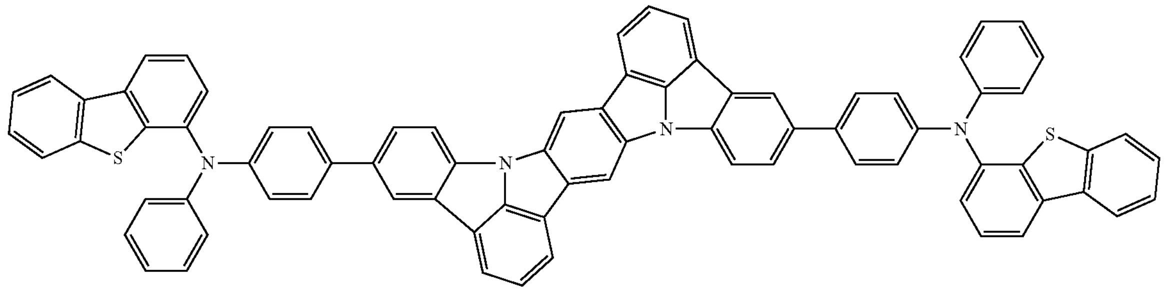
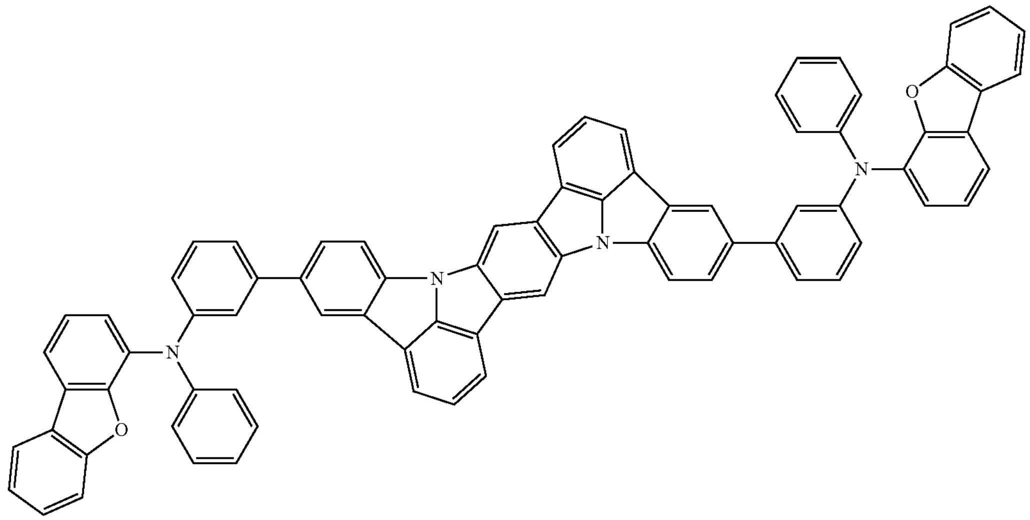
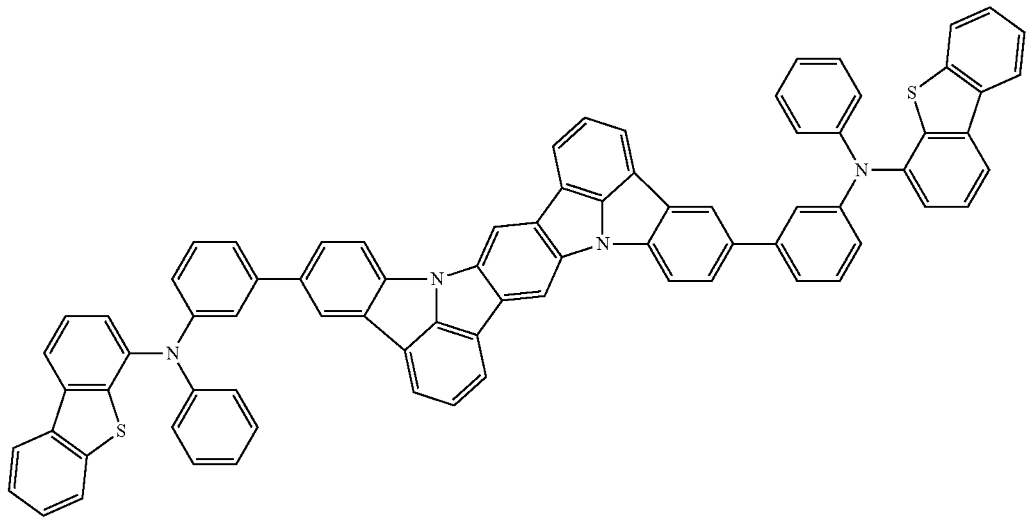
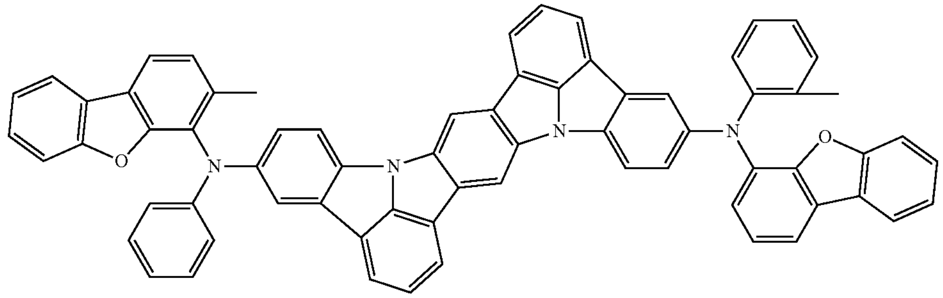

-continued
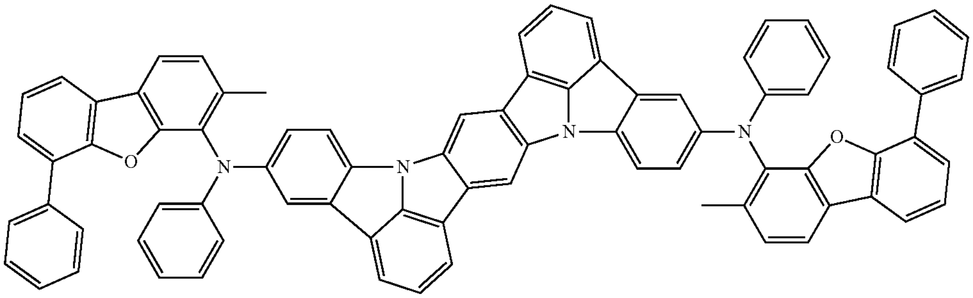
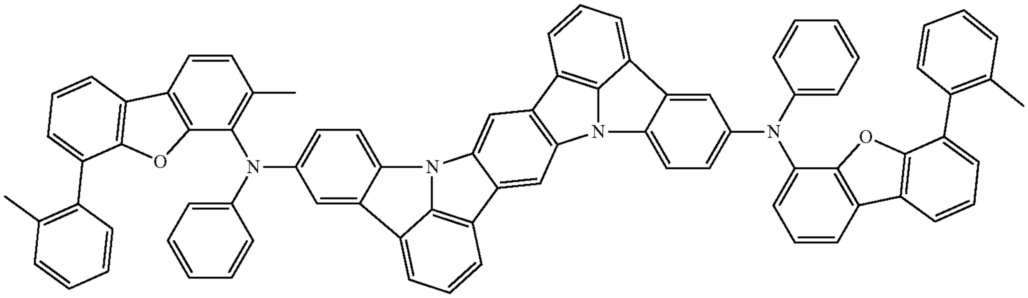
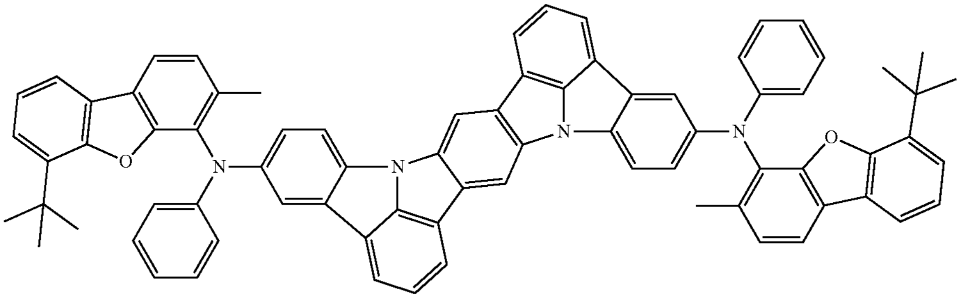
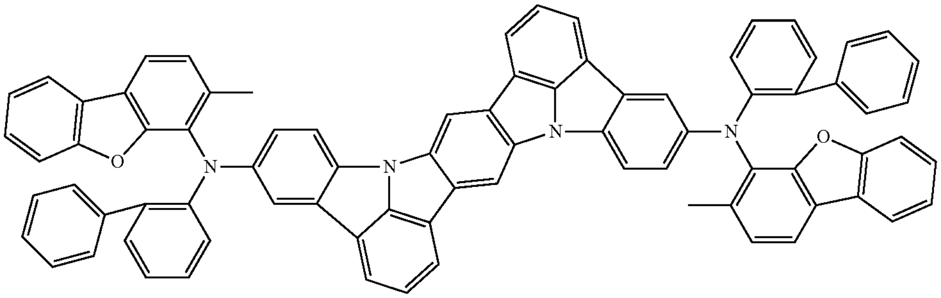
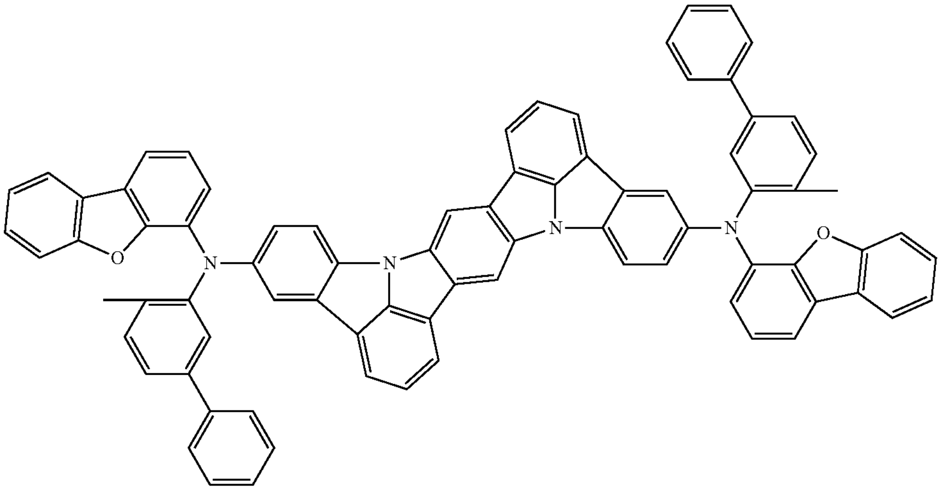

-continued
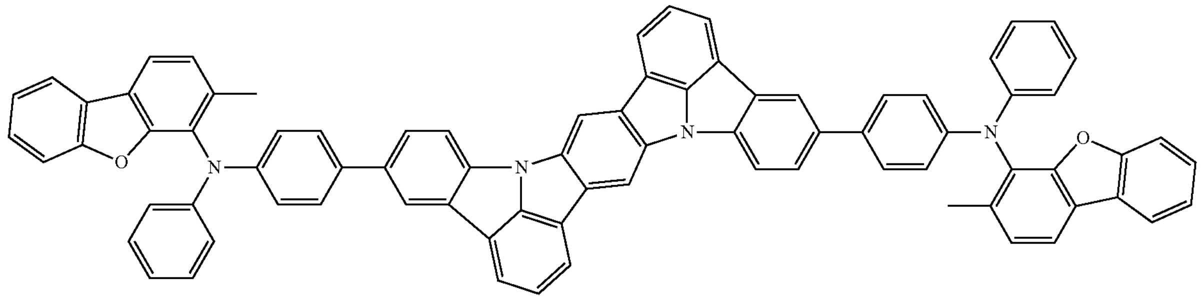
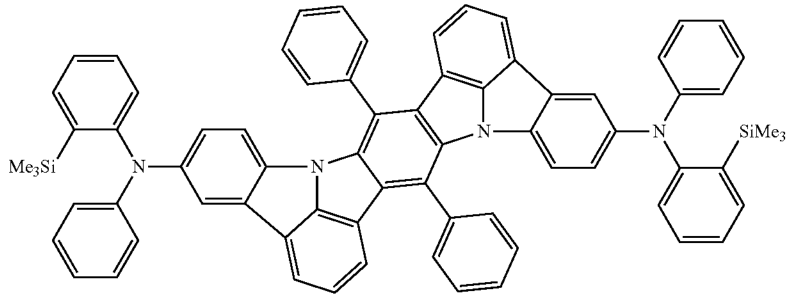
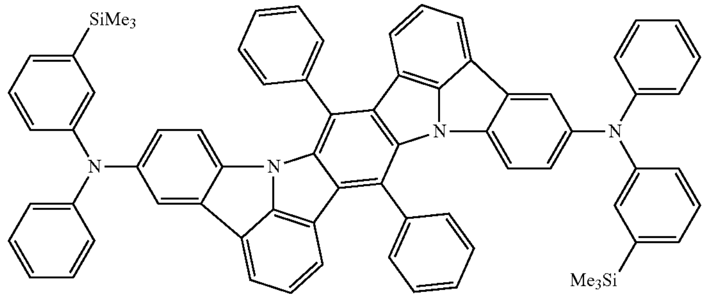
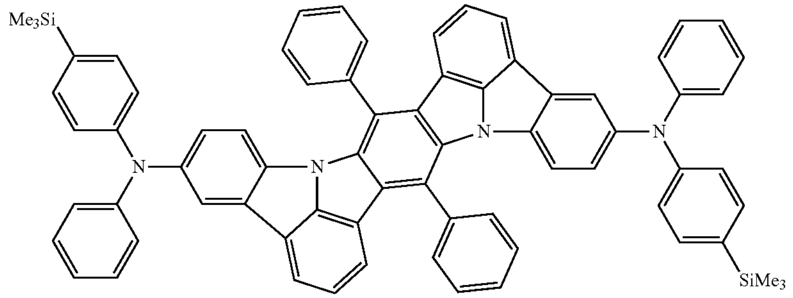
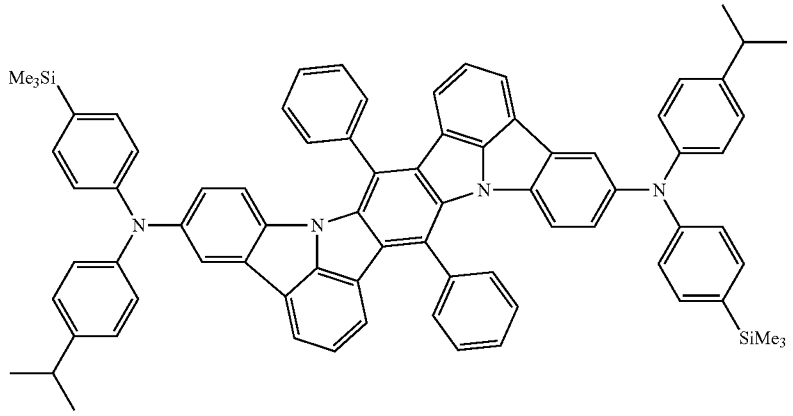

-continued
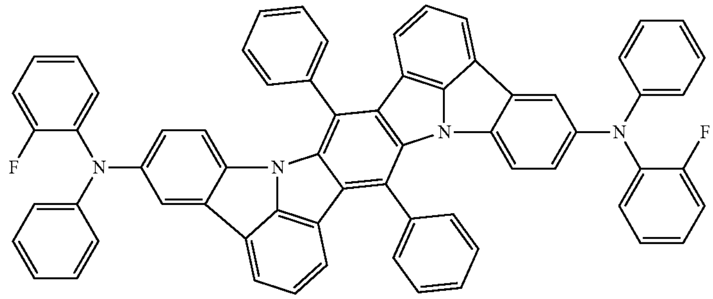
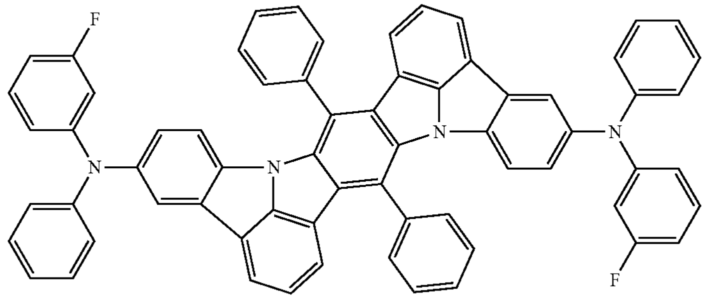
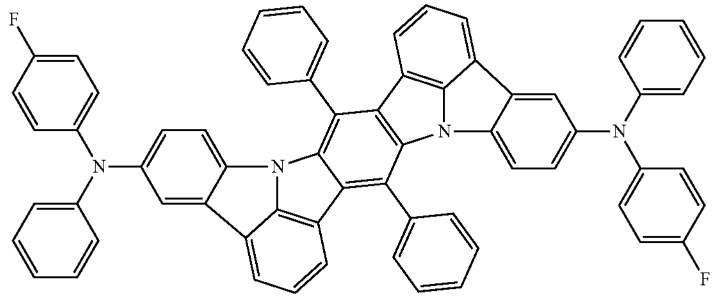
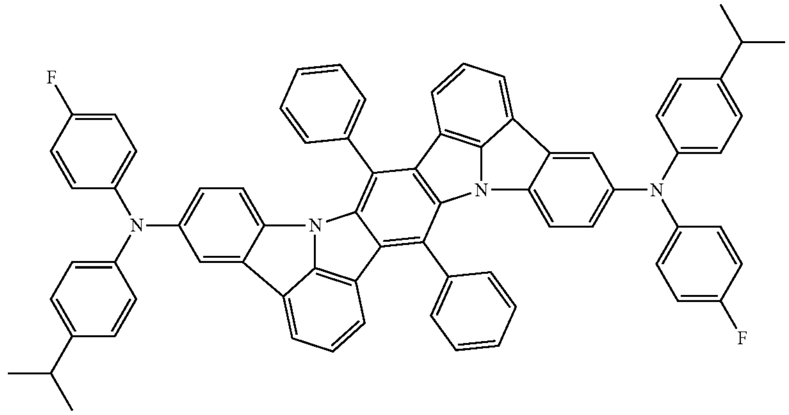
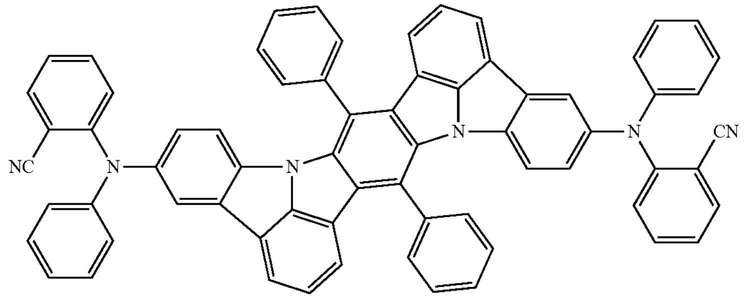

-continued
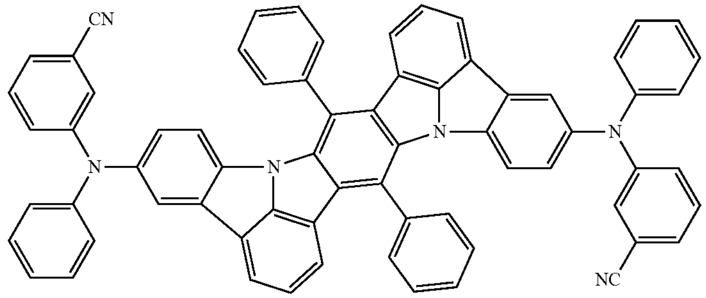
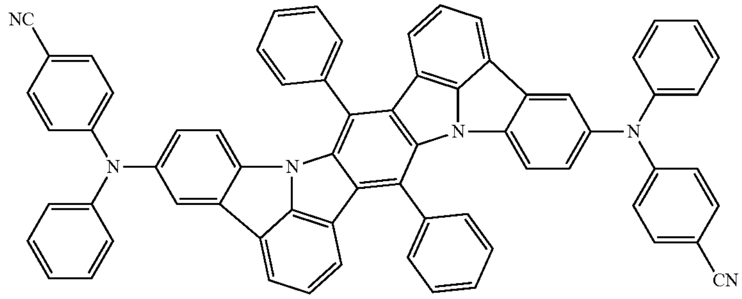
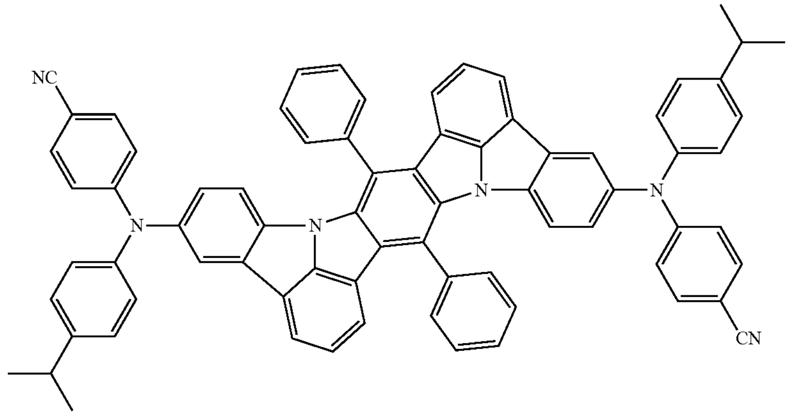
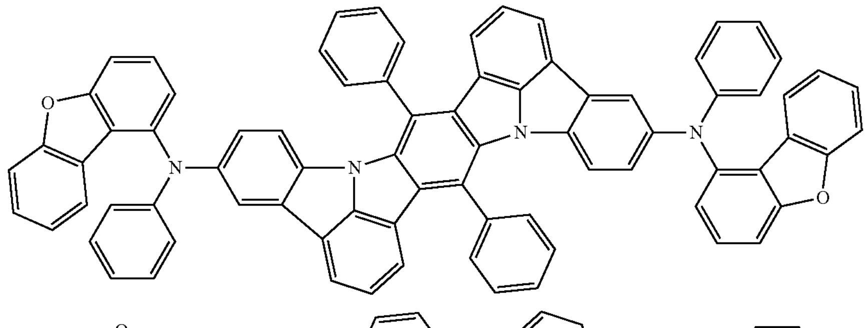
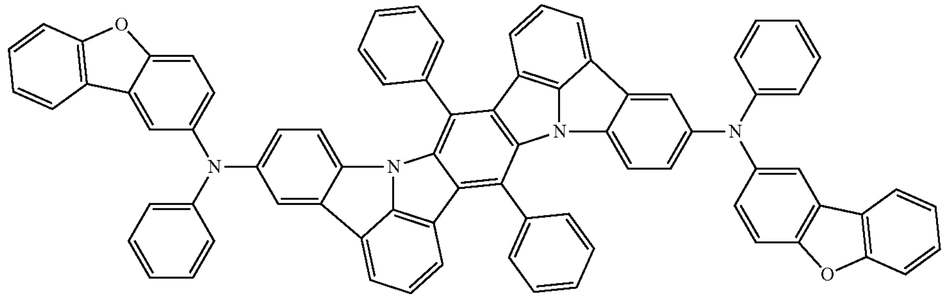

-continued
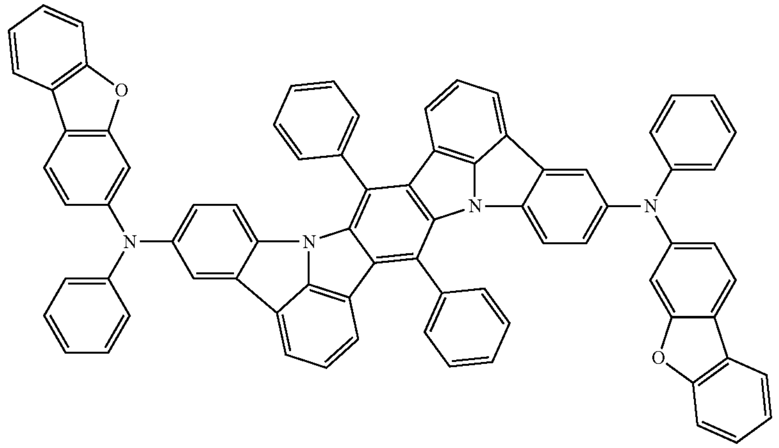
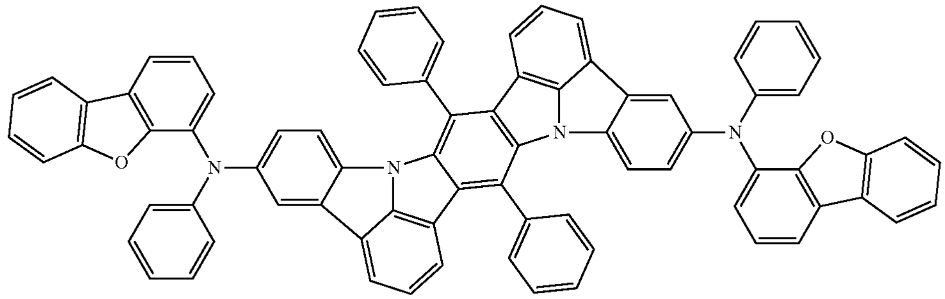
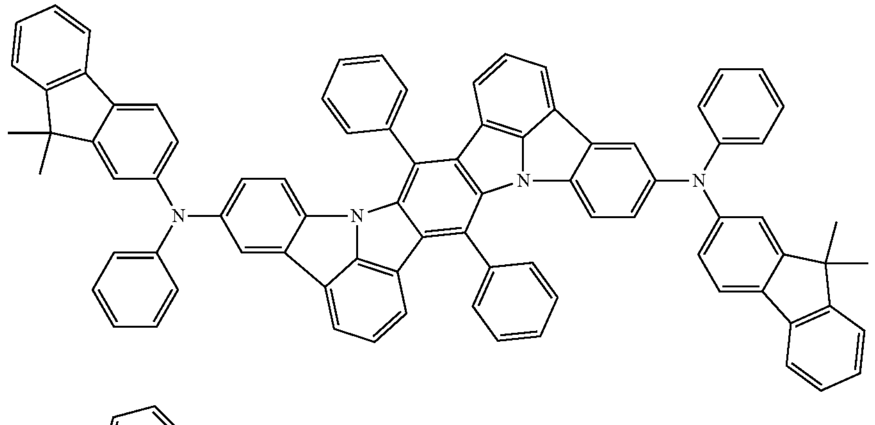
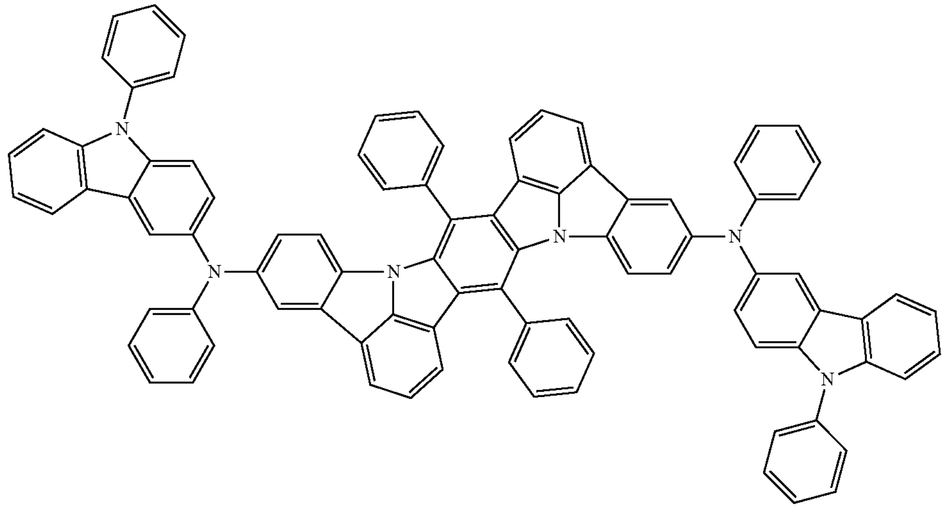

-continued
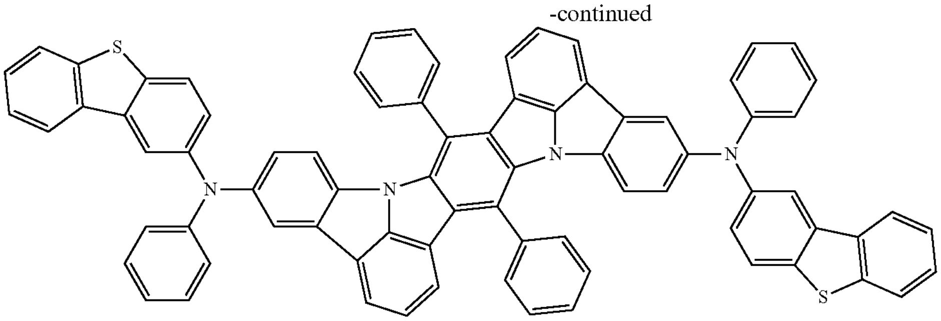
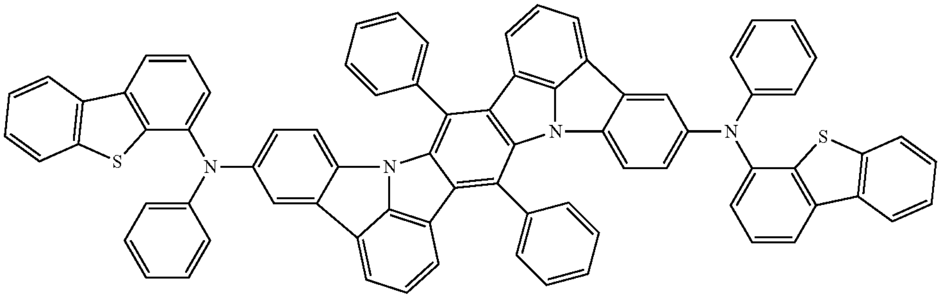
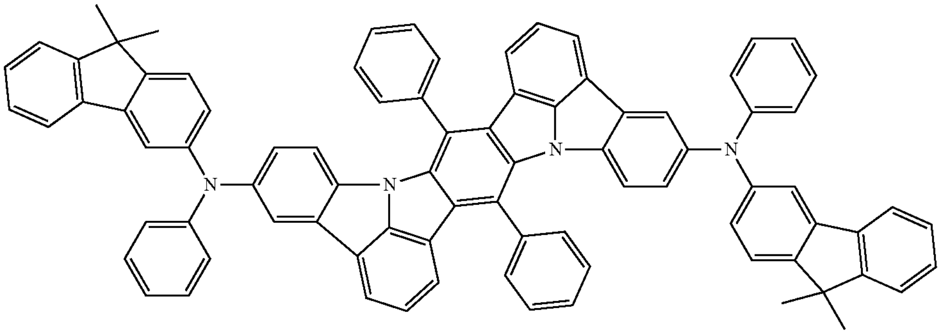
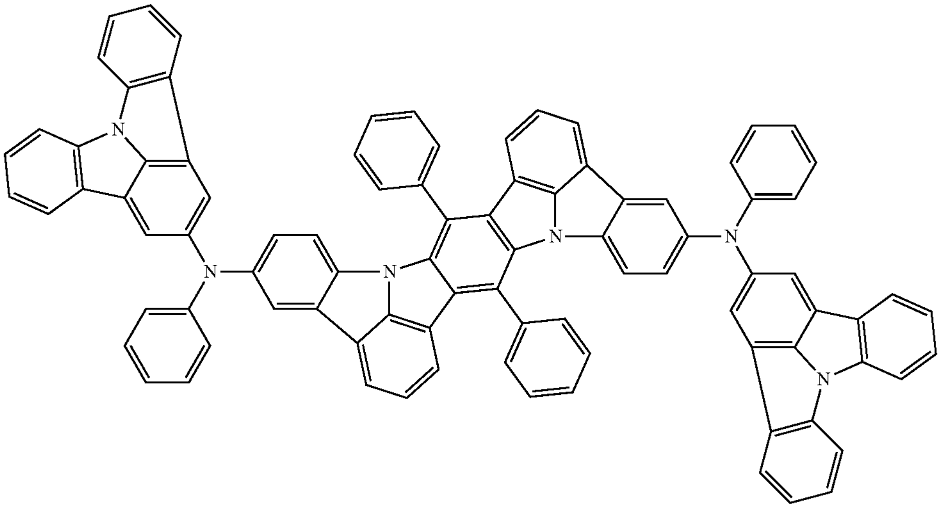

-continued
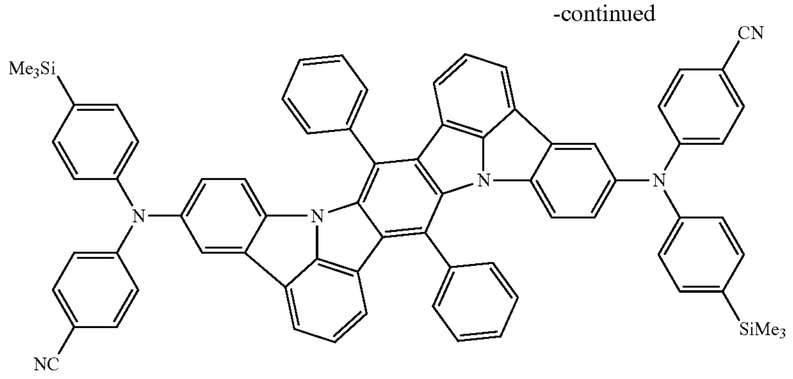
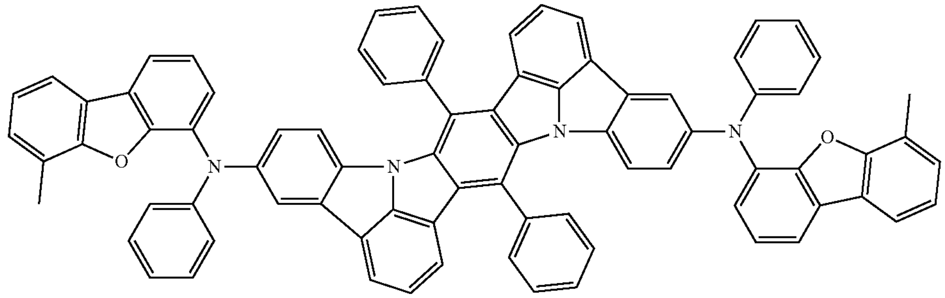
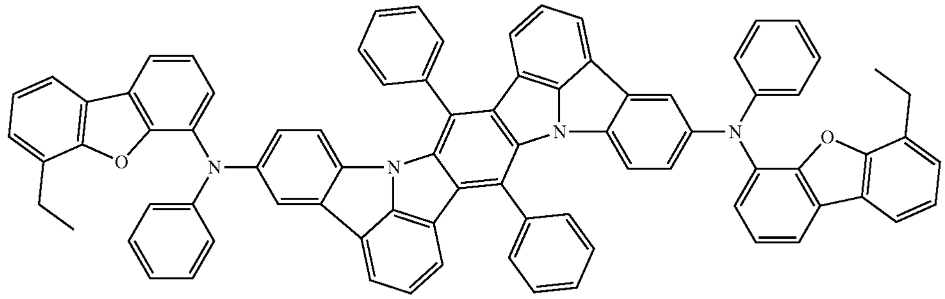
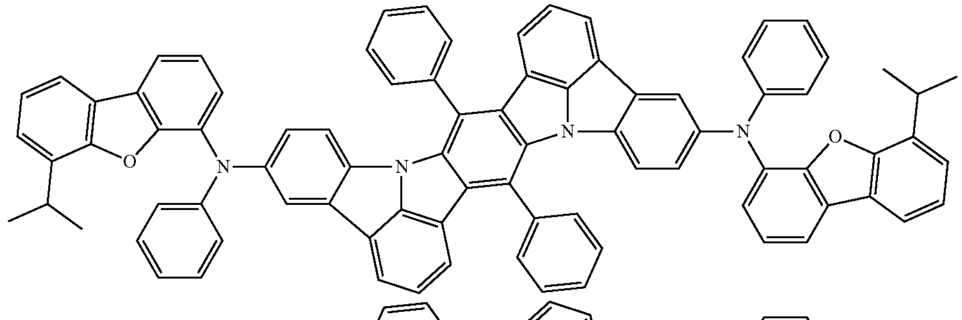
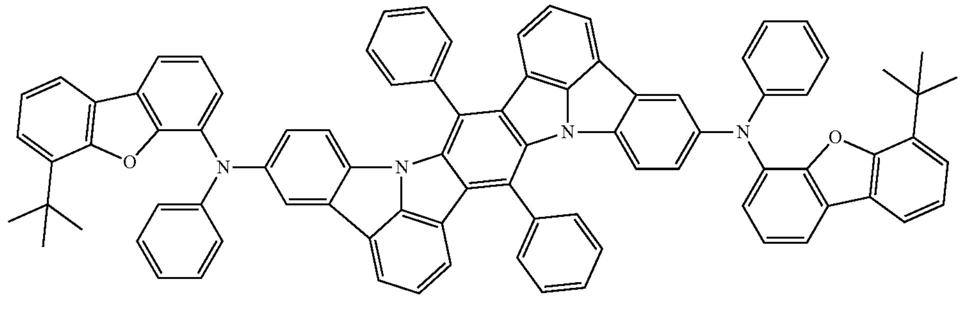

-continued
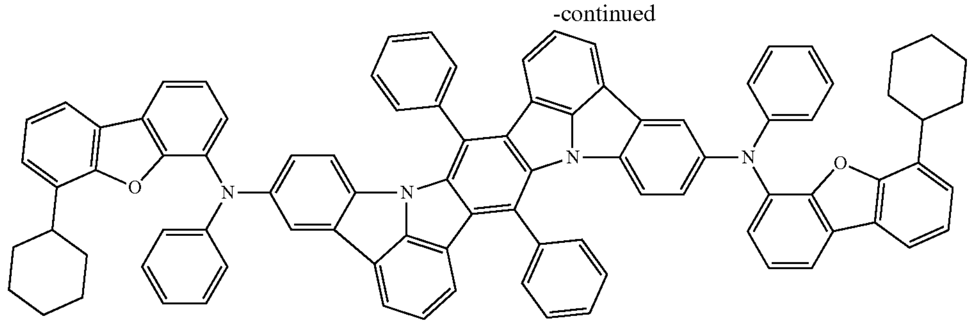
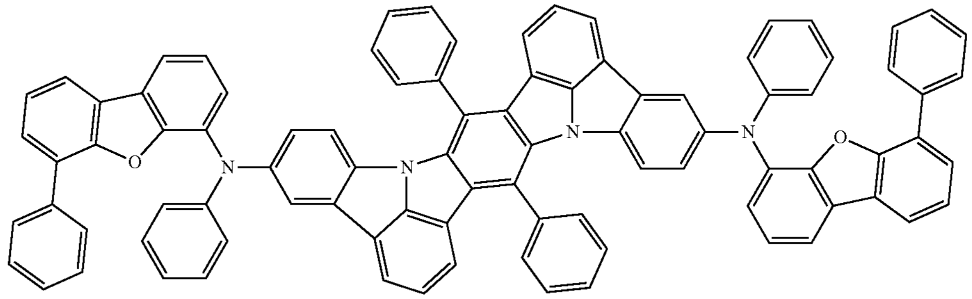
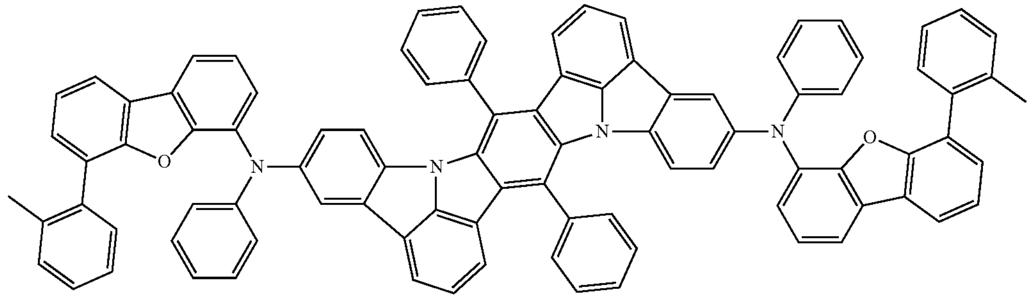
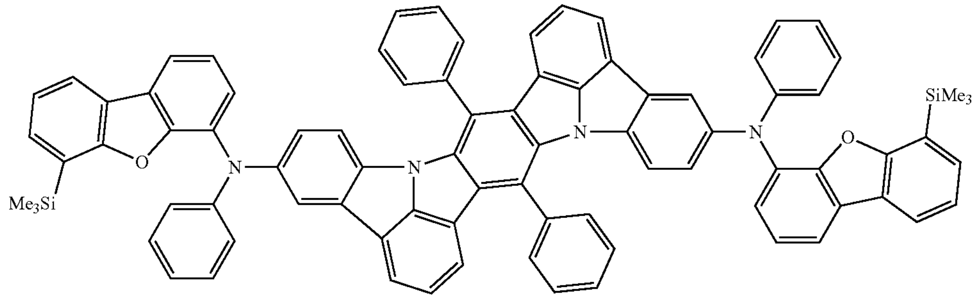
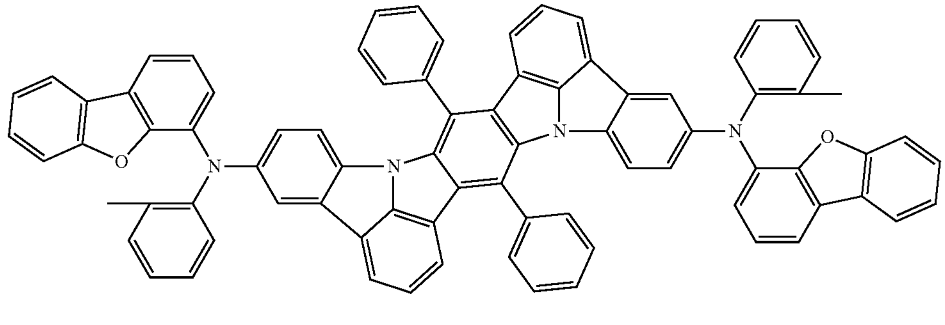

-continued
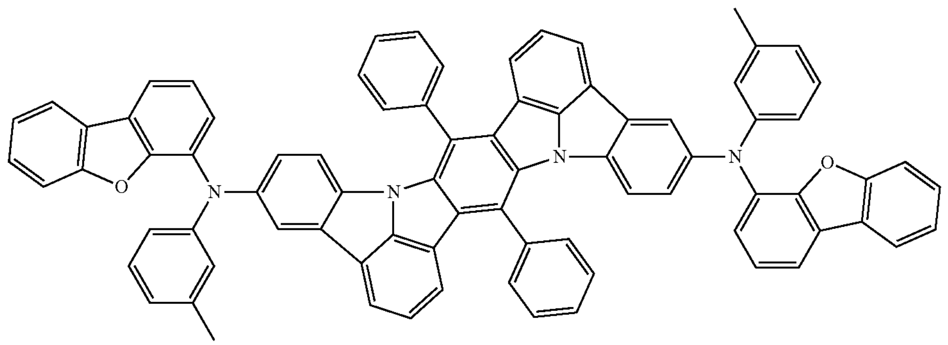
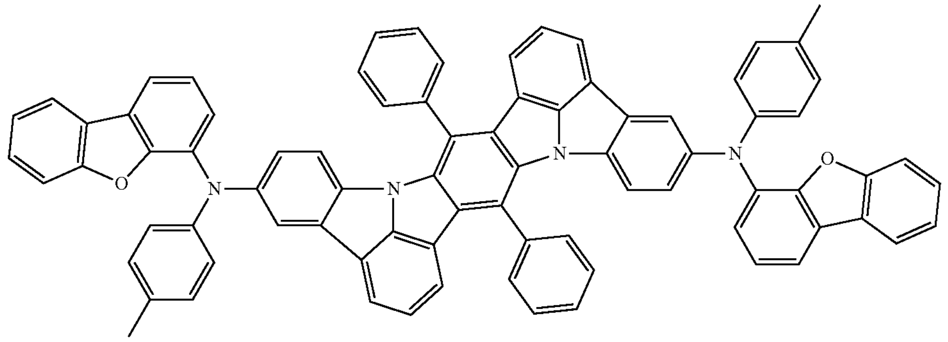
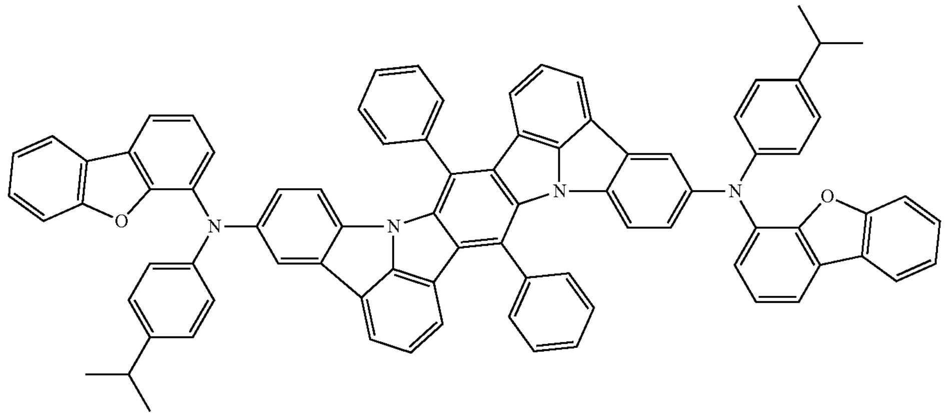
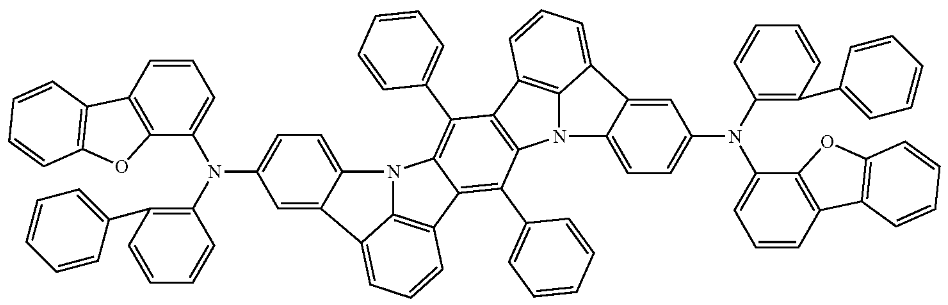

-continued
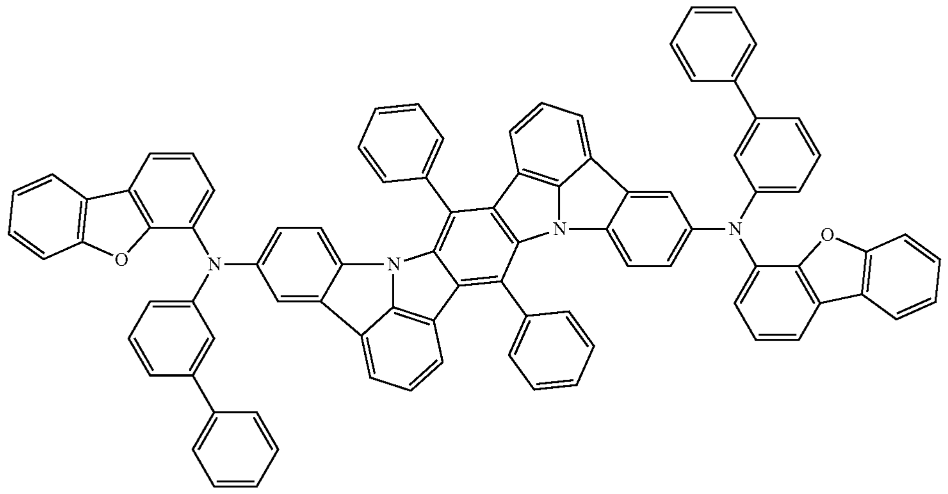
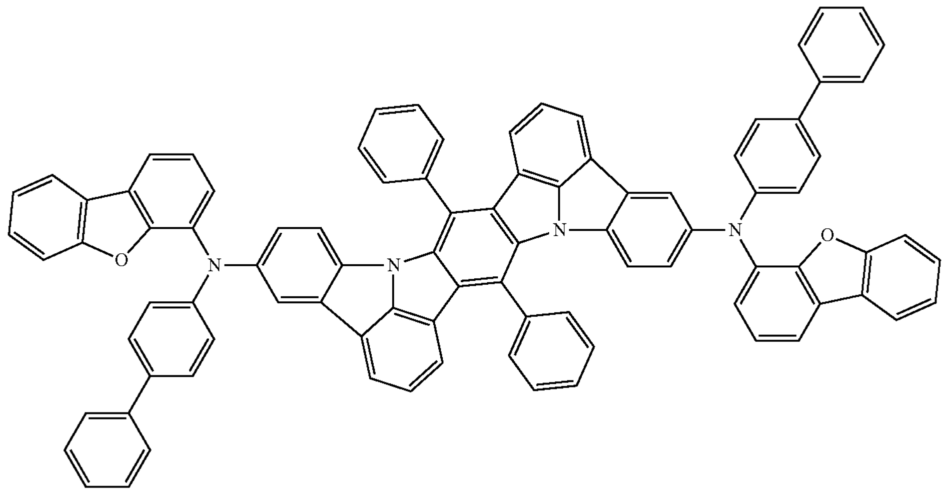
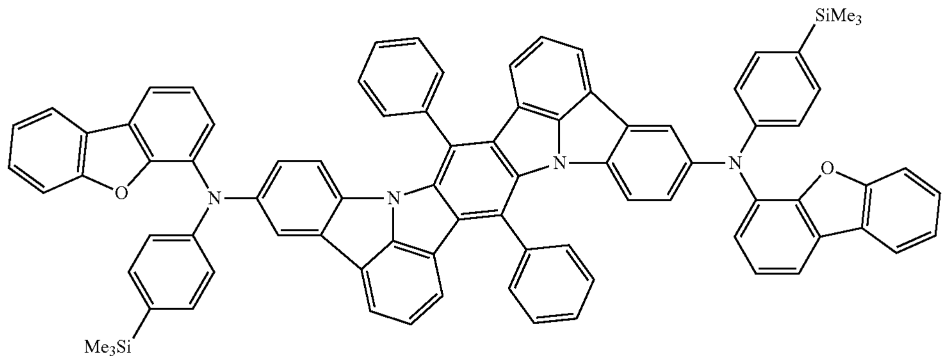
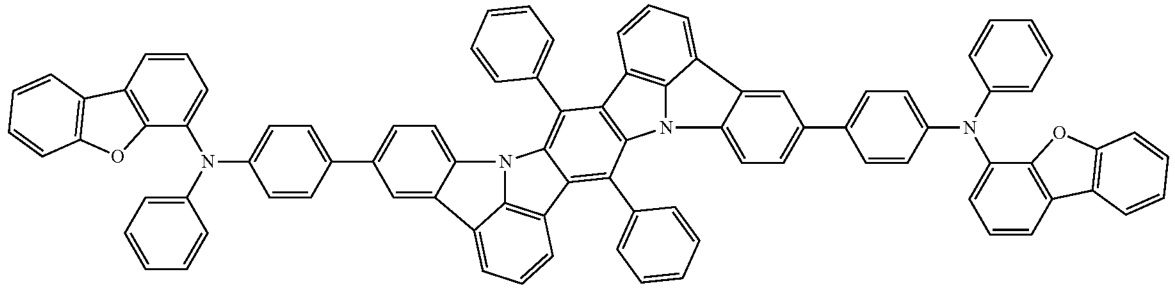

-continued
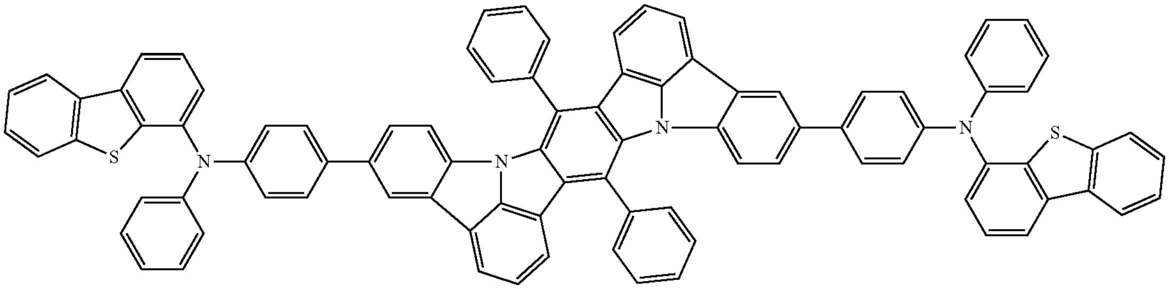
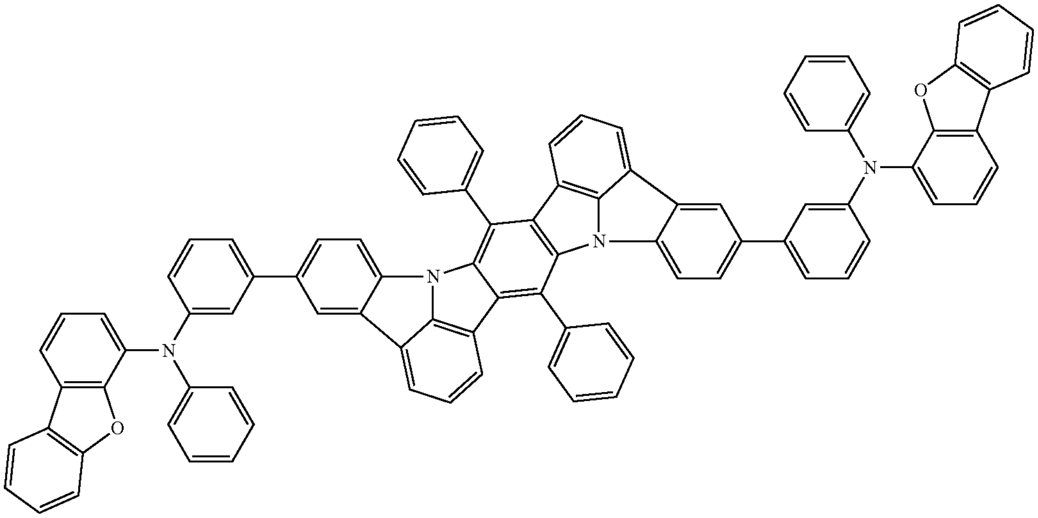
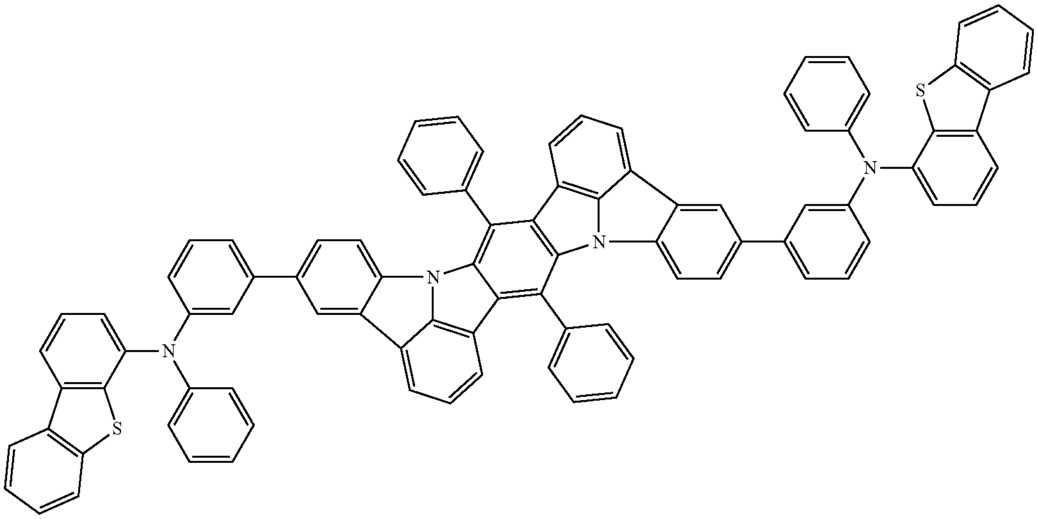
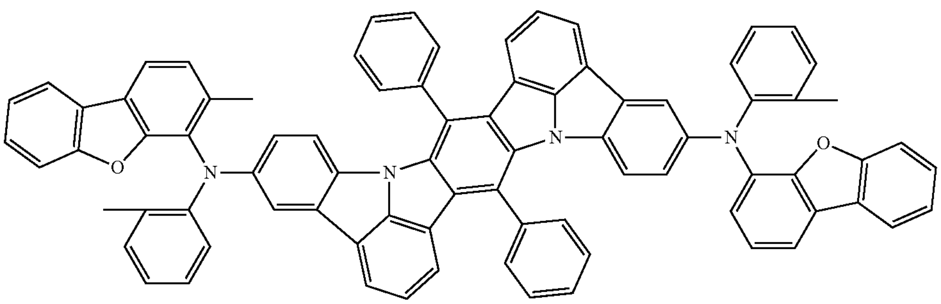

-continued
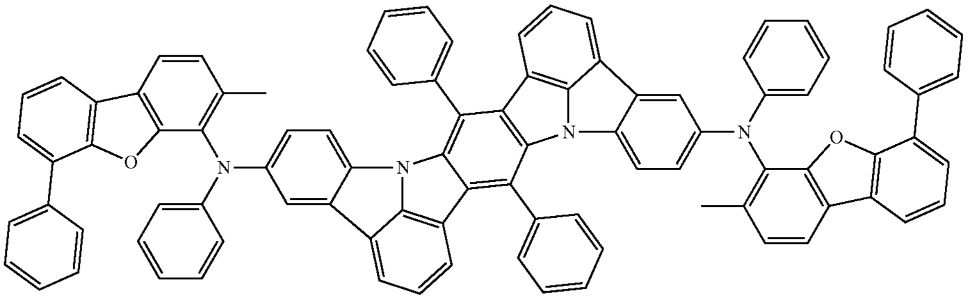
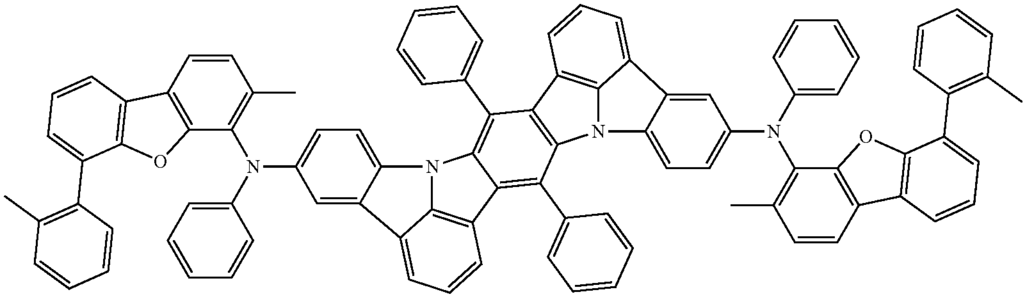
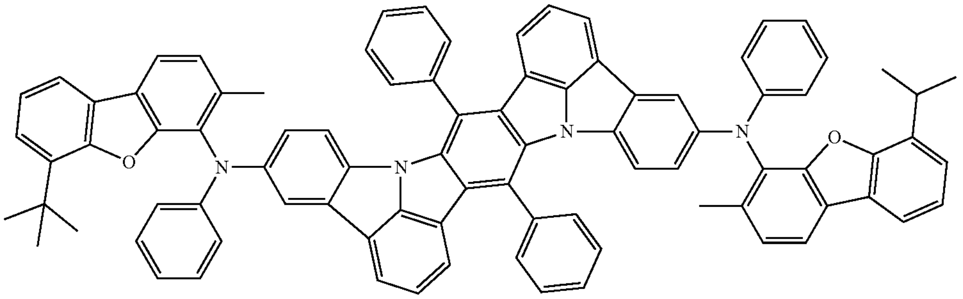
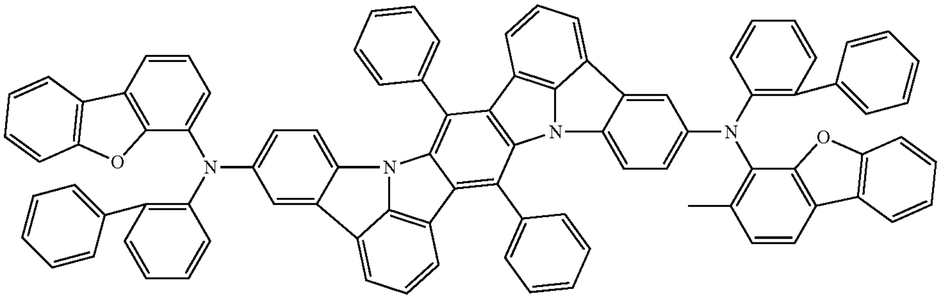
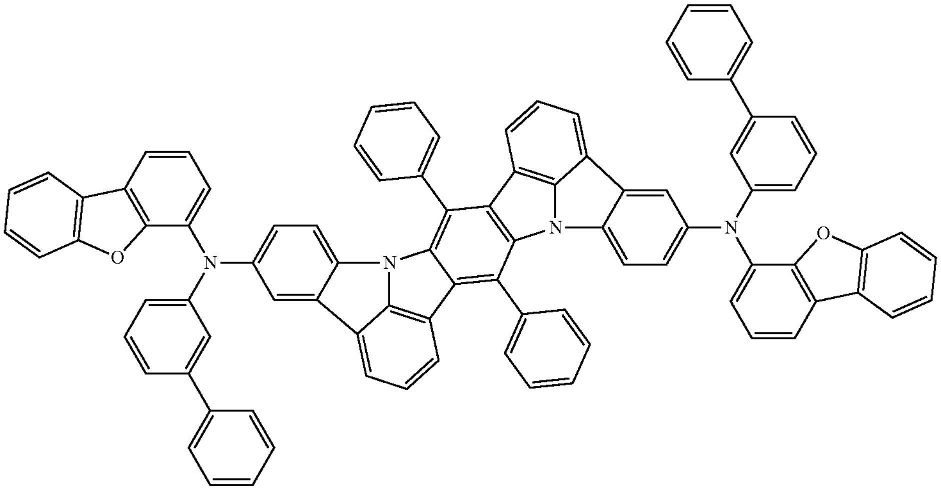

-continued
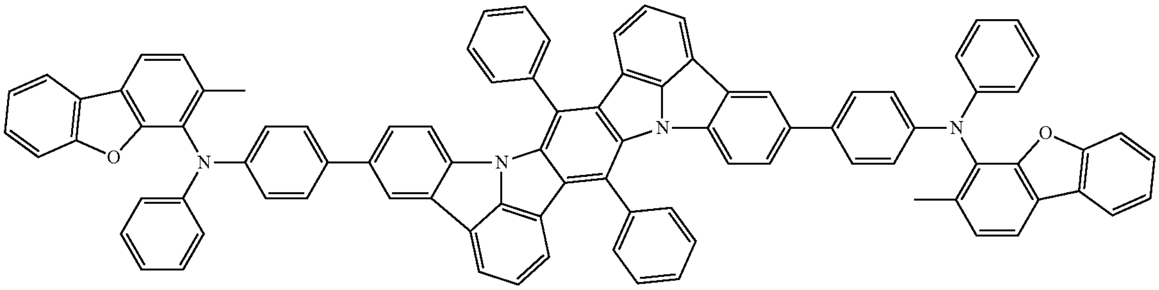
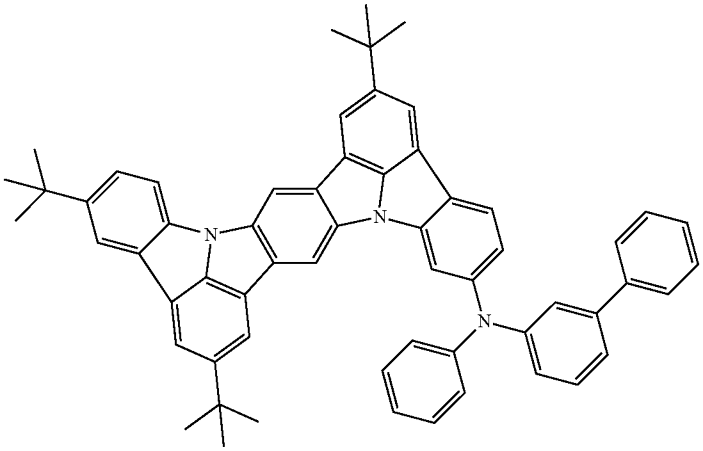
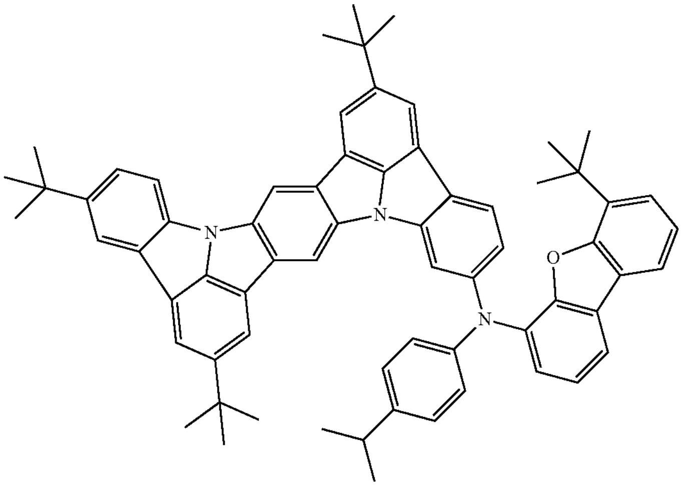
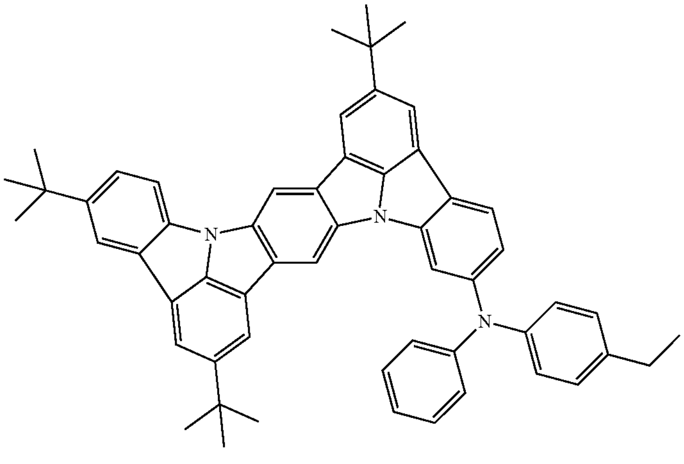

-continued
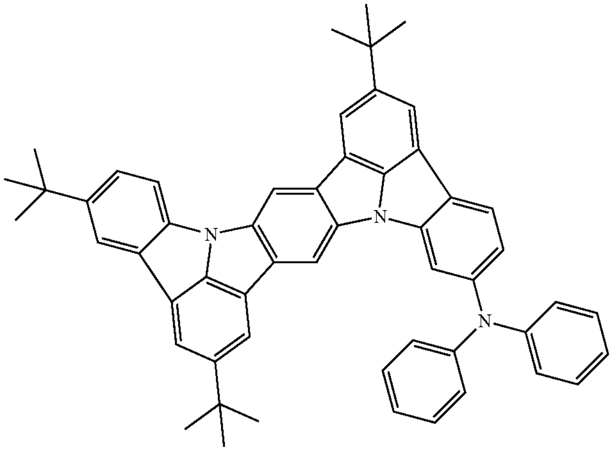
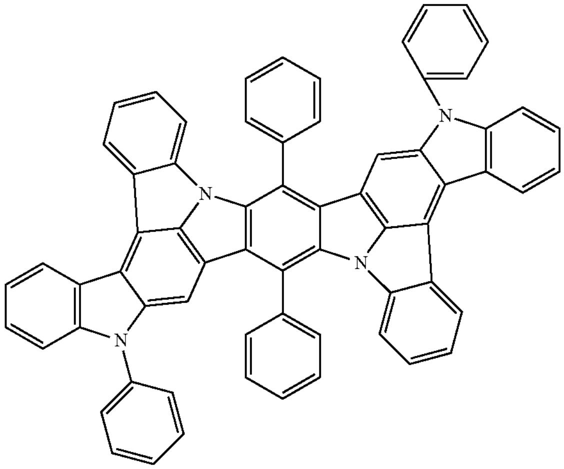
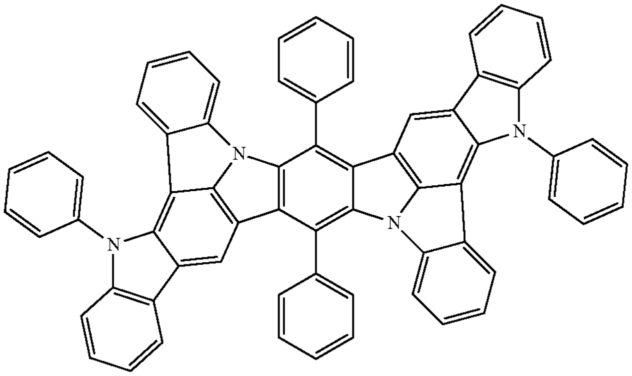
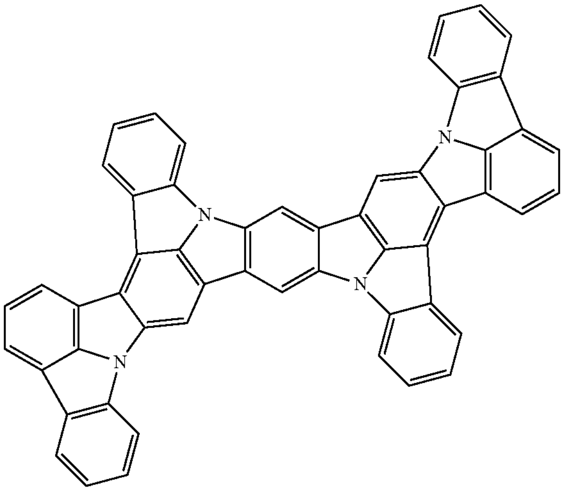
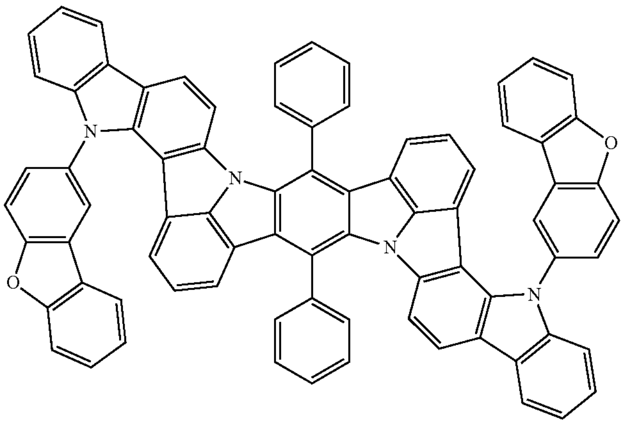

-continued

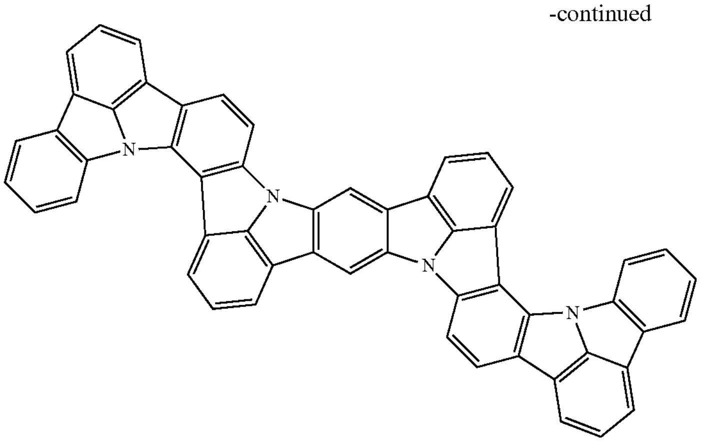

(Compound Represented by Formula (21))

(21)

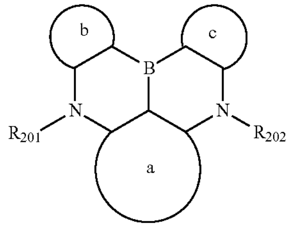

In the formula (21), a ring a, a ring b, and a ring c are independently a substituted or unsubstituted aromatic hydrocarbon ring including 6 to 50 ring carbon atoms, or a substituted or unsubstituted heterocycle including 5 to 50 ring atoms;

$R_{201}$ form a substituted or unsubstituted heterocycle by bonding with either or both of the ring a and the ring b, or do not form a substituted or unsubstituted heterocycle.

$R_{202}$ form a substituted or unsubstituted heterocycle by bonding with either or both of the ring a and the ring c, or do not form a substituted or unsubstituted heterocycle.

$R_{201}$ and $R_{202}$ that do not form the substituted or unsubstituted heterocycle are independently

- a substituted or unsubstituted alkyl group including 1 to 50 carbon atoms,
- a substituted or unsubstituted alkenyl group including 2 to 50 carbon atoms,
- a substituted or unsubstituted alkynyl group including 2 to 50 carbon atoms,
- a substituted or unsubstituted cycloalkyl group including 3 to 50 ring carbon atoms,
- —$Si(R_{901})(R_{902})(R_{903})$,
- a substituted or unsubstituted aryl group including 6 to 50 ring carbon atoms, or
- a substituted or unsubstituted monovalent heterocyclic group including 5 to 50 ring atoms.

$R_{901}$ to $R_{903}$ are as defined in the formula (1).

The ring a, the ring b, and the ring c are a ring (a substituted or unsubstituted aromatic hydrocarbon ring including 6 to 50 ring carbon atoms, or a substituted or unsubstituted heterocycle including 5 to 50 ring atoms) fused to the central fused bicyclic structure composed of a B atom and two N atoms in the formula (21).

The "aromatic hydrocarbon ring" for the ring a, the ring b, and the ring c has the structure same as a compound obtained by introducing a hydrogen atom to the "aryl group" described above. The "aromatic hydrocarbon ring" for the ring a contains three carbon atoms on the central fused bicyclic structure in the formula (21) as ring atoms. The "aromatic hydrocarbon ring" for the ring b and the ring c contains two carbon atoms on the central fused bicyclic structure in the formula (21) as ring atoms. Specific examples of the "substituted or unsubstituted aromatic hydrocarbon rings including 6 to 50 ring carbon atoms" include compounds obtained by introducing a hydrogen atom into the "aryl group" described in the specific example group G1, and the like.

The "heterocycle" for the ring a, the ring b, and the ring c has the structure same as a compound obtained by introducing a hydrogen atom into the "heterocyclic group" described above. The "heterocycle" for the ring a contains three carbon atoms on the central fused bicyclic structure in the formula (21) as ring atoms. The "heterocycle" of the ring b and the ring c contains two carbon atoms on the central fused bicyclic structure of the formula (21) as ring atoms. Specific examples of the "substituted or unsubstituted heterocycle including 5 to 50 ring atoms" include compounds obtained by introducing a hydrogen atom into the "heterocyclic group" described in the specific example group G2, and the like.

$R_{201}$ and $R_{202}$ may independently form a substituted or unsubstituted heterocycle by bonding with the ring a, the ring b, or the ring c. The heterocycle in this case contains the nitrogen atom on the central fused bicyclic structure in the formula (21). The heterocycle in this case may contain a hetero atom other than a nitrogen atom. The expression "$R_{201}$ and $R_{202}$ being bonded with the ring a, the ring b, or the ring c" specifically means that the atoms constituting the ring a, the ring b, or the ring care bonded with the atoms constituting $R_{201}$ and $R_{202}$. For example, $R_{201}$ may form a bicyclic (or tricyclic or more polycyclic) nitrogen-containing heterocycle in which the ring containing $R_{201}$ and the ring a are fused by bonding $R_{201}$ with the ring a. Specific examples of the nitrogen-containing heterocycle include a compound corresponding to a nitrogen-containing fused heterocyclic group containing a nitrogen atom in the specific example group G2.

The same as above can be applied to the cases where $R_{201}$ is bonded with the ring b, where $R_{202}$ is bonded with the ring a, and where $R_{202}$ is bonded with the ring c.

In one embodiment, the ring a, the ring b, and the ring c in the formula (21) are independently a substituted or unsubstituted aromatic hydrocarbon ring including 6 to 50 ring carbon atoms.

In one embodiment, the ring a, the ring b, and the ring c in the formula (21) are independently a substituted or unsubstituted benzene ring or a substituted or unsubstituted naphthalene ring.

In one embodiment, $R_{201}$ and $R_{202}$ in the formula (21) are independently a substituted or unsubstituted aryl group including 6 to 50 ring carbon atoms, or a substituted or unsubstituted monovalent heterocyclic group including 5 to 50 ring atoms, and preferably a substituted or unsubstituted aryl group including 6 to 50 ring carbon atoms.

In one embodiment, the ring a, the ring b, or the ring c in the formula (21) is the substituted aromatic hydrocarbon ring including 6 to 50 ring carbon atoms, or the substituted heterocycle including 5 to 50 ring atoms, and the substituent is one or more selected from

- a substituted or unsubstituted alkyl group including 1 to 50 carbon atoms,
- —Si($R_{901}$)($R_{902}$)($R_{903}$),
- —N($R_{906}$)($R_{907}$) (where $R_{901}$ to $R_{903}$, $R_{906}$, and $R_{907}$ are as defined in the formula (1)),
- a substituted or unsubstituted aryl group including 6 to 50 ring carbon atoms, and
- a substituted or unsubstituted monovalent heterocyclic group including 5 to 60 ring atoms.

In one embodiment, the compound represented by the formula (21) is a compound represented by the following formula (22).

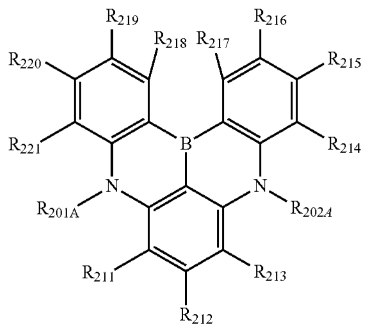

(22)

In the formula (22), $R_{201A}$ forms a substituted or unsubstituted heterocycle by bonding with one or more selected from the group consisting of $R_{211}$ and $R_{221}$, or do not form a substituted or unsubstituted heterocycle.

$R_{202A}$ forms a substituted or unsubstituted heterocycle by bonding with one or more selected from the group consisting of $R_{213}$ and $R_{214}$, or do not form a substituted or unsubstituted heterocycle.

$R_{201A}$ and $R_{202A}$ that do not form the substituted or unsubstituted heterocycle are independently

- a substituted or unsubstituted alkyl group including 1 to 50 carbon atoms,
- a substituted or unsubstituted alkenyl group including 2 to 50 carbon atoms,
- a substituted or unsubstituted alkynyl group including 2 to 50 carbon atoms,
- a substituted or unsubstituted cycloalkyl group including 3 to 50 ring carbon atoms,
- a substituted or unsubstituted aryl group including 6 to 50 ring carbon atoms, or
- a substituted or unsubstituted monovalent heterocyclic group including 5 to 50 ring atoms.

One or more sets of adjacent two or more of $R_{211}$ to $R_{221}$ form a substituted or unsubstituted, saturated or unsaturated ring by bonding with each other, or do not form a substituted or unsubstituted, saturated or unsaturated ring.

$R_{211}$ to $R_{221}$ that do not form the substituted or unsubstituted heterocycle, or the

- substituted or unsubstituted, saturated or unsaturated ring are independently a hydrogen atom,
- a substituted or unsubstituted alkyl group including 1 to 50 carbon atoms,
- a substituted or unsubstituted alkenyl group including 2 to 50 carbon atoms,
- a substituted or unsubstituted alkynyl group including 2 to 50 carbon atoms,
- a substituted or unsubstituted cycloalkyl group including 3 to 50 ring carbon atoms,
- —Si($R_{901}$)($R_{902}$)($R_{903}$),
- —O—($R_{904}$),
- —S—($R_{905}$),
- —N($R_{906}$)($R_{907}$),
- a halogen atom, a cyano group, a nitro group,
- a substituted or unsubstituted aryl group including 6 to 50 ring carbon atoms, or
- a substituted or unsubstituted monovalent heterocyclic group including 5 to 50 ring atoms.

$R_{901}$ to $R_{907}$ are as defined in the formula (1).

$R_{201A}$ and $R_{202A}$ in the formula (22) are groups corresponding to $R_{201}$ and $R_{202}$ in the formula (21), respectively.

For example, $R_{201A}$ and $R_{211}$ may be bonded with each other to form a bicyclic (or tricyclic or more polycyclic) nitrogen-containing heterocycle in which a ring containing $R_{201A}$ and $R_{211}$ and a benzene ring corresponding to the ring a are fused with each other. Specific examples of the nitrogen-containing heterocycle include compounds corresponding to bicyclic or more polycyclic nitrogen-containing fused heterocyclic groups in the specific example group G2. The same as above can be applied to cases where $R_{201A}$ and $R_{212}$ are bonded with each other, where $R_{22A}$ and $R_{213}$ are bonded with each other, and where $R_{202A}$ and $R_{214}$ are bonded with each other.

One or more sets of adjacent two or more of $R_{211}$ to $R_{221}$ may form a substituted or unsubstituted, saturated or unsaturated ring by bonding with each other. For example, $R_{211}$ and $R_{212}$ may form a structure in which a benzene ring, an indole ring, a pyrrole ring, a benzofuran ring, a benzothiophene ring, or the like are fused to a 6-membered ring with which $R_{211}$ and $R_{212}$ are bonded, and the formed fused ring is a naphthalene ring, a carbazole ring, an indole ring, a dibenzofuran ring, or a dibenzothiophene ring.

In one embodiment, $R_{211}$ to $R_{221}$ that are not involved in the ring formation are independently a hydrogen atom, a substituted or unsubstituted alkyl group including 1 to 50 carbon atoms, a substituted or unsubstituted aryl group including 6 to 50 ring carbon atoms, or a substituted or unsubstituted monovalent heterocyclic group including 5 to 50 ring atoms.

In one embodiment, $R_{211}$ to $R_{221}$ that are not involved in the ring formation are independently a hydrogen atom, a substituted or unsubstituted aryl group including 6 to 50 ring carbon atoms, or a substituted or unsubstituted monovalent heterocyclic group including 5 to 50 ring atoms.

In one embodiment, $R_{211}$ to $R_{221}$ that are not involved in the ring formation are independently a hydrogen atom, or a substituted or unsubstituted alkyl group including 1 to 50 carbon atoms.

In one embodiment, $R_{211}$ to $R_{221}$ that are not involved in the ring formation are independently a hydrogen atom, or a substituted or unsubstituted alkyl group including 1 to 50 carbon atoms, and at least one of $R_{211}$ to $R_{221}$ is a substituted or unsubstituted alkyl group including 1 to 50 carbon atoms.

In one embodiment, the compound represented by the formula (22) is a compound represented by the following formula (23).

(23)

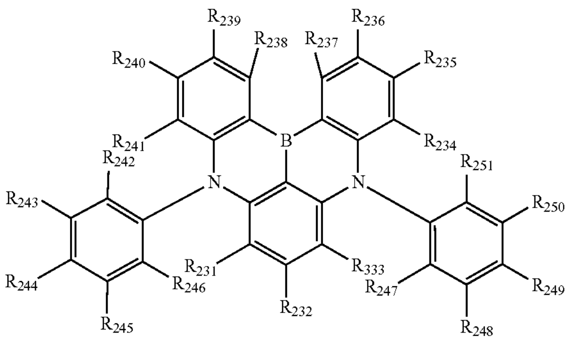

In the formula (23), $R_{231}$ forms a substituted or unsubstituted heterocycle by bonding with $R_{246}$, or does not form a substituted or unsubstituted heterocycle. $R_{233}$ forms a substituted or unsubstituted heterocycle by bonding with $R_{247}$, or does not form a substituted or unsubstituted heterocycle. $R_{234}$ forms a substituted or unsubstituted heterocycle by bonding with $R_{251}$, or does not form a substituted or unsubstituted heterocycle. $R_{241}$ forms a substituted or unsubstituted heterocycle by bonding with $R_{242}$, or does not form a substituted or unsubstituted heterocycle.

One or more sets of adjacent two or more of $R_{231}$ to $R_{251}$ form a substituted or unsubstituted, saturated or unsaturated ring by bonding with each other, or do not form a substituted or unsubstituted, saturated or unsaturated ring.

$R_{231}$ to $R_{251}$ that do not form the substituted or unsubstituted heterocycle, or the substituted or unsubstituted, saturated or unsaturated ring are independently a hydrogen atom, a substituted or unsubstituted alkyl group including 1 to 50 carbon atoms, a substituted or unsubstituted alkenyl group including 2 to 50 carbon atoms, a substituted or unsubstituted alkynyl group including 2 to 50 carbon atoms, a substituted or unsubstituted cycloalkyl group including 3 to 50 ring carbon atoms, —$Si(R_{901})(R_{902})(R_{903})$,

—O—$(R_{904})$,

—S—$(R_{905})$,

—$N(R_{906})(R_{907})$, a halogen atom, a cyano group, a nitro group, a substituted or unsubstituted aryl group including 6 to 50 ring carbon atoms, or a substituted or unsubstituted monovalent heterocyclic group including 5 to 50 ring atoms.

$R_{901}$ to $R_{907}$ are as defined in the formula (1).

$R_{231}$ may form a substituted or unsubstituted heterocycle by bonding with $R_{246}$. For example, a tricyclic or more polycyclic nitrogen-containing fused heterocycle in which a benzene ring with which $R_{246}$ is bonded, a ring containing N, and a benzene ring corresponding to the ring a are fused by bonding $R_{231}$ and $R_{246}$ with each other, may be formed. Specific examples of the nitrogen-containing heterocycle include a compound corresponding to a tricyclic or more polycyclic nitrogen-containing fused heterocyclic group in the specific example group G2. The same as above can be applied to cases where $R_{233}$ and $R_{247}$ are bonded with each other, where $R_{234}$ and $R_{251}$ are bonded with each other, and where $R_{241}$ and $R_{242}$ are bonded with each other.

In one embodiment, $R_{231}$ to $R_{251}$ that are not involved in the ring formation are independently a hydrogen atom, a substituted or unsubstituted alkyl group including 1 to 50 carbon atoms, a substituted or unsubstituted aryl group including 6 to 50 ring carbon atoms, or a substituted or unsubstituted monovalent heterocyclic group including 5 to 50 ring atoms.

In one embodiment, $R_{231}$ to $R_{251}$ that are not involved in the ring formation are independently a hydrogen atom, a substituted or unsubstituted aryl group including 6 to 50 ring carbon atoms, or a substituted or unsubstituted monovalent heterocyclic group including 5 to 50 ring atoms.

In one embodiment, $R_{231}$ to $R_{251}$ that are not involved in the ring formation are independently a hydrogen atom, or a substituted or unsubstituted alkyl group including 1 to 50 carbon atoms.

In one embodiment, $R_{231}$ to $R_{251}$ that are not involved in the ring formation are independently a hydrogen atom, or a substituted or unsubstituted alkyl group including 1 to 50 carbon atoms, and at least one of $R_{231}$ to $R_{251}$ is a substituted or unsubstituted alkyl group including 1 to 50, carbon atoms.

In one embodiment, the compound represented by the formula (21) is a compound represented by the following formula (23A).

(23A)

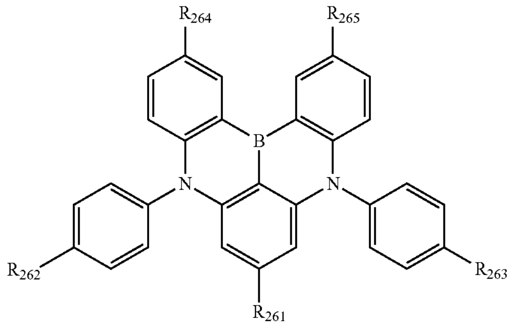

In the formula (23A), $R_{261}$ to $R_{265}$ are independently a hydrogen atom, a substituted or unsubstituted alkyl group including 1 to 50 carbon atoms, a substituted or unsubstituted alkenyl group including 2 to 50 carbon atoms, a substituted or unsubstituted alkynyl group including 2 to 50 carbon atoms,

—$N(R_{906})(R_{907})$, a substituted or unsubstituted cycloalkyl group including 3 to 50 ring carbon atoms, or
a substituted or unsubstituted aryl group including 6 to 50 ring carbon atoms.
$R_{906}$ and $R_{907}$ are as defined in the formula (1). When two or more of each of $R_{906}$ and $R_{907}$ are present, the two or more of each of $R_{906}$ and $R_{907}$ are the same as or different from each other.

In one embodiment, $R_{261}$ to $R_{265}$ are independently a substituted or unsubstituted alkyl group including 1 to 50 carbon atoms, or a substituted or unsubstituted aryl group including 6 to 50 ring carbon atoms.

In one embodiment, $R_{261}$ to $R_{265}$ are independently a substituted or unsubstituted alkyl group including 1 to 50 carbon atoms.

In one embodiment, the compound represented by the formula (23) is a compound represented by the following formula (23B).

(23B)

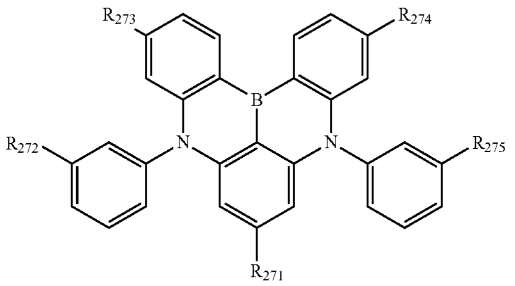

In the formula (23B),
$R_{271}$, $R_{272}$, and $R_{275}$ are independently
a hydrogen atom,
a substituted or unsubstituted alkyl group including 1 to 50 carbon atoms,
a substituted or unsubstituted alkenyl group including 2 to 50 carbon atoms,
a substituted or unsubstituted alkynyl group including 2 to 50 carbon atoms,
a substituted or unsubstituted cycloalkyl group including 3 to 50 ring carbon atoms,
—$N(R_{906})(R_{907})$, or
a substituted or unsubstituted aryl group including 6 to 50 ring carbon atoms.
$R_{273}$ and $R_{4274}$ are independently
a substituted or unsubstituted alkyl group including 1 to 50 carbon atoms,
a substituted or unsubstituted alkenyl group including 2 to 50 carbon atoms,
a substituted or unsubstituted alkynyl group including 2 to 50 carbon atoms,
a substituted or unsubstituted cycloalkyl group including 3 to 50 ring carbon atoms,
—$N(R_{906})(R_{907})$,
a substituted or unsubstituted aryl group including 6 to 50 ring carbon atoms, or
a substituted or unsubstituted monovalent heterocyclic group including 5 to 50 ring atoms.
$R_{906}$ and $R_{907}$ are as defined in the formula (1).

In one embodiment, the compound represented by the formula (23) is a compound represented by the following formula (23B').

(23B')

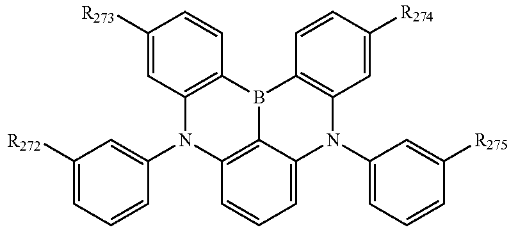

In the formula (23B'), $R_{272}$ to $R_{275}$ are as defined in the formula (23B).)

In one embodiment, at least one of $R_{271}$ to $R_{275}$ is
a substituted or unsubstituted alkyl group including 1 to 50 carbon atoms,
a substituted or unsubstituted alkenyl group including 2 to 50 carbon atoms,
a substituted or unsubstituted alkynyl group including 2 to 50 carbon atoms,
a substituted or unsubstituted cycloalkyl group including 3 to 50 ring carbon atoms,
—$N(R_{906})(R_{907})$, or
a substituted or unsubstituted aryl group including 6 to 50 ring carbon atoms.

In one embodiment,
$R_{272}$ is
a hydrogen atom,
a substituted or unsubstituted alkyl group including 1 to 50 carbon atoms,
—$N(R_{906})(R_{907})$, or
a substituted or unsubstituted aryl group including 6 to 50 ring carbon atoms.
$R_{271}$ and $R_{273}$ to $R_{275}$ are independently
a substituted or unsubstituted alkyl group including 1 to 50 carbon atoms, —$N(R_{906})(R_{907})$, or
a substituted or unsubstituted aryl group including 6 to 50 ring carbon atoms.

In one embodiment, the compound represented by the formula (23) is a compound represented by the following formula (23C).

(23C)

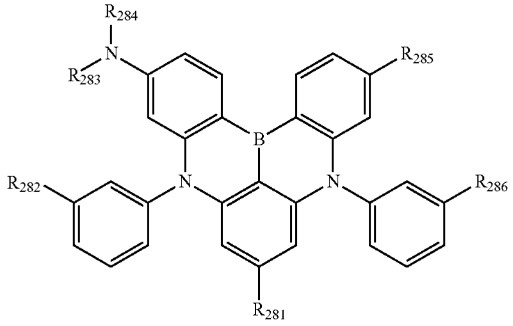

In the formula (23C),
$R_{281}$ and $R_{282}$ are independently
a hydrogen atom,
a substituted or unsubstituted alkyl group including 1 to 50 carbon atoms,
a substituted or unsubstituted alkenyl group including 2 to 50 carbon atoms, a substituted or unsubstituted alkynyl group including 2 to 50 carbon atoms, a substituted or unsubstituted cycloalkyl group including 3 to 50 ring carbon atoms, or a substituted or unsubstituted aryl group including 6 to 50 ring carbon atoms.

$R_{283}$ to $R_{286}$ are independently a substituted or unsubstituted alkyl group including 1 to 50 carbon atoms, a substituted or unsubstituted alkenyl group including 2 to 50 carbon atoms, a substituted or unsubstituted alkynyl group including 2 to 50 carbon atoms, a substituted or unsubstituted cycloalkyl group including 3 to 50 ring carbon atoms, or a substituted or unsubstituted aryl group including 6 to 50 ring carbon atoms.

In one embodiment, the compound represented by the formula (23) is a compound represented by the following formula (23C').

(23C')

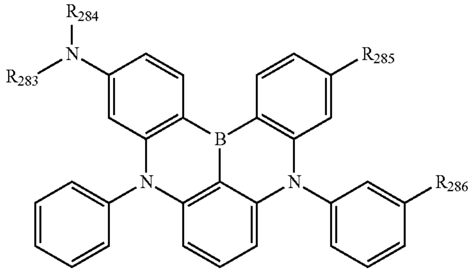

In the formula (23C'), $R_{283}$ to $R_{286}$ are as defined in the formula (23C).

In one embodiment, $R_{281}$ to $R_{286}$ are independently a substituted or unsubstituted alkyl group including 1 to 50 carbon atoms, or a substituted or unsubstituted aryl group including 6 to 50 ring carbon atoms.

In one embodiment, $R_{281}$ to $R_{286}$ are independently a substituted or unsubstituted aryl group including 6 to 50 ring carbon atoms.

The compound represented by the formula (21) can be produced by first bonding a ring a, a ring b, and a ring c through linking groups (a group containing N—$R_1$ and a group containing N—$R_2$) to form an intermediate (first reaction), followed by bonding of the ring a, the ring b, and the ring c through a linking group (a group containing B) to obtain a final product (second reaction). In the first reaction, an amination reaction such as a Buchwald-Hartwig reaction can be applied. In the second reaction, a tandem hetero-Friedel-Crafts reaction or the like can be applied.

Specific examples of the compound represented by the formula (21) will be described below, but these are merely examples, and the compound represented by the formula (21) is not limited to the following specific examples.

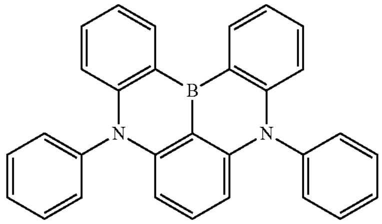

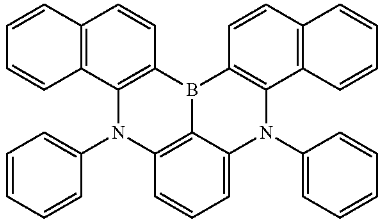

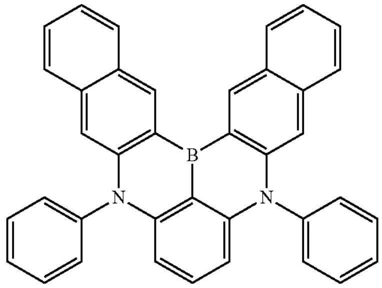

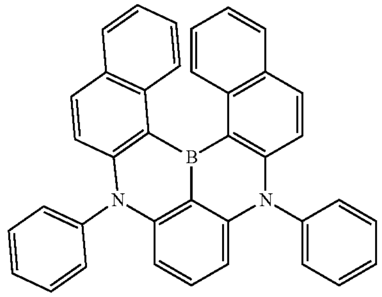

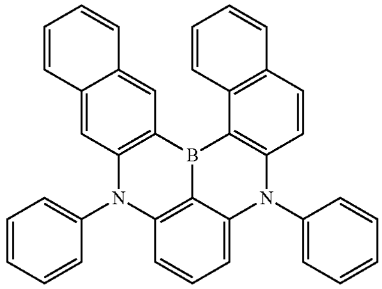

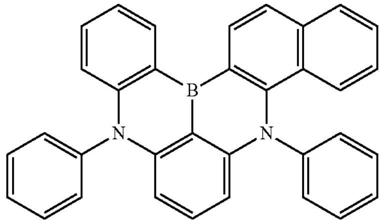

-continued
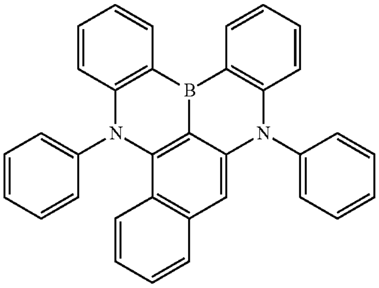
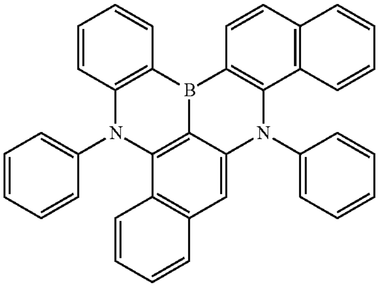
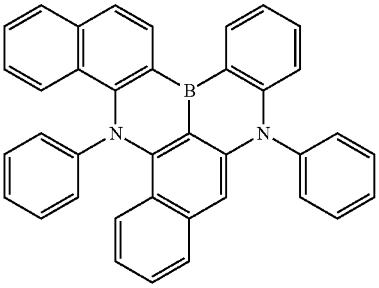
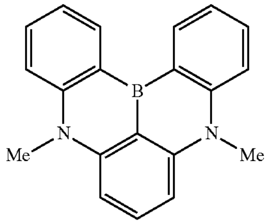
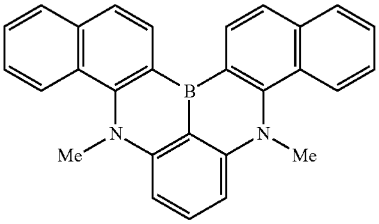
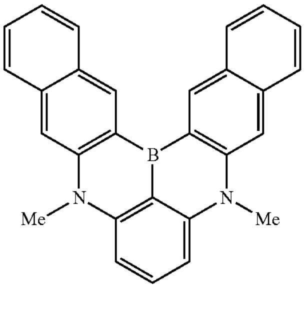
-continued
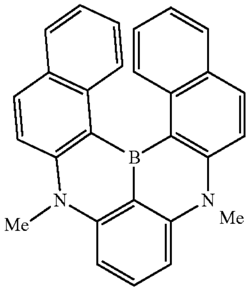
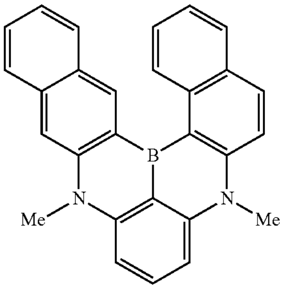
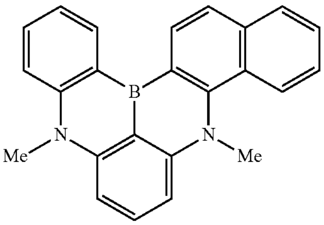
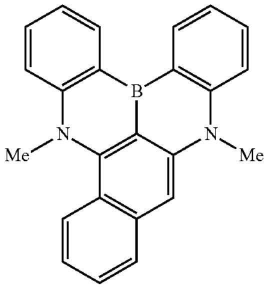
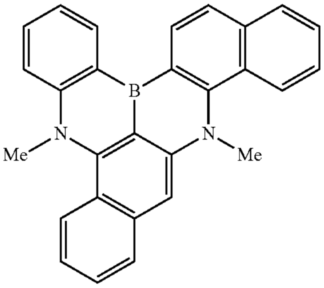
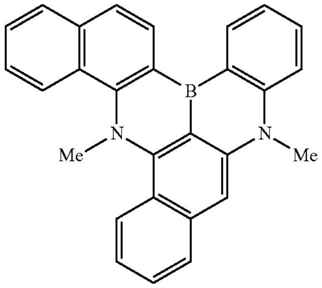

-continued
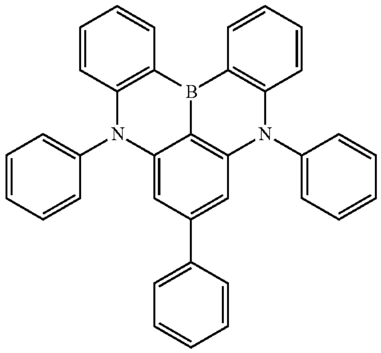
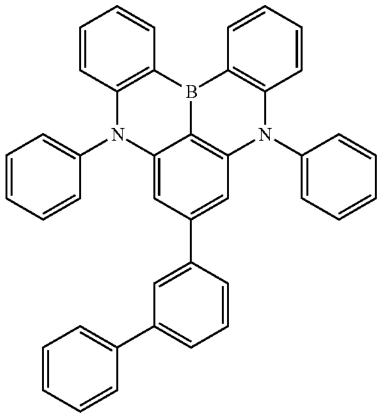
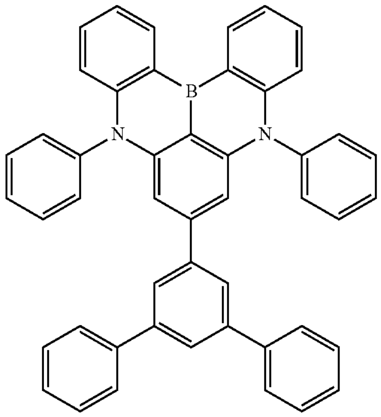
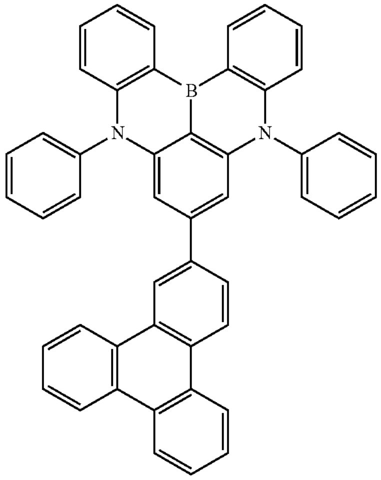
-continued
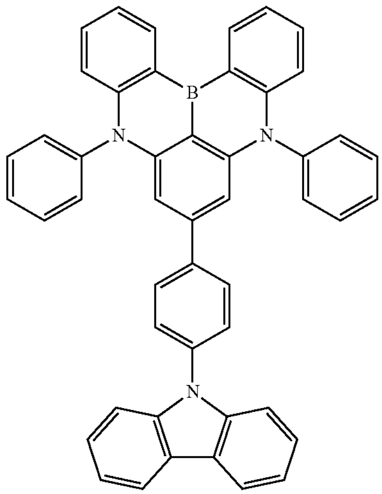
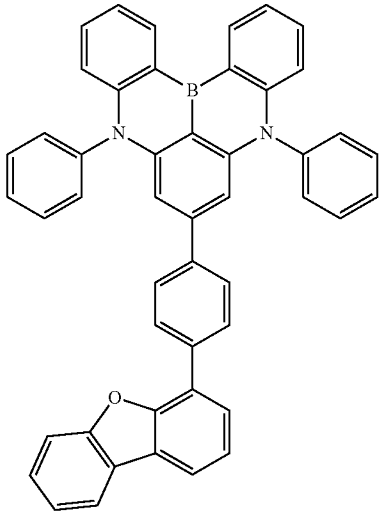
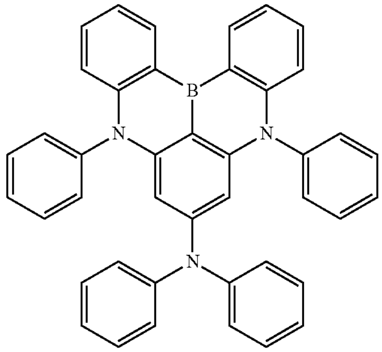
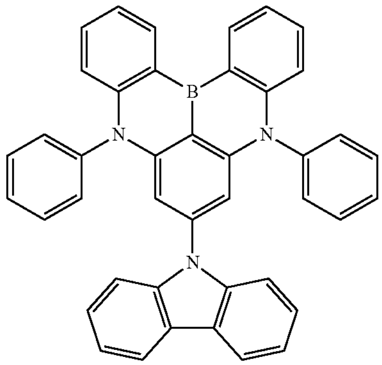

-continued
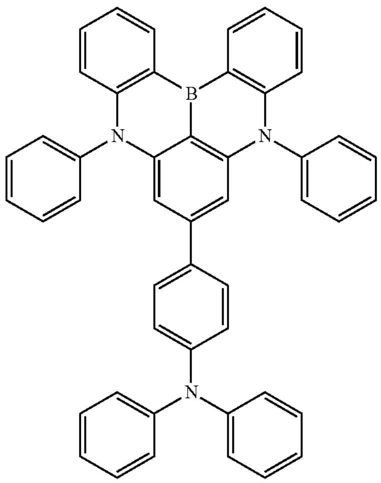
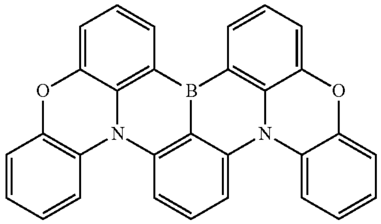
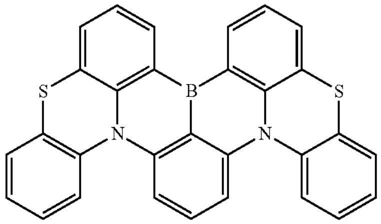
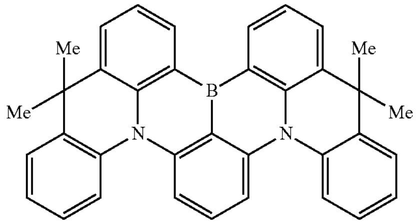
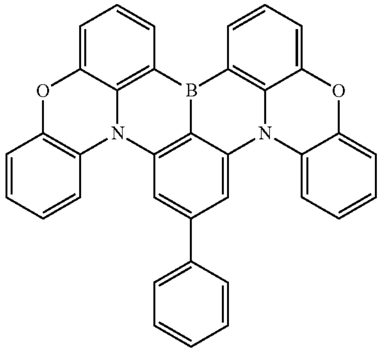
-continued
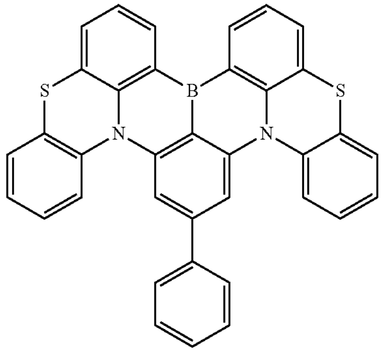
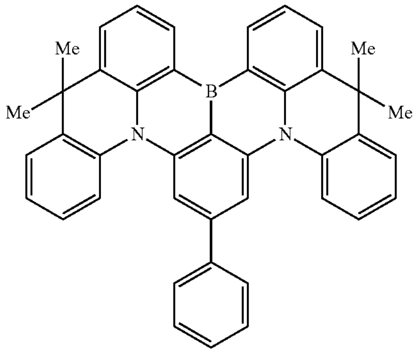
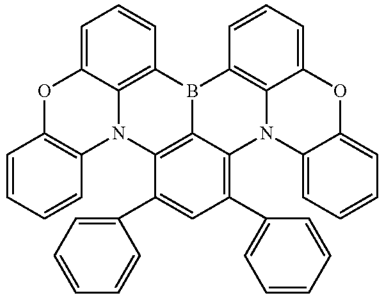
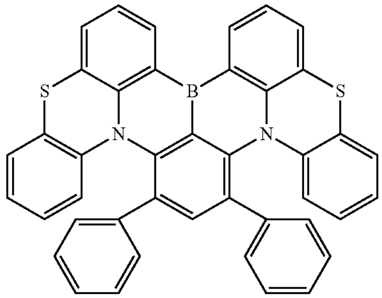
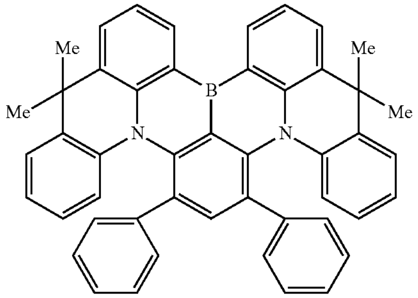

-continued
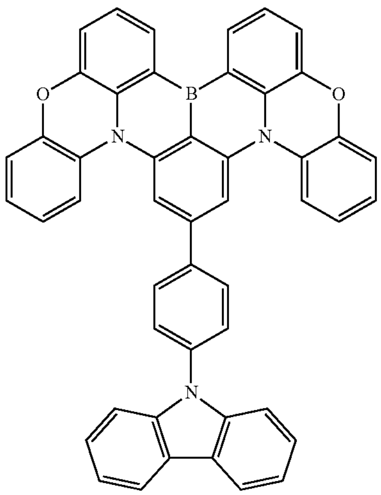
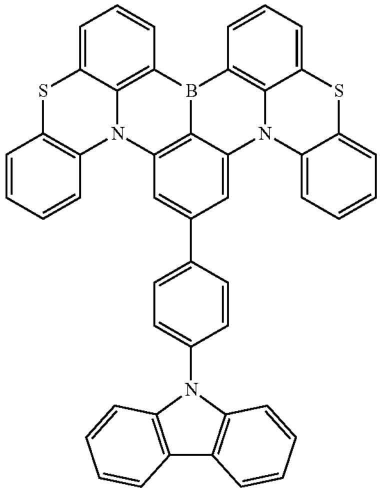
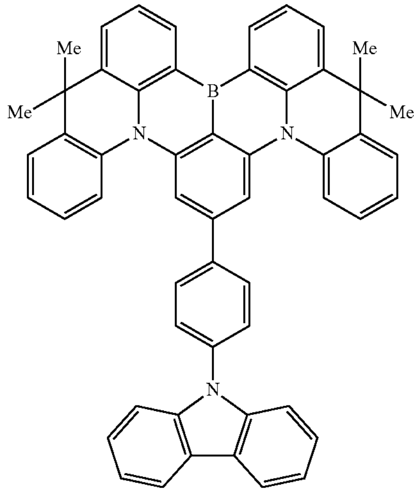
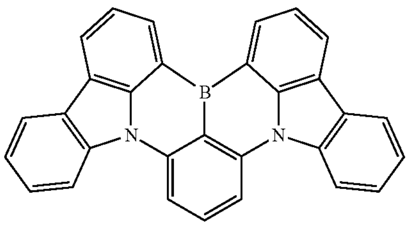
-continued
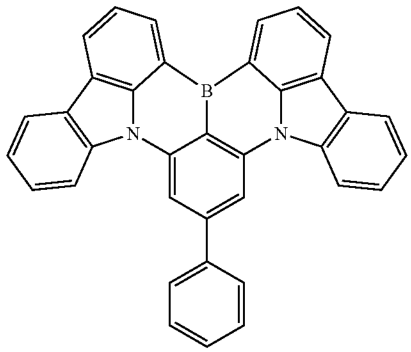
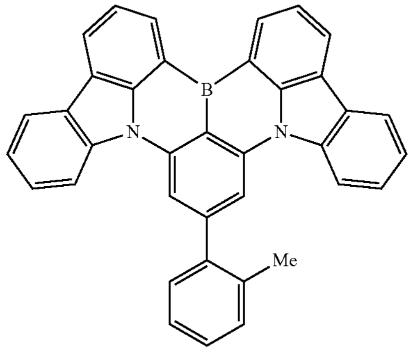
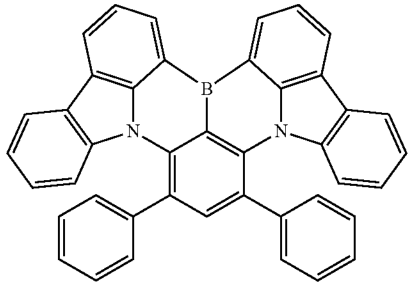
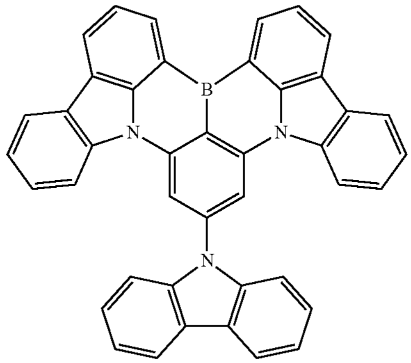
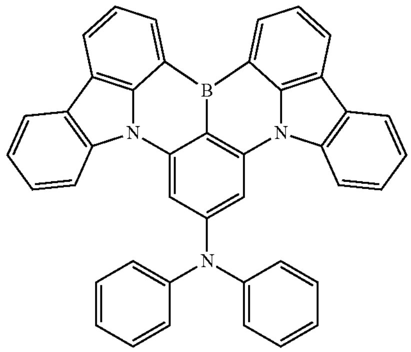

-continued
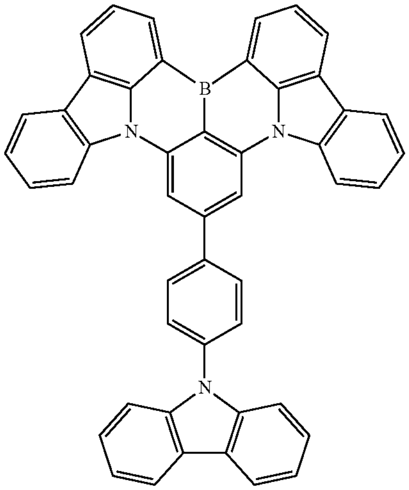
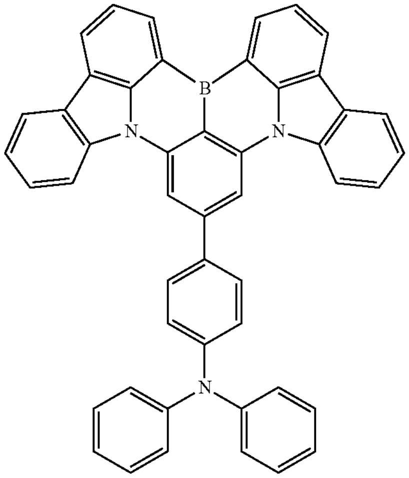
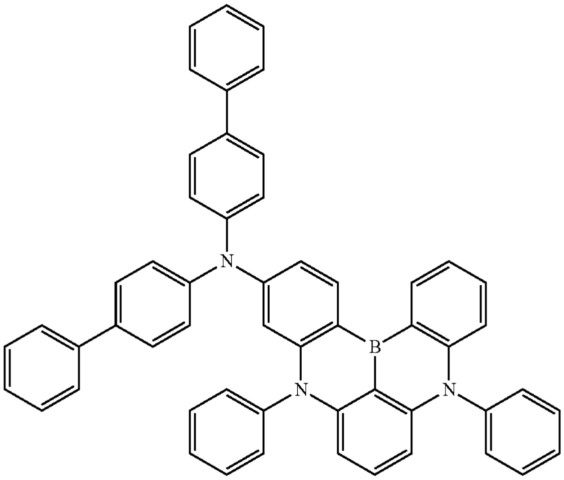
-continued
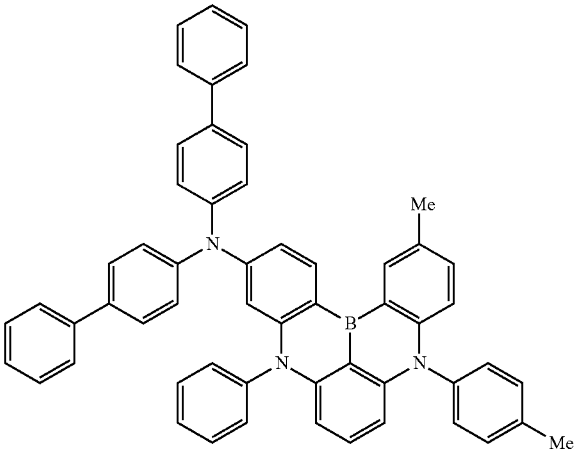
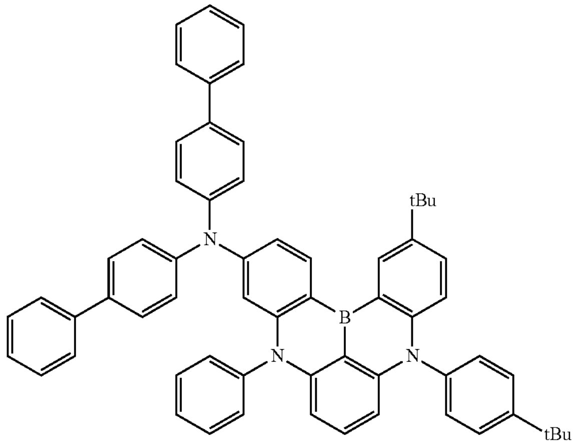
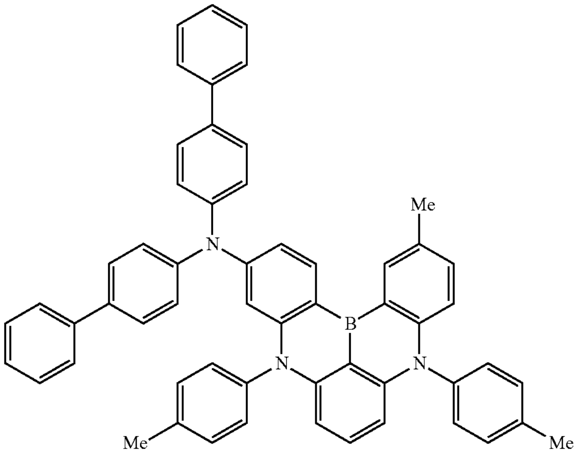
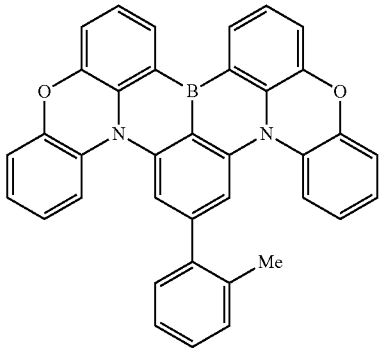

-continued
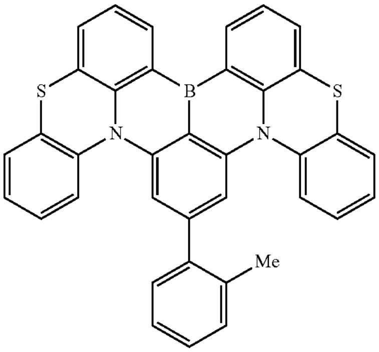
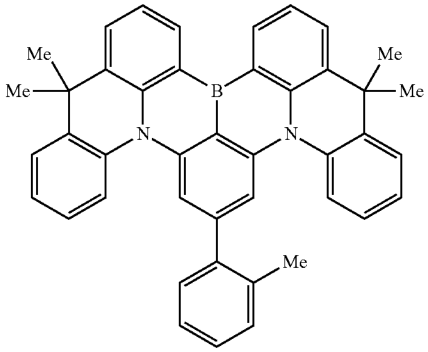
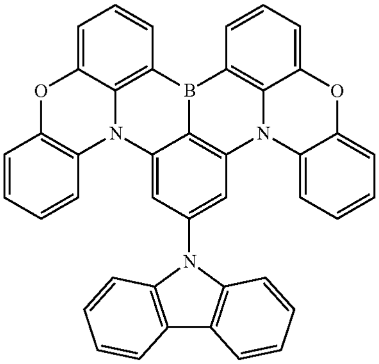
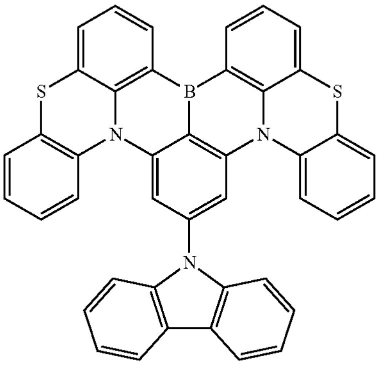
-continued
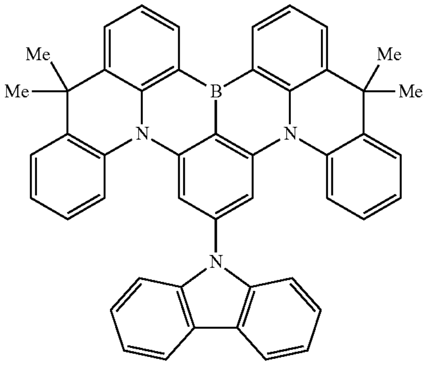
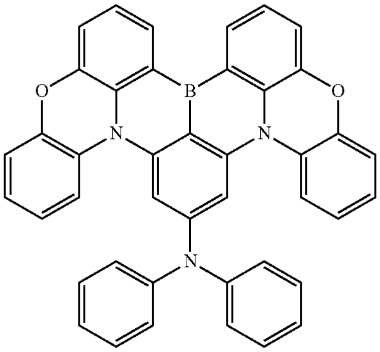
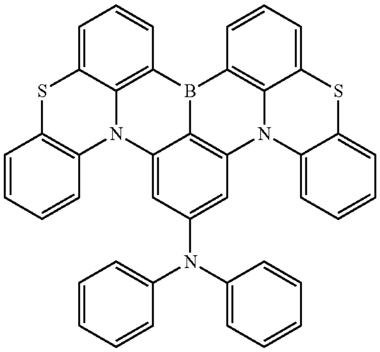
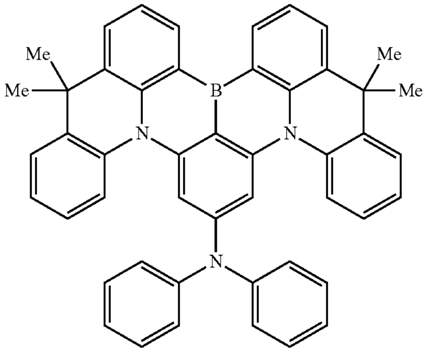

-continued
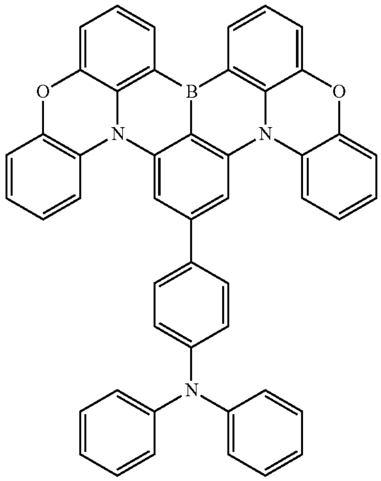
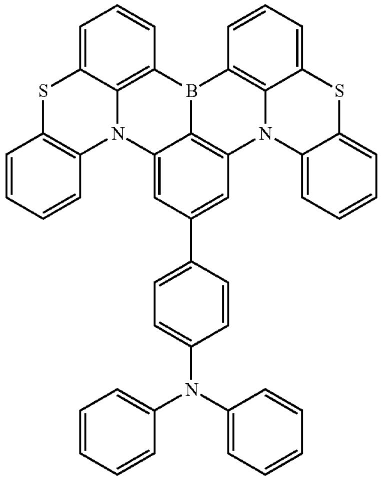
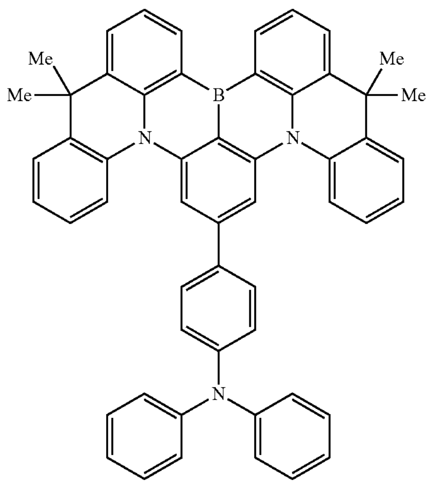
-continued
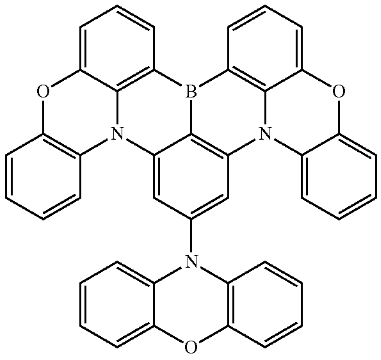
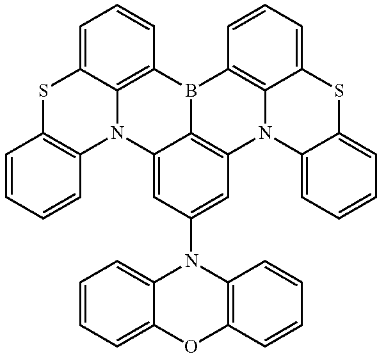
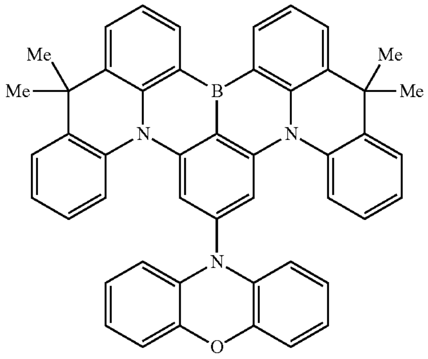
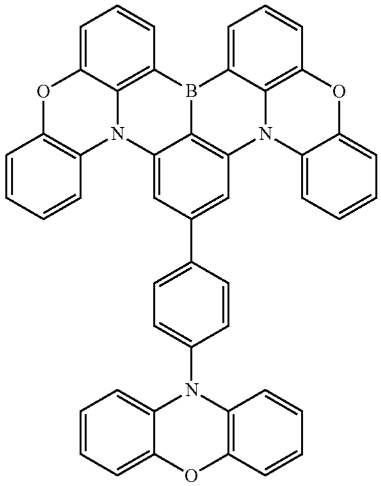

-continued
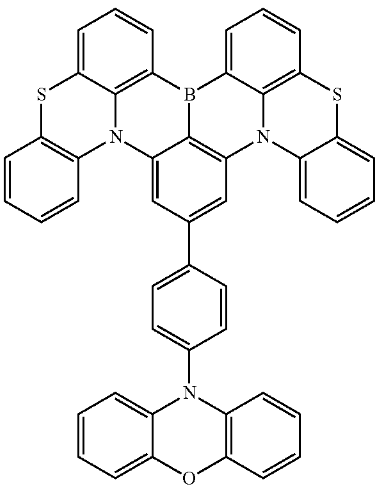
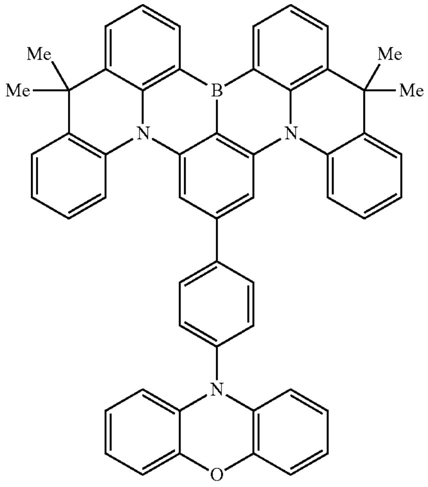
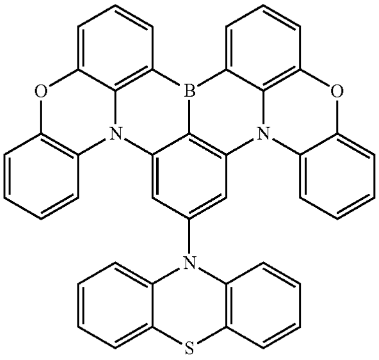
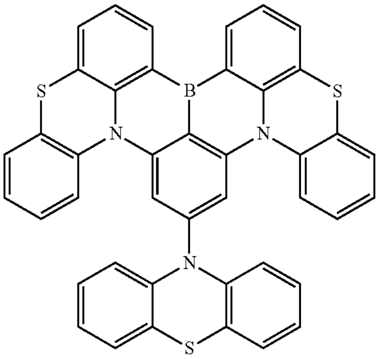
-continued
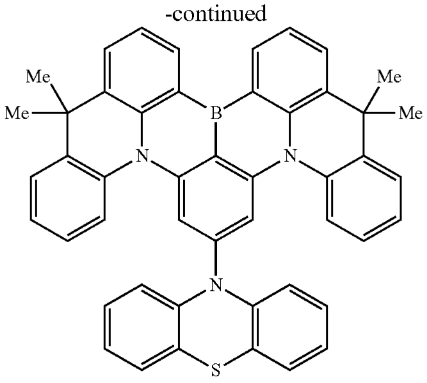
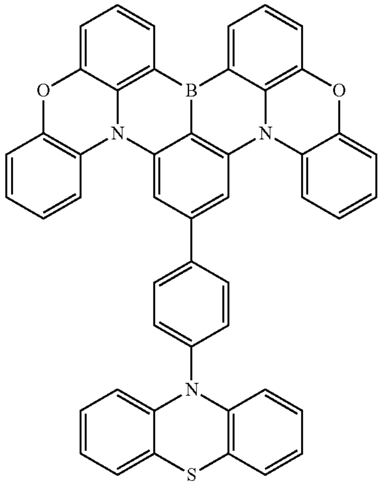
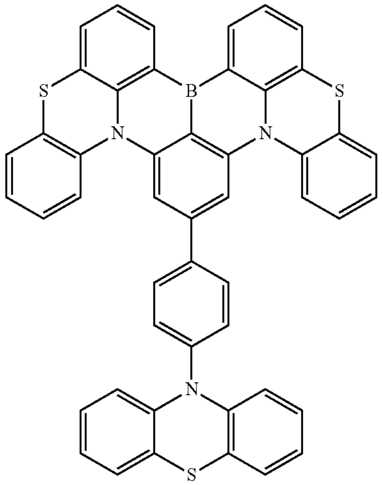

-continued
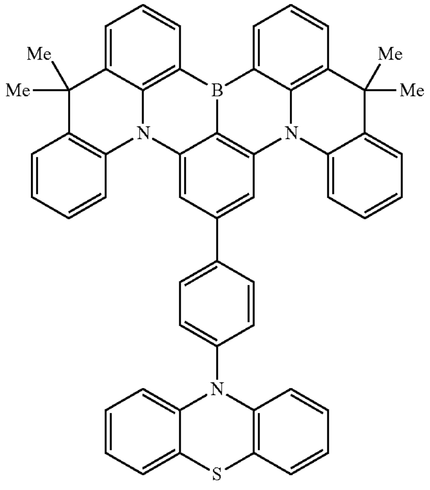
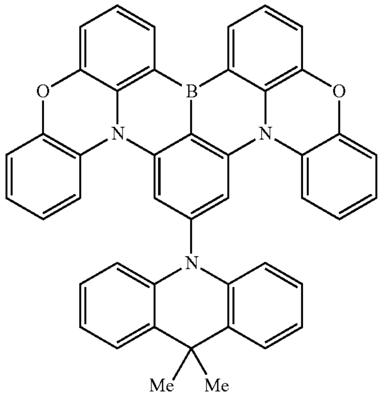
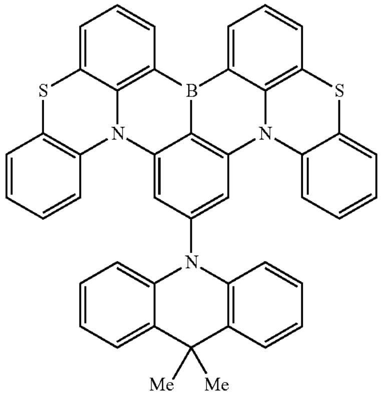
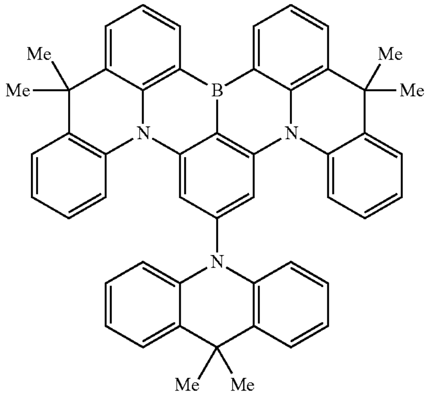
-continued
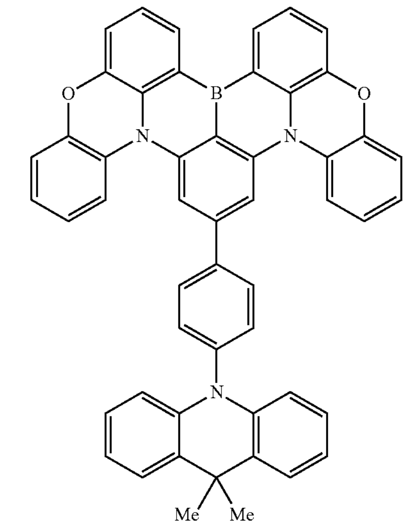
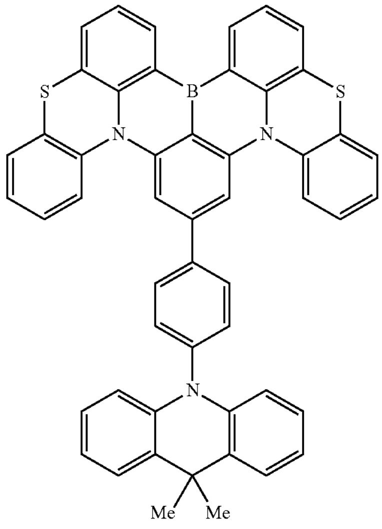
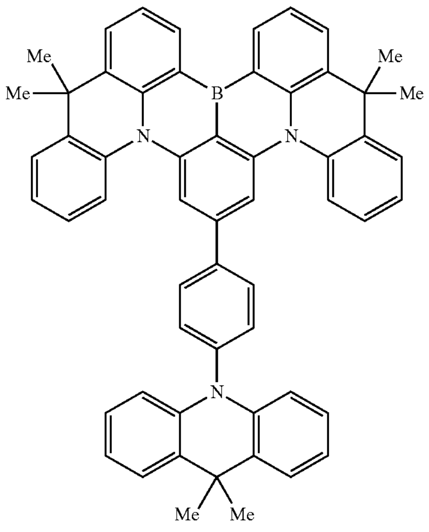

-continued
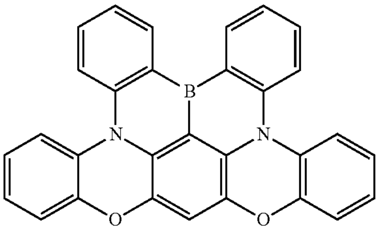
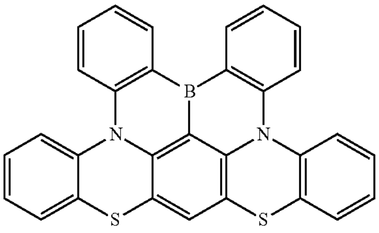
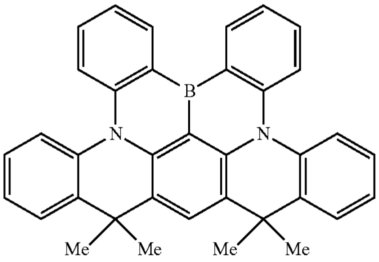
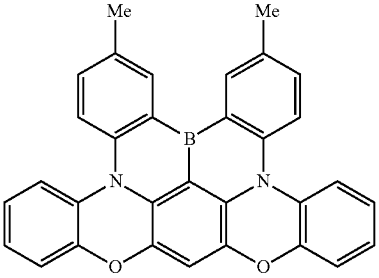
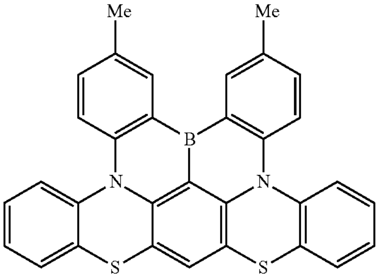
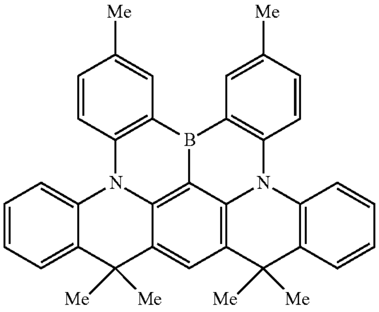
-continued
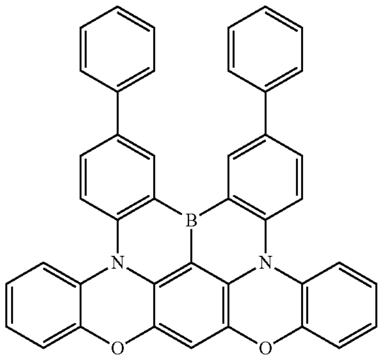
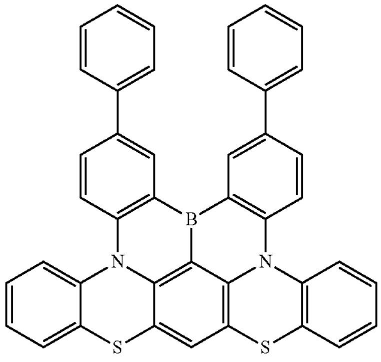
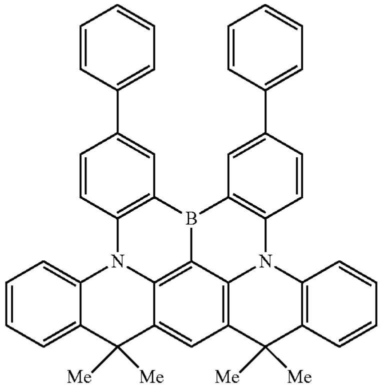
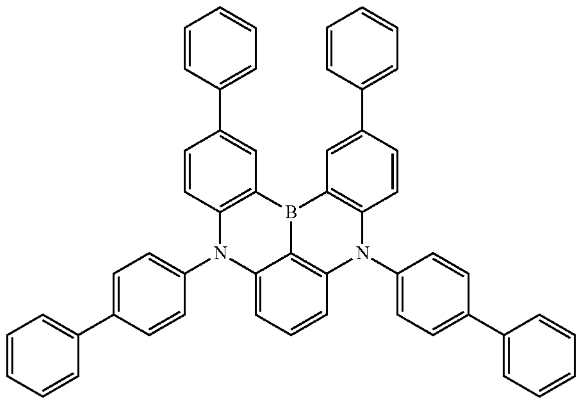

-continued
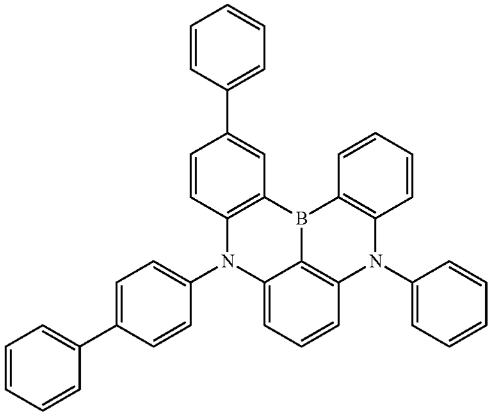
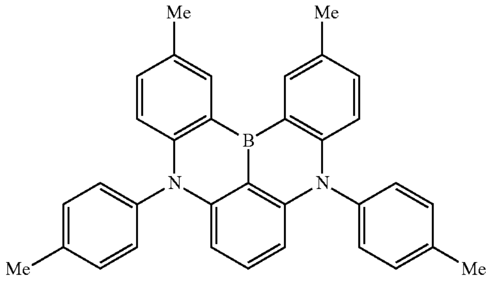
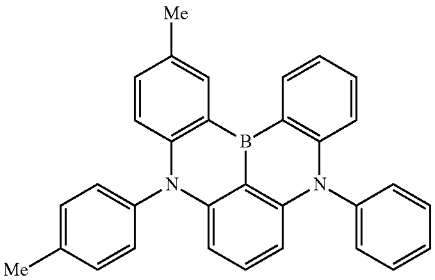
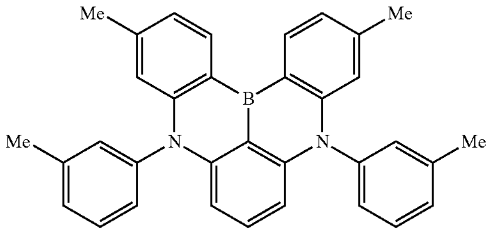
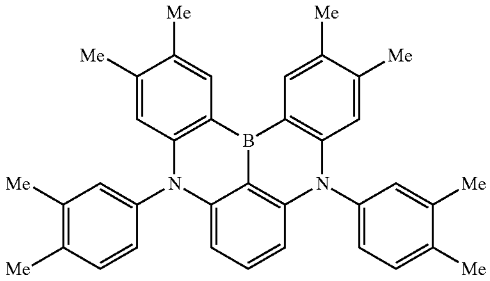
-continued
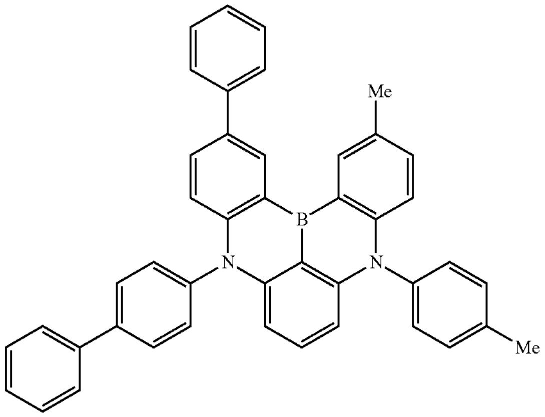
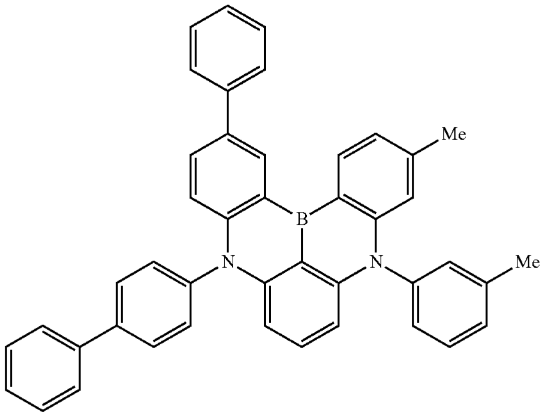
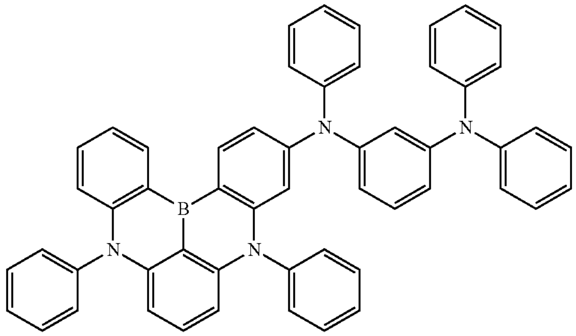
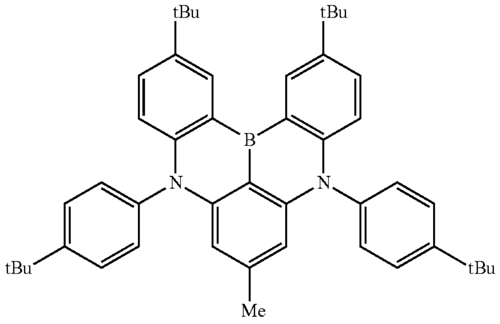

-continued
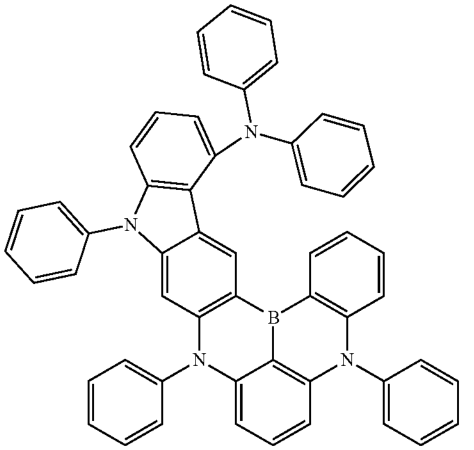
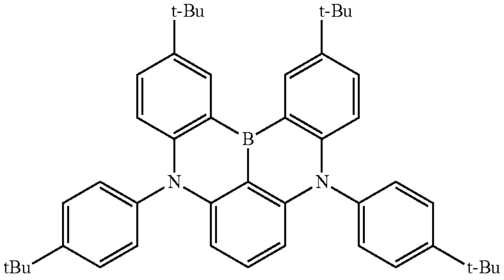
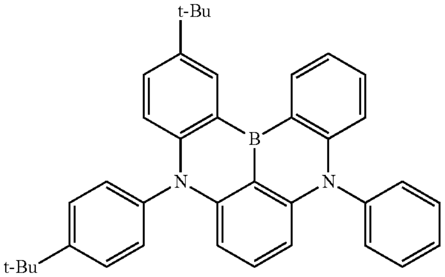
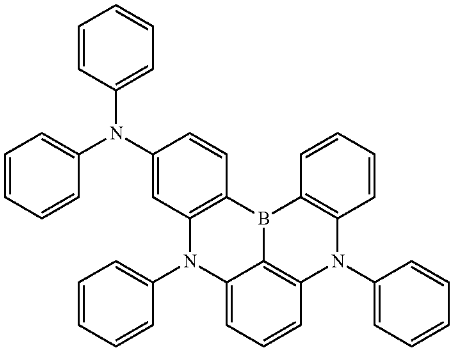
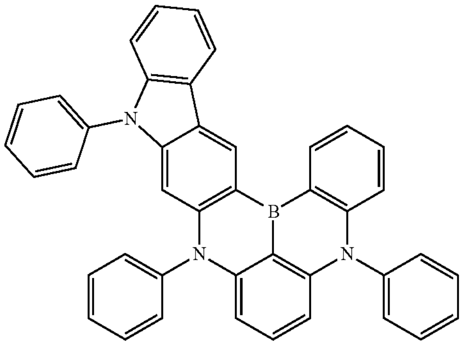
-continued
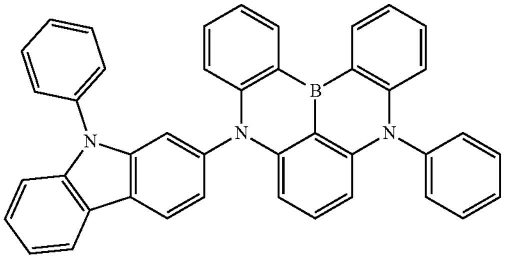
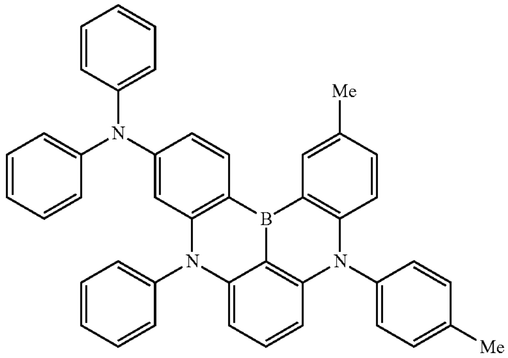
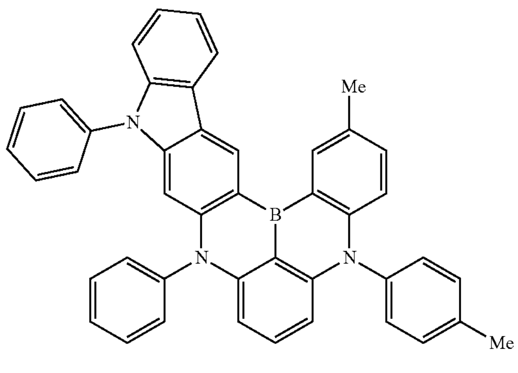
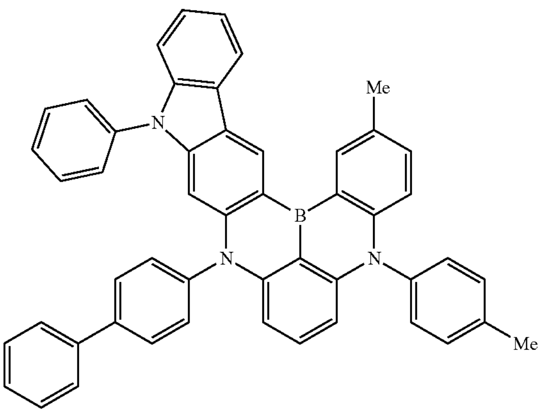

-continued
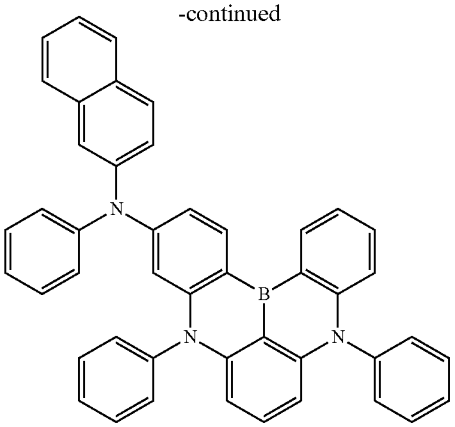
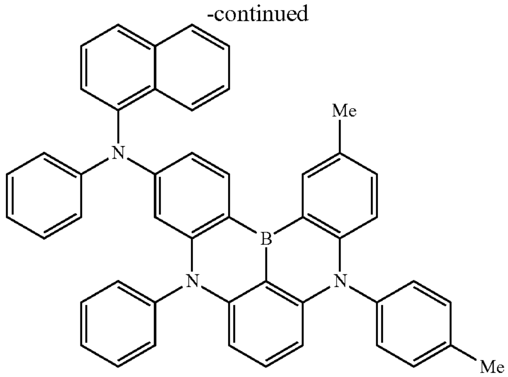
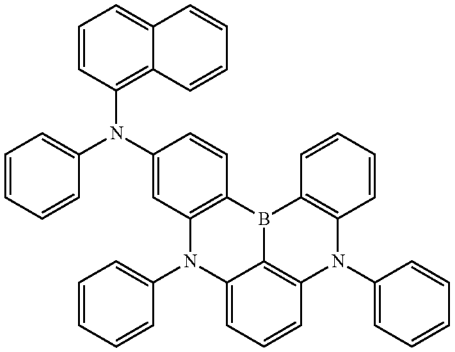
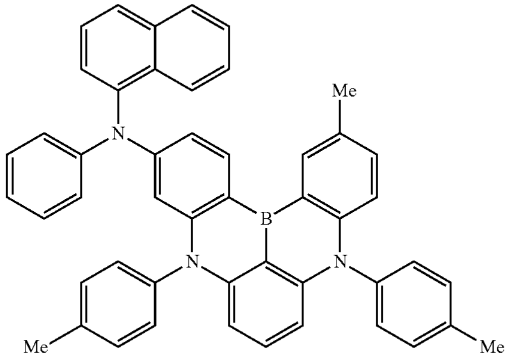
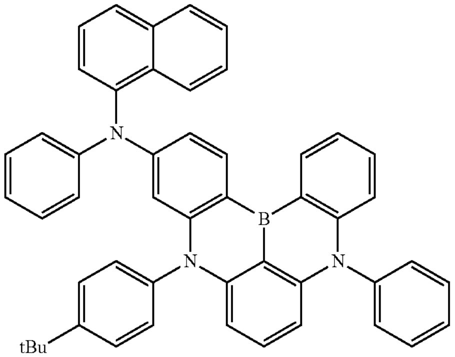
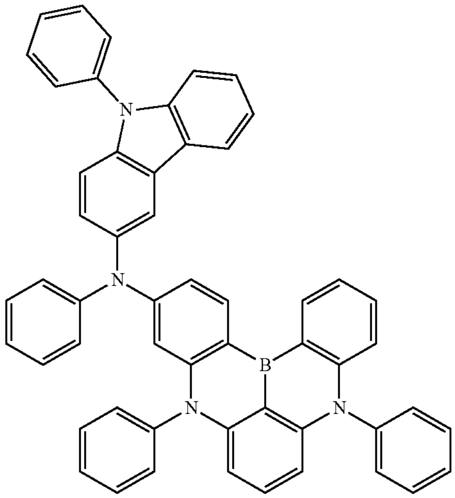
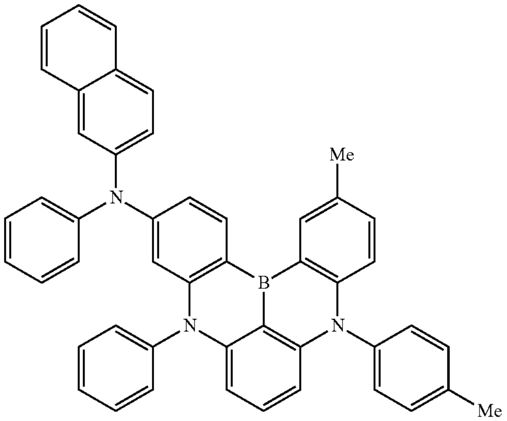
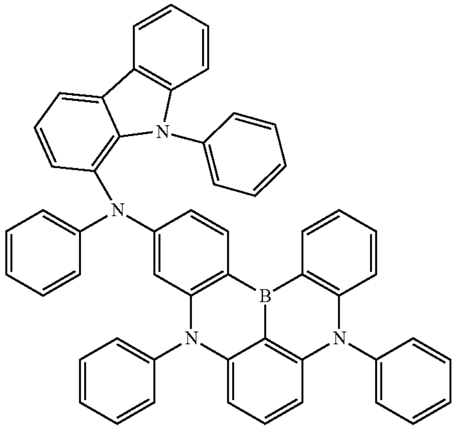

-continued
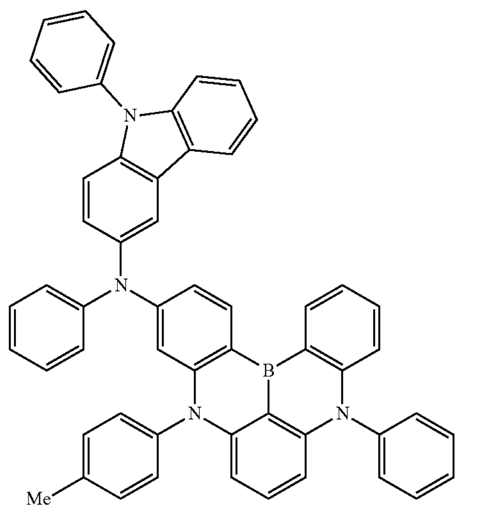
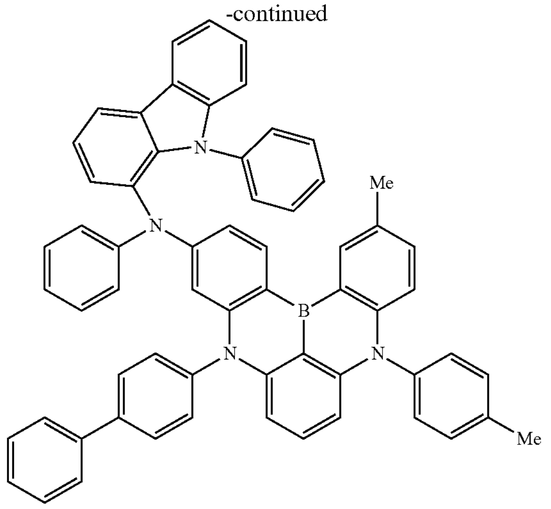
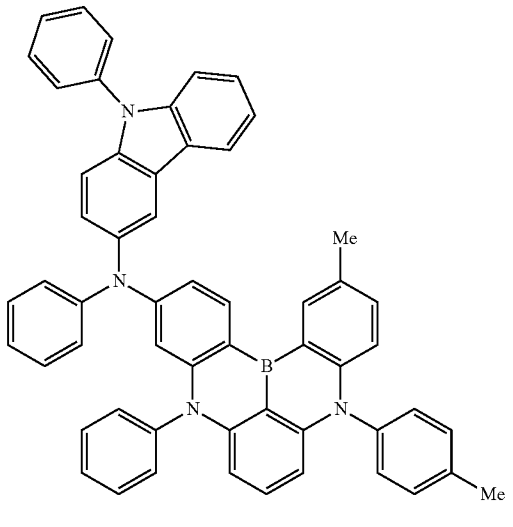
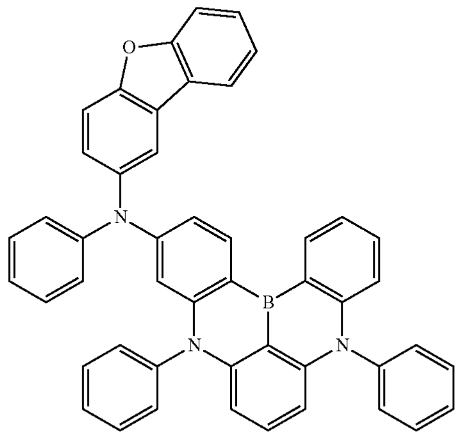
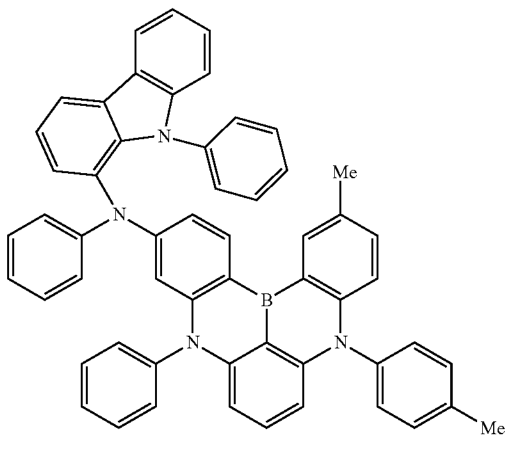
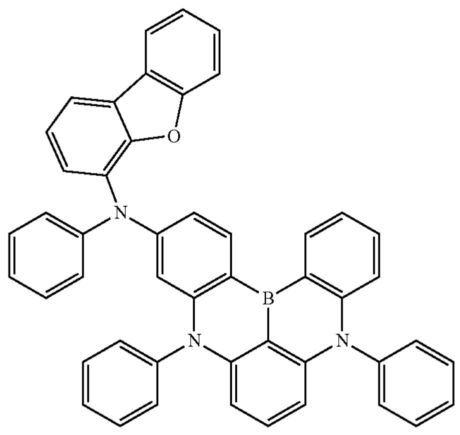

-continued
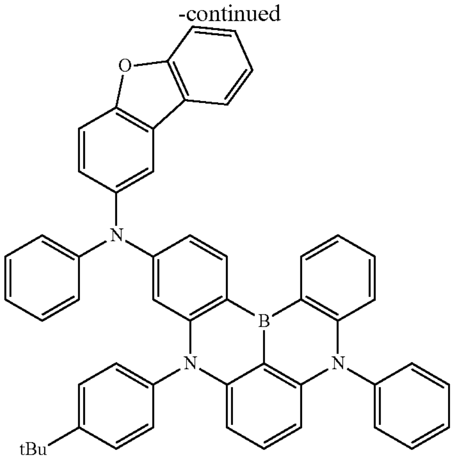
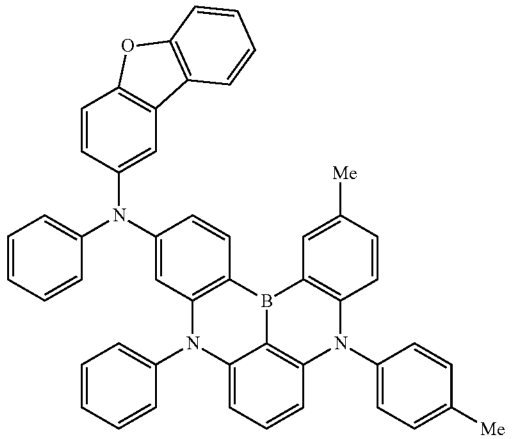
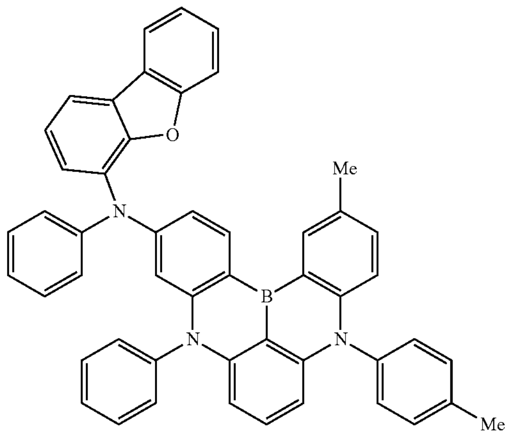
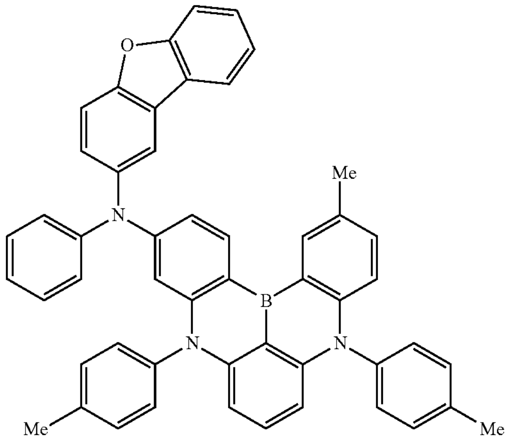
-continued
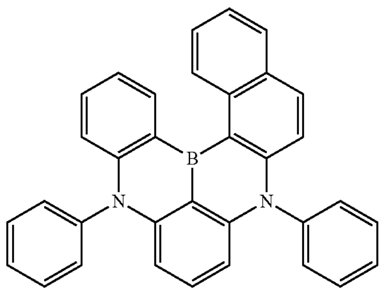
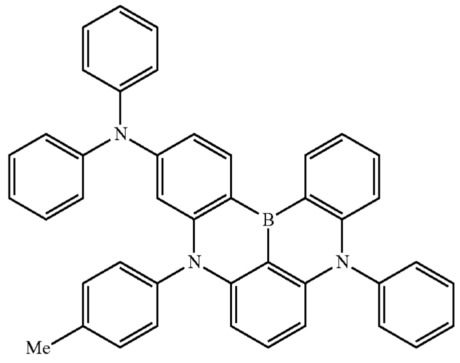
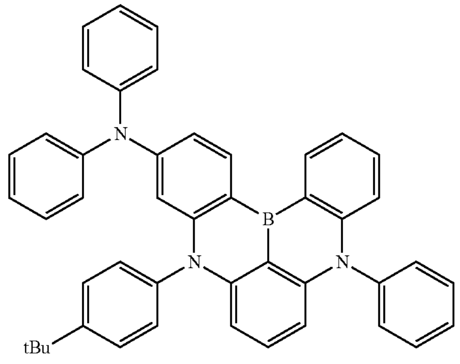

-continued
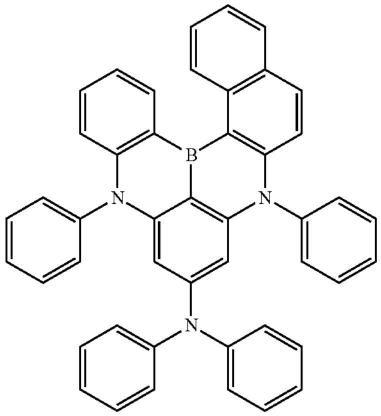
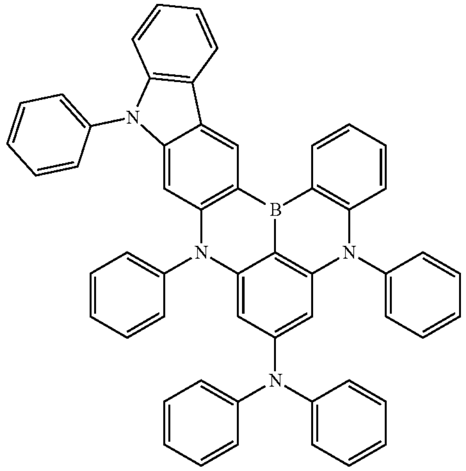
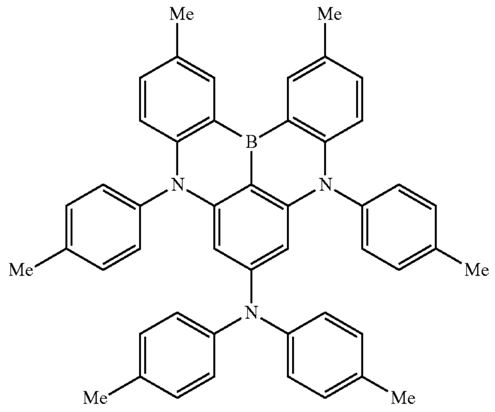
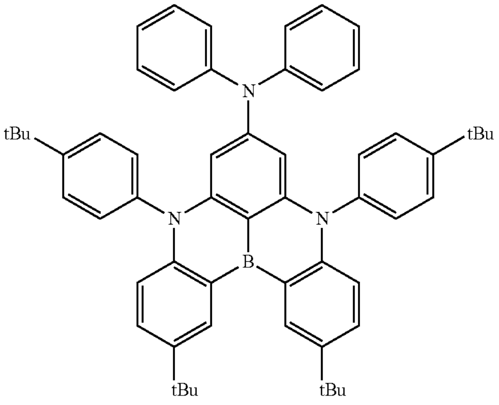
-continued
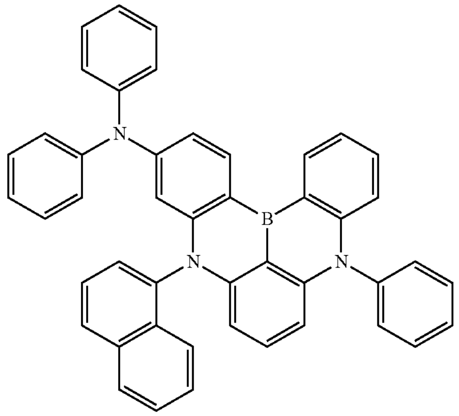
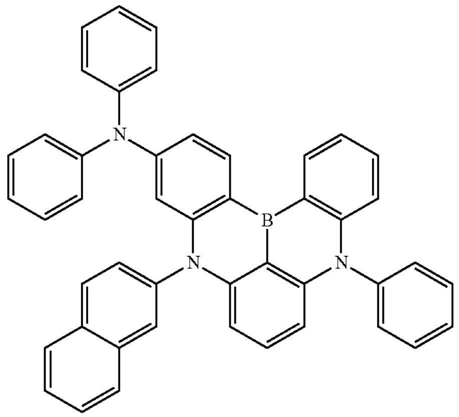
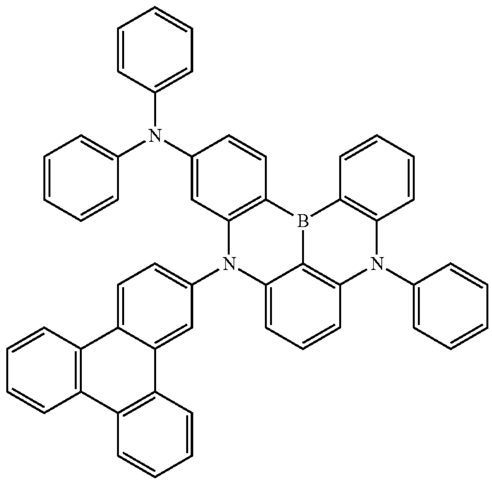

-continued
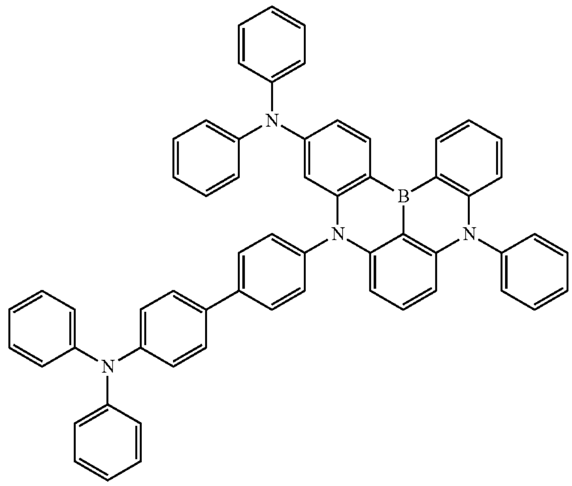
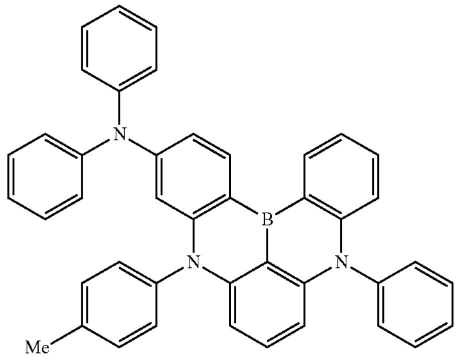
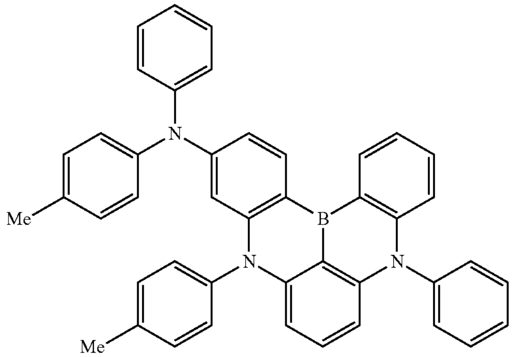
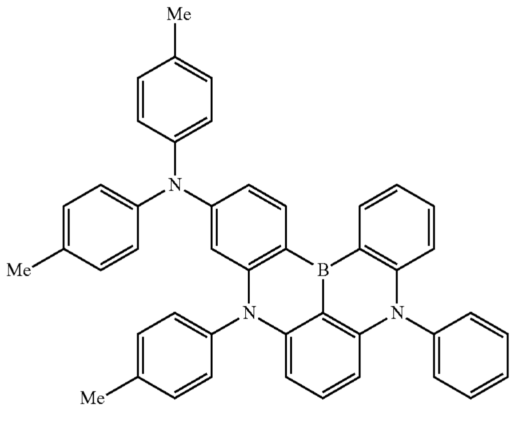
-continued
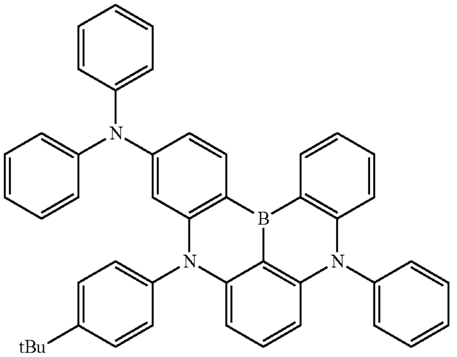
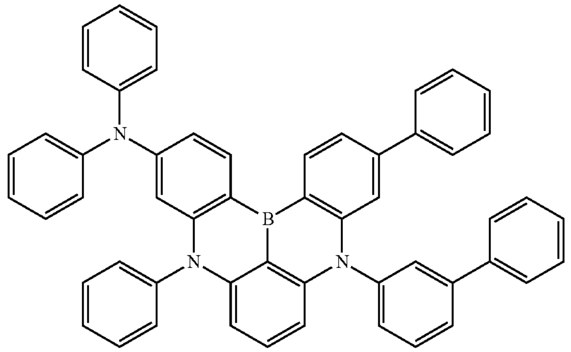
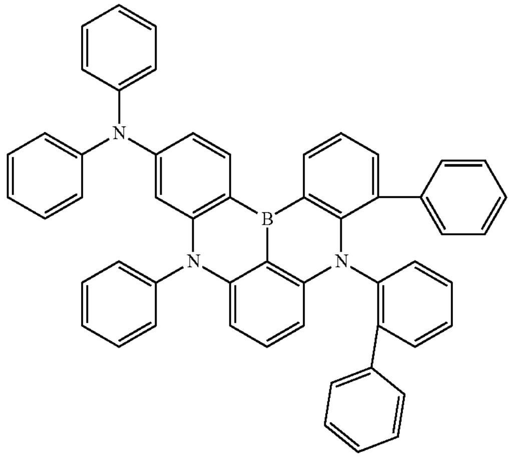
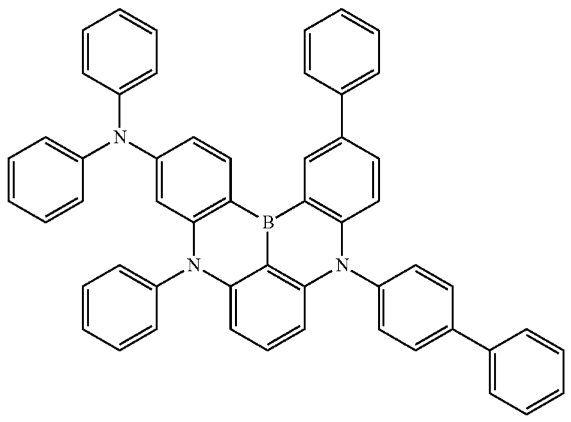

-continued
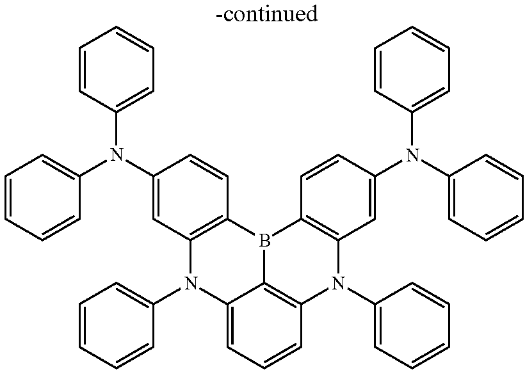
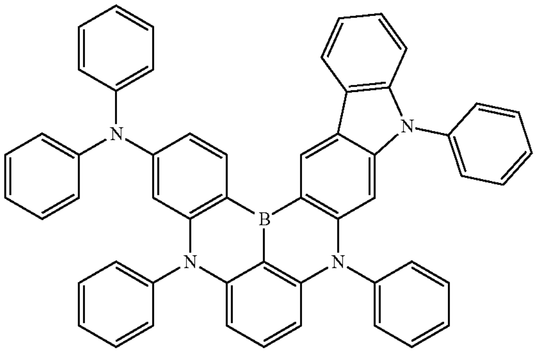
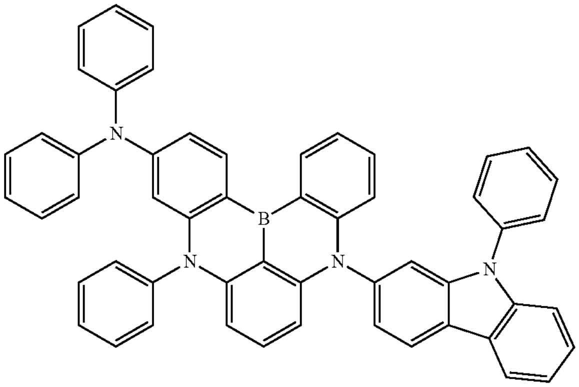
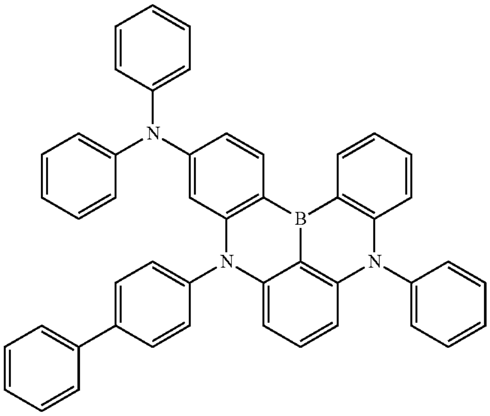
-continued
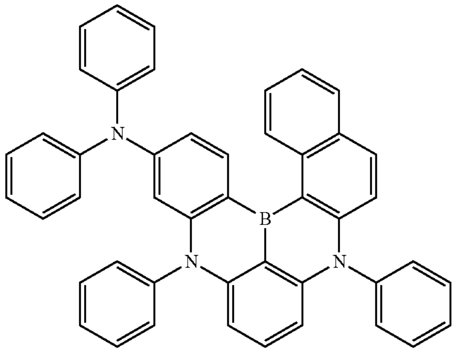
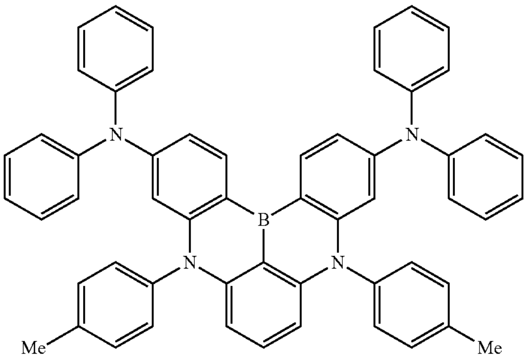
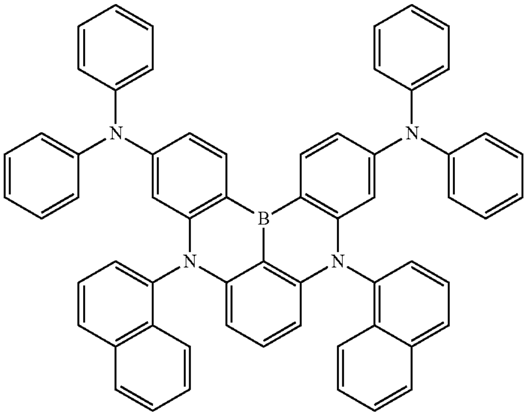
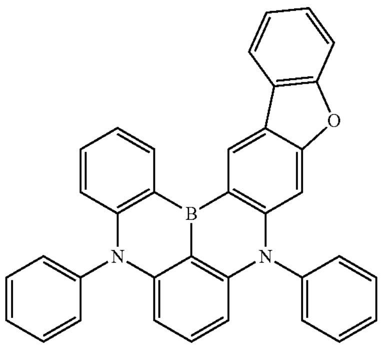

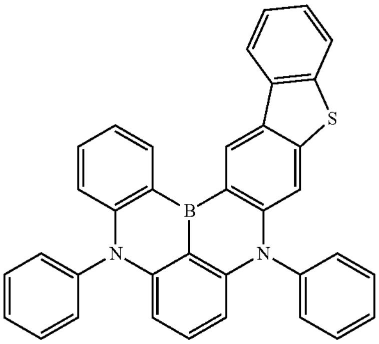
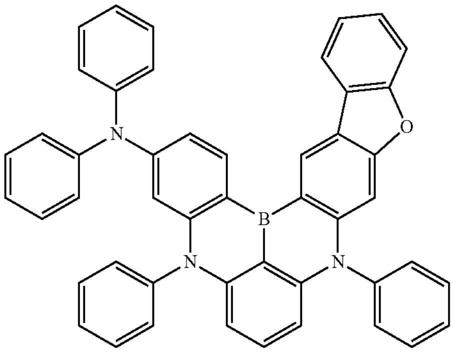
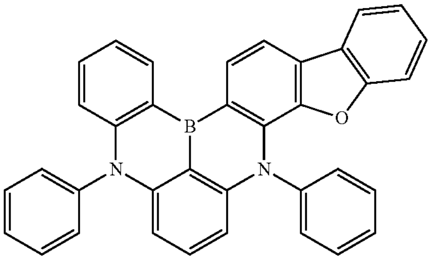
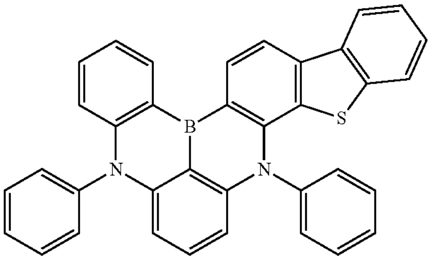
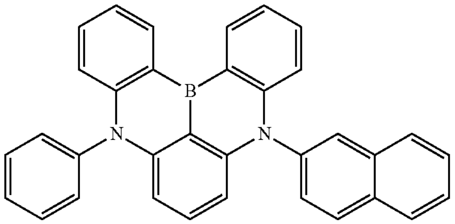
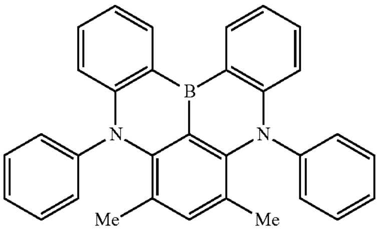
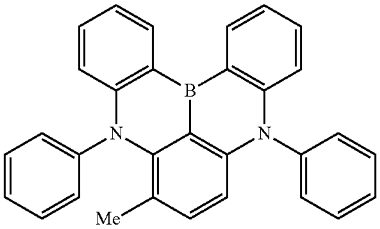
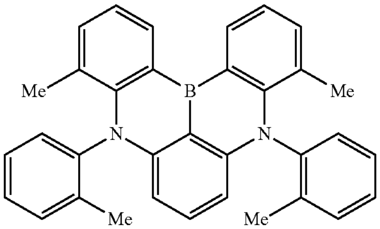
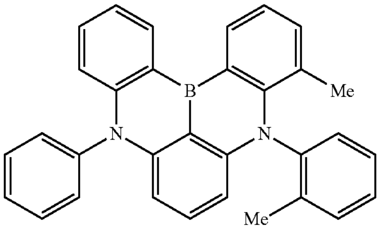
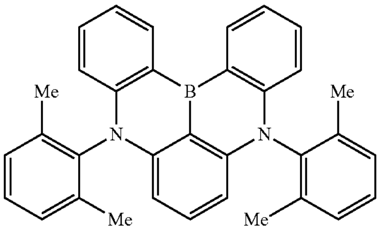
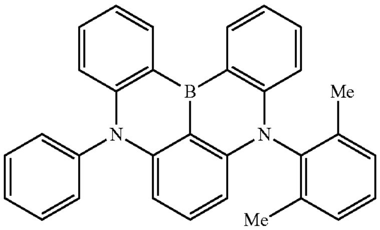
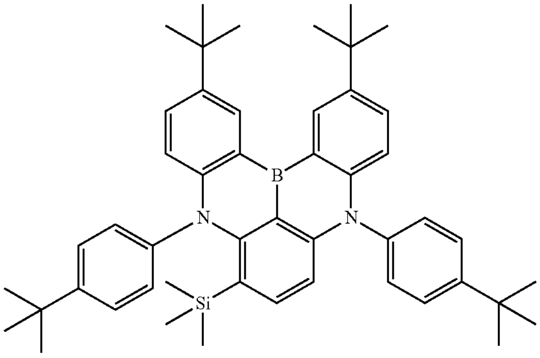

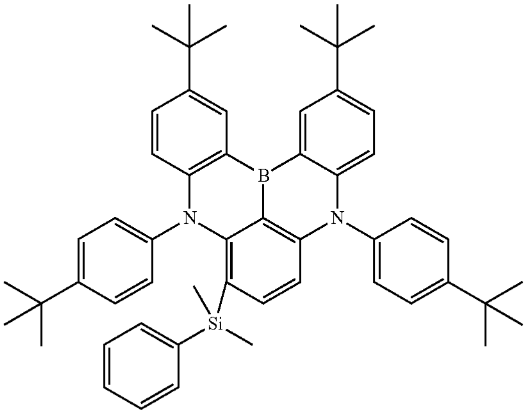
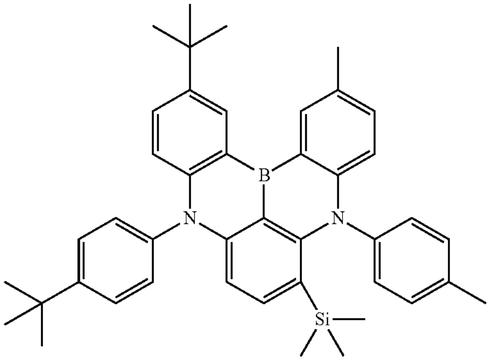
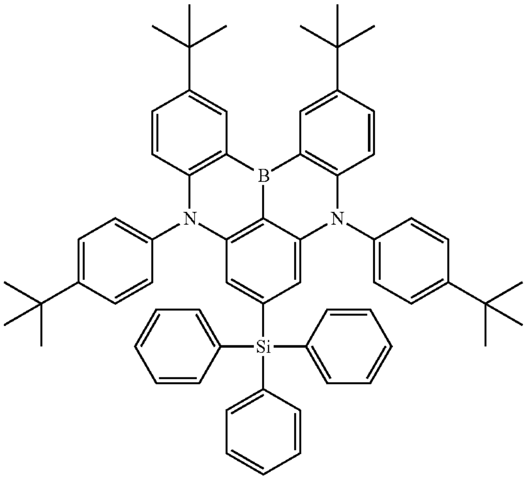
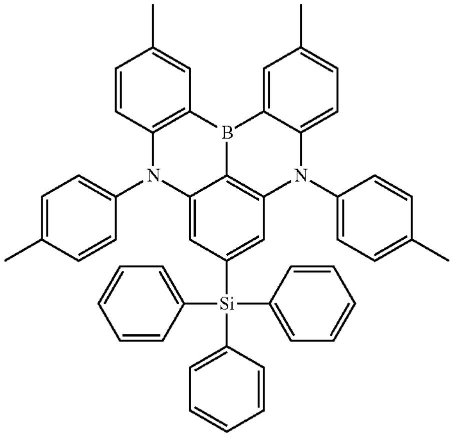
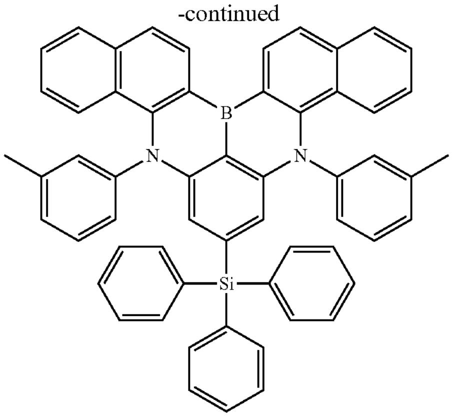
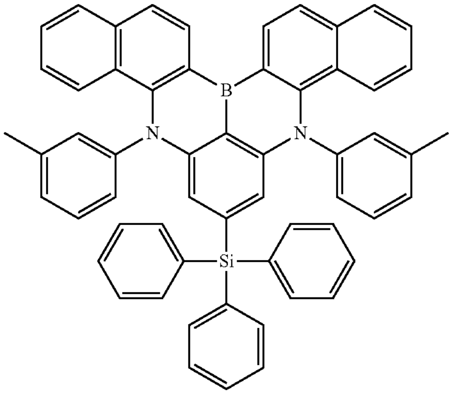
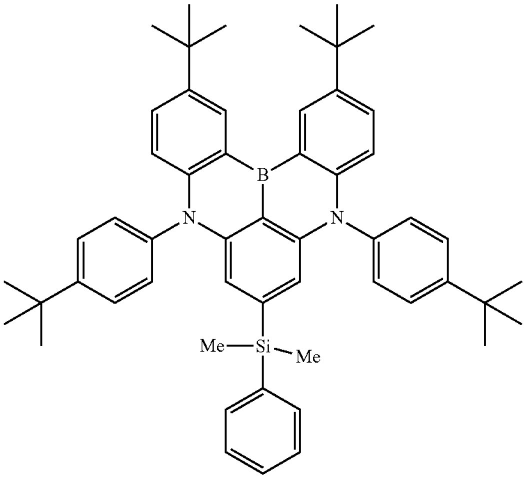
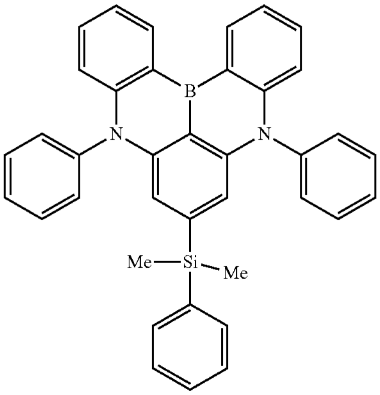

-continued
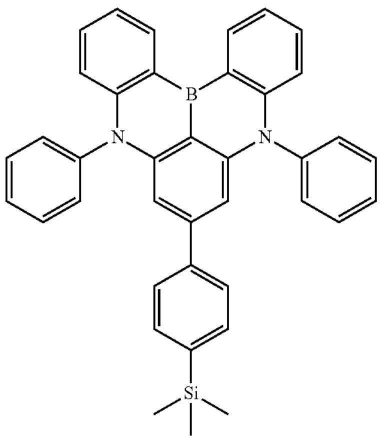
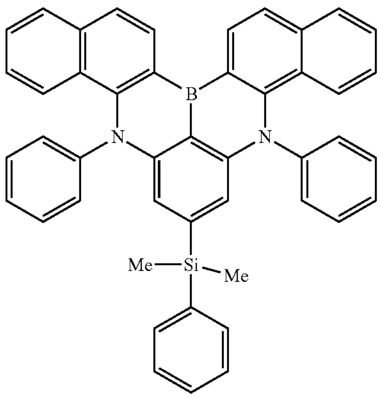
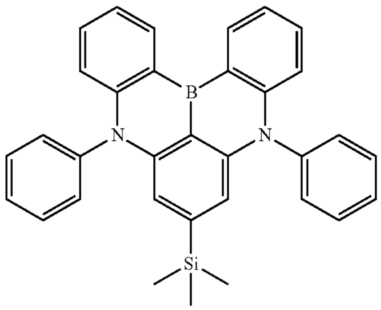
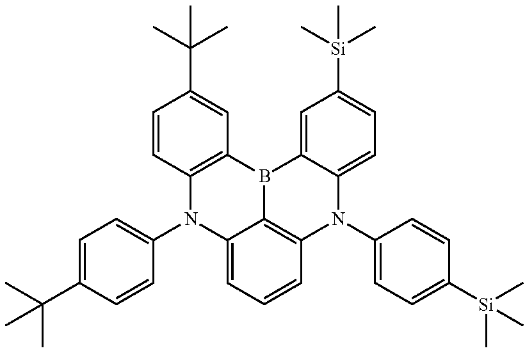
-continued
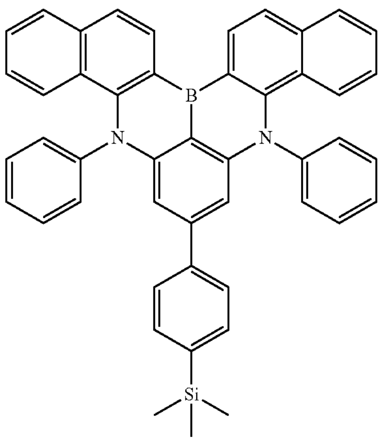
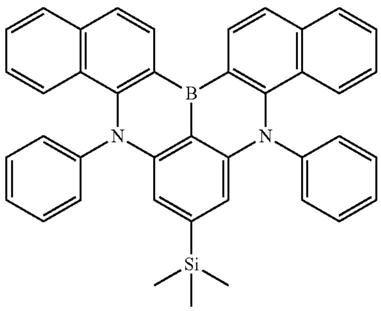
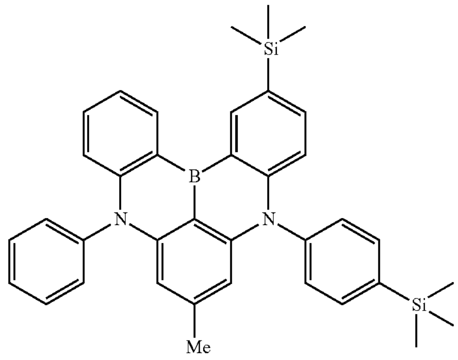
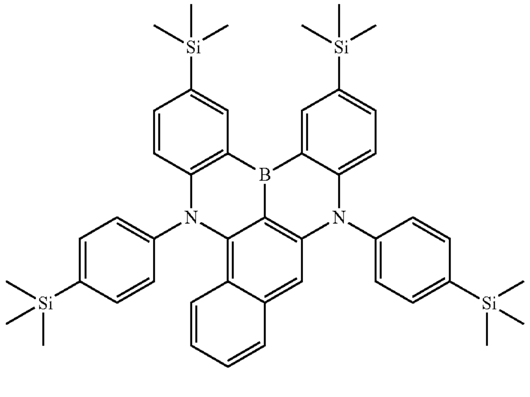

-continued
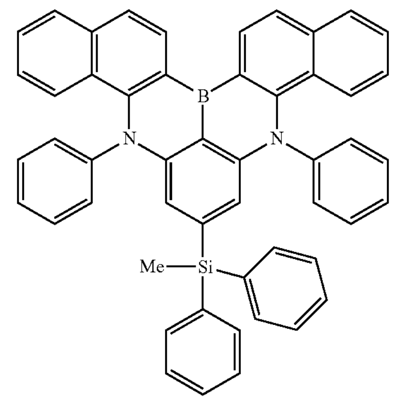
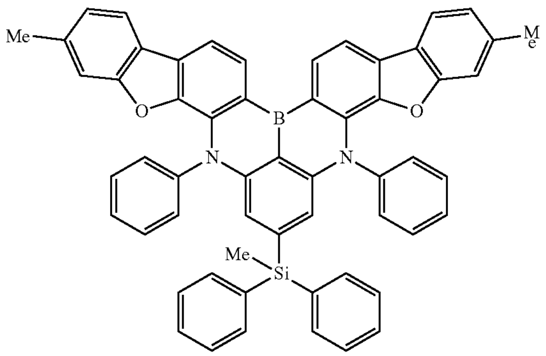
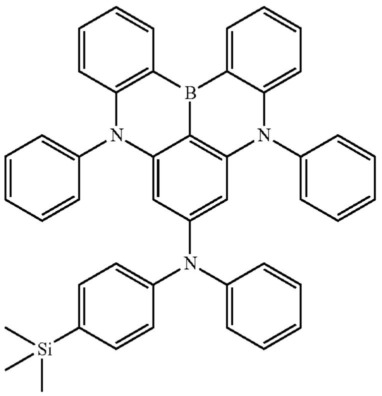
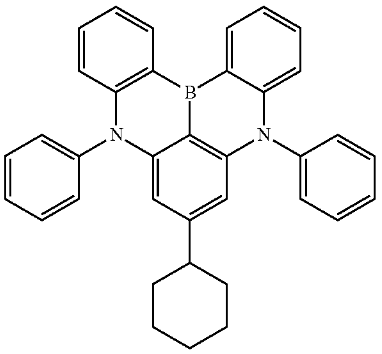
-continued
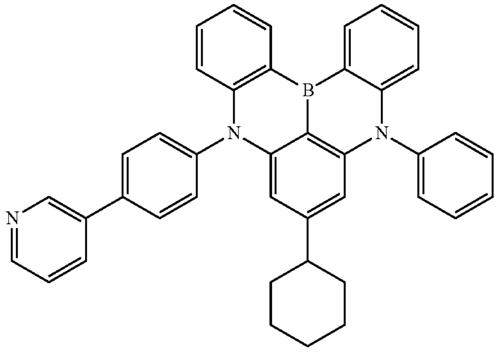
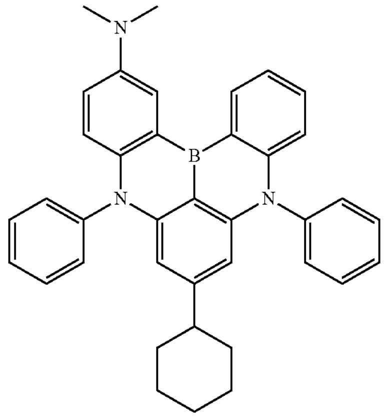
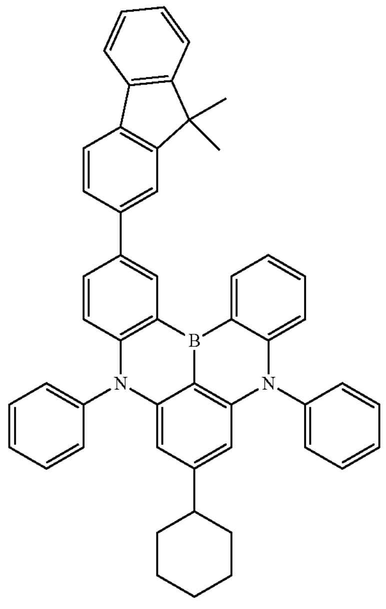

-continued
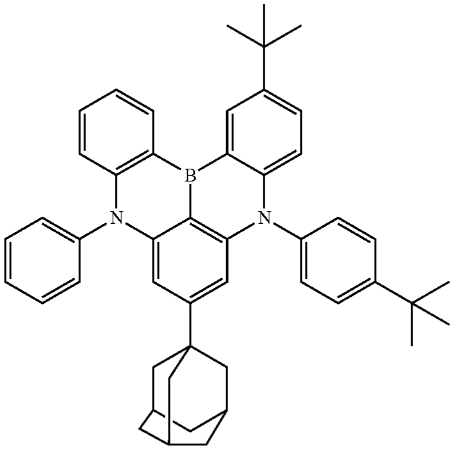
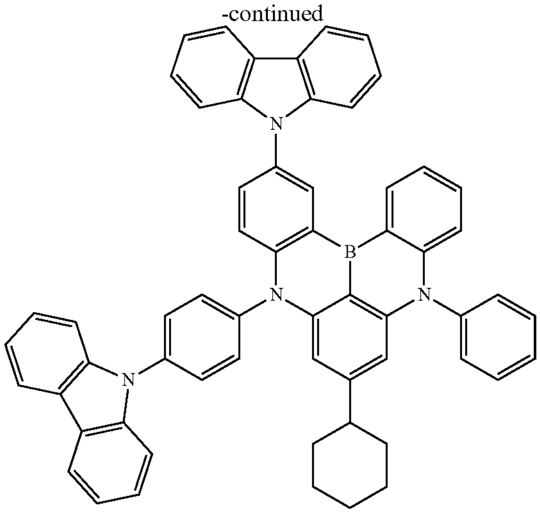
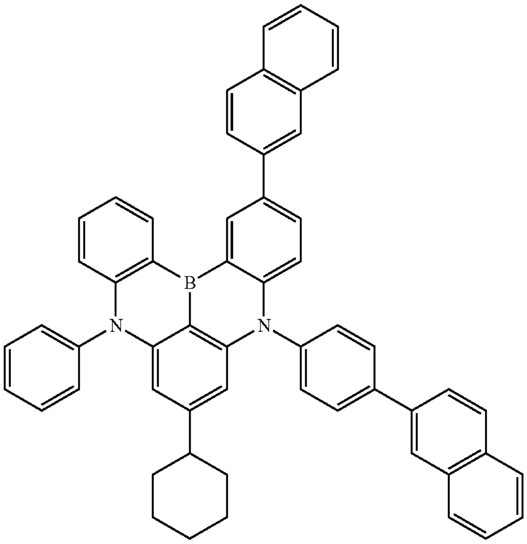
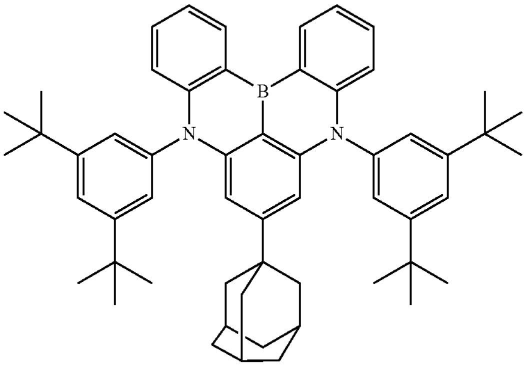
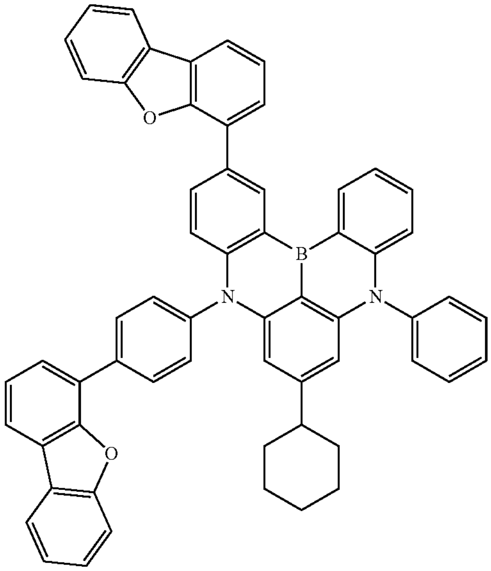
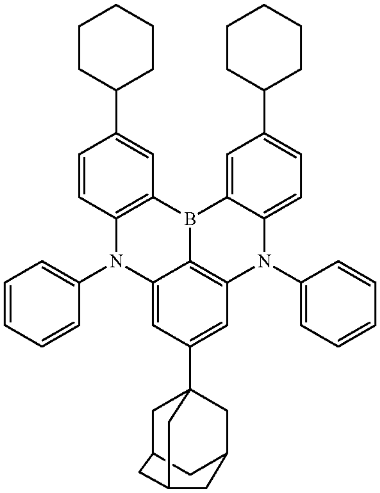
-continued -continued
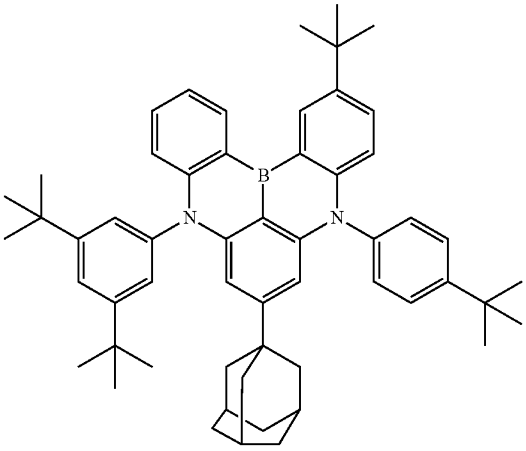
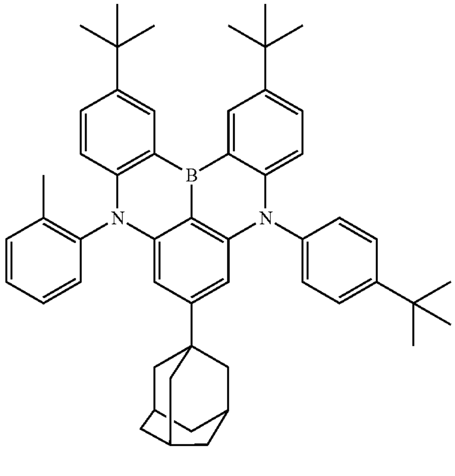
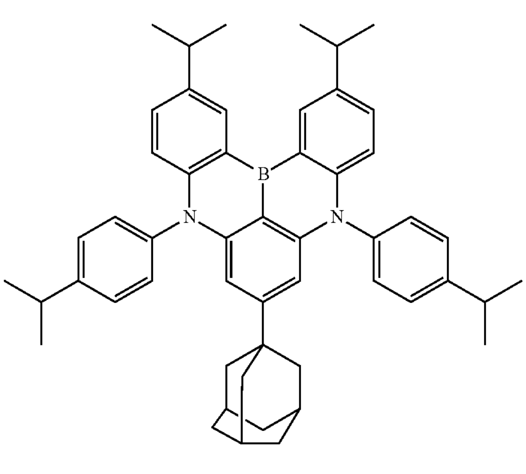
-continued
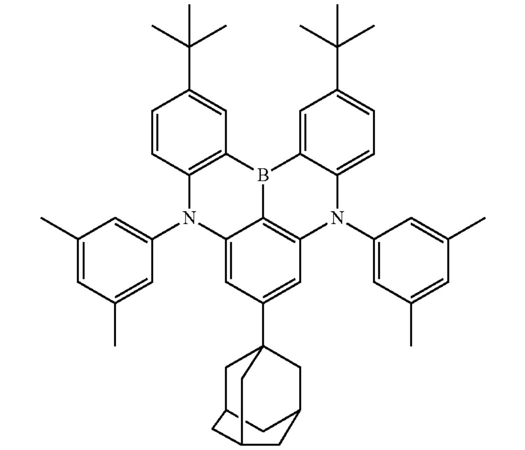
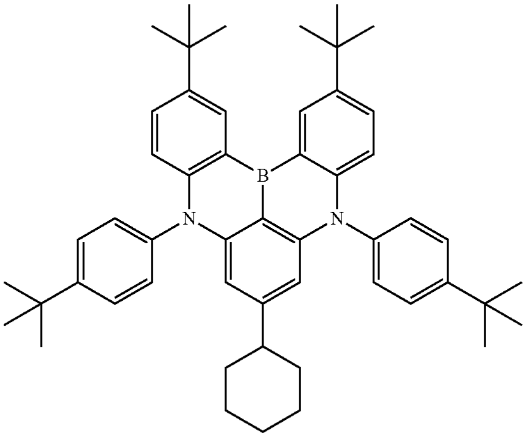
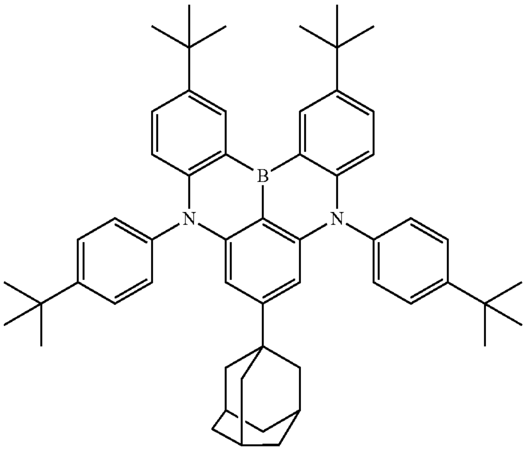

-continued
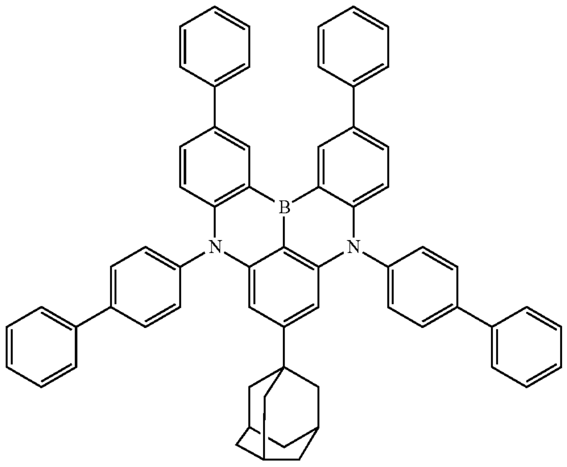
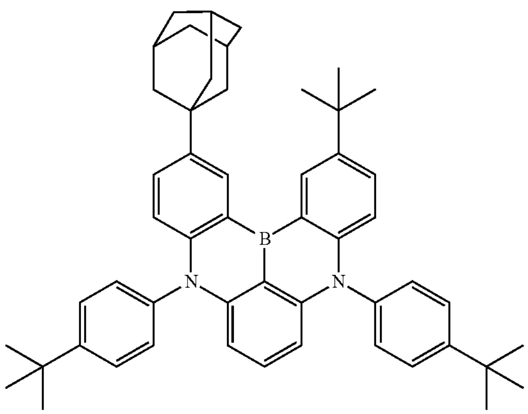
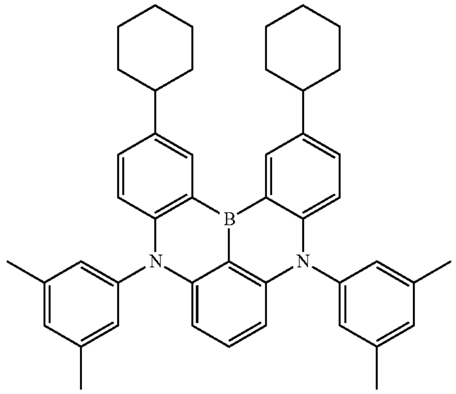
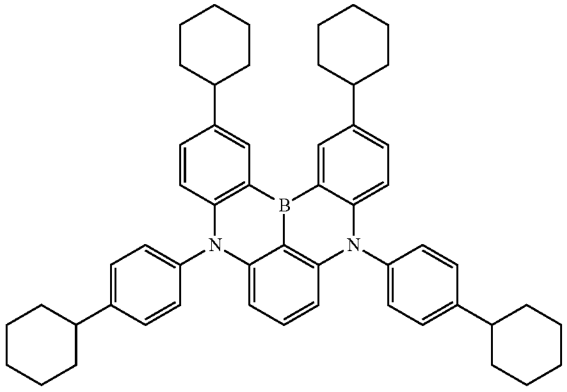
-continued
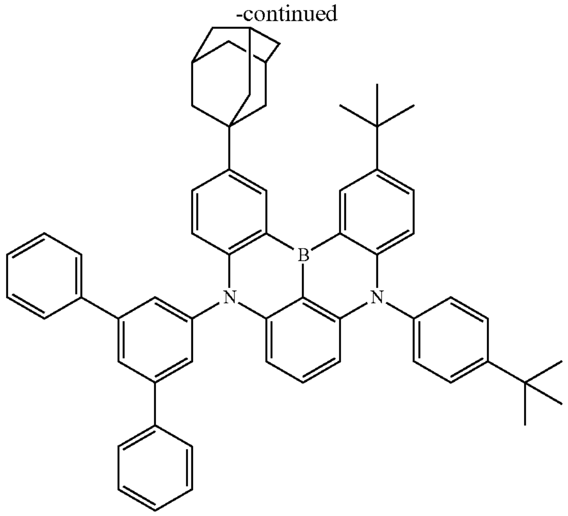
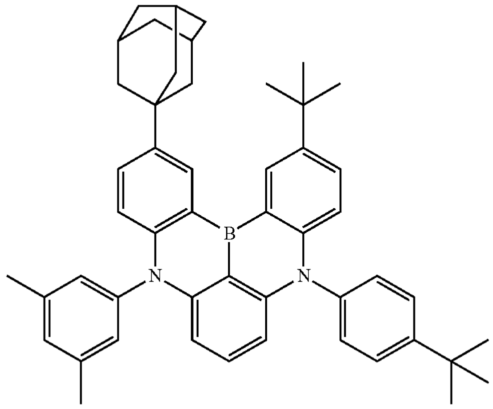
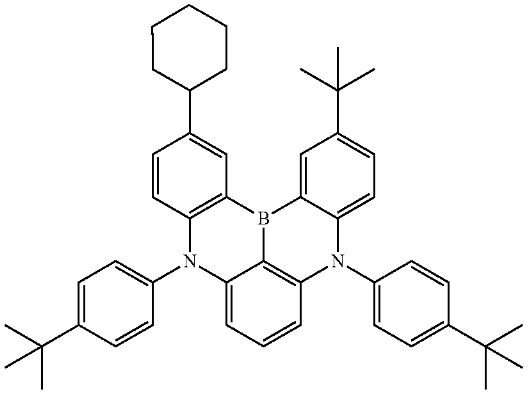
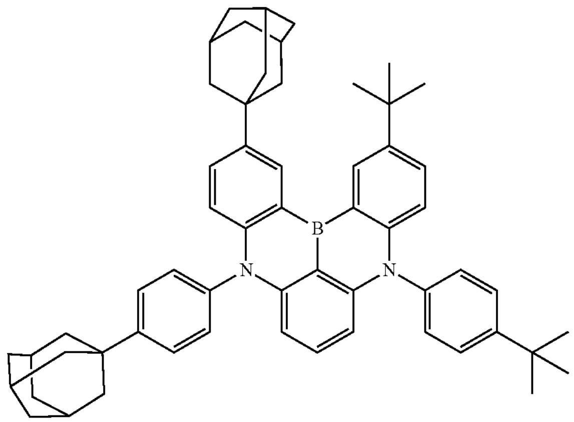

-continued
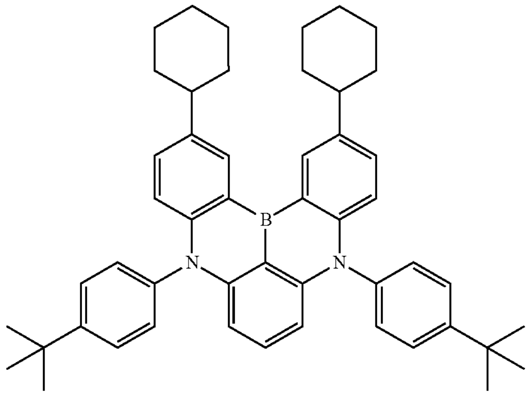
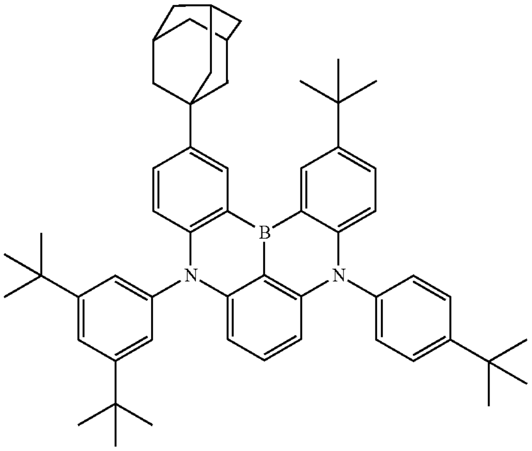
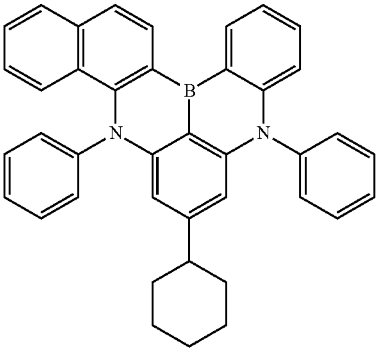
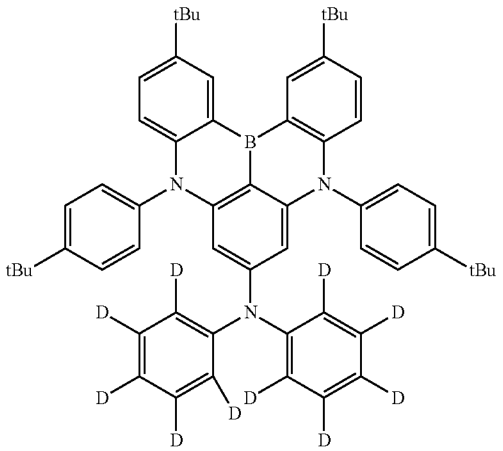
-continued
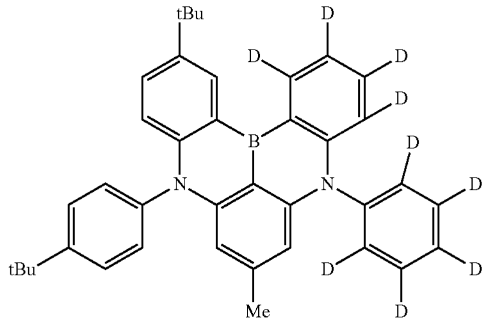
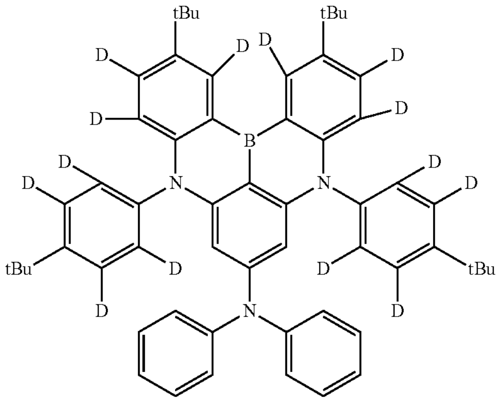
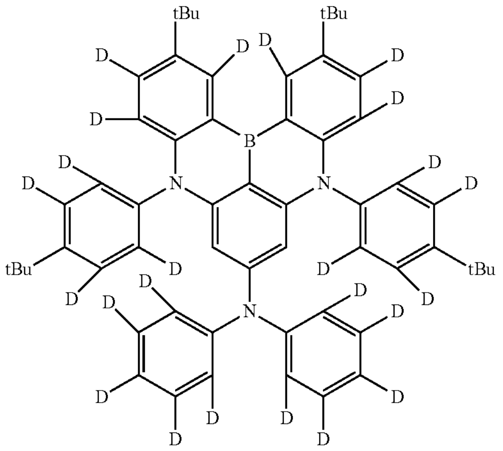
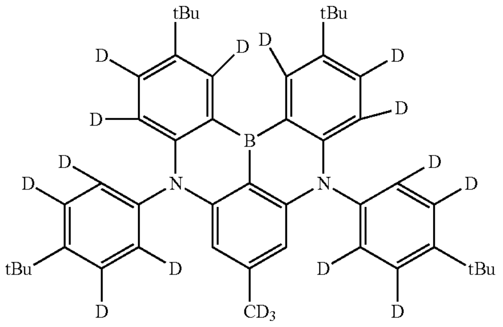

-continued

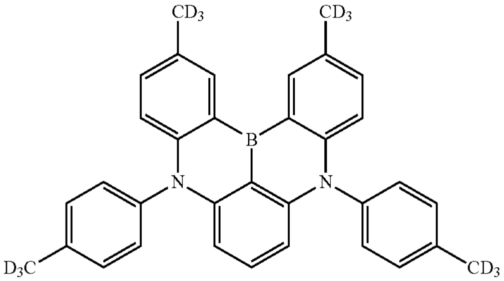

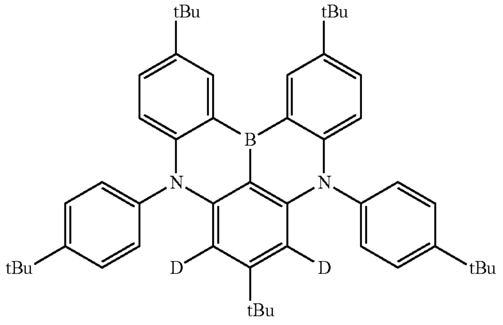

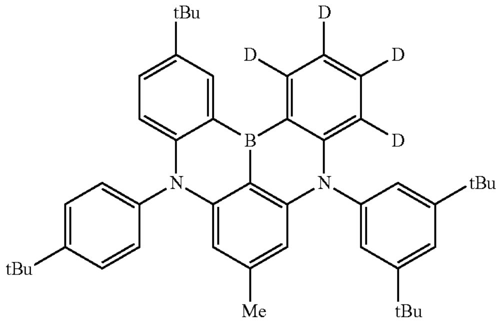

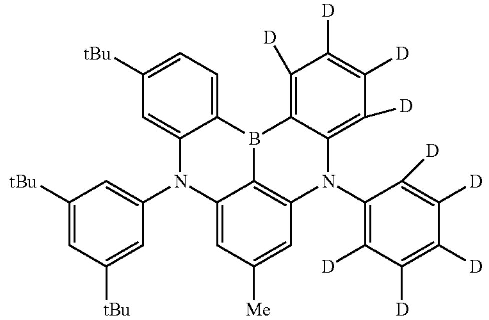

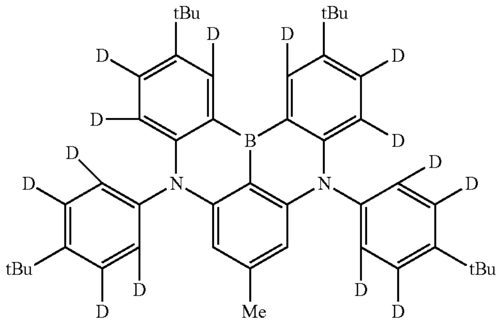

-continued

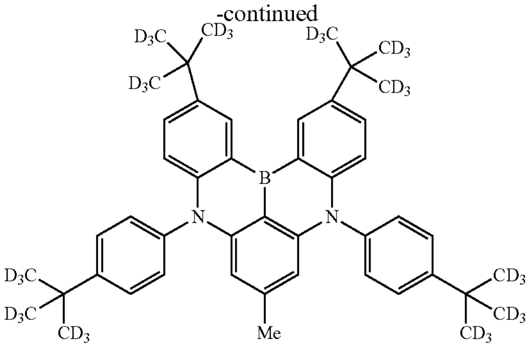

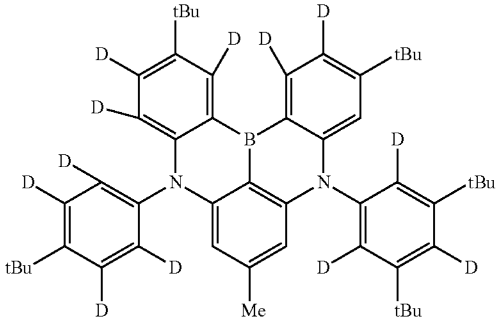

(Compound Represented by Formula (31))

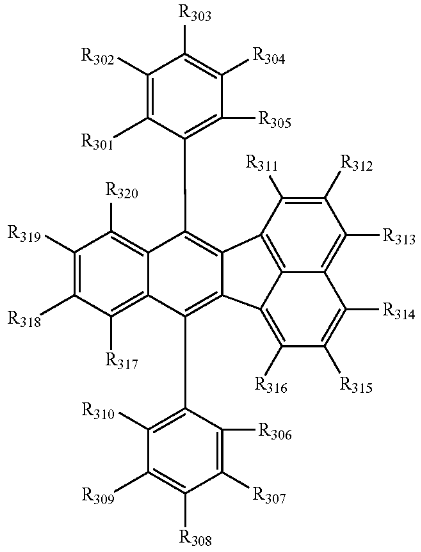

(31)

In the formula (31), any one or more sets among one or more sets of adjacent two or more of $R_{311}$ to $R_{320}$, one or more sets of adjacent two or more of $R_{301}$ to $R_{305}$, and one or more sets of adjacent two or more of $R_{30}$ to $R_{310}$ form a substituted or unsubstituted, saturated or unsaturated ring including 3 to 30 ring atoms by bonding with each other.

$R_{311}$ to $R_{320}$, $R_{301}$ to $R_{305}$, and $R_{306}$ to $R_{310}$ that do not form the substituted or unsubstituted, saturated or unsaturated ring are independently a hydrogen atom or a substituent $R_b$.

The substituent $R_b$ is a halogen atom, a cyano group, a nitro group, a carboxy group, a substituted or unsubstituted alkyl group including 1 to 50 carbon atoms, a substituted or unsubstituted alkenyl group including 2 to 50 carbon atoms, a substituted or unsubstituted alkynyl group including 2 to 50 carbon atoms, a substituted or unsubstituted cycloalkyl group including 3 to 50 ring carbon atoms, —Si $(R_{901})(R_{902})(R_{903})$,

—O—$(R_{904})$,

—S—$(R_{905})$,

—N$(R_{906})(R_{907})$, a substituted or unsubstituted aryl group including 6 to 50 ring carbon atoms, a substituted or unsubstituted monovalent heterocyclic group including 5 to 50 ring atoms, a substituted or unsubstituted phosphanyl group, a substituted or unsubstituted phosphoryl group, or a substituted or unsubstituted arylcarbonyl group including 6 to 50 ring carbon atoms.

$R_{901}$ to $R_{907}$ are as defined in the formula (1).

At least one set of adjacent two or more of $R_{311}$ to $R_{315}$, $R_{317}$ to $R_{320}$, $R_{301}$ to $R_{300}$, and $R_{305}$ to $R_{310}$ form a ring by bonding with each other.

Specific examples are described in which "one or more sets of adjacent two or more of $R_{311}$ to $R_{320}$, one or more sets of adjacent two or more of $R_{301}$ to $R_{305}$, and one or more sets of adjacent two or more of $R_{308}$ to $R_{310}$" form a substituted or unsubstituted, saturated or unsaturated ring including 3 to 30 ring atoms.

A specific example in which adjacent two or more forms a ring by bonding with each other includes the following partial structure, by taking $R_{317}$ to $R_{320}$ in the formula (31) as an example. In the following partial structure, adjacent three of $R_{318}$ and $R_{319}$ and $R_{320}$ form a ring by bonding with each other.

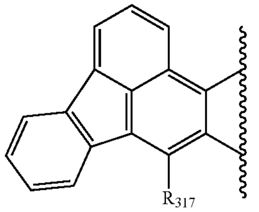

A specific example in which "one or more sets of adjacent two or more" forms a ring by bonding with each other includes the following substructure, by taking $R_{311}$ to $R_{316}$ in the formula (31) as an example. In the following partial structure, two sets of $R_{312}$ and $R_{313}$, and $R_{314}$ and $R_{315}$ form two separate rings by bonding with each other.

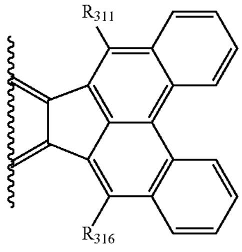

In one embodiment, $R_{312}$ and $R_{313}$ in the formula (31) are bonded together to form a substituted or unsubstituted, saturated or unsaturated ring including 3 to 30 ring atoms.

In one embodiment, $R_{312}$ and $R_{313}$ in the formula (31) form a substituted or unsubstituted, saturated or unsaturated ring including 3 to 30 ring atoms by bonding with each other.

In one embodiment, the compound represented by the formula (31) is a compound represented by the following formula (31-1).

(31-1)

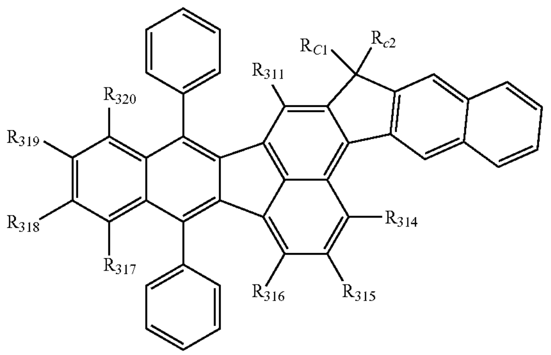

In the formula (31-1), $R_{311}$ and $R_{314}$ to $R_{320}$ are as defined in the formula (31).

$R_{c1}$ and $R_{c2}$ are independently a hydrogen atom, an unsubstituted alkyl group including 1 to 50 carbon atoms, an unsubstituted alkenyl group including 2 to 50 carbon atoms, an unsubstituted alkynyl group including 2 to 50 carbon atoms, an unsubstituted cycloalkyl group including 3 to 50 ring carbon atoms, —Si$(R_{901})(R_{902})(R_{903})$,

—O—$(R_{904})$,

—S—$(R_{905})$,

—N$(R_{906})(R_{907})$, a halogen atom, a cyano group, a nitro group, an unsubstituted aryl group including 6 to 50 ring carbon atoms, or an unsubstituted monovalent heterocyclic group including 5 to 50 ring atoms;

$R_{901}$ to $R_{907}$ are independently a hydrogen atom, a substituted or unsubstituted alkyl group including 1 to 50 carbon atoms, a substituted or unsubstituted cycloalkyl group including 3 to 50 ring carbon atoms, a substituted or unsubstituted aryl group including 6 to 50 ring carbon atoms, or a substituted or unsubstituted monovalent heterocyclic group including 5 to 50 ring atoms. When two or more of each of $R_{901}$ to $R_{907}$ are present, the two or more of each of $R_{901}$ to $R_{907}$ are the same as or different from each other.

In one embodiment, two or more of $R_{318}$ to $R_{320}$ in the formula (31) form a substituted or unsubstituted, saturated or unsaturated ring including 3 to 30 ring atoms by bonding with each other.

In one embodiment, the compound represented by the formula (31) is a compound represented by the following formula (31-2).

(31-2)

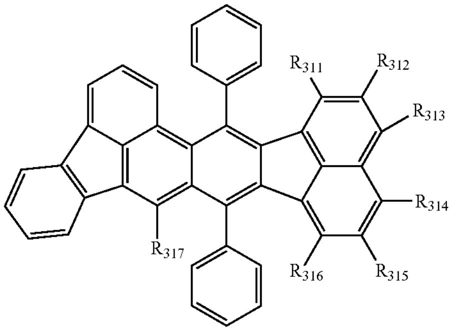

In the formula (31-2), $R_{311}$ to $R_{317}$ are as defined in the formula (31).

In one embodiment, $R_{311}$ to $R_{320}$, $R_{301}$ to $R_{305}$, and $R_{305}$ to $R_{310}$ that are not involved in the ring formation in the formula (31) are independently a hydrogen atom, an unsubstituted aryl group including 6 to 50 ring carbon atoms, or an unsubstituted monovalent heterocyclic group including 5 to 50 ring atoms.

Specific examples of the compound represented by the formula (31) will be described below, but these are merely examples, and the compound represented by the formula (31) is not limited to the following specific examples.

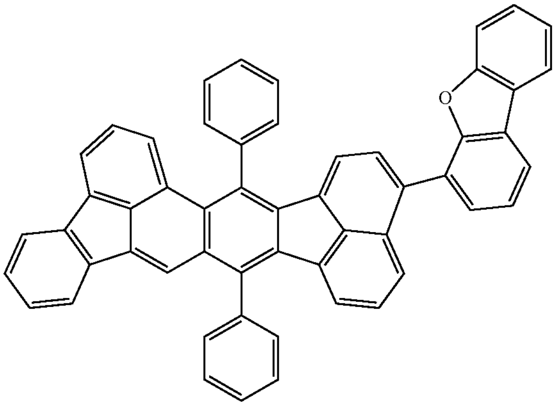

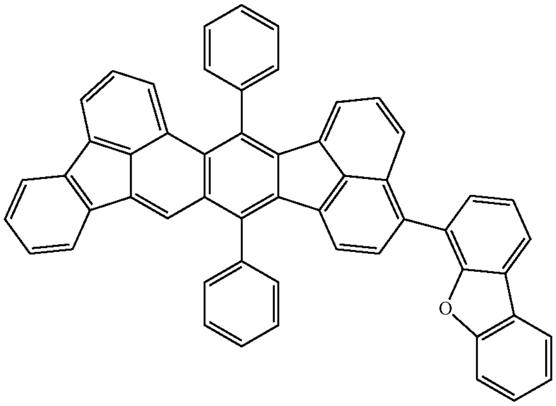

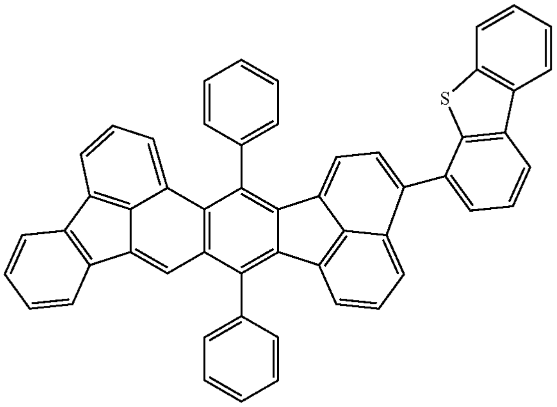

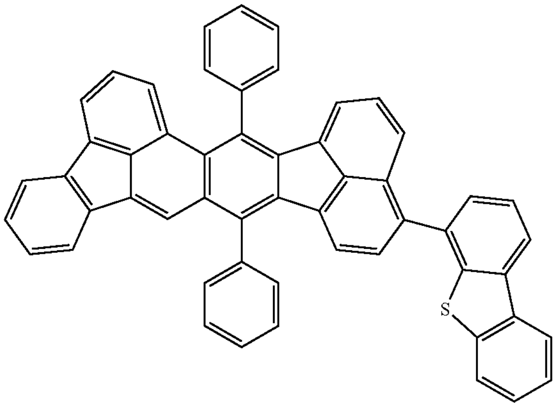

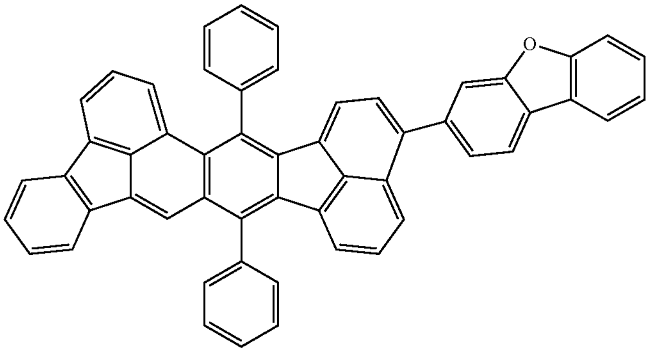

-continued
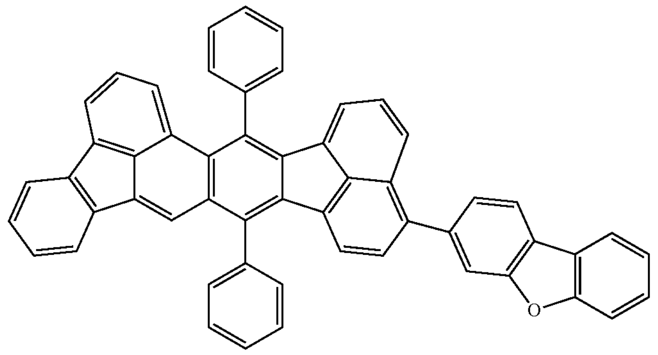
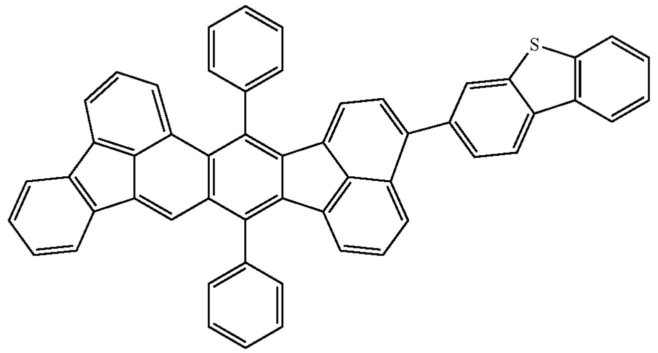
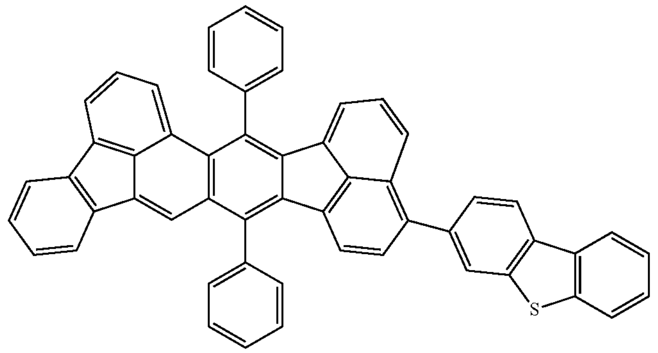
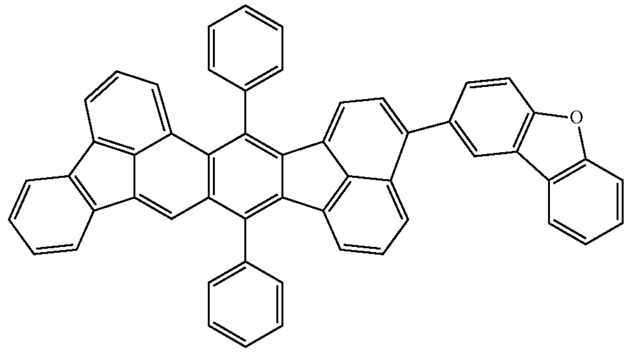

-continued
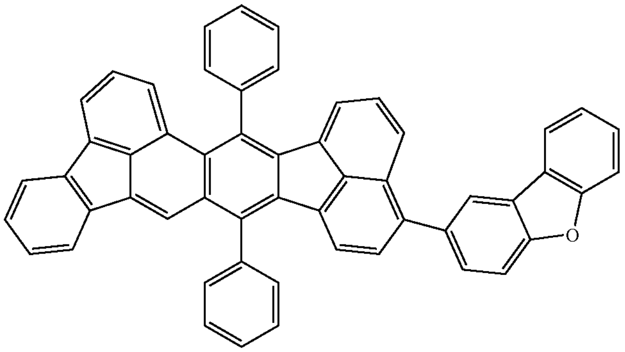
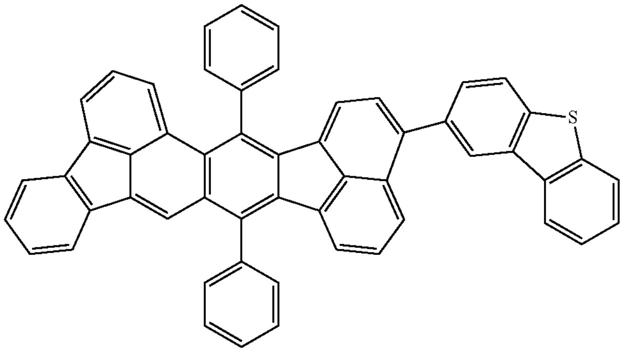
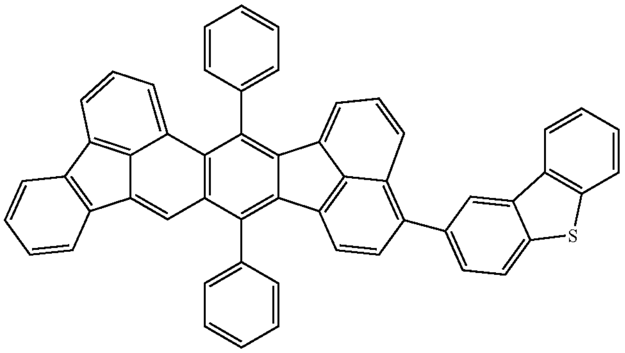
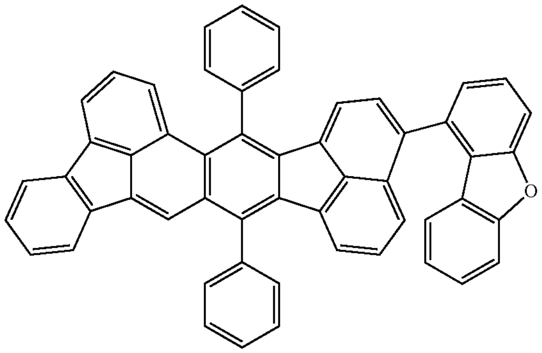
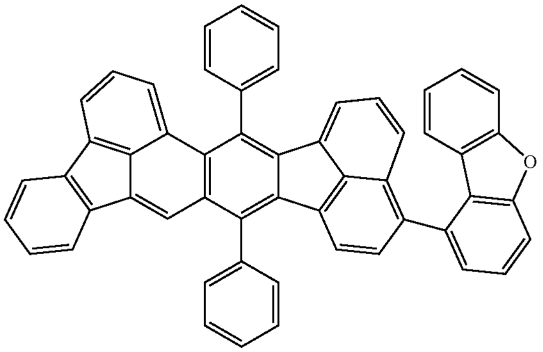
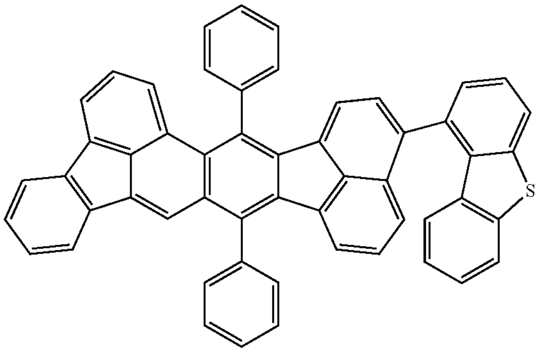

-continued
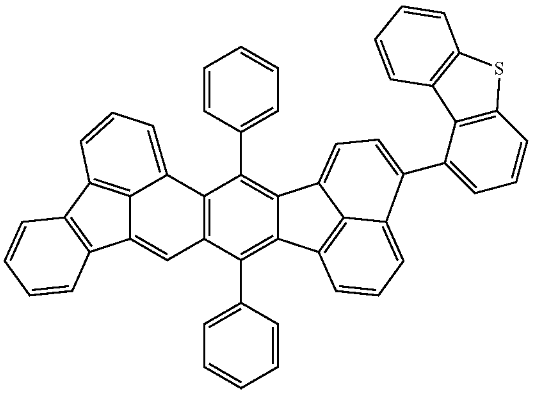
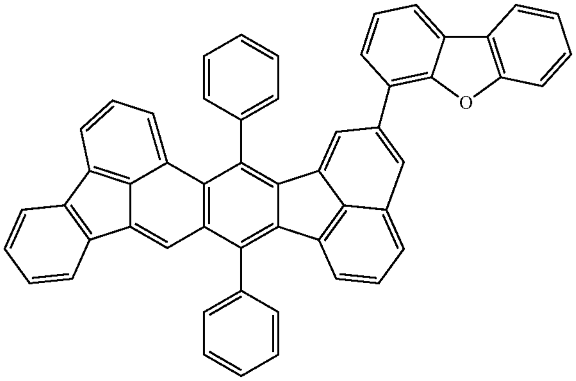
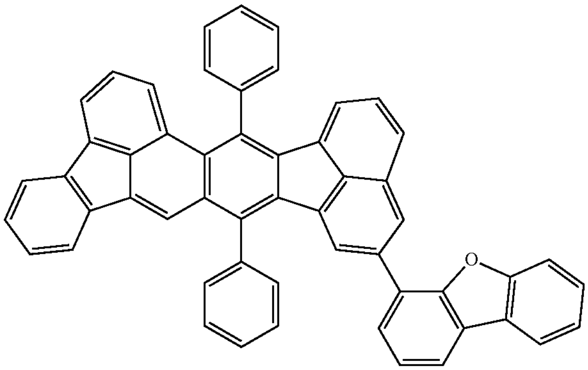
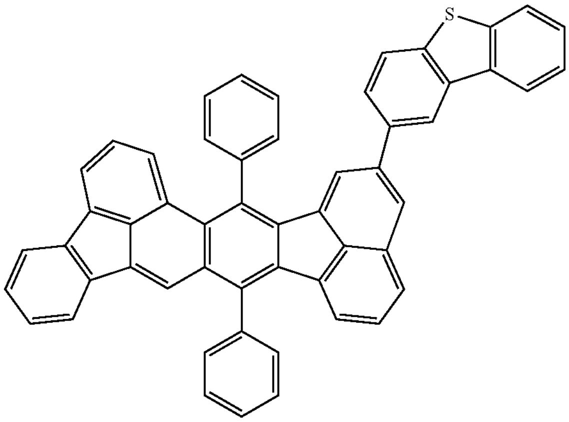
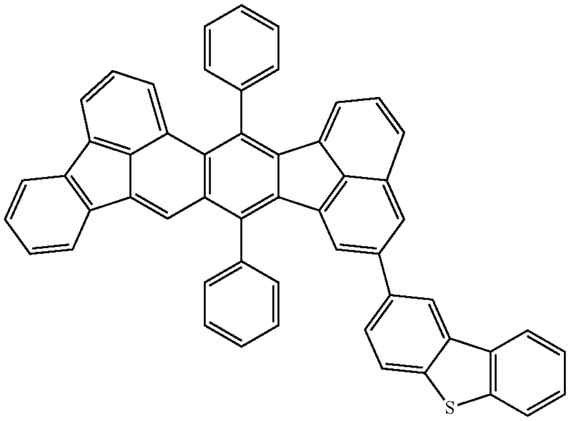
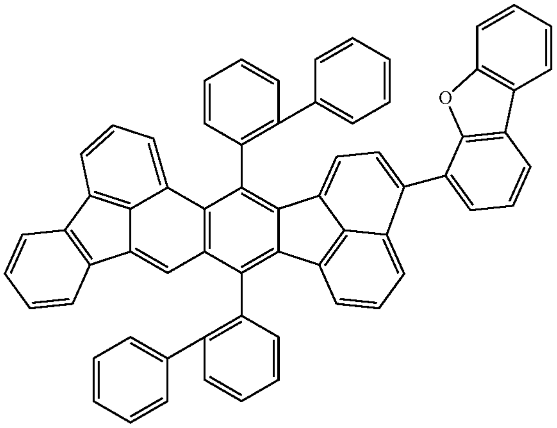
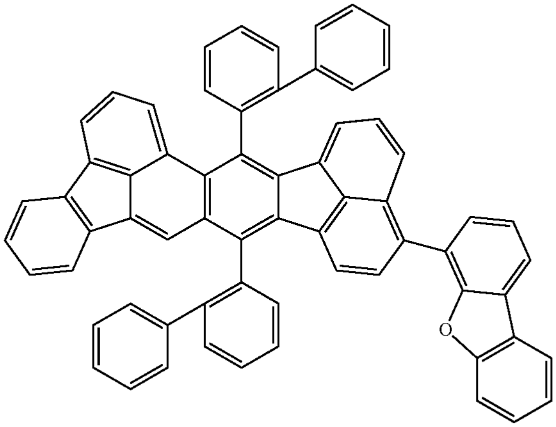

-continued
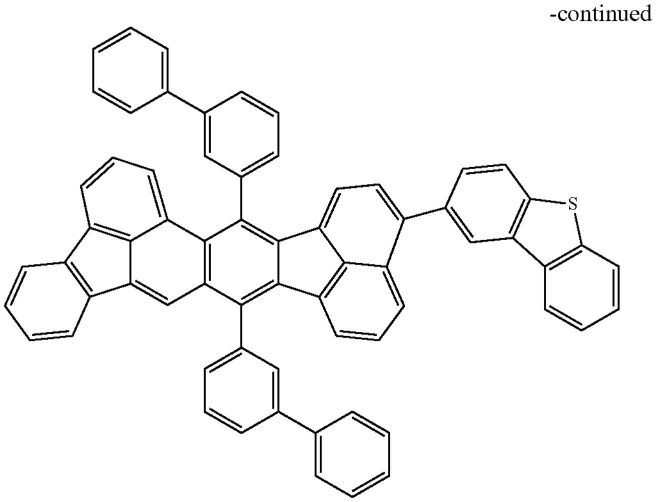
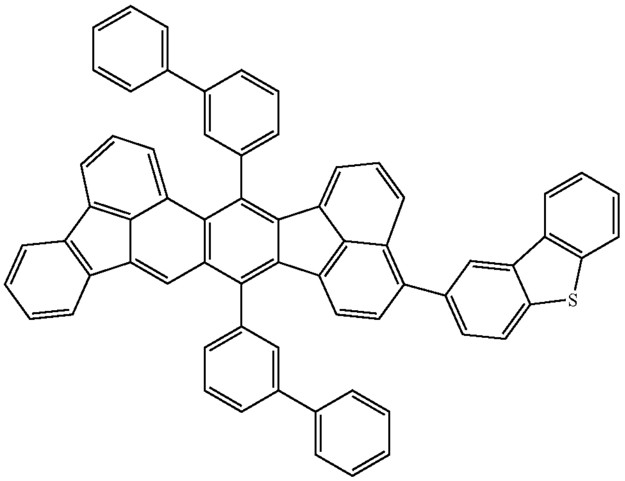
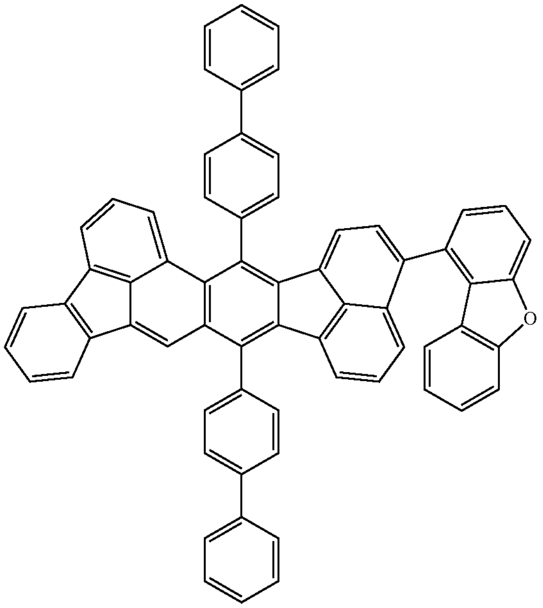
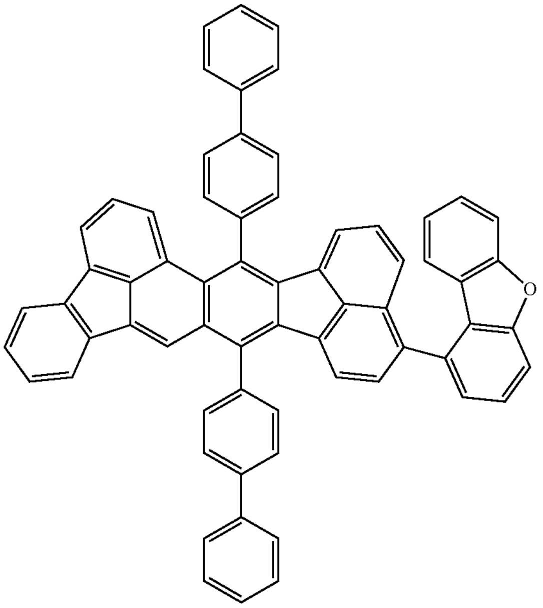

-continued
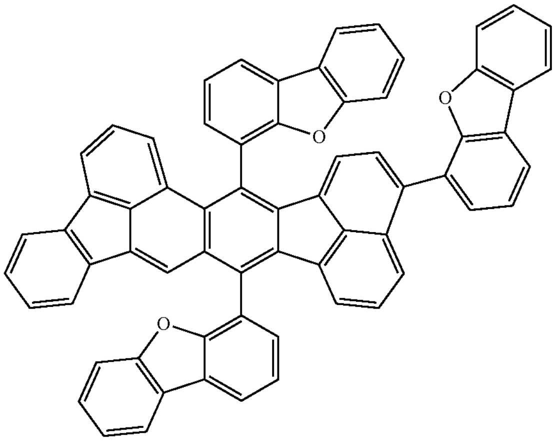
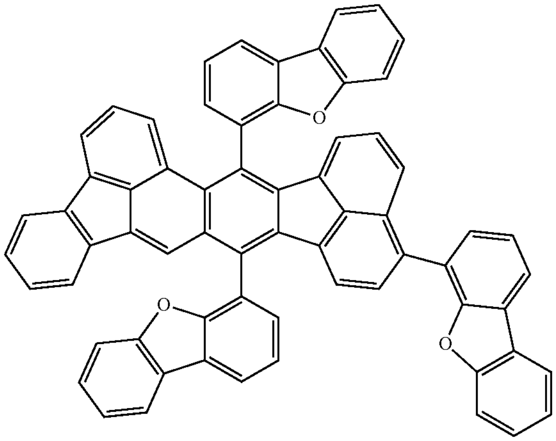
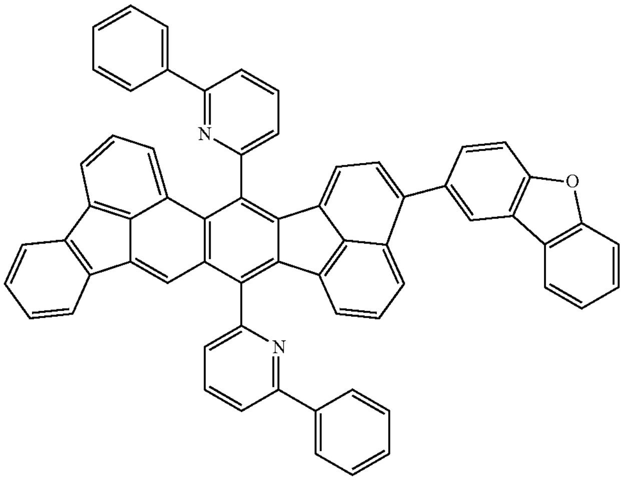
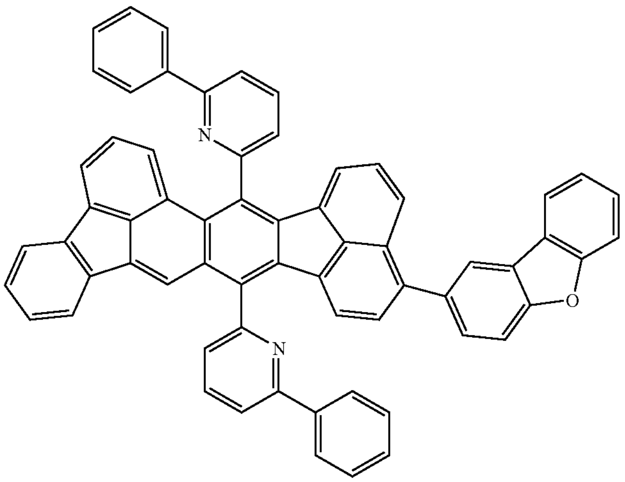

-continued
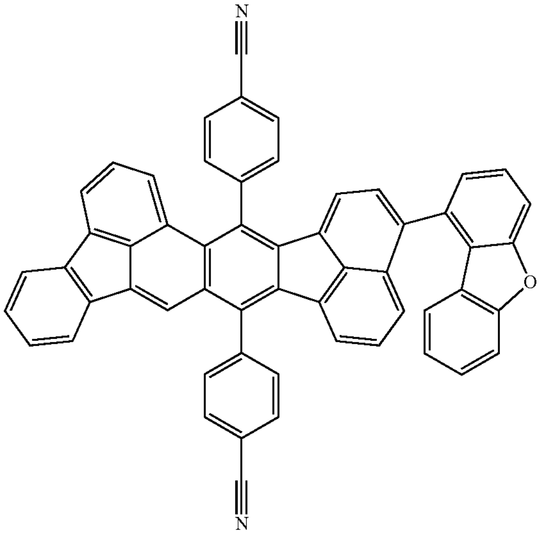
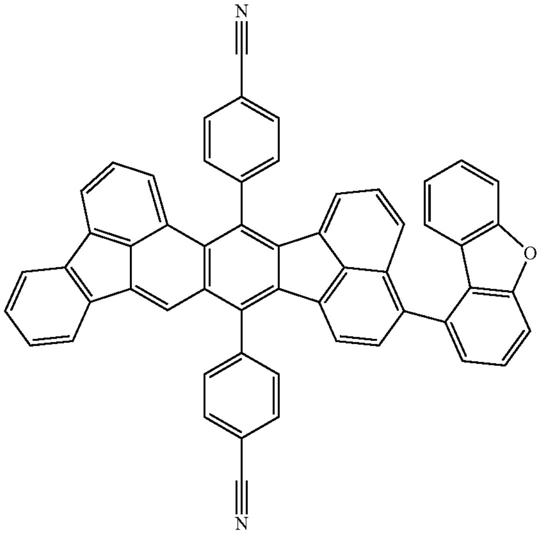
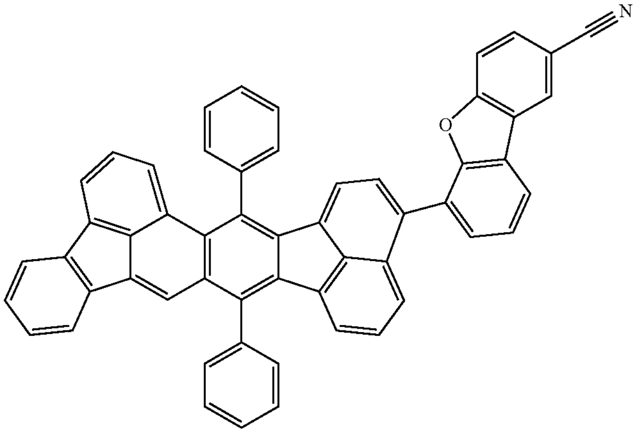
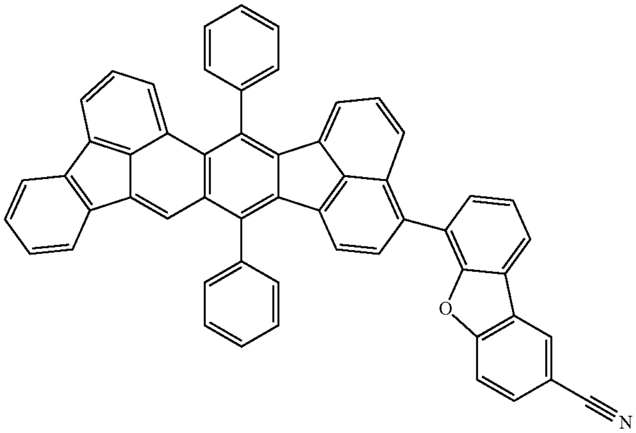

-continued
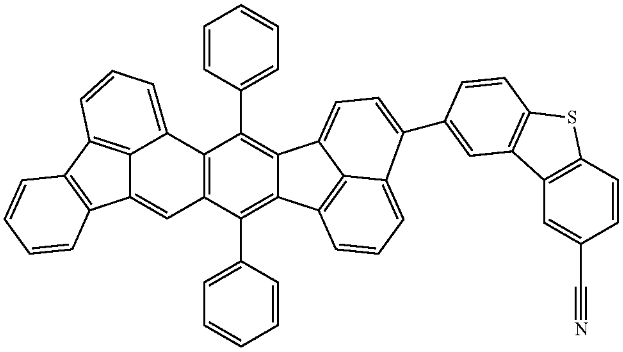
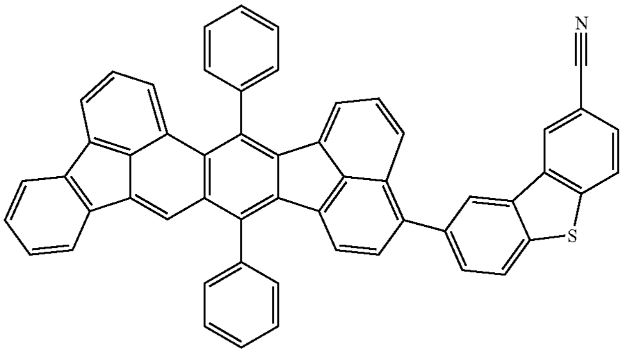
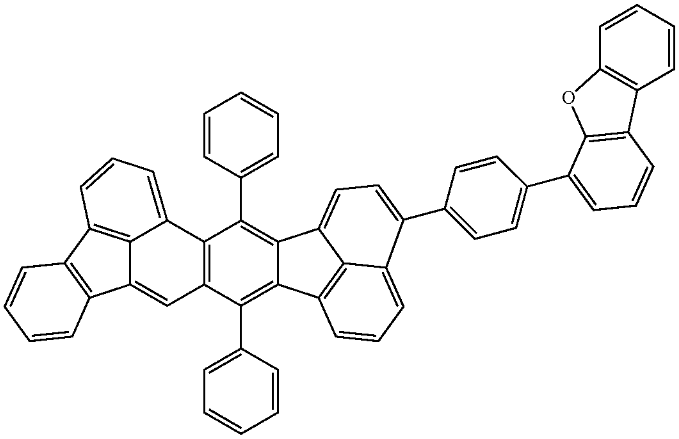
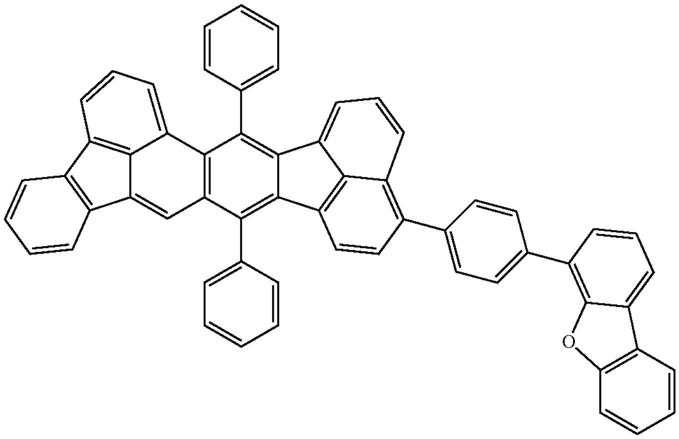

-continued
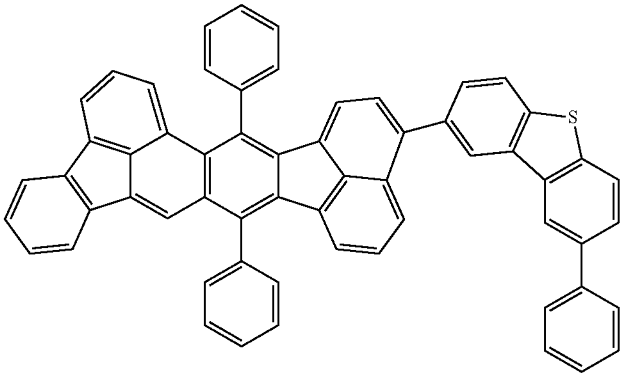
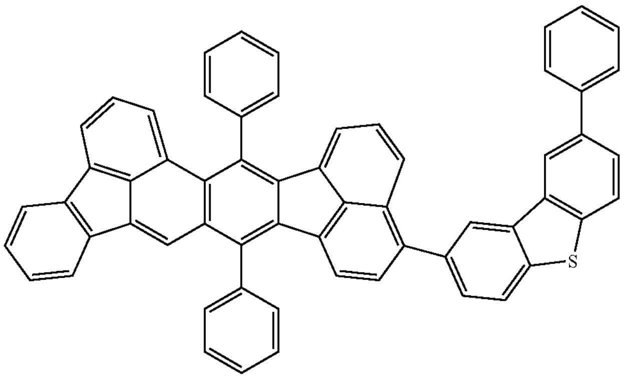
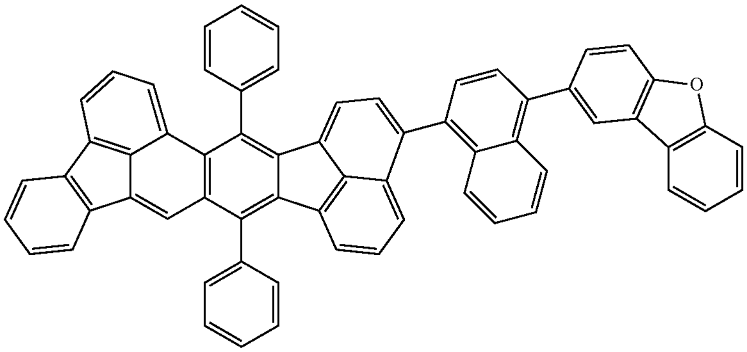
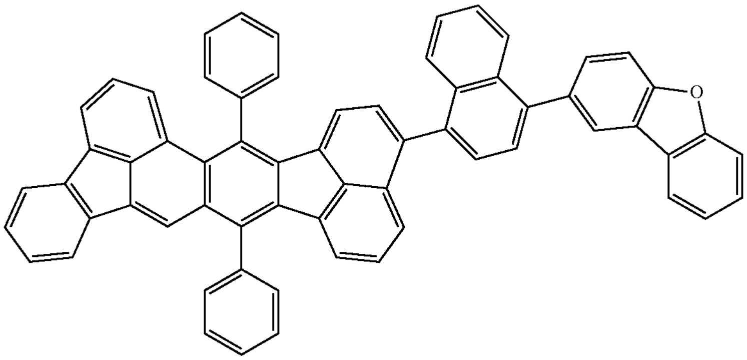

-continued
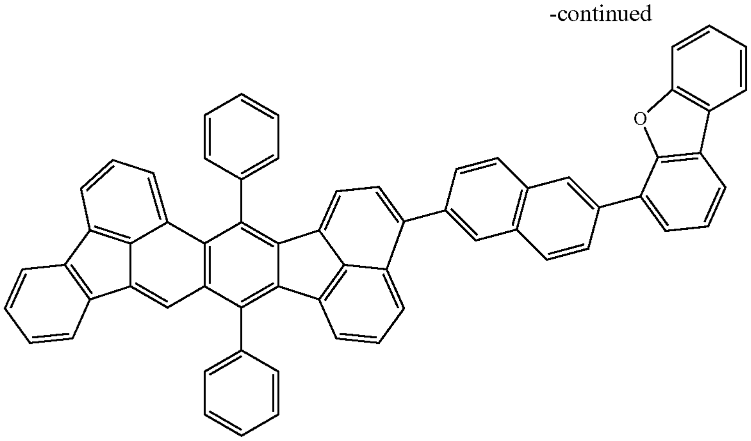
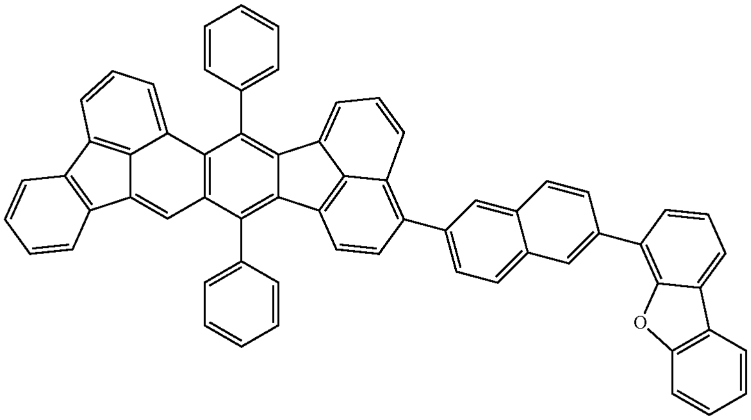
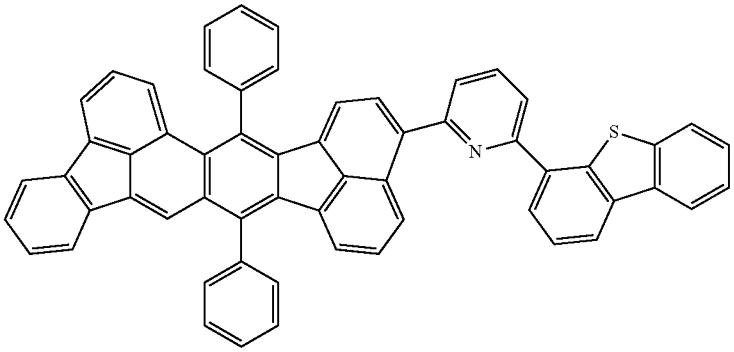
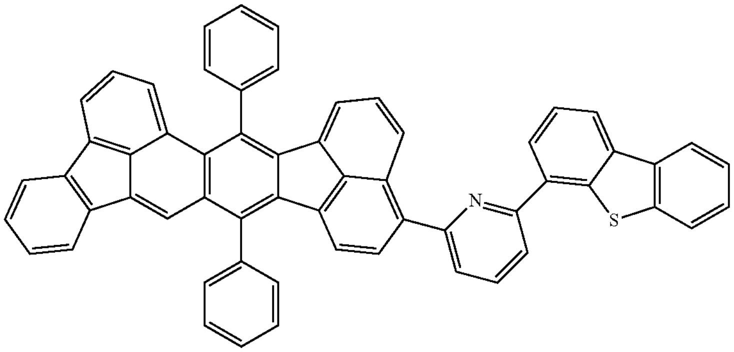

-continued
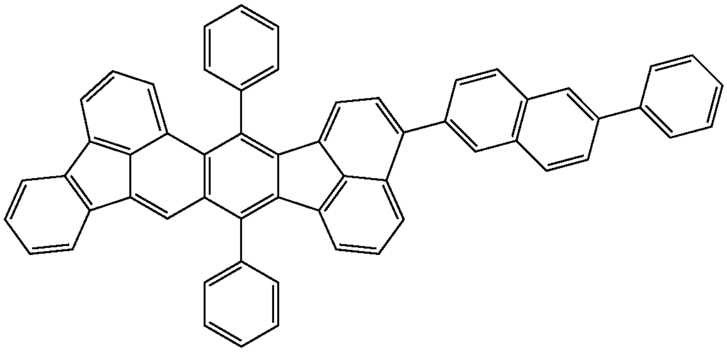
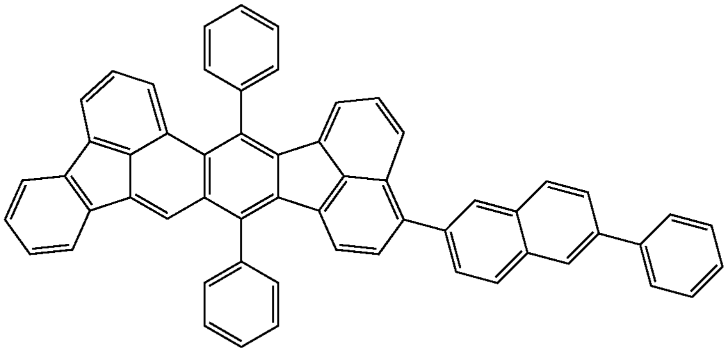
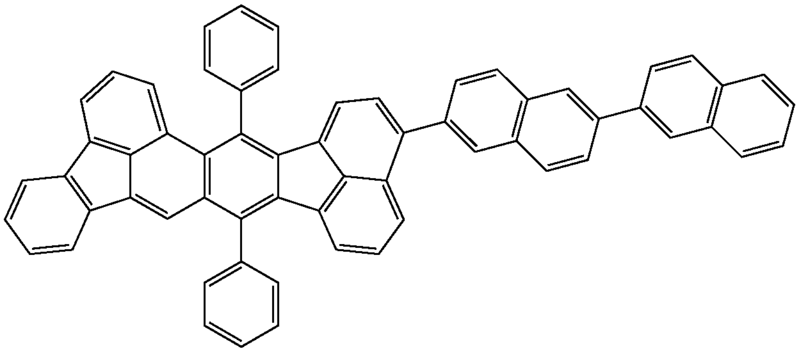
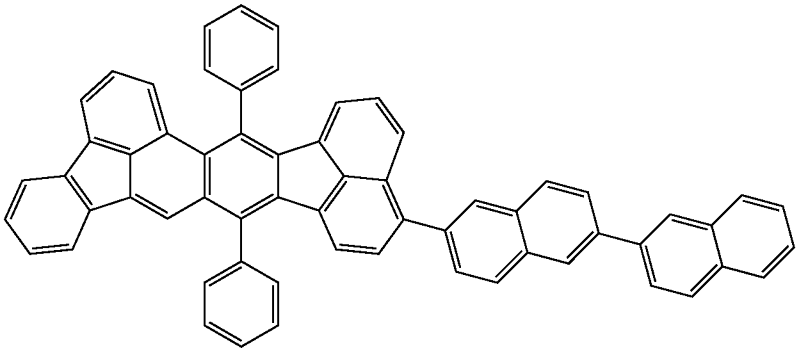

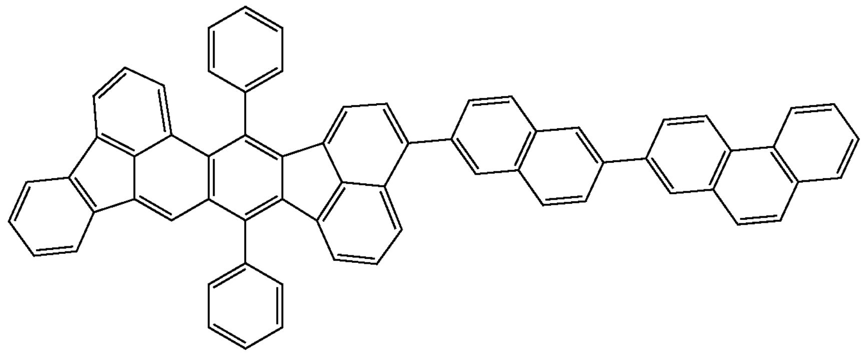
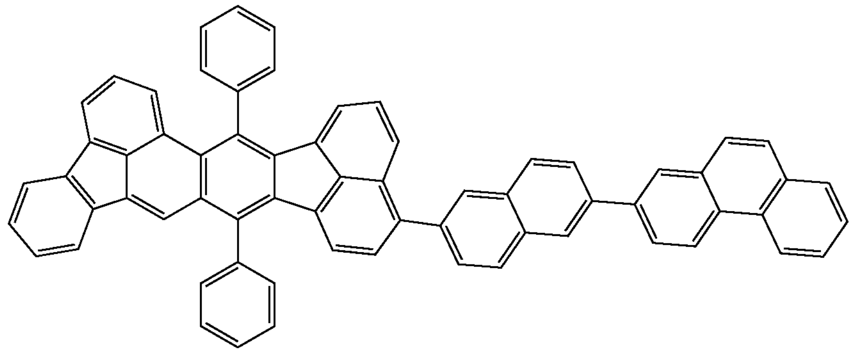
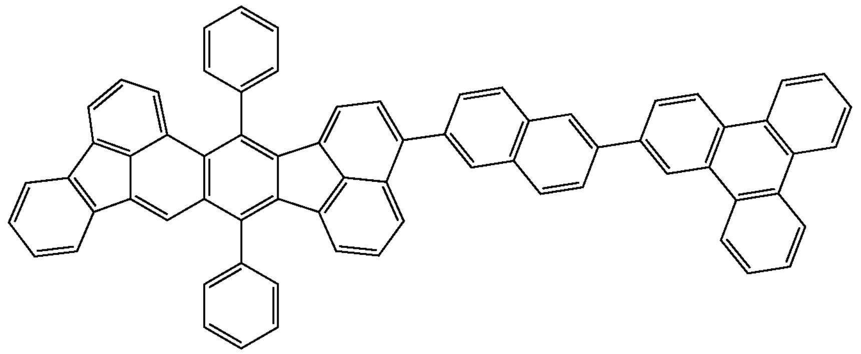
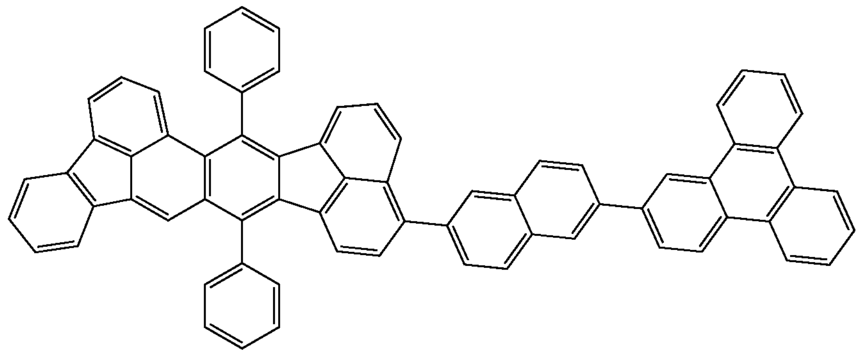

-continued
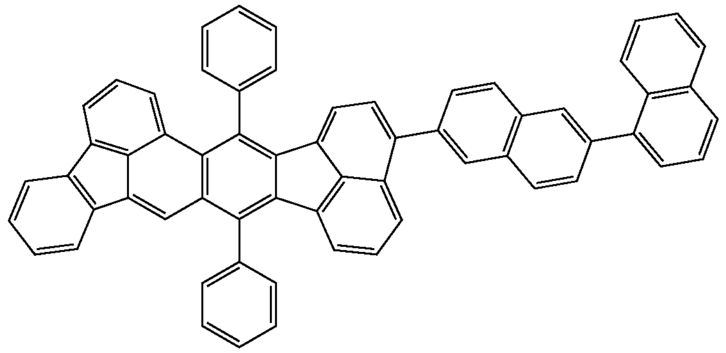
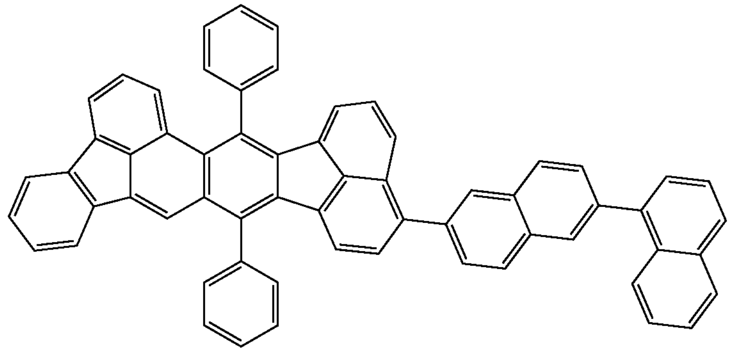
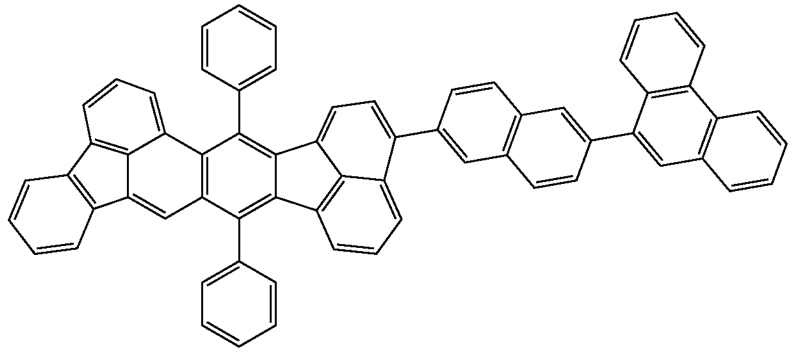
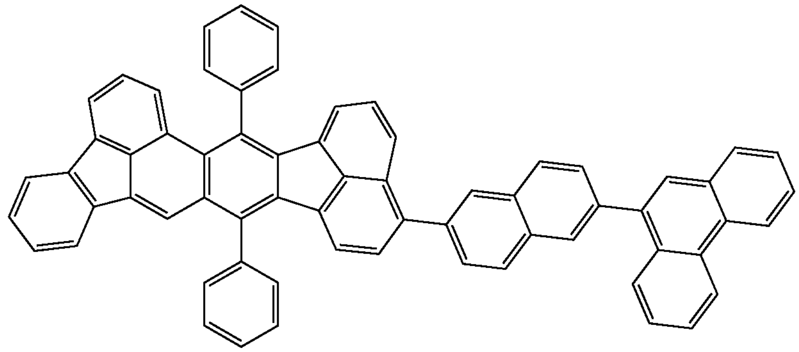

-continued
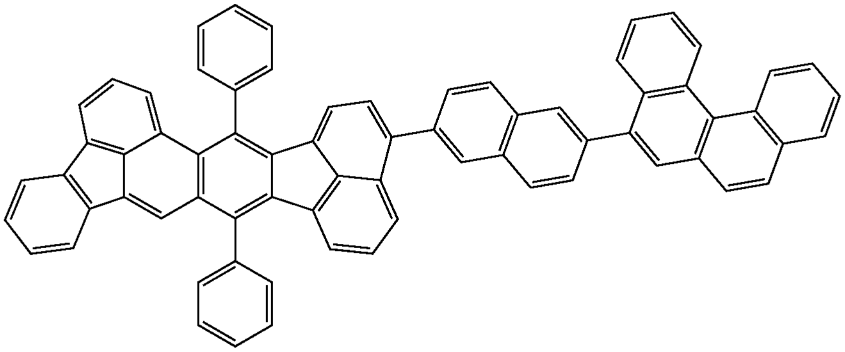
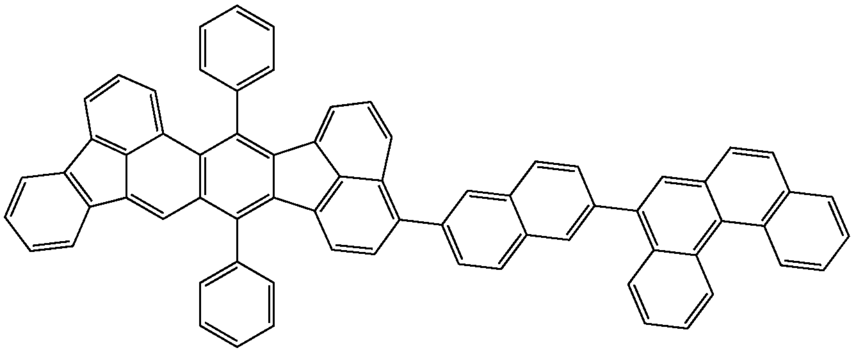
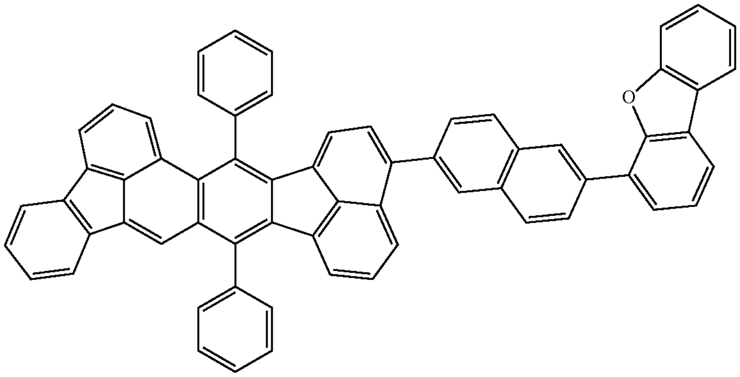
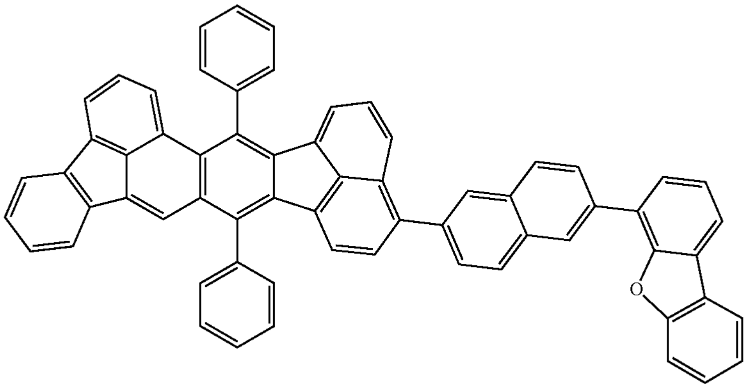

-continued
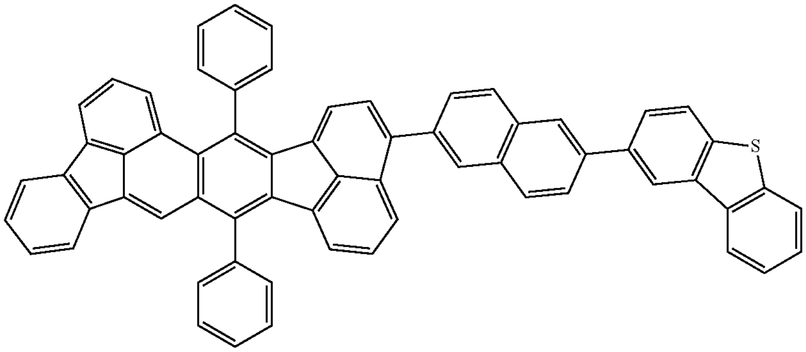
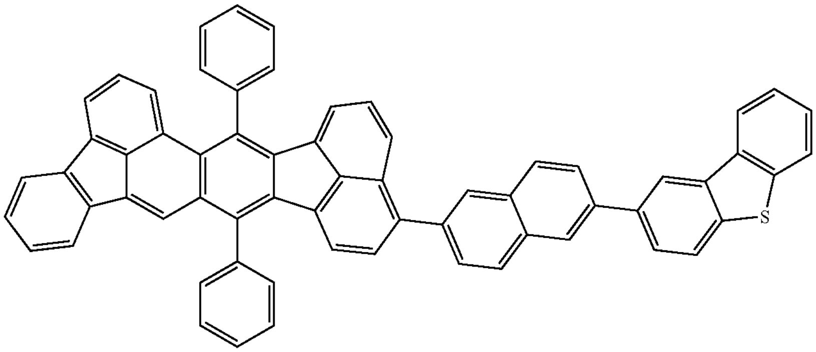
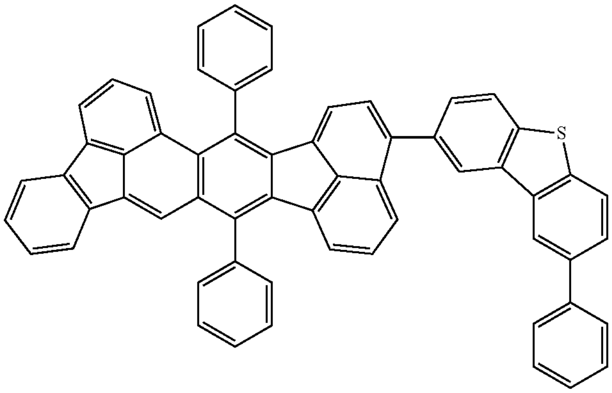
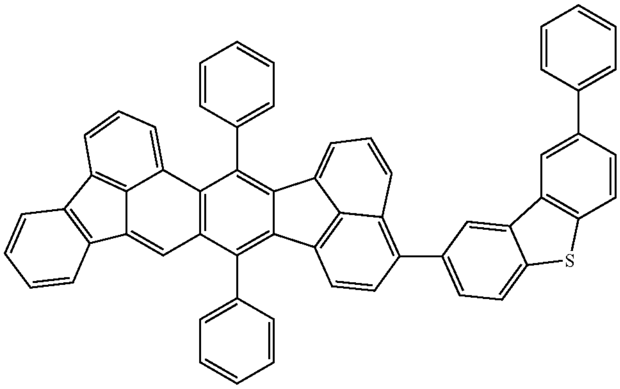

-continued
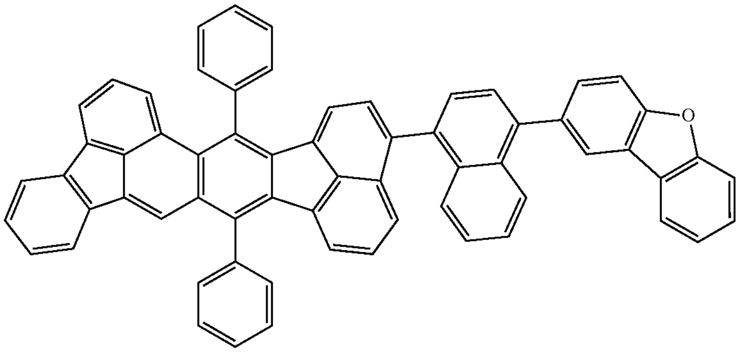
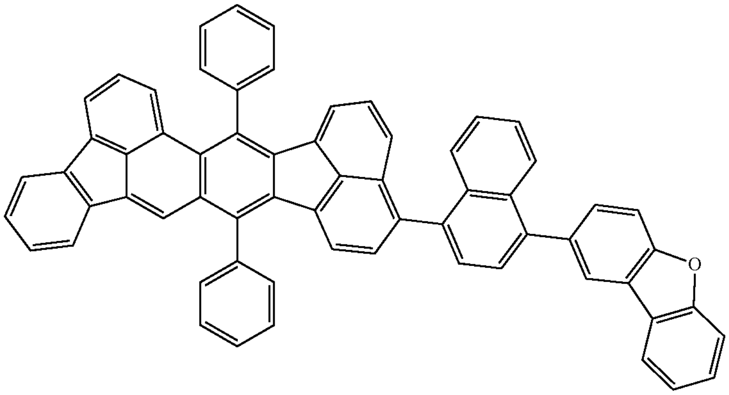
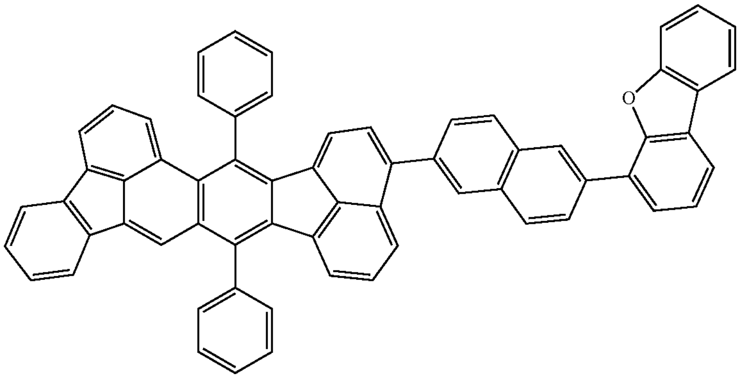
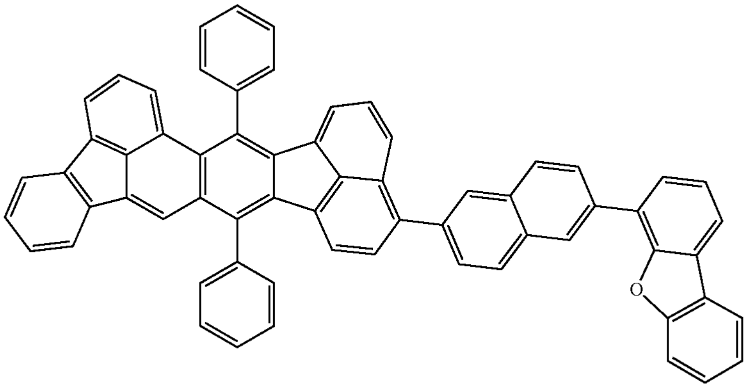

-continued
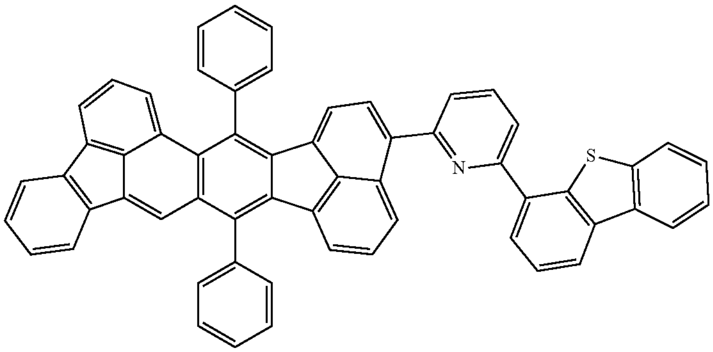
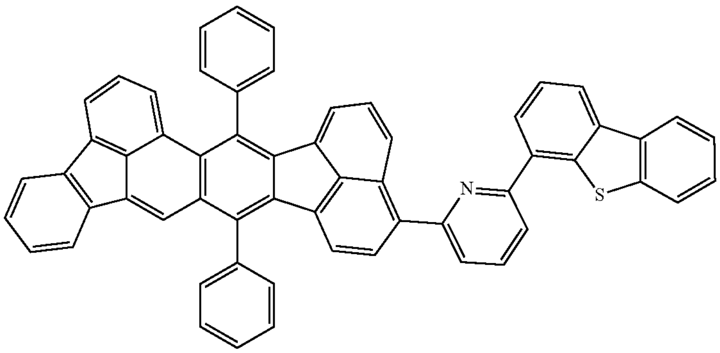
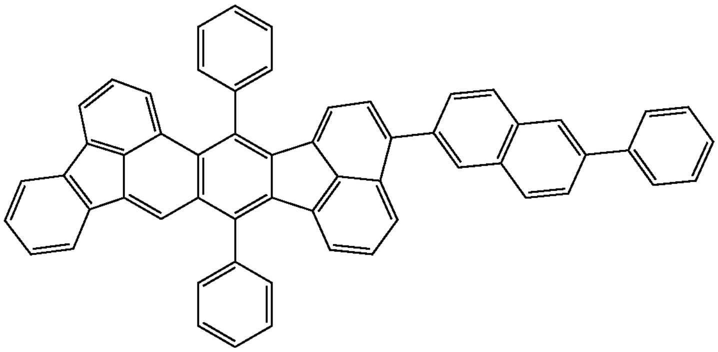
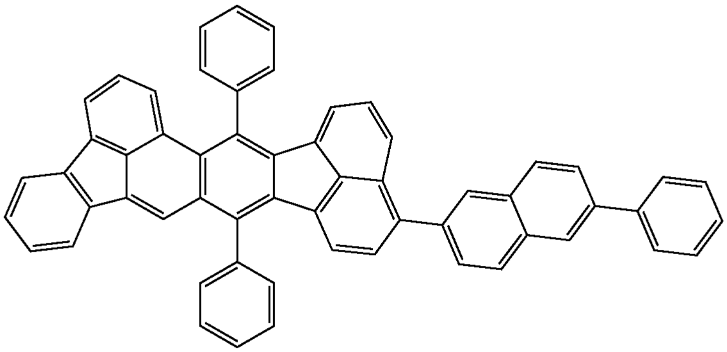

-continued
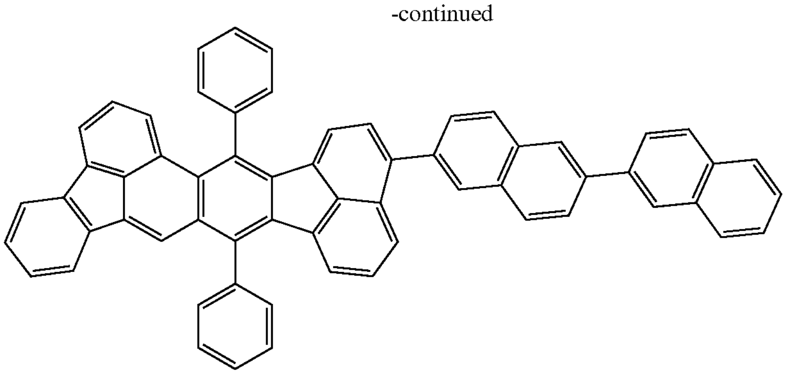
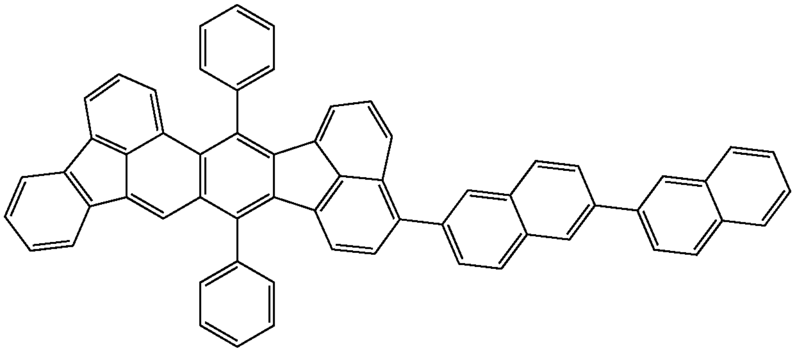
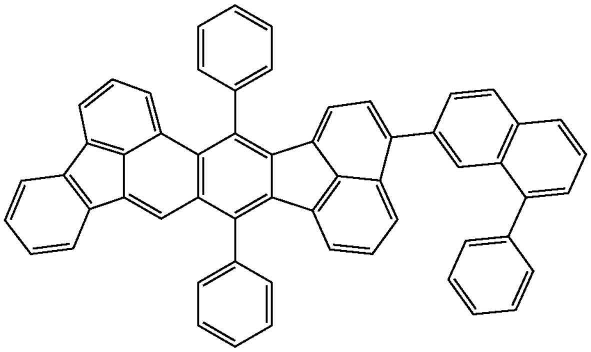
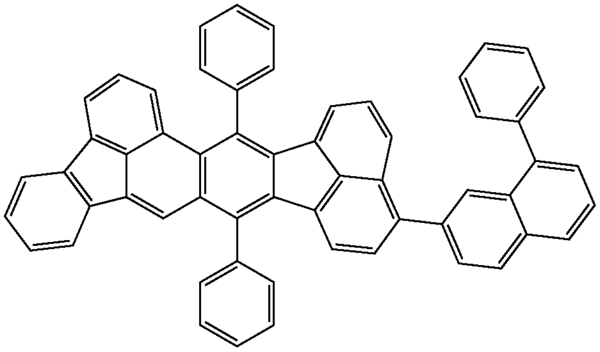

-continued
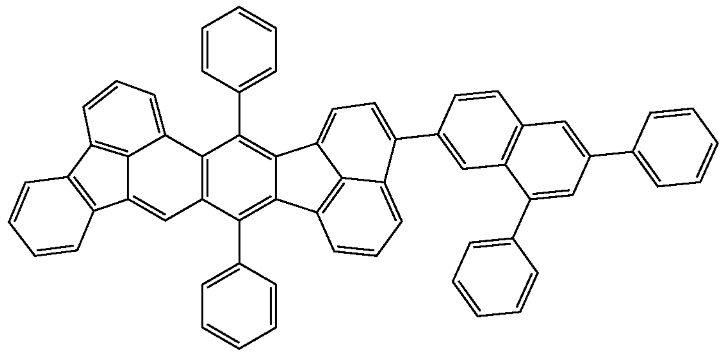
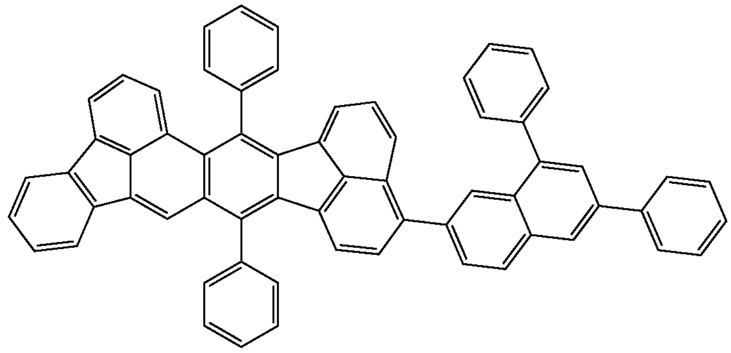
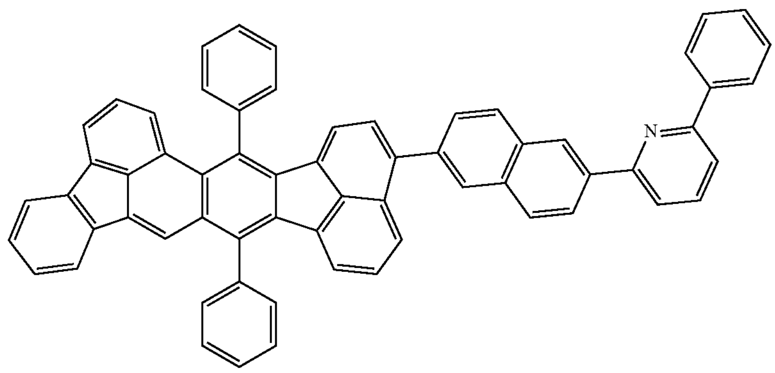
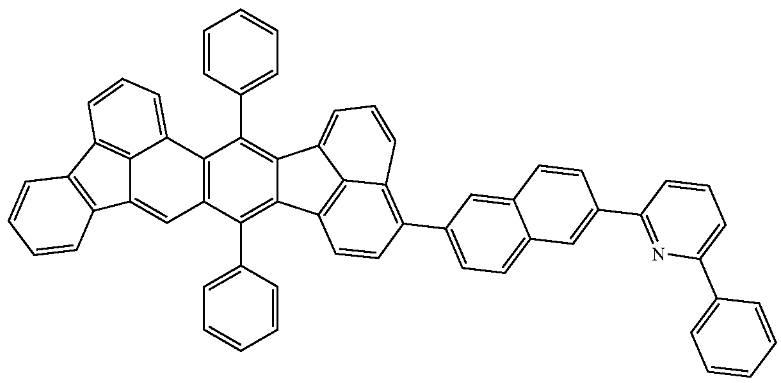

-continued
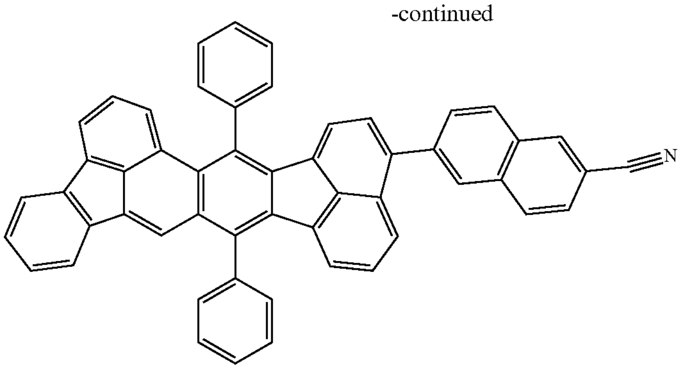
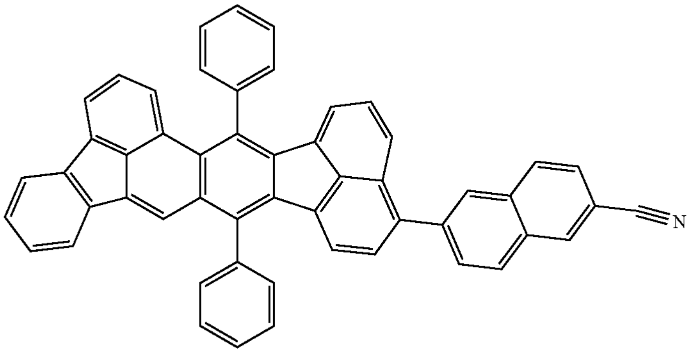
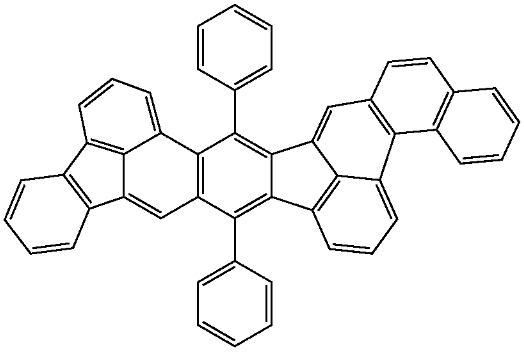
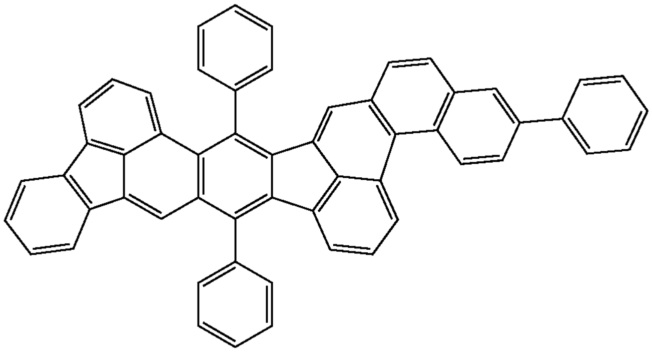

-continued
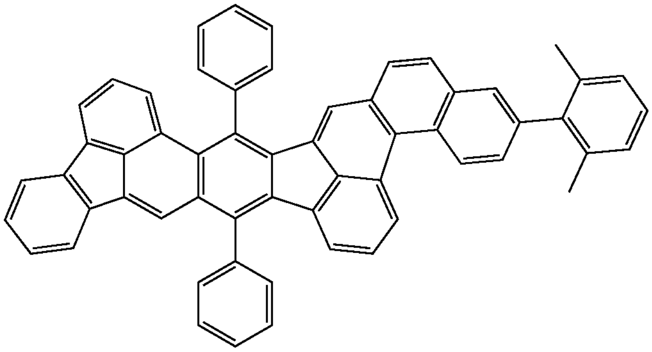
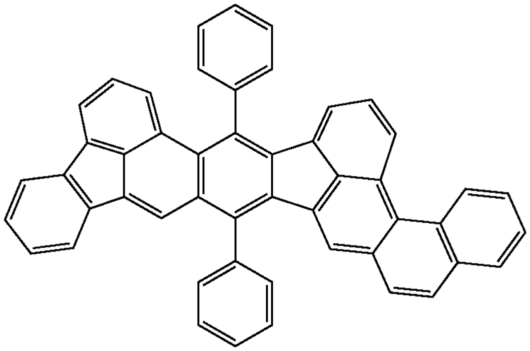
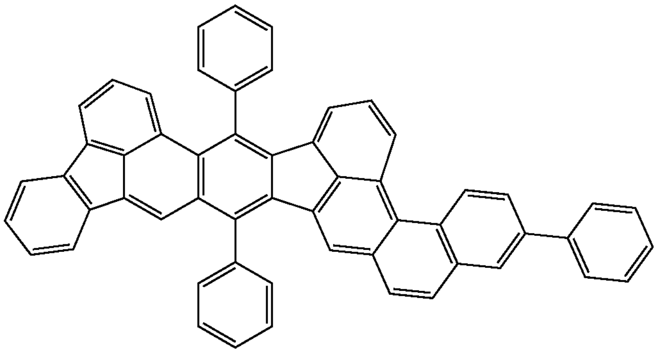
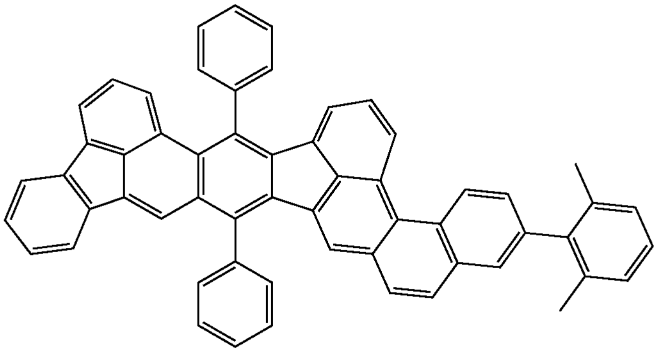

-continued
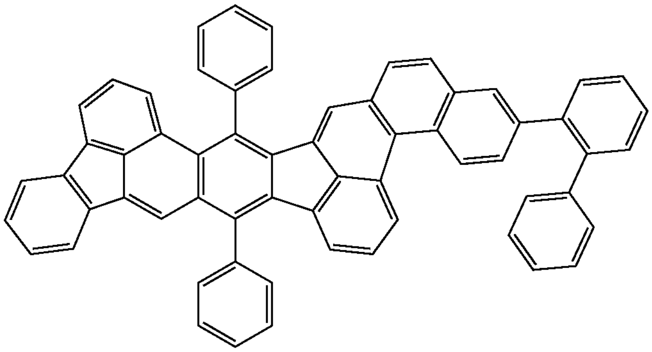
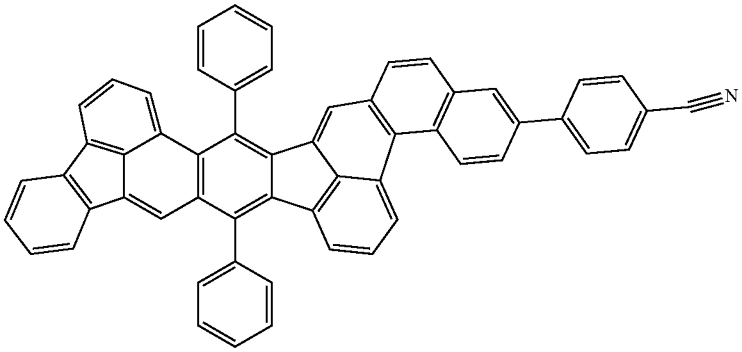
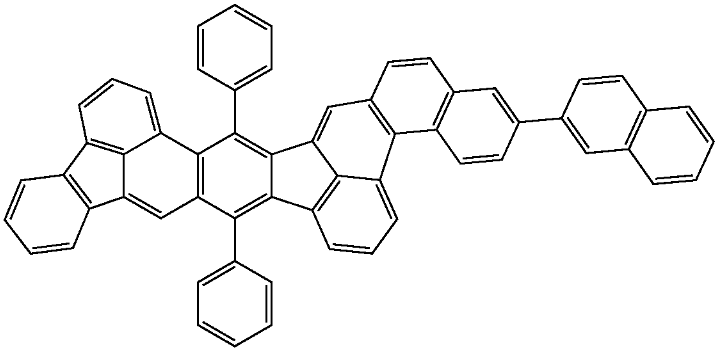
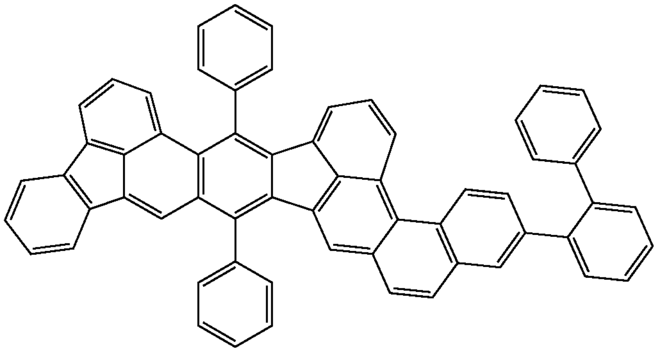

-continued
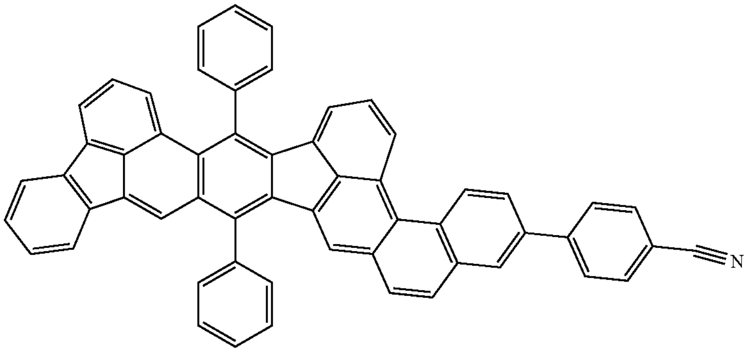
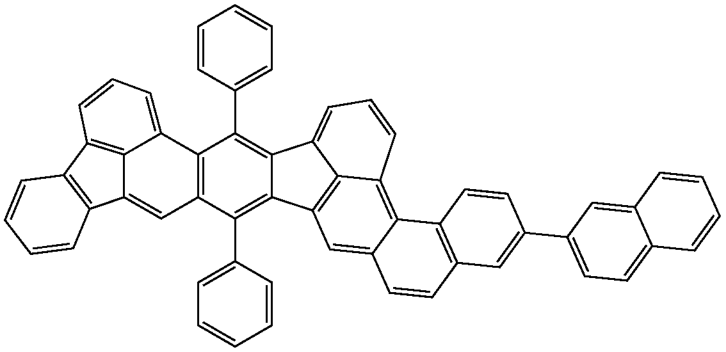
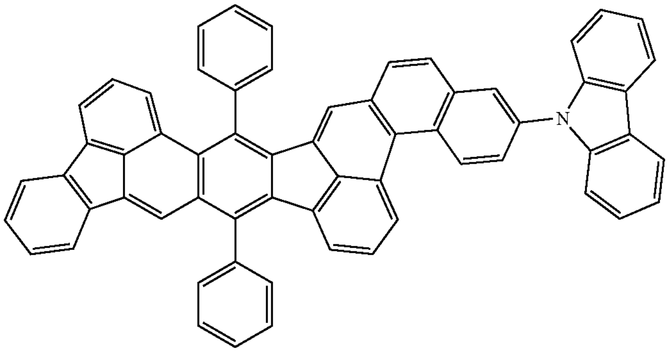
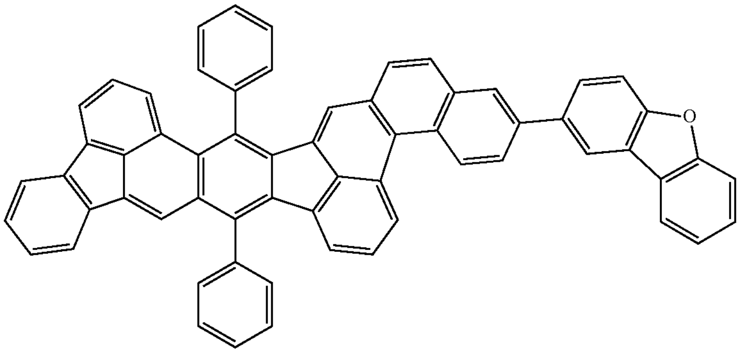

-continued
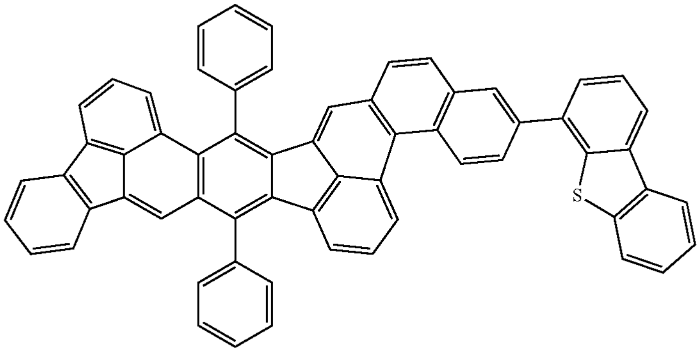
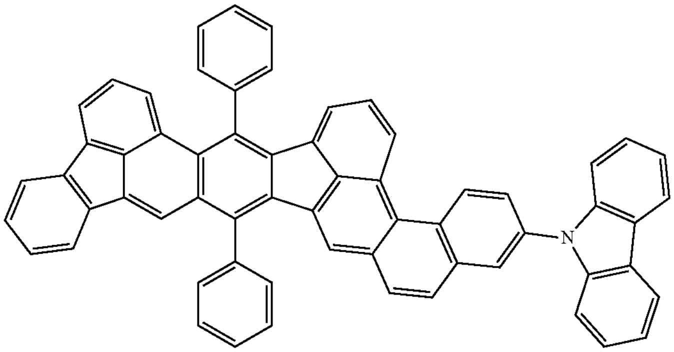
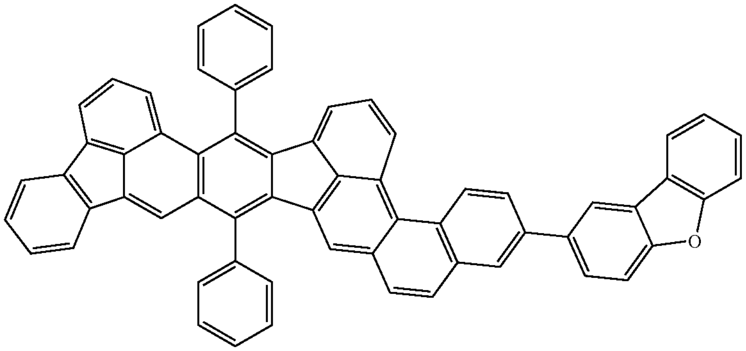
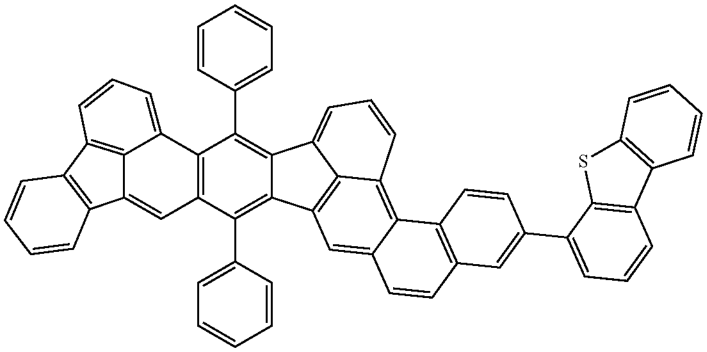

-continued
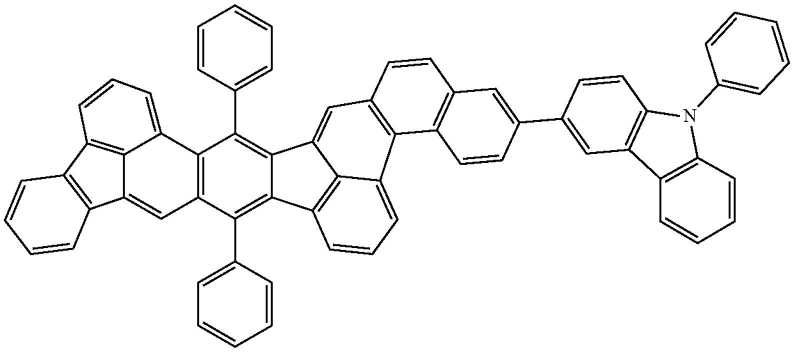
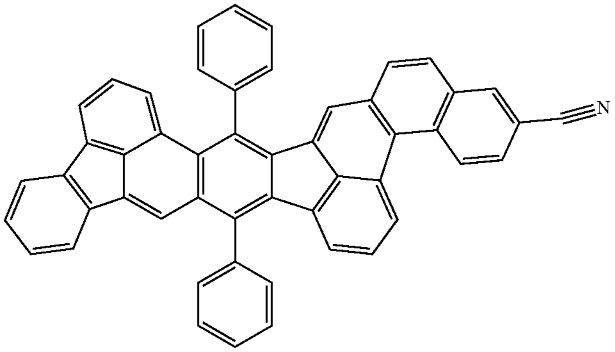
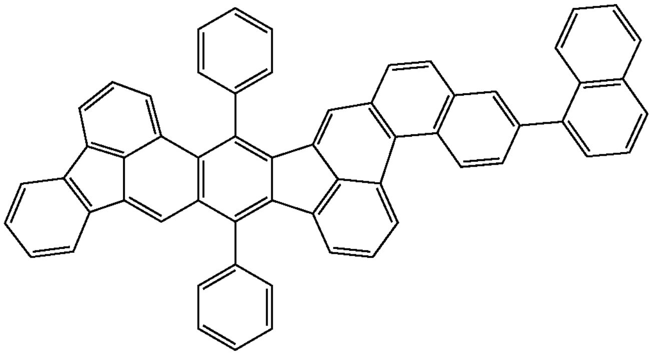
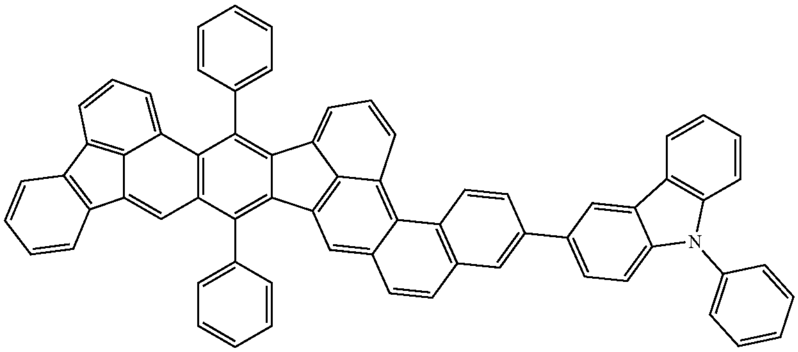

-continued
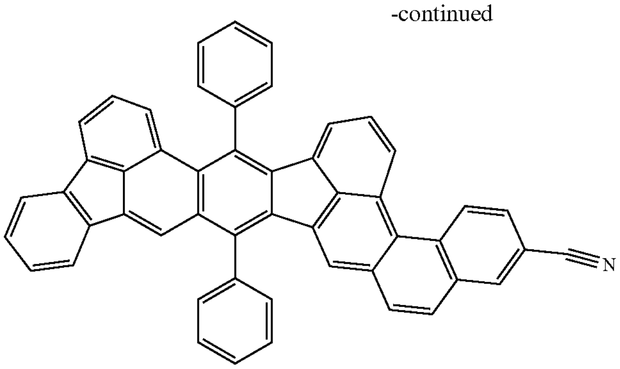
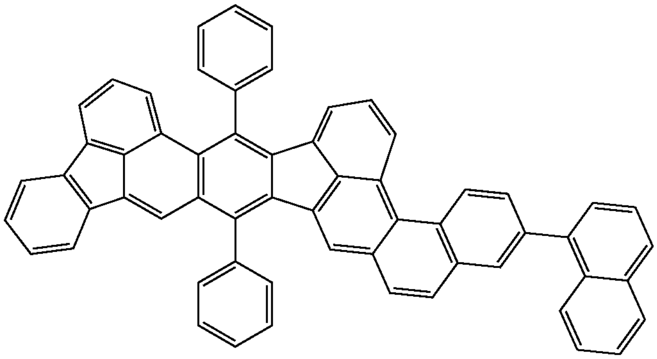
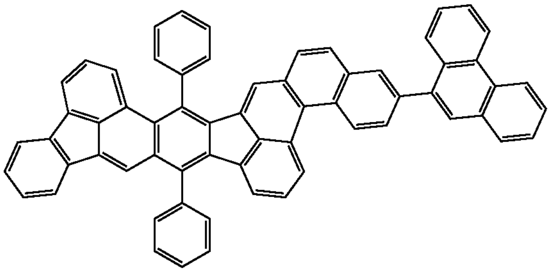
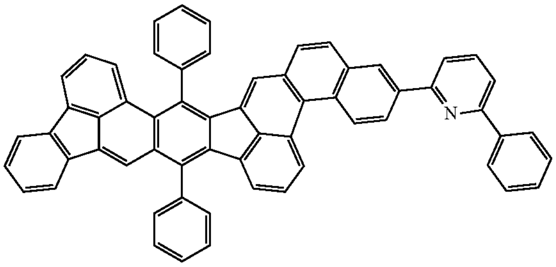
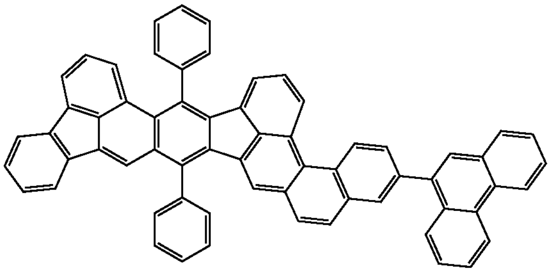
-continued
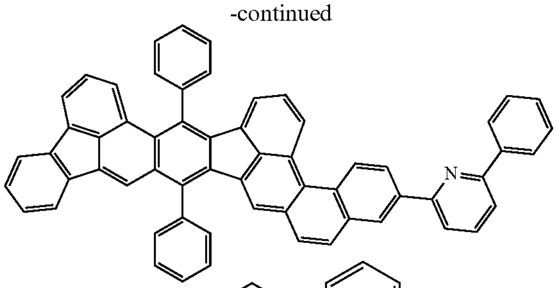
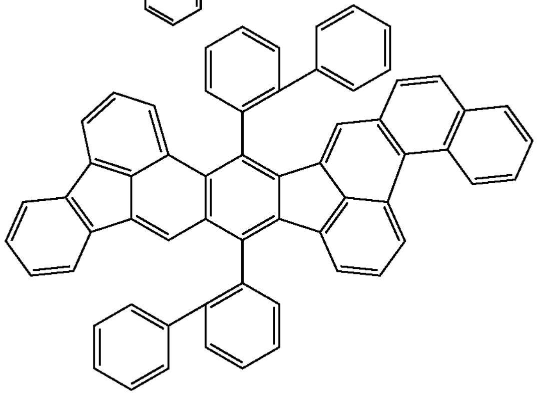
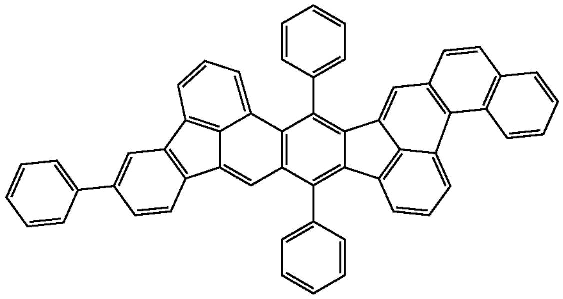

-continued
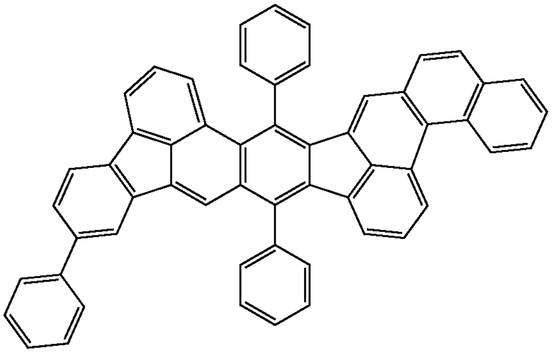
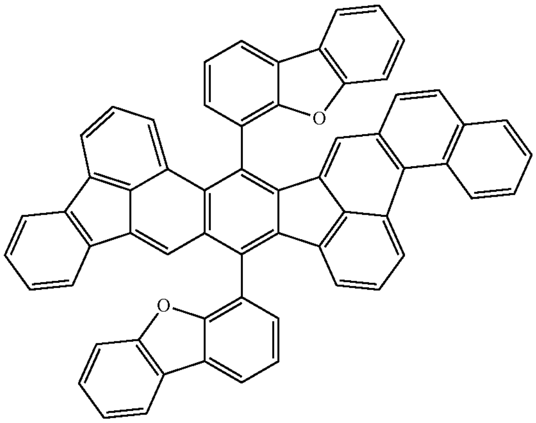
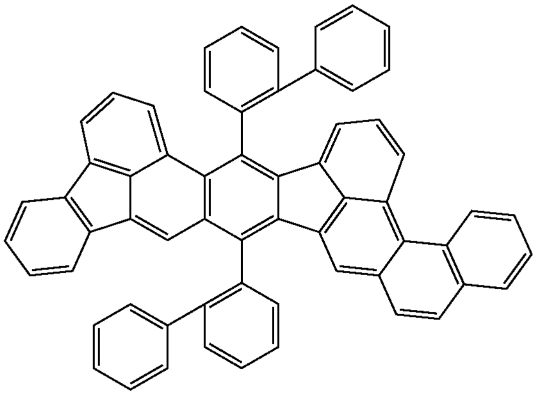
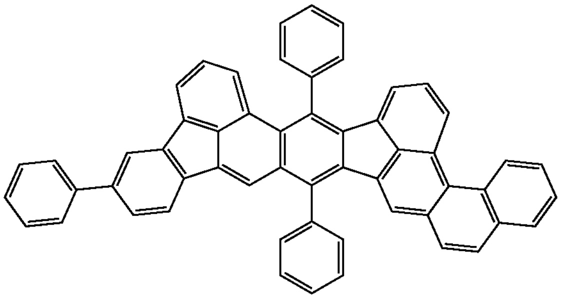
-continued
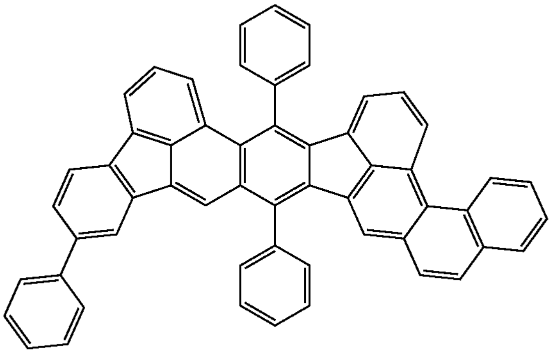
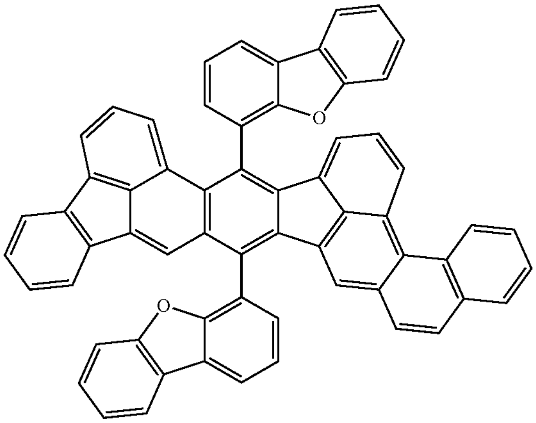
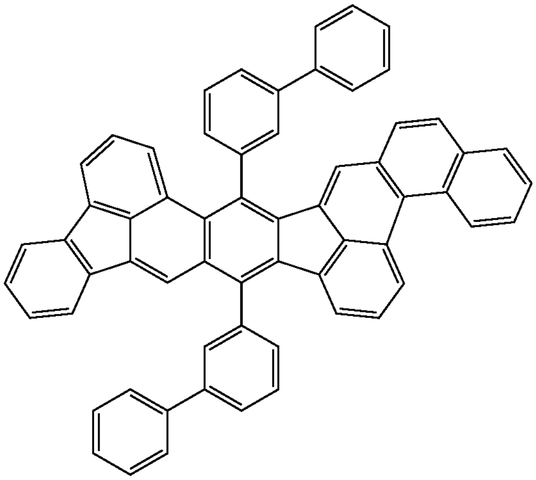

-continued
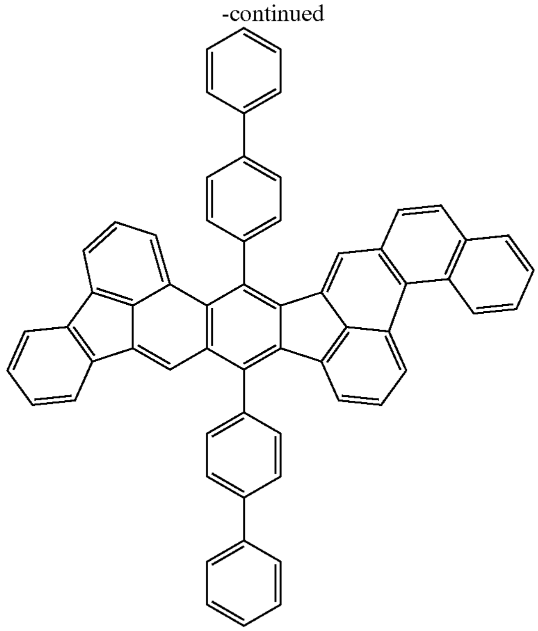
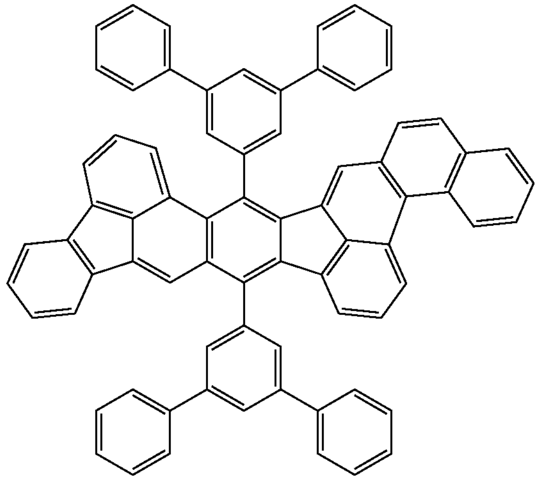
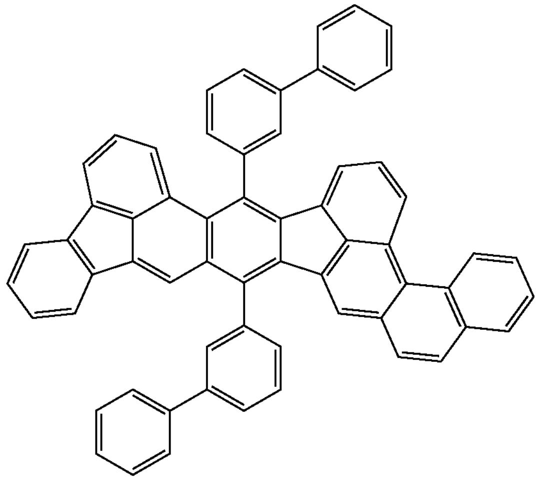
-continued
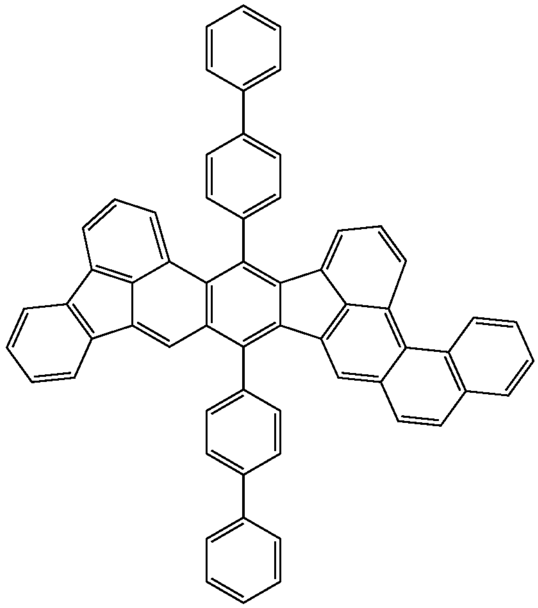
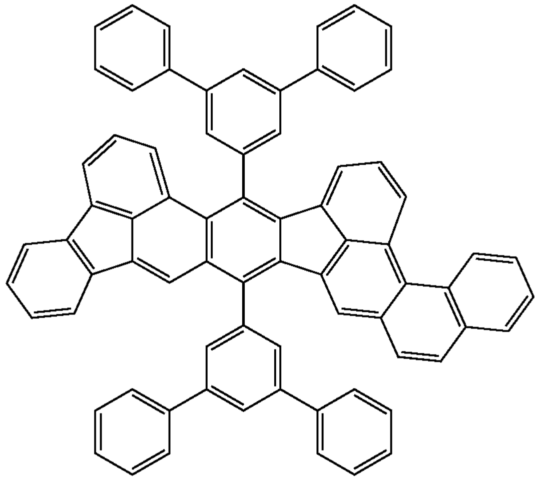
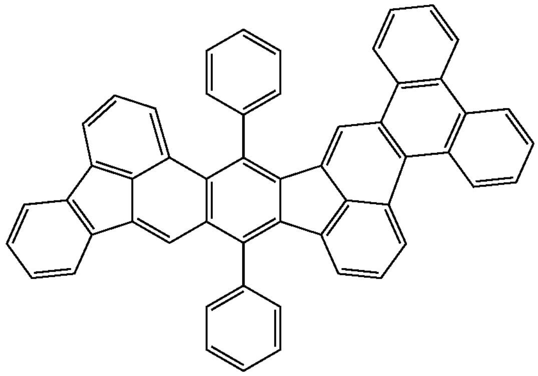

-continued
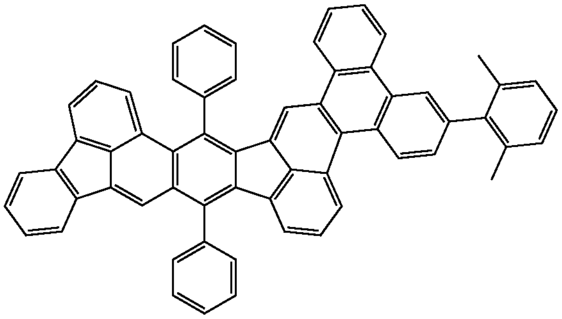
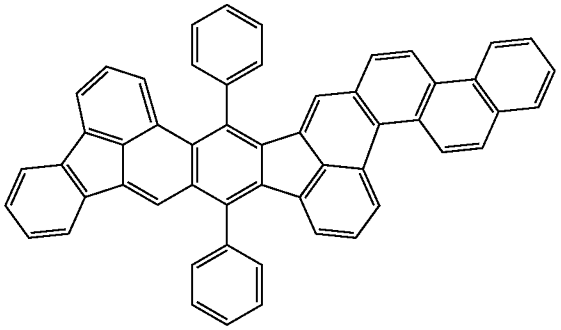
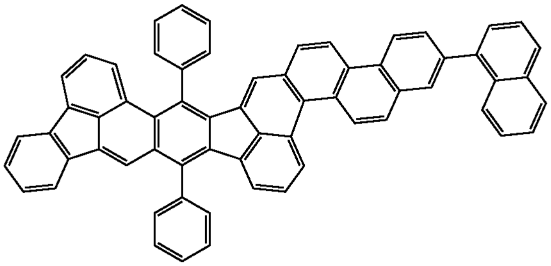
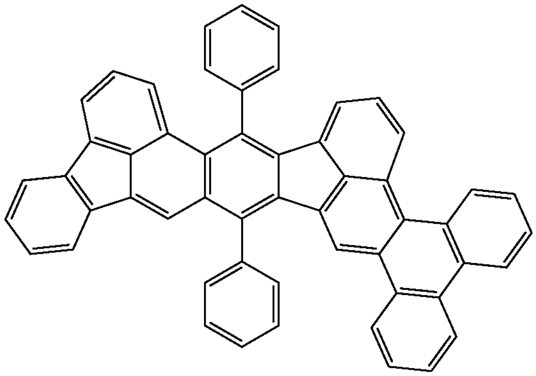
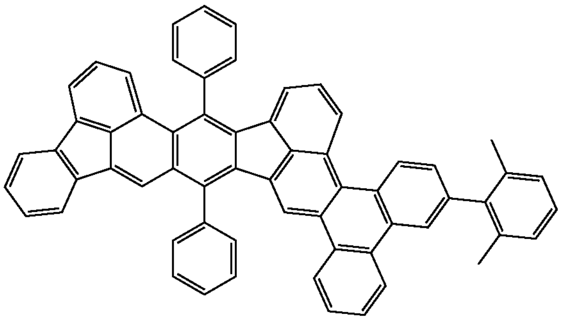
-continued
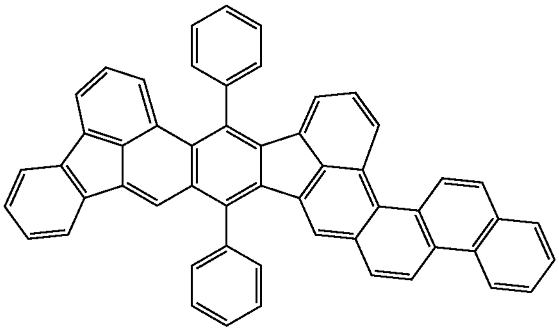
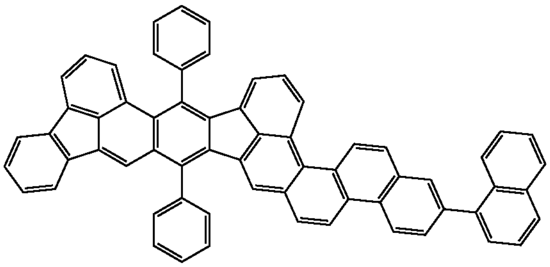
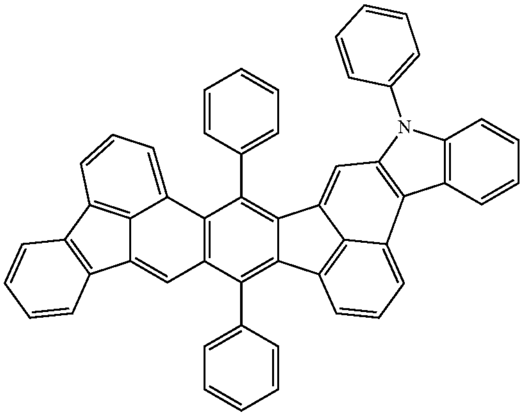
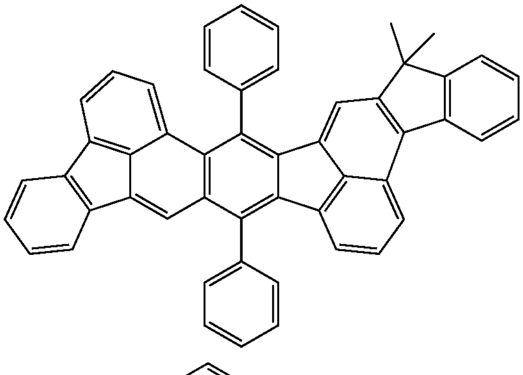
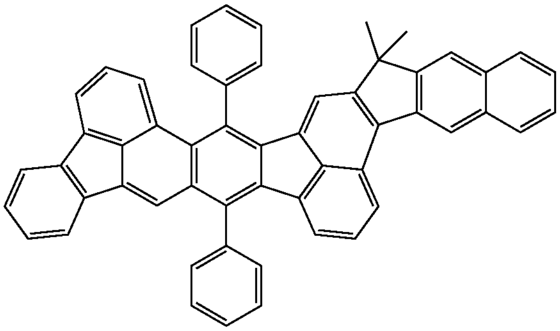

-continued
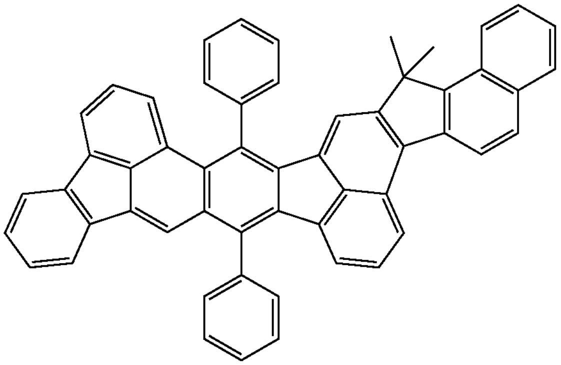
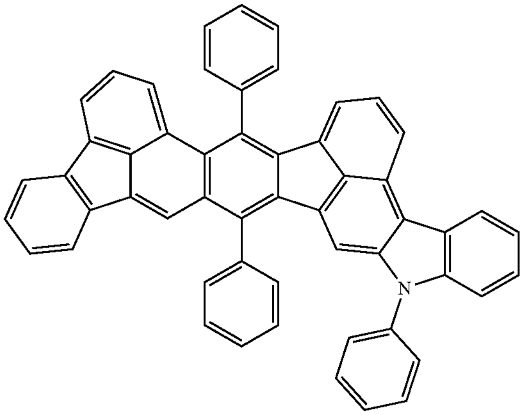
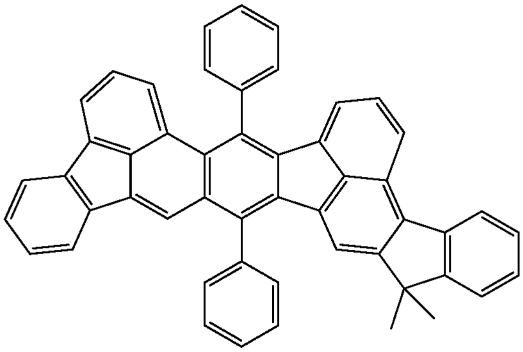
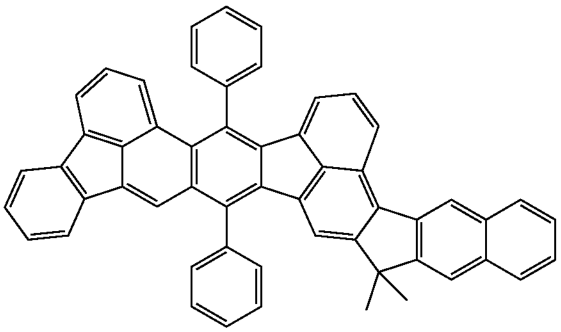
-continued
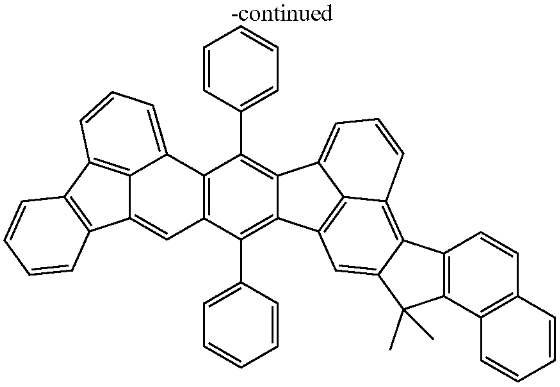
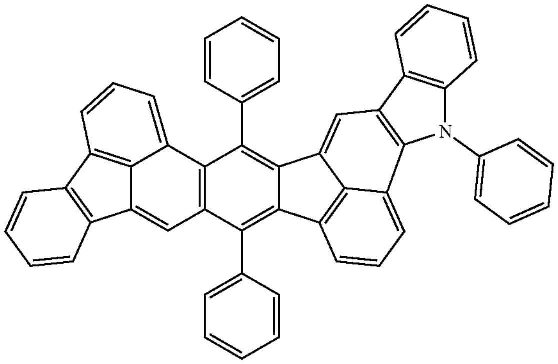
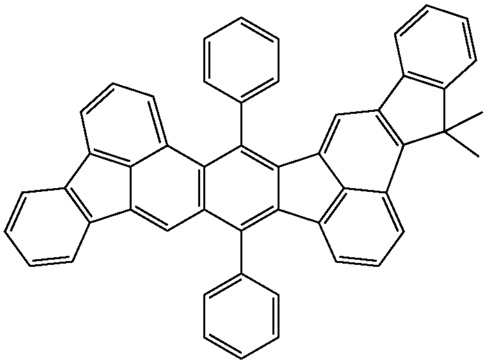
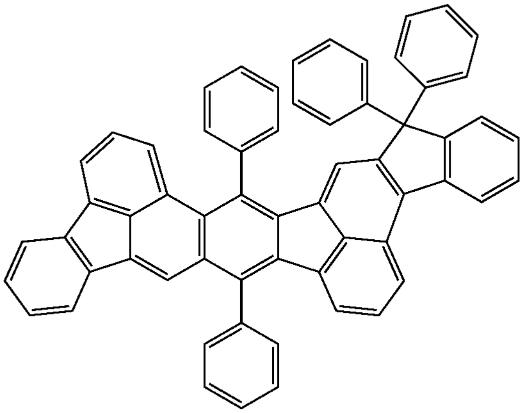

-continued
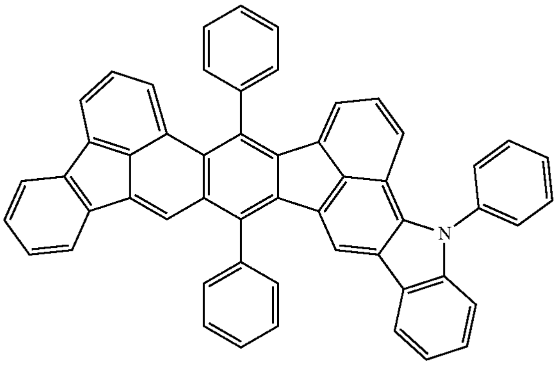
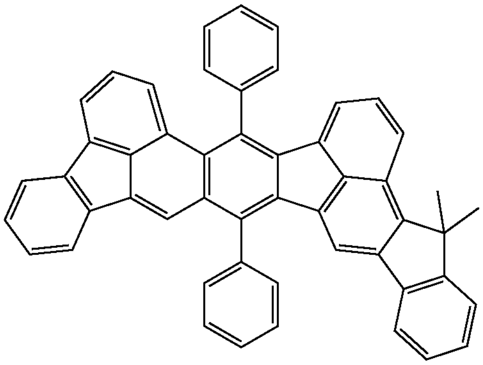
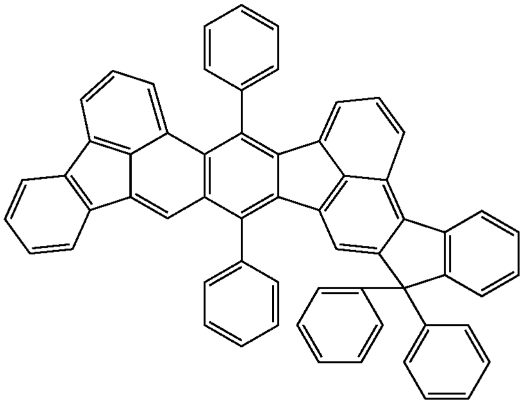
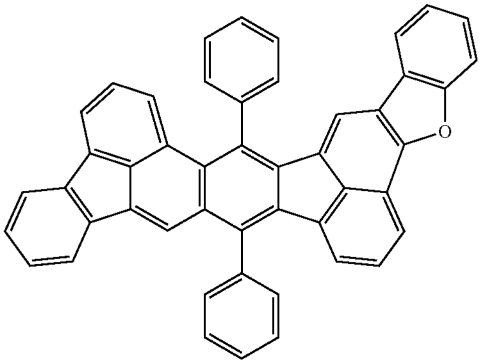
-continued
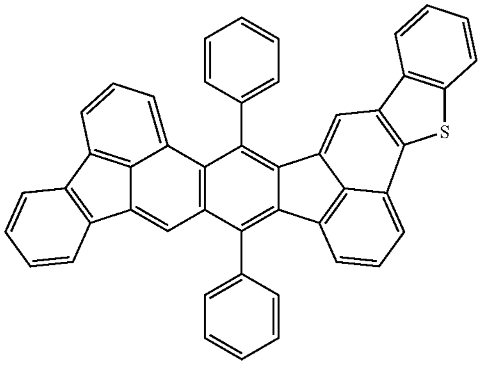
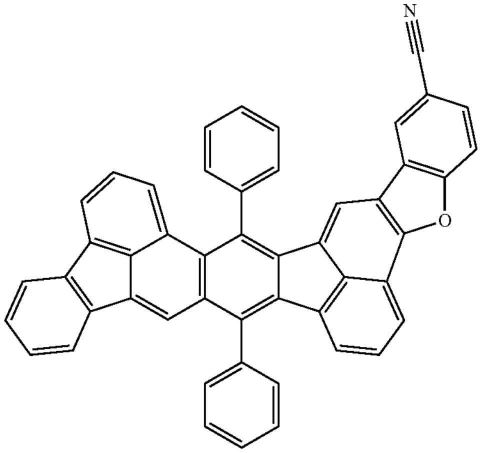
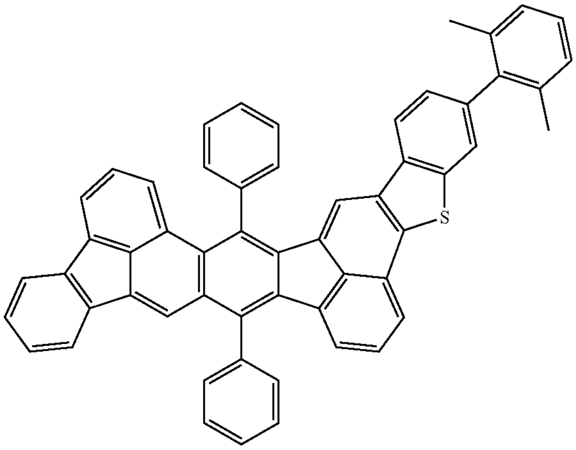
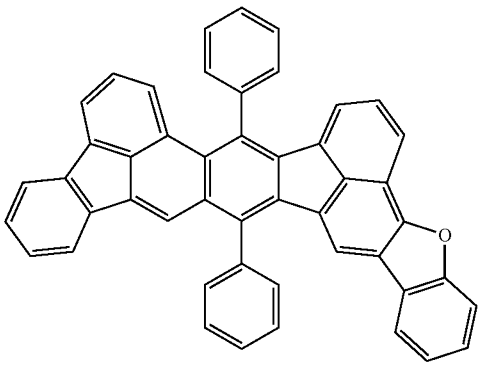

-continued
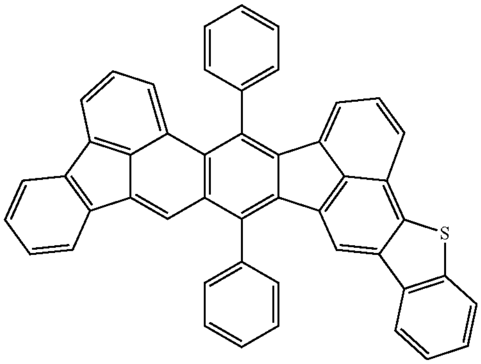
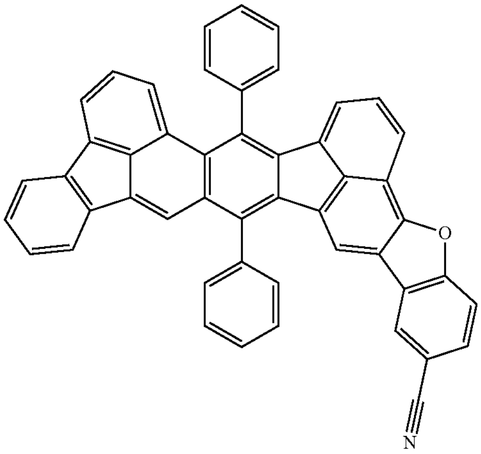
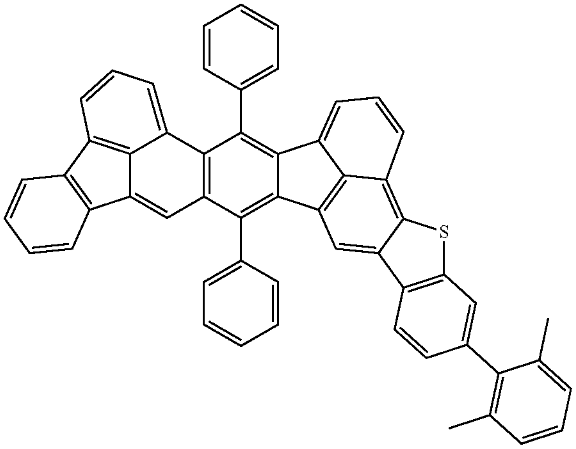
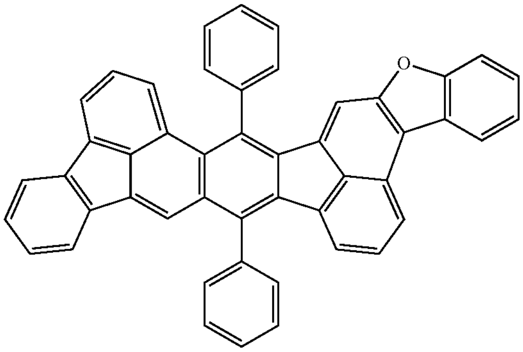
-continued
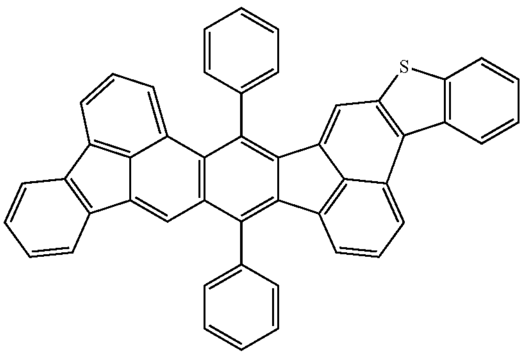
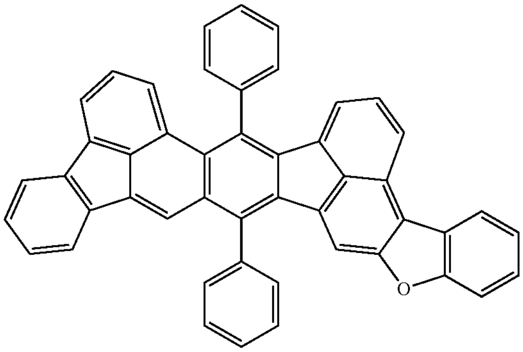
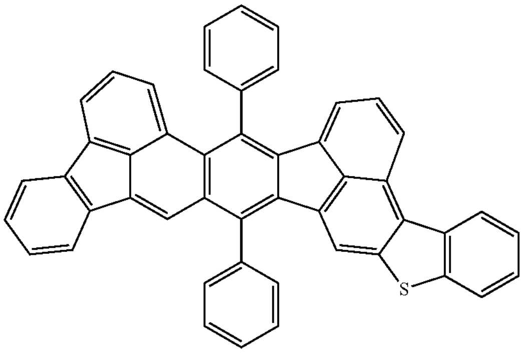
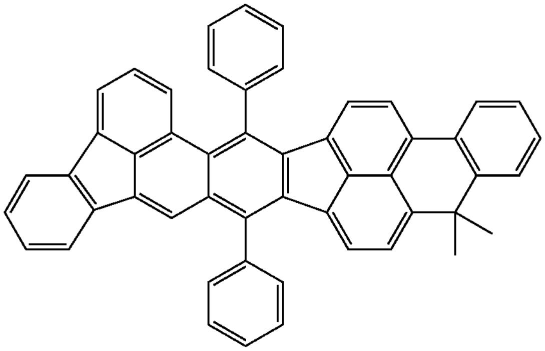

-continued
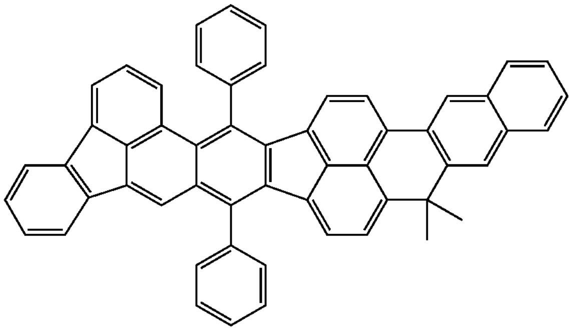
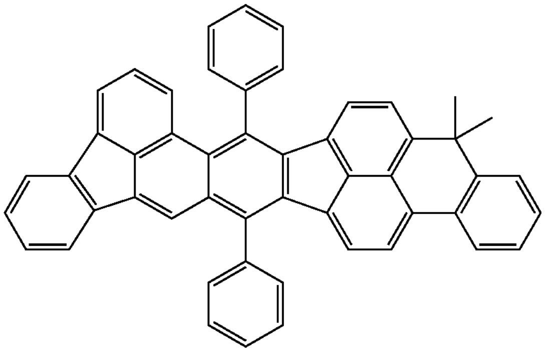
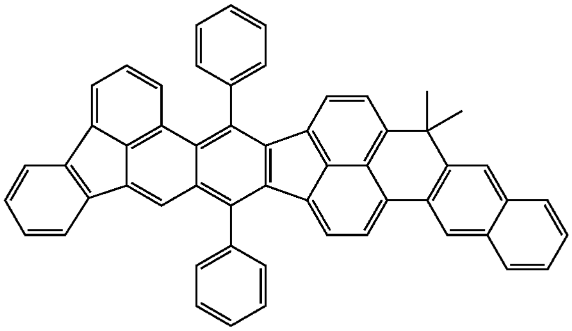
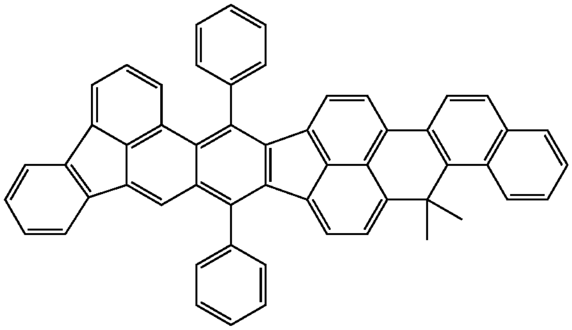
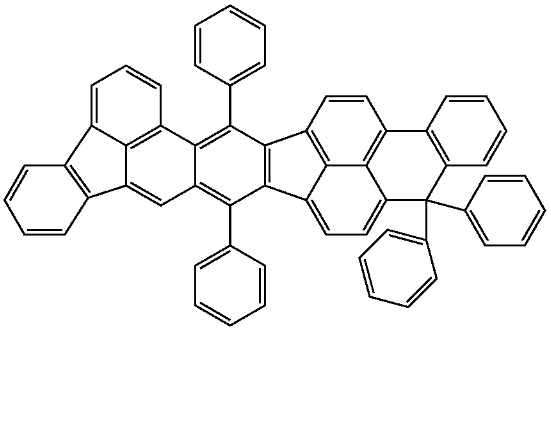
-continued
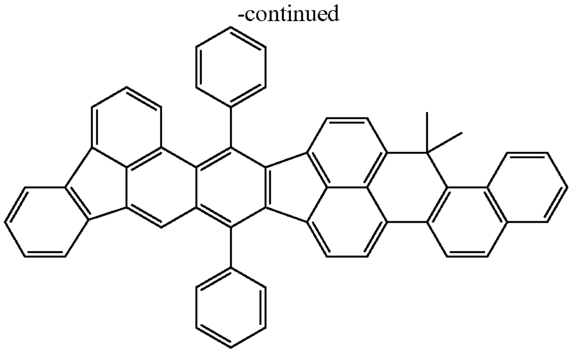
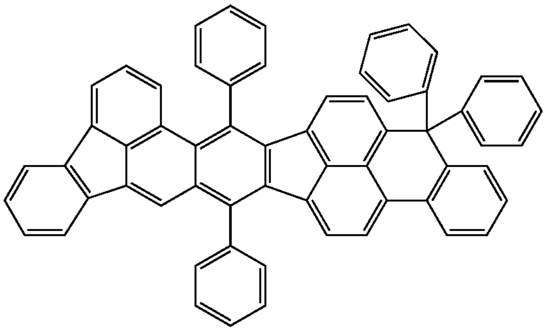
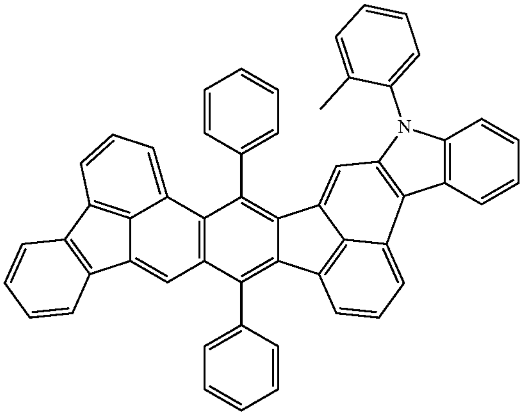
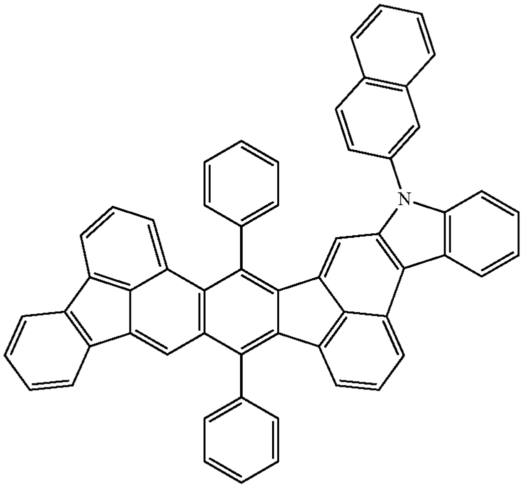

-continued
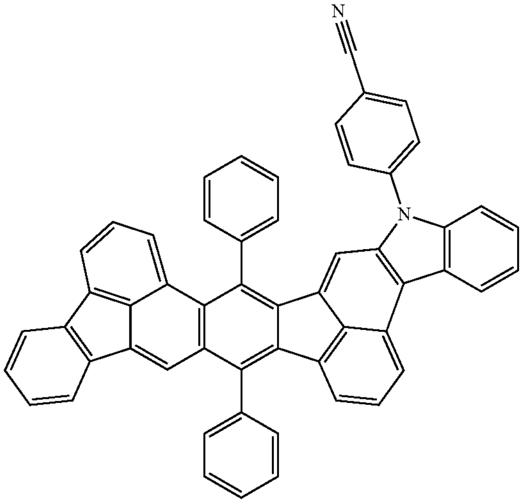
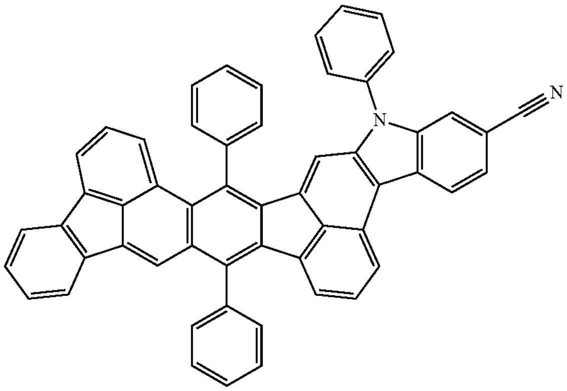
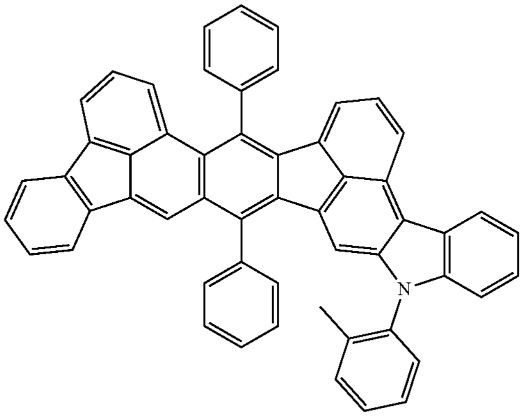
-continued
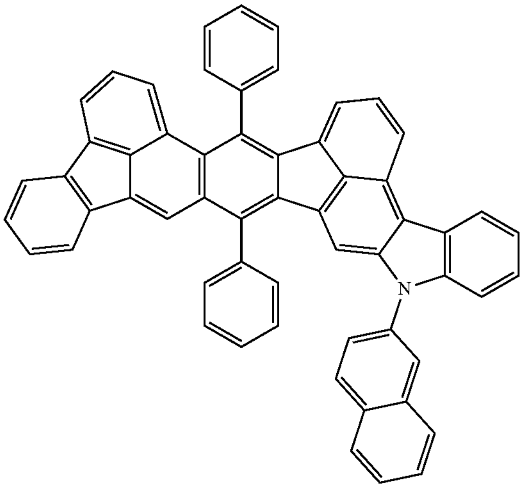
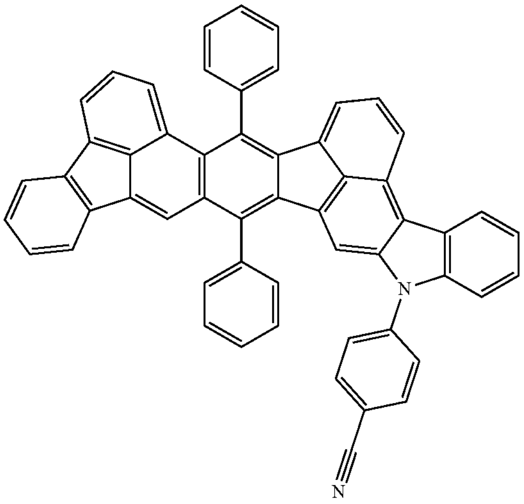
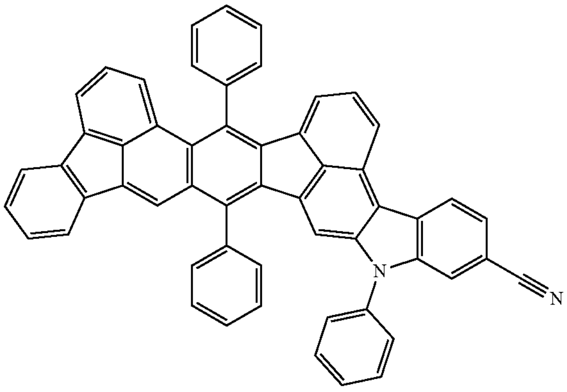

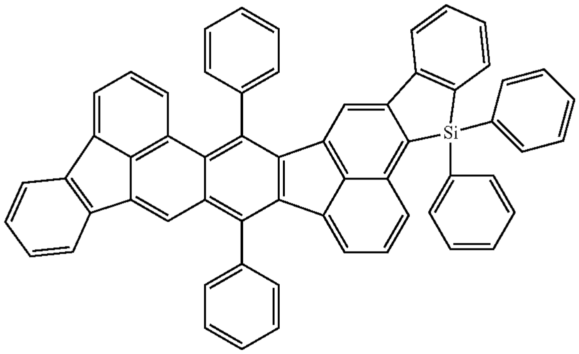
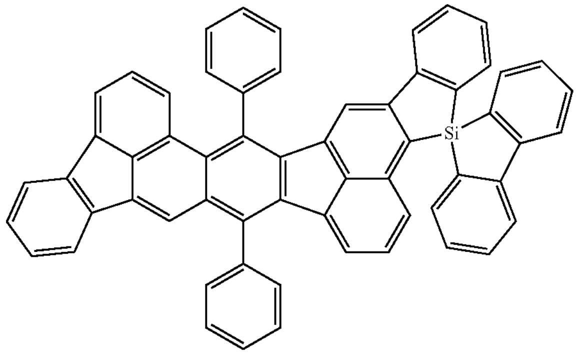
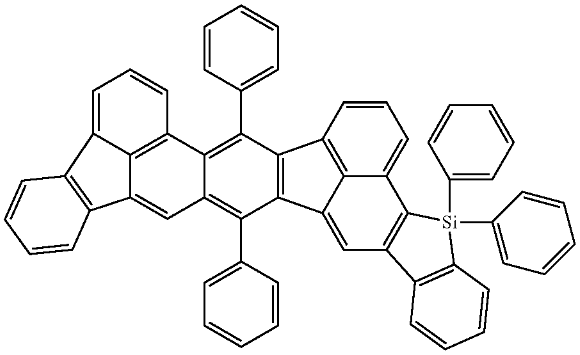
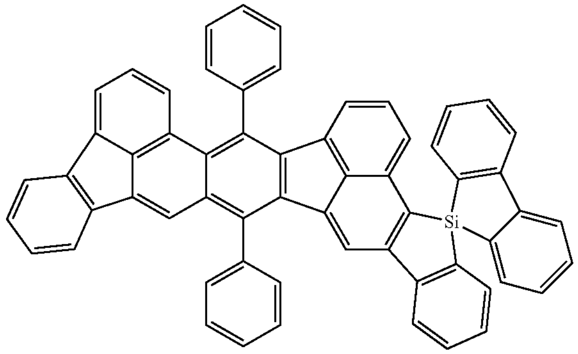
-continued
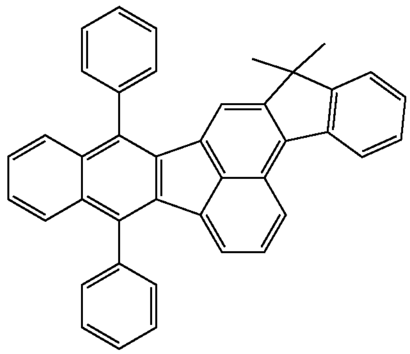
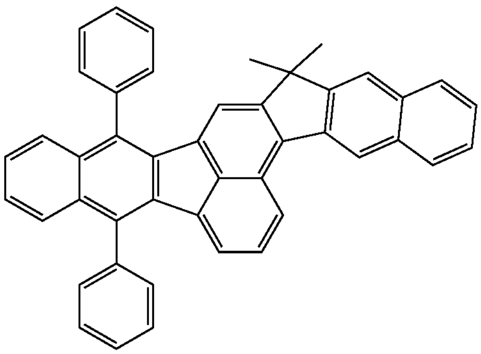
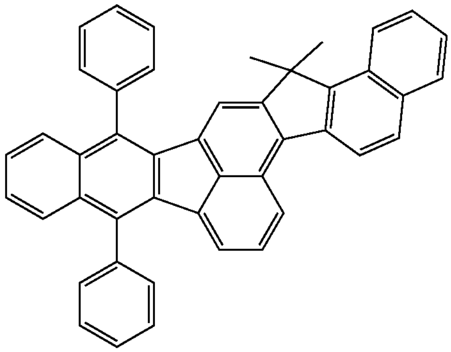
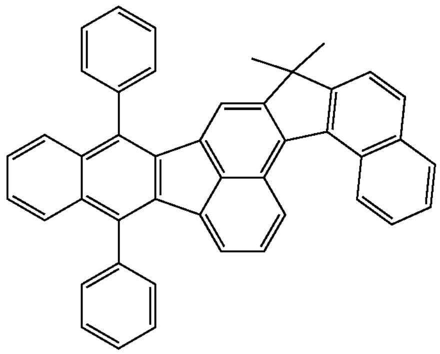

-continued
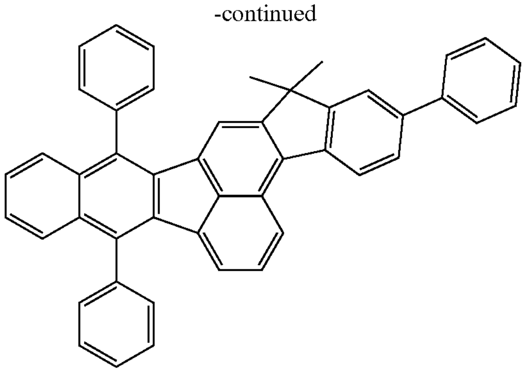
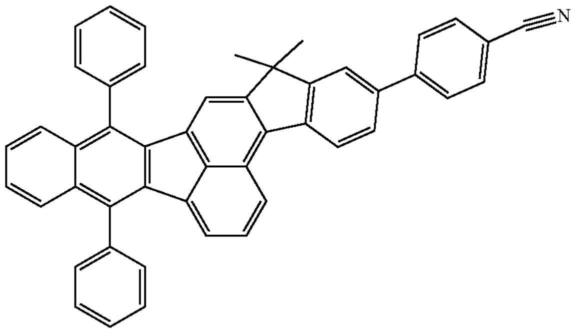
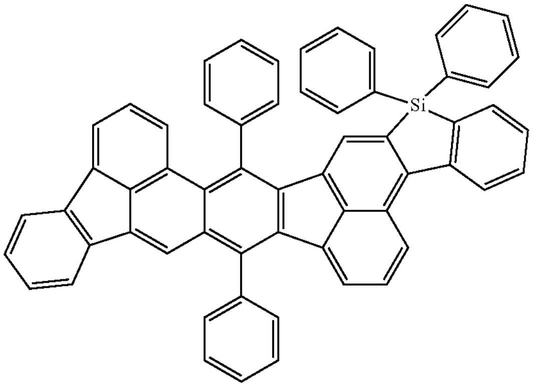
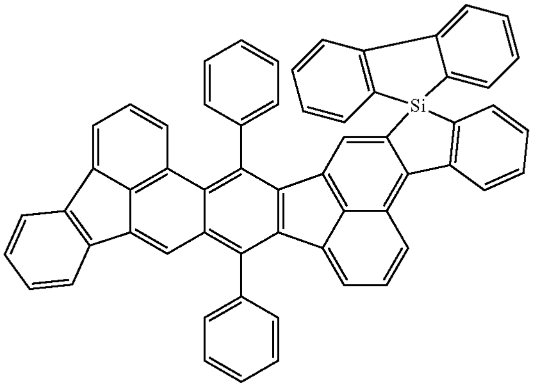
-continued
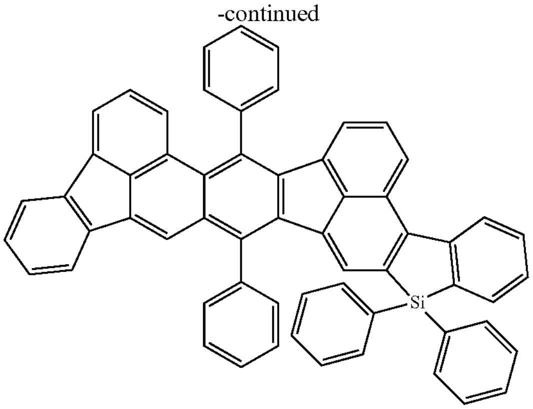
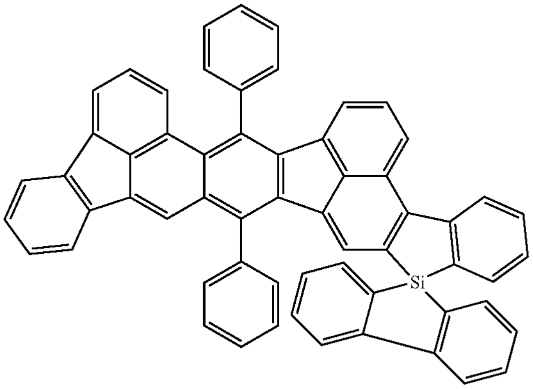
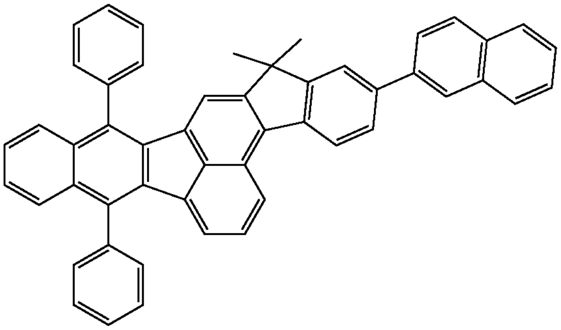
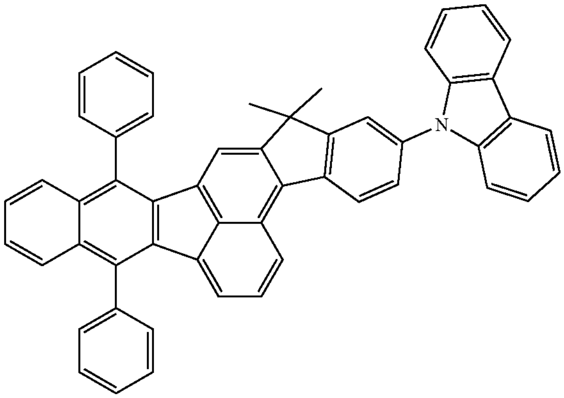

-continued
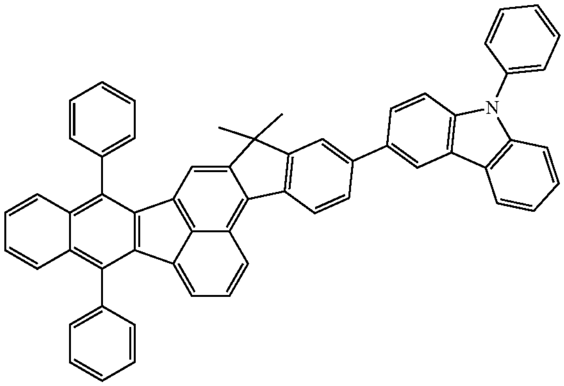
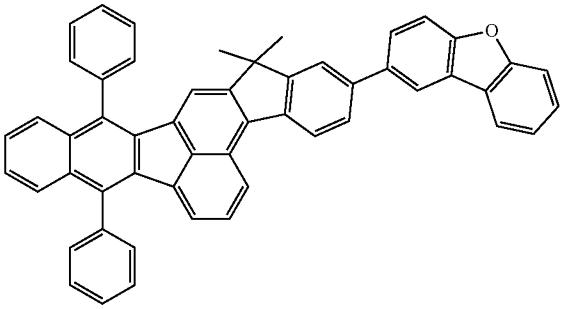
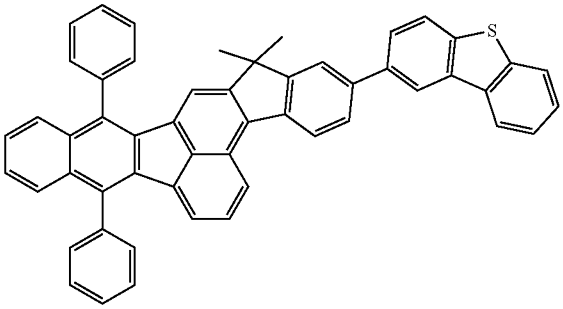
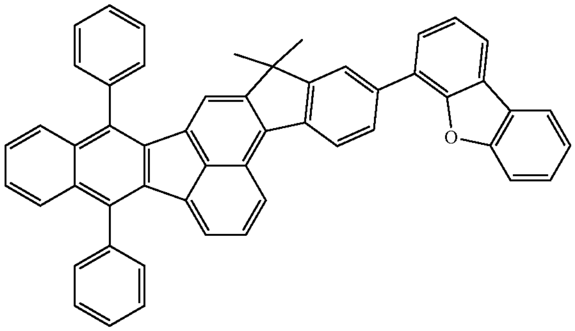
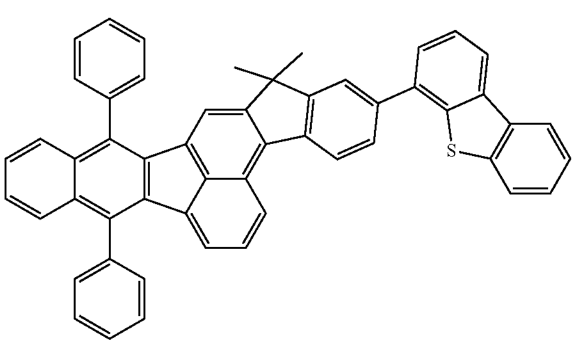
-continued
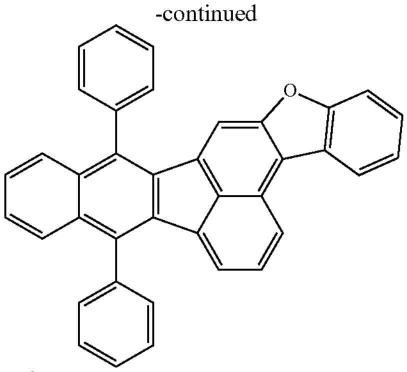
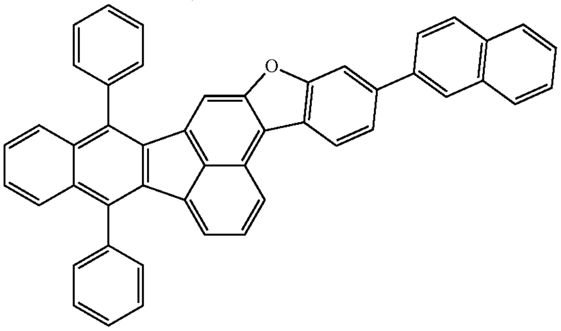
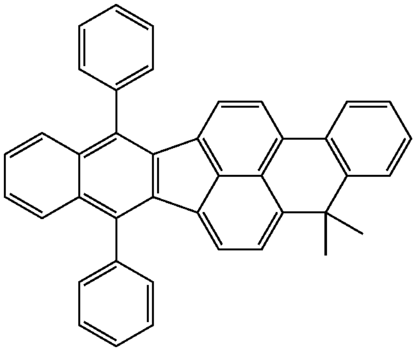
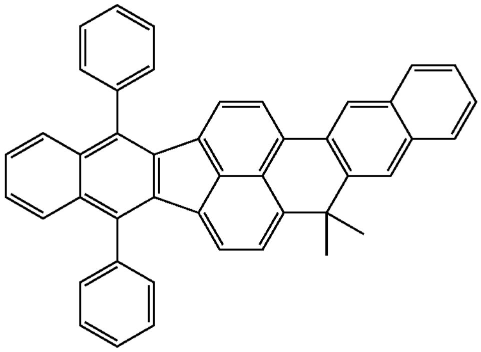
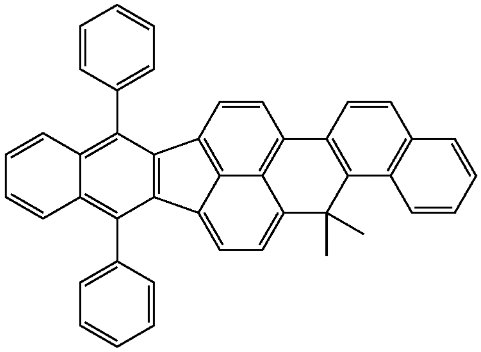

-continued
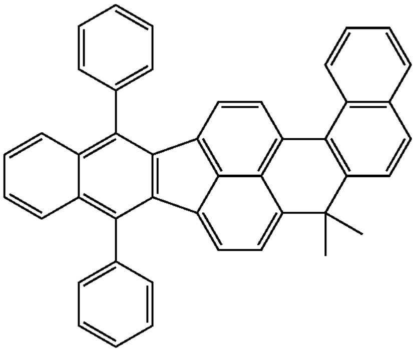
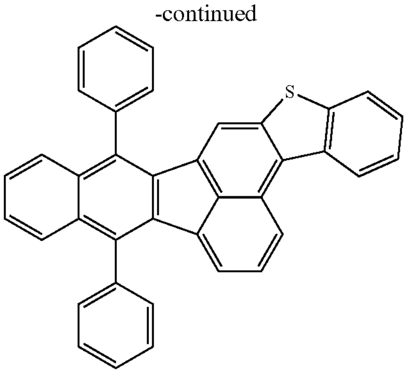
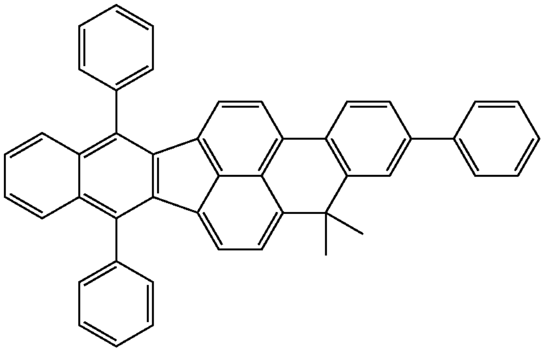
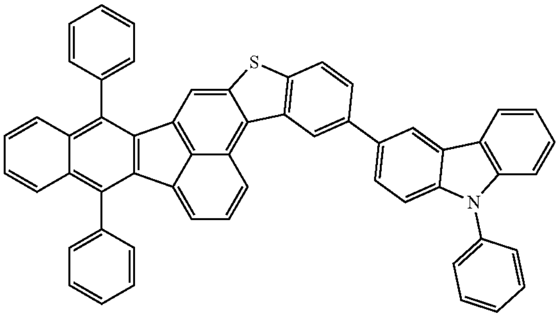
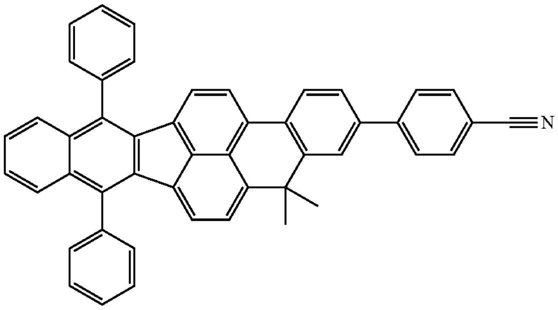
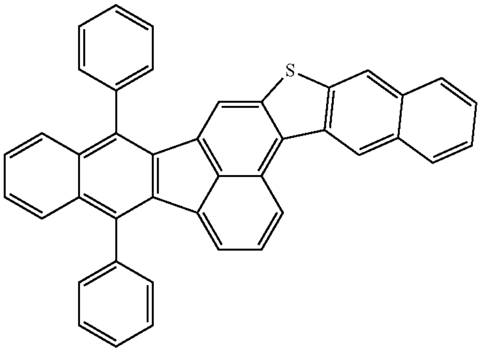
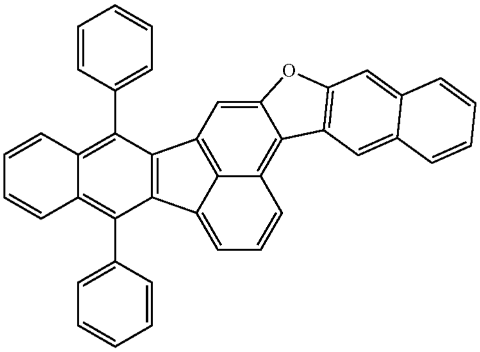
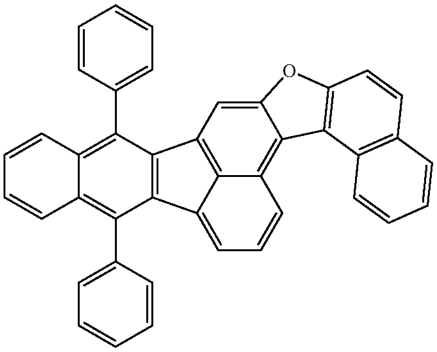
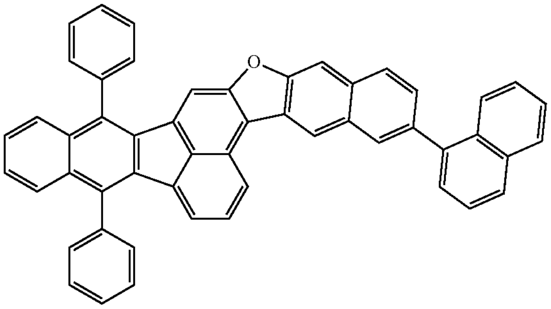
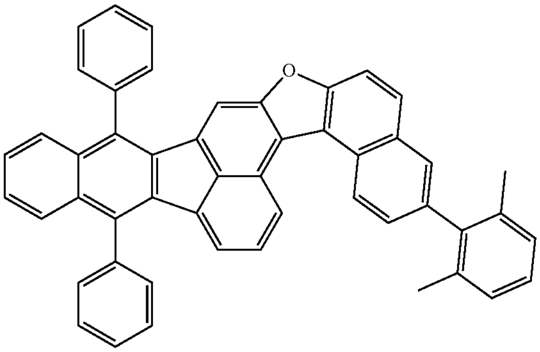

-continued
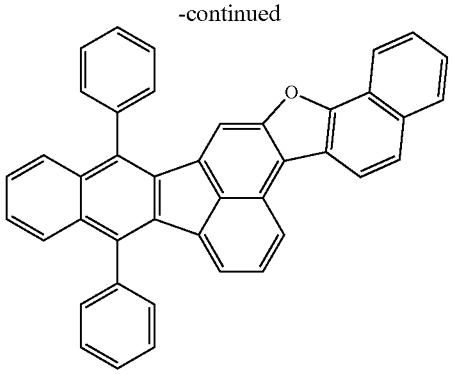
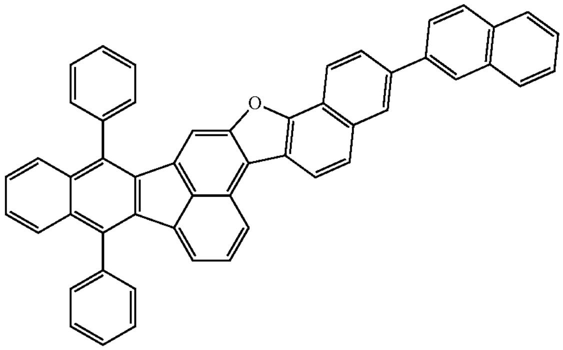
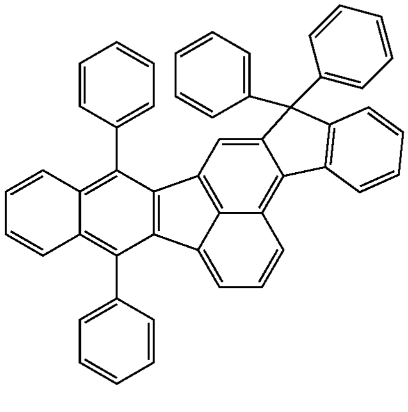
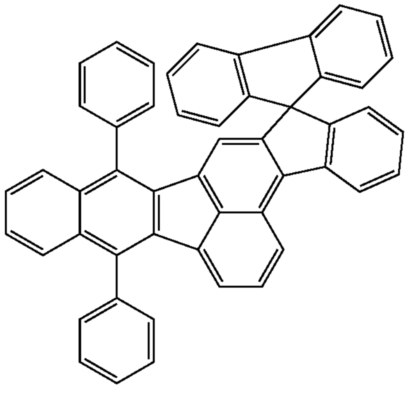
-continued
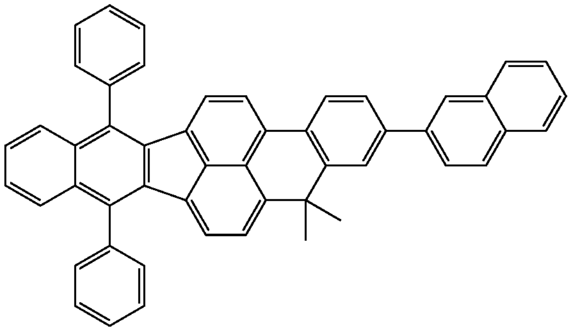
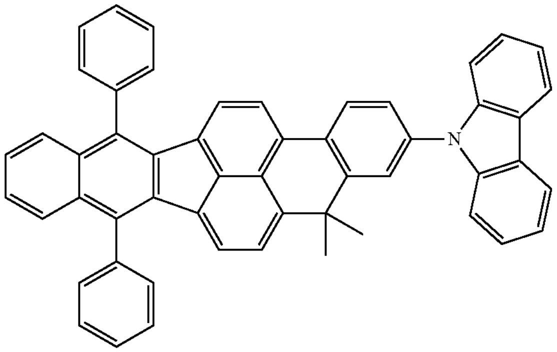
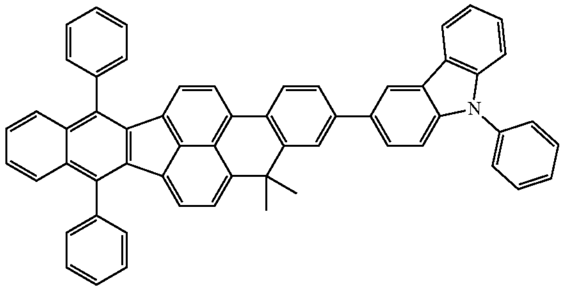
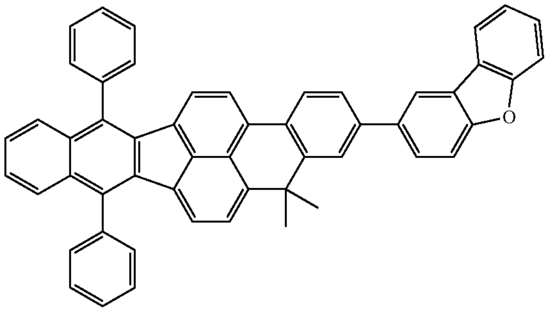
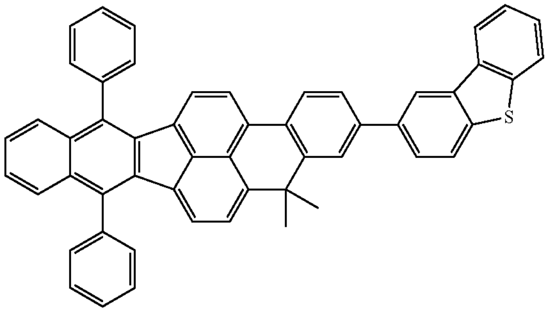

-continued
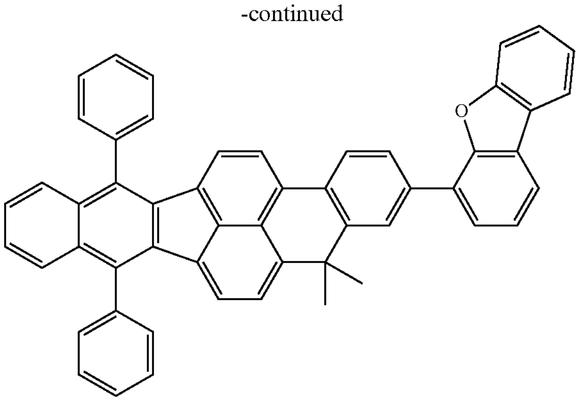
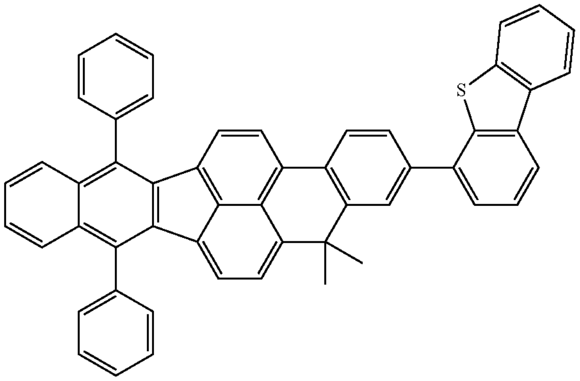
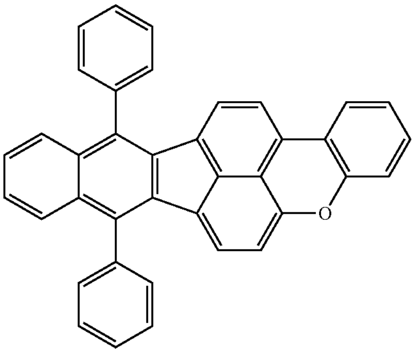
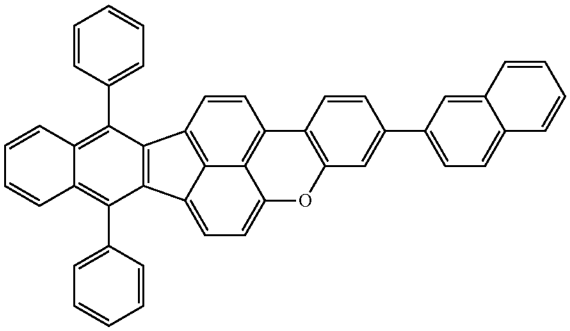
-continued
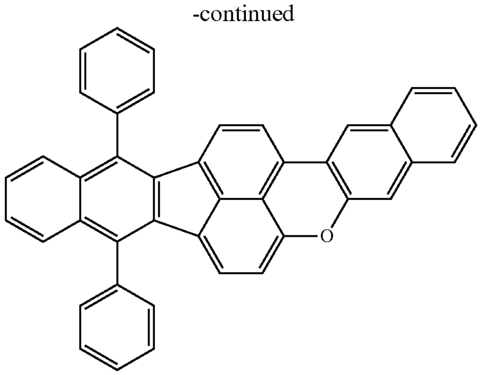
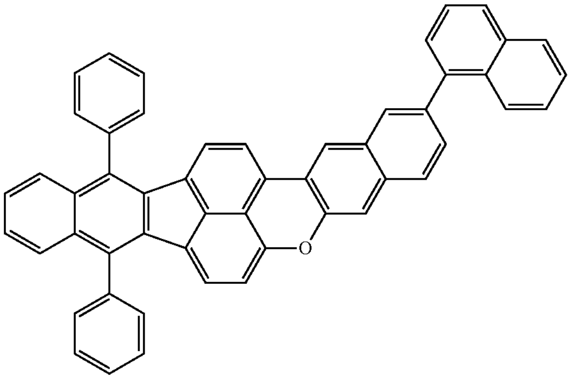
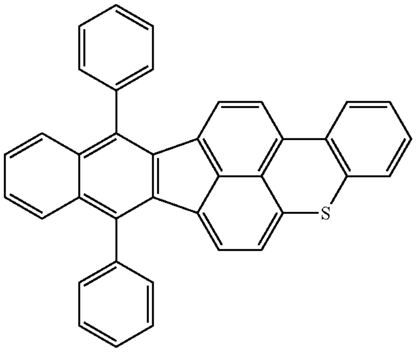
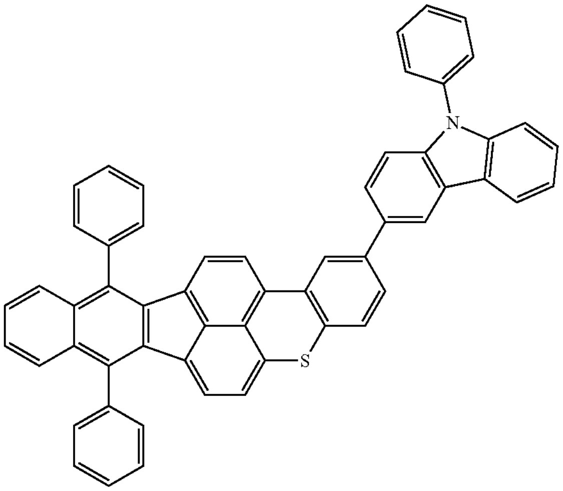

-continued
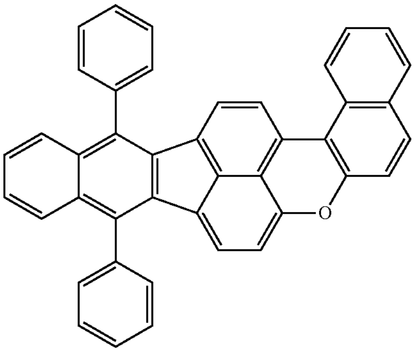
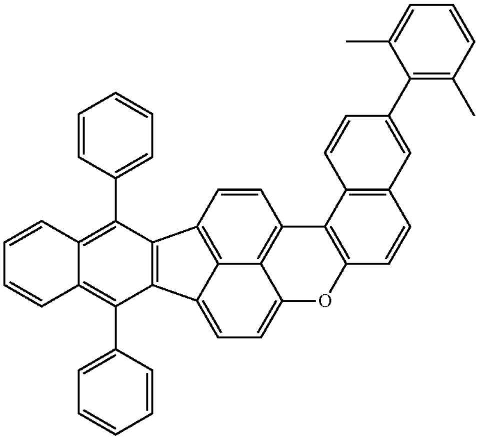
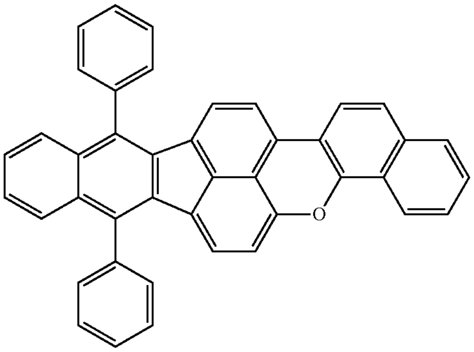
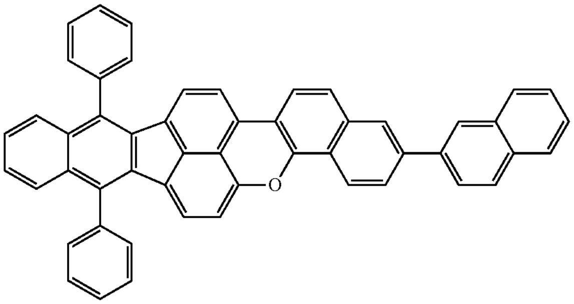
-continued
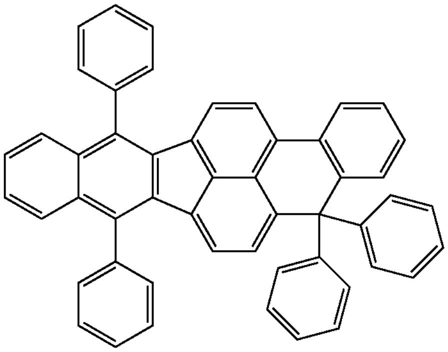
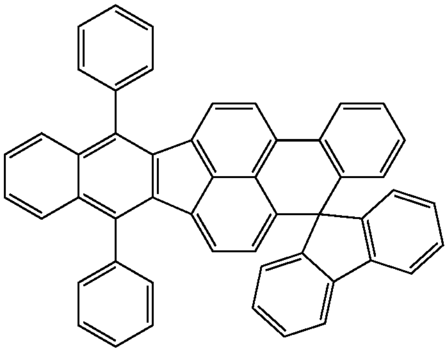
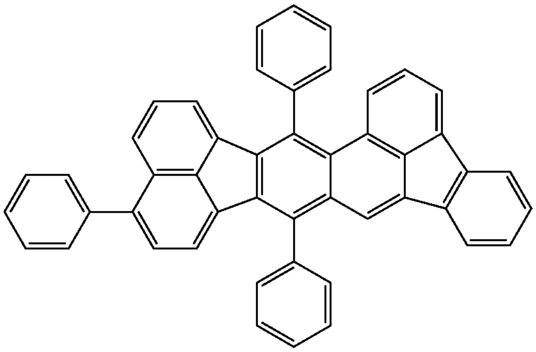
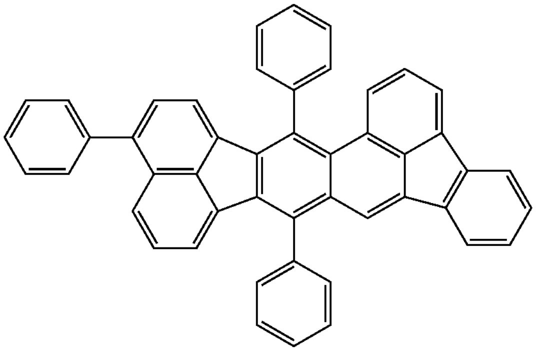

-continued
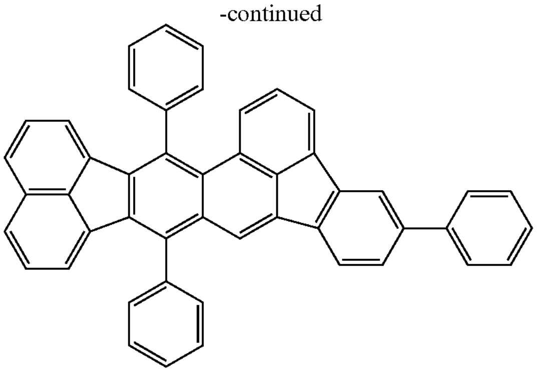
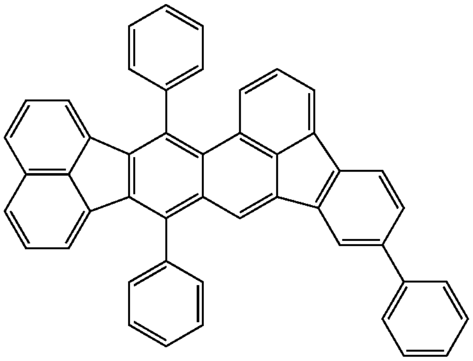
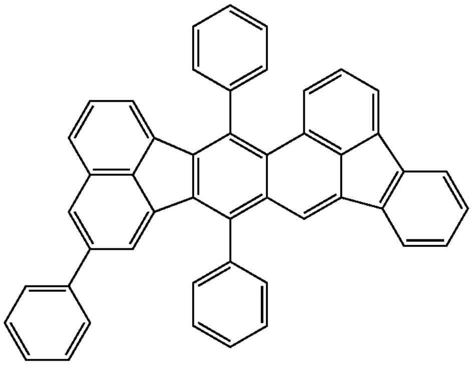
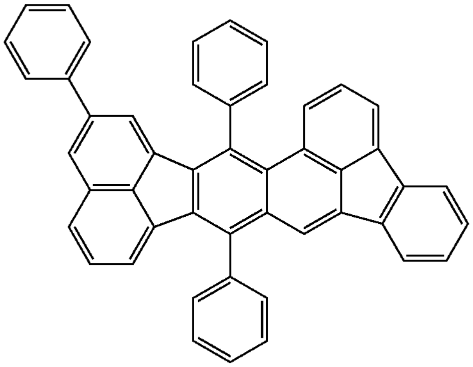
-continued
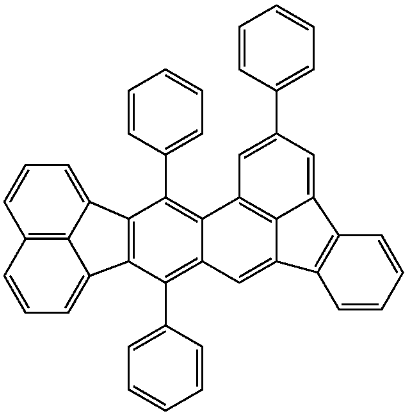
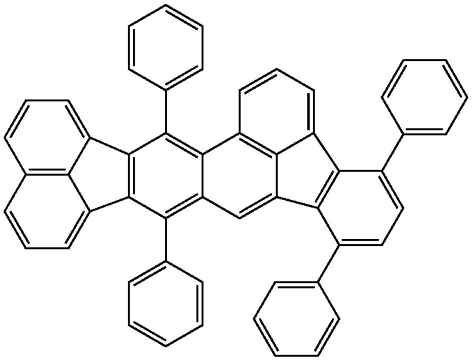
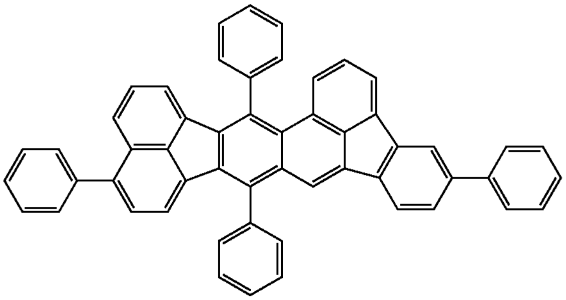
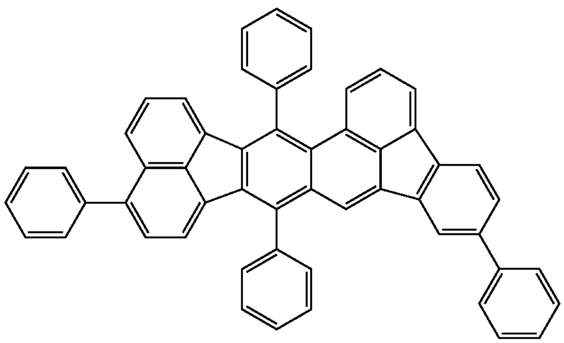

-continued
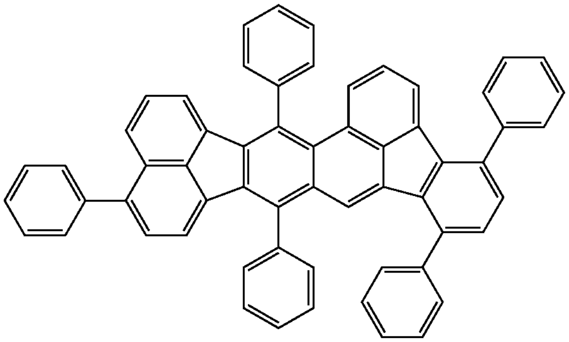
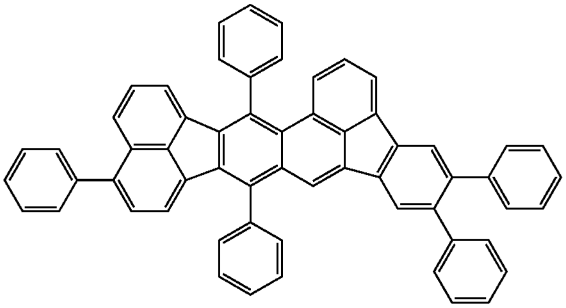
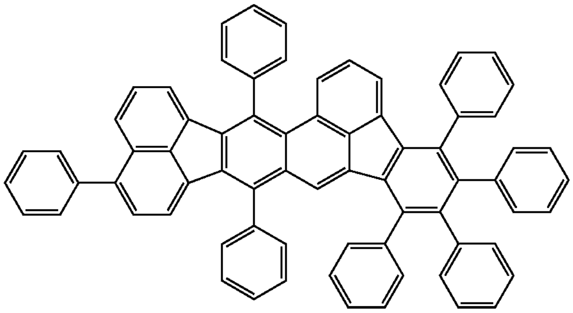
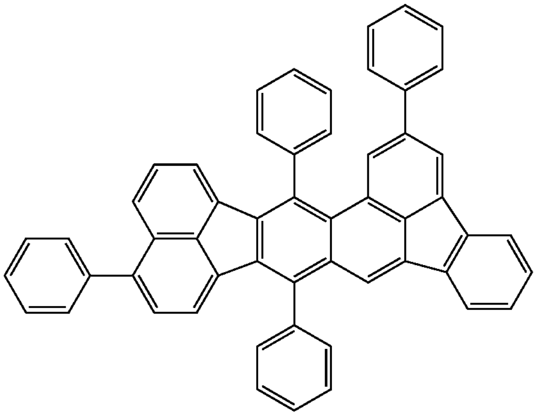
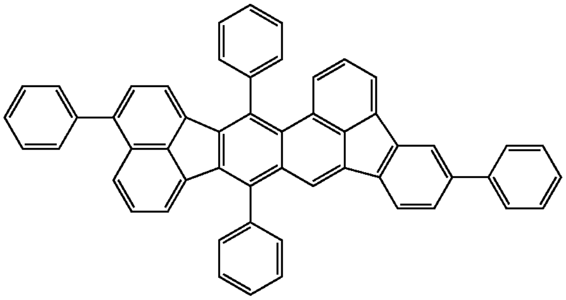
-continued
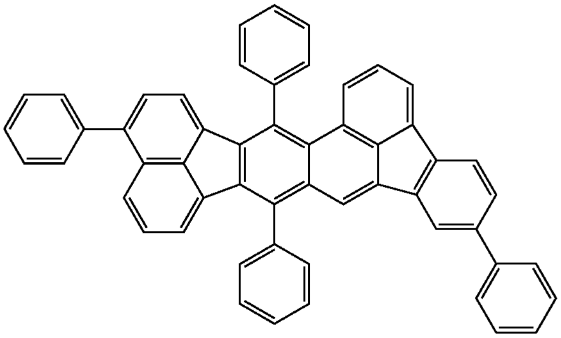
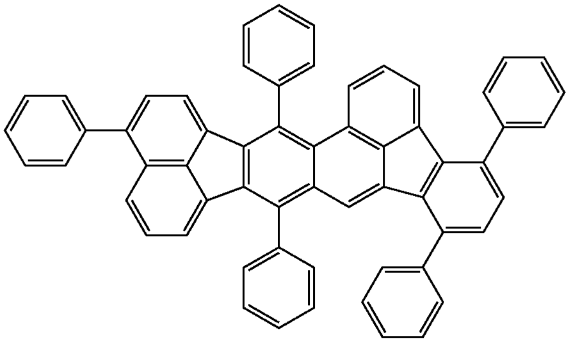
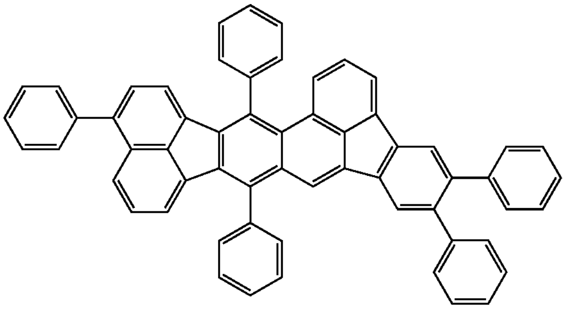
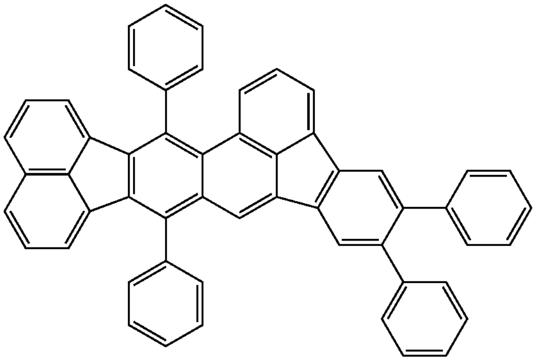
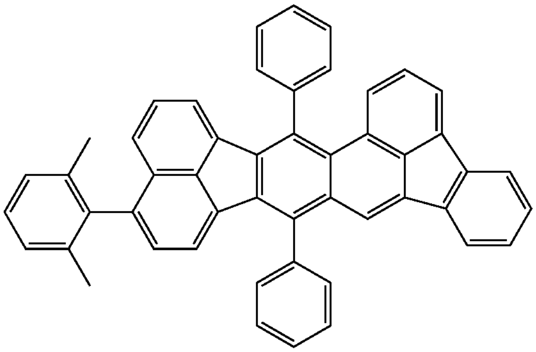

-continued
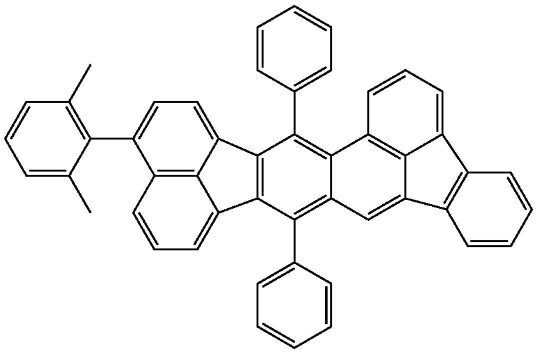
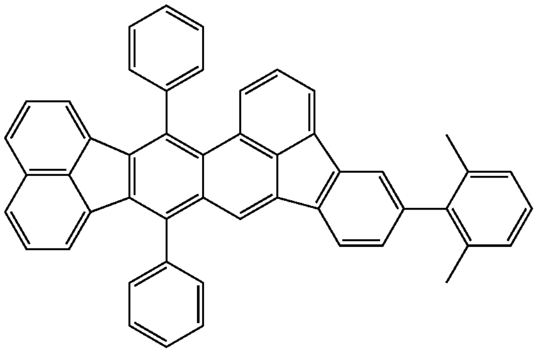
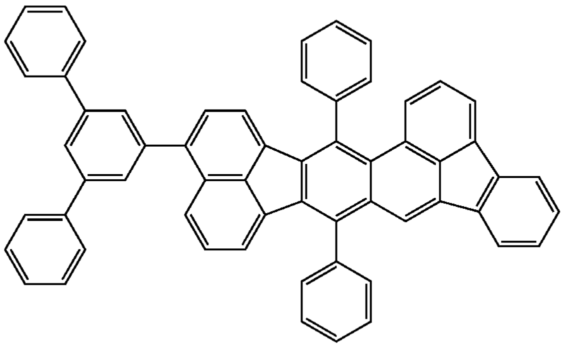
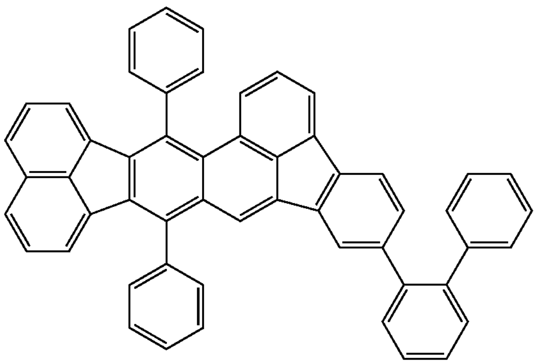
-continued
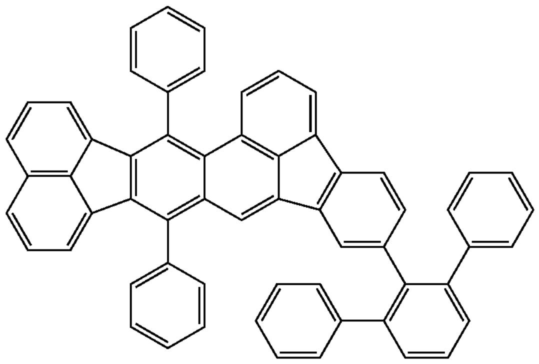
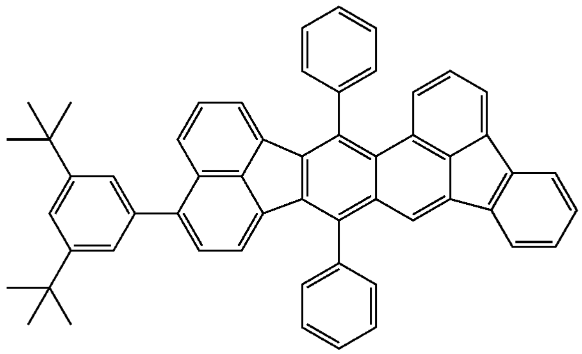
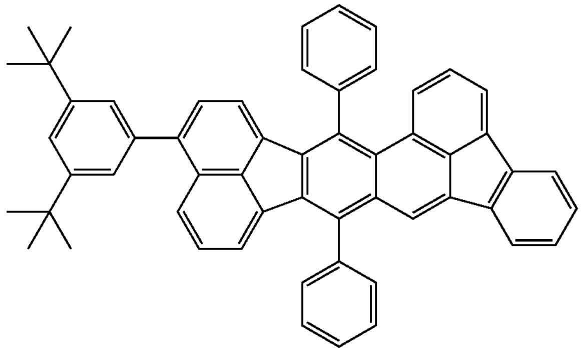
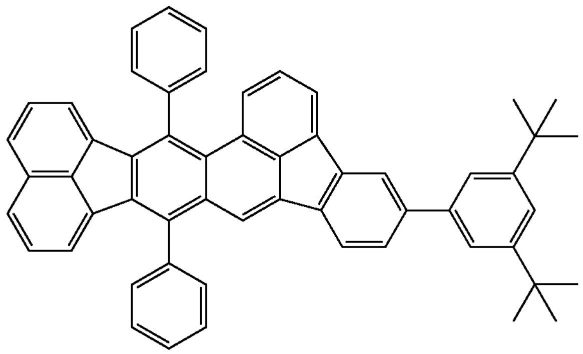

-continued
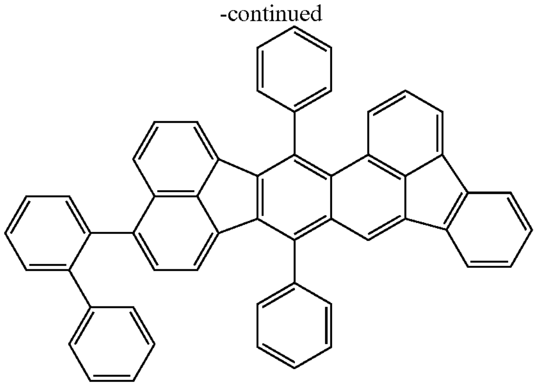
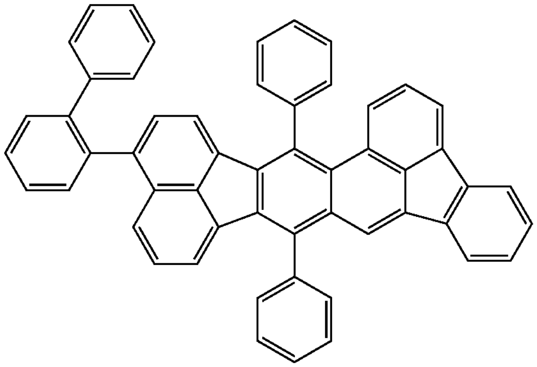
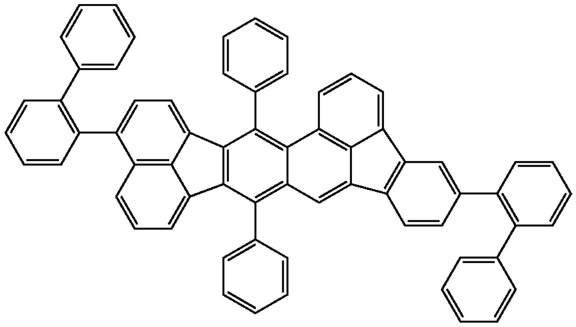
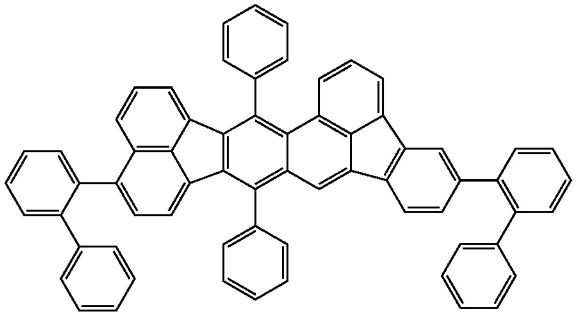
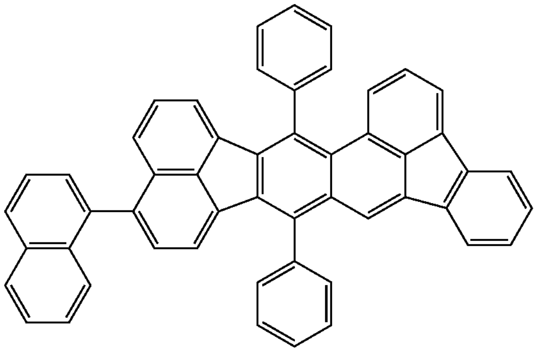
-continued
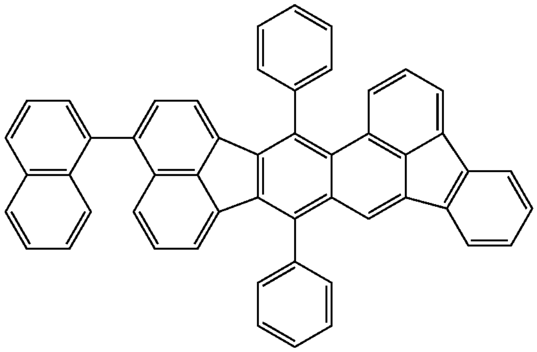
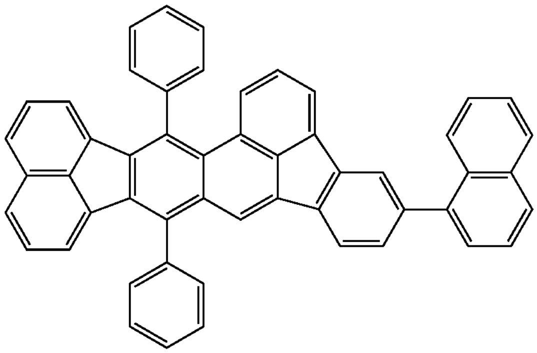
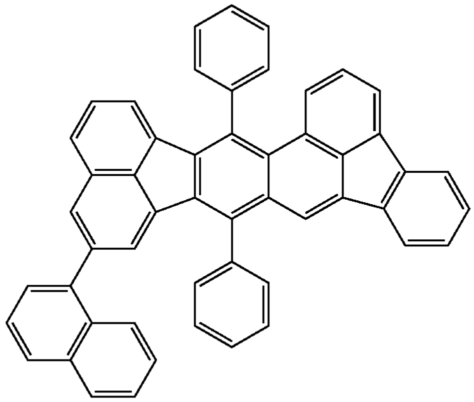
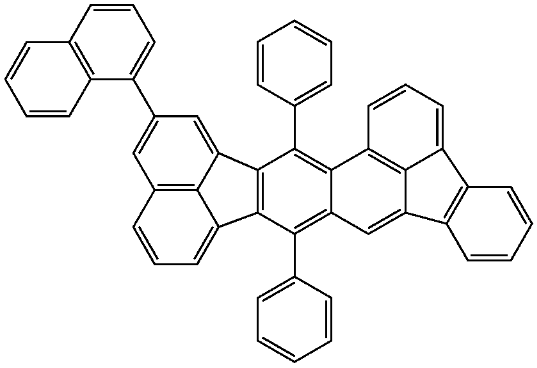

-continued
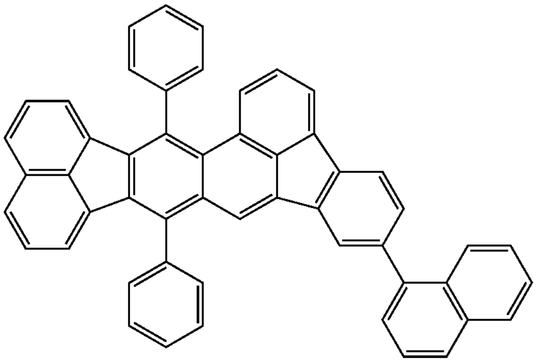
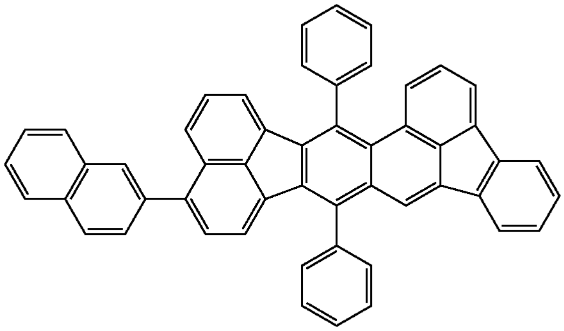
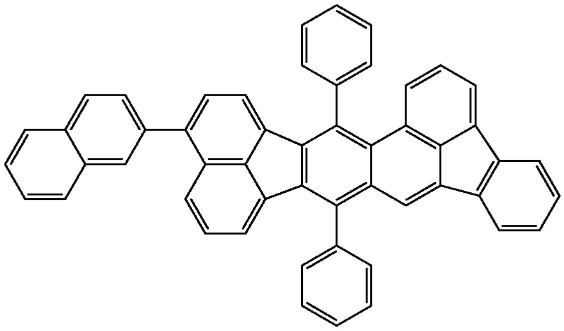
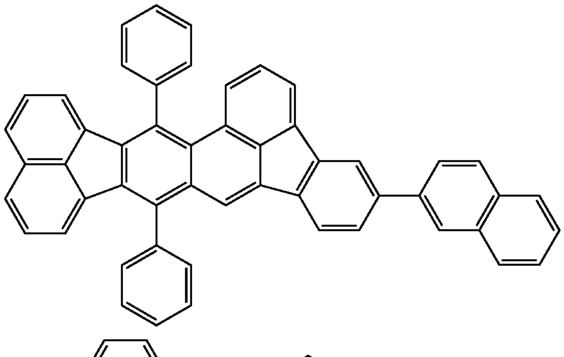
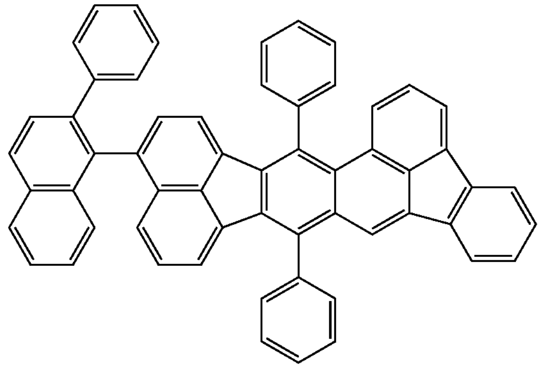
-continued
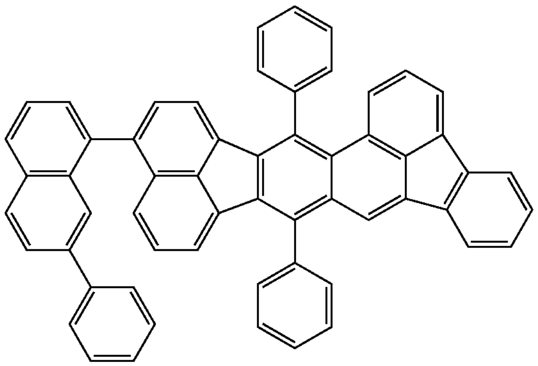
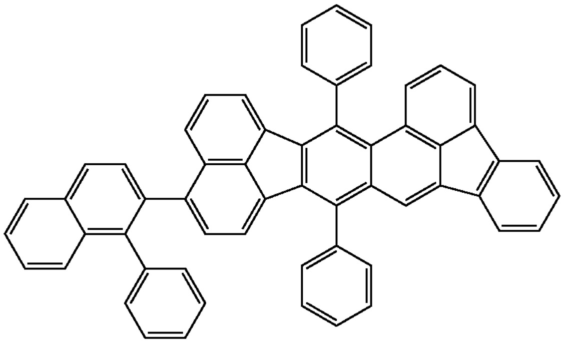
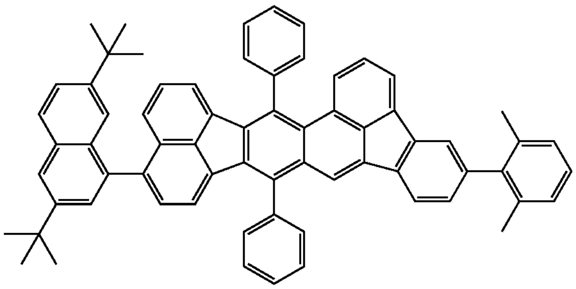
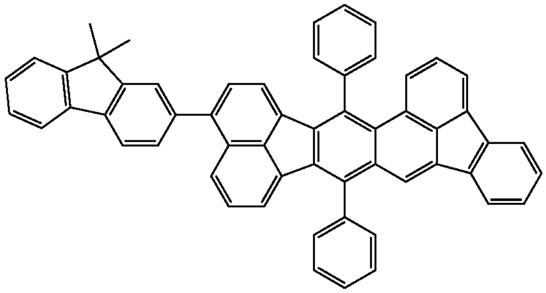
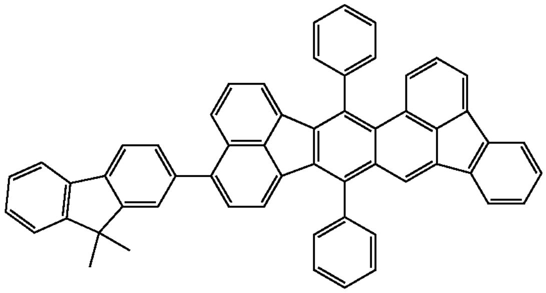

-continued
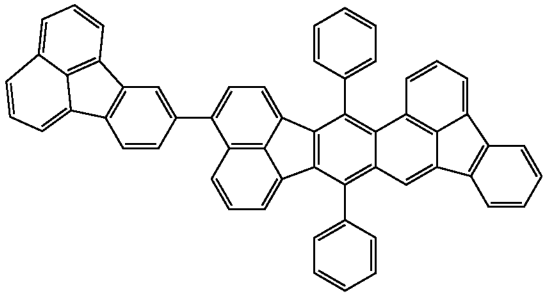
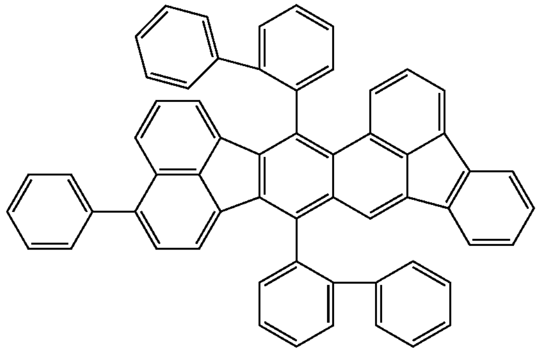
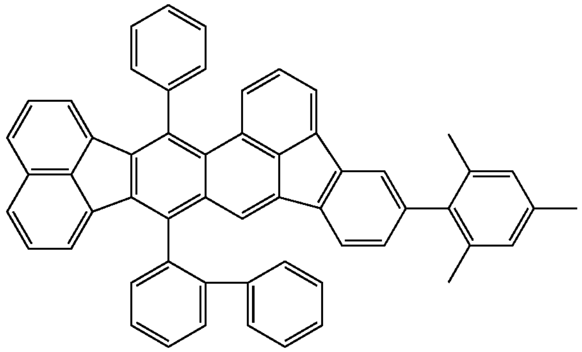
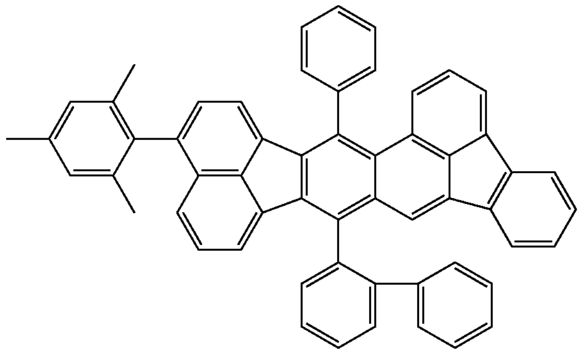
-continued
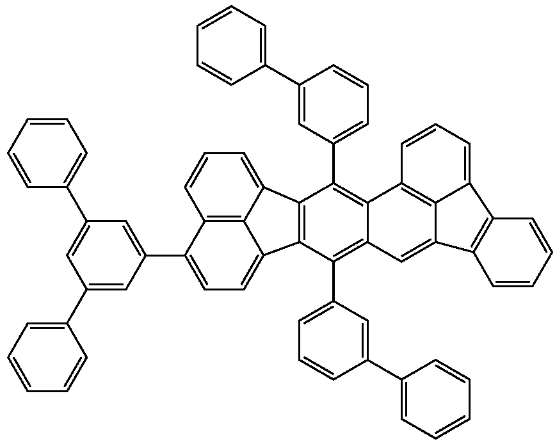
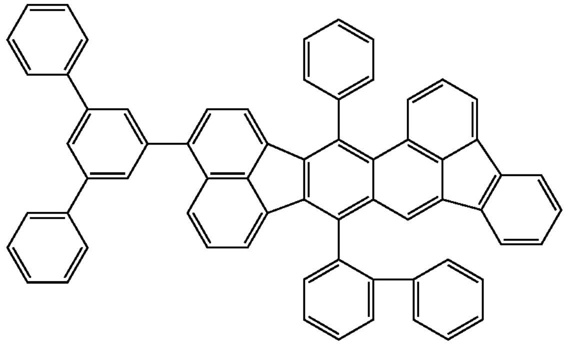
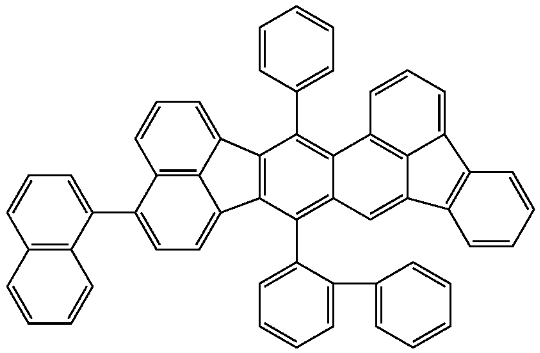
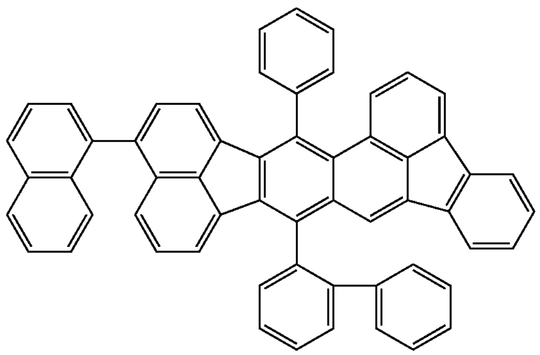

-continued
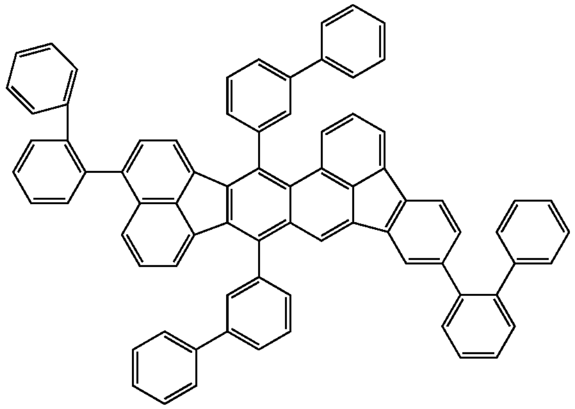
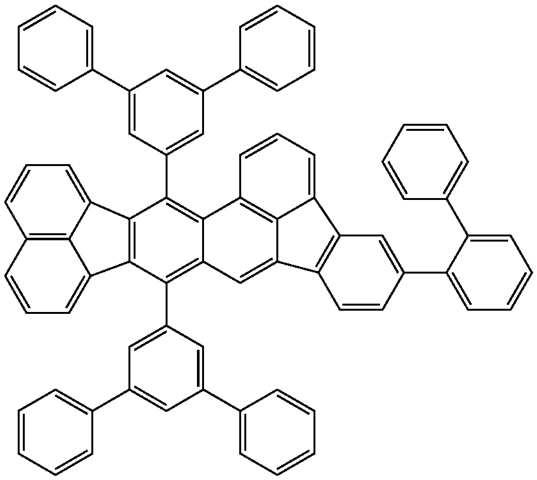
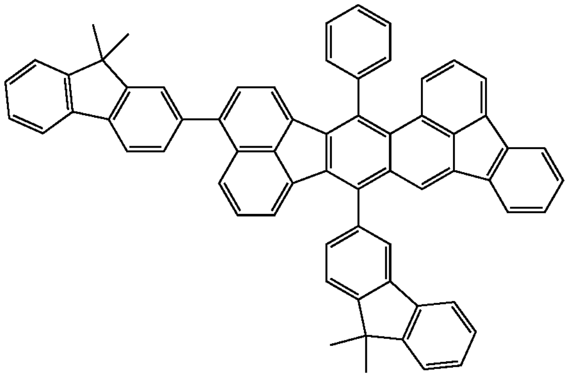
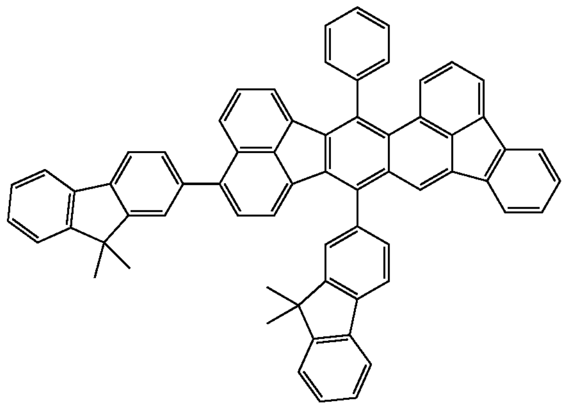
-continued
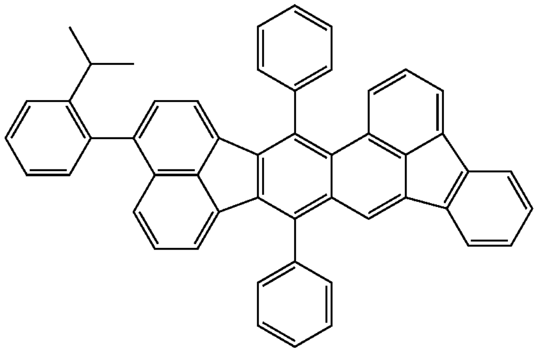
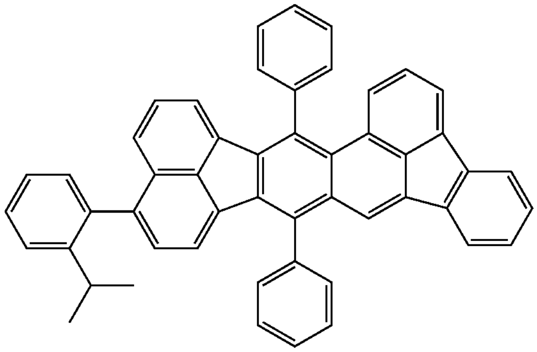
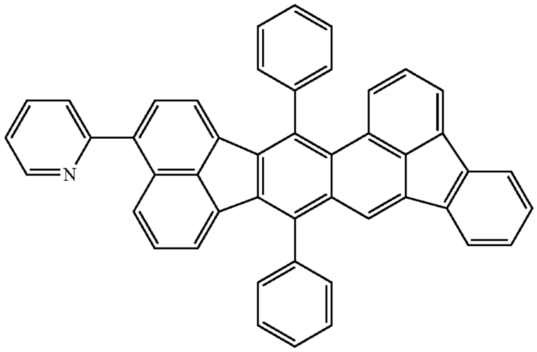
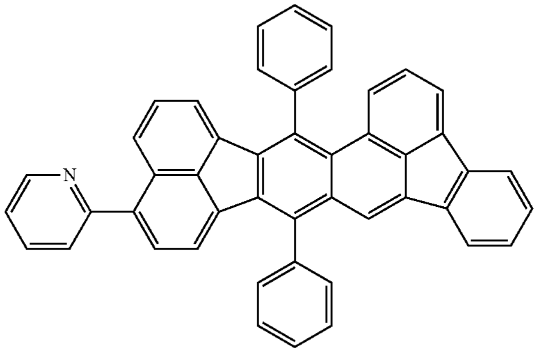

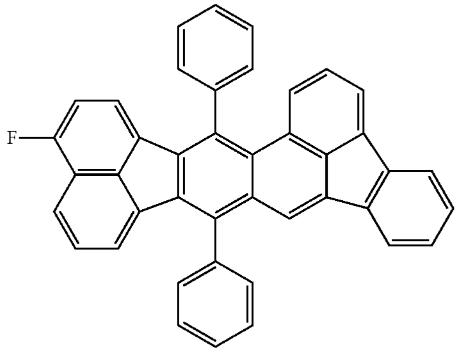
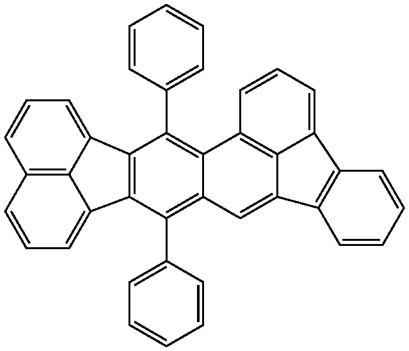
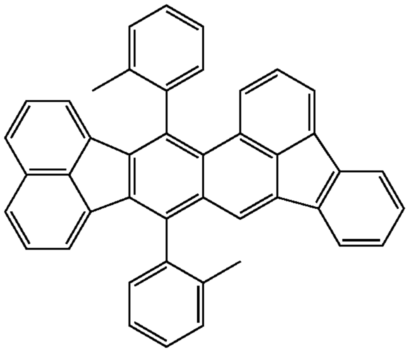
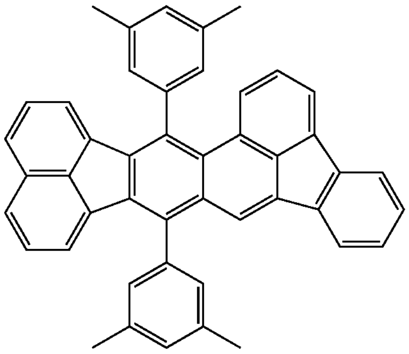
-continued
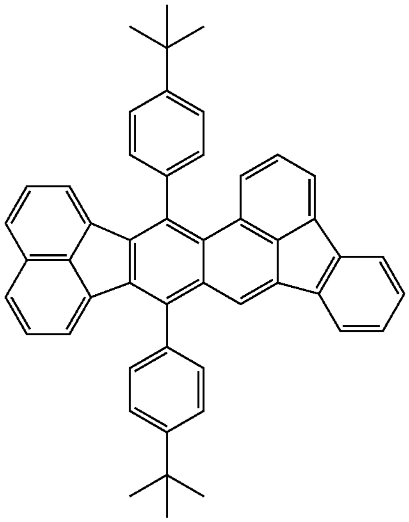
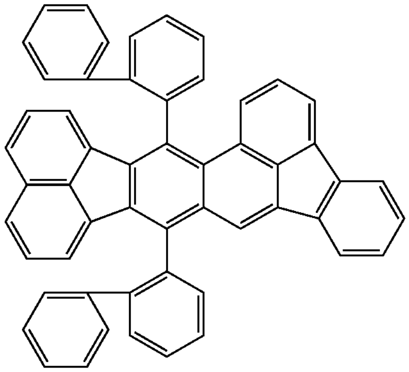
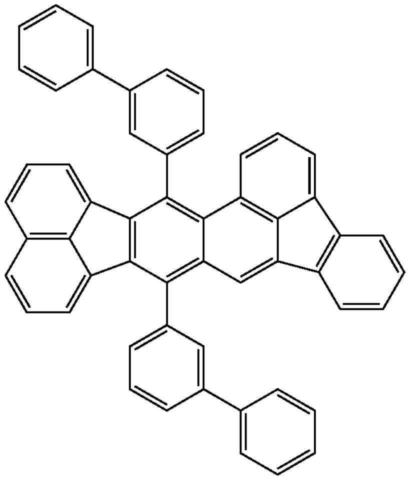

-continued
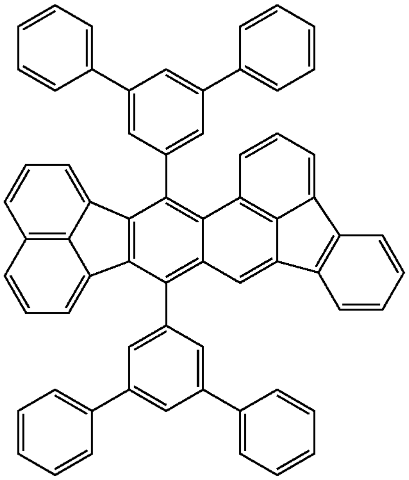
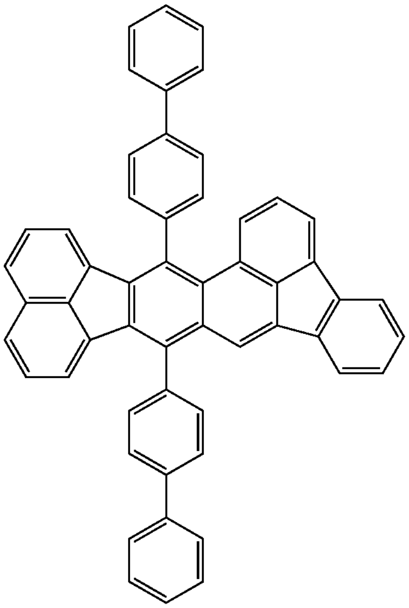
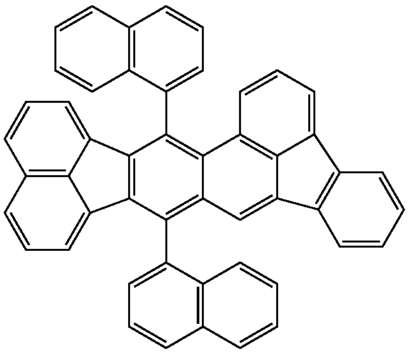
-continued
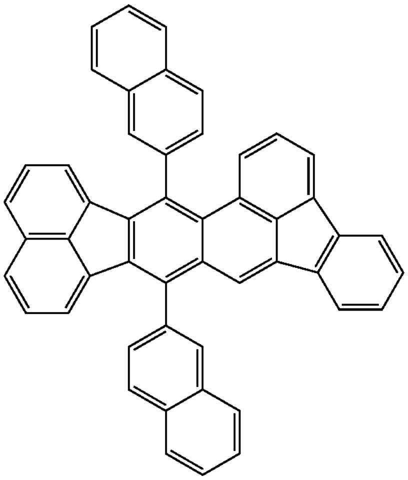
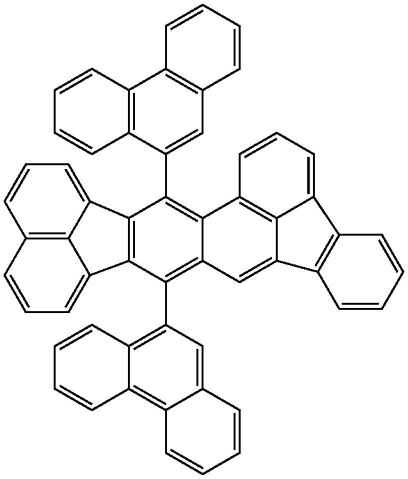
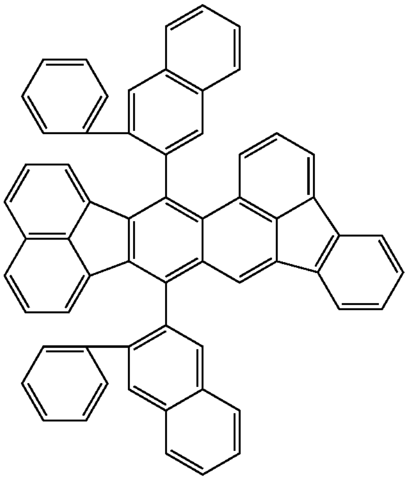

-continued
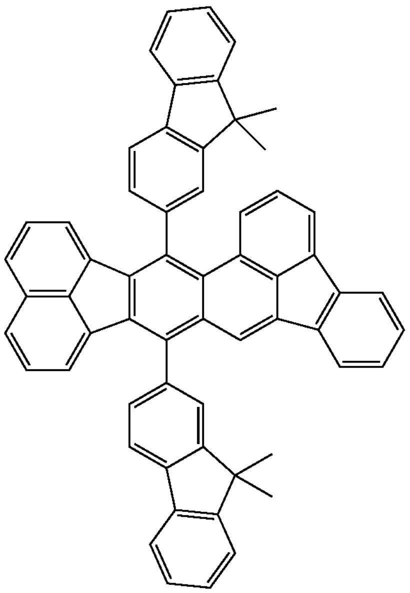
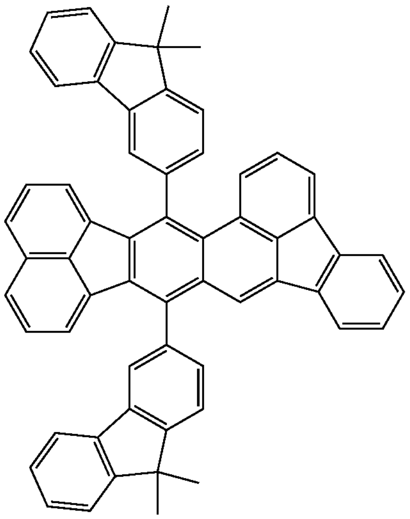
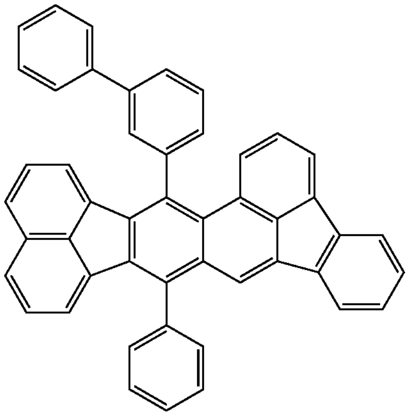
-continued
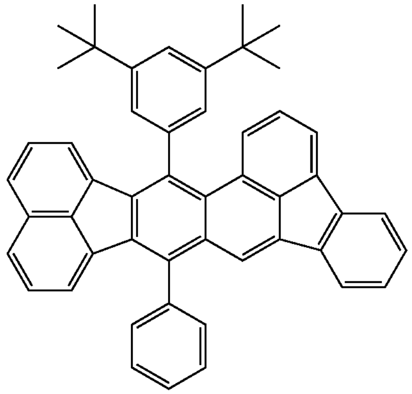
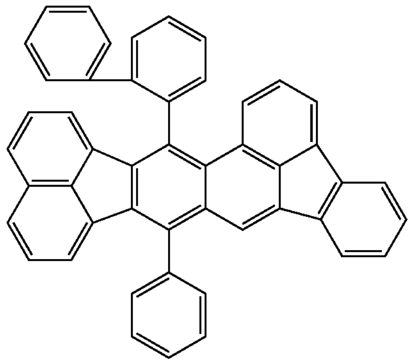
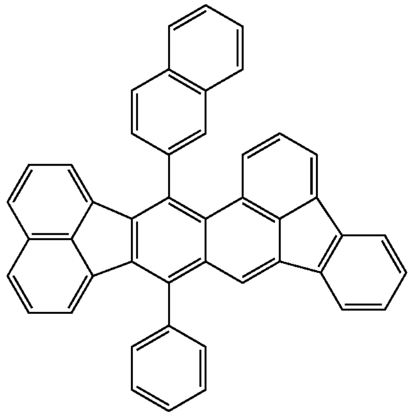
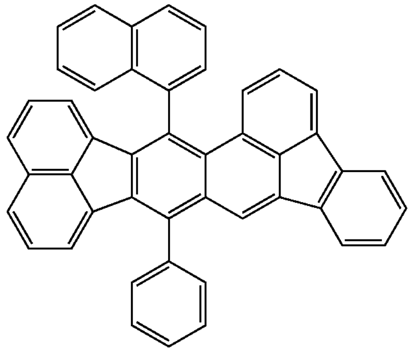

-continued
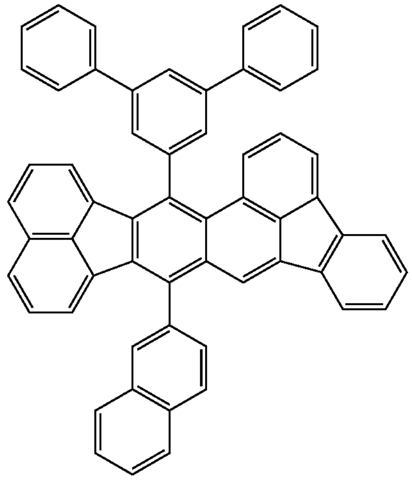
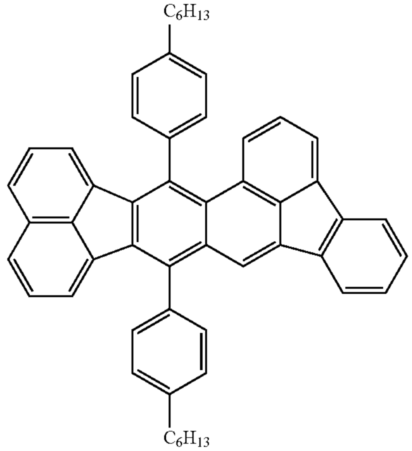
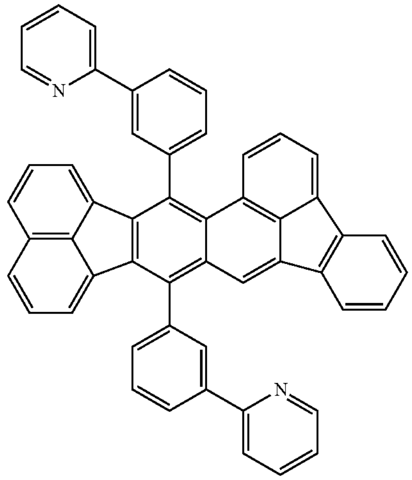
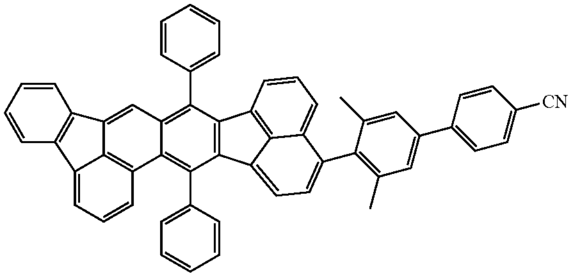
-continued
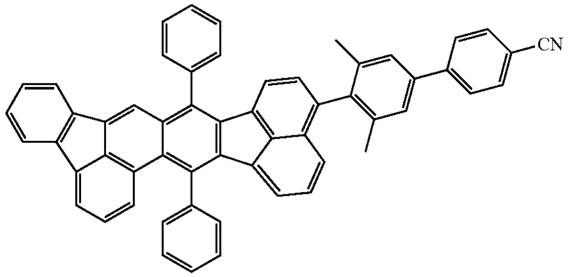
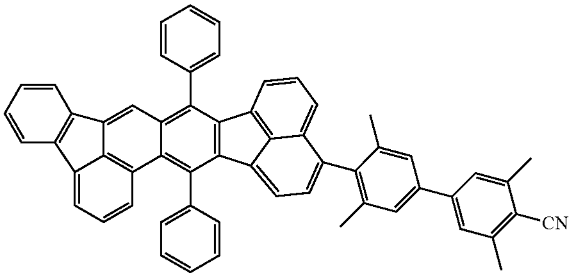
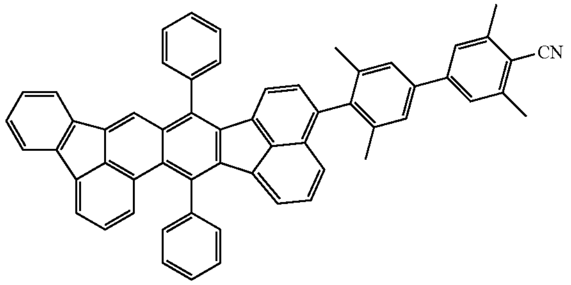
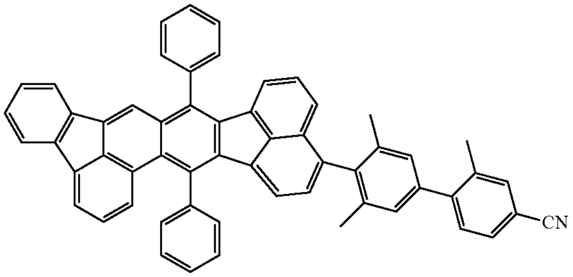
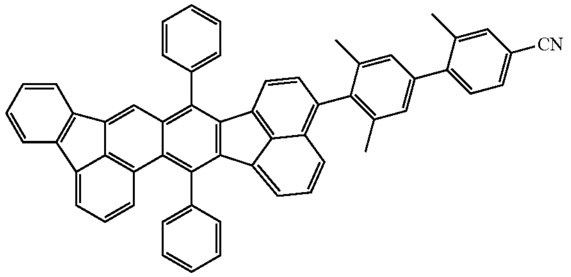
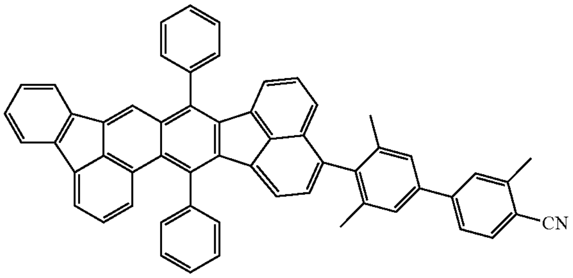

-continued

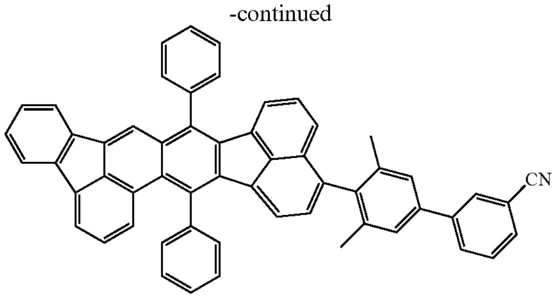

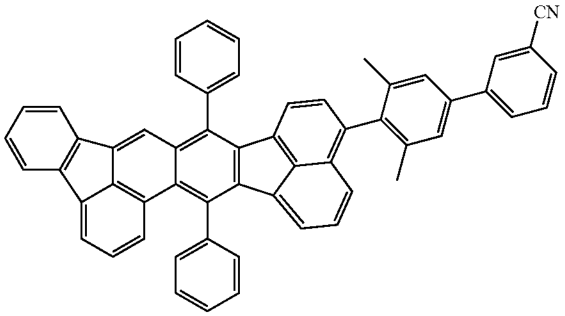

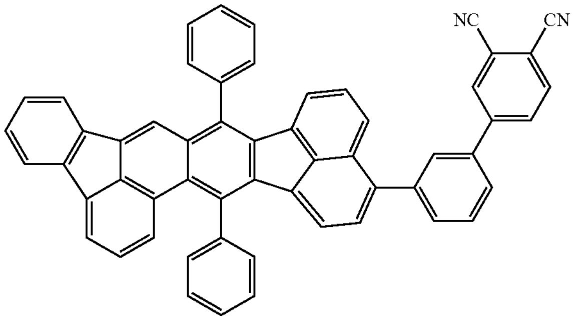

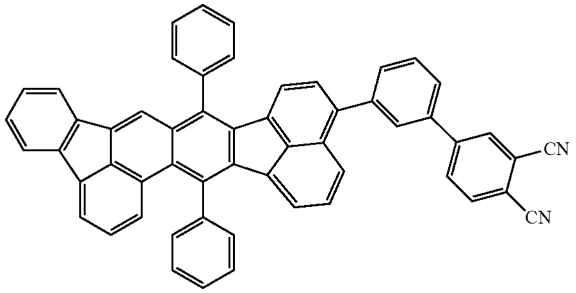

(Compound Represented by Formula (41))

(41)

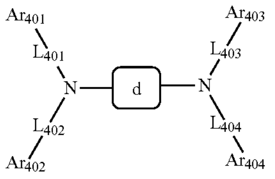

In the formula (41), a ring d is a substituted or unsubstituted aromatic hydrocarbon ring including 6 to 50 ring carbon atoms, or a substituted or unsubstituted heterocycle including 5 to 50 ring atoms.

$L_{401}$ to $L_{404}$ are independently a single bond, a substituted or unsubstituted arylene group including 6 to 50 ring carbon atoms, or a substituted or unsubstituted divalent heterocyclic group including 5 to 50 ring atoms.

$Ar_{401}$ to $Ar_{404}$ are independently a substituted or unsubstituted alkyl group including 1 to 50 carbon atoms, a substituted or unsubstituted cycloalkyl group including 3 to 50 ring carbon atoms, a substituted or unsubstituted aryl group including 6 to 50 ring carbon atoms, or a substituted or unsubstituted monovalent heterocyclic group including 5 to 50 ring atoms.

Provided that, when the ring d is a substituted or unsubstituted aromatic hydrocarbon ring including 10 to 50 ring carbon atoms, two or more of $Ar_{401}$ to $Ar_{404}$ are independently an aryl group including 6 to 50 carbon atoms substituted by an alkyl group including 1 to 50 carbon atoms, or a monovalent heterocyclic group including 5 to 50 ring atoms substituted by an alkyl group including 1 to 50 carbon atoms.

In one embodiment, the compound represented by the formula (41) is a compound represented by the following formula (41-1).

(41-1)

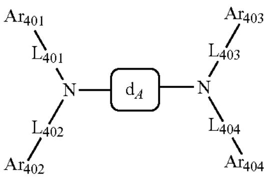

In the formula (41-1), $L_{401}$ to $L_{404}$ and $Ar_{401}$ to $Ar_{404}$ are as defined in the formula (41).

A ring $d_A$ is a substituted or unsubstituted aromatic hydrocarbon ring including 10 to 50 ring carbon atoms.

In one embodiment, the ring $d_A$ is a substituted or unsubstituted pyrene ring.

In one embodiment, the substituent of the ring $d_A$ is a substituted or unsubstituted alkyl group including 1 to 50 carbon atoms, a substituted or unsubstituted cycloalkyl group including 3 to 50 ring carbon atoms, —$Si(R_{901})(R_{902})(R_{903})$, a halogen atom, a cyano group, or a nitro group.

$R_{901}$ to $R_{903}$ are independently a hydrogen atom, a substituted or unsubstituted alkyl group including 1 to 50 carbon atoms, a substituted or unsubstituted cycloalkyl group including 3 to 50 ring carbon atoms, a substituted or unsubstituted aryl group including 6 to 50 ring carbon atoms, or a substituted or unsubstituted monovalent heterocyclic group including 5 to 50 ring atoms. When two or more of each of $R_{901}$ to $R_{903}$ are present, the two or more of each of $R_{901}$ to $R_{903}$ are the same as or different from each other.

In one embodiment, the compound represented by the formula (41) is a compound represented by the following formula (41-2).

(41-2)

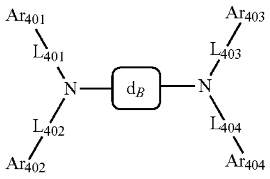

In the formula (41-2), $L_{401}$ to $L_{404}$ and $Ar_{401}$ to $Ar_{404}$ are as defined in the formula (41). A ring $d_B$ is a substituted or unsubstituted heterocycle including 12 to 50 ring atoms.

In one embodiment, the ring d in the formula (41) is a substituted or unsubstituted divalent group selected from the group consisting of structures represented by each of the following formulas.

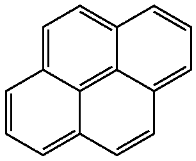

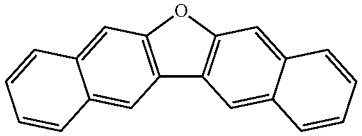

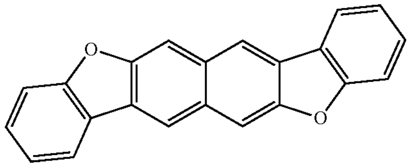

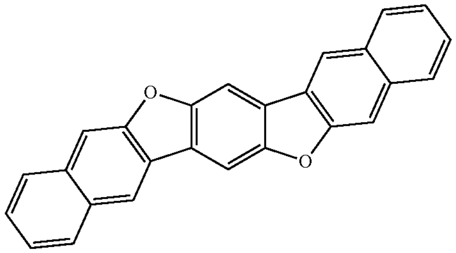

-continued

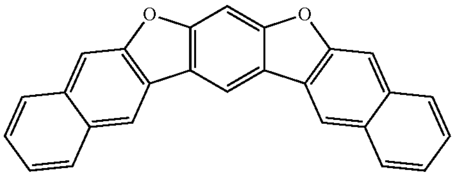

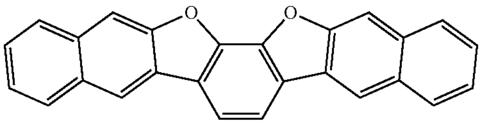

In one embodiment, the ring d in the formula (41) is a substituted or unsubstituted pyrene ring.

In one embodiment, the substituent of the ring d, the ring $d_A$, or the ring $d_B$ is a substituted or unsubstituted alkyl group including 1 to 50 carbon atoms, a substituted or unsubstituted cycloalkyl group including 3 to 50 ring carbon atoms, —$Si(R_{901})(R_{902})(R_{903})$, a halogen atom, a cyano group, or a nitro group.

$R_{901}$ to $R_{903}$ are independently a hydrogen atom, a substituted or unsubstituted alkyl group including 1 to 50 carbon atoms, a substituted or unsubstituted cycloalkyl group including 3 to 50 ring carbon atoms, a substituted or unsubstituted aryl group including 6 to 50 ring carbon atoms, or a substituted or unsubstituted monovalent heterocyclic group including 5 to 50 ring atoms. When two or more of each of $R_{901}$ to $R_{903}$ are present, the two or more of each of $R_{901}$ to $R_{903}$ are the same as or different from each other.

Specific examples of the compound represented by the formula (41) will be described, but are illustrative only, and the compound represented by the formula (41) is not limited to the following specific examples.

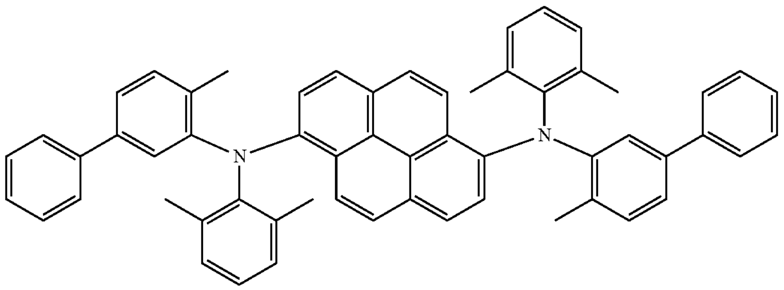

-continued
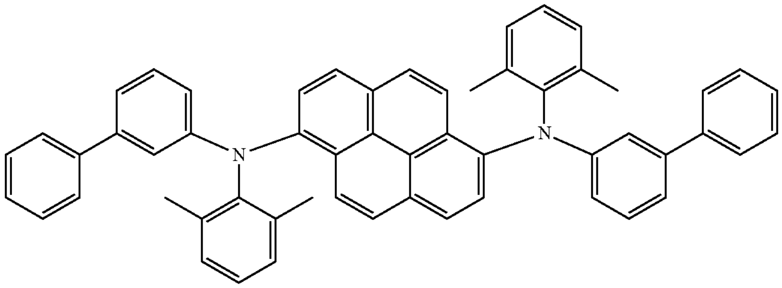
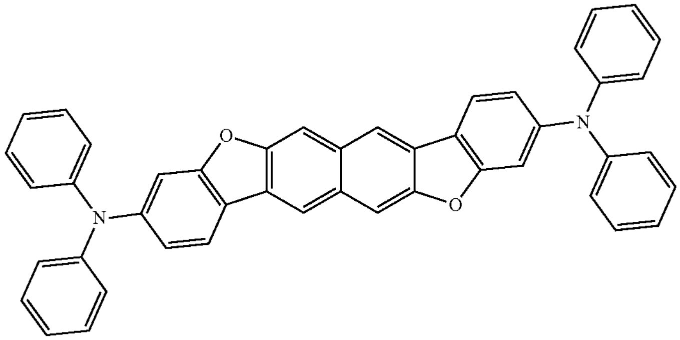
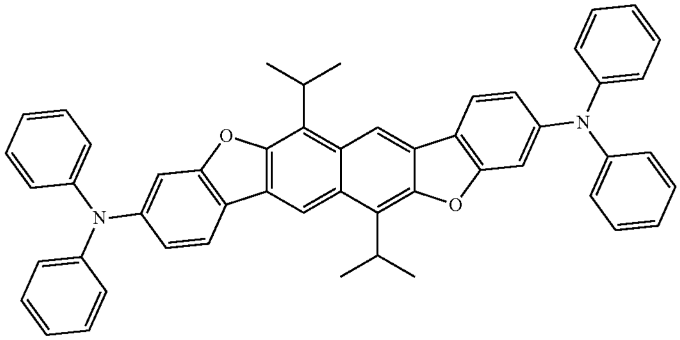
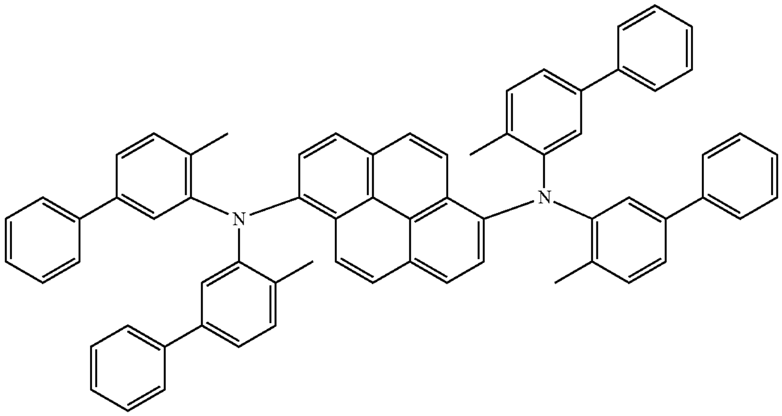
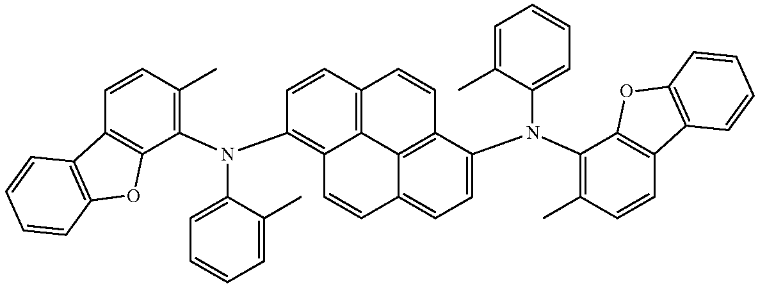

-continued
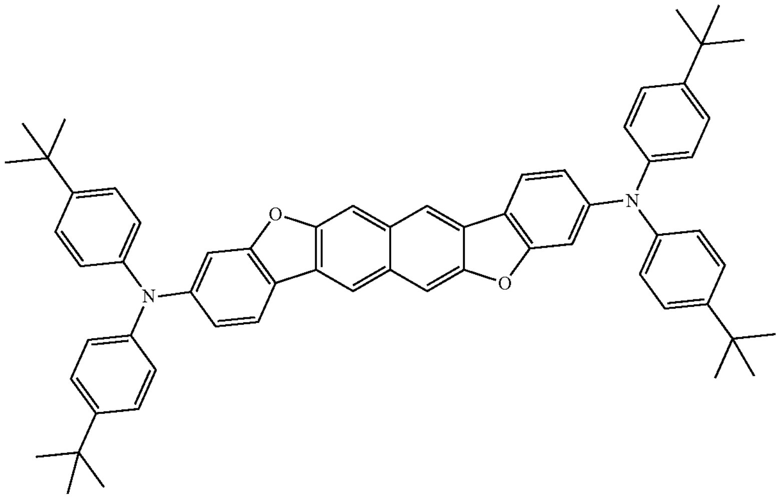
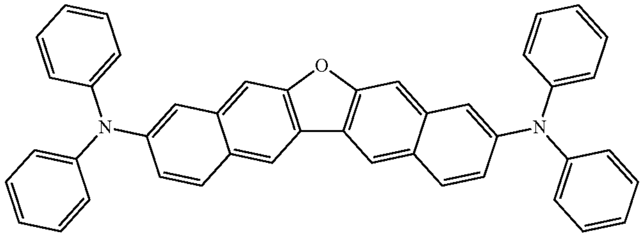
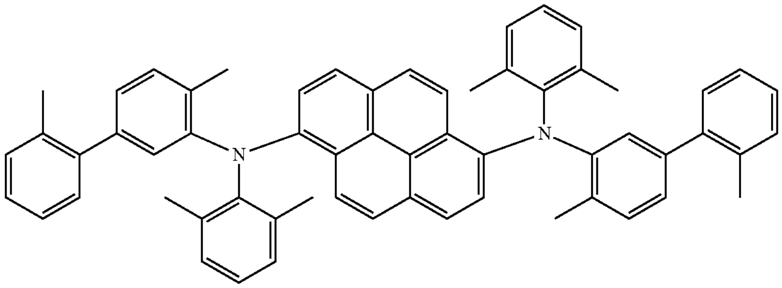
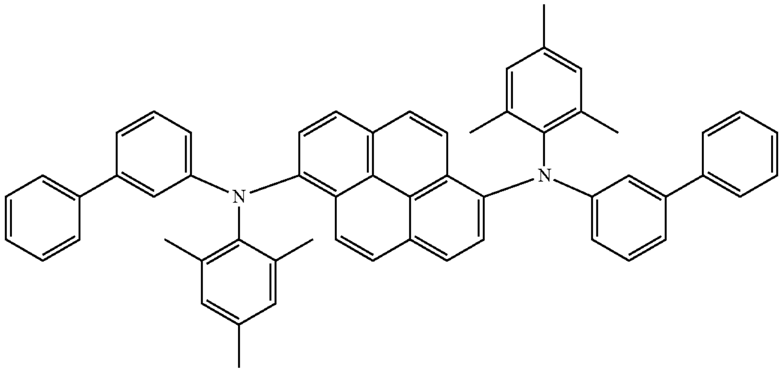
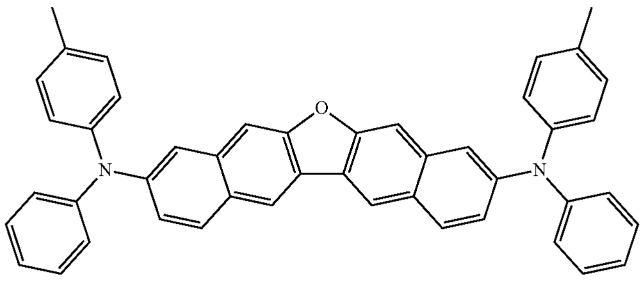

-continued
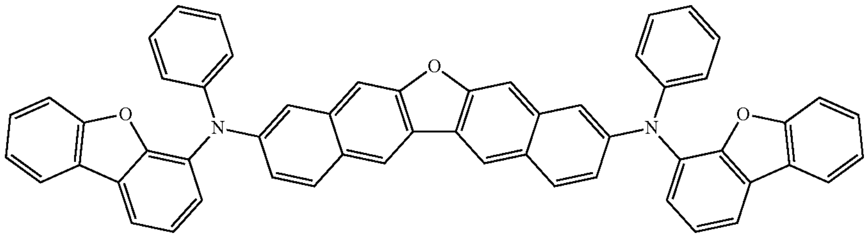
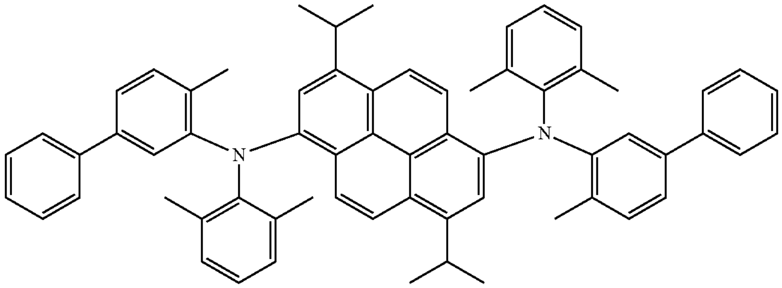
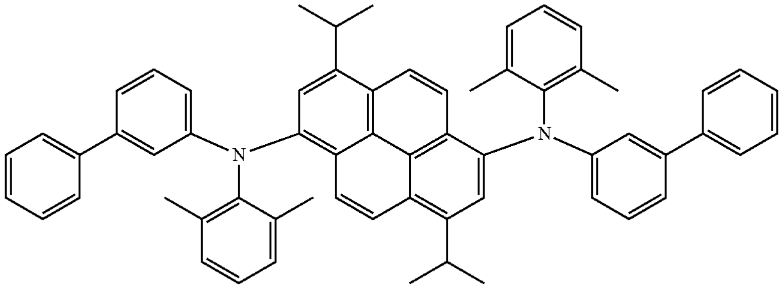
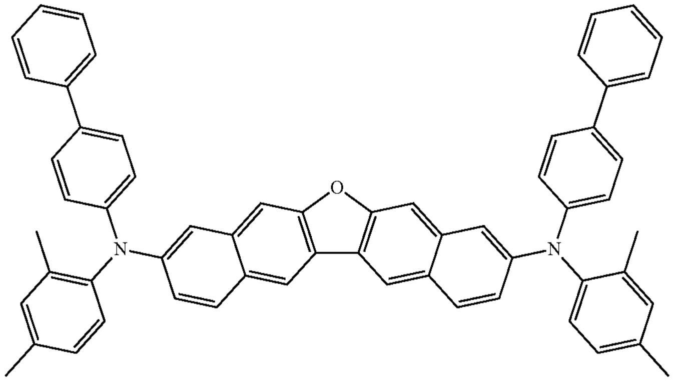
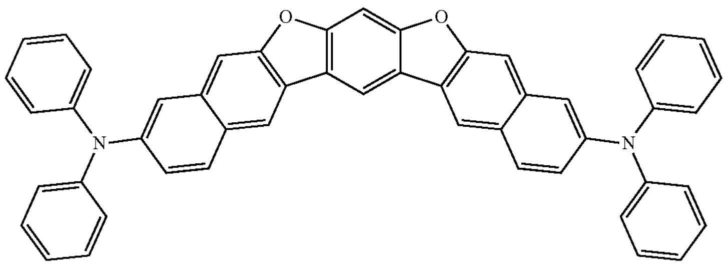

-continued
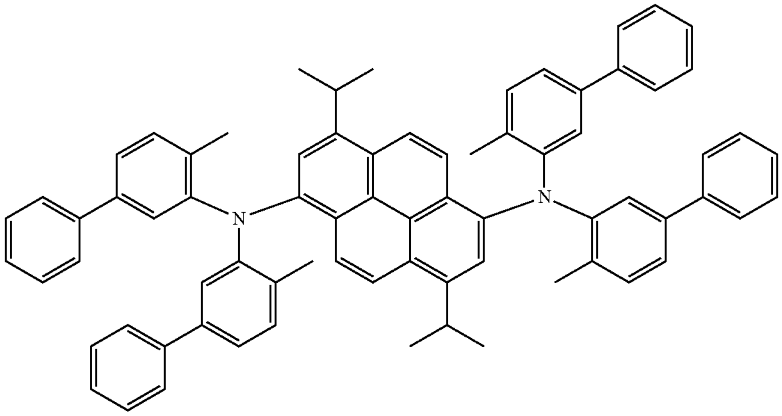
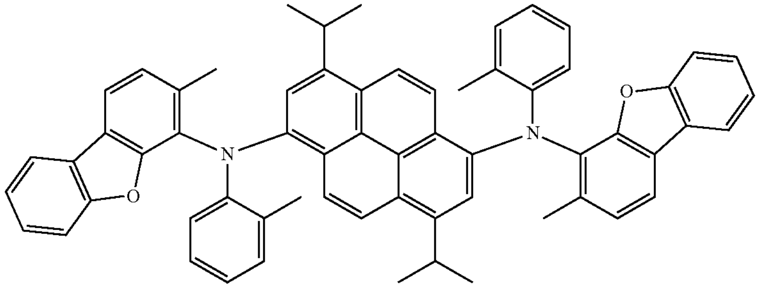
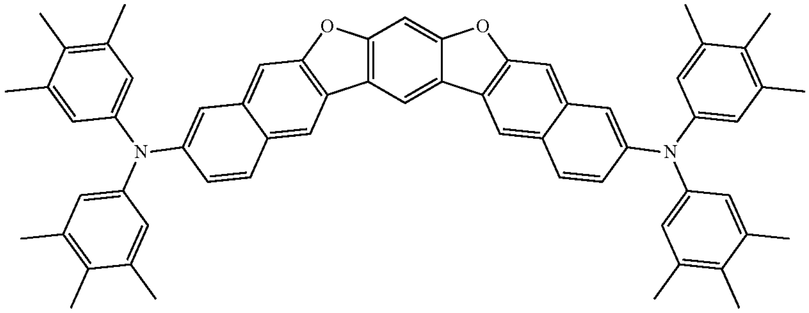
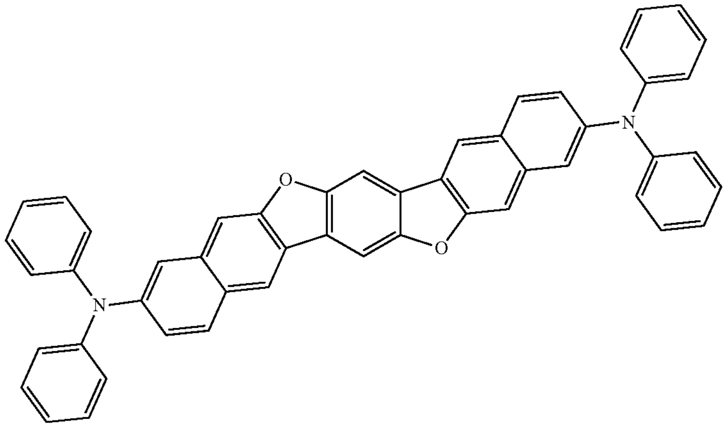
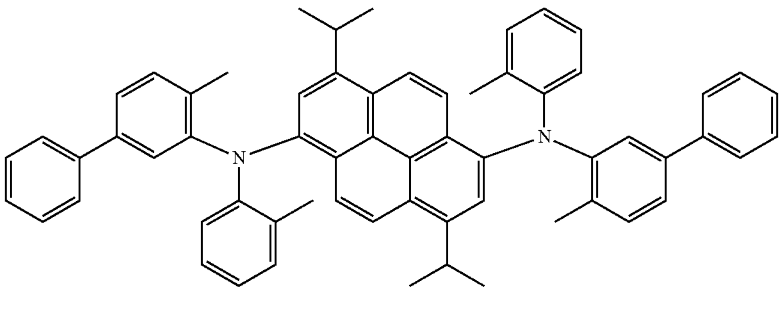

-continued
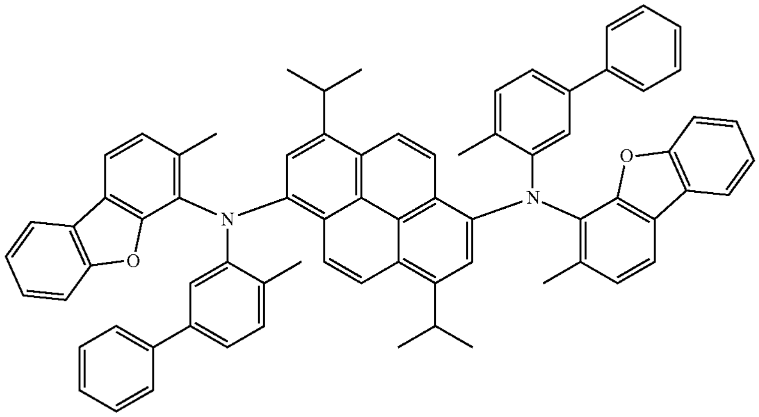
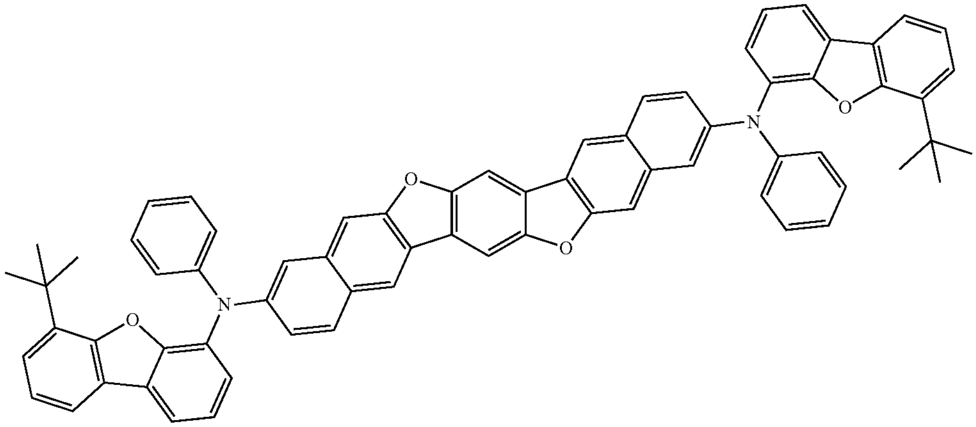
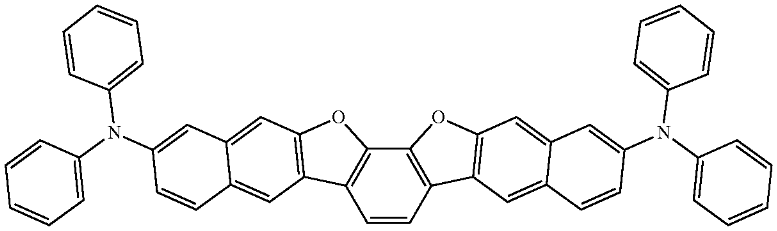
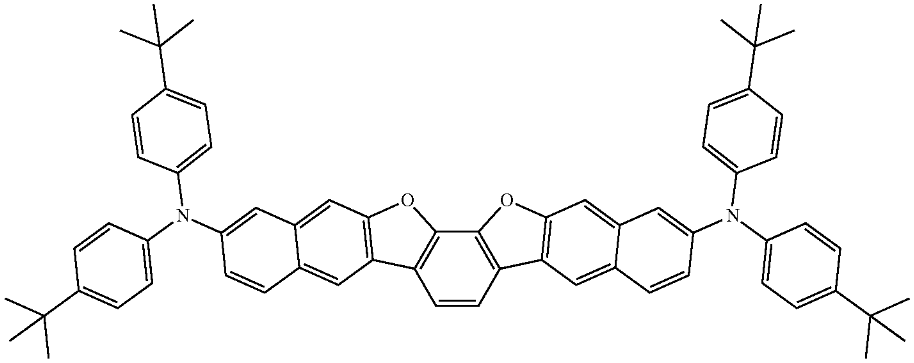

-continued

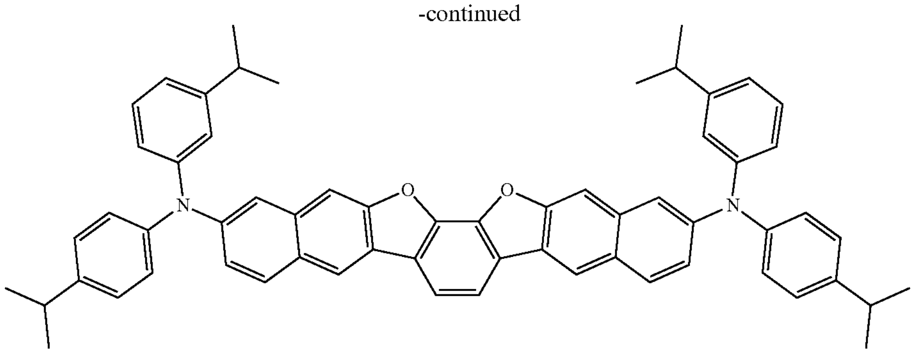

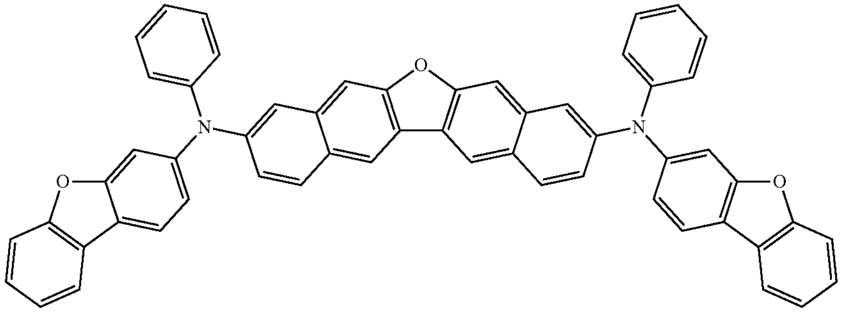

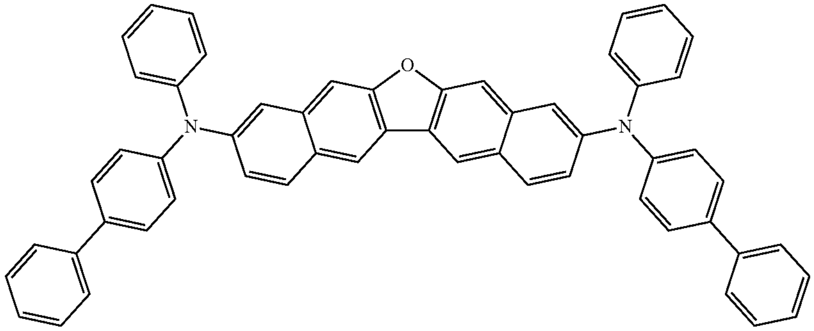

Details of each substituent in the formulas (1), (11), (21), (31), and (41) are as described in the section of [Definition] in this specification.

In one embodiment, in the compounds represented by each of the formulas (1), (11), (21), (31), and (41), the substituent in the case of "substituted or unsubstituted" is a group selected from the group consisting of an unsubstituted alkyl group including 1 to 50 carbon atoms, an unsubstituted alkenyl group including 2 to 50 carbon atoms, an unsubstituted alkynyl group including 2 to 50 carbon atoms, an unsubstituted cycloalkyl group including 3 to 50 ring carbon atoms, —$Si(R_{901})(R_{902})(R_{903})$,

—O—$(R_{904})$,

—S—$(R_{907})$,

—$N(R_{906})(R_{907})$ (where $R_{901}$ to $R_{907}$ are independently a hydrogen atom, a substituted or unsubstituted alkyl group including 1 to 50 carbon atoms, a substituted or unsubstituted cycloalkyl group including 3 to 50 ring carbon atoms, a substituted or unsubstituted aryl group including 6 to 50 ring carbon atoms, or a substituted or unsubstituted monovalent heterocyclic group including 5 to 50 ring atoms. When two or more of each of $R_{901}$ to $R_{907}$ are present, the two or more of each of $R_{901}$ to $R_{907}$ are the same as or different from each other.), a halogen atom, a cyano group, a nitro group, an unsubstituted aryl group including 6 to 50 ring carbon atoms, and an unsubstituted monovalent heterocyclic group including 5 to 50 ring atoms.

In one embodiment, in the compounds represented by each of the formulas (1), (11), (21), (31), and (41), the substituent in the case of "substituted or unsubstituted" is a group selected from the group, consisting of an alkyl group including 1 to 50 carbon atoms, an aryl group including 6 to 50 ring carbon atoms, and a monovalent heterocyclic group including 5 to 50 ring atoms.

In one embodiment, in the compounds represented by each of the formulas (1), (11), (21), (31), and (41), the substituent in the case of "substituted or unsubstituted" is a group selected from the group consisting of an alkyl group including 1 to 18 carbon atoms, an aryl group including 6 to 18 ring carbon atoms, and a monovalent heterocyclic group including 5 to 18 ring atoms.

Specific examples of the above groups are as described in the section of [Definitions] of this specification.

The organic EL device according to an aspect of the invention can be contain conventionally known materials and can be applied conventionally known device configurations as long as it is as described above an organic electroluminescence device including a cathode, an anode, and an organic layer disposed between the cathode and the anode, and the organic layer contains a compound represented by the formula (1) and a compound A having a Stokes shift of 20 nm or smaller and an emission peak wavelength of 440 nm to 465 nm, and the effect of the invention is not impaired by the conventionally known materials or the device configurations.

The compound represented by the formula (1) and the compound A may be contained in any layer of the plurality of organic layers when a plurality of organic layers are present between the cathode and the anode.

In one embodiment, the organic layer includes an emitting layer, and the emitting layer contains the compound represented by the formula (1) and the compound A.

Parts which can be used in the organic EL device according to an aspect of the invention, materials for forming respective layers, other than the above-mentioned compounds, and the like, will be described below.

(Substrate)

A substrate is used as a support of an emitting device. As the substrate, glass, quartz, plastics or the like can be used, for example. Further, a flexible substrate may be used. The flexible substrate means a bendable (flexible) substrate, and specific examples thereof include a plastic substrate formed of polycarbonate, polyvinyl chloride, or the like.

(Mode)

For the anode formed on the substrate, metals, alloys, electrically conductive compounds, mixtures thereof, and the like, which have a large work function (specifically 4.0 eV or more) are preferably used. Specific examples thereof include indium oxide-tin oxide (ITO: Indium Tin Oxide), indium oxide-zinc oxide, indium oxide-tin oxide containing silicon or silicon oxide, indium oxide containing zinc oxide, tungsten oxide, and graphene. In addition thereto, specific examples thereof include gold (Au), platinum (Pt), a nitride of a metallic material (for example, titanium nitride), and the like.

(Hole-Injecting Layer)

A hole-injecting layer is a layer containing a substance having high hole-injecting property. As such a substance having high hole-injecting property, molybdenum oxide, titanium oxide, vanadium oxide, rhenium oxide, ruthenium oxide, chromium oxide, zirconium oxide, hafnium oxide, tantalum oxide, silver oxide, tungsten oxide, manganese oxide, an aromatic amine compound, or a polymer compound (oligomers, dendrimers, polymers, etc.) can be given.

(Hole-Transporting Layer)

A hole-transporting layer is a layer containing a substance having high hole-transporting property. For the hole-transporting layer, an aromatic amine compound, a carbazole derivative, an anthracene derivative, or the like can be used. A polymer compound such as poly(N-vinylcarbazole) (abbreviation: PVK) and poly(4-vinyltriphenylamine) (abbreviation: PVTPA) can also be used. However, a substance other than the above-described substances may be used as long as the substance has a higher hole-transporting property in comparison with an electron-transporting property. It should be noted that the layer containing the material having a high hole-transporting property may be formed into not only a monolayer, but also a stacked layer in which two or more layers formed of the above-described materials are stacked.

(Guest Material for Emitting Layer)

The emitting layer is a layer containing a substance having a high emitting property, and various materials can be used for forming it. In addition to the compounds represented by each of the formulas (11) to (41) and the compound A, for example, a fluorescent compound that emits fluorescence or a phosphorescent compound that emits phosphorescence can be used as the substance having a high emitting property. The fluorescent compound is a compound which can emit from a singlet excited state, and the phosphorescent compound is a compound which can emit from a triplet excited state.

As a blue fluorescent emitting material which can be used for an emitting layer, pyrene derivatives, styrylamine derivatives, chrysene derivatives, fluoranthene derivatives, fluorene derivatives, diamine derivatives, triarylamine derivatives, and the like can be used. As a green fluorescent emitting material which can be used for an emitting layer, aromatic amine derivatives and the like can be used. As a red fluorescent emitting material which can be used for an emitting layer, tetracene derivatives, diamine derivatives and the like can be used.

As a blue phosphorescent emitting material which can be used for an emitting layer, metal complexes such as iridium complexes, osmium complexes, platinum complexes and the like are used. As a green phosphorescent emitting material which can be used for an emitting layer, iridium complexes and the like are used. As a red phosphorescent emitting material which can be used for an emitting layer, metal complexes such as iridium complexes, platinum complexes, terbium complexes, europium complexes and the like are used.

(Host Material for Emitting Layer)

The emitting layer may have a constitution in which the substance having a high emitting property (guest material) as mentioned above is dispersed in another substance (host material). As the substance for dispersing the substance having a high emitting property, a variety of substances can be used, and it is preferable to use a substance having a higher lowest unoccupied orbital level (LUMO level) and a lower highest occupied orbital level (HOMO level) rather than the substance having a high emitting property.

As the substance (host material) for dispersing the substance having a high luminous property, in addition to the compound represented by the formula (1), 1) a metal complex such as an aluminum complex, a beryllium complex, or a zinc complex, 2) a heterocyclic compound such as an oxadiazole derivative, a benzimidazole derivative, or a phenanthroline derivative, 3) a condensed aromatic compound such as a carbazole derivative, an anthracene derivative, a phenanthrene derivative, a pyrene derivative, or a chrysene derivative, and 4) an aromatic amine compound such as a triarylamine derivative or a condensed polycyclic aromatic amine derivative are used.

(Electron-Transporting Layer)

An electron-transporting layer is a layer that contains a substance having a high electron-transporting property. For the electron-transporting layer, 1) metal complexes such as aluminum complexes, beryllium complexes, zinc complexes, or the like; 2) heteroaromatic complexes such as imidazole derivatives, benzimidazole derivatives, azine derivatives, carbazole derivatives, phenanthroline derivatives, or the like; and 3) polymer compounds can be used.

(Electron-Injecting Layer)

An electron-injecting layer is a layer which contains a substance having a high electron-injecting property. As the electron injecting layer, a compound which can be used for the above-mentioned electron transporting layer, lithium (Li), ytterbium (Yb), lithium fluoride (LiF), cesium fluoride (CsF), calcium fluoride ($CaF_2$), a metal complex compound such as 8-hydroxyquinolinolato-lithium (Liq), an alkali metal, an alkaline earth metal, or a compound thereof such as lithium oxide ($LiO_x$) can be used.

(Cathode)

For the cathode, metals, alloys, electrically conductive compounds, mixtures thereof, and the like having a small work function (specifically, 3.8 eV or less) are preferably used. Specific examples of such a cathode material include elements belonging to Group 1 or Group 2 of the Periodic Table of the Elements, i.e., alkali metals such as lithium (Li) and cesium (Cs), alkaline earth metals such as magnesium (Mg), calcium (Ca) and strontium (Sr), and alloys containing these metals (e.g., MgAg and AlLi), rare earth metals such as europium (Eu) and ytterbium (Yb), and alloys containing these metals.

In the organic EL device according to an aspect of the invention, the methods for forming the respective layers are not particularly limited. A conventionally-known method for forming each layer according to a vacuum deposition process, a spin coating process or the like can be used. Each layer such as the emitting layer can be formed by a known method such as a vacuum deposition process, a molecular beam deposition process (MBE process), or an application process such as a dipping process, a spin coating process, a casting process, a bar coating process and a roll coating process, using a solution prepared by dissolving the material in a solvent.

In the organic EL device according to an aspect of the invention, the thickness of each layer is not particularly limited, but is generally preferable that the thickness be in the range of several nm to 1 μm in order to suppress defects such as pinholes, to suppress applied voltages to be low, and to improve luminous efficiency.

[Electronic Apparatus]

An electronic apparatus according to an aspect of the invention is equipped with an organic EL device according to an aspect of the invention.

Specific examples of the electronic apparatus include display components such as an organic EL panel module, and the like; display devices for a television, a cellular phone, a personal computer, and the like; and emitting devices such as a light, a vehicular lamp, and the like.

EXAMPLES

Hereinafter, the invention will be described in more detail by referring to Examples and Comparative Examples, but the like, and the invention is not limited in any way by these Examples.

<Compounds>

Compounds represented by the formula (1) used as host materials for fabricating the organic EL devices of Examples 1 to 5 and 8 to 13 are shown below.

BH-1

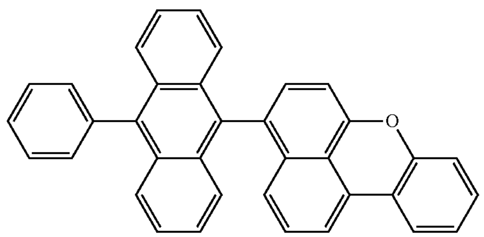

BH-3

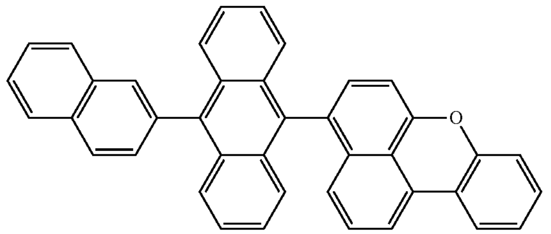

BH-4

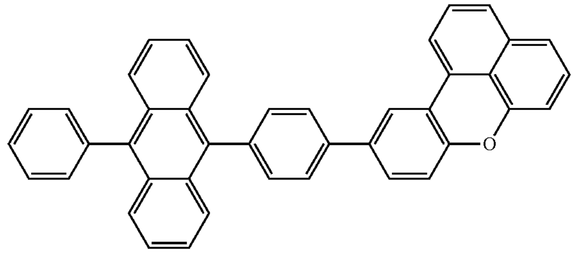

Compounds of the host material used for fabricating the organic EL devices of Comparative Examples 1 to 15 are shown below.

BH-R1

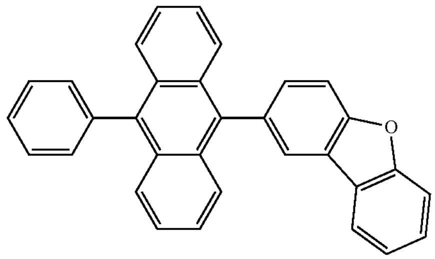

BH-R2

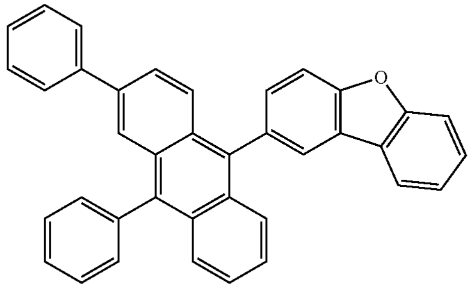

Compounds of the dopant material which are the compound A used for fabricating the organic EL devices of Examples 1 to 5 and 8 to 13, and Comparative Examples 1 to 9 and 12 to 13 are shown below.

BD-1
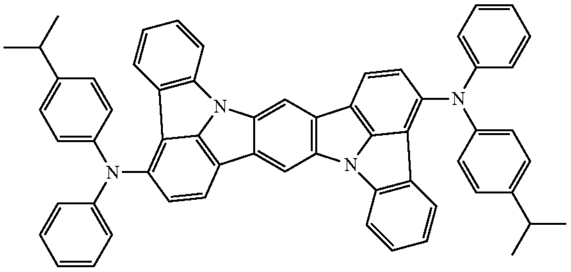
BD-2
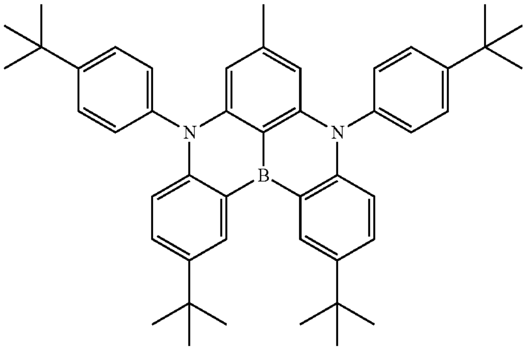
BD-3
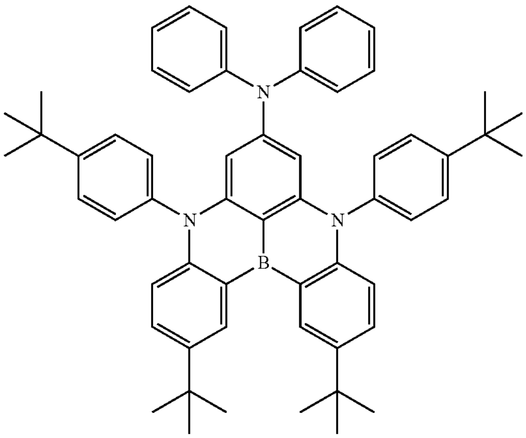
A compound of the dopant material which is not the compound A used for fabricating the organic EL devices of Comparative Examples 3 to 4, 10 to 11, 14, and 15 is shown below.
BD-R1
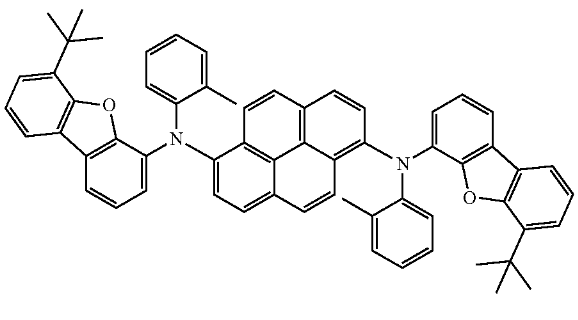
Other compounds used in the fabrication of the organic EL devices of Examples 1 to 13 and Comparative Examples 1 to 15 are shown below.
HI-1
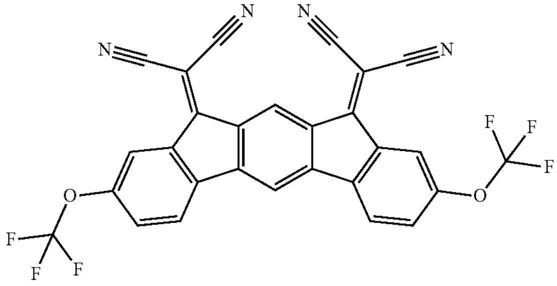
HT-1
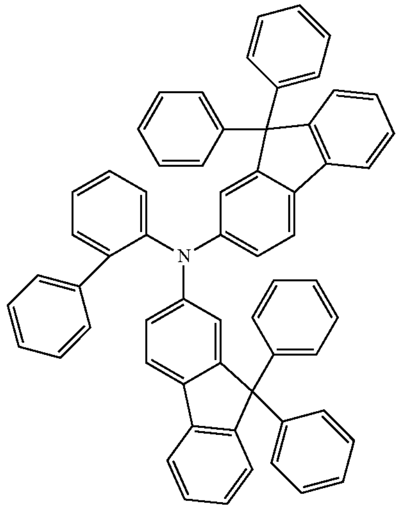
EBL-1
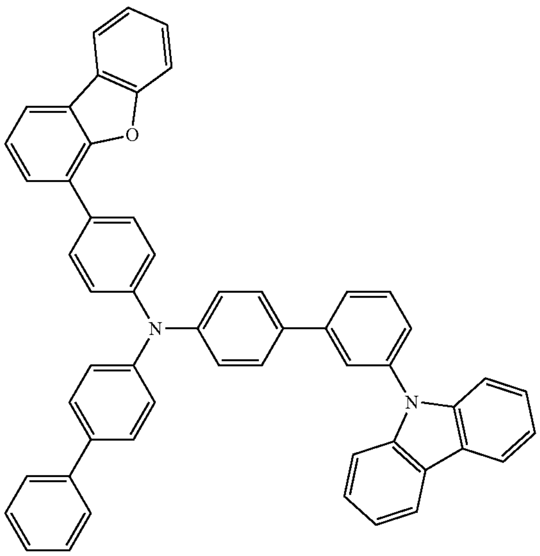

-continued aET-1

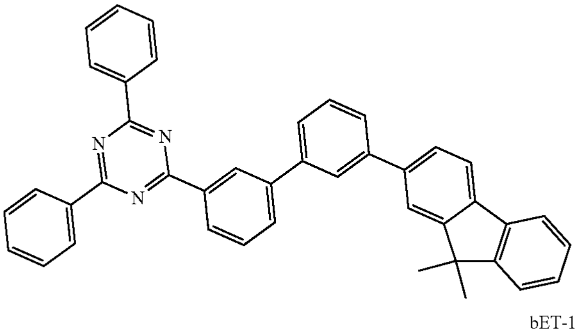

bET-1

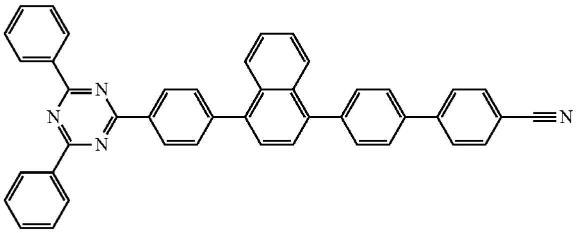

bET-2

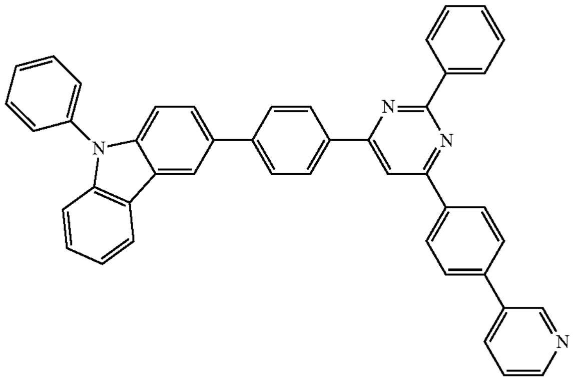

bET-3

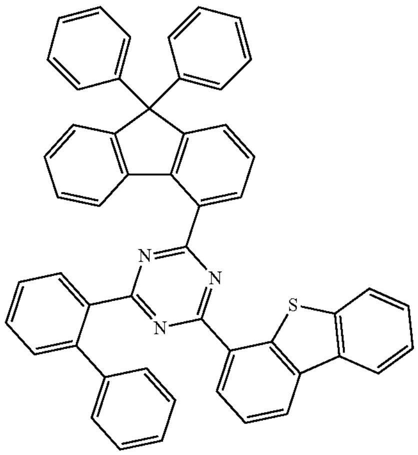

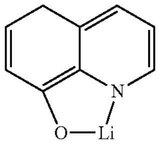

Liq

<Fabrication of Organic EL Device>

An organic EL device was fabricated and evaluated as follows.

Example 1

(Fabrication of Organic EL Device)

A 25 mm×75 mm×1.1 mm-thick glass substrate with an ITO transparent electrode (anode) (manufactured by GEOMATEC Co., Ltd.) was subjected to ultrasonic cleaning in isopropyl alcohol for 5 minutes, and then subjected to UV-ozone cleaning for 30 minutes. The thickness of the ITO film was 130 nm.

The glass substrate with the transparent electrode after being cleaned was mounted onto a substrate holder in a vacuum vapor deposition apparatus. First, a compound HI-1 was deposited on a surface of the glass substrate on the side on which the transparent electrode was formed so as to cover the transparent electrode to form a HI-1 film having a thickness of 5 nm. The HI-1 film functions as a hole-injecting layer.

Subsequent to the formation of the HI-1 film, a compound HT-1 was deposited on the HI-1 film to form an HT-1 film having a thickness of 80 nm. The HT-1 film functions as a hole-transporting layer (first hole-transporting layer).

Subsequent to the formation of the HT-1 film, a compound EBL-1 was deposited on the HT-1 film to form an EBL-1 film having a thickness of 10 nm. The EBL-1 film functions as an electron-blocking layer (second hole-transporting layer).

A compound BH-1 (host material) and a compound BD-1 (dopant material) were co-deposited on the EBL-1 film to be 4% by mass in a proportion of the compound BD-1, and a BH-1:BD-1 film having a thickness of 25 nm was formed. The BH-1:BD-1 film functions as an emitting layer.

A compound aET-1 was deposited on the emitting layer to form an aET-1 film having a thickness of 10 nm. The aET-1 film functions as a first electron-transporting layer.

A compound bET-1 and a compound Liq were co-deposited on the aET-1 film to be 50% by mass in a proportion of the compound Liq to form a bET-1:Liq film having a thickness of 15 nm. The bET-1:Liq film functions as an electron-transporting layer. LIF was deposited on this bET-1:Liq film to form a LiF film having a thickness of 1 nm. Metal Al was deposited on the LiF film to form a metal cathode having a thickness of 80 nm to fabricate an organic EL device.

The device configuration of the organic EL device of Example 1 is schematically shown as follows:

ITO(130/HI-1(5)/HT-1(80)/EBL-1(10)/BH-1:BD-1(25: 4%)/aET-1(10)/bET-1:Liq(15:50%)/LiF(1)/Al(80)

The numerical values in parentheses indicate the film thickness (unit: nm). The numerical value represented in percentages in parentheses indicates the proportion (mass %) of the latter compound in the layer.

<Evaluation of Organic EL Device>

The organic EL device fabricated in Example 1 was evaluated as follows. Evaluation results are shown in Table 1. The Stokes shift values and emission peak wavelength P of the dopant material used in Example 1 are also shown in Table 1.

External Quantum Efficiency EQE (%)

Voltage was applied to the organic EL device to be 10 $mA/cm^2$ in current density, and an EL emission spectrum was measured by using Spectroradiometer CS-1000 (manufactured by Konica Minolta, Inc.). External quantum efficiency (EQE) (%) was calculated from the obtained spectral radiance spectrum.

Stokes Shift (SS) of Dopant Material (Nm)

The dopant material was dissolved in toluene at a concentration of $10^{-5}$ mol/L or higher and $10^{-4}$ mol/L or lower to prepare a sample for measurement. A sample for measurement placed in a quartz cell was irradiated with continuous light in the ultraviolet-visible region at room temperature (300 K), and the absorption spectrum (vertical axis: absorbance, horizontal axis: wavelength) was measured. The spectrophotometer U-3900/3900H manufactured by Hitachi High-Tech Science Corporation was used for measuring the absorption spectrum. The dopant material was dissolved in toluene at a concentration of $10^{1}$ mol/L or higher and $10^{5}$ mol/L or lower to prepare another sample for measurement. The another sample for measurement placed in a quartz cell was irradiated with excitation light at room temperature (300 K), and the fluorescence spectrum (vertical axis: fluorescence intensity, horizontal axis: wavelength) was measured. The spectrofluorometer F-7000 manufactured by Hitachi High-Tech Science Corporation was used for measuring the fluorescence spectrum.

From the absorption spectrum and the fluorescence spectrum, the difference between the absorption local-maximum wavelength and the fluorescence local-maximum wavelength was calculated, and the Stokes shift (SS) was determined.

Emission Peak Wavelength a of Dopant Material (Nm)

Voltage was applied to the organic EL device to be 10 mA/$cm^2$ in current density, and an EL emission spectrum was measured by using Spectroradiometer CS-1000 (manufactured by Konica Minolta, Inc.). The emission peak wavelength was obtained from the obtained spectral radiance spectrum.

Comparative Examples 1 to 4

Organic EL devices of Comparative Examples 1 to 4 were fabricated and evaluated in the same manner as in Example 1, except that a host material and/or a dopant material contained in the emitting layer in Example 1 was replaced with materials described in Table 1. The results are shown in Table 1.

TABLE 1

| | | | Characteristics of dopant material | | |
|---|---|---|---|---|---|
| | Host material | Dopant material | Stokes Shift (nm) | Emission peak wavelength (nm) | EQE (%) |
| Ex. 1 | Compound BH-1 | Compound BD-1 | 15 | 456 | 9.8 |
| Comp. Ex. 1 | Compound BH-R1 | | | | 8.8 |
| Comp. Ex. 2 | Compound BH-R2 | | | | 9.0 |
| Comp. Ex. 3 | Compound BH-1 | Compound BD-R1 | 26 | 450 | 8.4 |
| Comp. Ex. 4 | Compound BH-R2 | | | | 8.1 |

The followings are seen from the results in Table 1.

The organic EL devices of Comparative Examples 1 and 2 in which either of compounds BH-$R_1$ and BH-$R_2$ was used as the host material of the emitting layer, and the compound BD-1 represented by the formula (11) was used as the dopant material of the emitting layer, have an EQE of 8.8 to 9.0%. On the other hand, it is found that the organic EL device of Example 1 in which the compound BH-1 represented by the formula (1) is used as the host material of the emitting layer and the compound BD-1 represented by the formula (11) is used as the dopant material of the emitting layer, has a remarkably improved EQE of 9.8%. This indicates that the compound represented by the formula (1) (host material) allows to exhibit the effect of the compound represented by the formula (11) (dopant material).

In addition, in both of the devices of Comparative Examples 3 and 4 in which the dopant material compound BD-$R_1$ having a Stokes shift as large as 26 nm was used, EQE was low in both devices. Even in Comparative Example 3 in which the compound BH-1 represented by the formula (1) is used as the host material, EQE was as low as 8.4%. This indicates that, even when the compound represented by the formula (1) is used as the host material, EQE is not improved unless the compound A (dopant material) having a Stokes shift of 20 nm or less and an emission peak wavelength of 440 nm to 465 nm is combined.

Example 2

An organic EL device was fabricated and evaluated in the same manner as in Example 1, except that a dopant material contained in the emitting layer in Example 1 was replaced with a material described in Table 2. The results are shown in Table 2.

Comparative Example 5

An organic EL device was fabricated and evaluated in the same manner as in Example 1, except that a host material and a dopant material contained in the emitting layer in Example 1 were replaced with materials described in Table 2. The results are shown in Table 2.

TABLE 2

| | | | Characteristics of dopant material | | |
|---|---|---|---|---|---|
| | Host material | Dopant material | Stokes Shift (nm) | Emission peak wavelength (nm) | EQE (%) |
| Ex. 2 | Compound BH-1 | Compound BD-2 | 17 | 455 | 8.8 |
| Comp. Ex. 5 | Compound BH-R1 | | | | 8.4 |

From the results shown in Table 2, in the organic EL device of Comparative Example 5 using the compound BH-$R_1$ as the host material of the emitting layer and a compound BD-2 represented by the formula (21) as the dopant material, EQE was 8.4%. On the other hand, in Examples 2 and 3 in which the compound BH-1 represented by the formula (1) is used as the host material of the emitting layer and the compound BD-2 represented by the formula (21) is used as the dopant material, it is found that EQE is remarkably improved to 8.8%. This indicates that the compound represented by the formula (1) (host material) allows the compound represented by the formula (21) (dopant material) to exhibit the effect thereof.

Example 3

An organic EL device was fabricated and evaluated in the same manner as in Example 1, except that the dopant material contained in the emitting layer in Example 1 was replaced with a material described in Table 3. The results are shown in Table 3.

Comparative Examples 6 to 7

Organic EL device were fabricated and evaluated in the same manner as in Example 1, except that the host material and the dopant material contained in the emitting layer in Example 1 were replaced with materials described in Table 3. The results are shown in Table 3.

TABLE 3

| | Host material | Dopant material | Characteristics of dopant material: Stokes Shift (nm) | Emission peak wavelength (nm) | EQE (%) |
|---|---|---|---|---|---|
| Ex. 3 | Compound BH-1 | Compound BD-3 | 16 | 453 | 8.4 |
| Comp. Ex. 6 | Compound BH-R1 | | | | 8.1 |
| Comp. Ex. 7 | Compound BH-R2 | | | | 7.9 |

From the results shown in Table 3, in the organic EL devices of Comparative Examples 6 and 7 using the compound $BH-R_1$ or $BH-R_2$ as the host material of the emitting layer and the compound BD-3 represented by the formula (21) as the dopant material, EQE were 7.9 to 8.1%. On the other hand, in Example 3 in which the compound BH-1 represented by the formula (1) is used as the host material of the emitting layer and the compound BD-3 represented by the formula (21) is used as the dopant material, it is found that EQE is remarkably improved to 8.4%. This indicates that the compound represented by the formula (1) (host material) allows the compound represented by the formula (21) (dopant material) to exhibit the effect thereof.

Example 4

(Fabrication of Organic EL Device)

A 25 mm×75 mm×1.1 mm-thick glass substrate with an ITO transparent electrode (anode) (manufactured by GEOMATEC Co., Ltd.) was subjected to ultrasonic cleaning in isopropyl alcohol for 5 minutes, and then subjected to UV-ozone cleaning for 30 minutes. The thickness of the ITO film was 130 nm.

The glass substrate with the transparent electrode after being cleaned was mounted onto a substrate holder in a vacuum vapor deposition apparatus. First, a compound HI-1 was deposited on a surface of the glass substrate on the side on which the transparent electrode was formed so as to cover the transparent electrode to form a HI-1 film having a thickness of 5 nm. The HI-1 film functions as a hole-injecting layer.

Subsequent to the formation of the HI-1 film, a compound HT-1 was deposited on the HI-1 film to form an HT-1 film having a thickness of 80 nm. The HT-1 film functions as a hole-transporting layer (first hole-transporting layer).

Subsequent to the formation of the HT-1 film, a compound EBL-1 was deposited on the HT-1 film to form an EBL-1 film having a thickness of 10 nm. The EBL-1 film functions as an electron-blocking layer (second hole-transporting layer).

A compound BH-1 (host material) and a compound BD-2 (dopant material) were co-deposited on the EBL-1 film to be 2% by mass in a proportion of the compound BD-2, and a BH-1:BD-2 film having a thickness of 25 nm was formed. The BH-1:BD-2 film functions as an emitting layer.

A compound aET-1 was deposited on the emitting layer to form an aET-1 film having a thickness of 10 nm. The aET-1 film functions as a first electron-transporting layer.

A compound bET-3 and a compound Liq were co-deposited on the aET-1 film to be 50% by mass in a proportion of the compound Liq to form a bET-3:Liq film having a thickness of 15 nm. The bET-3:Liq film functions as an electron-transporting layer. LiF was deposited on the bET-3:Liq film to form a LiF film having a thickness of 1 nm. Metal Al was deposited on the LIF film to form a metal cathode having a thickness of 80 nm to obtain an organic EL device.

The device configuration of the organic EL device of Example 4 is schematically shown as follows:

ITO(130)/HI-1(5)/HT-1(80)/EBL-1(10)/BH-1:BD-2(25:2%)/aET-1(10)/bET-3:Liq(15:50%)/LiF(1)/Al(80)

The numerical values in parentheses indicate the film thickness (unit: nm). The numerical value represented in percentages in parentheses indicates the proportion (mass %) of the latter compound in the layer.

<Evaluation of Organic EL Device>

The organic EL device fabricated in Example 4 was evaluated as follows. Evaluation results are shown in Table 4.

External Quantum Efficiency EQE (%)

Voltage was applied to the organic EL device to be 10 mA/cm$^2$ in current density, and an EL emission spectrum was measured by using Spectroradiometer CS-1000 (manufactured by Konica Minolta, Inc.). External quantum efficiency (EQE) (%) was calculated from the obtained spectral radiance spectrum.

Comparative Example 8

An organic EL device was fabricated and evaluated in the same manner as in Example 4, except that the material of each layer in Example 4 was replaced with materials described in Table 4. The results are shown in Table 4.

TABLE 4

| | HI | HT | EBL | BH | BD | HBL | ET | EQE(%) |
|---|---|---|---|---|---|---|---|---|
| Ex. 4 | HI-1 | HT-1 | EBL-1 | BH-1 | BD-2 | aET-1 | bET-3:Liq | 8.7 |
| Comp. Ex. 8 | | | | BH-R1 | | | | 8.4 |

From the results shown in Table 4, in the organic EL device of Comparative Example 8 using the compound $BH-R_1$ as the host material of the emitting layer and the compound BD-2 represented by the formula (21) as the dopant material, EQE was 8.4%. On the other hand, in Example 4 in which the compound BH-1 represented by the formula (1) is used as the host material of the emitting layer and the compound BD-2 represented by the formula (21) is used as the dopant material of the emitting layer, it is found that EQE is remarkably improved to 8.7%. This indicates that the compound represented by the formula (1) (host material) allows the compound represented by the formula (21) (dopant material) to exhibit the effect thereof.

Example 5 and Comparative Example 9

Organic EL devices were fabricated and evaluated in the same manner as in Example 4, except that the material of each layer in Example 4 was replaced with materials described in Table 5. The results are shown in Table 5.

TABLE 5

| | HI | HT | EBL | BH | BD | HBL | ET | EQE(%) |
|---|---|---|---|---|---|---|---|---|
| Ex. 5 | HI-1 | HT-1 | EBL-1 | BH-1 | BD-2 | aET-1 | bET-2:Liq | 9.2 |
| Comp. Ex. 9 | | | | BH-R1 | | | | 8.7 |

From the results shown in Table 5, in the organic EL device of Comparative Example 9 using the compound BH-$R_1$ as the host material of the emitting layer and the compound BD-2 represented by the formula (21) as the dopant material, EQE was 8.7%. On the other hand, in Example 5 in which the compound BH-1 represented by the formula (1) is used as the host material of the emitting layer and the compound BD-2 represented by the formula (21) is used as the dopant material of the emitting layer, it is found that EQE is remarkably improved to 9.2%. This indicates that the compound represented by the formula (1) (host material) allows the compound represented by the formula (21) (dopant material) to exhibit the effect thereof.

Comparative Example 14 and Comparative Example 10

Organic EL devices were fabricated and evaluated in the same manner as in Example 4, except that the material of each layer in Example 4 was replaced with materials described in Table 6. The results are shown in Table 6.

TABLE 6

| | HI | HT | EBL | BH | BD | HBL | ET | EQE(%) |
|---|---|---|---|---|---|---|---|---|
| Comp. Ex. 14 | HI-1 | HT-1 | EBL-1 | BH-1 | BD-R1 | aET-1 | bET-3:Liq | 8.2 |
| Comp. Ex. 10 | | | | BH-R1 | | | | 8.1 |

From the results shown in Table 6, in the organic EL device of Comparative Example 10 using the compound BH-$R_1$ as the host material of the emitting layer, and the compound BD-$R_1$, which is represented by the formula (41) but does not correspond to the compound A, as the dopant material of the emitting layer, EQE was 8.1%. On the other hand, in Comparative Example 14 using the compound BH-1 represented by the formula (1) as the host material of the emitting layer and the compound BD-$R_1$, which is represented by the formula (41) but does not correspond to the compound A, as the dopant material of the emitting layer, EQE is 8.2%. It can be seen that EQE is improved by only 0.1%. This indicates that when a dopant material which is not the compound A is used, EQE cannot be remarkably improved even when the compound represented by the formula (1) (host material) is combined therewith.

Comparative Example 15 and Comparative Example 11

Organic EL devices were fabricated and evaluated in the same manner as in Example 4, except that the material of each layer in Example 4 was replaced with materials described in Table 7. The results are shown in Table 7.

TABLE 7

| | HI | HT | EBL | BH | BD | HBL | ET | EQE(%) |
|---|---|---|---|---|---|---|---|---|
| Comp. Ex. 15 | HI-1 | HT-1 | EBL-1 | BH-1 | BD-R1 | aET-1 | bET-2:Liq | 8.8 |
| Comp. Ex. 11 | | | | BH-R1 | | | | 8.7 |

From the results shown in Table 7, in the organic EL device of Comparative Example 10 using the compound BH-$R_1$ as the host material of the emitting layer, and the compound BD-$R_1$, which is represented by the formula (41) but does not correspond to the compound A, as the dopant material of the emitting layer, EQE was 8.7%. On the other hand, in Comparative Example 15 using the compound BH-1 represented by the formula (1) as the host material of the emitting layer and the compound BD-$R_1$, which is represented by the formula (41) but does not correspond to the compound A, as the dopant material of the emitting layer, EQE is 8.8%. It can be seen that EQE is improved by only 0.1%. This indicates that when a dopant material which is not the compound A is used, EQE cannot be remarkably improved even when the compound represented by the formula (1) (host material) is combined therewith.

Example 8 and Comparative Example 12

Organic EL devices were fabricated and evaluated in the same manner as in Example 4, except that the material of each layer in Example 4 was replaced with materials described in Table 8. The results are shown in Table 8.

TABLE 8

| | HI | HT | EBL | BH | BD | HBL | ET | EQE(%) |
|---|---|---|---|---|---|---|---|---|
| Ex. 8 | HI-1 | HT-1 | EBL-1 | BH-1 | BD-1 | aET-1 | bET-1:Liq | 9.3 |
| Comp. Ex. 12 | | | | BH-R1 | | | | 8.8 |

From the results shown in Table 8, in the organic EL device of Comparative Example 12 using the compound BH-$R_1$ as the host material of the emitting layer and the compound BD-1 represented by the formula (11) as the dopant material, EQE was 8.8%. On the other hand, in Example 8 in which the compound BH-1 represented by the formula (1) is used as the host material of the emitting layer and the compound BD-1 represented by the formula (11) is used as the dopant material of the emitting layer, it is found that EQE is remarkably improved to 9.3%. This indicates that the compound represented by the formula (1) (host material) allows the compound represented by the formula (11) (dopant material) to exhibit the effect thereof.

Example 9 and Comparative Example 13

Organic EL devices were fabricated and evaluated in the same manner as in Example 4, except that the material of each layer in Example 4 was replaced with materials described in Table 9. The results are shown in Table 9.

TABLE 9

| | HI | HT | EBL | BH | BD | HBL | ET | EQE(%) |
|---|---|---|---|---|---|---|---|---|
| Ex. 9 | HI-1 | HT-2 | EBL-1 | BH-1 | BD-1 | aET-1 | bET-3:Liq | 9.6 |
| Comp. Ex. 13 | | | | BH-R1 | | | | 9.0 |

From the results shown in Table 9, in the organic EL device of Comparative Example 13 using the compound BH-$R_1$ as the host material of the emitting layer and a compound BD-1 represented by the formula (11) as the dopant material, EQE was 9.0%. On the other hand, in Example 9 in which the compound BH-1 represented by the formula (1) is used as the host material of the emitting layer and the compound BD-1 represented by the formula (11) is used as the dopant material of the emitting layer, it is found that EQE is remarkably improved to 9.6%. This indicates that the compound represented by the formula (1) (host material) allows the compound represented by the formula (11) (dopant material) to exhibit the effect thereof.

Examples 10 and 11

Organic EL devices were fabricated and evaluated in the same manner as in Example 4, except that the material of each layer in Example 4 was replaced with materials described in Table 10. The results are shown in Table 10.

TABLE 10

| | HI | HT | EBL | BH | BD | HBL | ET | EQE(%) |
|---|---|---|---|---|---|---|---|---|
| Ex. 10 | HI-1 | HT-1 | EBL-1 | BH-3 | BD-2 | aET-1 | bET-3:Liq | 8.6 |
| Ex. 11 | | | | BH-4 | | | | 8.7 |

From the results shown in Table 10, it can be seen that also when the compound BD-2 represented by the formula (21) is used as the dopant material of the emitting layer and the compound BH-3 or the compound BH-4 represented by the formula (1) is used as the host material, EQE as high as 8.6% and 8.7% can be obtained. This indicates that the compound represented by the formula (1) (host material) allows the compound represented by the formula (21) (dopant material) to exhibit the effect thereof.

Examples 12 and 13

Organic EL devices were fabricated and evaluated in the same manner as in Example 4, except that the material of each layer in Example 4 was replaced with materials described in Table 11. The results are shown in Table 11.

TABLE 11

| | HI | HT | EBL | BH | BD | HBL | ET | EQE(%) |
|---|---|---|---|---|---|---|---|---|
| Ex. 12 | HI-1 | HT-2 | EBL-1 | BH-3 | BD-1 | aET-1 | bET-1:Liq | 8.8 |
| Ex. 13 | | | | BH-4 | | | | 9.0 |

From the results shown in Table 11, it can be seen that also when the compound BD-1 represented by the formula (11) is used as the dopant material of the emitting layer and the compound BH-3 or the compound BH-4 represented by the formula (1) is used as the host material, EQE as high as 8.8% and 9.0% can be obtained. This indicates that the compound represented by the formula (1) (host material) allows the compound represented by the formula (11) (dopant material) to exhibit the effect thereof.

<Synthesis of Compounds>

Synthesis Example 1: Synthesis of Compound BH-1

A compound BH-1 was synthesized in accordance with the following synthetic scheme.

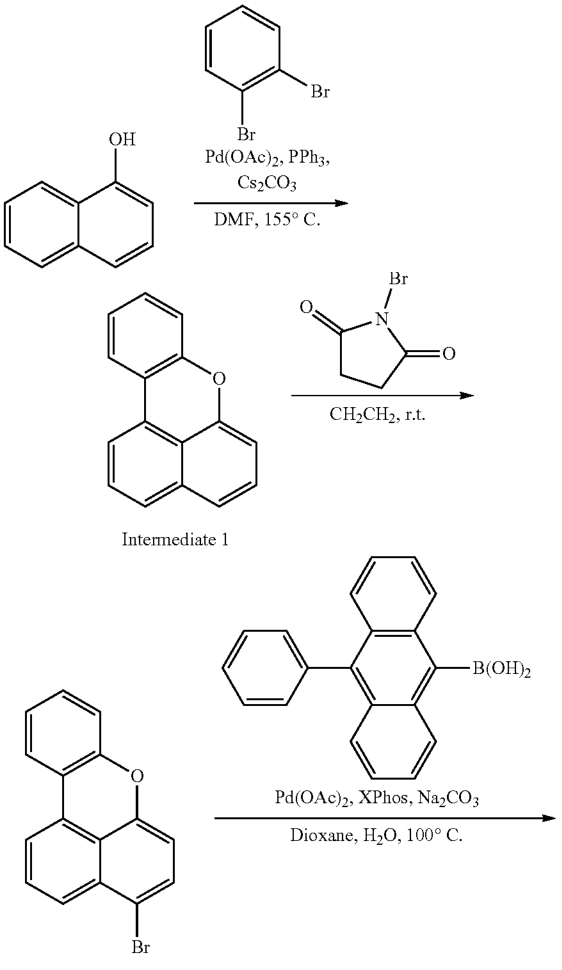

-continued

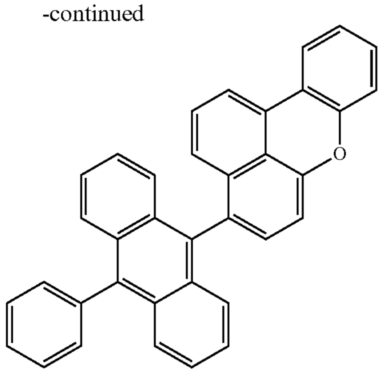

BH-1

(1) Synthesis of Benzo[Kl]Xanthene (Intermediate 1)

Under an argon atmosphere, 7.21 g of naphthalen-1-ol, 14.2 g of 1,2-dibromobenzene, 0.56 g of palladium(II) acetate ($Pd(OAc)_2$), 2.62 g of triphenylphosphine ($PPh_3$), 65.2 g of cesium carbonate, and 500 mL of N,N-dimethylformamide (DMF) (dehydrated) were placed in a flask and refluxed with stirring for 5 hours. After cooling to room temperature, the reaction solution was extracted using ethyl acetate, and after removing the aqueous phase, the organic phase was washed with saturated saline. After drying the organic phase with anhydrous sodium sulfate, the mixture was concentrated, and the residue was purified by silica gel column chromatography to obtain 6.77 g (yield: 62%) of a white solid of benzo[kl]xanthene (Intermediate 1).

(2) Synthesis of 4-Bromobenzo[Kl]Xanthene (Intermediate 2)

Under an argon atmosphere, 1.42 g of benzo[kl]xanthene (Intermediate 1) and 65 mL of dichloromethane (dehydrated) were placed in a flask and cooled to 0° C. 1.18 g of N-bromosuccinimide was added to the flask and then stirred at room temperature for 7 hours. After completion of the reaction, the reaction mixture was deactivated with a sufficient amount of water. The solution was transferred to a separatory funnel, extracted with dichloromethane. The extract was dried over anhydrous sodium sulfate, the origin impurity was removed by passing through a silica gel short column, followed by concentration. The obtained sample was dried under vacuum at room temperature for 3 hours to obtain 1.49 g (77%) of a white solid of 4-bromobenzo[k] xanthene (Intermediate 2).

(3) Synthesis of Anthracene Derivative (Compound BH-1)

Under an argon atmosphere, 6.00 g of 4-bromobenzo[kl] xanthene (Intermediate 2), 9.03 g of 10-phenylanthracene-9-boronic acid synthesized by a known method, 0.09 g of palladium(II) acetate ($Pd(OAc)_2$), 0.39 g of 2-dicyclohexylphosphino-2',4',6'-triisopropylbiphenyl (XPhos), 6.42 g of sodium carbonate, 270 mL of 1,4-dioxane, and 120 mL of ion-exchanged water were placed into a flask, and the mixture was refluxed with stirring for 18 hours. After cooling the mixture to room temperature, the precipitated solid was collected by filtration. The resulting solid was washed with water and acetone, and then recrystallized with a mixed solvent of toluene and hexane to obtain 7.60 g (80%) of a pale-yellow solid. As a result of mass spectrometric analysis, this pale-yellow solid was identified as a compound BH-1, based on m/e=471 relative to the molecular weight of 470.57.

Synthesis Example 2: Synthesis of Compound BH-3

A compound BH-3 was synthesized in accordance with the following synthetic scheme.

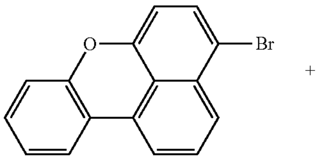

Intermediate 2

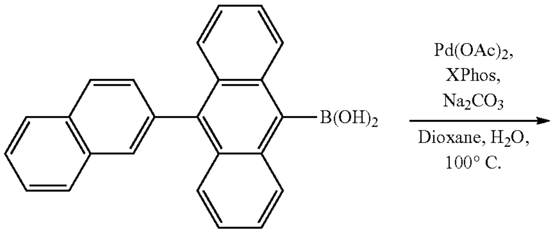

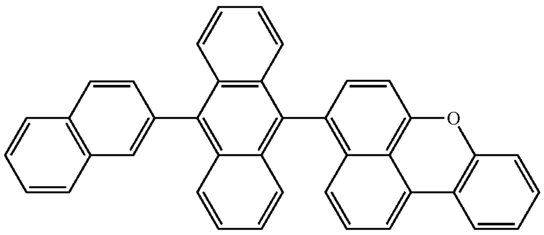

BH-3

Under an argon atmosphere, 4.20 g of 4-bromobenzo[kl]xanthene (Intermediate 2), 7.38 g of (10-(naphthalene-2-yl)anthracen-9-yl)boronic acid synthesized by a known method, 0.06 g of palladium(II) acetate (Pd(OAc)$_2$), 0.27 g of 2-dicyclohexylphosphino-2',4',6'-triisopropylbiphenyl (XPhos), 4.49 g of sodium carbonate, 250 mL of 1,4-dioxane, and 100 mL of ion-exchanged water were placed in a flask, and the mixture was refluxed with stirring at 100° C. for 18 hours. After cooling the reaction mixture to room temperature, precipitated solid was collected by filtration. The resulting solid was washed with water and then acetone, followed by recrystallization from a mixed solvent of toluene and hexane to obtain 5.67 g (77%) of a pale-yellow solid. As a result of mass spectrometric analysis, this pale-yellow solid was identified as a compound BH-3, based on m/e=521 relative to the molecular weight of 520.63.

Synthesis Example 3: Synthesis of Compound BH-4

A compound BH-4 was synthesized in accordance with the following synthetic scheme.

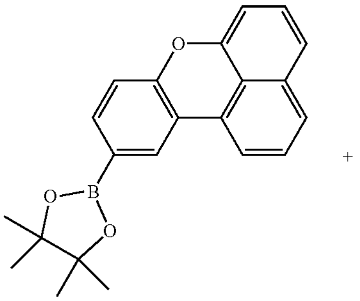

Intermediate 4

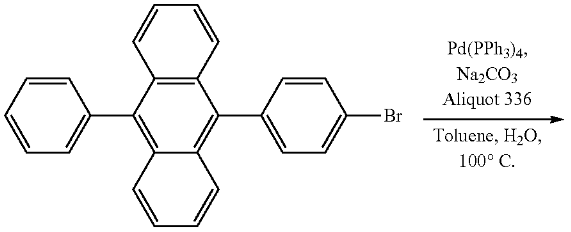

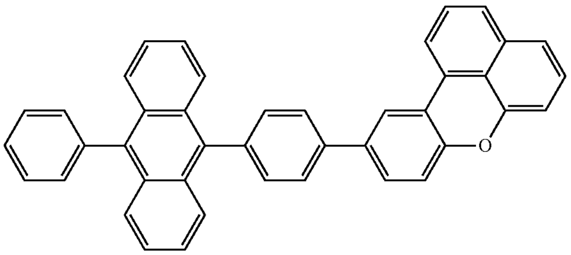

BH-4

Under an argon atmosphere, 0.66 g of 2-(benzo[kl]xanthen-10-yl)-4,4,5,5-tetramethyl-1,3,2-dioxaborane (Intermediate 4), 0.92 g of 9-(4-bromophenyl)-10-anthracene synthesized by a known method, 0.05 g of tetrakis (triphenylphosphine) palladium(0) (Pd (PPh$_3$)$_4$), 0:10 mL of Aliquot 336, 20 mL of toluene, and 1 mL of ion-exchanged water were placed in a flask, and the mixture was refluxed with stirring at 100° C. for 18 hours. After cooling the mixture to room temperature, the precipitated solid was collected by filtration. The resulting solid was washed with water and then acetone, followed by recrystallization from a mixed solvent of toluene and cyclohexane to obtain 0.72 g (66%) of a pale-yellow solid. As a result of mass spectrometric analysis, this pale-yellow solid was identified as a compound BH-4, based on m/e=547 relative to the molecular weight of 546.66.

Although only some exemplary embodiments and/or examples of this invention have been described in detail above, those skilled in the art will readily appreciate that many modifications are possible in the exemplary embodiments and/or examples without materially departing from the novel teachings and advantages of this invention. Accordingly, all such modifications are intended to be included within the scope of this invention.

The invention claimed is:

1. An organic electroluminescence device comprising:

a cathode;

an anode; and an organic layer disposed between the cathode and the anode, wherein the organic layer comprises a compound represented by the following formula (1-1) or the following formula (1-2), and a compound A having a Stokes shift of 20 nm or smaller and an emission peak wavelength of 440 nm to 465 nm (1-1)

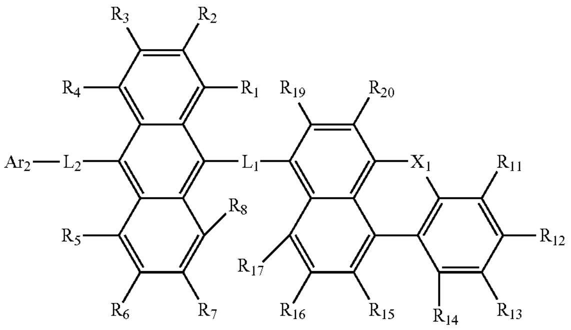

(1-2)

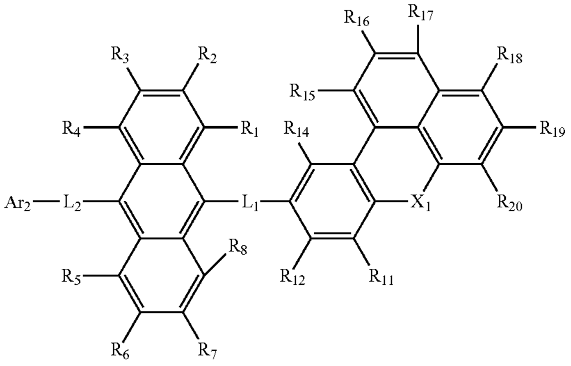

wherein in the formula (1-1) or (1-2), one or more sets of adjacent two or more of $R_1$ to $R_8$ form a substituted or unsubstituted, saturated or unsaturated ring by bonding with each other, or do not form a substituted or unsubstituted, saturated or unsaturated ring;

$R_1$ to $R_8$ that do not form the substituted or unsubstituted, saturated or unsaturated ring are independently a hydrogen atom or a substituent R;

the substituent R is a halogen atom, a cyano group, a nitro group, a substituted or unsubstituted alkyl group including 1 to 50 carbon atoms, a substituted or unsubstituted alkenyl group including 2 to 50 carbon atoms, a substituted or unsubstituted alkynyl group including 2 to 50 carbon atoms, a substituted or unsubstituted cycloalkyl group including 3 to 50 ring carbon atoms, $—Si(R_{901})(R_{902})(R_{903})$, $—O—(R_{904})$, $—S—(R_{905})$, $—N(R_{906})(R_{907})$, a substituted or unsubstituted aryl group including 6 to 50 ring carbon atoms, or a substituted or unsubstituted monovalent heterocyclic group including 5 to 50 ring atoms;

$R_{901}$ to $R_{907}$ are independently a hydrogen atom, a substituted or unsubstituted alkyl group including 1 to 50 carbon atoms, a substituted or unsubstituted cycloalkyl group including 3 to 50 ring carbon atoms, a substituted or unsubstituted aryl group including 6 to 50 ring carbon atoms, or a substituted or unsubstituted monovalent heterocyclic group including 5 to 50 ring atoms;

when two or more of each of $R_{901}$ to $R_{907}$ are present, the two or more of each of $R_{901}$ to $R_{907}$ are the same as or different from each other;

$L_1$ and $L_2$ are independently a single bond, a substituted or unsubstituted arylene group including 6 to 50 ring carbon atoms, or a substituted or unsubstituted divalent heterocyclic group including 5 to 50 ring atoms;

$X_1$ is O;

one or more sets of adjacent two or more of $R_{11}$ to $R_{14}$ and adjacent two or more of $R_{15}$ to $R_{20}$ form a substituted or unsubstituted, saturated or unsaturated ring by bonding with each other, or do not form a substituted or unsaturated, saturated or unsaturated ring;

$R_{11}$ to $R_{20}$ that do not form the substituted or unsubstituted, saturated or unsaturated ring are independently a hydrogen atom or a substituent R;

the substituent R is as defined in the formula (1-1) or (1-2);

$Ar_2$ is a substituted or unsubstituted aryl group including 6 to 50 ring carbon atoms, or a substituted or unsubstituted monovalent heterocyclic group including 5 to 50 ring atoms.

2. The organic electroluminescence device according to claim 1, wherein $L_1$ and $L_2$ are independently a single bond, or a substituted or unsubstituted arylene group including 6 to 14 ring carbon atoms.

3. The organic electroluminescence device according to according to claim 1, wherein $L_1$ and $L_2$ are independently a single bond, a substituted or unsubstituted phenylene group, a substituted or unsubstituted naphthylene group, a substituted or unsubstituted fluorenylene group, a substituted or unsubstituted phenanthrylene group, or a substituted or unsubstituted biphenyldiyl group.

4. The organic electroluminescence device according to claim 1, wherein either or both of $L_1$ and $L_2$ are single bonds.

5. The organic electroluminescence device according to claim 1, wherein the compound represented by the formula (1-1) or (1-2) is a compound represented by the following formula (1-1-1):

(1-1-1)

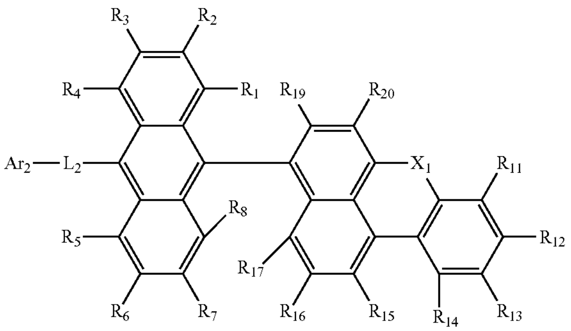

wherein in the formula (1-1-1), $R_1$ to $R_8$, $L_2$, $Ar_2$, $X_1$, $R_{11}$ to $R_{17}$, $R_{19}$, and $R_{20}$ are as defined in the formula (1-1) or (1-2).

6. The organic electroluminescence device according to claim 1, wherein $L_2$ is a single bond.

7. The organic electroluminescence device according to claim 1, wherein $Ar_2$ is a substituted or unsubstituted phenyl group,
a substituted or unsubstituted naphthyl group,
a substituted or unsubstituted fluorenyl group,
a substituted or unsubstituted phenanthryl group,
a substituted or unsubstituted biphenyl group,
a substituted or unsubstituted chrysenyl group,
a substituted or unsubstituted benzophenanthrenyl group,
a substituted or unsubstituted benzotriphenylenyl group,
a substituted or unsubstituted dibenzofuranyl group,
a substituted or unsubstituted naphthobenzofuranyl group,
a substituted or unsubstituted carbazolyl group, or
a substituted or unsubstituted benzo[def]carbazolyl group.

8. The organic electroluminescence device according to claim 1, wherein $Ar_2$ is a group represented by any of the following formulas ($Ar_2$-11) to ($Ar_2$-14):

($Ar_2$-11)

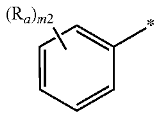

($Ar_2$-12)

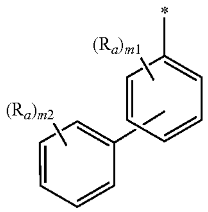

($Ar_2$-13)

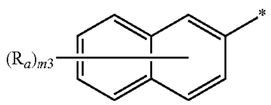

-continued ($Ar_2$-14)

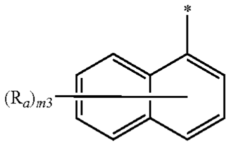

wherein in the formulas ($Ar_2$-11) to ($Ar_2$-14),
* is bonded with $L_2$;
$R_a$ is a substituent;
the substituent $R_a$ is
a halogen atom,
a cyano group,
a nitro group,
a substituted or unsubstituted alkyl group including 1 to 50 carbon atoms,
a substituted or unsubstituted alkenyl group including 2 to 50 carbon atoms,
a substituted or unsubstituted alkynyl group including 2 to 50 carbon atoms,
a substituted or unsubstituted cycloalkyl group including 3 to 50 ring carbon atoms,
—$Si(R_{901})(R_{902})(R_{903})$,
—O—$(R_{904})$,
—S—$(R_{905})$,
—$N(R_{906})(R_{907})$,
a substituted or unsubstituted aryl group including 6 to 50 ring carbon atoms, or
a substituted or unsubstituted monovalent heterocyclic group including 5 to 50 ring atoms;
$R_{901}$ to $R_{907}$ are as defined in the formula (1-1) or (1-2);
m1 is an integer of 0 to 4;
m2 is an integer of 0 to 5;
m3 is an integer of 0 to 7;
when each of m1 to m3 is 2 or more, a plurality of $R_a$'s may be the same as or different from each other;
when m1 to m3 are each 2 or more, a plurality of adjacent $R_a$'s form a substituted or unsubstituted, saturated or unsaturated ring by bonding with each other, or do not form a substituted or unsubstituted, saturated or unsaturated ring.

9. The organic electroluminescence device according to claim 1, wherein $Ar_2$-$L_2$-,
a substituted or unsubstituted phenyl group,
a substituted or unsubstituted naphthyl group,
a substituted or unsubstituted phenylnaphthyl group,
a substituted or unsubstituted biphenyl group,
a substituted or unsubstituted naphthylphenyl group,
a substituted or unsubstituted fluorenyl group,
a substituted or unsubstituted phenanthryl group,
a substituted or unsubstituted phenylphenanthryl group,
Substituted or unsubstituted benzophenanthryl groups
a substituted or unsubstituted benzotriphenylenyl group,
a substituted or unsubstituted chrysenyl group,
a substituted or unsubstituted dibenzofuranyl group,
a substituted or unsubstituted phenyldibenzofuranyl group,
a substituted or unsubstituted naphthobenzofuranyl group,
a substituted or unsubstituted carbazolyl group,
a substituted or unsubstituted carbazolyl-phenyl group, or
a substituted or unsubstituted benzo[def]carbazolyl-phenyl group.

10. The organic electroluminescence device according to claim 1, wherein one or more of $R_1$ to $R_8$ that are hydrogen atoms, $R_{11}$ to $R_{20}$ that are hydrogen atoms, hydrogen atoms possessed by the substituted or unsubstituted, saturated or unsaturated ring formed by bonding one or more sets of adjacent two or more of $R_1$ to $R_8$ with each other, hydrogen atoms possessed by $R_1$ to $R_8$ that are the substituents R, hydrogen atoms possessed by the substituted or unsubstituted, saturated or unsaturated ring formed by bonding one or more sets of adjacent two or more of $R_{11}$ to $R_{20}$ with each other, hydrogen atoms possessed by $R_{11}$ to $R_{20}$ that are the substituents R, hydrogen atoms possessed by $L_1$, hydrogen atoms possessed by $L_2$, and hydrogen atoms possessed by $Ar_2$ are deuterium atoms.

11. The organic electroluminescence device according to claim 1, wherein the compound A is one or more selected from the group consisting of a compound represented by the following formula (11), a compound represented by the following formula (21), a compound represented by the following formula (31), and a compound represented by the following formula (41):

(11)

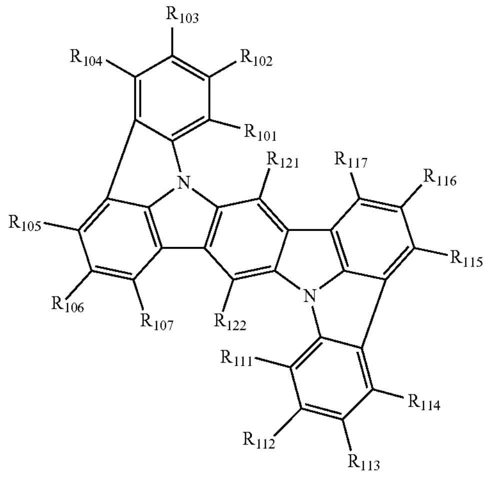

wherein in the formula (11), one or more sets of adjacent two or more of $R_{101}$ to $R_{107}$ and $R_{111}$ to $R_{117}$ form a substituted or unsubstituted, saturated or unsaturated ring by bonding with each other, or do not form a substituted or unsubstituted, saturated or unsaturated ring;

$R_{121}$ and $R_{122}$, and $R_{101}$ to $R_{107}$ and $R_{111}$ to $R_{117}$ that do not form the substituted or unsubstituted, saturated or unsaturated ring are independently a hydrogen atom or a substituent R; and the substituent R is as defined in the formula (1-1) or (1-2);

(21)

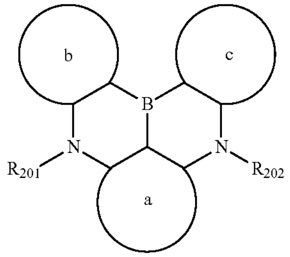

wherein in the formula (21), a ring a, a ring b, and a ring c are independently a substituted or unsubstituted aromatic hydrocarbon ring including 6 to 50 ring carbon atoms, or a substituted or unsubstituted heterocycle including 5 to 50 ring atoms;

$R_{201}$ forms a substituted or unsubstituted heterocycle by bonding with either or both of the ring a and the ring b, or do not form a substituted or unsubstituted heterocycle;

$R_{202}$ forms a substituted or unsubstituted heterocycle by bonding with either or both of the ring a and the ring c, or do not form a substituted or unsubstituted heterocycle;

$R_{201}$ and $R_{202}$ that do not form the substituted or unsubstituted heterocycle are independently a substituted or unsubstituted alkyl group including 1 to 50 carbon atoms, a substituted or unsubstituted alkenyl group including 2 to 50 carbon atoms, a substituted or unsubstituted alkynyl group including 2 to 50 carbon atoms, a substituted or unsubstituted cycloalkyl group including 3 to 50 ring carbon atoms, $-Si(R_{901})(R_{902})(R_{903})$, a substituted or unsubstituted aryl group including 6 to 50 ring carbon atoms, or a substituted or unsubstituted monovalent heterocyclic group including 5 to 50 ring atoms; and $R_{901}$ to $R_{903}$ are as defined in the formula (1-1) or (1-2);

(31)

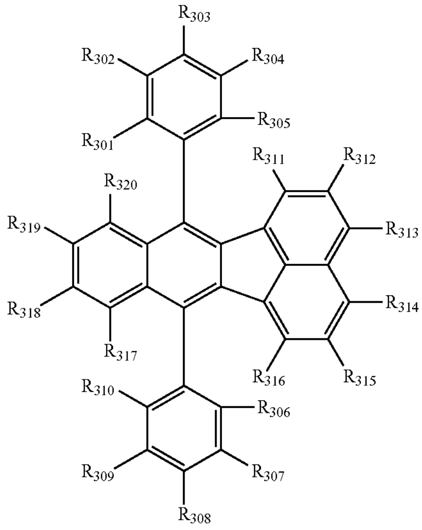

wherein in the formula (31), any one or more sets among one or more sets of adjacent two or more of $R_{311}$ to $R_{320}$, one or more sets of adjacent two or more of $R_{301}$ to $R_{305}$, and one or more sets of adjacent two or more of $R_{306}$ to $R_{310}$ form a substituted or unsubstituted, saturated or unsaturated ring including 3 to 30 ring atoms by bonding with each other;

$R_{311}$ to $R_{320}$, $R_{301}$ to $R_{305}$, and $R_{306}$ to $R_{310}$ that do not form the substituted or unsubstituted, saturated or unsaturated ring are independently a hydrogen atom or a substituent $R_b$;

the substituent $R_b$ is a halogen atom, a cyano group, a nitro group, a carboxy group, a substituted or unsubstituted alkyl group including 1 to 50 carbon atoms, a substituted or unsubstituted alkenyl group including 2 to 50 carbon atoms, a substituted or unsubstituted alkynyl group including 2 to 50 carbon atoms, a substituted or unsubstituted cycloalkyl group including 3 to 50 ring carbon atoms, —Si($R_{901}$)($R_{902}$)($R_{903}$),

—O—($R_{904}$),

—S—($R_{905}$),

—N($R_{906}$)($R_{907}$), a substituted or unsubstituted aryl group including 6 to 50 ring carbon atoms, a substituted or unsubstituted monovalent heterocyclic group including 5 to 50 ring atoms, a substituted or unsubstituted phosphanyl group, a substituted or unsubstituted phosphoryl group, or a substituted or unsubstituted arylcarbonyl group including 6 to 50 ring carbon atoms; and $R_{901}$ to $R_{907}$ are as defined in the formula (1-1) or (1-2); and (41)

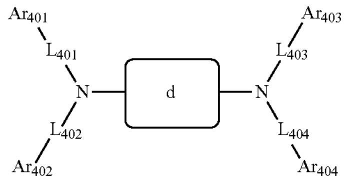

wherein in the formula (41), a ring d is a substituted or unsubstituted aromatic hydrocarbon ring including 6 to 50 ring carbon atoms, or a substituted or unsubstituted heterocycle including 5 to 50 ring atoms;

$L_{401}$ to $L_{404}$ are independently a single bond, a substituted or unsubstituted arylene group including 6 to 50 ring carbon atoms, or a substituted or unsubstituted divalent heterocyclic group including 5 to 50 ring atoms;

$Ar_{401}$ to $Ar_{404}$ are independently a substituted or unsubstituted alkyl group including 1 to 50 carbon atoms, a substituted or unsubstituted cycloalkyl group including 3 to 50 ring carbon atoms, a substituted or unsubstituted aryl group including 6 to 50 ring carbon atoms, or a substituted or unsubstituted monovalent heterocyclic group including 5 to 50 ring atoms; and provided that, when the ring d is a substituted or unsubstituted aromatic hydrocarbon ring including 10 to 50 ring carbon atoms, two or more of $Ar_{401}$ to $Ar_{404}$ are independently an aryl group including 6 to 50 carbon atoms substituted by an alkyl group including 1 to 50 carbon atoms, or a monovalent heterocyclic group including 5 to 50 ring atoms substituted by an alkyl group including 1 to 50 carbon atoms.

12. The organic electroluminescence device according to claim 11, wherein the compound represented by the formula (11) is a compound represented by the following formula (12):

(12)

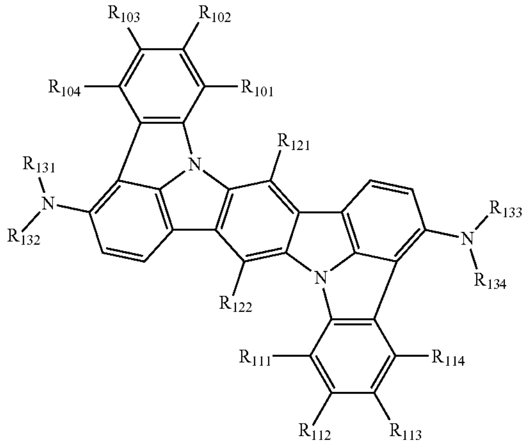

wherein in the formula (12), $R_{101}$ to $R_{104}$, $R_{111}$ to $R_{114}$, $R_{121}$, and $R_{122}$ are as defined in the formula (11); and $R_{131}$ to $R_{134}$ are independently a substituted or unsubstituted aryl group including 6 to 50 ring carbon atoms, or a substituted or unsubstituted monovalent heterocyclic group including 5 to 50 ring atoms.

13. The organic electroluminescence device according to claim 11, wherein the compound represented by the formula (11) is a compound represented by the following formula (13):

(13)

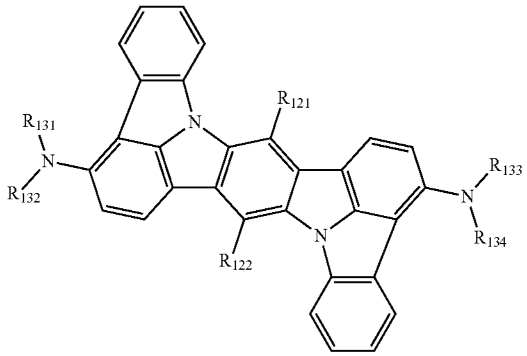

wherein in the formula (13), $R_{121}$ and $R_{122}$ are as defined in the formula (1-1) or (1-2), and $R_{131}$ to $R_{134}$ are as defined in the formula (12).

14. The organic electroluminescence device according to claim 11, wherein the ring a, the ring b, or the ring c in the formula (21) is the substituted aromatic hydrocarbon ring including 6 to 50 ring carbon atoms, or the substituted heterocycle including 5 to 50 ring atoms, and the substituent is one or more selected from the group consisting of:

a substituted or unsubstituted alkyl group including 1 to 50 carbon atoms,

—Si($R_{901}$)($R_{902}$)($R_{903}$),

—N($R_{906}$)($R_{907}$) (where $R_{901}$ to $R_{903}$, $R_{906}$, and $R_{907}$ are as defined in the formula (1-1) or (1-2), a substituted or unsubstituted aryl group including 6 to 50 ring carbon atoms, and a substituted or unsubstituted monovalent heterocyclic group including 5 to 60 ring atoms.

15. The organic electroluminescence device according to claim 11, wherein the compound represented by the formula (21) is a compound represented by the following formula (22):

(22)

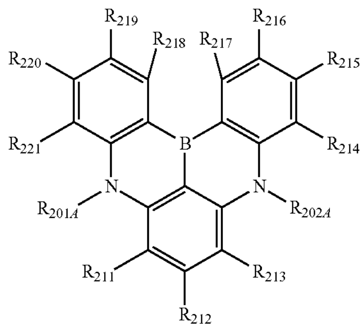

wherein in the formula (22), $R_{201A}$ forms a substituted or unsubstituted heterocycle by bonding with one or more selected from the group consisting of $R_{211}$ and $R_{221}$, or do not form a substituted or unsubstituted heterocycle;

$R_{202A}$ forms a substituted or unsubstituted heterocycle by bonding with one or more selected from the group consisting of $R_{213}$ and $R_{214}$, or do not form a substituted or unsubstituted heterocycle;

$R_{201A}$ and $R_{202A}$ that do not form the substituted or unsubstituted heterocycle are independently a substituted or unsubstituted alkyl group including 1 to 50 carbon atoms, a substituted or unsubstituted alkenyl group including 2 to 50 carbon atoms, a substituted or unsubstituted alkynyl group including 2 to 50 carbon atoms, a substituted or unsubstituted cycloalkyl group including 3 to 50 ring carbon atoms, a substituted or unsubstituted aryl group including 6 to 50 ring carbon atoms, or a substituted or unsubstituted monovalent heterocyclic group including 5 to 50 ring atoms;

one or more sets of adjacent two or more of $R_{211}$ to $R_{221}$ form a substituted or unsubstituted, saturated or unsaturated ring by bonding with each other, or do not form a substituted or unsubstituted, saturated or unsaturated ring;

$R_{211}$ to $R_{221}$ that do not form the substituted or unsubstituted heterocycle, or the substituted or unsubstituted, saturated or unsaturated ring are independently a hydrogen atom, a substituted or unsubstituted alkyl group including 1 to 50 carbon atoms, a substituted or unsubstituted alkenyl group including 2 to 50 carbon atoms, a substituted or unsubstituted alkynyl group including 2 to 50 carbon atoms, a substituted or unsubstituted cycloalkyl group including 3 to 50 ring carbon atoms, —Si($R_{901}$)($R_{902}$)($R_{903}$),

—O—($R_{904}$),

—S—($R_{905}$),

—N($R_{906}$)($R_{907}$), a halogen atom, a cyano group, a nitro group, a substituted or unsubstituted aryl group including 6 to 50 ring carbon atoms, or a substituted or unsubstituted monovalent heterocyclic group including 5 to 50 ring atoms; and $R_{901}$ to $R_{907}$ are as defined in the formula (1-1) or (1-2).

16. The organic electroluminescence device according to claim 11, wherein the compound represented by the formula (21) is a compound represented by the following formula (23A):

(23A)

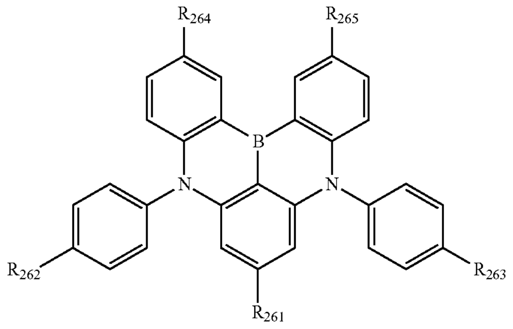

wherein in the formula (23A), $R_{261}$ to $R_{265}$ are a hydrogen atom, a substituted or unsubstituted alkyl group including 1 to 50 carbon atoms, a substituted or unsubstituted alkenyl group including 2 to 50 carbon atoms, a substituted or unsubstituted alkynyl group including 2 to 50 carbon atoms,

—N($R_{906}$)($R_{907}$), a substituted or unsubstituted cycloalkyl group including 3 to 50 ring carbon atoms, or a substituted or unsubstituted aryl group including 6 to 50 ring carbon atoms;

$R_{906}$ and $R_{907}$ are as defined in the formula (1-1) or (1-2); and when two or more of each of $R_{906}$ and $R_{907}$ are present, the two or more of each of $R_{906}$ and $R_{907}$ are the same as or different from each other.

17. The organic electroluminescence device according to claim 11, wherein the ring d in the formula (41) is a substituted or unsubstituted divalent group having a structure selected from the group consisting of structures represented by the following formulas.

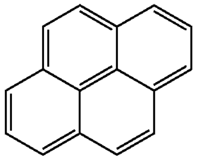

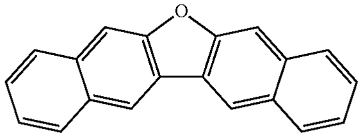

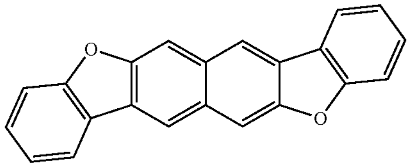

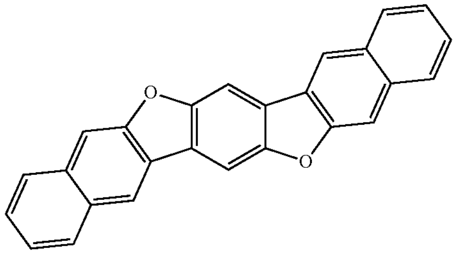

-continued

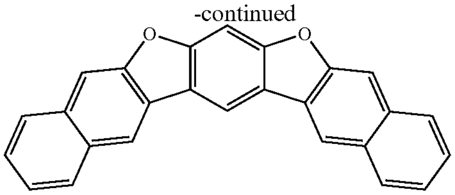

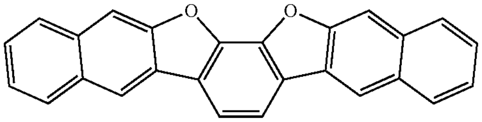

18. The organic electroluminescence device according to claim 11, wherein the ring d in the formula (41) is a substituted or unsubstituted pyrene ring.

19. The organic electroluminescence device according to claim 1, wherein the organic layer comprises an emitting layer, and the emitting layer comprises the compound represented by the formula (1-1) or (1-2) and the compound A.

20. An electronic apparatus equipped with the organic electroluminescence device according to claim 1.

* * * * *